United States Patent
Breidenbach et al.

(10) Patent No.: US 7,553,651 B2
(45) Date of Patent: Jun. 30, 2009

(54) CRYSTAL STRUCTURE OF SNAP-25 IN COMPLEX WITH BOTULINUM NEUROTOXIN AND USES THEREOF

(75) Inventors: Mark A. Breidenbach, San Francisco, CA (US); Axel T. Brunger, San Francisco, CA (US)

(73) Assignee: Board of Trustees of the Leland Stanford Junior University, Palo Alto, CA (US)

( * ) Notice: Subject to any disclaimer, the term of this patent is extended or adjusted under 35 U.S.C. 154(b) by 125 days.

(21) Appl. No.: 11/394,392

(22) Filed: Mar. 29, 2006

(65) Prior Publication Data

US 2006/0258846 A1     Nov. 16, 2006

Related U.S. Application Data

(60) Provisional application No. 60/668,771, filed on Apr. 5, 2005.

(51) Int. Cl.
*C12N 9/14* (2006.01)
*G06F 7/60* (2006.01)

(52) U.S. Cl. .......................... 435/195; 703/2
(58) Field of Classification Search ................ None
See application file for complete search history.

(56) References Cited

OTHER PUBLICATIONS

Lacy et al. Nat Struct Biol. Oct. 1998;5(10):898-902.*
Giege et al. (1994) Acta Cryst., D50, 339-350.*
Branden et al (1999) Introduction to Protein Structure, Second Edition, Garland Publishing Inc., New York, pp. 374-375 and 382.*
Drenth (1995) Principles of X-ray Crystallography, Springer, New York, p. 1.*
Kierzek et al. (2001) Biophys Chem, 91:1-20.*
Wiencek (1999) Ann Rev Biomed Eng., 1:505-534.*
Breidenbach et al., Substrate recognition strategy for botulinum neurotoxin serotype A., Dec. 16, 2004, Nature, vol. 432, pp. 925-929.*

* cited by examiner

*Primary Examiner*—Suzanne M. Noakes
*Assistant Examiner*—Alexander D Kim
(74) *Attorney, Agent, or Firm*—Thomas, Kayden, Horstemeyer & Risley, LLP

(57) ABSTRACT

The present invention provides a crystallized form of the E223Q Y365F mutant of the light chain of botulinum neurotoxin serotype A (BoNT/A) protein as well as the atomic structure of this mutant protein. The present invention also provides crystals of the E223Q Y365F mutant of the BoNT/A light chain in complex with the SNARE (soluble N-ethylmaleimide-sensitive factor attachment protein receptor) domain of the SNAP-25 (synaptosome-associated protein-25 kDa) protein as well as the atomic structure of this complex. The present invention further provides a method of determining whether an agent mimics a region of the SNAP-25 protein that interacts with BoNT/A. With this method, a three-dimensional representation of the SNAP-25 region is used to computationally compare the agent with the three-dimensional representation of the SNAP-25 region.

2 Claims, 2 Drawing Sheets

CRYSTAL STRUCTURE OF SNAP-25 IN COMPLEX WITH BOTULINUM NEUROTOXIN AND USES THEREOF

CROSS-REFERENCE TO RELATED APPLICATIONS

This application claims priority from U.S. Provisional Patent Application No. 60/668,771, filed Apr. 5, 2005, which is incorporated herein by reference.

STATEMENT REGARDING FEDERALLY SPONSORED RESEARCH OR DEVELOPMENT

This invention was made in part with government support under grant no. NIH R01-MH63105-01 awarded by the National Institutes of Health (NIH). The government has certain rights in this invention.

FIELD OF THE INVENTION

The present invention relates generally to neurotoxins. More particularly, the present invention relates to the crystallization and structure determination of SNAP-25 in complex with botulinum neurotoxin.

BACKGROUND

Clostridal neurotoxins (CNTs) are the causative agents of the neuroparalytic diseases botulism and tetanus. CNTs impair neuronal exocytosis through specific proteolysis of essential proteins called SNAREs (soluble N-ethylmaleimide-sensitive factor attachment protein receptor). This proteolysis prevents the release of neurotransmitter at neuromuscular junctions, resulting in muscle paralysis. The identification of the means by which a CNT properly identifies and cleaves its target SNARE is therefore of clinical and biological significance.

Site-specific SNARE hydrolysis is catalysed by the CNT light chains, a unique group of zinc-dependent endopeptidases. The structures of three CNT light chains suggest that substrate recognition cannot occur at the active sites of these proteases, because the catalytic pocket composition and geometries of BoNTs A, B, and E are essentially identical. Furthermore (and atypically for endopeptidases), light-chain activity can be strongly influenced by remote substitutions and deletions. for example, conserved motifs containing acidic residues in the substrates were shown to be required for normal levels of light-chain activity and led to the proposal that the light chains may use exosites for efficient substrate recognition and cleavage. However, structural data concerning the locations and functions of these exosites have remained elusive. Accordingly, there is a need in the art to determine the precise structure and amino acids involved in the binding of CNT light chains to exosites on the target SNAREs.

SUMMARY OF THE INVENTION

The present invention provides a crystallized form of the E223Q Y365F (amino acid numbering according to SEQ ID NO: 1) mutant of the light chain of botulinum neurotoxin serotype A (BoNT/A) protein. The E223Q Y365F mutant of BoNT/A light chain eliminates substrate turnover at the conditions required for crystallization. In one embodiment, the E223Q Y365F mutant of the BoNT/A light chain has the amino acid sequence listed in SEQ ID NO: 1. In another embodiment, the E223Q Y365F mutant of the BoNT/A light chain has an amino acid sequence that is at least 50% identical to the amino acid sequence listed in SEQ ID NO: 1. In this embodiment, the amino acid sequence of the E223Q Y365F mutant of the BoNT/A light chain preferably has Lys at position 41, Tyr at position 312, Asn at position 40, Thr at position 109, Val at position 316, Ile at position 115, Arg at position 113, Met at position 106, Met at position 344, Lys at position 337, Leu at position 341, Leu at position 322, Lys at position 340, Ile at position 348, Leu at position 103, Phe at position 357, Lys at position 356, Tyr at position 250, Phe at position 369, Leu at position 256, His at position 227, Thr at position 176, Lys at position 166, Phe at position 168, Asn at position 136, Pro at position 25, Cys at position 134, Val at position 129, Trp at position 118, and Glu at position 148 (numbering of the amino acid positions is according to SEQ ID NO.: 1 plus one position e.g., Tyr is at position 312 according to Table 1, chain A, but at position 311 of SEQ ID NO.: 1, Asn is at position 40 according to Table 1. but at position 39 of SEQ ID NO.: 1, and so forth).

Crystals of the E223Q Y365F mutant of the BoNT/A light chain are preferably indexed in space group P2. In addition, the crystals preferably have unit cell dimensions ranging from about 53 to about 61 Å for dimension a, about 39 to about 43 Å for dimension b, and about 185 to about 205 Å for dimension c. More preferably, the crystals have unit cell dimensions of about 58 Å for dimension a, about 41 Å for dimension b, and about 196 Å for dimension c. Crystals of the E223Q Y365F mutant of the BoNT/A light chain preferably have atoms arranged in a spatial relationship represented by the structure coordinates listed in Table 1. (Numbering of the amino acid positions in Table 1 is according to SEQ ID NO: 1 plus one position e.g., E223Q of SEQ ID NO: 1 corresponds to position 224 of Table 1, Y365F of SEQ ID NO: 1 is position 366 of Table 1, and so forth).

The present invention also provides crystals of the E223Q Y365F mutant of the BoNT/A light chain in complex with the SNARE (soluble N-ethylmaleimide-sensitive factor attachment protein receptor) domain of the SNAP-25 (synaptosome-associated protein-25 kDa) protein, referred to hereafter as sn2. In one embodiment, sn2 contains residues 146-204 of SNAP-25 of the sequence listed in SEQ ID NO: 2. In another embodiment, sn2 has a sequence that is at least 50% identical to SEQ ID NO: 2. In this embodiment, the amino acid sequence of sn2 preferably has Gln at position 152, Val at position 153, Ile at position 156, Ile at position 157, Leu at position 160, Met at position 163, Asp at position 166, Met at position 167, Glu at position 170, Ile at position 171, Asp at position 172, Arg at position 176, Ile at position 178, Ile at position 181, Glu at position 183, Ile at position 192, Asp at position 193, Asn at position 196, and Met at position 202 (numbering of the amino acid positions is according to SEQ ID NO.: 2).

Crystals of the E223Q Y365F mutant of the BoNT/A light chain in complex with sn2 are preferably indexed in space group $P4_32_12$. In addition, crystals of the E223Q Y365F mutant of the BoNT/A light chain in complex with sn2 preferably have unit cell dimensions of about 80 to about 90 Å for dimensions a and b, and about 154 to about 174 Å for dimension c. More preferably, crystals of the E223Q Y365F mutant of the BoNT/A light chain in complex with sn2 have unit cell dimensions of about 85 Å for dimensions a and b, and about 165 Å for dimension c. Crystals of the E223Q Y365F mutant of BoNT/A light chain in complex with sn2 preferably have atoms arranged in a spatial relationship represented by the structure coordinates listed in Table 2.

The present invention further provides a method of determining whether an agent mimics a region of the SNAP-25 protein that interacts with BoNT/A light chain. With this method, a three-dimensional representation of the SNAP-25 region is used to computationally compare the agent with the three-dimensional representation of the SNAP-25 region. Preferably, the three-dimensional representation of the SNAP-25 region is based on the atomic coordinates of amino acids in the SNAP-25 region. These atomic coordinates can be found in Table 2. Several amino acid sequences within sn2 represent regions of interaction with BoNT/A, as determined using the crystals of the present invention. Examples include amino acids 148 through 167, amino acids 168 through 182, amino acids 192 through 193, and amino acids 201 through 204 (see SEQ ID NO: 2).

BRIEF DESCRIPTION OF THE FIGURES

The present invention together with its objectives and advantages will be understood by reading the following description in conjunction with the drawings, in which.

BRIEF DESCRIPTION OF THE TABLES

Figure 1:
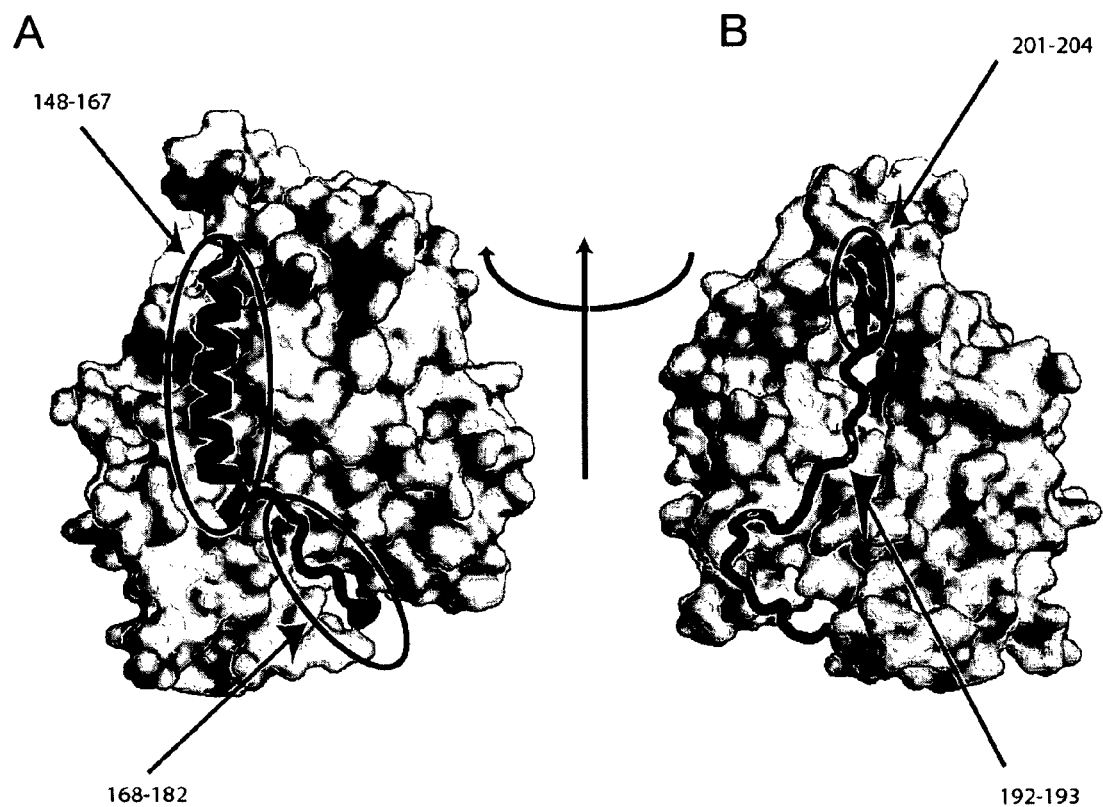
FIG. 1 shows a three dimensional structure of the SNARE domain of SNAP-25 in complex with the E223Q Y365F mutant of BoNT/A light chain according to the present invention.

TABLE 1 Atomic coordinates of the E223Q Y365F mutant of the BoNT/A light chain. Numbering of the amino acid positions of chain A in Table 1 is according to SEQ ID NO: 1 plus one position e.g., E223Q of SEQ ID NO: 1 corresponds to position 224 of Table 1, Y365F of SEQ ID NO: 1 is position 366 of Table 1, and so forth. Numbering of the amino acid positions of chain B of Table 1 is according to SEQ ID NO.: 1 plus 429 positions e.g., E223Q of SEQ ID NO.: 1 corresponds to position 652 of Table 1. Y365F of SEQ ID NO.: 1 is position 794 of Table 1, and so forth. Each of chain A and B includes the tag Pro-Gly-His-His-His-His-His-His— (SEQ ID NO.: 7) at positions 421-428 (chain A) and 849-856 (chain B), according to the numbering of Table 1. The amino acid sequences of the individual chains A and B are identical (SEQ ID NO.: 9), each comprising sequence SEQ ID NO.: 1 and sequence SEQ ID NO.: 7

TABLE 2 Atomic coordinates of the E223Q Y365F mutant of the BoNT/A light chain in complex with sn2. Numbering of the amino acid positions in Table 2, for Chain A, is according to SEQ ID NO.: 1 plus one position e.g., E223Q of SEQ ID NO.: 1 corresponds to position 224 of Table 2. Y365F of SEQ ID NO.: 1 is position 366 of Table 2. and so forth. Chain A further includes the tag Pro-Leu-Val-Pro-Arg (SEQ ID NO.: 8) at positions 421-425 according to Table 2. Numbering of the amino acid positions for Chain B (sn2) in Table 2 (positions 146-204) is in accordance with SEQ ID NO.: 2. The amino acid sequence of the chain A (SEQ ID NO.: 10), therefore, comprises sequence SEQ ID NO.: 1 and sequence SEQ ID NO.: 8.

DETAILED DESCRIPTION OF THE INVENTION

Crystals of the E223Q Y365F Mutant of the BoNT/A Light Chain

The present invention provides crystals of the E223Q Y365F mutant of the BoNT/A light chain. This mutant was created to eliminate substrate turnover at the conditions required for crystallization (see "Substrate Recognition Strategy for Botulinum Neurotoxin Serotype A", by Breidenbach and Brunger, Nature, vol. 432, pages 925-929, December 2004, including "Supplementary Information", which is incorporated by reference herein). The mutant polypeptide may be obtained and purified using techniques well known in the art. The purified mutant polypeptide may then be crystallized using any methods known in the art, but is preferably crystallized using a hanging-drop vapor diffusion technique. For example, the crystals may be grown by hanging-drop vapor diffusion over reservoirs of 15-18% PRG 3350 and 200 mM di-sodium hydrogen phosphate dihydrate. The amino acid sequence of the purified mutant polypeptide may be the amino acid sequence listed in SEQ ID NO: 1. Alternatively, the amino acid sequence may be a variant of SEQ ID NO: 1 that includes Lys at position 41, Tyr at position 312, Asn at position 40, Thr at position 109, Val at position 316, Ile at position 115, Arg at position 113, Met at position 106, Met at position 344, Lys at position 337, Leu at position 341, Leu at position 322, Lys at position 340, Ile at position 348, Leu at position 103, Phe at position 357, Lys at position 356, Tyr at position 250, Phe at position 369, Leu at position 256, His at position 227, Thr at position 176, Lys at position 166, Phe at position 168, Asn at position 136, Pro at position 25, Cys at position 134, Val at position 129, Trp at position 118, and Glu at position 148, but varies at other residues within SEQ ID NO: 1 (numbering of the amino acid positions is in accordance with the numbering of chain A of Tables 1 and 2, corresponding to SEQ ID NO.: 1 plus one position e.g., Tyr at position 311 of SEQ ID NO.: 1 corresponds to position 312 of Tables 1 and 2, Asn at position 39 of SEQ ID NO.: 1 is position 40 of chain A of Tables 1 and 2, and so forth). Preferably, the variant would have at least 50% identity to the amino acid sequence listed in SEQ ID NO.: 1.

Crystals of the E223Q Y365F mutant of the BoNT/A light chain are preferably indexed in space group P2. In addition, the crystals preferably have unit cell dimensions ranging from about 53 to about 61 Å for dimension a, about 39 to about 43 Å for dimension b, and about 185 to about 205 Å for dimension c. More preferably, the crystals have unit cell dimensions of about 58 Å for dimension a, about 41 Å for dimension b, and about 196 Å for dimension c. Most preferably, the crystals have near-orthorhombic unit cell dimensions a=57.90 Å, b=40.49 Å, c=195.89 Å, and β=90.25°.

Crystals of the E223Q Y365F mutant of the BoNT/A light chain may be characterized using x-ray diffraction techniques known in the art. Data from x-ray diffraction may then be used to solve the atomic structure of the E223Q Y365F mutant of the BoNT/A light chain. In a preferred embodiment, crystals according to the present invention can be used to define the structure of the E223Q Y365F mutant of the BoNT/A light chain to within about 0.2 Å coordinate accuracy. Crystals of the E223Q Y365F mutant of the BoNT/A light chain according to the present invention preferably have atoms arranged in a spatial relationship represented by the structure coordinates listed in Table 1,± a root mean square deviation from the conserved backbone atoms of the amino acids of about 0.2 Å. In Table 1, the first column is an identifier. The second column indicates the number of the atom. The third column indicates the type of atom [N=backbone amide nitrogen, CA=backbone alpha carbon, C=backbone carbonyl carbon, O=backbone carbonyl oxygen, CB=sidechain beta carbon, CG=sidechain gamma carbon (if multiple gamma carbons exist in sidechain, they are numbered CG1, CG2, etc.), CD=sidechain delta carbon (if multiple delta carbons exist in sidechain, they are numbered CD1, CD2, etc.), CE=sidechain epsilon carbon (if multiple epsilon carbons exist in sidechain, they are numbered CE1, CE2, etc.), CZ=sidechain zeta carbon, CZ2=zeta carbon in tryptophan sidechains, CH2=eta carbon in tryptophan sidechains, OD=sidechain delta oxygen (if multiple delta oxygens exist in sidechain, they are numbered OD1, OD2, etc.), OG=sidechain gamma oxygen (if multiple gamma oxygens exist in sidechain, they are numbered OG1, OG2, etc.), OE=sidechain epsilon oxygen (if multiple epsilon oxygens exist in sidechain, they are numbered OE1, OE2, etc.), OH=eta oxygen in tyrosine sidechains, ND=sidechain delta nitrogen (if multiple delta nitrogens exist in sidechain, they are numbered ND1, ND2, etc.), NE=sidechain epsilon nitrogen (if multiple epsilon nitrogens exist in sidechain, they are numbered NE1, NE2,etc.), NZ=sidechain zeta nitrogen (if multiple zeta nitrogens exist in sidechain, they are numbered NZ1, NZ2, etc.), NH=sidechain eta nitrogen (if multiple eta nitrogens exist in sidechain, they are numbered NH1, NH2, etc.), SD=delta sulfur present in methionine sidechains, SG=gamma sulfur present in cysteine sidechains, OXT=backbone carboxy terminal oxygen]. The fourth column indicates the type of amino acid the atom is in. The fifth column indicates the polypeptide chain identifier. (There are two copies of the E223Q Y365F mutant of the BoNT/A light chain in the crystallographic asymmetric unit. Chain A includes atoms from the first copy of the light chain and chain B includes atoms from the second copy). The sixth column indicates the number of the amino acid from SEQ ID NO: 1 that the atom is contained in plus one (e.g., Pro2 of Table 1 corresponds to Pro1 of SEQ ID NO: 1). The seventh through ninth columns indicate the Cartesian coordinates of each measured atom's location in the unit cell (in Å). The tenth column indicates the occupancy factor. The eleventh column indicates the B-value, which is a measure of how mobile the atom is in the atomic structure. The twelfth column lists the element type for each atom according to the standard notation used in a periodic table of elements.

Crystals of the E223Q Y365F Mutant of the BoNT/A Light Chain in Complex With the SNARE Domain of SNAP-25

The present invention also provides crystals of the E223Q Y365F mutant of the BoNT/A light chain in complex with the SNARE domain of SNAP-25, sn2 (amino acids 141 through 204 of SEQ ID NO: 2). Sn2 may be obtained and purified using techniques well known in the art. A mixture of purified sn2 and the E223Q Y365F mutant of the BoNT/A light chain may then be crystallized using any methods known in the art, but is preferably crystallized using a hanging-drop vapor diffusion technique. For example, the crystals may be grown by hanging-drop vapor diffusion over reservoirs of about 10% (w/v) PEG 8000, 200 mM magnesium acetate, and 100 mM sodium cacodylate pH 6.5. The amino acid sequence of sn2 may be amino acids 141 through 204 of SEQ ID NO: 2. Alternatively, the amino acid sequence may be a variant of this sequence that includes Lys at position 41, Tyr at position 312, Asn at position 40, Thr at position 109, Val at position 316, Ile at position 115, Arg at position 113, Met at position 106, Met at position 344, Lys at position 337, Leu at position 341, Leu at position 322, Lys at position 340, Ile at position 348, Leu at position 103, Phe at position 357, Lys at position 356, Tyr at position 250, Phe at position 369, Leu at position 256, His at position 227, Thr at position 176, Lys at position 166, Phe at position 168, Asn at position 136, Pro at position 25, Cys at position 134, Val at position 129, Trp at position 118, and Glu at position 148, but varies at other residues from amino acids 141-204 of SEQ ID NO:2. Preferably, the variant would have at least 50% identity to amino acids 141 through 204 of the amino acid sequence listed in SEQ ID NO: 2.

Crystals of the E223Q Y365F mutant of the BoNT/A light chain in complex with sn2 are preferably indexed in space group P4$_3$2$_1$2. In addition, the crystals preferably have unit cell dimensions ranging from about 80 to about 90 Å for dimensions a and b, and about 154 to about 174 Å for dimension c. More preferably, the crystals have unit cell dimensions of about 85 Å for dimensions a and b, and about 165 Å for dimension c. Most preferably, the crystals have near-orthorhombic unit cell dimensions a=b=86.0 Å, and c=165.4 Å.

Crystals of the E223Q Y365F mutant of the BoNT/A light chain in complex with sn2 may be characterized using x-ray diffraction techniques known in the art. Data from x-ray diffraction may then be used to solve the atomic structure of the E223Q Y365F mutant of the BoNT/A light chain in complex with sn2. In a preferred embodiment, the structure of the E223Q Y365F mutant of the BoNT/A light chain in complex with sn2 may be solved using crystals according to the present invention to within about 2.0 and about 30 Å. Crystals according to the present invention of the E223Q Y365F mutant of the BoNT/A light chain in complex with sn2 preferably have atoms arranged in a spatial relationship represented by the structure coordinates listed in Table 2.±.a root mean square deviation from the conserved backbone atoms of the amino acids of about 0.2 Å. In Table 2, the first column is an identifier. The second column indicates the number of the atom. The third column indicates the type of atom [N=backbone amide nitrogen, CA=backbone alpha carbon, C=backbone carbonyl carbon, O=backbone carbonyl oxygen, CB=sidechain beta carbon, CG=sidechain gamma carbon (if multiple gamma carbons exist in sidechain, they are numbered CG1, CG2, etc.), CD=sidechain delta carbon (if multiple delta carbons exist in sidechain, they are numbered CD1, CD2, etc.), CE=sidechain epsilon carbon (if multiple epsilon carbons exist in sidechain, they are numbered CE1, CE2, etc.), CZ=sidechain zeta carbon, CZ2=zeta carbon in tryptophan sidechains, CH2=eta carbon in tryptophan sidechains, OD=sidechain delta oxygen (if multiple delta oxygens exist in sidechain, they are numbered OD1, OD2, etc.), OG=sidechain gamma oxygen (if multiple gamma oxygens exist in sidechain, they are numbered OG1, OG2, etc.), OE=sidechain epsilon oxygen (if multiple epsilon oxygens exist in sidechain, they are numbered OE1, OE2, etc.), OH=eta oxygen in tyrosine sidechains, ND=sidechain delta nitrogen (if multiple delta nitrogens exist in sidechain, they are numbered ND1, ND2, etc.), NE=sidechain epsilon nitrogen (if multiple epsilon nitrogens exist in sidechain, they are numbered NE1, NE2, etc.), NZ=sidechain zeta nitrogen (if multiple zeta nitrogens exist in sidechain, they are numbered NZ1, NZ2, etc.), NH=sidechain eta nitrogen (if multiple eta nitrogens exist in sidechain, they are numbered NH1, NH2, etc.), SD=delta sulfur present in methionine sidechains, SG=gamma sulfur present in cysteine sidechains, OXT=backbone carboxy terminal oxygen]. The fourth column indicates the type of amino acid the atom is in. The fifth column indicates whether the atom is from the E223Q Y365F mutant of the BoNT/A light chain polypeptide (A) or from sn2 (B). The sixth column indicates the number of the amino acid from SEQ ID NO: 1 plus one (e.g. Pro2 of Table 1 corresponds to Pro1 of SEQ ID NO: 1) (for the E223Q Y365F mutant of the BoNT/A light chain) or SEQ ID NO: 2 (for sn2) that the atom is contained in. The seventh through ninth columns indicate the Cartesian coordinates of each measured atom's location in the unit cell (in Å). The tenth column indicates the occupancy factor. The eleventh column indicates the B-value, which is a measure of how mobile the atom is in the atomic structure. The twelfth column lists the element type for each atom according to the standard notation used in a periodic table of elements.

Method of Determining Whether an Agent Mimics a Region of SNAP-25 That Interacts With BoNT/A Crystals according to the present invention of the E223Q Y365F mutant of the BoNT/A light chain in complex with sn2, as well as kinetic data, were used to identify substrate recognition sites of BoNT/A (see "Substrate Recognition Strategy for Botulinum Neurotoxin Serotype A", by Breidenbach and Brunger, Nature, vol. 432, pages 925-929, December 2004, including "Supplementary Information"). FIG. 1 illustrates regions of SNAP-25 (colored black) that interact with these substrate recognition sites. As shown in FIG. 1A, SNAP-25 amino acids 148-167 form an alpha-helix that binds to a hydrophobic patch on BoNT/A (represented by a gray surface). SNAP-25 amino acids 168-182 adopt a unique extended conformation, which binds to the toxin with mixed hydrophobic and polar interactions. On the opposite side face of the toxin, shown in FIG. 1B, amino acids 192-193 anchor SNAP-25 leading into the active site of BoNT/A. Amino acids 201-204 form part of a beta-sheet structure that is required for activation of the toxin.

Figure 2:
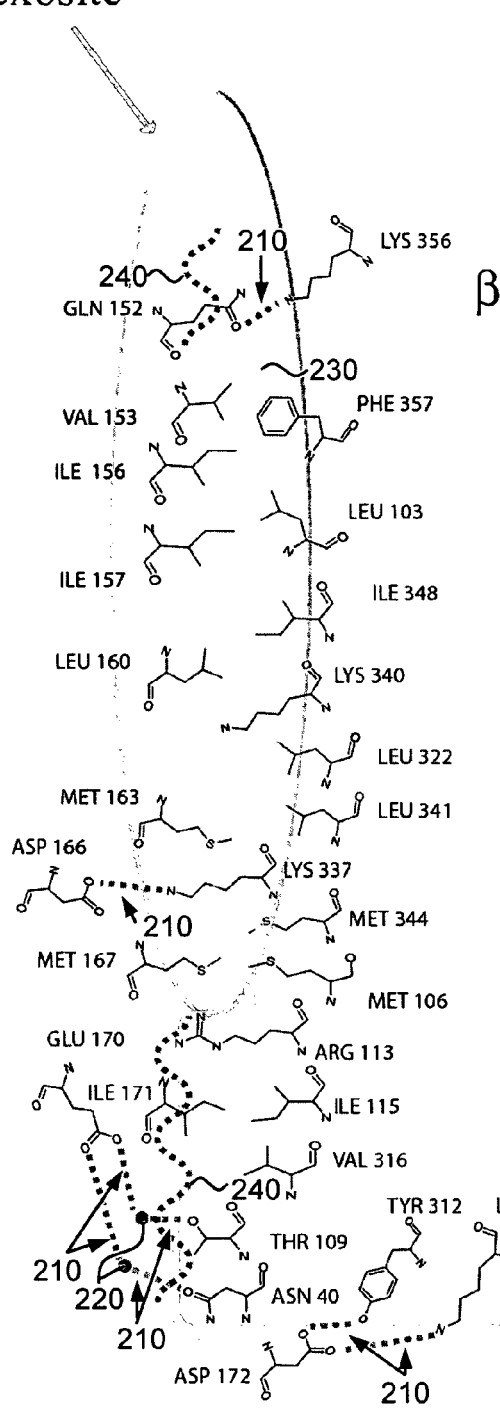
FIG. 2 shows regions of interaction between SNAP-25 and BoNT/A light chain according to the present invention.
Figure 2:
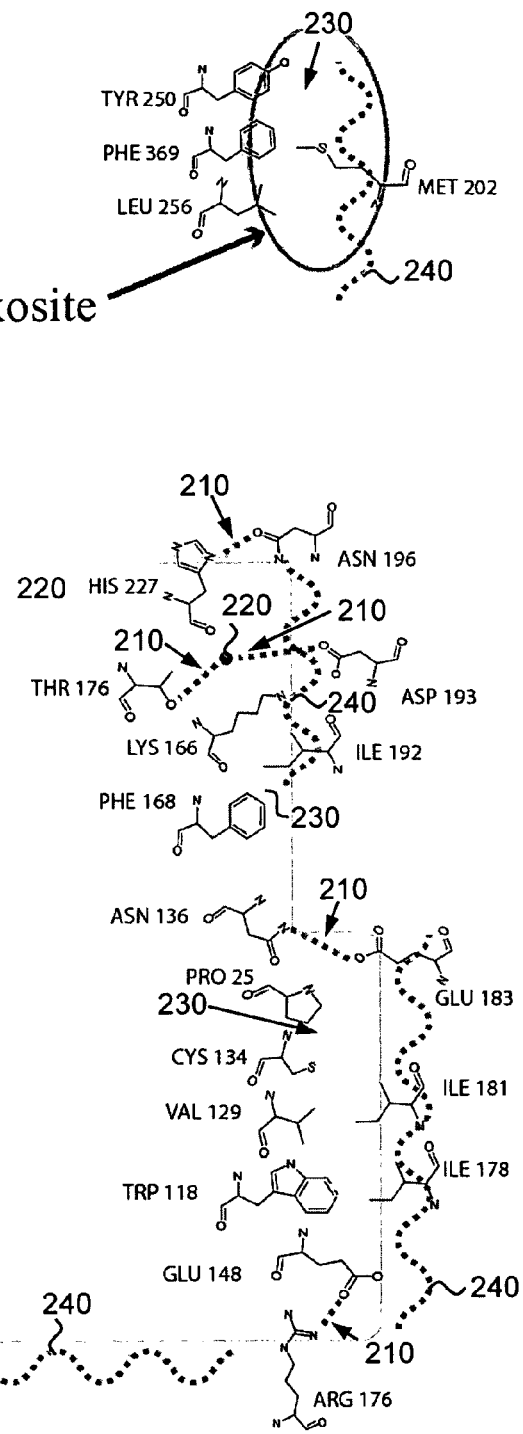

A schematic of the sn2 (colored light gray) interface with BoNT/A (colored dark gray) shows the extensive network of contacts used in substrate recognition (FIG. 2). Two exosites important for substrate recognition, called the alpha exosite and the beta exosite, are indicated. Residues involved in side-chain/side-chain interactions are explicitly shown. Straight dashed lines 210 indicate polar side-chain contacts, with water mediation indicated by dots 220. Wavy dashed lines 230 indicate regions of hydrophobic side-chain interaction. Wavy dashed lines 240 indicate regions of backbone polar contacts.

The structure of regions of SNAP-25 that interact with BoNT/A may be used to design, screen for and/or identify inhibitors specific to BoNT/A. These inhibitors would potentially compete with substrate binding at exosites, as opposed to the active site of BoNT/A. Thus, inhibitors designed according to the present invention could potentially be very specific against the intended target.

In a preferred method according to the present invention, agents are tested to determine whether they mimic a region of SNAP-25 that interacts with BoNT/A. By mimic, it is meant that the agent has a similar shape (the agent is within 2 Å of the coordinates of SNAP-25) and chemical nature (similar hydrophobicity, charged, or polar character) to the region. Agents may be any type of compound or molecule, including but not limited to a small molecule (e.g., a small organic molecule), a peptide (a D-peptide or an L-peptide), or a peptidomimetic compound.

The test is accomplished by computationally comparing agents with a three dimensional representation of the region of interest. The computational comparison may be accomplished using techniques known in the art. The three-dimensional representations of the region of interest can be generated using the atomic coordinates, according to Table 2, of the amino acids in the region using techniques known in the art. The regions of interest may be any of the amino acid regions illustrated in FIG. 1.

The tested agents may be agents from a random library of chemical compounds, or from a pre-screened library of compounds that are known to have a similar shape and/or chemical nature to a given region of SNAP-25. In this case, the test would be used to screen for candidate inhibitors. Alternatively, the test could be used to evaluate compounds that were designed based on the shape and chemical nature of the region of interest. Preferably, once an agent is identified using the above method, it is tested for its ability to inhibit binding of BoNT/A to its substrate (SNAP-25). This test may be any computational, biochemical, etc. test known in the art to be suitable for this purpose, for example, binding may be determined using co-immunoprecipitation techniques.

The agent is also preferably tested for its ability to inhibit cleavage of SNAP-25 by BoNT/A. Again, the test may be any computational, biochemical, etc. test known in the art to be suitable for this purpose. In one example, the presence of cleaved SNAP-25 is detected by incubating sn2 with BoNT/A and quantifying proteolysis products from the digestions following fractionation on a column with reverse-phase high-performance liquid chromatography. Any type of column, including but not limited to a 218TP54 column (Vydac) used with a 0-90% acetonitrile gradient, may be used to separate the small C-terminal cleavage product from the N-terminal and uncut moieties. Initial substrate concentrations, as well as the relation between $A_{214}$ peak area and C-terminal protein yield may be determined by any type of quantitative amino-acid analysis, such as with the Beckman 7300 Analyzer. In another example, Matrix-Assisted Laser Desorption/Ionization (MALDI) mass spectrometry is used to detect the cleavage products. The SNAP-25 used in the binding and cleavage tests may be derived from mammals, birds, amphibians, or fishes, as the residues important for interaction of SNAP-25 with BoNT/A are conserved in these animals.

EXAMPLES

Protein Purification of the Light Chain of BoNT/A and SNAP-25 BoNT/A-LC and BoNT/A E223/Y365F Plasmid DNA pBN3 encoding wt-BoNT/A-LC was provided by Thomas Binz (Medizinische Hoschule Hannover, Germany). Truncation of the LC C-terminus was achieved by amplifying residues 1-420 from the original construct by polymerase chain reaction (PCR) using the primers a) 5'-ACAGAATTCGCAATTAAGGAGATAATAGGTATG-3' (SEQ ID NO: 3) corresponding to the 5' end and b) 5'-GCTC-CCGGGAGTAAAATTTTTTAGTTTAG-TAAAATTCATATTATTMTTTCTGTATTTT GAC-3' (SEQ ID NO: 4) corresponding to the 3' end. The resulting PCR product was digested with EcoRI and SmaI and re-inserted into the original pBN3 vector that had been digested with the same restriction enzymes. A variant of this construct with a thrombin-cleavable affinity tag was prepared by digesting the plasmid with SmaI and inserting the following sequence: 5'-CTGGTTCCGCGTGGATCT-3' (SEQ ID NO:5) paired with 5'-AGATCCACGCGGAACCAG-3' (SEQ ID NO:6). Constructs encoding point mutant E223Q and double mutant E223Q/Y365F were prepared using the Quickchange protocol (Stratagene).

All BoNT/A-LC constructs were expressed at 20° in M15 [pREP4] cells (Qiagen) and affinity purified according to protocols previously described, with minor modifications (Li, L. & Singh, B. R. "High-level expression, purification, and characterization of recombinant type A botulinum neurotoxin light chain". Protein Expr Purif 17, 339-44 (1999)). Cells were lysed via two passes through a M-110 EH Microfluidizer Processor (Microfluidics) at 18,000 psi. Insoluble debris was removed from the lysate by centrifugation in a JA-20 rotor (Beckman) at 19,500 rpm for 45 min. Protease inhibitors added to the lysate include 1 mM phenylmethylsulfonyl fluoride (PMSF) and EDTA-free Complete Protease Inhibitor Cocktail Tablets (Roche). The affinity tag was removed with bovine a-thrombin (Haematologic Technologies), and additional purification (>95%) was achieved with cation-exchange (Amersham-Pharmacia, mono-S resin) chromatography. BoNT/A-LC was quantified by UV/Vis spectroscopy at 280 nm, based on its theoretical extinction coefficient in denaturing conditions. Proteolytic activity of the BoNT/A-LC was qualitatively verified by incubation with SNAP-25 residues 141-204; cleavage products were observed with an Omni-Flex Matrix-Assisted Laser Desorption/Ionization (MALDI) mass spectrometer (Bruker).

SNAP-25

Plasmid DNA encoding human SNAP-25a residues 141-204 (SN2) in a pET-28a expression vector was obtained from J. Ernst (Stanford University). The peptide was expressed and purified as previously described (Ernst, J. A. & Brunger, A. T. "High resolution structure, stability, and synaptotagmin binding of a truncated neuronal SNARE complex". J Biol Chem 278, 8630-6 (2003)). Purified SNAP-25 peptide for crystallization was quantified by the BCA colorimetric assay (Pierce).

Crystallization and Data Collection

BoNT/A-LC E223Q/Y365F SNAP-25 complex

Concentrated stocks of BoNT/A E223Q/Y365F and SNAP-25 in 20 mM HEPES pH 7.4 were diluted into a crystallization mix to final concentrations of 242 .μm and 484 .μM respectively. Crystals were grown from this mix by hanging-drop vapour diffusion over 1 mL reservoirs of 10% (w/v) PEG 8000, 200 mM magnesium acetate, and 100 mM sodium cacodylate pH 6.5 at 4° over the course of 2-3 weeks. Crystals typically grew in clusters of blade-shapes with approximate dimensions of 0.3×0.05×0.05 mm$^3$. Thoroughly washed crystals were confirmed to contain both enzyme and uncleaved substrate by both MALDI and analysis on a Phastgel SDS-PAGE system (Amersham-Pharmacia). Nucleation events were unusually rare and it was necessary to propagate crystal growth by macroseeding to obtain a large a large population of high-quality single crystals. Individual blades were harvested and flash-frozen after brief exposure to 25% ethylene glycol cryoprotectant.

Crystals were characterized at beamline 8.2.2 of the Advanced Light Source (ALS). Data indexed in space group P4$_3$2$_1$2 with unit cell dimensions a=b=86.0 Å, c=165.4 Å, and diffraction extended to $d_{min}$=2.0 Å. A native high-resolution dataset was collected at 11,500 eV. A second, low-resolution dataset was collected on a different crystal at Stanford Synchrotron Radiation Laboratory (SSRL) beamline 9-2. This inverse-beam dataset was collected at a lower energy (7,500 eV) in 1° wedges with high multiplicity to record the weak anomalous signal from the sulphur atoms. Both datasets were collected on CCD Quantum-315 detectors (Area Detector Systems). All diffraction datasets were integrated and scaled using MOSFLM and SCALA in the CCP4 computational suite. Low-resolution reflections (30-2.6 Å) from the anomalous dataset were scaled with high-resolution reflections (3.2-2.1 Å) from the native dataset.

apo BoNT/A-LC E223Q/Y365F

BoNT/A-LC 1-420 E223Q/Y365F with C-terminal hexahistidine tag attached was concentrated to 10 mg mL$^{-1}$ in 20 mM HEPES pH 7.4. Crystals were grown by hanging-drop vapour diffusion over 1 mL reservoirs of 15-18% PEG 3350 and 200 mM di-sodium hydrogen phosphate dihydrate. Crystals appeared over the course of 4-5 days, typically assuming a cubic morphology with approximately 0.25 mm edges. Individual crystals were flash-frozen in a 20% glycerol cryoprotectant.

Diffraction data was collected at 11,500 eV on a Quantum-210 CCD detector (Area Detector Systems) at beamline 8.2.1 at ALS. Reflections extended to approximately $d_{min}$=2.2 Å, and indexed in space group P2 with near-orthorhombic unit cell dimensions a=57.90 Å, b=40.49 Å, c=195.89 Å, and β=90.25°. A total of 150° of data were collected in 0.5° oscillations before high-resolution reflections were no longer detectable due to radiation damage.

Crystallographic Refinement and Structure Determination

All phasing and refinement calculations were performed using the Crystallography and NMR System version 1.1 (CNS). Progress of refinement for both apo and holo structures was monitored by the cross-validated $R_{free}$ value which was computed from a randomly assigned test set comprising 5% of the data. Model building was performed using the program O. Model stereochemical quality was evaluated with PROCHECK. FIG. 1 was prepared using PyMOL.

BoNT/A-LC E223Q/Y365F SNAP-25 complex

A molecular replacement (MR) solution was found with coordinates of the BoNT/A-LC extracted from 3 BTA.pdb (Lacy, D. B., Tepp, W., Cohen, A. C., DasGupta, B. R. & Stevens, R. C. "Crystal structure of botulinum neurotoxin type A and implications for toxicity". Nat Struct Biol 5, 898-902 (1998)). Anomalously scattering sulphur atoms (as well as the Zn$^{2+}$ and one chloride) were located with an anomalous difference Fourier map calculated using reflections from 20 to 3.2 Å resolution. Experimental single-wavelength anomalous dispersion (SAD) phases were computed from these low-resolution reflections and, after density modification, used as an independent confirmation of the sn2 trace. Electron density for both enzyme and sn2 substrate was easily interpretable in a $σ_A$-weighted MR (2m|F$_o$|Ψ$_{calc}$-D|F$_c$|Ψ$_{calc}$) map. The register of the sn2 peptide was double-checked by matching anomalous difference peaks to methionine residues. The model was refined with alternate cycles of simulated annealing with torsion angle dynamics and restrained B-factor refinement using the maximum likelihood target function with amplitudes and phase probability distributions followed by manual rebuilding. In addition to the MR map described above, a MR/SAD phase-combined (2m|F$_o$|Ψ$_{comb}$-D|F$_c$|Ψ$_{calc}$) map was also used to further reduce model bias; little change was observed between the two maps. Weak electron density was observed in three regions of the complex including BoNT/A residues 200-205, and sn2 residues 183-190 and 197-199. The fragmented electron density allowed for approximate main-chain trace for these regions, but side chain occupancies were set to zero. The coordinates and structure factors of the BoNT/A-LC E223Q/Y365F SNAP-25 complex can be found in the Protein Data Bank under the accession code 1XTG.

apo BoNT/A-LC E223Q/Y365F

MR solutions were found for two molecules of BoNT/A LC per asymmetric unit using light chain coordinates extracted from 3BTA.pdb. A near-perfect two-fold screw axis related the two molecules. A plausible orientation for one molecule was located and fixed before an additional translation search could locate the second molecule.

The initial model, derived from the MR solution, was refined with alternate cycles of simulated annealing with torsion angle dynamics and restrained B-factor refinement using the maximum likelihood target function followed by manual rebuilding. Poorly ordered regions of the endopeptidase included residues 201-205 and 247-254 in both molecules of the asymmetric unit. Fragmented electron density allowed for approximate main-chain trace for these regions, but side chain occupancies were set to zero. The substrate-bound structure has a significantly lower $R_{free}$ than the apo-structure presumably due to stabilization of some of the loops (especially the 250 and 370 loops) by bound substrate. The coordinates and structure factors for BoNT/A-LC E223Q/Y365F can be found in the Protein Data Bank under the accession code 1XTF.

TABLE 2

| | | | | | | | | | | | |
|---|---|---|---|---|---|---|---|---|---|---|---|
| ATOM | 1 | N | PRO | A | 2 | 52.853 | 16.250 | −77.548 | 1.00 | 30.07 | N |
| ATOM | 2 | CA | PRO | A | 2 | 52.012 | 16.618 | −76.386 | 1.00 | 31.68 | C |
| ATOM | 3 | C | PRO | A | 2 | 51.375 | 15.379 | −75.822 | 1.00 | 32.52 | C |
| ATOM | 4 | O | PRO | A | 2 | 51.958 | 14.300 | −75.885 | 1.00 | 36.94 | O |
| ATOM | 5 | CB | PRO | A | 2 | 50.948 | 17.563 | −76.894 | 1.00 | 28.26 | C |
| ATOM | 6 | CG | PRO | A | 2 | 51.667 | 18.194 | −78.061 | 1.00 | 27.29 | C |
| ATOM | 7 | CD | PRO | A | 2 | 52.480 | 17.080 | −78.704 | 1.00 | 27.52 | C |
| ATOM | 8 | N | PHE | A | 3 | 50.178 | 15.544 | −75.269 | 1.00 | 33.99 | N |
| ATOM | 9 | CA | PHE | A | 3 | 49.424 | 14.433 | −74.717 | 1.00 | 31.60 | C |
| ATOM | 10 | C | PHE | A | 3 | 49.394 | 13.384 | −75.825 | 1.00 | 29.72 | C |
| ATOM | 11 | O | PHE | A | 3 | 49.193 | 13.705 | −77.003 | 1.00 | 24.65 | O |
| ATOM | 12 | CB | PHE | A | 3 | 47.990 | 14.869 | −74.394 | 1.00 | 35.96 | C |
| ATOM | 13 | CG | PHE | A | 3 | 47.268 | 13.965 | −73.426 | 1.00 | 40.84 | C |
| ATOM | 14 | CD1 | PHE | A | 3 | 47.479 | 12.591 | −73.429 | 1.00 | 43.52 | C |
| ATOM | 15 | CD2 | PHE | A | 3 | 46.361 | 14.493 | −72.515 | 1.00 | 43.47 | C |
| ATOM | 16 | CE1 | PHE | A | 3 | 46.797 | 11.760 | −72.536 | 1.00 | 44.20 | C |
| ATOM | 17 | CE2 | PHE | A | 3 | 45.675 | 13.671 | −71.623 | 1.00 | 43.79 | C |
| ATOM | 18 | CZ | PHE | A | 3 | 45.895 | 12.304 | −71.633 | 1.00 | 44.99 | C |
| ATOM | 19 | N | VAL | A | 4 | 49.620 | 12.137 | −75.437 | 1.00 | 28.75 | N |
| ATOM | 20 | CA | VAL | A | 4 | 49.612 | 11.017 | −76.358 | 1.00 | 30.03 | C |
| ATOM | 21 | C | VAL | A | 4 | 48.355 | 10.234 | −75.989 | 1.00 | 33.16 | C |
| ATOM | 22 | O | VAL | A | 4 | 48.322 | 9.561 | −74.962 | 1.00 | 32.04 | O |
| ATOM | 23 | CB | VAL | A | 4 | 50.871 | 10.141 | −76.155 | 1.00 | 27.51 | C |
| ATOM | 24 | CG1 | VAL | A | 4 | 50.891 | 9.000 | −77.147 | 1.00 | 26.42 | C |
| ATOM | 25 | CG2 | VAL | A | 4 | 52.117 | 10.999 | −76.300 | 1.00 | 27.05 | C |
| ATOM | 26 | N | ASN | A | 5 | 47.315 | 10.349 | −76.811 | 1.00 | 36.69 | N |
| ATOM | 27 | CA | ASN | A | 5 | 46.056 | 9.661 | −76.541 | 1.00 | 41.83 | C |
| ATOM | 28 | C | ASN | A | 5 | 45.998 | 8.285 | −77.177 | 1.00 | 44.15 | C |
| ATOM | 29 | O | ASN | A | 5 | 44.976 | 7.894 | −77.735 | 1.00 | 46.74 | O |
| ATOM | 30 | CB | ASN | A | 5 | 44.875 | 10.494 | −77.042 | 1.00 | 42.90 | C |
| ATOM | 31 | CG | ASN | A | 5 | 44.681 | 11.760 | −76.242 | 1.00 | 45.67 | C |
| ATOM | 32 | OD1 | ASN | A | 5 | 44.591 | 11.721 | −75.013 | 1.00 | 47.61 | O |
| ATOM | 33 | ND2 | ASN | A | 5 | 44.608 | 12.893 | −76.933 | 1.00 | 47.11 | N |
| ATOM | 34 | N | LYS | A | 6 | 47.092 | 7.545 | −77.086 | 1.00 | 46.34 | N |
| ATOM | 35 | CA | LYS | A | 6 | 47.140 | 6.223 | −77.676 | 1.00 | 48.41 | C |
| ATOM | 36 | C | LYS | A | 6 | 47.966 | 5.320 | −76.786 | 1.00 | 49.40 | C |
| ATOM | 37 | O | LYS | A | 6 | 48.973 | 5.744 | −76.220 | 1.00 | 49.83 | O |
| ATOM | 38 | CB | LYS | A | 6 | 47.775 | 6.299 | −79.064 | 1.00 | 50.73 | C |
| ATOM | 39 | CG | LYS | A | 6 | 47.398 | 5.169 | −80.011 | 1.00 | 52.56 | C |
| ATOM | 40 | CD | LYS | A | 6 | 46.013 | 5.370 | −80.607 | 1.00 | 53.40 | C |
| ATOM | 41 | CE | LYS | A | 6 | 45.765 | 4.393 | −81.748 | 1.00 | 54.95 | C |
| ATOM | 42 | NZ | LYS | A | 6 | 44.421 | 4.561 | −82.367 | 1.00 | 56.05 | N |
| ATOM | 43 | N | GLN | A | 7 | 47.526 | 4.075 | −76.661 | 1.00 | 50.30 | N |
| ATOM | 44 | CA | GLN | A | 7 | 48.216 | 3.084 | −75.851 | 1.00 | 51.18 | C |
| ATOM | 45 | C | GLN | A | 7 | 49.130 | 2.297 | −76.789 | 1.00 | 49.34 | C |
| ATOM | 46 | O | GLN | A | 7 | 48.744 | 1.247 | −77.308 | 1.00 | 51.47 | O |
| ATOM | 47 | CB | GLN | A | 7 | 47.187 | 2.153 | −75.209 | 1.00 | 54.16 | C |
| ATOM | 48 | CG | GLN | A | 7 | 46.070 | 2.883 | −74.475 | 1.00 | 58.11 | C |
| ATOM | 49 | CD | GLN | A | 7 | 44.882 | 1.983 | −74.179 | 1.00 | 61.71 | C |
| ATOM | 50 | OE1 | GLN | A | 7 | 45.018 | 0.948 | −73.523 | 1.00 | 62.85 | O |
| ATOM | 51 | NE2 | GLN | A | 7 | 43.707 | 2.374 | −74.666 | 1.00 | 62.82 | N |
| ATOM | 52 | N | PHE | A | 8 | 50.339 | 2.806 | −77.007 | 1.00 | 45.50 | N |
| ATOM | 53 | CA | PHE | A | 8 | 51.282 | 2.152 | −77.907 | 1.00 | 40.62 | C |
| ATOM | 54 | C | PHE | A | 8 | 52.193 | 1.098 | −77.297 | 1.00 | 38.78 | C |
| ATOM | 55 | O | PHE | A | 8 | 52.810 | 1.305 | −76.250 | 1.00 | 38.26 | O |
| ATOM | 56 | CB | PHE | A | 8 | 52.168 | 3.190 | −78.610 | 1.00 | 39.48 | C |
| ATOM | 57 | CG | PHE | A | 8 | 51.475 | 3.955 | −79.702 | 1.00 | 37.99 | C |
| ATOM | 58 | CD1 | PHE | A | 8 | 50.784 | 3.289 | −80.710 | 1.00 | 35.89 | C |
| ATOM | 59 | CD2 | PHE | A | 8 | 51.547 | 5.344 | −79.745 | 1.00 | 37.88 | C |
| ATOM | 60 | CE1 | PHE | A | 8 | 50.175 | 3.995 | −81.744 | 1.00 | 35.74 | C |
| ATOM | 61 | CE2 | PHE | A | 8 | 50.942 | 6.061 | −80.778 | 1.00 | 37.30 | C |
| ATOM | 62 | CZ | PHE | A | 8 | 50.255 | 5.385 | −81.778 | 1.00 | 35.84 | C |
| ATOM | 63 | N | ASN | A | 9 | 52.274 | −0.035 | −77.985 | 1.00 | 36.68 | N |
| ATOM | 64 | CA | ASN | A | 9 | 53.140 | −1.137 | −77.594 | 1.00 | 33.87 | C |
| ATOM | 65 | C | ASN | A | 9 | 53.997 | −1.342 | −78.827 | 1.00 | 31.77 | C |

TABLE 2-continued

| | | | | | | | | | | | |
|---|---|---|---|---|---|---|---|---|---|---|---|
| ATOM | 66 | O | ASN | A | 9 | 53.479 | −1.357 | −79.945 | 1.00 | 30.81 | O |
| ATOM | 67 | CB | ASN | A | 9 | 52.329 | −2.399 | −77.309 | 1.00 | 35.30 | C |
| ATOM | 68 | CG | ASN | A | 9 | 51.347 | −2.209 | −76.182 | 1.00 | 37.56 | C |
| ATOM | 69 | OD1 | ASN | A | 9 | 51.734 | −1.915 | −75.048 | 1.00 | 40.98 | O |
| ATOM | 70 | ND2 | ASN | A | 9 | 50.064 | −2.367 | −76.483 | 1.00 | 36.71 | N |
| ATOM | 71 | N | TYR | A | 10 | 55.300 | −1.493 | −78.636 | 1.00 | 29.22 | N |
| ATOM | 72 | CA | TYR | A | 10 | 56.192 | −1.660 | −79.771 | 1.00 | 29.38 | C |
| ATOM | 73 | C | TYR | A | 10 | 55.756 | −2.734 | −80.755 | 1.00 | 30.41 | C |
| ATOM | 74 | O | TYR | A | 10 | 55.872 | −2.545 | −81.967 | 1.00 | 28.98 | O |
| ATOM | 75 | CB | TYR | A | 10 | 57.612 | −1.972 | −79.316 | 1.00 | 25.24 | C |
| ATOM | 76 | CG | TYR | A | 10 | 58.592 | −1.900 | −80.460 | 1.00 | 26.86 | C |
| ATOM | 77 | CD1 | TYR | A | 10 | 58.845 | −0.688 | −81.100 | 1.00 | 25.34 | C |
| ATOM | 78 | CD2 | TYR | A | 10 | 59.227 | −3.044 | −80.941 | 1.00 | 26.98 | C |
| ATOM | 79 | CE1 | TYR | A | 10 | 59.696 | −0.613 | −82.186 | 1.00 | 26.40 | C |
| ATOM | 80 | CE2 | TYR | A | 10 | 60.086 | −2.977 | −82.039 | 1.00 | 29.70 | C |
| ATOM | 81 | CZ | TYR | A | 10 | 60.312 | −1.751 | −82.654 | 1.00 | 28.53 | C |
| ATOM | 82 | OH | TYR | A | 10 | 61.156 | −1.653 | −83.738 | 1.00 | 32.34 | O |
| ATOM | 83 | N | LYS | A | 11 | 55.258 | −3.854 | −80.237 | 1.00 | 31.84 | N |
| ATOM | 84 | CA | LYS | A | 11 | 54.829 | −4.963 | −81.085 | 1.00 | 35.25 | C |
| ATOM | 85 | C | LYS | A | 11 | 53.522 | −4.744 | −81.859 | 1.00 | 34.80 | C |
| ATOM | 86 | O | LYS | A | 11 | 53.148 | −5.582 | −82.682 | 1.00 | 35.56 | O |
| ATOM | 87 | CB | LYS | A | 11 | 54.720 | −6.245 | −80.249 | 1.00 | 36.23 | C |
| ATOM | 88 | CG | LYS | A | 11 | 53.761 | −6.149 | −79.067 | 1.00 | 42.88 | C |
| ATOM | 89 | CD | LYS | A | 11 | 52.311 | −5.969 | −79.514 | 1.00 | 45.19 | C |
| ATOM | 90 | CE | LYS | A | 11 | 51.384 | −5.764 | −78.327 | 1.00 | 48.20 | C |
| ATOM | 91 | NZ | LYS | A | 11 | 49.974 | −5.538 | −78.758 | 1.00 | 50.42 | N |
| ATOM | 92 | N | ASP | A | 12 | 52.822 | −3.643 | −81.591 | 1.00 | 34.43 | N |
| ATOM | 93 | CA | ASP | A | 12 | 51.567 | −3.357 | −82.292 | 1.00 | 34.49 | C |
| ATOM | 94 | C | ASP | A | 12 | 51.789 | −3.395 | −83.798 | 1.00 | 34.72 | C |
| ATOM | 95 | O | ASP | A | 12 | 52.739 | −2.801 | −84.307 | 1.00 | 36.04 | O |
| ATOM | 96 | CB | ASP | A | 12 | 51.012 | −1.983 | −81.893 | 1.00 | 35.44 | C |
| ATOM | 97 | CG | ASP | A | 12 | 50.369 | −1.985 | −80.512 | 1.00 | 37.18 | C |
| ATOM | 98 | OD1 | ASP | A | 12 | 50.428 | −3.024 | −79.823 | 1.00 | 38.51 | O |
| ATOM | 99 | OD2 | ASP | A | 12 | 49.803 | −0.946 | −80.110 | 1.00 | 39.39 | O |
| ATOM | 100 | N | PRO | A | 13 | 50.915 | −4.102 | −84.533 | 1.00 | 33.76 | N |
| ATOM | 101 | CA | PRO | A | 13 | 51.045 | −4.202 | −85.991 | 1.00 | 33.21 | C |
| ATOM | 102 | C | PRO | A | 13 | 50.951 | −2.836 | −86.667 | 1.00 | 31.00 | C |
| ATOM | 103 | O | PRO | A | 13 | 50.221 | −1.960 | −86.209 | 1.00 | 29.07 | O |
| ATOM | 104 | CB | PRO | A | 13 | 49.880 | −5.116 | −86.386 | 1.00 | 33.23 | C |
| ATOM | 105 | CG | PRO | A | 13 | 49.645 | −5.939 | −85.140 | 1.00 | 35.19 | C |
| ATOM | 106 | CD | PRO | A | 13 | 49.779 | −4.906 | −84.050 | 1.00 | 34.55 | C |
| ATOM | 107 | N | VAL | A | 14 | 51.692 | −2.660 | −87.754 | 1.00 | 30.03 | N |
| ATOM | 108 | CA | VAL | A | 14 | 51.666 | −1.401 | −88.480 | 1.00 | 30.92 | C |
| ATOM | 109 | C | VAL | A | 14 | 50.291 | −1.223 | −89.100 | 1.00 | 31.08 | C |
| ATOM | 110 | O | VAL | A | 14 | 49.618 | −2.202 | −89.411 | 1.00 | 31.96 | O |
| ATOM | 111 | CB | VAL | A | 14 | 52.720 | −1.380 | −89.599 | 1.00 | 31.55 | C |
| ATOM | 112 | CG1 | VAL | A | 14 | 54.113 | −1.494 | −89.001 | 1.00 | 30.91 | C |
| ATOM | 113 | CG2 | VAL | A | 14 | 52.460 | −2.520 | −90.573 | 1.00 | 33.82 | C |
| ATOM | 114 | N | ASN | A | 15 | 49.870 | 0.026 | −89.265 | 1.00 | 30.47 | N |
| ATOM | 115 | CA | ASN | A | 15 | 48.572 | 0.317 | −89.856 | 1.00 | 28.56 | C |
| ATOM | 116 | C | ASN | A | 15 | 48.676 | 1.416 | −90.904 | 1.00 | 27.19 | C |
| ATOM | 117 | O | ASN | A | 15 | 47.666 | 1.864 | −91.429 | 1.00 | 27.44 | O |
| ATOM | 118 | CB | ASN | A | 15 | 47.574 | 0.740 | −88.782 | 1.00 | 28.55 | C |
| ATOM | 119 | CG | ASN | A | 15 | 48.078 | 1.896 | −87.940 | 1.00 | 29.07 | C |
| ATOM | 120 | OD1 | ASN | A | 15 | 48.705 | 2.827 | −88.453 | 1.00 | 27.97 | O |
| ATOM | 121 | ND2 | ASN | A | 15 | 47.789 | 1.854 | −86.642 | 1.00 | 26.47 | N |
| ATOM | 122 | N | GLY | A | 16 | 49.900 | 1.855 | −91.190 | 1.00 | 25.59 | N |
| ATOM | 123 | CA | GLY | A | 16 | 50.111 | 2.895 | −92.185 | 1.00 | 23.78 | C |
| ATOM | 124 | C | GLY | A | 16 | 49.593 | 4.273 | −91.807 | 1.00 | 23.10 | C |
| ATOM | 125 | O | GLY | A | 16 | 49.688 | 5.217 | −92.598 | 1.00 | 22.07 | O |
| ATOM | 126 | N | VAL | A | 17 | 49.062 | 4.391 | −90.595 | 1.00 | 23.91 | N |
| ATOM | 127 | CA | VAL | A | 17 | 48.508 | 5.648 | −90.095 | 1.00 | 24.39 | C |
| ATOM | 128 | C | VAL | A | 17 | 49.342 | 6.232 | −88.951 | 1.00 | 24.45 | C |
| ATOM | 129 | O | VAL | A | 17 | 49.992 | 7.267 | −89.119 | 1.00 | 24.24 | O |
| ATOM | 130 | CB | VAL | A | 17 | 47.060 | 5.448 | −89.613 | 1.00 | 24.02 | C |
| ATOM | 131 | CG1 | VAL | A | 17 | 46.522 | 6.738 | −89.010 | 1.00 | 26.33 | C |
| ATOM | 132 | CG2 | VAL | A | 17 | 46.184 | 5.003 | −90.788 | 1.00 | 28.20 | C |
| ATOM | 133 | N | ASP | A | 18 | 49.318 | 5.591 | −87.785 | 1.00 | 22.64 | N |
| ATOM | 134 | CA | ASP | A | 18 | 50.117 | 6.091 | −86.669 | 1.00 | 22.32 | C |
| ATOM | 135 | C | ASP | A | 18 | 51.159 | 5.084 | −86.185 | 1.00 | 22.04 | C |
| ATOM | 136 | O | ASP | A | 18 | 51.882 | 5.337 | −85.223 | 1.00 | 21.63 | O |
| ATOM | 137 | CB | ASP | A | 18 | 49.221 | 6.558 | −85.518 | 1.00 | 24.28 | C |
| ATOM | 138 | CG | ASP | A | 18 | 48.314 | 5.472 | −85.007 | 1.00 | 27.62 | C |
| ATOM | 139 | OD1 | ASP | A | 18 | 48.231 | 4.406 | −85.651 | 1.00 | 29.00 | O |
| ATOM | 140 | OD2 | ASP | A | 18 | 47.675 | 5.693 | −83.962 | 1.00 | 33.00 | O |
| ATOM | 141 | N | ILE | A | 19 | 51.231 | 3.942 | −86.865 | 1.00 | 21.70 | N |
| ATOM | 142 | CA | ILE | A | 19 | 52.227 | 2.915 | −86.568 | 1.00 | 20.75 | C |
| ATOM | 143 | C | ILE | A | 19 | 52.649 | 2.416 | −87.930 | 1.00 | 21.86 | C |
| ATOM | 144 | O | ILE | A | 19 | 51.853 | 1.789 | −88.633 | 1.00 | 21.44 | O |

TABLE 2-continued

| | | | | | | | | | | |
|---|---|---|---|---|---|---|---|---|---|---|
| ATOM | 145 | CB | ILE | A | 19 | 51.656 | 1.723 | −85.789 | 1.00 | 22.18 C |
| ATOM | 146 | CG1 | ILE | A | 19 | 51.005 | 2.201 | −84.498 | 1.00 | 21.18 C |
| ATOM | 147 | CG2 | ILE | A | 19 | 52.779 | 0.733 | −85.466 | 1.00 | 23.27 C |
| ATOM | 148 | CD1 | ILE | A | 19 | 50.357 | 1.075 | −83.708 | 1.00 | 24.42 C |
| ATOM | 149 | N | ALA | A | 20 | 53.889 | 2.691 | −88.318 | 1.00 | 20.74 N |
| ATOM | 150 | CA | ALA | A | 20 | 54.341 | 2.269 | −89.630 | 1.00 | 21.59 C |
| ATOM | 151 | C | ALA | A | 20 | 55.841 | 2.275 | −89.800 | 1.00 | 22.92 C |
| ATOM | 152 | O | ALA | A | 20 | 56.579 | 2.853 | −89.005 | 1.00 | 22.89 O |
| ATOM | 153 | CB | ALA | A | 20 | 53.718 | 3.174 | −90.695 | 1.00 | 22.81 C |
| ATOM | 154 | N | TYR | A | 21 | 56.286 | 1.609 | −90.856 | 1.00 | 24.43 N |
| ATOM | 155 | CA | TYR | A | 21 | 57.692 | 1.589 | −91.202 | 1.00 | 23.92 C |
| ATOM | 156 | C | TYR | A | 21 | 57.814 | 2.844 | −92.057 | 1.00 | 24.60 C |
| ATOM | 157 | O | TYR | A | 21 | 56.967 | 3.106 | −92.917 | 1.00 | 23.27 O |
| ATOM | 158 | CB | TYR | A | 21 | 58.016 | 0.320 | −91.992 | 1.00 | 28.82 C |
| ATOM | 159 | CG | TYR | A | 21 | 58.164 | −0.890 | −91.085 | 1.00 | 30.45 C |
| ATOM | 160 | CD1 | TYR | A | 21 | 59.322 | −1.074 | −90.333 | 1.00 | 33.37 C |
| ATOM | 161 | CD2 | TYR | A | 21 | 57.125 | −1.808 | −90.927 | 1.00 | 34.26 C |
| ATOM | 162 | CE1 | TYR | A | 21 | 59.451 | −2.135 | −89.442 | 1.00 | 35.24 C |
| ATOM | 163 | CE2 | TYR | A | 21 | 57.240 | −2.882 | −90.029 | 1.00 | 36.43 C |
| ATOM | 164 | CZ | TYR | A | 21 | 58.410 | −3.032 | −89.290 | 1.00 | 37.38 C |
| ATOM | 165 | OH | TYR | A | 21 | 58.549 | −4.065 | −88.386 | 1.00 | 41.56 O |
| ATOM | 166 | N | ILE | A | 22 | 58.844 | 3.641 | −91.814 | 1.00 | 23.63 N |
| ATOM | 167 | CA | ILE | A | 22 | 58.986 | 4.870 | −92.561 | 1.00 | 25.06 C |
| ATOM | 168 | C | ILE | A | 22 | 60.387 | 5.059 | −93.096 | 1.00 | 27.39 C |
| ATOM | 169 | O | ILE | A | 22 | 61.320 | 4.363 | −92.702 | 1.00 | 26.15 O |
| ATOM | 170 | CB | ILE | A | 22 | 58.639 | 6.088 | −91.673 | 1.00 | 24.87 C |
| ATOM | 171 | CG1 | ILE | A | 22 | 59.702 | 6.244 | −90.586 | 1.00 | 24.23 C |
| ATOM | 172 | CG2 | ILE | A | 22 | 57.264 | 5.898 | −91.015 | 1.00 | 21.46 C |
| ATOM | 173 | CD1 | ILE | A | 22 | 59.488 | 7.438 | −89.697 | 1.00 | 26.24 C |
| ATOM | 174 | N | LYS | A | 23 | 60.518 | 6.017 | −94.003 | 1.00 | 29.88 N |
| ATOM | 175 | CA | LYS | A | 23 | 61.801 | 6.362 | −94.590 | 1.00 | 34.35 C |
| ATOM | 176 | C | LYS | A | 23 | 61.898 | 7.875 | −94.643 | 1.00 | 37.24 C |
| ATOM | 177 | O | LYS | A | 23 | 60.900 | 8.565 | −94.869 | 1.00 | 36.05 O |
| ATOM | 178 | CB | LYS | A | 23 | 61.931 | 5.815 | −96.015 | 1.00 | 36.36 C |
| ATOM | 179 | CG | LYS | A | 23 | 62.443 | 4.393 | −96.125 | 1.00 | 38.72 C |
| ATOM | 180 | CD | LYS | A | 23 | 62.871 | 4.117 | −97.560 | 1.00 | 42.04 C |
| ATOM | 181 | CE | LYS | A | 23 | 63.466 | 2.733 | −97.726 | 1.00 | 44.54 C |
| ATOM | 182 | NZ | LYS | A | 23 | 63.896 | 2.512 | −99.134 | 1.00 | 45.33 N |
| ATOM | 183 | N | ILE | A | 24 | 63.099 | 8.392 | −94.423 | 1.00 | 40.72 N |
| ATOM | 184 | CA | ILE | A | 24 | 63.329 | 9.821 | −94.483 | 1.00 | 45.99 C |
| ATOM | 185 | C | ILE | A | 24 | 64.054 | 10.068 | −95.803 | 1.00 | 50.23 C |
| ATOM | 186 | O | ILE | A | 24 | 65.271 | 9.920 | −95.886 | 1.00 | 52.74 O |
| ATOM | 187 | CB | ILE | A | 24 | 64.162 | 10.294 | −93.270 | 1.00 | 46.87 C |
| ATOM | 188 | CG1 | ILE | A | 24 | 65.292 | 9.309 | −92.973 | 1.00 | 47.69 C |
| ATOM | 189 | CG2 | ILE | A | 24 | 63.271 | 10.383 | −92.041 | 1.00 | 48.27 C |
| ATOM | 190 | CD1 | ILE | A | 24 | 66.018 | 9.595 | −91.663 | 1.00 | 47.95 C |
| ATOM | 191 | N | PRO | A | 25 | 63.297 | 10.433 | −96.860 | 1.00 | 54.37 N |
| ATOM | 192 | CA | PRO | A | 25 | 63.762 | 10.714 | −98.228 | 1.00 | 57.23 C |
| ATOM | 193 | C | PRO | A | 25 | 65.097 | 11.437 | −98.273 | 1.00 | 59.85 C |
| ATOM | 194 | O | PRO | A | 25 | 65.906 | 11.242 | −99.185 | 1.00 | 60.02 O |
| ATOM | 195 | CB | PRO | A | 25 | 62.639 | 11.572 | −98.801 | 1.00 | 56.70 C |
| ATOM | 196 | CG | PRO | A | 25 | 61.437 | 11.034 | −98.124 | 1.00 | 56.48 C |
| ATOM | 197 | CD | PRO | A | 25 | 61.905 | 10.896 | −96.697 | 1.00 | 55.29 C |
| ATOM | 198 | N | ASN | A | 26 | 65.301 | 12.280 | −97.271 | 1.00 | 62.20 N |
| ATOM | 199 | CA | ASN | A | 26 | 66.507 | 13.075 | −97.130 | 1.00 | 64.75 C |
| ATOM | 200 | C | ASN | A | 26 | 67.714 | 12.180 | −96.869 | 1.00 | 65.60 C |
| ATOM | 201 | O | ASN | A | 26 | 68.720 | 12.248 | −97.581 | 1.00 | 66.11 O |
| ATOM | 202 | CB | ASN | A | 26 | 66.318 | 14.045 | −95.964 | 1.00 | 65.75 C |
| ATOM | 203 | CG | ASN | A | 26 | 64.924 | 13.952 | −95.352 | 1.00 | 67.19 C |
| ATOM | 204 | OD1 | ASN | A | 26 | 63.961 | 14.514 | −95.879 | 1.00 | 67.36 O |
| ATOM | 205 | ND2 | ASN | A | 26 | 64.809 | 13.223 | −94.244 | 1.00 | 67.50 N |
| ATOM | 206 | N | ALA | A | 27 | 67.601 | 11.338 | −95.846 | 1.00 | 65.83 N |
| ATOM | 207 | CA | ALA | A | 27 | 68.682 | 10.438 | −95.469 | 1.00 | 67.05 C |
| ATOM | 208 | C | ALA | A | 27 | 68.829 | 9.267 | −96.429 | 1.00 | 67.59 C |
| ATOM | 209 | O | ALA | A | 27 | 68.386 | 8.156 | −96.139 | 1.00 | 67.42 O |
| ATOM | 210 | CB | ALA | A | 27 | 68.460 | 9.926 | −94.058 | 1.00 | 66.89 C |
| ATOM | 211 | N | GLY | A | 28 | 69.457 | 9.529 | −97.571 | 1.00 | 68.62 N |
| ATOM | 212 | CA | GLY | A | 28 | 69.673 | 8.497 | −98.570 | 1.00 | 69.52 C |
| ATOM | 213 | C | GLY | A | 28 | 68.549 | 7.487 | −98.683 | 1.00 | 69.99 C |
| ATOM | 214 | O | GLY | A | 28 | 67.382 | 7.810 | −98.449 | 1.00 | 70.82 O |
| ATOM | 215 | N | GLN | A | 29 | 68.904 | 6.257 | −99.038 | 1.00 | 69.55 N |
| ATOM | 216 | CA | GLN | A | 29 | 67.922 | 5.191 | −99.191 | 1.00 | 69.26 C |
| ATOM | 217 | C | GLN | A | 29 | 68.126 | 4.129 | −98.115 | 1.00 | 68.01 C |
| ATOM | 218 | O | GLN | A | 29 | 68.266 | 2.944 | −98.419 | 1.00 | 68.37 O |
| ATOM | 219 | CB | GLN | A | 29 | 68.058 | 4.547 | −100.574 | 1.00 | 70.74 C |
| ATOM | 220 | CG | GLN | A | 29 | 68.267 | 5.535 | −101.722 | 1.00 | 73.20 C |
| ATOM | 221 | CD | GLN | A | 29 | 67.097 | 6.485 | −101.925 | 1.00 | 74.63 C |
| ATOM | 222 | OE1 | GLN | A | 29 | 66.782 | 7.301 | −101.057 | 1.00 | 75.05 O |
| ATOM | 223 | NE2 | GLN | A | 29 | 66.448 | 6.383 | −103.081 | 1.00 | 74.99 N |

TABLE 2-continued

| | | | | | | | | | | |
|---|---|---|---|---|---|---|---|---|---|---|
| ATOM | 224 | N | MET | A | 30 | 68.145 | 4.559 | −96.856 | 1.00 | 65.84 N |
| ATOM | 225 | CA | MET | A | 30 | 68.331 | 3.637 | −95.740 | 1.00 | 62.92 C |
| ATOM | 226 | C | MET | A | 30 | 67.223 | 2.590 | −95.655 | 1.00 | 60.50 C |
| ATOM | 227 | O | MET | A | 30 | 66.319 | 2.551 | −96.494 | 1.00 | 59.83 O |
| ATOM | 228 | CB | MET | A | 30 | 68.439 | 4.415 | −94.414 | 1.00 | 63.72 C |
| ATOM | 229 | CG | MET | A | 30 | 67.539 | 5.657 | −94.285 | 1.00 | 65.19 C |
| ATOM | 230 | SD | MET | A | 30 | 65.800 | 5.377 | −93.838 | 1.00 | 66.54 S |
| ATOM | 231 | CE | MET | A | 30 | 65.789 | 5.865 | −92.134 | 1.00 | 64.10 C |
| ATOM | 232 | N | GLN | A | 31 | 67.311 | 1.731 | −94.644 | 1.00 | 57.17 N |
| ATOM | 233 | CA | GLN | A | 31 | 66.324 | 0.675 | −94.437 | 1.00 | 53.98 C |
| ATOM | 234 | C | GLN | A | 31 | 65.130 | 1.257 | −93.683 | 1.00 | 49.95 C |
| ATOM | 235 | O | GLN | A | 31 | 65.301 | 2.082 | −92.787 | 1.00 | 50.07 O |
| ATOM | 236 | CB | GLN | A | 31 | 66.946 | −0.459 | −93.618 | 1.00 | 55.52 C |
| ATOM | 237 | CG | GLN | A | 31 | 66.286 | −1.809 | −93.812 | 1.00 | 57.71 C |
| ATOM | 238 | CD | GLN | A | 31 | 66.513 | −2.363 | −95.206 | 1.00 | 60.09 C |
| ATOM | 239 | OE1 | GLN | A | 31 | 67.654 | −2.478 | −95.659 | 1.00 | 60.75 O |
| ATOM | 240 | NE2 | GLN | A | 31 | 65.429 | −2.713 | −95.892 | 1.00 | 59.93 N |
| ATOM | 241 | N | PRO | A | 32 | 63.904 | 0.838 | −94.035 | 1.00 | 46.43 N |
| ATOM | 242 | CA | PRO | A | 32 | 62.721 | 1.363 | −93.344 | 1.00 | 43.02 C |
| ATOM | 243 | C | PRO | A | 32 | 62.710 | 0.993 | −91.862 | 1.00 | 39.36 C |
| ATOM | 244 | O | PRO | A | 32 | 63.007 | −0.143 | −91.501 | 1.00 | 39.35 O |
| ATOM | 245 | CB | PRO | A | 32 | 61.565 | 0.734 | −94.118 | 1.00 | 43.73 C |
| ATOM | 246 | CG | PRO | A | 32 | 62.142 | −0.571 | −94.572 | 1.00 | 45.37 C |
| ATOM | 247 | CD | PRO | A | 32 | 63.521 | −0.169 | −95.039 | 1.00 | 45.82 C |
| ATOM | 248 | N | VAL | A | 33 | 62.376 | 1.960 | −91.010 | 1.00 | 34.81 N |
| ATOM | 249 | CA | VAL | A | 33 | 62.335 | 1.740 | −89.566 | 1.00 | 29.75 C |
| ATOM | 250 | C | VAL | A | 33 | 60.924 | 1.927 | −89.030 | 1.00 | 27.68 C |
| ATOM | 251 | O | VAL | A | 33 | 60.182 | 2.798 | −89.493 | 1.00 | 25.11 O |
| ATOM | 252 | CB | VAL | A | 33 | 63.279 | 2.712 | −88.825 | 1.00 | 29.78 C |
| ATOM | 253 | CG1 | VAL | A | 33 | 64.709 | 2.454 | −89.239 | 1.00 | 29.05 C |
| ATOM | 254 | CG2 | VAL | A | 33 | 62.891 | 4.156 | −89.138 | 1.00 | 27.08 C |
| ATOM | 255 | N | LYS | A | 34 | 60.558 | 1.110 | −88.049 | 1.00 | 24.10 N |
| ATOM | 256 | CA | LYS | A | 34 | 59.225 | 1.189 | −87.470 | 1.00 | 24.26 C |
| ATOM | 257 | C | LYS | A | 34 | 59.108 | 2.432 | −86.593 | 1.00 | 23.31 C |
| ATOM | 258 | O | LYS | A | 34 | 59.942 | 2.681 | −85.723 | 1.00 | 22.73 O |
| ATOM | 259 | CB | LYS | A | 34 | 58.922 | −0.073 | −86.658 | 1.00 | 21.79 C |
| ATOM | 260 | CG | LYS | A | 34 | 57.441 | −0.264 | −86.344 | 1.00 | 20.19 C |
| ATOM | 261 | CD | LYS | A | 34 | 57.165 | −1.612 | −85.660 | 1.00 | 20.88 C |
| ATOM | 262 | CE | LYS | A | 34 | 55.690 | −1.750 | −85.321 | 1.00 | 19.52 C |
| ATOM | 263 | NZ | LYS | A | 34 | 55.368 | −3.036 | −84.616 | 1.00 | 23.34 N |
| ATOM | 264 | N | ALA | A | 35 | 58.065 | 3.217 | −86.830 | 1.00 | 22.72 N |
| ATOM | 265 | CA | ALA | A | 35 | 57.874 | 4.442 | −86.075 | 1.00 | 20.13 C |
| ATOM | 266 | C | ALA | A | 35 | 56.455 | 4.566 | −85.540 | 1.00 | 20.61 C |
| ATOM | 267 | O | ALA | A | 35 | 55.550 | 3.839 | −85.963 | 1.00 | 19.71 O |
| ATOM | 268 | CB | ALA | A | 35 | 58.224 | 5.640 | −86.953 | 1.00 | 20.89 C |
| ATOM | 269 | N | PHE | A | 36 | 56.269 | 5.499 | −84.611 | 1.00 | 18.12 N |
| ATOM | 270 | CA | PHE | A | 36 | 54.974 | 5.718 | −83.979 | 1.00 | 17.56 C |
| ATOM | 271 | C | PHE | A | 36 | 54.646 | 7.205 | −83.930 | 1.00 | 18.07 C |
| ATOM | 272 | O | PHE | A | 36 | 55.456 | 8.014 | −83.467 | 1.00 | 17.18 O |
| ATOM | 273 | CB | PHE | A | 36 | 54.991 | 5.147 | −82.547 | 1.00 | 19.72 C |
| ATOM | 274 | CG | PHE | A | 36 | 55.360 | 3.679 | −82.474 | 1.00 | 20.68 C |
| ATOM | 275 | CD1 | PHE | A | 36 | 56.665 | 3.260 | −82.712 | 1.00 | 20.79 C |
| ATOM | 276 | CD2 | PHE | A | 36 | 54.389 | 2.717 | −82.215 | 1.00 | 20.45 C |
| ATOM | 277 | CE1 | PHE | A | 36 | 56.999 | 1.902 | −82.702 | 1.00 | 21.46 C |
| ATOM | 278 | CE2 | PHE | A | 36 | 54.711 | 1.353 | −82.201 | 1.00 | 18.48 C |
| ATOM | 279 | CZ | PHE | A | 36 | 56.010 | 0.946 | −82.445 | 1.00 | 20.14 C |
| ATOM | 280 | N | LYS | A | 37 | 53.459 | 7.565 | −84.411 | 1.00 | 18.16 N |
| ATOM | 281 | CA | LYS | A | 37 | 53.022 | 8.960 | −84.398 | 1.00 | 17.11 C |
| ATOM | 282 | C | LYS | A | 37 | 52.289 | 9.168 | −83.085 | 1.00 | 18.50 C |
| ATOM | 283 | O | LYS | A | 37 | 51.156 | 8.727 | −82.918 | 1.00 | 20.20 O |
| ATOM | 284 | CB | LYS | A | 37 | 52.085 | 9.241 | −85.576 | 1.00 | 16.00 C |
| ATOM | 285 | CG | LYS | A | 37 | 51.652 | 10.704 | −85.707 | 1.00 | 20.62 C |
| ATOM | 286 | CD | LYS | A | 37 | 50.871 | 10.915 | −87.001 | 1.00 | 22.70 C |
| ATOM | 287 | CE | LYS | A | 37 | 50.457 | 12.361 | −87.181 | 1.00 | 26.57 C |
| ATOM | 288 | NZ | LYS | A | 37 | 49.839 | 12.601 | −88.521 | 1.00 | 26.96 N |
| ATOM | 289 | N | ILE | A | 38 | 52.932 | 9.844 | −82.145 | 1.00 | 19.20 N |
| ATOM | 290 | CA | ILE | A | 38 | 52.316 | 10.047 | −80.843 | 1.00 | 18.87 C |
| ATOM | 291 | C | ILE | A | 38 | 51.428 | 11.277 | −80.754 | 1.00 | 19.16 C |
| ATOM | 292 | O | ILE | A | 38 | 50.693 | 11.448 | −79.779 | 1.00 | 19.92 O |
| ATOM | 293 | CB | ILE | A | 38 | 53.391 | 10.137 | −79.753 | 1.00 | 19.94 C |
| ATOM | 294 | CG1 | ILE | A | 38 | 54.301 | 11.339 | −80.016 | 1.00 | 18.99 C |
| ATOM | 295 | CG2 | ILE | A | 38 | 54.202 | 8.852 | −79.738 | 1.00 | 18.72 C |
| ATOM | 296 | CD1 | ILE | A | 38 | 55.225 | 11.672 | −78.853 | 1.00 | 22.83 C |
| ATOM | 297 | N | HIS | A | 39 | 51.484 | 12.125 | −81.777 | 1.00 | 19.15 N |
| ATOM | 298 | CA | HIS | A | 39 | 50.701 | 13.355 | −81.789 | 1.00 | 20.71 C |
| ATOM | 299 | C | HIS | A | 39 | 50.810 | 13.941 | −83.191 | 1.00 | 19.19 C |
| ATOM | 300 | O | HIS | A | 39 | 51.742 | 13.610 | −83.918 | 1.00 | 20.61 O |
| ATOM | 301 | CB | HIS | A | 39 | 51.292 | 14.330 | −80.749 | 1.00 | 19.21 C |
| ATOM | 302 | CG | HIS | A | 39 | 50.357 | 15.420 | −80.321 | 1.00 | 18.05 C |

TABLE 2-continued

| | | | | | | | | | | |
|---|---|---|---|---|---|---|---|---|---|---|
| ATOM | 303 | ND1 | HIS | A | 39 | 50.263 | 16.629 | −80.981 | 1.00 | 21.39 N |
| ATOM | 304 | CD2 | HIS | A | 39 | 49.482 | 15.487 | −79.288 | 1.00 | 14.39 C |
| ATOM | 305 | CE1 | HIS | A | 39 | 49.374 | 17.394 | −80.372 | 1.00 | 18.56 C |
| ATOM | 306 | NE2 | HIS | A | 39 | 48.885 | 16.724 | −79.341 | 1.00 | 21.32 N |
| ATOM | 307 | N | ASN | A | 40 | 49.866 | 14.788 | −83.587 | 1.00 | 18.11 N |
| ATOM | 308 | CA | ASN | A | 40 | 49.951 | 15.399 | −84.913 | 1.00 | 19.27 C |
| ATOM | 309 | C | ASN | A | 40 | 51.307 | 16.093 | −85.044 | 1.00 | 17.69 C |
| ATOM | 310 | O | ASN | A | 40 | 51.732 | 16.805 | −84.131 | 1.00 | 16.97 O |
| ATOM | 311 | CB | ASN | A | 40 | 48.834 | 16.434 | −85.132 | 1.00 | 21.18 C |
| ATOM | 312 | CG | ASN | A | 40 | 47.454 | 15.798 | −85.246 | 1.00 | 23.69 C |
| ATOM | 313 | OD1 | ASN | A | 40 | 47.322 | 14.619 | −85.572 | 1.00 | 22.45 O |
| ATOM | 314 | ND2 | ASN | A | 40 | 46.421 | 16.587 | −84.997 | 1.00 | 23.40 N |
| ATOM | 315 | N | LYS | A | 41 | 51.978 | 15.856 | −86.172 | 1.00 | 15.88 N |
| ATOM | 316 | CA | LYS | A | 41 | 53.279 | 16.444 | −86.484 | 1.00 | 15.85 C |
| ATOM | 317 | C | LYS | A | 41 | 54.483 | 15.856 | −85.724 | 1.00 | 16.75 C |
| ATOM | 318 | O | LYS | A | 41 | 55.611 | 16.266 | −85.965 | 1.00 | 16.45 O |
| ATOM | 319 | CB | LYS | A | 41 | 53.239 | 17.953 | −86.242 | 1.00 | 16.91 C |
| ATOM | 320 | CG | LYS | A | 41 | 52.104 | 18.687 | −86.937 | 1.00 | 18.86 C |
| ATOM | 321 | CD | LYS | A | 41 | 52.217 | 18.570 | −88.445 | 1.00 | 20.61 C |
| ATOM | 322 | CE | LYS | A | 41 | 51.217 | 19.483 | −89.134 | 1.00 | 20.66 C |
| ATOM | 323 | NZ | LYS | A | 41 | 51.448 | 19.513 | −90.601 | 1.00 | 20.50 N |
| ATOM | 324 | N | ILE | A | 42 | 54.251 | 14.890 | −84.840 | 1.00 | 16.30 N |
| ATOM | 325 | CA | ILE | A | 42 | 55.336 | 14.311 | −84.040 | 1.00 | 16.79 C |
| ATOM | 326 | C | ILE | A | 42 | 55.429 | 12.780 | −84.067 | 1.00 | 18.19 C |
| ATOM | 327 | O | ILE | A | 42 | 54.496 | 12.078 | −83.662 | 1.00 | 18.18 O |
| ATOM | 328 | CB | ILE | A | 42 | 55.203 | 14.755 | −82.563 | 1.00 | 17.11 C |
| ATOM | 329 | CG1 | ILE | A | 42 | 55.111 | 16.283 | −82.488 | 1.00 | 17.04 C |
| ATOM | 330 | CG2 | ILE | A | 42 | 56.405 | 14.269 | −81.756 | 1.00 | 15.85 C |
| ATOM | 331 | CD1 | ILE | A | 42 | 54.940 | 16.827 | −81.085 | 1.00 | 18.95 C |
| ATOM | 332 | N | TRP | A | 43 | 56.567 | 12.272 | −84.534 | 1.00 | 17.01 N |
| ATOM | 333 | CA | TRP | A | 43 | 56.801 | 10.835 | −84.607 | 1.00 | 16.48 C |
| ATOM | 334 | C | TRP | A | 43 | 57.953 | 10.395 | −83.701 | 1.00 | 17.31 C |
| ATOM | 335 | O | TRP | A | 43 | 58.841 | 11.183 | −83.370 | 1.00 | 17.78 O |
| ATOM | 336 | CB | TRP | A | 43 | 57.127 | 10.417 | −86.045 | 1.00 | 15.64 C |
| ATOM | 337 | CG | TRP | A | 43 | 55.961 | 10.444 | −86.996 | 1.00 | 20.23 C |
| ATOM | 338 | CD1 | TRP | A | 43 | 55.359 | 11.551 | −87.543 | 1.00 | 21.33 C |
| ATOM | 339 | CD2 | TRP | A | 43 | 55.270 | 9.311 | −87.528 | 1.00 | 19.35 C |
| ATOM | 340 | NE1 | TRP | A | 43 | 54.342 | 11.168 | −88.387 | 1.00 | 17.78 N |
| ATOM | 341 | CE2 | TRP | A | 43 | 54.266 | 9.800 | −88.397 | 1.00 | 21.71 C |
| ATOM | 342 | CE3 | TRP | A | 43 | 55.399 | 7.927 | −87.356 | 1.00 | 20.85 C |
| ATOM | 343 | CZ2 | TRP | A | 43 | 53.398 | 8.949 | −89.098 | 1.00 | 21.08 C |
| ATOM | 344 | CZ3 | TRP | A | 43 | 54.533 | 7.080 | −88.053 | 1.00 | 21.70 C |
| ATOM | 345 | CH2 | TRP | A | 43 | 53.549 | 7.597 | −88.912 | 1.00 | 20.95 C |
| ATOM | 346 | N | VAL | A | 44 | 57.930 | 9.131 | −83.296 | 1.00 | 17.02 N |
| ATOM | 347 | CA | VAL | A | 44 | 58.987 | 8.587 | −82.458 | 1.00 | 15.70 C |
| ATOM | 348 | C | VAL | A | 44 | 59.540 | 7.314 | −83.111 | 1.00 | 19.16 C |
| ATOM | 349 | O | VAL | A | 44 | 58.788 | 6.399 | −83.470 | 1.00 | 18.70 O |
| ATOM | 350 | CB | VAL | A | 44 | 58.473 | 8.267 | −81.031 | 1.00 | 15.98 C |
| ATOM | 351 | CG1 | VAL | A | 44 | 59.584 | 7.655 | −80.191 | 1.00 | 16.68 C |
| ATOM | 352 | CG2 | VAL | A | 44 | 57.985 | 9.540 | −80.361 | 1.00 | 17.70 C |
| ATOM | 353 | N | ILE | A | 45 | 60.857 | 7.276 | −83.287 | 1.00 | 18.76 N |
| ATOM | 354 | CA | ILE | A | 45 | 61.529 | 6.120 | −83.876 | 1.00 | 19.90 C |
| ATOM | 355 | C | ILE | A | 45 | 62.437 | 5.537 | −82.797 | 1.00 | 21.62 C |
| ATOM | 356 | O | ILE | A | 45 | 63.522 | 6.052 | −82.552 | 1.00 | 22.03 O |
| ATOM | 357 | CB | ILE | A | 45 | 62.406 | 6.527 | −85.087 | 1.00 | 20.03 C |
| ATOM | 358 | CG1 | ILE | A | 45 | 61.559 | 7.267 | −86.129 | 1.00 | 18.38 C |
| ATOM | 359 | CG2 | ILE | A | 45 | 63.035 | 5.279 | −85.721 | 1.00 | 16.47 C |
| ATOM | 360 | CD1 | ILE | A | 45 | 62.375 | 7.836 | −87.283 | 1.00 | 19.52 C |
| ATOM | 361 | N | PRO | A | 46 | 61.999 | 4.456 | −82.133 | 1.00 | 23.67 N |
| ATOM | 362 | CA | PRO | A | 46 | 62.805 | 3.833 | −81.077 | 1.00 | 23.88 C |
| ATOM | 363 | C | PRO | A | 46 | 63.993 | 3.008 | −81.575 | 1.00 | 25.00 C |
| ATOM | 364 | O | PRO | A | 46 | 64.077 | 1.810 | −81.309 | 1.00 | 27.17 O |
| ATOM | 365 | CB | PRO | A | 46 | 61.783 | 2.985 | −80.329 | 1.00 | 24.68 C |
| ATOM | 366 | CG | PRO | A | 46 | 60.862 | 2.548 | −81.420 | 1.00 | 26.36 C |
| ATOM | 367 | CD | PRO | A | 46 | 60.679 | 3.810 | −82.244 | 1.00 | 23.01 C |
| ATOM | 368 | N | GLU | A | 47 | 64.913 | 3.659 | −82.285 | 1.00 | 24.05 N |
| ATOM | 369 | CA | GLU | A | 47 | 66.105 | 3.000 | −82.824 | 1.00 | 23.80 C |
| ATOM | 370 | C | GLU | A | 47 | 67.316 | 3.898 | −82.596 | 1.00 | 22.54 C |
| ATOM | 371 | O | GLU | A | 47 | 67.178 | 5.120 | −82.514 | 1.00 | 22.35 O |
| ATOM | 372 | CB | GLU | A | 47 | 65.987 | 2.789 | −84.343 | 1.00 | 23.69 C |
| ATOM | 373 | CG | GLU | A | 47 | 64.827 | 1.938 | −84.844 | 1.00 | 27.69 C |
| ATOM | 374 | CD | GLU | A | 47 | 65.090 | 0.453 | −84.718 | 1.00 | 28.02 C |
| ATOM | 375 | OE1 | GLU | A | 47 | 66.275 | 0.066 | −84.597 | 1.00 | 31.14 O |
| ATOM | 376 | OE2 | GLU | A | 47 | 64.114 | −0.325 | −84.754 | 1.00 | 28.60 O |
| ATOM | 377 | N | ARG | A | 48 | 68.497 | 3.291 | −82.512 | 1.00 | 20.80 N |
| ATOM | 378 | CA | ARG | A | 48 | 69.734 | 4.052 | −82.362 | 1.00 | 19.98 C |
| ATOM | 379 | C | ARG | A | 48 | 69.848 | 4.821 | −83.671 | 1.00 | 20.58 C |
| ATOM | 380 | O | ARG | A | 48 | 69.562 | 4.268 | −84.729 | 1.00 | 21.22 O |
| ATOM | 381 | CB | ARG | A | 48 | 70.928 | 3.103 | −82.204 | 1.00 | 20.92 C |

TABLE 2-continued

| | | | | | | | | | | |
|---|---|---|---|---|---|---|---|---|---|---|
| ATOM | 382 | CG | ARG | A | 48 | 70.916 | 2.316 | −80.898 | 1.00 | 17.93 | C |
| ATOM | 383 | CD | ARG | A | 48 | 70.978 | 3.261 | −79.705 | 1.00 | 18.12 | C |
| ATOM | 384 | NE | ARG | A | 48 | 72.307 | 3.844 | −79.545 | 1.00 | 19.75 | N |
| ATOM | 385 | CZ | ARG | A | 48 | 73.351 | 3.189 | −79.041 | 1.00 | 20.82 | C |
| ATOM | 386 | NH1 | ARG | A | 48 | 73.218 | 1.932 | −78.644 | 1.00 | 18.69 | N |
| ATOM | 387 | NH2 | ARG | A | 48 | 74.529 | 3.789 | −78.940 | 1.00 | 20.06 | N |
| ATOM | 388 | N | ASP | A | 49 | 70.251 | 6.085 | −83.621 | 1.00 | 20.92 | N |
| ATOM | 389 | CA | ASP | A | 49 | 70.340 | 6.844 | −84.860 | 1.00 | 25.31 | C |
| ATOM | 390 | C | ASP | A | 49 | 71.558 | 6.572 | −85.726 | 1.00 | 27.59 | C |
| ATOM | 391 | O | ASP | A | 49 | 72.638 | 7.111 | −85.497 | 1.00 | 27.12 | O |
| ATOM | 392 | CB | ASP | A | 49 | 70.249 | 8.348 | −84.608 | 1.00 | 23.46 | C |
| ATOM | 393 | CG | ASP | A | 49 | 70.294 | 9.152 | −85.900 | 1.00 | 26.55 | C |
| ATOM | 394 | OD1 | ASP | A | 49 | 70.066 | 8.566 | −86.986 | 1.00 | 28.36 | O |
| ATOM | 395 | OD2 | ASP | A | 49 | 70.538 | 10.371 | −85.837 | 1.00 | 26.63 | O |
| ATOM | 396 | N | THR | A | 50 | 71.359 | 5.736 | −86.738 | 1.00 | 30.85 | N |
| ATOM | 397 | CA | THR | A | 50 | 72.404 | 5.406 | −87.693 | 1.00 | 34.21 | C |
| ATOM | 398 | C | THR | A | 50 | 71.831 | 5.709 | −89.074 | 1.00 | 36.72 | C |
| ATOM | 399 | O | THR | A | 50 | 72.329 | 5.210 | −90.079 | 1.00 | 38.76 | O |
| ATOM | 400 | CB | THR | A | 50 | 72.763 | 3.917 | −87.638 | 1.00 | 34.95 | C |
| ATOM | 401 | OG1 | THR | A | 50 | 71.573 | 3.138 | −87.812 | 1.00 | 35.35 | O |
| ATOM | 402 | CG2 | THR | A | 50 | 73.412 | 3.568 | −86.310 | 1.00 | 34.65 | C |
| ATOM | 403 | N | PHE | A | 51 | 70.786 | 6.536 | −89.112 | 1.00 | 39.22 | N |
| ATOM | 404 | CA | PHE | A | 51 | 70.110 | 6.880 | −90.365 | 1.00 | 41.26 | C |
| ATOM | 405 | C | PHE | A | 51 | 70.297 | 8.322 | −90.830 | 1.00 | 41.20 | C |
| ATOM | 406 | O | PHE | A | 51 | 70.535 | 8.578 | −92.010 | 1.00 | 42.09 | O |
| ATOM | 407 | CB | PHE | A | 51 | 68.604 | 6.631 | −90.233 | 1.00 | 43.82 | C |
| ATOM | 408 | CG | PHE | A | 51 | 68.258 | 5.453 | −89.380 | 1.00 | 46.30 | C |
| ATOM | 409 | CD1 | PHE | A | 51 | 68.551 | 4.160 | −89.802 | 1.00 | 48.72 | C |
| ATOM | 410 | CD2 | PHE | A | 51 | 67.661 | 5.637 | −88.139 | 1.00 | 47.13 | C |
| ATOM | 411 | CE1 | PHE | A | 51 | 68.254 | 3.061 | −88.995 | 1.00 | 50.28 | C |
| ATOM | 412 | CE2 | PHE | A | 51 | 67.360 | 4.553 | −87.324 | 1.00 | 49.22 | C |
| ATOM | 413 | CZ | PHE | A | 51 | 67.658 | 3.259 | −87.751 | 1.00 | 49.85 | C |
| ATOM | 414 | N | THR | A | 52 | 70.160 | 9.263 | −89.905 | 1.00 | 40.82 | N |
| ATOM | 415 | CA | THR | A | 52 | 70.281 | 10.674 | −90.239 | 1.00 | 41.60 | C |
| ATOM | 416 | C | THR | A | 52 | 71.642 | 11.045 | −90.807 | 1.00 | 43.63 | C |
| ATOM | 417 | O | THR | A | 52 | 71.746 | 11.948 | −91.633 | 1.00 | 43.04 | O |
| ATOM | 418 | CB | THR | A | 52 | 69.997 | 11.554 | −89.016 | 1.00 | 39.00 | C |
| ATOM | 419 | OG1 | THR | A | 52 | 71.055 | 11.410 | −88.065 | 1.00 | 38.91 | O |
| ATOM | 420 | CG2 | THR | A | 52 | 68.685 | 11.145 | −88.374 | 1.00 | 38.22 | C |
| ATOM | 421 | N | ASN | A | 53 | 72.685 | 10.352 | −90.368 | 1.00 | 46.51 | N |
| ATOM | 422 | CA | ASN | A | 53 | 74.027 | 10.631 | −90.856 | 1.00 | 49.89 | C |
| ATOM | 423 | C | ASN | A | 53 | 74.799 | 9.341 | −91.098 | 1.00 | 53.22 | C |
| ATOM | 424 | O | ASN | A | 53 | 75.179 | 8.652 | −90.152 | 1.00 | 53.55 | O |
| ATOM | 425 | CB | ASN | A | 53 | 74.790 | 11.498 | −89.853 | 1.00 | 48.90 | C |
| ATOM | 426 | CG | ASN | A | 53 | 76.162 | 11.915 | −90.362 | 1.00 | 49.71 | C |
| ATOM | 427 | OD1 | ASN | A | 53 | 76.947 | 12.522 | −89.633 | 1.00 | 49.39 | O |
| ATOM | 428 | ND2 | ASN | A | 53 | 76.454 | 11.595 | −91.619 | 1.00 | 49.99 | N |
| ATOM | 429 | N | PRO | A | 54 | 75.038 | 8.997 | −92.374 | 1.00 | 56.49 | N |
| ATOM | 430 | CA | PRO | A | 54 | 75.772 | 7.784 | −92.757 | 1.00 | 58.55 | C |
| ATOM | 431 | C | PRO | A | 54 | 77.147 | 7.734 | −92.094 | 1.00 | 60.16 | C |
| ATOM | 432 | O | PRO | A | 54 | 77.685 | 6.658 | −91.829 | 1.00 | 60.74 | O |
| ATOM | 433 | CB | PRO | A | 54 | 75.869 | 7.908 | −94.275 | 1.00 | 58.72 | C |
| ATOM | 434 | CG | PRO | A | 54 | 74.597 | 8.624 | −94.624 | 1.00 | 58.67 | C |
| ATOM | 435 | CD | PRO | A | 54 | 74.539 | 9.702 | −93.569 | 1.00 | 57.46 | C |
| ATOM | 436 | N | GLU | A | 55 | 77.702 | 8.913 | −91.832 | 1.00 | 61.89 | N |
| ATOM | 437 | CA | GLU | A | 55 | 79.009 | 9.049 | −91.195 | 1.00 | 63.33 | C |
| ATOM | 438 | C | GLU | A | 55 | 79.017 | 8.449 | −89.789 | 1.00 | 62.92 | C |
| ATOM | 439 | O | GLU | A | 55 | 80.070 | 8.091 | −89.263 | 1.00 | 62.99 | O |
| ATOM | 440 | CB | GLU | A | 55 | 79.393 | 10.532 | −91.121 | 1.00 | 65.72 | C |
| ATOM | 441 | CG | GLU | A | 55 | 80.706 | 10.824 | −90.402 | 1.00 | 68.83 | C |
| ATOM | 442 | CD | GLU | A | 55 | 81.907 | 10.209 | −91.098 | 1.00 | 70.53 | C |
| ATOM | 443 | OE1 | GLU | A | 55 | 82.106 | 10.488 | −92.302 | 1.00 | 71.20 | O |
| ATOM | 444 | OE2 | GLU | A | 55 | 82.655 | 9.454 | −90.438 | 1.00 | 70.58 | O |
| ATOM | 445 | N | GLU | A | 56 | 77.837 | 8.344 | −89.185 | 1.00 | 62.29 | N |
| ATOM | 446 | CA | GLU | A | 56 | 77.710 | 7.795 | −87.840 | 1.00 | 61.11 | C |
| ATOM | 447 | C | GLU | A | 56 | 76.954 | 6.469 | −87.863 | 1.00 | 60.24 | C |
| ATOM | 448 | O | GLU | A | 56 | 75.863 | 6.355 | −87.301 | 1.00 | 60.64 | O |
| ATOM | 449 | CB | GLU | A | 56 | 76.977 | 8.792 | −86.939 | 1.00 | 61.71 | C |
| ATOM | 450 | CG | GLU | A | 56 | 77.550 | 10.199 | −86.984 | 1.00 | 62.62 | C |
| ATOM | 451 | CD | GLU | A | 56 | 76.754 | 11.182 | −86.146 | 1.00 | 63.74 | C |
| ATOM | 452 | OE1 | GLU | A | 56 | 76.681 | 10.997 | −84.913 | 1.00 | 65.29 | O |
| ATOM | 453 | OE2 | GLU | A | 56 | 76.202 | 12.144 | −86.720 | 1.00 | 64.77 | O |
| ATOM | 454 | N | GLY | A | 57 | 77.542 | 5.468 | −88.513 | 1.00 | 58.95 | N |
| ATOM | 455 | CA | GLY | A | 57 | 76.910 | 4.162 | −88.602 | 1.00 | 56.62 | C |
| ATOM | 456 | C | GLY | A | 57 | 77.284 | 3.213 | −87.478 | 1.00 | 55.62 | C |
| ATOM | 457 | O | GLY | A | 57 | 76.464 | 2.399 | −87.047 | 1.00 | 55.51 | O |
| ATOM | 458 | N | ASP | A | 58 | 78.523 | 3.309 | −87.001 | 1.00 | 54.20 | N |
| ATOM | 459 | CA | ASP | A | 58 | 78.994 | 2.448 | −85.920 | 1.00 | 51.99 | C |
| ATOM | 460 | C | ASP | A | 58 | 78.496 | 2.972 | −84.576 | 1.00 | 48.53 | C |

TABLE 2-continued

| | | | | | | | | | | |
|---|---|---|---|---|---|---|---|---|---|---|
| ATOM | 461 | O | ASP | A | 58 | 78.213 | 4.161 | −84.431 | 1.00 | 48.14 O |
| ATOM | 462 | CB | ASP | A | 58 | 80.523 | 2.391 | −85.913 | 1.00 | 54.95 C |
| ATOM | 463 | CG | ASP | A | 58 | 81.152 | 3.720 | −85.548 | 1.00 | 58.47 C |
| ATOM | 464 | OD1 | ASP | A | 58 | 81.018 | 4.138 | −84.376 | 1.00 | 60.71 O |
| ATOM | 465 | OD2 | ASP | A | 58 | 81.773 | 4.350 | −86.433 | 1.00 | 60.34 O |
| ATOM | 466 | N | LEU | A | 59 | 78.397 | 2.083 | −83.595 | 1.00 | 43.59 N |
| ATOM | 467 | CA | LEU | A | 59 | 77.920 | 2.469 | −82.276 | 1.00 | 39.96 C |
| ATOM | 468 | C | LEU | A | 59 | 78.969 | 2.246 | −81.188 | 1.00 | 38.60 C |
| ATOM | 469 | O | LEU | A | 59 | 78.653 | 2.250 | −79.998 | 1.00 | 36.99 O |
| ATOM | 470 | CB | LEU | A | 59 | 76.639 | 1.694 | −81.941 | 1.00 | 37.14 C |
| ATOM | 471 | CG | LEU | A | 59 | 75.453 | 1.964 | −82.875 | 1.00 | 37.03 C |
| ATOM | 472 | CD1 | LEU | A | 59 | 74.232 | 1.182 | −82.409 | 1.00 | 35.04 C |
| ATOM | 473 | CD2 | LEU | A | 59 | 75.147 | 3.450 | −82.887 | 1.00 | 33.33 C |
| ATOM | 474 | N | ASN | A | 60 | 80.218 | 2.054 | −81.596 | 1.00 | 37.67 N |
| ATOM | 475 | CA | ASN | A | 60 | 81.294 | 1.837 | −80.635 | 1.00 | 36.92 C |
| ATOM | 476 | C | ASN | A | 60 | 82.054 | 3.125 | −80.363 | 1.00 | 35.15 C |
| ATOM | 477 | O | ASN | A | 60 | 81.972 | 4.078 | −81.136 | 1.00 | 34.00 O |
| ATOM | 478 | CB | ASN | A | 60 | 82.257 | 0.774 | −81.157 | 1.00 | 38.53 C |
| ATOM | 479 | CG | ASN | A | 60 | 81.667 | −0.613 | −81.100 | 1.00 | 39.76 C |
| ATOM | 480 | OD1 | ASN | A | 60 | 81.448 | −1.162 | −80.018 | 1.00 | 40.47 O |
| ATOM | 481 | ND2 | ASN | A | 60 | 81.395 | −1.189 | −82.265 | 1.00 | 40.54 N |
| ATOM | 482 | N | PRO | A | 61 | 82.795 | 3.179 | −79.246 | 1.00 | 34.63 N |
| ATOM | 483 | CA | PRO | A | 61 | 83.542 | 4.404 | −78.956 | 1.00 | 34.51 C |
| ATOM | 484 | C | PRO | A | 61 | 84.482 | 4.770 | −80.101 | 1.00 | 35.29 C |
| ATOM | 485 | O | PRO | A | 61 | 85.140 | 3.905 | −80.680 | 1.00 | 34.33 O |
| ATOM | 486 | CB | PRO | A | 61 | 84.273 | 4.073 | −77.647 | 1.00 | 36.93 C |
| ATOM | 487 | CG | PRO | A | 61 | 84.261 | 2.568 | −77.584 | 1.00 | 36.23 C |
| ATOM | 488 | CD | PRO | A | 61 | 82.924 | 2.207 | −78.150 | 1.00 | 34.95 C |
| ATOM | 489 | N | PRO | A | 62 | 84.545 | 6.063 | −80.452 | 1.00 | 34.80 N |
| ATOM | 490 | CA | PRO | A | 62 | 85.410 | 6.523 | −81.541 | 1.00 | 35.00 C |
| ATOM | 491 | C | PRO | A | 62 | 86.895 | 6.373 | −81.222 | 1.00 | 35.88 C |
| ATOM | 492 | O | PRO | A | 62 | 87.287 | 6.280 | −80.055 | 1.00 | 34.02 O |
| ATOM | 493 | CB | PRO | A | 62 | 84.995 | 7.982 | −81.708 | 1.00 | 35.42 C |
| ATOM | 494 | CG | PRO | A | 62 | 84.667 | 8.381 | −80.298 | 1.00 | 34.17 C |
| ATOM | 495 | CD | PRO | A | 62 | 83.866 | 7.200 | −79.804 | 1.00 | 33.48 C |
| ATOM | 496 | N | PRO | A | 63 | 87.740 | 6.341 | −82.264 | 1.00 | 38.44 N |
| ATOM | 497 | CA | PRO | A | 63 | 89.194 | 6.203 | −82.105 | 1.00 | 39.60 C |
| ATOM | 498 | C | PRO | A | 63 | 89.749 | 7.296 | −81.189 | 1.00 | 40.66 C |
| ATOM | 499 | O | PRO | A | 63 | 90.586 | 7.036 | −80.324 | 1.00 | 41.68 O |
| ATOM | 500 | CB | PRO | A | 63 | 89.707 | 6.335 | −83.537 | 1.00 | 40.08 C |
| ATOM | 501 | CG | PRO | A | 63 | 88.580 | 5.767 | −84.347 | 1.00 | 41.05 C |
| ATOM | 502 | CD | PRO | A | 63 | 87.372 | 6.394 | −83.690 | 1.00 | 38.59 C |
| ATOM | 503 | N | GLU | A | 64 | 89.274 | 8.522 | −81.396 | 1.00 | 40.38 N |
| ATOM | 504 | CA | GLU | A | 64 | 89.690 | 9.664 | −80.588 | 1.00 | 41.66 C |
| ATOM | 505 | C | GLU | A | 64 | 88.530 | 9.995 | −79.650 | 1.00 | 38.27 C |
| ATOM | 506 | O | GLU | A | 64 | 87.519 | 10.548 | −80.078 | 1.00 | 37.77 O |
| ATOM | 507 | CB | GLU | A | 64 | 89.983 | 10.879 | −81.479 | 1.00 | 45.09 C |
| ATOM | 508 | CG | GLU | A | 64 | 90.854 | 10.588 | −82.697 | 1.00 | 51.92 C |
| ATOM | 509 | CD | GLU | A | 64 | 92.249 | 10.103 | −82.336 | 1.00 | 54.74 C |
| ATOM | 510 | OE1 | GLU | A | 64 | 93.007 | 10.865 | −81.695 | 1.00 | 55.59 O |
| ATOM | 511 | OE2 | GLU | A | 64 | 92.585 | 8.955 | −82.700 | 1.00 | 56.76 O |
| ATOM | 512 | N | ALA | A | 65 | 88.672 | 9.646 | −78.378 | 1.00 | 35.88 N |
| ATOM | 513 | CA | ALA | A | 65 | 87.624 | 9.904 | −77.396 | 1.00 | 33.38 C |
| ATOM | 514 | C | ALA | A | 65 | 87.225 | 11.379 | −77.363 | 1.00 | 31.28 C |
| ATOM | 515 | O | ALA | A | 65 | 88.086 | 12.260 | −77.389 | 1.00 | 30.00 O |
| ATOM | 516 | CB | ALA | A | 65 | 88.091 | 9.464 | −76.022 | 1.00 | 31.31 C |
| ATOM | 517 | N | LYS | A | 66 | 85.922 | 11.646 | −77.300 | 1.00 | 28.27 N |
| ATOM | 518 | CA | LYS | A | 66 | 85.432 | 13.023 | −77.251 | 1.00 | 27.61 C |
| ATOM | 519 | C | LYS | A | 66 | 85.892 | 13.693 | −75.960 | 1.00 | 26.47 C |
| ATOM | 520 | O | LYS | A | 66 | 85.841 | 13.090 | −74.896 | 1.00 | 24.98 O |
| ATOM | 521 | CB | LYS | A | 66 | 83.904 | 13.065 | −77.309 | 1.00 | 26.52 C |
| ATOM | 522 | CG | LYS | A | 66 | 83.299 | 12.259 | −78.447 | 1.00 | 29.08 C |
| ATOM | 523 | CD | LYS | A | 66 | 81.882 | 12.716 | −78.756 | 1.00 | 30.22 C |
| ATOM | 524 | CE | LYS | A | 66 | 80.976 | 12.669 | −77.533 | 1.00 | 29.34 C |
| ATOM | 525 | NZ | LYS | A | 66 | 79.624 | 13.248 | −77.804 | 1.00 | 28.83 N |
| ATOM | 526 | N | GLN | A | 67 | 86.336 | 14.941 | −76.057 | 1.00 | 25.70 N |
| ATOM | 527 | CA | GLN | A | 67 | 86.794 | 15.674 | −74.879 | 1.00 | 26.87 C |
| ATOM | 528 | C | GLN | A | 67 | 85.615 | 16.312 | −74.148 | 1.00 | 24.42 C |
| ATOM | 529 | O | GLN | A | 67 | 85.489 | 17.533 | −74.120 | 1.00 | 23.83 O |
| ATOM | 530 | CB | GLN | A | 67 | 87.782 | 16.773 | −75.289 | 1.00 | 31.21 C |
| ATOM | 531 | CG | GLN | A | 67 | 88.945 | 16.300 | −76.141 | 1.00 | 37.34 C |
| ATOM | 532 | CD | GLN | A | 67 | 89.865 | 15.361 | −75.399 | 1.00 | 42.04 C |
| ATOM | 533 | OE1 | GLN | A | 67 | 90.400 | 15.701 | −74.342 | 1.00 | 45.66 O |
| ATOM | 534 | NE2 | GLN | A | 67 | 90.067 | 14.170 | −75.954 | 1.00 | 46.66 N |
| ATOM | 535 | N | VAL | A | 68 | 84.748 | 15.490 | −73.564 | 1.00 | 23.90 N |
| ATOM | 536 | CA | VAL | A | 68 | 83.590 | 16.003 | −72.834 | 1.00 | 21.29 C |
| ATOM | 537 | C | VAL | A | 68 | 83.593 | 15.427 | −71.421 | 1.00 | 20.70 C |
| ATOM | 538 | O | VAL | A | 68 | 84.133 | 14.353 | −71.190 | 1.00 | 20.10 O |
| ATOM | 539 | CB | VAL | A | 68 | 82.256 | 15.620 | −73.525 | 1.00 | 21.96 C |

TABLE 2-continued

| | | | | | | | | | | |
|---|---|---|---|---|---|---|---|---|---|---|
| ATOM | 540 | CG1 | VAL | A | 68 | 82.179 | 16.257 | −74.908 | 1.00 | 23.60 C |
| ATOM | 541 | CG2 | VAL | A | 68 | 82.132 | 14.114 | −73.630 | 1.00 | 19.77 C |
| ATOM | 542 | N | PRO | A | 69 | 82.994 | 16.144 | −70.457 | 1.00 | 20.84 N |
| ATOM | 543 | CA | PRO | A | 69 | 82.917 | 15.725 | −69.052 | 1.00 | 20.05 C |
| ATOM | 544 | C | PRO | A | 69 | 82.379 | 14.307 | −68.843 | 1.00 | 20.68 C |
| ATOM | 545 | O | PRO | A | 69 | 82.913 | 13.549 | −68.031 | 1.00 | 19.98 O |
| ATOM | 546 | CB | PRO | A | 69 | 81.999 | 16.774 | −68.436 | 1.00 | 20.99 C |
| ATOM | 547 | CG | PRO | A | 69 | 82.311 | 17.994 | −69.231 | 1.00 | 22.69 C |
| ATOM | 548 | CD | PRO | A | 69 | 82.362 | 17.463 | −70.641 | 1.00 | 20.73 C |
| ATOM | 549 | N | VAL | A | 70 | 81.327 | 13.946 | −69.576 | 1.00 | 18.05 N |
| ATOM | 550 | CA | VAL | A | 70 | 80.730 | 12.619 | −69.427 | 1.00 | 18.32 C |
| ATOM | 551 | C | VAL | A | 70 | 80.253 | 12.045 | −70.758 | 1.00 | 19.61 C |
| ATOM | 552 | O | VAL | A | 70 | 79.645 | 12.745 | −71.560 | 1.00 | 21.26 O |
| ATOM | 553 | CB | VAL | A | 70 | 79.508 | 12.659 | −68.455 | 1.00 | 20.21 C |
| ATOM | 554 | CG1 | VAL | A | 70 | 79.115 | 11.252 | −68.055 | 1.00 | 23.61 C |
| ATOM | 555 | CG2 | VAL | A | 70 | 79.838 | 13.467 | −67.217 | 1.00 | 19.26 C |
| ATOM | 556 | N | SER | A | 71 | 80.538 | 10.768 | −70.988 | 1.00 | 19.22 N |
| ATOM | 557 | CA | SER | A | 71 | 80.116 | 10.083 | −72.203 | 1.00 | 18.67 C |
| ATOM | 558 | C | SER | A | 71 | 79.870 | 8.630 | −71.839 | 1.00 | 19.32 C |
| ATOM | 559 | O | SER | A | 71 | 80.411 | 8.126 | −70.850 | 1.00 | 17.63 O |
| ATOM | 560 | CB | SER | A | 71 | 81.196 | 10.178 | −73.295 | 1.00 | 20.19 C |
| ATOM | 561 | OG | SER | A | 71 | 82.436 | 9.627 | −72.852 | 1.00 | 20.70 O |
| ATOM | 562 | N | TYR | A | 72 | 79.040 | 7.955 | −72.625 | 1.00 | 18.78 N |
| ATOM | 563 | CA | TYR | A | 72 | 78.740 | 6.560 | −72.359 | 1.00 | 20.05 C |
| ATOM | 564 | C | TYR | A | 72 | 78.460 | 5.826 | −73.667 | 1.00 | 22.72 C |
| ATOM | 565 | O | TYR | A | 72 | 77.737 | 6.325 | −74.531 | 1.00 | 21.77 O |
| ATOM | 566 | CB | TYR | A | 72 | 77.531 | 6.454 | −71.416 | 1.00 | 20.90 C |
| ATOM | 567 | CG | TYR | A | 72 | 77.186 | 5.031 | −71.046 | 1.00 | 20.35 C |
| ATOM | 568 | CD1 | TYR | A | 72 | 78.026 | 4.282 | −70.216 | 1.00 | 19.31 C |
| ATOM | 569 | CD2 | TYR | A | 72 | 76.057 | 4.407 | −71.583 | 1.00 | 17.73 C |
| ATOM | 570 | CE1 | TYR | A | 72 | 77.751 | 2.939 | −69.938 | 1.00 | 18.11 C |
| ATOM | 571 | CE2 | TYR | A | 72 | 75.778 | 3.069 | −71.311 | 1.00 | 19.88 C |
| ATOM | 572 | CZ | TYR | A | 72 | 76.628 | 2.343 | −70.494 | 1.00 | 19.52 C |
| ATOM | 573 | OH | TYR | A | 72 | 76.358 | 1.012 | −70.256 | 1.00 | 23.71 O |
| ATOM | 574 | N | TYR | A | 73 | 79.037 | 4.637 | −73.810 | 1.00 | 21.63 N |
| ATOM | 575 | CA | TYR | A | 73 | 78.865 | 3.851 | −75.021 | 1.00 | 20.63 C |
| ATOM | 576 | C | TYR | A | 73 | 78.454 | 2.426 | −74.688 | 1.00 | 21.25 C |
| ATOM | 577 | O | TYR | A | 73 | 78.836 | 1.883 | −73.653 | 1.00 | 20.62 O |
| ATOM | 578 | CB | TYR | A | 73 | 80.169 | 3.802 | −75.828 | 1.00 | 20.61 C |
| ATOM | 579 | CG | TYR | A | 73 | 80.649 | 5.142 | −76.334 | 1.00 | 24.02 C |
| ATOM | 580 | CD1 | TYR | A | 73 | 81.316 | 6.032 | −75.491 | 1.00 | 22.55 C |
| ATOM | 581 | CD2 | TYR | A | 73 | 80.412 | 5.534 | −77.654 | 1.00 | 22.70 C |
| ATOM | 582 | CE1 | TYR | A | 73 | 81.734 | 7.285 | −75.952 | 1.00 | 23.62 C |
| ATOM | 583 | CE2 | TYR | A | 73 | 80.824 | 6.784 | −78.123 | 1.00 | 21.76 C |
| ATOM | 584 | CZ | TYR | A | 73 | 81.484 | 7.652 | −77.266 | 1.00 | 23.24 C |
| ATOM | 585 | OH | TYR | A | 73 | 81.892 | 8.885 | −77.726 | 1.00 | 21.40 O |
| ATOM | 586 | N | ASP | A | 74 | 77.681 | 1.832 | −75.586 | 1.00 | 19.91 N |
| ATOM | 587 | CA | ASP | A | 74 | 77.208 | 0.459 | −75.442 | 1.00 | 21.89 C |
| ATOM | 588 | C | ASP | A | 74 | 76.432 | 0.146 | −76.706 | 1.00 | 22.27 C |
| ATOM | 589 | O | ASP | A | 74 | 75.254 | 0.474 | −76.817 | 1.00 | 21.25 O |
| ATOM | 590 | CB | ASP | A | 74 | 76.292 | 0.308 | −74.227 | 1.00 | 23.18 C |
| ATOM | 591 | CG | ASP | A | 74 | 75.709 | −1.090 | −74.117 | 1.00 | 26.21 C |
| ATOM | 592 | OD1 | ASP | A | 74 | 76.046 | −1.948 | −74.965 | 1.00 | 27.53 O |
| ATOM | 593 | OD2 | ASP | A | 74 | 74.916 | −1.336 | −73.191 | 1.00 | 28.61 O |
| ATOM | 594 | N | SER | A | 75 | 77.103 | −0.489 | −77.658 | 1.00 | 24.86 N |
| ATOM | 595 | CA | SER | A | 75 | 76.499 | −0.813 | −78.945 | 1.00 | 26.28 C |
| ATOM | 596 | C | SER | A | 75 | 75.260 | −1.693 | −78.900 | 1.00 | 26.74 C |
| ATOM | 597 | O | SER | A | 75 | 74.538 | −1.783 | −79.893 | 1.00 | 28.76 O |
| ATOM | 598 | CB | SER | A | 75 | 77.544 | −1.461 | −79.855 | 1.00 | 27.90 C |
| ATOM | 599 | OG | SER | A | 75 | 78.058 | −2.637 | −79.260 | 1.00 | 29.43 O |
| ATOM | 600 | N | THR | A | 76 | 75.002 | −2.335 | −77.764 | 1.00 | 26.40 N |
| ATOM | 601 | CA | THR | A | 76 | 73.838 | −3.214 | −77.655 | 1.00 | 26.73 C |
| ATOM | 602 | C | THR | A | 76 | 72.576 | −2.526 | −77.140 | 1.00 | 25.95 C |
| ATOM | 603 | O | THR | A | 76 | 71.481 | −3.076 | −77.255 | 1.00 | 24.86 O |
| ATOM | 604 | CB | THR | A | 76 | 74.108 | −4.418 | −76.722 | 1.00 | 27.89 C |
| ATOM | 605 | OG1 | THR | A | 76 | 74.343 | −3.943 | −75.393 | 1.00 | 26.50 O |
| ATOM | 606 | CG2 | THR | A | 76 | 75.316 | −5.215 | −77.200 | 1.00 | 28.11 C |
| ATOM | 607 | N | TYR | A | 77 | 72.720 | −1.343 | −76.555 | 1.00 | 23.68 N |
| ATOM | 608 | CA | TYR | A | 77 | 71.554 | −0.635 | −76.041 | 1.00 | 23.23 C |
| ATOM | 609 | C | TYR | A | 77 | 70.535 | −0.310 | −77.139 | 1.00 | 21.71 C |
| ATOM | 610 | O | TYR | A | 77 | 70.901 | 0.182 | −78.204 | 1.00 | 22.04 O |
| ATOM | 611 | CB | TYR | A | 77 | 71.988 | 0.658 | −75.352 | 1.00 | 24.51 C |
| ATOM | 612 | CG | TYR | A | 77 | 70.846 | 1.619 | −75.125 | 1.00 | 23.77 C |
| ATOM | 613 | CD1 | TYR | A | 77 | 69.752 | 1.262 | −74.340 | 1.00 | 22.63 C |
| ATOM | 614 | CD2 | TYR | A | 77 | 70.855 | 2.884 | −75.710 | 1.00 | 24.90 C |
| ATOM | 615 | CE1 | TYR | A | 77 | 68.687 | 2.146 | −74.143 | 1.00 | 24.26 C |
| ATOM | 616 | CE2 | TYR | A | 77 | 69.801 | 3.773 | −75.523 | 1.00 | 24.76 C |
| ATOM | 617 | CZ | TYR | A | 77 | 68.722 | 3.399 | −74.743 | 1.00 | 24.21 C |
| ATOM | 618 | OH | TYR | A | 77 | 67.676 | 4.274 | −74.587 | 1.00 | 21.48 O |

TABLE 2-continued

| ATOM | 619 | N | LEU | A | 78 | 69.264 | −0.603 | −76.872 | 1.00 | 23.08 | N |
| ATOM | 620 | CA | LEU | A | 78 | 68.164 | −0.337 | −77.808 | 1.00 | 24.95 | C |
| ATOM | 621 | C | LEU | A | 78 | 68.124 | −1.267 | −79.016 | 1.00 | 25.57 | C |
| ATOM | 622 | O | LEU | A | 78 | 67.736 | −0.852 | −80.115 | 1.00 | 26.19 | O |
| ATOM | 623 | CB | LEU | A | 78 | 68.218 | 1.114 | −78.318 | 1.00 | 24.90 | C |
| ATOM | 624 | CG | LEU | A | 78 | 67.097 | 2.082 | −77.925 | 1.00 | 26.49 | C |
| ATOM | 625 | CD1 | LEU | A | 78 | 67.098 | 3.259 | −78.893 | 1.00 | 20.99 | C |
| ATOM | 626 | CD2 | LEU | A | 78 | 65.745 | 1.382 | −77.949 | 1.00 | 22.79 | C |
| ATOM | 627 | N | SER | A | 79 | 68.504 | −2.522 | −78.812 | 1.00 | 26.37 | N |
| ATOM | 628 | CA | SER | A | 79 | 68.520 | −3.488 | −79.900 | 1.00 | 28.67 | C |
| ATOM | 629 | C | SER | A | 79 | 67.444 | −4.564 | −79.782 | 1.00 | 28.96 | C |
| ATOM | 630 | O | SER | A | 79 | 67.251 | −5.343 | −80.707 | 1.00 | 31.88 | O |
| ATOM | 631 | CB | SER | A | 79 | 69.892 | −4.156 | −79.974 | 1.00 | 26.98 | C |
| ATOM | 632 | OG | SER | A | 79 | 70.210 | −4.773 | −78.741 | 1.00 | 24.14 | O |
| ATOM | 633 | N | THR | A | 80 | 66.749 | −4.613 | −78.651 | 1.00 | 30.15 | N |
| ATOM | 634 | CA | THR | A | 80 | 65.705 | −5.617 | −78.455 | 1.00 | 30.25 | C |
| ATOM | 635 | C | THR | A | 80 | 64.321 | −4.973 | −78.456 | 1.00 | 29.82 | C |
| ATOM | 636 | O | THR | A | 80 | 64.196 | −3.778 | −78.198 | 1.00 | 27.97 | O |
| ATOM | 637 | CB | THR | A | 80 | 65.892 | −6.347 | −77.121 | 1.00 | 29.03 | C |
| ATOM | 638 | OG1 | THR | A | 80 | 65.712 | −5.423 | −76.045 | 1.00 | 30.95 | O |
| ATOM | 639 | CG2 | THR | A | 80 | 67.291 | −6.941 | −77.032 | 1.00 | 31.44 | C |
| ATOM | 640 | N | ASP | A | 81 | 63.288 | −5.764 | −78.745 | 1.00 | 29.87 | N |
| ATOM | 641 | CA | ASP | A | 81 | 61.919 | −5.254 | −78.768 | 1.00 | 30.58 | C |
| ATOM | 642 | C | ASP | A | 81 | 61.492 | −4.736 | −77.398 | 1.00 | 29.09 | C |
| ATOM | 643 | O | ASP | A | 81 | 60.781 | −3.738 | −77.304 | 1.00 | 28.72 | O |
| ATOM | 644 | CB | ASP | A | 81 | 60.927 | −6.335 | −79.222 | 1.00 | 32.44 | C |
| ATOM | 645 | CG | ASP | A | 81 | 61.052 | −6.669 | −80.699 | 1.00 | 35.53 | C |
| ATOM | 646 | OD1 | ASP | A | 81 | 61.664 | −5.880 | −81.449 | 1.00 | 37.78 | O |
| ATOM | 647 | OD2 | ASP | A | 81 | 60.522 | −7.719 | −81.117 | 1.00 | 39.77 | O |
| ATOM | 648 | N | ASN | A | 82 | 61.916 | −5.414 | −76.337 | 1.00 | 27.07 | N |
| ATOM | 649 | CA | ASN | A | 82 | 61.554 | −4.983 | −74.994 | 1.00 | 27.35 | C |
| ATOM | 650 | C | ASN | A | 82 | 62.163 | −3.620 | −74.671 | 1.00 | 25.14 | C |
| ATOM | 651 | O | ASN | A | 82 | 61.538 | −2.798 | −74.008 | 1.00 | 23.72 | O |
| ATOM | 652 | CB | ASN | A | 82 | 62.000 | −6.017 | −73.952 | 1.00 | 29.88 | C |
| ATOM | 653 | CG | ASN | A | 82 | 61.160 | −7.286 | −73.997 | 1.00 | 35.79 | C |
| ATOM | 654 | OD1 | ASN | A | 82 | 59.931 | −7.227 | −74.066 | 1.00 | 36.44 | O |
| ATOM | 655 | ND2 | ASN | A | 82 | 61.820 | −8.438 | −73.949 | 1.00 | 38.21 | N |
| ATOM | 656 | N | GLU | A | 83 | 63.388 | −3.385 | −75.132 | 1.00 | 25.26 | N |
| ATOM | 657 | CA | GLU | A | 83 | 64.035 | −2.101 | −74.885 | 1.00 | 25.64 | C |
| ATOM | 658 | C | GLU | A | 83 | 63.309 | −1.031 | −75.681 | 1.00 | 22.69 | C |
| ATOM | 659 | O | GLU | A | 83 | 63.018 | 0.047 | −75.172 | 1.00 | 21.95 | O |
| ATOM | 660 | CB | GLU | A | 83 | 65.494 | −2.133 | −75.324 | 1.00 | 26.26 | C |
| ATOM | 661 | CG | GLU | A | 83 | 66.439 | −2.798 | −74.356 | 1.00 | 30.49 | C |
| ATOM | 662 | CD | GLU | A | 83 | 67.853 | −2.787 | −74.887 | 1.00 | 33.13 | C |
| ATOM | 663 | OE1 | GLU | A | 83 | 68.113 | −3.501 | −75.885 | 1.00 | 30.77 | O |
| ATOM | 664 | OE2 | GLU | A | 83 | 68.691 | −2.048 | −74.321 | 1.00 | 32.37 | O |
| ATOM | 665 | N | LYS | A | 84 | 63.023 | −1.335 | −76.939 | 1.00 | 22.66 | N |
| ATOM | 666 | CA | LYS | A | 84 | 62.328 | −0.384 | −77.792 | 1.00 | 22.82 | C |
| ATOM | 667 | C | LYS | A | 84 | 60.954 | −0.073 | −77.222 | 1.00 | 22.79 | C |
| ATOM | 668 | O | LYS | A | 84 | 60.470 | 1.060 | −77.329 | 1.00 | 21.61 | O |
| ATOM | 669 | CB | LYS | A | 84 | 62.225 | −0.933 | −79.212 | 1.00 | 21.15 | C |
| ATOM | 670 | CG | LYS | A | 84 | 63.597 | −1.126 | −79.826 | 1.00 | 26.37 | C |
| ATOM | 671 | CD | LYS | A | 84 | 63.556 | −1.625 | −81.257 | 1.00 | 26.21 | C |
| ATOM | 672 | CE | LYS | A | 84 | 64.971 | −1.894 | −81.736 | 1.00 | 25.83 | C |
| ATOM | 673 | NZ | LYS | A | 84 | 65.034 | −2.259 | −83.169 | 1.00 | 27.83 | N |
| ATOM | 674 | N | ASP | A | 85 | 60.324 | −1.068 | −76.602 | 1.00 | 22.89 | N |
| ATOM | 675 | CA | ASP | A | 85 | 59.012 | −0.840 | −76.009 | 1.00 | 22.61 | C |
| ATOM | 676 | C | ASP | A | 85 | 59.157 | 0.056 | −74.790 | 1.00 | 21.16 | C |
| ATOM | 677 | O | ASP | A | 85 | 58.359 | 0.965 | −74.582 | 1.00 | 21.52 | O |
| ATOM | 678 | CB | ASP | A | 85 | 58.359 | −2.148 | −75.582 | 1.00 | 24.72 | C |
| ATOM | 679 | CG | ASP | A | 85 | 56.966 | −1.933 | −75.027 | 1.00 | 28.67 | C |
| ATOM | 680 | OD1 | ASP | A | 85 | 56.072 | −1.535 | −75.806 | 1.00 | 30.48 | O |
| ATOM | 681 | OD2 | ASP | A | 85 | 56.766 | −2.140 | −73.813 | 1.00 | 30.52 | O |
| ATOM | 682 | N | ASN | A | 86 | 60.180 | −0.201 | −73.980 | 1.00 | 22.03 | N |
| ATOM | 683 | CA | ASN | A | 86 | 60.411 | 0.607 | −72.780 | 1.00 | 22.08 | C |
| ATOM | 684 | C | ASN | A | 86 | 60.825 | 2.036 | −73.165 | 1.00 | 22.13 | C |
| ATOM | 685 | O | ASN | A | 86 | 60.505 | 2.990 | −72.459 | 1.00 | 21.54 | O |
| ATOM | 686 | CB | ASN | A | 86 | 61.486 | −0.050 | −71.908 | 1.00 | 23.59 | C |
| ATOM | 687 | CG | ASN | A | 86 | 61.615 | 0.604 | −70.544 | 1.00 | 26.88 | C |
| ATOM | 688 | OD1 | ASN | A | 86 | 62.668 | 1.145 | −70.206 | 1.00 | 31.59 | O |
| ATOM | 689 | ND2 | ASN | A | 86 | 60.545 | 0.559 | −69.756 | 1.00 | 24.35 | N |
| ATOM | 690 | N | TYR | A | 87 | 61.537 | 2.176 | −74.284 | 1.00 | 20.04 | N |
| ATOM | 691 | CA | TYR | A | 87 | 61.959 | 3.490 | −74.776 | 1.00 | 20.49 | C |
| ATOM | 692 | C | TYR | A | 87 | 60.720 | 4.287 | −75.199 | 1.00 | 21.12 | C |
| ATOM | 693 | O | TYR | A | 87 | 60.552 | 5.448 | −74.815 | 1.00 | 20.62 | O |
| ATOM | 694 | CB | TYR | A | 87 | 62.922 | 3.324 | −75.969 | 1.00 | 18.09 | C |
| ATOM | 695 | CG | TYR | A | 87 | 63.325 | 4.611 | −76.670 | 1.00 | 18.98 | C |
| ATOM | 696 | CD1 | TYR | A | 87 | 62.459 | 5.245 | −77.572 | 1.00 | 14.99 | C |
| ATOM | 697 | CD2 | TYR | A | 87 | 64.572 | 5.197 | −76.434 | 1.00 | 15.56 | C |

TABLE 2-continued

| | | | | | | | | | | |
|---|---|---|---|---|---|---|---|---|---|---|
| ATOM | 698 | CE1 | TYR | A | 87 | 62.830 | 6.432 | −78.219 | 1.00 | 16.59 C |
| ATOM | 699 | CE2 | TYR | A | 87 | 64.947 | 6.386 | −77.077 | 1.00 | 16.90 C |
| ATOM | 700 | CZ | TYR | A | 87 | 64.070 | 6.995 | −77.964 | 1.00 | 17.13 C |
| ATOM | 701 | OH | TYR | A | 87 | 64.427 | 8.173 | −78.580 | 1.00 | 19.87 O |
| ATOM | 702 | N | LEU | A | 88 | 59.843 | 3.651 | −75.973 | 1.00 | 20.26 N |
| ATOM | 703 | CA | LEU | A | 88 | 58.638 | 4.317 | −76.439 | 1.00 | 20.96 C |
| ATOM | 704 | C | LEU | A | 88 | 57.807 | 4.804 | −75.262 | 1.00 | 19.54 C |
| ATOM | 705 | O | LEU | A | 88 | 57.303 | 5.922 | −75.274 | 1.00 | 19.68 O |
| ATOM | 706 | CB | LEU | A | 88 | 57.795 | 3.371 | −77.306 | 1.00 | 22.25 C |
| ATOM | 707 | CG | LEU | A | 88 | 56.526 | 4.006 | −77.887 | 1.00 | 23.50 C |
| ATOM | 708 | CD1 | LEU | A | 88 | 56.901 | 5.160 | −78.804 | 1.00 | 25.29 C |
| ATOM | 709 | CD2 | LEU | A | 88 | 55.733 | 2.963 | −78.653 | 1.00 | 26.77 C |
| ATOM | 710 | N | LYS | A | 89 | 57.661 | 3.957 | −74.247 | 1.00 | 20.52 N |
| ATOM | 711 | CA | LYS | A | 89 | 56.887 | 4.308 | −73.059 | 1.00 | 19.53 C |
| ATOM | 712 | C | LYS | A | 89 | 57.575 | 5.392 | −72.231 | 1.00 | 18.33 C |
| ATOM | 713 | O | LYS | A | 89 | 56.910 | 6.216 | −71.605 | 1.00 | 18.10 O |
| ATOM | 714 | CB | LYS | A | 89 | 56.656 | 3.071 | −72.182 | 1.00 | 21.21 C |
| ATOM | 715 | CG | LYS | A | 89 | 55.635 | 2.077 | −72.741 | 1.00 | 25.39 C |
| ATOM | 716 | CD | LYS | A | 89 | 55.425 | 0.910 | −71.780 | 1.00 | 27.53 C |
| ATOM | 717 | CE | LYS | A | 89 | 54.289 | −0.006 | −72.237 | 1.00 | 30.28 C |
| ATOM | 718 | NZ | LYS | A | 89 | 54.568 | −0.706 | −73.524 | 1.00 | 32.20 N |
| ATOM | 719 | N | GLY | A | 90 | 58.905 | 5.384 | −72.222 | 1.00 | 16.29 N |
| ATOM | 720 | CA | GLY | A | 90 | 59.639 | 6.383 | −71.461 | 1.00 | 17.09 C |
| ATOM | 721 | C | GLY | A | 90 | 59.517 | 7.749 | −72.115 | 1.00 | 17.78 C |
| ATOM | 722 | O | GLY | A | 90 | 59.259 | 8.747 | −71.446 | 1.00 | 20.19 O |
| ATOM | 723 | N | VAL | A | 91 | 59.716 | 7.799 | −73.427 | 1.00 | 16.50 N |
| ATOM | 724 | CA | VAL | A | 91 | 59.607 | 9.061 | −74.154 | 1.00 | 16.62 C |
| ATOM | 725 | C | VAL | A | 91 | 58.182 | 9.608 | −74.035 | 1.00 | 17.00 C |
| ATOM | 726 | O | VAL | A | 91 | 57.984 | 10.813 | −73.888 | 1.00 | 14.85 O |
| ATOM | 727 | CB | VAL | A | 91 | 59.986 | 8.866 | −75.639 | 1.00 | 16.97 C |
| ATOM | 728 | CG1 | VAL | A | 91 | 59.563 | 10.071 | −76.468 | 1.00 | 16.04 C |
| ATOM | 729 | CG2 | VAL | A | 91 | 61.493 | 8.665 | −75.744 | 1.00 | 14.55 C |
| ATOM | 730 | N | THR | A | 92 | 57.191 | 8.718 | −74.074 | 1.00 | 17.59 N |
| ATOM | 731 | CA | THR | A | 92 | 55.789 | 9.132 | −73.955 | 1.00 | 18.53 C |
| ATOM | 732 | C | THR | A | 92 | 55.503 | 9.749 | −72.592 | 1.00 | 17.34 C |
| ATOM | 733 | O | THR | A | 92 | 54.826 | 10.772 | −72.489 | 1.00 | 18.41 O |
| ATOM | 734 | CB | THR | A | 92 | 54.822 | 7.938 | −74.135 | 1.00 | 19.82 C |
| ATOM | 735 | OG1 | THR | A | 92 | 54.940 | 7.429 | −75.467 | 1.00 | 24.40 O |
| ATOM | 736 | CG2 | THR | A | 92 | 53.381 | 8.376 | −73.889 | 1.00 | 22.15 C |
| ATOM | 737 | N | LYS | A | 93 | 56.009 | 9.107 | −71.545 | 1.00 | 17.51 N |
| ATOM | 738 | CA | LYS | A | 93 | 55.810 | 9.577 | −70.180 | 1.00 | 16.80 C |
| ATOM | 739 | C | LYS | A | 93 | 56.435 | 10.956 | −69.974 | 1.00 | 17.04 C |
| ATOM | 740 | O | LYS | A | 93 | 55.879 | 11.803 | −69.268 | 1.00 | 17.03 O |
| ATOM | 741 | CB | LYS | A | 93 | 56.421 | 8.564 | −69.203 | 1.00 | 19.02 C |
| ATOM | 742 | CG | LYS | A | 93 | 56.071 | 8.779 | −67.743 | 1.00 | 18.33 C |
| ATOM | 743 | CD | LYS | A | 93 | 56.412 | 7.536 | −66.917 | 1.00 | 20.80 C |
| ATOM | 744 | CE | LYS | A | 93 | 55.936 | 7.669 | −65.476 | 1.00 | 19.49 C |
| ATOM | 745 | NZ | LYS | A | 93 | 56.197 | 6.443 | −64.666 | 1.00 | 18.94 N |
| ATOM | 746 | N | LEU | A | 94 | 57.594 | 11.185 | −70.587 | 1.00 | 16.00 N |
| ATOM | 747 | CA | LEU | A | 94 | 58.265 | 12.472 | −70.441 | 1.00 | 16.77 C |
| ATOM | 748 | C | LEU | A | 94 | 57.480 | 13.561 | −71.180 | 1.00 | 16.03 C |
| ATOM | 749 | O | LEU | A | 94 | 57.403 | 14.697 | −70.714 | 1.00 | 13.28 O |
| ATOM | 750 | CB | LEU | A | 94 | 59.713 | 12.380 | −70.950 | 1.00 | 17.26 C |
| ATOM | 751 | CG | LEU | A | 94 | 60.628 | 11.461 | −70.122 | 1.00 | 14.55 C |
| ATOM | 752 | CD1 | LEU | A | 94 | 62.042 | 11.470 | −70.696 | 1.00 | 16.29 C |
| ATOM | 753 | CD2 | LEU | A | 94 | 60.650 | 11.926 | −68.674 | 1.00 | 13.03 C |
| ATOM | 754 | N | PHE | A | 95 | 56.903 | 13.224 | −72.331 | 1.00 | 14.26 N |
| ATOM | 755 | CA | PHE | A | 95 | 56.092 | 14.206 | −73.052 | 1.00 | 15.99 C |
| ATOM | 756 | C | PHE | A | 95 | 54.904 | 14.574 | −72.157 | 1.00 | 15.46 C |
| ATOM | 757 | O | PHE | A | 95 | 54.512 | 15.737 | −72.075 | 1.00 | 18.75 O |
| ATOM | 758 | CB | PHE | A | 95 | 55.582 | 13.639 | −74.385 | 1.00 | 15.38 C |
| ATOM | 759 | CG | PHE | A | 95 | 56.446 | 13.995 | −75.564 | 1.00 | 18.07 C |
| ATOM | 760 | CD1 | PHE | A | 95 | 56.348 | 15.251 | −76.164 | 1.00 | 20.09 C |
| ATOM | 761 | CD2 | PHE | A | 95 | 57.372 | 13.086 | −76.066 | 1.00 | 17.77 C |
| ATOM | 762 | CE1 | PHE | A | 95 | 57.165 | 15.596 | −77.250 | 1.00 | 21.18 C |
| ATOM | 763 | CE2 | PHE | A | 95 | 58.194 | 13.419 | −77.149 | 1.00 | 18.54 C |
| ATOM | 764 | CZ | PHE | A | 95 | 58.089 | 14.678 | −77.742 | 1.00 | 19.09 C |
| ATOM | 765 | N | GLU | A | 96 | 54.332 | 13.587 | −71.474 | 1.00 | 16.97 N |
| ATOM | 766 | CA | GLU | A | 96 | 53.198 | 13.874 | −70.597 | 1.00 | 16.69 C |
| ATOM | 767 | C | GLU | A | 96 | 53.656 | 14.741 | −69.423 | 1.00 | 18.24 C |
| ATOM | 768 | O | GLU | A | 96 | 52.947 | 15.656 | −69.013 | 1.00 | 19.65 O |
| ATOM | 769 | CB | GLU | A | 96 | 52.564 | 12.577 | −70.083 | 1.00 | 17.39 C |
| ATOM | 770 | CG | GLU | A | 96 | 51.970 | 11.664 | −71.171 | 1.00 | 18.74 C |
| ATOM | 771 | CD | GLU | A | 96 | 50.847 | 12.330 | −71.983 | 1.00 | 23.75 C |
| ATOM | 772 | OE1 | GLU | A | 96 | 50.414 | 13.454 | −71.625 | 1.00 | 19.71 O |
| ATOM | 773 | OE2 | GLU | A | 96 | 50.397 | 11.717 | −72.980 | 1.00 | 22.02 O |
| ATOM | 774 | N | ARG | A | 97 | 54.844 | 14.469 | −68.884 | 1.00 | 17.56 N |
| ATOM | 775 | CA | ARG | A | 97 | 55.346 | 15.267 | −67.769 | 1.00 | 15.02 C |
| ATOM | 776 | C | ARG | A | 97 | 55.521 | 16.712 | −68.236 | 1.00 | 15.27 C |

TABLE 2-continued

| ATOM | 777 | O | ARG | A | 97 | 55.176 | 17.653 | −67.529 | 1.00 | 13.68 | O |
| ATOM | 778 | CB | ARG | A | 97 | 56.665 | 14.679 | −67.243 | 1.00 | 15.44 | C |
| ATOM | 779 | CG | ARG | A | 97 | 57.317 | 15.479 | −66.101 | 1.00 | 14.65 | C |
| ATOM | 780 | CD | ARG | A | 97 | 58.126 | 14.555 | −65.172 | 1.00 | 13.56 | C |
| ATOM | 781 | NE | ARG | A | 97 | 58.976 | 15.287 | −64.234 | 1.00 | 11.28 | N |
| ATOM | 782 | CZ | ARG | A | 97 | 58.531 | 16.061 | −63.248 | 1.00 | 15.43 | C |
| ATOM | 783 | NH1 | ARG | A | 97 | 57.228 | 16.209 | −63.050 | 1.00 | 15.54 | N |
| ATOM | 784 | NH2 | ARG | A | 97 | 59.395 | 16.699 | −62.464 | 1.00 | 15.71 | N |
| ATOM | 785 | N | ILE | A | 98 | 56.049 | 16.897 | −69.436 | 1.00 | 16.90 | N |
| ATOM | 786 | CA | ILE | A | 98 | 56.209 | 18.245 | −69.966 | 1.00 | 17.84 | C |
| ATOM | 787 | C | ILE | A | 98 | 54.808 | 18.874 | −70.133 | 1.00 | 19.43 | C |
| ATOM | 788 | O | ILE | A | 98 | 54.574 | 20.041 | −69.787 | 1.00 | 18.80 | O |
| ATOM | 789 | CB | ILE | A | 98 | 56.963 | 18.209 | −71.322 | 1.00 | 17.75 | C |
| ATOM | 790 | CG1 | ILE | A | 98 | 58.448 | 17.906 | −71.069 | 1.00 | 19.53 | C |
| ATOM | 791 | CG2 | ILE | A | 98 | 56.772 | 19.528 | −72.064 | 1.00 | 16.30 | C |
| ATOM | 792 | CD1 | ILE | A | 98 | 59.261 | 17.639 | −72.301 | 1.00 | 22.03 | C |
| ATOM | 793 | N | TYR | A | 99 | 53.876 | 18.077 | −70.636 | 1.00 | 19.02 | N |
| ATOM | 794 | CA | TYR | A | 99 | 52.500 | 18.519 | −70.858 | 1.00 | 21.83 | C |
| ATOM | 795 | C | TYR | A | 99 | 51.739 | 18.808 | −69.550 | 1.00 | 23.37 | C |
| ATOM | 796 | O | TYR | A | 99 | 50.650 | 19.388 | −69.583 | 1.00 | 22.44 | O |
| ATOM | 797 | CB | TYR | A | 99 | 51.757 | 17.439 | −71.651 | 1.00 | 25.43 | C |
| ATOM | 798 | CG | TYR | A | 99 | 50.367 | 17.810 | −72.131 | 1.00 | 28.29 | C |
| ATOM | 799 | CD1 | TYR | A | 99 | 50.183 | 18.700 | −73.187 | 1.00 | 30.00 | C |
| ATOM | 800 | CD2 | TYR | A | 99 | 49.237 | 17.228 | −71.554 | 1.00 | 30.34 | C |
| ATOM | 801 | CE1 | TYR | A | 99 | 48.902 | 18.996 | −73.665 | 1.00 | 34.24 | C |
| ATOM | 802 | CE2 | TYR | A | 99 | 47.960 | 17.515 | −72.019 | 1.00 | 32.96 | C |
| ATOM | 803 | CZ | TYR | A | 99 | 47.797 | 18.395 | −73.074 | 1.00 | 34.87 | C |
| ATOM | 804 | OH | TYR | A | 99 | 46.531 | 18.651 | −73.546 | 1.00 | 39.44 | O |
| ATOM | 805 | N | SER | A | 100 | 52.316 | 18.431 | −68.408 | 1.00 | 21.80 | N |
| ATOM | 806 | CA | SER | A | 100 | 51.649 | 18.625 | −67.113 | 1.00 | 23.42 | C |
| ATOM | 807 | C | SER | A | 100 | 51.657 | 20.045 | −66.553 | 1.00 | 23.46 | C |
| ATOM | 808 | O | SER | A | 100 | 51.051 | 20.302 | −65.513 | 1.00 | 22.48 | O |
| ATOM | 809 | CB | SER | A | 100 | 52.238 | 17.681 | −66.057 | 1.00 | 23.90 | C |
| ATOM | 810 | OG | SER | A | 100 | 53.529 | 18.112 | −65.644 | 1.00 | 22.03 | O |
| ATOM | 811 | N | THR | A | 101 | 52.352 | 20.963 | −67.216 | 1.00 | 22.77 | N |
| ATOM | 812 | CA | THR | A | 101 | 52.380 | 22.348 | −66.750 | 1.00 | 22.98 | C |
| ATOM | 813 | C | THR | A | 101 | 52.049 | 23.260 | −67.923 | 1.00 | 23.05 | C |
| ATOM | 814 | O | THR | A | 101 | 52.173 | 22.850 | −69.082 | 1.00 | 21.58 | O |
| ATOM | 815 | CB | THR | A | 101 | 53.759 | 22.754 | −66.203 | 1.00 | 23.37 | C |
| ATOM | 816 | OG1 | THR | A | 101 | 54.663 | 22.970 | −67.293 | 1.00 | 26.04 | O |
| ATOM | 817 | CG2 | THR | A | 101 | 54.311 | 21.665 | −65.296 | 1.00 | 24.26 | C |
| ATOM | 818 | N | ASP | A | 102 | 51.627 | 24.488 | −67.630 | 1.00 | 21.88 | N |
| ATOM | 819 | CA | ASP | A | 102 | 51.283 | 25.438 | −68.683 | 1.00 | 22.82 | C |
| ATOM | 820 | C | ASP | A | 102 | 52.465 | 25.737 | −69.596 | 1.00 | 22.62 | C |
| ATOM | 821 | O | ASP | A | 102 | 52.294 | 25.885 | −70.808 | 1.00 | 20.12 | O |
| ATOM | 822 | CB | ASP | A | 102 | 50.772 | 26.754 | −68.093 | 1.00 | 25.32 | C |
| ATOM | 823 | CG | ASP | A | 102 | 49.392 | 26.623 | −67.486 | 1.00 | 29.00 | C |
| ATOM | 824 | OD1 | ASP | A | 102 | 48.524 | 25.975 | −68.109 | 1.00 | 32.13 | O |
| ATOM | 825 | OD2 | ASP | A | 102 | 49.171 | 27.176 | −66.391 | 1.00 | 30.10 | O |
| ATOM | 826 | N | LEU | A | 103 | 53.660 | 25.833 | −69.018 | 1.00 | 19.74 | N |
| ATOM | 827 | CA | LEU | A | 103 | 54.848 | 26.133 | −69.809 | 1.00 | 19.60 | C |
| ATOM | 828 | C | LEU | A | 103 | 55.062 | 25.060 | −70.867 | 1.00 | 18.97 | C |
| ATOM | 829 | O | LEU | A | 103 | 55.278 | 25.363 | −72.046 | 1.00 | 20.26 | O |
| ATOM | 830 | CB | LEU | A | 103 | 56.088 | 26.225 | −68.911 | 1.00 | 19.44 | C |
| ATOM | 831 | CG | LEU | A | 103 | 57.403 | 26.635 | −69.590 | 1.00 | 19.98 | C |
| ATOM | 832 | CD1 | LEU | A | 103 | 57.260 | 28.019 | −70.219 | 1.00 | 19.10 | C |
| ATOM | 833 | CD2 | LEU | A | 103 | 58.533 | 26.643 | −68.555 | 1.00 | 22.64 | C |
| ATOM | 834 | N | GLY | A | 104 | 55.001 | 23.808 | −70.435 | 1.00 | 17.03 | N |
| ATOM | 835 | CA | GLY | A | 104 | 55.199 | 22.698 | −71.343 | 1.00 | 16.98 | C |
| ATOM | 836 | C | GLY | A | 104 | 54.096 | 22.584 | −72.380 | 1.00 | 18.10 | C |
| ATOM | 837 | O | GLY | A | 104 | 54.373 | 22.328 | −73.551 | 1.00 | 16.12 | O |
| ATOM | 838 | N | ARG | A | 105 | 52.847 | 22.763 | −71.957 | 1.00 | 17.40 | N |
| ATOM | 839 | CA | ARG | A | 105 | 51.719 | 22.677 | −72.877 | 1.00 | 19.57 | C |
| ATOM | 840 | C | ARG | A | 105 | 51.853 | 23.728 | −73.971 | 1.00 | 19.81 | C |
| ATOM | 841 | O | ARG | A | 105 | 51.588 | 23.460 | −75.140 | 1.00 | 20.46 | O |
| ATOM | 842 | CB | ARG | A | 105 | 50.390 | 22.874 | −72.131 | 1.00 | 19.47 | C |
| ATOM | 843 | CG | ARG | A | 105 | 49.908 | 21.628 | −71.400 | 1.00 | 22.89 | C |
| ATOM | 844 | CD | ARG | A | 105 | 48.449 | 21.758 | −70.962 | 1.00 | 26.59 | C |
| ATOM | 845 | NE | ARG | A | 105 | 48.265 | 22.746 | −69.900 | 1.00 | 28.03 | N |
| ATOM | 846 | CZ | ARG | A | 105 | 48.410 | 22.488 | −68.603 | 1.00 | 28.65 | C |
| ATOM | 847 | NH1 | ARG | A | 105 | 48.742 | 21.271 | −68.194 | 1.00 | 29.20 | N |
| ATOM | 848 | NH2 | ARG | A | 105 | 48.216 | 23.450 | −67.712 | 1.00 | 30.11 | N |
| ATOM | 849 | N | MET | A | 106 | 52.286 | 24.921 | −73.587 | 1.00 | 19.93 | N |
| ATOM | 850 | CA | MET | A | 106 | 52.454 | 26.006 | −74.543 | 1.00 | 22.05 | C |
| ATOM | 851 | C | MET | A | 106 | 53.597 | 25.700 | −75.520 | 1.00 | 21.11 | C |
| ATOM | 852 | O | MET | A | 106 | 53.447 | 25.889 | −76.731 | 1.00 | 20.63 | O |
| ATOM | 853 | CB | MET | A | 106 | 52.709 | 27.312 | −73.790 | 1.00 | 23.29 | C |
| ATOM | 854 | CG | MET | A | 106 | 51.971 | 28.521 | −74.339 | 1.00 | 34.82 | C |
| ATOM | 855 | SD | MET | A | 106 | 50.172 | 28.319 | −74.479 | 1.00 | 35.16 | S |

TABLE 2-continued

| | | | | | | | | | | |
|---|---|---|---|---|---|---|---|---|---|---|
| ATOM | 856 | CE | MET | A | 106 | 49.927 | 28.811 | −76.140 | 1.00 | 39.14 | C |
| ATOM | 857 | N | LEU | A | 107 | 54.724 | 25.207 | −75.001 | 1.00 | 19.03 | N |
| ATOM | 858 | CA | LEU | A | 107 | 55.871 | 24.868 | −75.848 | 1.00 | 18.43 | C |
| ATOM | 859 | C | LEU | A | 107 | 55.510 | 23.804 | −76.884 | 1.00 | 16.43 | C |
| ATOM | 860 | O | LEU | A | 107 | 55.842 | 23.935 | −78.060 | 1.00 | 14.65 | O |
| ATOM | 861 | CB | LEU | A | 107 | 57.049 | 24.347 | −75.007 | 1.00 | 16.49 | C |
| ATOM | 862 | CG | LEU | A | 107 | 58.180 | 23.694 | −75.822 | 1.00 | 18.57 | C |
| ATOM | 863 | CD1 | LEU | A | 107 | 58.786 | 24.712 | −76.792 | 1.00 | 19.60 | C |
| ATOM | 864 | CD2 | LEU | A | 107 | 59.256 | 23.150 | −74.885 | 1.00 | 21.41 | C |
| ATOM | 865 | N | LEU | A | 108 | 54.848 | 22.740 | −76.441 | 1.00 | 13.10 | N |
| ATOM | 866 | CA | LEU | A | 108 | 54.464 | 21.658 | −77.349 | 1.00 | 16.44 | C |
| ATOM | 867 | C | LEU | A | 108 | 53.497 | 22.142 | −78.434 | 1.00 | 16.37 | C |
| ATOM | 868 | O | LEU | A | 108 | 53.573 | 21.710 | −79.585 | 1.00 | 17.27 | O |
| ATOM | 869 | CB | LEU | A | 108 | 53.844 | 20.503 | −76.553 | 1.00 | 14.35 | C |
| ATOM | 870 | CG | LEU | A | 108 | 54.855 | 19.766 | −75.668 | 1.00 | 14.63 | C |
| ATOM | 871 | CD1 | LEU | A | 108 | 54.127 | 18.870 | −74.687 | 1.00 | 15.53 | C |
| ATOM | 872 | CD2 | LEU | A | 108 | 55.808 | 18.962 | −76.534 | 1.00 | 14.90 | C |
| ATOM | 873 | N | THR | A | 109 | 52.584 | 23.035 | −78.067 | 1.00 | 16.23 | N |
| ATOM | 874 | CA | THR | A | 109 | 51.635 | 23.582 | −79.037 | 1.00 | 16.06 | C |
| ATOM | 875 | C | THR | A | 109 | 52.384 | 24.462 | −80.035 | 1.00 | 15.39 | C |
| ATOM | 876 | O | THR | A | 109 | 52.073 | 24.469 | −81.224 | 1.00 | 16.37 | O |
| ATOM | 877 | CB | THR | A | 109 | 50.536 | 24.416 | −78.327 | 1.00 | 16.48 | C |
| ATOM | 878 | OG1 | THR | A | 109 | 49.804 | 23.558 | −77.450 | 1.00 | 16.59 | O |
| ATOM | 879 | CG2 | THR | A | 109 | 49.566 | 25.042 | −79.345 | 1.00 | 17.74 | C |
| ATOM | 880 | N | SER | A | 110 | 53.373 | 25.210 | −79.551 | 1.00 | 16.96 | N |
| ATOM | 881 | CA | SER | A | 110 | 54.153 | 26.065 | −80.438 | 1.00 | 18.43 | C |
| ATOM | 882 | C | SER | A | 110 | 54.884 | 25.186 | −81.438 | 1.00 | 18.07 | C |
| ATOM | 883 | O | SER | A | 110 | 54.984 | 25.525 | −82.618 | 1.00 | 17.74 | O |
| ATOM | 884 | CB | SER | A | 110 | 55.172 | 26.902 | −79.653 | 1.00 | 19.60 | C |
| ATOM | 885 | OG | SER | A | 110 | 54.537 | 27.944 | −78.931 | 1.00 | 20.92 | O |
| ATOM | 886 | N | ILE | A | 111 | 55.393 | 24.055 | −80.956 | 1.00 | 16.24 | N |
| ATOM | 887 | CA | ILE | A | 111 | 56.111 | 23.119 | −81.807 | 1.00 | 16.85 | C |
| ATOM | 888 | C | ILE | A | 111 | 55.186 | 22.504 | −82.864 | 1.00 | 17.32 | C |
| ATOM | 889 | O | ILE | A | 111 | 55.562 | 22.405 | −84.033 | 1.00 | 18.19 | O |
| ATOM | 890 | CB | ILE | A | 111 | 56.770 | 22.000 | −80.959 | 1.00 | 13.41 | C |
| ATOM | 891 | CG1 | ILE | A | 111 | 58.034 | 22.556 | −80.282 | 1.00 | 15.59 | C |
| ATOM | 892 | CG2 | ILE | A | 111 | 57.095 | 20.795 | −81.831 | 1.00 | 16.18 | C |
| ATOM | 893 | CD1 | ILE | A | 111 | 58.640 | 21.634 | −79.240 | 1.00 | 15.48 | C |
| ATOM | 894 | N | VAL | A | 112 | 53.983 | 22.107 | −82.459 | 1.00 | 15.00 | N |
| ATOM | 895 | CA | VAL | A | 112 | 53.037 | 21.523 | −83.401 | 1.00 | 16.20 | C |
| ATOM | 896 | C | VAL | A | 112 | 52.593 | 22.575 | −84.423 | 1.00 | 17.27 | C |
| ATOM | 897 | O | VAL | A | 112 | 52.312 | 22.250 | −85.570 | 1.00 | 16.99 | O |
| ATOM | 898 | CB | VAL | A | 112 | 51.818 | 20.938 | −82.667 | 1.00 | 17.57 | C |
| ATOM | 899 | CG1 | VAL | A | 112 | 50.801 | 20.396 | −83.669 | 1.00 | 16.66 | C |
| ATOM | 900 | CG2 | VAL | A | 112 | 52.276 | 19.820 | −81.745 | 1.00 | 16.04 | C |
| ATOM | 901 | N | ARG | A | 113 | 52.572 | 23.839 | −84.008 | 1.00 | 18.16 | N |
| ATOM | 902 | CA | ARG | A | 113 | 52.194 | 24.946 | −84.894 | 1.00 | 18.00 | C |
| ATOM | 903 | C | ARG | A | 113 | 53.346 | 25.350 | −85.817 | 1.00 | 16.28 | C |
| ATOM | 904 | O | ARG | A | 113 | 53.130 | 25.993 | −86.839 | 1.00 | 16.95 | O |
| ATOM | 905 | CB | ARG | A | 113 | 51.839 | 26.198 | −84.094 | 1.00 | 16.22 | C |
| ATOM | 906 | CG | ARG | A | 113 | 50.541 | 26.234 | −83.331 | 1.00 | 20.28 | C |
| ATOM | 907 | CD | ARG | A | 113 | 50.438 | 27.644 | −82.729 | 1.00 | 22.98 | C |
| ATOM | 908 | NE | ARG | A | 113 | 49.061 | 28.075 | −82.575 | 1.00 | 30.93 | N |
| ATOM | 909 | CZ | ARG | A | 113 | 48.504 | 29.088 | −83.229 | 1.00 | 25.82 | C |
| ATOM | 910 | NH1 | ARG | A | 113 | 49.203 | 29.805 | −84.100 | 1.00 | 27.12 | N |
| ATOM | 911 | NH2 | ARG | A | 113 | 47.237 | 29.380 | −83.000 | 1.00 | 29.92 | N |
| ATOM | 912 | N | GLY | A | 114 | 54.565 | 24.994 | −85.434 | 1.00 | 16.85 | N |
| ATOM | 913 | CA | GLY | A | 114 | 55.738 | 25.368 | −86.208 | 1.00 | 16.34 | C |
| ATOM | 914 | C | GLY | A | 114 | 55.984 | 24.658 | −87.524 | 1.00 | 16.87 | C |
| ATOM | 915 | O | GLY | A | 114 | 57.090 | 24.187 | −87.786 | 1.00 | 17.51 | O |
| ATOM | 916 | N | ILE | A | 115 | 54.969 | 24.601 | −88.371 | 1.00 | 17.84 | N |
| ATOM | 917 | CA | ILE | A | 115 | 55.111 | 23.934 | −89.651 | 1.00 | 18.56 | C |
| ATOM | 918 | C | ILE | A | 115 | 56.160 | 24.585 | −90.555 | 1.00 | 18.67 | C |
| ATOM | 919 | O | ILE | A | 115 | 56.129 | 25.794 | −90.800 | 1.00 | 18.64 | O |
| ATOM | 920 | CB | ILE | A | 115 | 53.755 | 23.901 | −90.372 | 1.00 | 23.40 | C |
| ATOM | 921 | CG1 | ILE | A | 115 | 52.759 | 23.095 | −89.528 | 1.00 | 24.13 | C |
| ATOM | 922 | CG2 | ILE | A | 115 | 53.914 | 23.288 | −91.757 | 1.00 | 23.21 | C |
| ATOM | 923 | CD1 | ILE | A | 115 | 51.334 | 23.435 | −89.777 | 1.00 | 26.56 | C |
| ATOM | 924 | N | PRO | A | 116 | 57.129 | 23.789 | −91.038 | 1.00 | 17.72 | N |
| ATOM | 925 | CA | PRO | A | 116 | 58.177 | 24.316 | −91.923 | 1.00 | 17.27 | C |
| ATOM | 926 | C | PRO | A | 116 | 57.553 | 24.996 | −93.148 | 1.00 | 18.96 | C |
| ATOM | 927 | O | PRO | A | 116 | 56.656 | 24.439 | −93.786 | 1.00 | 17.17 | O |
| ATOM | 928 | CB | PRO | A | 116 | 58.965 | 23.067 | −92.301 | 1.00 | 16.83 | C |
| ATOM | 929 | CG | PRO | A | 116 | 58.875 | 22.226 | −91.048 | 1.00 | 15.43 | C |
| ATOM | 930 | CD | PRO | A | 116 | 57.420 | 22.398 | −90.637 | 1.00 | 16.49 | C |
| ATOM | 931 | N | PHE | A | 117 | 58.043 | 26.189 | −93.477 | 1.00 | 17.70 | N |
| ATOM | 932 | CA | PHE | A | 117 | 57.517 | 26.963 | −94.598 | 1.00 | 20.19 | C |
| ATOM | 933 | C | PHE | A | 117 | 57.573 | 26.267 | −95.951 | 1.00 | 19.89 | C |
| ATOM | 934 | O | PHE | A | 117 | 58.476 | 25.473 | −96.229 | 1.00 | 20.53 | O |

TABLE 2-continued

| | | | | | | | | | | |
|---|---|---|---|---|---|---|---|---|---|---|
| ATOM | 935 | CB | PHE | A | 117 | 58.247 | 28.306 | −94.692 | 1.00 | 21.28 | C |
| ATOM | 936 | CG | PHE | A | 117 | 57.681 | 29.236 | −95.733 | 1.00 | 20.87 | C |
| ATOM | 937 | CD1 | PHE | A | 117 | 56.367 | 29.675 | −95.647 | 1.00 | 22.24 | C |
| ATOM | 938 | CD2 | PHE | A | 117 | 58.466 | 29.675 | −96.789 | 1.00 | 21.03 | C |
| ATOM | 939 | CE1 | PHE | A | 117 | 55.835 | 30.543 | −96.595 | 1.00 | 22.60 | C |
| ATOM | 940 | CE2 | PHE | A | 117 | 57.950 | 30.541 | −97.745 | 1.00 | 24.20 | C |
| ATOM | 941 | CZ | PHE | A | 117 | 56.626 | 30.978 | −97.647 | 1.00 | 24.28 | C |
| ATOM | 942 | N | TRP | A | 118 | 56.589 | 26.572 | −96.789 | 1.00 | 21.44 | N |
| ATOM | 943 | CA | TRP | A | 118 | 56.512 | 26.005 | −98.129 | 1.00 | 21.27 | C |
| ATOM | 944 | C | TRP | A | 118 | 57.277 | 26.903 | −99.094 | 1.00 | 22.79 | C |
| ATOM | 945 | O | TRP | A | 118 | 56.682 | 27.674 | −99.846 | 1.00 | 24.67 | O |
| ATOM | 946 | CB | TRP | A | 118 | 55.047 | 25.882 | −98.563 | 1.00 | 20.14 | C |
| ATOM | 947 | CG | TRP | A | 118 | 54.426 | 24.546 | −98.224 | 1.00 | 23.00 | C |
| ATOM | 948 | CD1 | TRP | A | 118 | 54.534 | 23.865 | −97.043 | 1.00 | 21.74 | C |
| ATOM | 949 | CD2 | TRP | A | 118 | 53.673 | 23.700 | −99.105 | 1.00 | 22.15 | C |
| ATOM | 950 | NE1 | TRP | A | 118 | 53.905 | 22.649 | −97.138 | 1.00 | 20.51 | N |
| ATOM | 951 | CE2 | TRP | A | 118 | 53.367 | 22.521 | −98.390 | 1.00 | 23.11 | C |
| ATOM | 952 | CE3 | TRP | A | 118 | 53.227 | 23.824 | −100.426 | 1.00 | 23.22 | C |
| ATOM | 953 | CZ2 | TRP | A | 118 | 52.641 | 21.469 | −98.955 | 1.00 | 21.26 | C |
| ATOM | 954 | CZ3 | TRP | A | 118 | 52.503 | 22.774 | −100.989 | 1.00 | 23.51 | C |
| ATOM | 955 | CH2 | TRP | A | 118 | 52.217 | 21.615 | −100.250 | 1.00 | 23.29 | C |
| ATOM | 956 | N | GLY | A | 119 | 58.601 | 26.806 | −99.070 | 1.00 | 24.02 | N |
| ATOM | 957 | CA | GLY | A | 119 | 59.400 | 27.633 | −99.952 | 1.00 | 26.76 | C |
| ATOM | 958 | C | GLY | A | 119 | 60.423 | 26.852 | −100.746 | 1.00 | 26.54 | C |
| ATOM | 959 | O | GLY | A | 119 | 61.558 | 27.285 | −100.872 | 1.00 | 28.32 | O |
| ATOM | 960 | N | GLY | A | 120 | 60.029 | 25.703 | −101.282 | 1.00 | 27.98 | N |
| ATOM | 961 | CA | GLY | A | 120 | 60.961 | 24.901 | −102.052 | 1.00 | 29.63 | C |
| ATOM | 962 | C | GLY | A | 120 | 60.844 | 25.019 | −103.566 | 1.00 | 31.21 | C |
| ATOM | 963 | O | GLY | A | 120 | 61.352 | 24.163 | −104.293 | 1.00 | 30.78 | O |
| ATOM | 964 | N | SER | A | 121 | 60.192 | 26.072 | −104.051 | 1.00 | 31.29 | N |
| ATOM | 965 | CA | SER | A | 121 | 60.024 | 26.258 | −105.491 | 1.00 | 34.33 | C |
| ATOM | 966 | C | SER | A | 121 | 61.042 | 27.198 | −106.125 | 1.00 | 34.91 | C |
| ATOM | 967 | O | SER | A | 121 | 61.543 | 28.116 | −105.482 | 1.00 | 34.36 | O |
| ATOM | 968 | CB | SER | A | 121 | 58.617 | 26.779 | −105.798 | 1.00 | 36.77 | C |
| ATOM | 969 | OG | SER | A | 121 | 58.493 | 27.118 | −107.169 | 1.00 | 38.09 | O |
| ATOM | 970 | N | THR | A | 122 | 61.349 | 26.958 | −107.395 | 1.00 | 38.15 | N |
| ATOM | 971 | CA | THR | A | 122 | 62.284 | 27.811 | −108.120 | 1.00 | 40.22 | C |
| ATOM | 972 | C | THR | A | 122 | 61.502 | 29.010 | −108.652 | 1.00 | 40.78 | C |
| ATOM | 973 | O | THR | A | 122 | 62.080 | 30.008 | −109.080 | 1.00 | 43.30 | O |
| ATOM | 974 | CB | THR | A | 122 | 62.952 | 27.051 | −109.295 | 1.00 | 39.87 | C |
| ATOM | 975 | OG1 | THR | A | 122 | 61.947 | 26.449 | −110.121 | 1.00 | 42.34 | O |
| ATOM | 976 | CG2 | THR | A | 122 | 63.875 | 25.970 | −108.767 | 1.00 | 38.90 | C |
| ATOM | 977 | N | ILE | A | 123 | 60.180 | 28.907 | −108.601 | 1.00 | 40.71 | N |
| ATOM | 978 | CA | ILE | A | 123 | 59.300 | 29.971 | −109.069 | 1.00 | 41.12 | C |
| ATOM | 979 | C | ILE | A | 123 | 58.861 | 30.806 | −107.870 | 1.00 | 41.40 | C |
| ATOM | 980 | O | ILE | A | 123 | 57.999 | 30.386 | −107.103 | 1.00 | 41.71 | O |
| ATOM | 981 | CB | ILE | A | 123 | 58.052 | 29.381 | −109.754 | 1.00 | 40.12 | C |
| ATOM | 982 | CG1 | ILE | A | 123 | 58.477 | 28.394 | −110.841 | 1.00 | 40.92 | C |
| ATOM | 983 | CG2 | ILE | A | 123 | 57.209 | 30.497 | −110.347 | 1.00 | 40.63 | C |
| ATOM | 984 | CD1 | ILE | A | 123 | 57.322 | 27.665 | −111.501 | 1.00 | 40.77 | C |
| ATOM | 985 | N | ASP | A | 124 | 59.448 | 31.990 | −107.723 | 1.00 | 42.12 | N |
| ATOM | 986 | CA | ASP | A | 124 | 59.152 | 32.880 | −106.599 | 1.00 | 42.97 | C |
| ATOM | 987 | C | ASP | A | 124 | 57.671 | 33.078 | −106.284 | 1.00 | 42.38 | C |
| ATOM | 988 | O | ASP | A | 124 | 57.316 | 33.420 | −105.156 | 1.00 | 44.53 | O |
| ATOM | 989 | CB | ASP | A | 124 | 59.800 | 34.253 | −106.828 | 1.00 | 47.11 | C |
| ATOM | 990 | CG | ASP | A | 124 | 59.020 | 35.118 | −107.811 | 1.00 | 50.05 | C |
| ATOM | 991 | OD1 | ASP | A | 124 | 58.723 | 34.646 | −108.931 | 1.00 | 52.38 | O |
| ATOM | 992 | OD2 | ASP | A | 124 | 58.707 | 36.278 | −107.465 | 1.00 | 52.45 | O |
| ATOM | 993 | N | THR | A | 125 | 56.807 | 32.869 | −107.269 | 1.00 | 39.41 | N |
| ATOM | 994 | CA | THR | A | 125 | 55.376 | 33.051 | −107.053 | 1.00 | 38.35 | C |
| ATOM | 995 | C | THR | A | 125 | 54.640 | 31.743 | −106.766 | 1.00 | 36.27 | C |
| ATOM | 996 | O | THR | A | 125 | 53.416 | 31.729 | −106.656 | 1.00 | 34.90 | O |
| ATOM | 997 | CB | THR | A | 125 | 54.711 | 33.725 | −108.273 | 1.00 | 38.90 | C |
| ATOM | 998 | OG1 | THR | A | 125 | 54.920 | 32.917 | −109.437 | 1.00 | 38.35 | O |
| ATOM | 999 | CG2 | THR | A | 125 | 55.295 | 35.112 | −108.506 | 1.00 | 39.24 | C |
| ATOM | 1000 | N | GLU | A | 126 | 55.385 | 30.649 | −106.633 | 1.00 | 34.73 | N |
| ATOM | 1001 | CA | GLU | A | 126 | 54.780 | 29.348 | −106.375 | 1.00 | 33.16 | C |
| ATOM | 1002 | C | GLU | A | 126 | 55.143 | 28.760 | −105.010 | 1.00 | 31.75 | C |
| ATOM | 1003 | O | GLU | A | 126 | 56.319 | 28.646 | −104.672 | 1.00 | 31.42 | O |
| ATOM | 1004 | CB | GLU | A | 126 | 55.201 | 28.356 | −107.465 | 1.00 | 33.11 | C |
| ATOM | 1005 | CG | GLU | A | 126 | 54.590 | 26.978 | −107.316 | 1.00 | 36.07 | C |
| ATOM | 1006 | CD | GLU | A | 126 | 55.255 | 25.942 | −108.203 | 1.00 | 40.52 | C |
| ATOM | 1007 | OE1 | GLU | A | 126 | 56.401 | 25.539 | −107.902 | 1.00 | 42.40 | O |
| ATOM | 1008 | OE2 | GLU | A | 126 | 54.635 | 25.530 | −109.207 | 1.00 | 42.27 | O |
| ATOM | 1009 | N | LEU | A | 127 | 54.131 | 28.384 | −104.231 | 1.00 | 30.73 | N |
| ATOM | 1010 | CA | LEU | A | 127 | 54.371 | 27.766 | −102.930 | 1.00 | 28.79 | C |
| ATOM | 1011 | C | LEU | A | 127 | 54.554 | 26.269 | −103.163 | 1.00 | 27.73 | C |
| ATOM | 1012 | O | LEU | A | 127 | 53.719 | 25.620 | −103.797 | 1.00 | 28.18 | O |
| ATOM | 1013 | CB | LEU | A | 127 | 53.196 | 28.002 | −101.975 | 1.00 | 25.14 | C |

TABLE 2-continued

| ATOM | 1014 | CG  | LEU | A | 127 | 52.907 | 29.438 | −101.527 | 1.00 | 24.55 | C |
|------|------|-----|-----|---|-----|--------|--------|----------|------|-------|---|
| ATOM | 1015 | CD1 | LEU | A | 127 | 51.887 | 29.398 | −100.396 | 1.00 | 21.43 | C |
| ATOM | 1016 | CD2 | LEU | A | 127 | 54.191 | 30.127 | −101.046 | 1.00 | 24.06 | C |
| ATOM | 1017 | N   | LYS | A | 128 | 55.659 | 25.731 | −102.663 | 1.00 | 27.24 | N |
| ATOM | 1018 | CA  | LYS | A | 128 | 55.970 | 24.313 | −102.819 | 1.00 | 26.34 | C |
| ATOM | 1019 | C   | LYS | A | 128 | 56.656 | 23.795 | −101.560 | 1.00 | 26.36 | C |
| ATOM | 1020 | O   | LYS | A | 128 | 57.445 | 24.505 | −100.942 | 1.00 | 23.97 | O |
| ATOM | 1021 | CB  | LYS | A | 128 | 56.892 | 24.097 | −104.019 | 1.00 | 27.27 | C |
| ATOM | 1022 | CG  | LYS | A | 128 | 57.206 | 22.634 | −104.294 | 1.00 | 28.75 | C |
| ATOM | 1023 | CD  | LYS | A | 128 | 58.069 | 22.472 | −105.532 | 1.00 | 34.08 | C |
| ATOM | 1024 | CE  | LYS | A | 128 | 58.319 | 21.003 | −105.826 | 1.00 | 36.20 | C |
| ATOM | 1025 | NZ  | LYS | A | 128 | 59.052 | 20.822 | −107.104 | 1.00 | 43.14 | N |
| ATOM | 1026 | N   | VAL | A | 129 | 56.353 | 22.554 | −101.193 | 1.00 | 25.13 | N |
| ATOM | 1027 | CA  | VAL | A | 129 | 56.924 | 21.932 | −100.005 | 1.00 | 25.35 | C |
| ATOM | 1028 | C   | VAL | A | 129 | 58.408 | 21.646 | −100.192 | 1.00 | 26.30 | C |
| ATOM | 1029 | O   | VAL | A | 129 | 58.900 | 21.584 | −101.321 | 1.00 | 26.71 | O |
| ATOM | 1030 | CB  | VAL | A | 129 | 56.227 | 20.582 | −99.708  | 1.00 | 26.07 | C |
| ATOM | 1031 | CG1 | VAL | A | 129 | 56.723 | 19.520 | −100.692 | 1.00 | 23.30 | C |
| ATOM | 1032 | CG2 | VAL | A | 129 | 56.483 | 20.148 | −98.264  | 1.00 | 22.23 | C |
| ATOM | 1033 | N   | ILE | A | 130 | 59.117 | 21.477 | −99.081  | 1.00 | 26.86 | N |
| ATOM | 1034 | CA  | ILE | A | 130 | 60.531 | 21.132 | −99.120  | 1.00 | 26.28 | C |
| ATOM | 1035 | C   | ILE | A | 130 | 60.580 | 19.678 | −98.654  | 1.00 | 27.81 | C |
| ATOM | 1036 | O   | ILE | A | 130 | 60.257 | 19.382 | −97.509  | 1.00 | 25.94 | O |
| ATOM | 1037 | CB  | ILE | A | 130 | 61.369 | 22.031 | −98.183  | 1.00 | 26.45 | C |
| ATOM | 1038 | CG1 | ILE | A | 130 | 61.353 | 23.475 | −98.704  | 1.00 | 27.38 | C |
| ATOM | 1039 | CG2 | ILE | A | 130 | 62.799 | 21.518 | −98.117  | 1.00 | 23.09 | C |
| ATOM | 1040 | CD1 | ILE | A | 130 | 62.222 | 24.456 | −97.925  | 1.00 | 26.21 | C |
| ATOM | 1041 | N   | ASP | A | 131 | 60.949 | 18.776 | −99.563  | 1.00 | 29.59 | N |
| ATOM | 1042 | CA  | ASP | A | 131 | 61.004 | 17.334 | −99.292  | 1.00 | 31.92 | C |
| ATOM | 1043 | C   | ASP | A | 131 | 61.690 | 16.931 | −97.989  | 1.00 | 32.06 | C |
| ATOM | 1044 | O   | ASP | A | 131 | 61.376 | 15.893 | −97.404  | 1.00 | 31.74 | O |
| ATOM | 1045 | CB  | ASP | A | 131 | 61.687 | 16.608 | −100.455 | 1.00 | 34.11 | C |
| ATOM | 1046 | CG  | ASP | A | 131 | 60.790 | 16.481 | −101.669 | 1.00 | 37.87 | C |
| ATOM | 1047 | OD1 | ASP | A | 131 | 59.694 | 17.088 | −101.670 | 1.00 | 38.09 | O |
| ATOM | 1048 | OD2 | ASP | A | 131 | 61.182 | 15.778 | −102.628 | 1.00 | 42.08 | O |
| ATOM | 1049 | N   | THR | A | 132 | 62.626 | 17.761 | −97.550  | 1.00 | 30.72 | N |
| ATOM | 1050 | CA  | THR | A | 132 | 63.387 | 17.535 | −96.330  | 1.00 | 31.53 | C |
| ATOM | 1051 | C   | THR | A | 132 | 62.528 | 17.691 | −95.061  | 1.00 | 29.74 | C |
| ATOM | 1052 | O   | THR | A | 132 | 62.979 | 17.396 | −93.951  | 1.00 | 28.91 | O |
| ATOM | 1053 | CB  | THR | A | 132 | 64.595 | 18.517 | −96.293  | 1.00 | 31.97 | C |
| ATOM | 1054 | OG1 | THR | A | 132 | 65.795 | 17.773 | −96.068  | 1.00 | 39.77 | O |
| ATOM | 1055 | CG2 | THR | A | 132 | 64.436 | 19.578 | −95.195  | 1.00 | 32.62 | C |
| ATOM | 1056 | N   | ASN | A | 133 | 61.294 | 18.153 | −95.233  | 1.00 | 25.83 | N |
| ATOM | 1057 | CA  | ASN | A | 133 | 60.390 | 18.357 | −94.104  | 1.00 | 22.76 | C |
| ATOM | 1058 | C   | ASN | A | 133 | 59.251 | 17.331 | −94.117  | 1.00 | 21.47 | C |
| ATOM | 1059 | O   | ASN | A | 133 | 58.183 | 17.575 | −93.553  | 1.00 | 18.46 | O |
| ATOM | 1060 | CB  | ASN | A | 133 | 59.798 | 19.773 | −94.153  | 1.00 | 22.86 | C |
| ATOM | 1061 | CG  | ASN | A | 133 | 60.857 | 20.872 | −94.088  | 1.00 | 24.90 | C |
| ATOM | 1062 | OD1 | ASN | A | 133 | 60.716 | 21.920 | −94.733  | 1.00 | 28.38 | O |
| ATOM | 1063 | ND2 | ASN | A | 133 | 61.908 | 20.650 | −93.308  | 1.00 | 13.33 | N |
| ATOM | 1064 | N   | CYS | A | 134 | 59.479 | 16.192 | −94.768  | 1.00 | 19.79 | N |
| ATOM | 1065 | CA  | CYS | A | 134 | 58.474 | 15.129 | −94.848  | 1.00 | 19.46 | C |
| ATOM | 1066 | C   | CYS | A | 134 | 59.132 | 13.771 | −94.615  | 1.00 | 19.99 | C |
| ATOM | 1067 | O   | CYS | A | 134 | 60.353 | 13.670 | −94.526  | 1.00 | 21.29 | O |
| ATOM | 1068 | CB  | CYS | A | 134 | 57.833 | 15.075 | −96.244  | 1.00 | 17.00 | C |
| ATOM | 1069 | SG  | CYS | A | 134 | 57.205 | 16.630 | −96.953  | 1.00 | 22.56 | S |
| ATOM | 1070 | N   | ILE | A | 135 | 58.304 | 12.735 | −94.518  | 1.00 | 19.98 | N |
| ATOM | 1071 | CA  | ILE | A | 135 | 58.774 | 11.359 | −94.399  | 1.00 | 19.63 | C |
| ATOM | 1072 | C   | ILE | A | 135 | 57.827 | 10.547 | −95.272  | 1.00 | 21.34 | C |
| ATOM | 1073 | O   | ILE | A | 135 | 56.732 | 11.004 | −95.606  | 1.00 | 21.14 | O |
| ATOM | 1074 | CB  | ILE | A | 135 | 58.689 | 10.779 | −92.963  | 1.00 | 21.55 | C |
| ATOM | 1075 | CG1 | ILE | A | 135 | 57.244 | 10.813 | −92.465  | 1.00 | 19.85 | C |
| ATOM | 1076 | CG2 | ILE | A | 135 | 59.644 | 11.523 | −92.038  | 1.00 | 19.01 | C |
| ATOM | 1077 | CD1 | ILE | A | 135 | 57.051 | 10.095 | −91.138  | 1.00 | 21.55 | C |
| ATOM | 1078 | N   | ASN | A | 136 | 58.264 | 9.364  | −95.675  | 1.00 | 20.75 | N |
| ATOM | 1079 | CA  | ASN | A | 136 | 57.423 | 8.491  | −96.466  | 1.00 | 22.08 | C |
| ATOM | 1080 | C   | ASN | A | 136 | 56.926 | 7.409  | −95.525  | 1.00 | 21.55 | C |
| ATOM | 1081 | O   | ASN | A | 136 | 57.713 | 6.750  | −94.849  | 1.00 | 22.41 | O |
| ATOM | 1082 | CB  | ASN | A | 136 | 58.202 | 7.893  | −97.628  | 1.00 | 21.67 | C |
| ATOM | 1083 | CG  | ASN | A | 136 | 58.465 | 8.904  | −98.709  | 1.00 | 25.49 | C |
| ATOM | 1084 | OD1 | ASN | A | 136 | 57.665 | 9.820  | −98.922  | 1.00 | 25.25 | O |
| ATOM | 1085 | ND2 | ASN | A | 136 | 59.580 | 8.751  | −99.407  | 1.00 | 23.70 | N |
| ATOM | 1086 | N   | VAL | A | 137 | 55.609 | 7.262  | −95.464  | 1.00 | 18.83 | N |
| ATOM | 1087 | CA  | VAL | A | 137 | 54.982 | 6.287  | −94.590  | 1.00 | 18.67 | C |
| ATOM | 1088 | C   | VAL | A | 137 | 54.542 | 5.081  | −95.416  | 1.00 | 22.28 | C |
| ATOM | 1089 | O   | VAL | A | 137 | 53.668 | 5.190  | −96.277  | 1.00 | 21.68 | O |
| ATOM | 1090 | CB  | VAL | A | 137 | 53.740 | 6.896  | −93.891  | 1.00 | 18.05 | C |
| ATOM | 1091 | CG1 | VAL | A | 137 | 53.259 | 5.973  | −92.802  | 1.00 | 16.13 | C |
| ATOM | 1092 | CG2 | VAL | A | 137 | 54.073 | 8.274  | −93.315  | 1.00 | 15.49 | C |

TABLE 2-continued

| | | | | | | | | | | | |
|---|---|---|---|---|---|---|---|---|---|---|---|
| ATOM | 1093 | N | ILE | A | 138 | 55.150 | 3.932 | −95.151 | 1.00 | 24.53 | N |
| ATOM | 1094 | CA | ILE | A | 138 | 54.813 | 2.712 | −95.868 | 1.00 | 27.27 | C |
| ATOM | 1095 | C | ILE | A | 138 | 53.493 | 2.164 | −95.343 | 1.00 | 27.93 | C |
| ATOM | 1096 | O | ILE | A | 138 | 53.252 | 2.165 | −94.143 | 1.00 | 27.14 | O |
| ATOM | 1097 | CB | ILE | A | 138 | 55.908 | 1.659 | −95.681 | 1.00 | 29.49 | C |
| ATOM | 1098 | CG1 | ILE | A | 138 | 57.216 | 2.186 | −96.272 | 1.00 | 29.68 | C |
| ATOM | 1099 | CG2 | ILE | A | 138 | 55.484 | 0.341 | −96.327 | 1.00 | 30.91 | C |
| ATOM | 1100 | CD1 | ILE | A | 138 | 58.438 | 1.383 | −95.874 | 1.00 | 33.50 | C |
| ATOM | 1101 | N | GLN | A | 139 | 52.642 | 1.705 | −96.257 | 1.00 | 29.73 | N |
| ATOM | 1102 | CA | GLN | A | 139 | 51.338 | 1.154 | −95.912 | 1.00 | 32.40 | C |
| ATOM | 1103 | C | GLN | A | 139 | 51.382 | −0.369 | −95.852 | 1.00 | 34.85 | C |
| ATOM | 1104 | O | GLN | A | 139 | 52.305 | −0.991 | −96.363 | 1.00 | 34.70 | O |
| ATOM | 1105 | CB | GLN | A | 139 | 50.300 | 1.568 | −96.955 | 1.00 | 32.39 | C |
| ATOM | 1106 | CG | GLN | A | 139 | 50.168 | 3.059 | −97.134 | 1.00 | 32.32 | C |
| ATOM | 1107 | CD | GLN | A | 139 | 49.834 | 3.761 | −95.840 | 1.00 | 30.59 | C |
| ATOM | 1108 | OE1 | GLN | A | 139 | 48.773 | 3.544 | −95.256 | 1.00 | 30.10 | O |
| ATOM | 1109 | NE2 | GLN | A | 139 | 50.747 | 4.607 | −95.379 | 1.00 | 32.24 | N |
| ATOM | 1110 | N | PRO | A | 140 | 50.379 | −0.988 | −95.212 | 1.00 | 37.62 | N |
| ATOM | 1111 | CA | PRO | A | 140 | 50.336 | −2.450 | −95.113 | 1.00 | 40.23 | C |
| ATOM | 1112 | C | PRO | A | 140 | 50.219 | −3.128 | −96.486 | 1.00 | 42.97 | C |
| ATOM | 1113 | O | PRO | A | 140 | 50.665 | −4.262 | −96.663 | 1.00 | 44.01 | O |
| ATOM | 1114 | CB | PRO | A | 140 | 49.111 | −2.693 | −94.239 | 1.00 | 39.21 | C |
| ATOM | 1115 | CG | PRO | A | 140 | 49.122 | −1.505 | −93.330 | 1.00 | 37.18 | C |
| ATOM | 1116 | CD | PRO | A | 140 | 49.413 | −0.374 | −94.283 | 1.00 | 36.55 | C |
| ATOM | 1117 | N | ASP | A | 141 | 49.624 | −2.434 | −97.455 | 1.00 | 44.54 | N |
| ATOM | 1118 | CA | ASP | A | 141 | 49.466 | −2.996 | −98.795 | 1.00 | 45.81 | C |
| ATOM | 1119 | C | ASP | A | 141 | 50.761 | −2.917 | −99.589 | 1.00 | 45.63 | C |
| ATOM | 1120 | O | ASP | A | 141 | 50.840 | −3.425 | −100.706 | 1.00 | 46.98 | O |
| ATOM | 1121 | CB | ASP | A | 141 | 48.360 | −2.271 | −99.567 | 1.00 | 48.12 | C |
| ATOM | 1122 | CG | ASP | A | 141 | 48.601 | −0.776 | −99.670 | 1.00 | 50.44 | C |
| ATOM | 1123 | OD1 | ASP | A | 141 | 49.773 | −0.369 | −99.828 | 1.00 | 52.22 | O |
| ATOM | 1124 | OD2 | ASP | A | 141 | 47.617 | −0.009 | −99.606 | 1.00 | 51.80 | O |
| ATOM | 1125 | N | GLY | A | 142 | 51.771 | −2.265 | −99.020 | 1.00 | 43.23 | N |
| ATOM | 1126 | CA | GLY | A | 142 | 53.047 | −2.160 | −99.706 | 1.00 | 40.39 | C |
| ATOM | 1127 | C | GLY | A | 142 | 53.328 | −0.803 | −100.320 | 1.00 | 39.06 | C |
| ATOM | 1128 | O | GLY | A | 142 | 54.486 | −0.443 | −100.538 | 1.00 | 38.61 | O |
| ATOM | 1129 | N | SER | A | 143 | 52.275 | −0.049 | −100.616 | 1.00 | 36.29 | N |
| ATOM | 1130 | CA | SER | A | 143 | 52.446 | 1.278 | −101.191 | 1.00 | 35.70 | C |
| ATOM | 1131 | C | SER | A | 143 | 52.873 | 2.228 | −100.073 | 1.00 | 35.00 | C |
| ATOM | 1132 | O | SER | A | 143 | 53.110 | 1.800 | −98.946 | 1.00 | 33.81 | O |
| ATOM | 1133 | CB | SER | A | 143 | 51.130 | 1.770 | −101.796 | 1.00 | 35.37 | C |
| ATOM | 1134 | OG | SER | A | 143 | 50.143 | 1.954 | −100.789 | 1.00 | 34.83 | O |
| ATOM | 1135 | N | TYR | A | 144 | 52.979 | 3.514 | −100.389 | 1.00 | 34.57 | N |
| ATOM | 1136 | CA | TYR | A | 144 | 53.349 | 4.496 | −99.384 | 1.00 | 34.56 | C |
| ATOM | 1137 | C | TYR | A | 144 | 52.818 | 5.875 | −99.745 | 1.00 | 34.41 | C |
| ATOM | 1138 | O | TYR | A | 144 | 52.435 | 6.141 | −100.889 | 1.00 | 33.42 | O |
| ATOM | 1139 | CB | TYR | A | 144 | 54.871 | 4.570 | −99.220 | 1.00 | 36.87 | C |
| ATOM | 1140 | CG | TYR | A | 144 | 55.572 | 5.333 | −100.317 | 1.00 | 40.03 | C |
| ATOM | 1141 | CD1 | TYR | A | 144 | 55.710 | 4.793 | −101.594 | 1.00 | 42.26 | C |
| ATOM | 1142 | CD2 | TYR | A | 144 | 56.073 | 6.612 | −100.085 | 1.00 | 41.95 | C |
| ATOM | 1143 | CE1 | TYR | A | 144 | 56.332 | 5.512 | −102.618 | 1.00 | 43.92 | C |
| ATOM | 1144 | CE2 | TYR | A | 144 | 56.693 | 7.339 | −101.095 | 1.00 | 43.11 | C |
| ATOM | 1145 | CZ | TYR | A | 144 | 56.820 | 6.784 | −102.358 | 1.00 | 44.74 | C |
| ATOM | 1146 | OH | TYR | A | 144 | 57.435 | 7.504 | −103.354 | 1.00 | 46.09 | O |
| ATOM | 1147 | N | ARG | A | 145 | 52.784 | 6.748 | −98.750 | 1.00 | 33.16 | N |
| ATOM | 1148 | CA | ARG | A | 145 | 52.335 | 8.111 | −98.951 | 1.00 | 31.66 | C |
| ATOM | 1149 | C | ARG | A | 145 | 53.278 | 9.019 | −98.181 | 1.00 | 30.05 | C |
| ATOM | 1150 | O | ARG | A | 145 | 53.836 | 8.626 | −97.155 | 1.00 | 29.34 | O |
| ATOM | 1151 | CB | ARG | A | 145 | 50.904 | 8.288 | −98.447 | 1.00 | 32.83 | C |
| ATOM | 1152 | CG | ARG | A | 145 | 50.714 | 7.972 | −96.989 | 1.00 | 33.55 | C |
| ATOM | 1153 | CD | ARG | A | 145 | 49.285 | 8.252 | −96.548 | 1.00 | 35.23 | C |
| ATOM | 1154 | NE | ARG | A | 145 | 49.086 | 7.930 | −95.136 | 1.00 | 35.58 | N |
| ATOM | 1155 | CZ | ARG | A | 145 | 49.653 | 8.587 | −94.128 | 1.00 | 35.14 | C |
| ATOM | 1156 | NH1 | ARG | A | 145 | 50.458 | 9.616 | −94.365 | 1.00 | 35.59 | N |
| ATOM | 1157 | NH2 | ARG | A | 145 | 49.423 | 8.209 | −92.880 | 1.00 | 34.11 | N |
| ATOM | 1158 | N | SER | A | 146 | 53.467 | 10.230 | −98.682 | 1.00 | 27.61 | N |
| ATOM | 1159 | CA | SER | A | 146 | 54.345 | 11.176 | −98.014 | 1.00 | 25.47 | C |
| ATOM | 1160 | C | SER | A | 146 | 53.518 | 12.015 | −97.061 | 1.00 | 24.65 | C |
| ATOM | 1161 | O | SER | A | 146 | 52.332 | 12.256 | −97.301 | 1.00 | 23.06 | O |
| ATOM | 1162 | CB | SER | A | 146 | 55.044 | 12.054 | −99.043 | 1.00 | 25.05 | C |
| ATOM | 1163 | OG | SER | A | 146 | 55.794 | 11.244 | −99.928 | 1.00 | 28.19 | O |
| ATOM | 1164 | N | GLU | A | 147 | 54.155 | 12.464 | −95.983 | 1.00 | 23.78 | N |
| ATOM | 1165 | CA | GLU | A | 147 | 53.481 | 13.255 | −94.959 | 1.00 | 22.52 | C |
| ATOM | 1166 | C | GLU | A | 147 | 54.440 | 14.281 | −94.344 | 1.00 | 21.17 | C |
| ATOM | 1167 | O | GLU | A | 147 | 55.601 | 13.970 | −94.092 | 1.00 | 19.68 | O |
| ATOM | 1168 | CB | GLU | A | 147 | 52.982 | 12.301 | −93.871 | 1.00 | 23.35 | C |
| ATOM | 1169 | CG | GLU | A | 147 | 52.199 | 12.930 | −92.741 | 1.00 | 29.33 | C |
| ATOM | 1170 | CD | GLU | A | 147 | 51.850 | 11.920 | −91.652 | 1.00 | 28.32 | C |
| ATOM | 1171 | OE1 | GLU | A | 147 | 51.405 | 10.805 | −91.992 | 1.00 | 28.66 | O |

TABLE 2-continued

| | | | | | | | | | | |
|---|---|---|---|---|---|---|---|---|---|---|
| ATOM | 1172 | OE2 | GLU | A | 147 | 52.010 | 12.244 | −90.456 | 1.00 | 27.86 | O |
| ATOM | 1173 | N | GLU | A | 148 | 53.954 | 15.499 | −94.114 | 1.00 | 18.96 | N |
| ATOM | 1174 | CA | GLU | A | 148 | 54.767 | 16.541 | −93.489 | 1.00 | 19.07 | C |
| ATOM | 1175 | C | GLU | A | 148 | 54.717 | 16.327 | −91.981 | 1.00 | 18.84 | C |
| ATOM | 1176 | O | GLU | A | 148 | 53.719 | 15.836 | −91.449 | 1.00 | 18.92 | O |
| ATOM | 1177 | CB | GLU | A | 148 | 54.203 | 17.931 | −93.793 | 1.00 | 19.92 | C |
| ATOM | 1178 | CG | GLU | A | 148 | 54.352 | 18.382 | −95.229 | 1.00 | 22.12 | C |
| ATOM | 1179 | CD | GLU | A | 148 | 53.505 | 19.602 | −95.527 | 1.00 | 23.91 | C |
| ATOM | 1180 | OE1 | GLU | A | 148 | 53.901 | 20.723 | −95.134 | 1.00 | 26.30 | O |
| ATOM | 1181 | OE2 | GLU | A | 148 | 52.432 | 19.433 | −96.142 | 1.00 | 22.23 | O |
| ATOM | 1182 | N | LEU | A | 149 | 55.793 | 16.699 | −91.297 | 1.00 | 18.40 | N |
| ATOM | 1183 | CA | LEU | A | 149 | 55.859 | 16.573 | −89.848 | 1.00 | 16.51 | C |
| ATOM | 1184 | C | LEU | A | 149 | 56.849 | 17.607 | −89.337 | 1.00 | 16.34 | C |
| ATOM | 1185 | O | LEU | A | 149 | 57.674 | 18.114 | −90.104 | 1.00 | 13.92 | O |
| ATOM | 1186 | CB | LEU | A | 149 | 56.303 | 15.163 | −89.440 | 1.00 | 16.79 | C |
| ATOM | 1187 | CG | LEU | A | 149 | 57.776 | 14.765 | −89.533 | 1.00 | 15.82 | C |
| ATOM | 1188 | CD1 | LEU | A | 149 | 57.923 | 13.311 | −89.101 | 1.00 | 17.26 | C |
| ATOM | 1189 | CD2 | LEU | A | 149 | 58.289 | 14.944 | −90.941 | 1.00 | 18.11 | C |
| ATOM | 1190 | N | ASN | A | 150 | 56.764 | 17.916 | −88.046 | 1.00 | 14.99 | N |
| ATOM | 1191 | CA | ASN | A | 150 | 57.633 | 18.914 | −87.428 | 1.00 | 14.82 | C |
| ATOM | 1192 | C | ASN | A | 150 | 58.749 | 18.346 | −86.559 | 1.00 | 15.73 | C |
| ATOM | 1193 | O | ASN | A | 150 | 59.846 | 18.907 | −86.499 | 1.00 | 13.68 | O |
| ATOM | 1194 | CB | ASN | A | 150 | 56.800 | 19.860 | −86.557 | 1.00 | 14.87 | C |
| ATOM | 1195 | CG | ASN | A | 150 | 55.752 | 20.621 | −87.356 | 1.00 | 15.14 | C |
| ATOM | 1196 | OD1 | ASN | A | 150 | 55.635 | 20.448 | −88.573 | 1.00 | 15.67 | O |
| ATOM | 1197 | ND2 | ASN | A | 150 | 54.990 | 21.472 | −86.674 | 1.00 | 13.52 | N |
| ATOM | 1198 | N | LEU | A | 151 | 58.476 | 17.232 | −85.887 | 1.00 | 15.34 | N |
| ATOM | 1199 | CA | LEU | A | 151 | 59.461 | 16.674 | −84.980 | 1.00 | 16.03 | C |
| ATOM | 1200 | C | LEU | A | 151 | 59.529 | 15.159 | −84.976 | 1.00 | 17.17 | C |
| ATOM | 1201 | O | LEU | A | 151 | 58.513 | 14.470 | −85.077 | 1.00 | 17.42 | O |
| ATOM | 1202 | CB | LEU | A | 151 | 59.157 | 17.178 | −83.559 | 1.00 | 17.69 | C |
| ATOM | 1203 | CG | LEU | A | 151 | 59.979 | 16.670 | −82.366 | 1.00 | 19.41 | C |
| ATOM | 1204 | CD1 | LEU | A | 151 | 61.385 | 17.239 | −82.449 | 1.00 | 20.76 | C |
| ATOM | 1205 | CD2 | LEU | A | 151 | 59.311 | 17.106 | −81.049 | 1.00 | 15.34 | C |
| ATOM | 1206 | N | VAL | A | 152 | 60.748 | 14.648 | −84.861 | 1.00 | 16.79 | N |
| ATOM | 1207 | CA | VAL | A | 152 | 60.985 | 13.218 | −84.785 | 1.00 | 16.81 | C |
| ATOM | 1208 | C | VAL | A | 152 | 61.932 | 12.996 | −83.604 | 1.00 | 17.56 | C |
| ATOM | 1209 | O | VAL | A | 152 | 62.969 | 13.655 | −83.516 | 1.00 | 17.24 | O |
| ATOM | 1210 | CB | VAL | A | 152 | 61.679 | 12.679 | −86.051 | 1.00 | 16.23 | C |
| ATOM | 1211 | CG1 | VAL | A | 152 | 61.997 | 11.195 | −85.865 | 1.00 | 15.87 | C |
| ATOM | 1212 | CG2 | VAL | A | 152 | 60.800 | 12.888 | −87.276 | 1.00 | 17.37 | C |
| ATOM | 1213 | N | ILE | A | 153 | 61.569 | 12.096 | −82.692 | 1.00 | 17.97 | N |
| ATOM | 1214 | CA | ILE | A | 153 | 62.419 | 11.770 | −81.540 | 1.00 | 16.06 | C |
| ATOM | 1215 | C | ILE | A | 153 | 63.067 | 10.434 | −81.900 | 1.00 | 18.07 | C |
| ATOM | 1216 | O | ILE | A | 153 | 62.364 | 9.466 | −82.209 | 1.00 | 18.54 | O |
| ATOM | 1217 | CB | ILE | A | 153 | 61.598 | 11.552 | −80.239 | 1.00 | 18.30 | C |
| ATOM | 1218 | CG1 | ILE | A | 153 | 60.774 | 12.794 | −79.902 | 1.00 | 17.23 | C |
| ATOM | 1219 | CG2 | ILE | A | 153 | 62.543 | 11.209 | −79.078 | 1.00 | 19.31 | C |
| ATOM | 1220 | CD1 | ILE | A | 153 | 61.595 | 14.043 | −79.610 | 1.00 | 17.37 | C |
| ATOM | 1221 | N | ILE | A | 154 | 64.392 | 10.370 | −81.869 | 1.00 | 16.32 | N |
| ATOM | 1222 | CA | ILE | A | 154 | 65.078 | 9.134 | −82.208 | 1.00 | 16.74 | C |
| ATOM | 1223 | C | ILE | A | 154 | 66.118 | 8.758 | −81.154 | 1.00 | 15.72 | C |
| ATOM | 1224 | O | ILE | A | 154 | 66.544 | 9.600 | −80.370 | 1.00 | 15.89 | O |
| ATOM | 1225 | CB | ILE | A | 154 | 65.734 | 9.249 | −83.604 | 1.00 | 19.26 | C |
| ATOM | 1226 | CG1 | ILE | A | 154 | 66.228 | 7.872 | −84.060 | 1.00 | 21.86 | C |
| ATOM | 1227 | CG2 | ILE | A | 154 | 66.863 | 10.280 | −83.575 | 1.00 | 18.91 | C |
| ATOM | 1228 | CD1 | ILE | A | 154 | 66.516 | 7.771 | −85.548 | 1.00 | 25.73 | C |
| ATOM | 1229 | N | GLY | A | 155 | 66.498 | 7.483 | −81.123 | 1.00 | 17.00 | N |
| ATOM | 1230 | CA | GLY | A | 155 | 67.481 | 7.012 | −80.158 | 1.00 | 15.61 | C |
| ATOM | 1231 | C | GLY | A | 155 | 68.842 | 7.629 | −80.418 | 1.00 | 18.06 | C |
| ATOM | 1232 | O | GLY | A | 155 | 69.085 | 8.138 | −81.506 | 1.00 | 16.61 | O |
| ATOM | 1233 | N | PRO | A | 156 | 69.763 | 7.582 | −79.446 | 1.00 | 17.77 | N |
| ATOM | 1234 | CA | PRO | A | 156 | 71.086 | 8.175 | −79.656 | 1.00 | 19.77 | C |
| ATOM | 1235 | C | PRO | A | 156 | 71.988 | 7.430 | −80.637 | 1.00 | 21.20 | C |
| ATOM | 1236 | O | PRO | A | 156 | 71.690 | 6.310 | −81.065 | 1.00 | 21.60 | O |
| ATOM | 1237 | CB | PRO | A | 156 | 71.669 | 8.206 | −78.247 | 1.00 | 19.75 | C |
| ATOM | 1238 | CG | PRO | A | 156 | 71.090 | 6.941 | −77.632 | 1.00 | 19.92 | C |
| ATOM | 1239 | CD | PRO | A | 156 | 69.644 | 6.989 | −78.100 | 1.00 | 17.83 | C |
| ATOM | 1240 | N | SER | A | 157 | 73.084 | 8.079 | −81.010 | 1.00 | 20.84 | N |
| ATOM | 1241 | CA | SER | A | 157 | 74.056 | 7.462 | −81.898 | 1.00 | 22.43 | C |
| ATOM | 1242 | C | SER | A | 157 | 75.074 | 6.777 | −80.969 | 1.00 | 20.99 | C |
| ATOM | 1243 | O | SER | A | 157 | 74.712 | 6.357 | −79.865 | 1.00 | 18.27 | O |
| ATOM | 1244 | CB | SER | A | 157 | 74.728 | 8.525 | −82.772 | 1.00 | 24.74 | C |
| ATOM | 1245 | OG | SER | A | 157 | 75.498 | 7.918 | −83.793 | 1.00 | 31.10 | O |
| ATOM | 1246 | N | ALA | A | 158 | 76.333 | 6.675 | −81.393 | 1.00 | 21.22 | N |
| ATOM | 1247 | CA | ALA | A | 158 | 77.370 | 6.018 | −80.580 | 1.00 | 23.43 | C |
| ATOM | 1248 | C | ALA | A | 158 | 77.398 | 6.470 | −79.109 | 1.00 | 22.50 | C |
| ATOM | 1249 | O | ALA | A | 158 | 77.285 | 5.643 | −78.206 | 1.00 | 24.25 | O |
| ATOM | 1250 | CB | ALA | A | 158 | 78.756 | 6.222 | −81.222 | 1.00 | 24.91 | C |

TABLE 2-continued

| | | | | | | | | | | |
|---|---|---|---|---|---|---|---|---|---|---|
| ATOM | 1251 | N | ASP | A | 159 | 77.569 | 7.767 | −78.862 | 1.00 | 21.34 | N |
| ATOM | 1252 | CA | ASP | A | 159 | 77.583 | 8.273 | −77.487 | 1.00 | 21.67 | C |
| ATOM | 1253 | C | ASP | A | 159 | 76.129 | 8.343 | −77.028 | 1.00 | 22.28 | C |
| ATOM | 1254 | O | ASP | A | 159 | 75.372 | 9.236 | −77.428 | 1.00 | 22.18 | O |
| ATOM | 1255 | CB | ASP | A | 159 | 78.220 | 9.664 | −77.426 | 1.00 | 22.16 | C |
| ATOM | 1256 | CG | ASP | A | 159 | 78.269 | 10.243 | −76.006 | 1.00 | 23.60 | C |
| ATOM | 1257 | OD1 | ASP | A | 159 | 77.728 | 9.638 | −75.053 | 1.00 | 21.55 | O |
| ATOM | 1258 | OD2 | ASP | A | 159 | 78.859 | 11.332 | −75.846 | 1.00 | 24.92 | O |
| ATOM | 1259 | N | ILE | A | 160 | 75.749 | 7.389 | −76.191 | 1.00 | 19.79 | N |
| ATOM | 1260 | CA | ILE | A | 160 | 74.392 | 7.289 | −75.686 | 1.00 | 20.65 | C |
| ATOM | 1261 | C | ILE | A | 160 | 73.805 | 8.529 | −75.023 | 1.00 | 19.96 | C |
| ATOM | 1262 | O | ILE | A | 160 | 72.599 | 8.760 | −75.111 | 1.00 | 20.27 | O |
| ATOM | 1263 | CB | ILE | A | 160 | 74.275 | 6.100 | −74.709 | 1.00 | 21.57 | C |
| ATOM | 1264 | CG1 | ILE | A | 160 | 74.505 | 4.795 | −75.479 | 1.00 | 23.74 | C |
| ATOM | 1265 | CG2 | ILE | A | 160 | 72.903 | 6.101 | −74.027 | 1.00 | 19.64 | C |
| ATOM | 1266 | CD1 | ILE | A | 160 | 74.515 | 3.536 | −74.612 | 1.00 | 23.99 | C |
| ATOM | 1267 | N | ILE | A | 161 | 74.630 | 9.332 | −74.363 | 1.00 | 19.85 | N |
| ATOM | 1268 | CA | ILE | A | 161 | 74.090 | 10.513 | −73.703 | 1.00 | 21.60 | C |
| ATOM | 1269 | C | ILE | A | 161 | 74.336 | 11.813 | −74.456 | 1.00 | 22.20 | C |
| ATOM | 1270 | O | ILE | A | 161 | 74.158 | 12.901 | −73.914 | 1.00 | 22.69 | O |
| ATOM | 1271 | CB | ILE | A | 161 | 74.601 | 10.629 | −72.249 | 1.00 | 22.76 | C |
| ATOM | 1272 | CG1 | ILE | A | 161 | 76.127 | 10.630 | −72.217 | 1.00 | 23.09 | C |
| ATOM | 1273 | CG2 | ILE | A | 161 | 74.060 | 9.453 | −71.435 | 1.00 | 23.03 | C |
| ATOM | 1274 | CD1 | ILE | A | 161 | 76.707 | 10.730 | −70.811 | 1.00 | 23.18 | C |
| ATOM | 1275 | N | GLN | A | 162 | 74.731 | 11.695 | −75.718 | 1.00 | 22.44 | N |
| ATOM | 1276 | CA | GLN | A | 162 | 74.940 | 12.868 | −76.556 | 1.00 | 22.56 | C |
| ATOM | 1277 | C | GLN | A | 162 | 73.568 | 13.189 | −77.163 | 1.00 | 22.50 | C |
| ATOM | 1278 | O | GLN | A | 162 | 73.197 | 12.630 | −78.190 | 1.00 | 23.29 | O |
| ATOM | 1279 | CB | GLN | A | 162 | 75.930 | 12.560 | −77.678 | 1.00 | 24.04 | C |
| ATOM | 1280 | CG | GLN | A | 162 | 76.104 | 13.695 | −78.685 | 1.00 | 29.76 | C |
| ATOM | 1281 | CD | GLN | A | 162 | 76.615 | 13.205 | −80.037 | 1.00 | 34.52 | C |
| ATOM | 1282 | OE1 | GLN | A | 162 | 77.697 | 12.619 | −80.135 | 1.00 | 35.54 | O |
| ATOM | 1283 | NE2 | GLN | A | 162 | 75.829 | 13.439 | −81.085 | 1.00 | 35.96 | N |
| ATOM | 1284 | N | PHE | A | 163 | 72.806 | 14.056 | −76.506 | 1.00 | 21.19 | N |
| ATOM | 1285 | CA | PHE | A | 163 | 71.494 | 14.430 | −77.001 | 1.00 | 21.54 | C |
| ATOM | 1286 | C | PHE | A | 163 | 71.616 | 15.724 | −77.795 | 1.00 | 23.29 | C |
| ATOM | 1287 | O | PHE | A | 163 | 72.324 | 16.647 | −77.388 | 1.00 | 22.74 | O |
| ATOM | 1288 | CB | PHE | A | 163 | 70.520 | 14.612 | −75.837 | 1.00 | 21.59 | C |
| ATOM | 1289 | CG | PHE | A | 163 | 70.446 | 13.424 | −74.915 | 1.00 | 22.15 | C |
| ATOM | 1290 | CD1 | PHE | A | 163 | 70.606 | 12.131 | −75.405 | 1.00 | 21.63 | C |
| ATOM | 1291 | CD2 | PHE | A | 163 | 70.179 | 13.598 | −73.559 | 1.00 | 22.04 | C |
| ATOM | 1292 | CE1 | PHE | A | 163 | 70.499 | 11.021 | −74.549 | 1.00 | 21.94 | C |
| ATOM | 1293 | CE2 | PHE | A | 163 | 70.068 | 12.502 | −72.699 | 1.00 | 20.60 | C |
| ATOM | 1294 | CZ | PHE | A | 163 | 70.227 | 11.217 | −73.192 | 1.00 | 19.71 | C |
| ATOM | 1295 | N | GLU | A | 164 | 70.929 | 15.797 | −78.928 | 1.00 | 21.83 | N |
| ATOM | 1296 | CA | GLU | A | 164 | 71.012 | 16.981 | −79.764 | 1.00 | 23.96 | C |
| ATOM | 1297 | C | GLU | A | 164 | 69.765 | 17.131 | −80.608 | 1.00 | 24.52 | C |
| ATOM | 1298 | O | GLU | A | 164 | 68.916 | 16.240 | −80.644 | 1.00 | 24.89 | O |
| ATOM | 1299 | CB | GLU | A | 164 | 72.232 | 16.880 | −80.683 | 1.00 | 25.36 | C |
| ATOM | 1300 | CG | GLU | A | 164 | 72.282 | 15.576 | −81.470 | 1.00 | 32.17 | C |
| ATOM | 1301 | CD | GLU | A | 164 | 73.466 | 15.496 | −82.416 | 1.00 | 37.54 | C |
| ATOM | 1302 | OE1 | GLU | A | 164 | 74.609 | 15.726 | −81.968 | 1.00 | 41.05 | O |
| ATOM | 1303 | OE2 | GLU | A | 164 | 73.256 | 15.195 | −83.610 | 1.00 | 42.91 | O |
| ATOM | 1304 | N | CYS | A | 165 | 69.673 | 18.263 | −81.297 | 1.00 | 22.55 | N |
| ATOM | 1305 | CA | CYS | A | 165 | 68.537 | 18.554 | −82.151 | 1.00 | 23.29 | C |
| ATOM | 1306 | C | CYS | A | 165 | 69.105 | 18.944 | −83.510 | 1.00 | 23.67 | C |
| ATOM | 1307 | O | CYS | A | 165 | 69.709 | 20.004 | −83.654 | 1.00 | 22.35 | O |
| ATOM | 1308 | CB | CYS | A | 165 | 67.724 | 19.701 | −81.540 | 1.00 | 23.74 | C |
| ATOM | 1309 | SG | CYS | A | 165 | 66.175 | 20.093 | −82.386 | 1.00 | 25.90 | S |
| ATOM | 1310 | N | LYS | A | 166 | 68.922 | 18.079 | −84.502 | 1.00 | 22.90 | N |
| ATOM | 1311 | CA | LYS | A | 166 | 69.440 | 18.333 | −85.843 | 1.00 | 24.93 | C |
| ATOM | 1312 | C | LYS | A | 166 | 68.356 | 18.279 | −86.911 | 1.00 | 24.35 | C |
| ATOM | 1313 | O | LYS | A | 166 | 67.224 | 17.867 | −86.650 | 1.00 | 21.10 | O |
| ATOM | 1314 | CB | LYS | A | 166 | 70.522 | 17.301 | −86.178 | 1.00 | 28.17 | C |
| ATOM | 1315 | CG | LYS | A | 166 | 70.012 | 15.864 | −86.108 | 1.00 | 29.65 | C |
| ATOM | 1316 | CD | LYS | A | 166 | 71.143 | 14.843 | −86.176 | 1.00 | 35.80 | C |
| ATOM | 1317 | CE | LYS | A | 166 | 71.864 | 14.880 | −87.511 | 1.00 | 35.45 | C |
| ATOM | 1318 | NZ | LYS | A | 166 | 72.837 | 13.764 | −87.612 | 1.00 | 39.77 | N |
| ATOM | 1319 | N | SER | A | 167 | 68.711 | 18.695 | −88.123 | 1.00 | 22.06 | N |
| ATOM | 1320 | CA | SER | A | 167 | 67.762 | 18.673 | −89.221 | 1.00 | 22.21 | C |
| ATOM | 1321 | C | SER | A | 167 | 68.461 | 18.649 | −90.573 | 1.00 | 23.18 | C |
| ATOM | 1322 | O | SER | A | 167 | 69.658 | 18.910 | −90.676 | 1.00 | 23.38 | O |
| ATOM | 1323 | CB | SER | A | 167 | 66.823 | 19.876 | −89.130 | 1.00 | 20.18 | C |
| ATOM | 1324 | OG | SER | A | 167 | 67.537 | 21.094 | −89.159 | 1.00 | 23.04 | O |
| ATOM | 1325 | N | PHE | A | 168 | 67.704 | 18.320 | −91.610 | 1.00 | 23.70 | N |
| ATOM | 1326 | CA | PHE | A | 168 | 68.248 | 18.263 | −92.958 | 1.00 | 25.38 | C |
| ATOM | 1327 | C | PHE | A | 168 | 68.256 | 19.658 | −93.567 | 1.00 | 25.62 | C |
| ATOM | 1328 | O | PHE | A | 168 | 67.286 | 20.403 | −93.469 | 1.00 | 23.80 | O |
| ATOM | 1329 | CB | PHE | A | 168 | 67.424 | 17.285 | −93.793 | 1.00 | 25.84 | C |

TABLE 2-continued

| | | | | | | | | | | |
|---|---|---|---|---|---|---|---|---|---|---|
| ATOM | 1330 | CG | PHE | A | 168 | 67.571 | 15.856 | −93.349 | 1.00 | 28.00 | C |
| ATOM | 1331 | CD1 | PHE | A | 168 | 68.623 | 15.074 | −93.816 | 1.00 | 28.85 | C |
| ATOM | 1332 | CD2 | PHE | A | 168 | 66.692 | 15.308 | −92.414 | 1.00 | 29.51 | C |
| ATOM | 1333 | CE1 | PHE | A | 168 | 68.800 | 13.764 | −93.359 | 1.00 | 29.88 | C |
| ATOM | 1334 | CE2 | PHE | A | 168 | 66.861 | 14.001 | −91.950 | 1.00 | 28.38 | C |
| ATOM | 1335 | CZ | PHE | A | 168 | 67.918 | 13.229 | −92.423 | 1.00 | 27.74 | C |
| ATOM | 1336 | N | GLY | A | 169 | 69.371 | 20.021 | −94.181 | 1.00 | 27.77 | N |
| ATOM | 1337 | CA | GLY | A | 169 | 69.464 | 21.344 | −94.756 | 1.00 | 30.81 | C |
| ATOM | 1338 | C | GLY | A | 169 | 69.078 | 21.429 | −96.213 | 1.00 | 32.88 | C |
| ATOM | 1339 | O | GLY | A | 169 | 68.881 | 20.421 | −96.895 | 1.00 | 30.57 | O |
| ATOM | 1340 | N | HIS | A | 170 | 68.963 | 22.664 | −96.676 | 1.00 | 34.45 | N |
| ATOM | 1341 | CA | HIS | A | 170 | 68.635 | 22.959 | −98.054 | 1.00 | 37.64 | C |
| ATOM | 1342 | C | HIS | A | 170 | 69.989 | 23.231 | −98.706 | 1.00 | 40.83 | C |
| ATOM | 1343 | O | HIS | A | 170 | 70.935 | 23.643 | −98.029 | 1.00 | 41.43 | O |
| ATOM | 1344 | CB | HIS | A | 170 | 67.767 | 24.211 | −98.119 | 1.00 | 37.86 | C |
| ATOM | 1345 | CG | HIS | A | 170 | 67.179 | 24.467 | −99.469 | 1.00 | 39.03 | C |
| ATOM | 1346 | ND1 | HIS | A | 170 | 66.075 | 23.790 | −99.939 | 1.00 | 39.64 | N |
| ATOM | 1347 | CD2 | HIS | A | 170 | 67.545 | 25.322 | −100.454 | 1.00 | 38.80 | C |
| ATOM | 1348 | CE1 | HIS | A | 170 | 65.783 | 24.218 | −101.154 | 1.00 | 39.89 | C |
| ATOM | 1349 | NE2 | HIS | A | 170 | 66.660 | 25.148 | −101.490 | 1.00 | 40.46 | N |
| ATOM | 1350 | N | GLU | A | 171 | 70.095 | 23.006 | −100.010 | 1.00 | 41.85 | N |
| ATOM | 1351 | CA | GLU | A | 171 | 71.363 | 23.243 | −100.683 | 1.00 | 43.68 | C |
| ATOM | 1352 | C | GLU | A | 171 | 71.802 | 24.708 | −100.651 | 1.00 | 41.26 | C |
| ATOM | 1353 | O | GLU | A | 171 | 72.993 | 24.996 | −100.670 | 1.00 | 41.47 | O |
| ATOM | 1354 | CB | GLU | A | 171 | 71.295 | 22.740 | −102.128 | 1.00 | 47.04 | C |
| ATOM | 1355 | CG | GLU | A | 171 | 71.252 | 21.216 | −102.230 | 1.00 | 53.12 | C |
| ATOM | 1356 | CD | GLU | A | 171 | 71.194 | 20.713 | −103.662 | 1.00 | 56.42 | C |
| ATOM | 1357 | OE1 | GLU | A | 171 | 72.111 | 21.040 | −104.448 | 1.00 | 59.09 | O |
| ATOM | 1358 | OE2 | GLU | A | 171 | 70.232 | 19.987 | −103.999 | 1.00 | 58.32 | O |
| ATOM | 1359 | N | VAL | A | 172 | 70.848 | 25.631 | −100.583 | 1.00 | 39.92 | N |
| ATOM | 1360 | CA | VAL | A | 172 | 71.180 | 27.053 | −100.564 | 1.00 | 38.13 | C |
| ATOM | 1361 | C | VAL | A | 172 | 70.622 | 27.800 | −99.351 | 1.00 | 36.61 | C |
| ATOM | 1362 | O | VAL | A | 172 | 71.316 | 28.600 | −98.723 | 1.00 | 38.11 | O |
| ATOM | 1363 | CB | VAL | A | 172 | 70.670 | 27.753 | −101.852 | 1.00 | 38.49 | C |
| ATOM | 1364 | CG1 | VAL | A | 172 | 71.007 | 29.242 | −101.813 | 1.00 | 38.77 | C |
| ATOM | 1365 | CG2 | VAL | A | 172 | 71.298 | 27.098 | −103.083 | 1.00 | 38.53 | C |
| ATOM | 1366 | N | LEU | A | 173 | 69.365 | 27.539 | −99.022 | 1.00 | 33.94 | N |
| ATOM | 1367 | CA | LEU | A | 173 | 68.718 | 28.206 | −97.900 | 1.00 | 32.34 | C |
| ATOM | 1368 | C | LEU | A | 173 | 69.221 | 27.731 | −96.535 | 1.00 | 29.71 | C |
| ATOM | 1369 | O | LEU | A | 173 | 69.638 | 26.588 | −96.387 | 1.00 | 30.64 | O |
| ATOM | 1370 | CB | LEU | A | 173 | 67.211 | 27.981 | −97.989 | 1.00 | 31.48 | C |
| ATOM | 1371 | CG | LEU | A | 173 | 66.517 | 28.494 | −99.254 | 1.00 | 34.26 | C |
| ATOM | 1372 | CD1 | LEU | A | 173 | 65.082 | 27.967 | −99.302 | 1.00 | 32.45 | C |
| ATOM | 1373 | CD2 | LEU | A | 173 | 66.546 | 30.020 | −99.271 | 1.00 | 34.99 | C |
| ATOM | 1374 | N | ASN | A | 174 | 69.197 | 28.624 | −95.549 | 1.00 | 28.60 | N |
| ATOM | 1375 | CA | ASN | A | 174 | 69.594 | 28.287 | −94.177 | 1.00 | 24.50 | C |
| ATOM | 1376 | C | ASN | A | 174 | 68.263 | 28.229 | −93.426 | 1.00 | 21.69 | C |
| ATOM | 1377 | O | ASN | A | 174 | 67.891 | 29.167 | −92.718 | 1.00 | 19.32 | O |
| ATOM | 1378 | CB | ASN | A | 174 | 70.478 | 29.381 | −93.577 | 1.00 | 26.14 | C |
| ATOM | 1379 | CG | ASN | A | 174 | 71.830 | 29.479 | −94.253 | 1.00 | 28.64 | C |
| ATOM | 1380 | OD1 | ASN | A | 174 | 72.223 | 30.548 | −94.712 | 1.00 | 29.57 | O |
| ATOM | 1381 | ND2 | ASN | A | 174 | 72.551 | 28.365 | −94.310 | 1.00 | 27.69 | N |
| ATOM | 1382 | N | LEU | A | 175 | 67.550 | 27.119 | −93.587 | 1.00 | 19.77 | N |
| ATOM | 1383 | CA | LEU | A | 175 | 66.224 | 26.960 | −92.987 | 1.00 | 19.27 | C |
| ATOM | 1384 | C | LEU | A | 175 | 66.054 | 27.240 | −91.496 | 1.00 | 19.56 | C |
| ATOM | 1385 | O | LEU | A | 175 | 65.034 | 27.802 | −91.092 | 1.00 | 18.34 | O |
| ATOM | 1386 | CB | LEU | A | 175 | 65.668 | 25.570 | −93.317 | 1.00 | 18.55 | C |
| ATOM | 1387 | CG | LEU | A | 175 | 65.529 | 25.279 | −94.818 | 1.00 | 18.83 | C |
| ATOM | 1388 | CD1 | LEU | A | 175 | 65.058 | 23.847 | −95.031 | 1.00 | 19.74 | C |
| ATOM | 1389 | CD2 | LEU | A | 175 | 64.544 | 26.263 | −95.451 | 1.00 | 18.03 | C |
| ATOM | 1390 | N | THR | A | 176 | 67.025 | 26.868 | −90.669 | 1.00 | 18.08 | N |
| ATOM | 1391 | CA | THR | A | 176 | 66.866 | 27.116 | −89.237 | 1.00 | 20.32 | C |
| ATOM | 1392 | C | THR | A | 176 | 67.088 | 28.572 | −88.836 | 1.00 | 21.54 | C |
| ATOM | 1393 | O | THR | A | 176 | 66.825 | 28.940 | −87.690 | 1.00 | 21.84 | O |
| ATOM | 1394 | CB | THR | A | 176 | 67.815 | 26.242 | −88.385 | 1.00 | 21.13 | C |
| ATOM | 1395 | OG1 | THR | A | 176 | 69.174 | 26.579 | −88.683 | 1.00 | 26.05 | O |
| ATOM | 1396 | CG2 | THR | A | 176 | 67.581 | 24.763 | −88.663 | 1.00 | 18.77 | C |
| ATOM | 1397 | N | ARG | A | 177 | 67.544 | 29.403 | −89.775 | 1.00 | 20.48 | N |
| ATOM | 1398 | CA | ARG | A | 177 | 67.808 | 30.807 | −89.469 | 1.00 | 24.44 | C |
| ATOM | 1399 | C | ARG | A | 177 | 67.221 | 31.831 | −90.446 | 1.00 | 24.26 | C |
| ATOM | 1400 | O | ARG | A | 177 | 67.576 | 33.005 | −90.385 | 1.00 | 24.45 | O |
| ATOM | 1401 | CB | ARG | A | 177 | 69.318 | 31.050 | −89.375 | 1.00 | 23.52 | C |
| ATOM | 1402 | CG | ARG | A | 177 | 70.092 | 29.892 | −88.807 | 1.00 | 29.53 | C |
| ATOM | 1403 | CD | ARG | A | 177 | 71.567 | 30.223 | −88.635 | 1.00 | 35.15 | C |
| ATOM | 1404 | NE | ARG | A | 177 | 72.369 | 29.008 | −88.731 | 1.00 | 39.63 | N |
| ATOM | 1405 | CZ | ARG | A | 177 | 72.969 | 28.602 | −89.844 | 1.00 | 37.77 | C |
| ATOM | 1406 | NH1 | ARG | A | 177 | 72.871 | 29.321 | −90.955 | 1.00 | 39.09 | N |
| ATOM | 1407 | NH2 | ARG | A | 177 | 73.649 | 27.466 | −89.848 | 1.00 | 39.49 | N |
| ATOM | 1408 | N | ASN | A | 178 | 66.341 | 31.408 | −91.347 | 1.00 | 23.90 | N |

TABLE 2-continued

| | | | | | | | | | | |
|---|---|---|---|---|---|---|---|---|---|---|
| ATOM | 1409 | CA | ASN | A | 178 | 65.756 | 32.358 | −92.286 | 1.00 | 22.76 | C |
| ATOM | 1410 | C | ASN | A | 178 | 64.257 | 32.474 | −92.056 | 1.00 | 22.32 | C |
| ATOM | 1411 | O | ASN | A | 178 | 63.520 | 32.956 | −92.921 | 1.00 | 21.64 | O |
| ATOM | 1412 | CB | ASN | A | 178 | 66.037 | 31.925 | −93.729 | 1.00 | 24.50 | C |
| ATOM | 1413 | CG | ASN | A | 178 | 65.219 | 30.722 | −94.143 | 1.00 | 27.01 | C |
| ATOM | 1414 | OD1 | ASN | A | 178 | 64.621 | 30.052 | −93.305 | 1.00 | 24.11 | O |
| ATOM | 1415 | ND2 | ASN | A | 178 | 65.192 | 30.438 | −95.444 | 1.00 | 26.19 | N |
| ATOM | 1416 | N | GLY | A | 179 | 63.812 | 32.026 | −90.883 | 1.00 | 20.15 | N |
| ATOM | 1417 | CA | GLY | A | 179 | 62.403 | 32.090 | −90.550 | 1.00 | 19.06 | C |
| ATOM | 1418 | C | GLY | A | 179 | 61.552 | 30.957 | −91.111 | 1.00 | 19.61 | C |
| ATOM | 1419 | O | GLY | A | 179 | 60.419 | 30.757 | −90.660 | 1.00 | 21.59 | O |
| ATOM | 1420 | N | TYR | A | 180 | 62.088 | 30.211 | −92.075 | 1.00 | 17.49 | N |
| ATOM | 1421 | CA | TYR | A | 180 | 61.355 | 29.098 | −92.700 | 1.00 | 19.70 | C |
| ATOM | 1422 | C | TYR | A | 180 | 61.067 | 27.917 | −91.763 | 1.00 | 19.98 | C |
| ATOM | 1423 | O | TYR | A | 180 | 59.934 | 27.432 | −91.672 | 1.00 | 18.20 | O |
| ATOM | 1424 | CB | TYR | A | 180 | 62.135 | 28.562 | −93.906 | 1.00 | 20.84 | C |
| ATOM | 1425 | CG | TYR | A | 180 | 62.031 | 29.398 | −95.169 | 1.00 | 24.22 | C |
| ATOM | 1426 | CD1 | TYR | A | 180 | 61.804 | 30.770 | −95.108 | 1.00 | 25.61 | C |
| ATOM | 1427 | CD2 | TYR | A | 180 | 62.193 | 28.814 | −96.427 | 1.00 | 24.50 | C |
| ATOM | 1428 | CE1 | TYR | A | 180 | 61.738 | 31.544 | −96.265 | 1.00 | 27.32 | C |
| ATOM | 1429 | CE2 | TYR | A | 180 | 62.133 | 29.577 | −97.590 | 1.00 | 26.68 | C |
| ATOM | 1430 | CZ | TYR | A | 180 | 61.906 | 30.940 | −97.498 | 1.00 | 27.98 | C |
| ATOM | 1431 | OH | TYR | A | 180 | 61.853 | 31.701 | −98.637 | 1.00 | 32.13 | O |
| ATOM | 1432 | N | GLY | A | 181 | 62.109 | 27.446 | −91.087 | 1.00 | 19.02 | N |
| ATOM | 1433 | CA | GLY | A | 181 | 61.959 | 26.309 | −90.202 | 1.00 | 18.79 | C |
| ATOM | 1434 | C | GLY | A | 181 | 62.126 | 25.042 | −91.024 | 1.00 | 18.69 | C |
| ATOM | 1435 | O | GLY | A | 181 | 62.047 | 25.082 | −92.254 | 1.00 | 18.79 | O |
| ATOM | 1436 | N | SER | A | 182 | 62.381 | 23.929 | −90.347 | 1.00 | 16.53 | N |
| ATOM | 1437 | CA | SER | A | 182 | 62.560 | 22.633 | −90.987 | 1.00 | 15.88 | C |
| ATOM | 1438 | C | SER | A | 182 | 62.292 | 21.561 | −89.935 | 1.00 | 17.38 | C |
| ATOM | 1439 | O | SER | A | 182 | 62.421 | 21.815 | −88.730 | 1.00 | 16.43 | O |
| ATOM | 1440 | CB | SER | A | 182 | 63.989 | 22.479 | −91.501 | 1.00 | 16.88 | C |
| ATOM | 1441 | OG | SER | A | 182 | 64.915 | 22.610 | −90.439 | 1.00 | 15.07 | O |
| ATOM | 1442 | N | THR | A | 183 | 61.919 | 20.371 | −90.391 | 1.00 | 15.97 | N |
| ATOM | 1443 | CA | THR | A | 183 | 61.626 | 19.263 | −89.497 | 1.00 | 16.56 | C |
| ATOM | 1444 | C | THR | A | 183 | 62.843 | 18.939 | −88.633 | 1.00 | 17.46 | C |
| ATOM | 1445 | O | THR | A | 183 | 63.949 | 18.743 | −89.141 | 1.00 | 18.01 | O |
| ATOM | 1446 | CB | THR | A | 183 | 61.227 | 18.030 | −90.307 | 1.00 | 17.81 | C |
| ATOM | 1447 | OG1 | THR | A | 183 | 60.061 | 18.347 | −91.072 | 1.00 | 17.76 | O |
| ATOM | 1448 | CG2 | THR | A | 183 | 60.944 | 16.853 | −89.399 | 1.00 | 13.23 | C |
| ATOM | 1449 | N | GLN | A | 184 | 62.623 | 18.869 | −87.326 | 1.00 | 17.64 | N |
| ATOM | 1450 | CA | GLN | A | 184 | 63.694 | 18.598 | −86.373 | 1.00 | 17.69 | C |
| ATOM | 1451 | C | GLN | A | 184 | 63.739 | 17.155 | −85.901 | 1.00 | 19.52 | C |
| ATOM | 1452 | O | GLN | A | 184 | 62.702 | 16.540 | −85.630 | 1.00 | 17.14 | O |
| ATOM | 1453 | CB | GLN | A | 184 | 63.550 | 19.517 | −85.158 | 1.00 | 15.68 | C |
| ATOM | 1454 | CG | GLN | A | 184 | 63.606 | 20.980 | −85.511 | 1.00 | 18.93 | C |
| ATOM | 1455 | CD | GLN | A | 184 | 64.914 | 21.341 | −86.179 | 1.00 | 20.26 | C |
| ATOM | 1456 | OE1 | GLN | A | 184 | 65.984 | 21.051 | −85.649 | 1.00 | 18.97 | O |
| ATOM | 1457 | NE2 | GLN | A | 184 | 64.839 | 21.975 | −87.344 | 1.00 | 18.28 | N |
| ATOM | 1458 | N | TYR | A | 185 | 64.962 | 16.637 | −85.804 | 1.00 | 19.75 | N |
| ATOM | 1459 | CA | TYR | A | 185 | 65.227 | 15.277 | −85.356 | 1.00 | 18.24 | C |
| ATOM | 1460 | C | TYR | A | 185 | 66.022 | 15.380 | −84.058 | 1.00 | 18.83 | C |
| ATOM | 1461 | O | TYR | A | 185 | 67.114 | 15.957 | −84.023 | 1.00 | 16.62 | O |
| ATOM | 1462 | CB | TYR | A | 185 | 66.033 | 14.511 | −86.410 | 1.00 | 17.30 | C |
| ATOM | 1463 | CG | TYR | A | 185 | 65.237 | 14.167 | −87.653 | 1.00 | 16.61 | C |
| ATOM | 1464 | CD1 | TYR | A | 185 | 64.878 | 15.149 | −88.578 | 1.00 | 19.22 | C |
| ATOM | 1465 | CD2 | TYR | A | 185 | 64.790 | 12.870 | −87.870 | 1.00 | 17.91 | C |
| ATOM | 1466 | CE1 | TYR | A | 185 | 64.080 | 14.841 | −89.690 | 1.00 | 19.44 | C |
| ATOM | 1467 | CE2 | TYR | A | 185 | 63.998 | 12.545 | −88.970 | 1.00 | 18.47 | C |
| ATOM | 1468 | CZ | TYR | A | 185 | 63.644 | 13.534 | −89.874 | 1.00 | 21.68 | C |
| ATOM | 1469 | OH | TYR | A | 185 | 62.849 | 13.205 | −90.950 | 1.00 | 23.09 | O |
| ATOM | 1470 | N | ILE | A | 186 | 65.458 | 14.851 | −82.980 | 1.00 | 16.68 | N |
| ATOM | 1471 | CA | ILE | A | 186 | 66.118 | 14.905 | −81.683 | 1.00 | 17.78 | C |
| ATOM | 1472 | C | ILE | A | 186 | 66.611 | 13.532 | −81.239 | 1.00 | 17.47 | C |
| ATOM | 1473 | O | ILE | A | 186 | 65.822 | 12.597 | −81.123 | 1.00 | 16.34 | O |
| ATOM | 1474 | CB | ILE | A | 186 | 65.160 | 15.443 | −80.587 | 1.00 | 14.80 | C |
| ATOM | 1475 | CG1 | ILE | A | 186 | 64.774 | 16.896 | −80.884 | 1.00 | 15.63 | C |
| ATOM | 1476 | CG2 | ILE | A | 186 | 65.821 | 15.338 | −79.217 | 1.00 | 16.29 | C |
| ATOM | 1477 | CD1 | ILE | A | 186 | 63.799 | 17.487 | −79.874 | 1.00 | 13.31 | C |
| ATOM | 1478 | N | ARG | A | 187 | 67.916 | 13.418 | −81.015 | 1.00 | 17.92 | N |
| ATOM | 1479 | CA | ARG | A | 187 | 68.514 | 12.178 | −80.527 | 1.00 | 17.65 | C |
| ATOM | 1480 | C | ARG | A | 187 | 68.339 | 12.295 | −79.026 | 1.00 | 17.68 | C |
| ATOM | 1481 | O | ARG | A | 187 | 68.837 | 13.243 | −78.411 | 1.00 | 18.54 | O |
| ATOM | 1482 | CB | ARG | A | 187 | 70.007 | 12.110 | −80.855 | 1.00 | 19.76 | C |
| ATOM | 1483 | CG | ARG | A | 187 | 70.328 | 11.806 | −82.308 | 1.00 | 22.91 | C |
| ATOM | 1484 | CD | ARG | A | 187 | 71.834 | 11.784 | −82.542 | 1.00 | 23.64 | C |
| ATOM | 1485 | NE | ARG | A | 187 | 72.155 | 11.359 | −83.901 | 1.00 | 27.05 | N |
| ATOM | 1486 | CZ | ARG | A | 187 | 73.373 | 11.410 | −84.430 | 1.00 | 27.04 | C |
| ATOM | 1487 | NH1 | ARG | A | 187 | 74.393 | 11.874 | −83.713 | 1.00 | 24.58 | N |

TABLE 2-continued

| ATOM | 1488 | NH2 | ARG | A | 187 | 73.575 | 10.989 | −85.672 | 1.00 | 26.03 | N |
|---|---|---|---|---|---|---|---|---|---|---|---|
| ATOM | 1489 | N | PHE | A | 188 | 67.643 | 11.334 | −78.437 | 1.00 | 17.35 | N |
| ATOM | 1490 | CA | PHE | A | 188 | 67.360 | 11.366 | −77.008 | 1.00 | 18.34 | C |
| ATOM | 1491 | C | PHE | A | 188 | 67.119 | 9.964 | −76.469 | 1.00 | 19.18 | C |
| ATOM | 1492 | O | PHE | A | 188 | 66.755 | 9.059 | −77.218 | 1.00 | 20.75 | O |
| ATOM | 1493 | CB | PHE | A | 188 | 66.099 | 12.198 | −76.773 | 1.00 | 16.47 | C |
| ATOM | 1494 | CG | PHE | A | 188 | 65.679 | 12.284 | −75.335 | 1.00 | 17.10 | C |
| ATOM | 1495 | CD1 | PHE | A | 188 | 66.352 | 13.120 | −74.449 | 1.00 | 16.28 | C |
| ATOM | 1496 | CD2 | PHE | A | 188 | 64.601 | 11.538 | −74.864 | 1.00 | 15.63 | C |
| ATOM | 1497 | CE1 | PHE | A | 188 | 65.953 | 13.216 | −73.109 | 1.00 | 18.17 | C |
| ATOM | 1498 | CE2 | PHE | A | 188 | 64.196 | 11.627 | −73.525 | 1.00 | 13.67 | C |
| ATOM | 1499 | CZ | PHE | A | 188 | 64.869 | 12.464 | −72.651 | 1.00 | 14.40 | C |
| ATOM | 1500 | N | SER | A | 189 | 67.314 | 9.802 | −75.164 | 1.00 | 19.16 | N |
| ATOM | 1501 | CA | SER | A | 189 | 67.092 | 8.531 | −74.490 | 1.00 | 17.00 | C |
| ATOM | 1502 | C | SER | A | 189 | 66.551 | 8.807 | −73.091 | 1.00 | 15.78 | C |
| ATOM | 1503 | O | SER | A | 189 | 67.116 | 9.614 | −72.361 | 1.00 | 17.02 | O |
| ATOM | 1504 | CB | SER | A | 189 | 68.397 | 7.741 | −74.367 | 1.00 | 15.98 | C |
| ATOM | 1505 | OG | SER | A | 189 | 68.198 | 6.608 | −73.532 | 1.00 | 16.99 | O |
| ATOM | 1506 | N | PRO | A | 190 | 65.444 | 8.151 | −72.707 | 1.00 | 14.40 | N |
| ATOM | 1507 | CA | PRO | A | 190 | 64.844 | 8.335 | −71.384 | 1.00 | 14.99 | C |
| ATOM | 1508 | C | PRO | A | 190 | 65.395 | 7.307 | −70.386 | 1.00 | 16.04 | C |
| ATOM | 1509 | O | PRO | A | 190 | 64.991 | 7.288 | −69.226 | 1.00 | 14.32 | O |
| ATOM | 1510 | CB | PRO | A | 190 | 63.372 | 8.080 | −71.654 | 1.00 | 16.36 | C |
| ATOM | 1511 | CG | PRO | A | 190 | 63.456 | 6.898 | −72.583 | 1.00 | 15.88 | C |
| ATOM | 1512 | CD | PRO | A | 190 | 64.567 | 7.315 | −73.554 | 1.00 | 16.03 | C |
| ATOM | 1513 | N | ASP | A | 191 | 66.311 | 6.460 | −70.846 | 1.00 | 15.89 | N |
| ATOM | 1514 | CA | ASP | A | 191 | 66.867 | 5.400 | −70.006 | 1.00 | 16.88 | C |
| ATOM | 1515 | C | ASP | A | 191 | 68.151 | 5.726 | −69.266 | 1.00 | 16.93 | C |
| ATOM | 1516 | O | ASP | A | 191 | 68.680 | 4.884 | −68.545 | 1.00 | 18.48 | O |
| ATOM | 1517 | CB | ASP | A | 191 | 67.066 | 4.138 | −70.853 | 1.00 | 16.52 | C |
| ATOM | 1518 | CG | ASP | A | 191 | 65.803 | 3.740 | −71.590 | 1.00 | 16.76 | C |
| ATOM | 1519 | OD1 | ASP | A | 191 | 64.760 | 3.607 | −70.924 | 1.00 | 20.96 | O |
| ATOM | 1520 | OD2 | ASP | A | 191 | 65.848 | 3.565 | −72.829 | 1.00 | 17.56 | O |
| ATOM | 1521 | N | PHE | A | 192 | 68.666 | 6.935 | −69.458 | 1.00 | 15.63 | N |
| ATOM | 1522 | CA | PHE | A | 192 | 69.885 | 7.354 | −68.776 | 1.00 | 16.81 | C |
| ATOM | 1523 | C | PHE | A | 192 | 69.744 | 8.811 | −68.389 | 1.00 | 16.49 | C |
| ATOM | 1524 | O | PHE | A | 192 | 68.864 | 9.512 | −68.898 | 1.00 | 17.44 | O |
| ATOM | 1525 | CB | PHE | A | 192 | 71.114 | 7.235 | −69.692 | 1.00 | 15.81 | C |
| ATOM | 1526 | CG | PHE | A | 192 | 71.343 | 5.858 | −70.241 | 1.00 | 19.48 | C |
| ATOM | 1527 | CD1 | PHE | A | 192 | 70.597 | 5.396 | −71.319 | 1.00 | 19.30 | C |
| ATOM | 1528 | CD2 | PHE | A | 192 | 72.325 | 5.033 | −69.701 | 1.00 | 18.59 | C |
| ATOM | 1529 | CE1 | PHE | A | 192 | 70.829 | 4.125 | −71.856 | 1.00 | 21.94 | C |
| ATOM | 1530 | CE2 | PHE | A | 192 | 72.567 | 3.763 | −70.228 | 1.00 | 20.01 | C |
| ATOM | 1531 | CZ | PHE | A | 192 | 71.819 | 3.307 | −71.307 | 1.00 | 20.17 | C |
| ATOM | 1532 | N | THR | A | 193 | 70.600 | 9.263 | −67.480 | 1.00 | 14.17 | N |
| ATOM | 1533 | CA | THR | A | 193 | 70.598 | 10.666 | −67.086 | 1.00 | 16.84 | C |
| ATOM | 1534 | C | THR | A | 193 | 71.943 | 11.040 | −66.483 | 1.00 | 17.75 | C |
| ATOM | 1535 | O | THR | A | 193 | 72.761 | 10.165 | −66.183 | 1.00 | 18.91 | O |
| ATOM | 1536 | CB | THR | A | 193 | 69.456 | 11.015 | −66.112 | 1.00 | 17.31 | C |
| ATOM | 1537 | OG1 | THR | A | 193 | 69.311 | 12.443 | −66.076 | 1.00 | 18.82 | O |
| ATOM | 1538 | CG2 | THR | A | 193 | 69.745 | 10.506 | −64.702 | 1.00 | 13.96 | C |
| ATOM | 1539 | N | PHE | A | 194 | 72.180 | 12.337 | −66.317 | 1.00 | 18.07 | N |
| ATOM | 1540 | CA | PHE | A | 194 | 73.462 | 12.827 | −65.798 | 1.00 | 19.21 | C |
| ATOM | 1541 | C | PHE | A | 194 | 73.511 | 13.052 | −64.289 | 1.00 | 18.94 | C |
| ATOM | 1542 | O | PHE | A | 194 | 72.485 | 13.249 | −63.637 | 1.00 | 20.57 | O |
| ATOM | 1543 | CB | PHE | A | 194 | 73.840 | 14.142 | −66.490 | 1.00 | 20.28 | C |
| ATOM | 1544 | CG | PHE | A | 194 | 73.639 | 14.128 | −67.976 | 1.00 | 25.90 | C |
| ATOM | 1545 | CD1 | PHE | A | 194 | 72.386 | 14.380 | −68.524 | 1.00 | 26.71 | C |
| ATOM | 1546 | CD2 | PHE | A | 194 | 74.697 | 13.836 | −68.831 | 1.00 | 27.34 | C |
| ATOM | 1547 | CE1 | PHE | A | 194 | 72.190 | 14.338 | −69.900 | 1.00 | 28.40 | C |
| ATOM | 1548 | CE2 | PHE | A | 194 | 74.509 | 13.793 | −70.209 | 1.00 | 25.92 | C |
| ATOM | 1549 | CZ | PHE | A | 194 | 73.252 | 14.043 | −70.743 | 1.00 | 26.50 | C |
| ATOM | 1550 | N | GLY | A | 195 | 74.723 | 13.032 | −63.746 | 1.00 | 17.97 | N |
| ATOM | 1551 | CA | GLY | A | 195 | 74.915 | 13.266 | −62.328 | 1.00 | 17.48 | C |
| ATOM | 1552 | C | GLY | A | 195 | 75.720 | 14.543 | −62.147 | 1.00 | 19.05 | C |
| ATOM | 1553 | O | GLY | A | 195 | 76.701 | 14.765 | −62.857 | 1.00 | 16.48 | O |
| ATOM | 1554 | N | PHE | A | 196 | 75.313 | 15.384 | −61.201 | 1.00 | 20.49 | N |
| ATOM | 1555 | CA | PHE | A | 196 | 76.009 | 16.639 | −60.951 | 1.00 | 22.69 | C |
| ATOM | 1556 | C | PHE | A | 196 | 76.041 | 16.934 | −59.463 | 1.00 | 26.07 | C |
| ATOM | 1557 | O | PHE | A | 196 | 75.349 | 16.282 | −58.684 | 1.00 | 24.35 | O |
| ATOM | 1558 | CB | PHE | A | 196 | 75.312 | 17.802 | −61.673 | 1.00 | 20.39 | C |
| ATOM | 1559 | CG | PHE | A | 196 | 73.915 | 18.073 | −61.188 | 1.00 | 19.93 | C |
| ATOM | 1560 | CD1 | PHE | A | 196 | 72.842 | 17.316 | −61.646 | 1.00 | 20.46 | C |
| ATOM | 1561 | CD2 | PHE | A | 196 | 73.678 | 19.061 | −60.241 | 1.00 | 19.90 | C |
| ATOM | 1562 | CE1 | PHE | A | 196 | 71.554 | 17.538 | −61.164 | 1.00 | 19.11 | C |
| ATOM | 1563 | CE2 | PHE | A | 196 | 72.392 | 19.290 | −59.751 | 1.00 | 21.12 | C |
| ATOM | 1564 | CZ | PHE | A | 196 | 71.330 | 18.528 | −60.214 | 1.00 | 21.09 | C |
| ATOM | 1565 | N | GLU | A | 197 | 76.861 | 17.911 | −59.079 | 1.00 | 27.55 | N |
| ATOM | 1566 | CA | GLU | A | 197 | 76.978 | 18.326 | −57.685 | 1.00 | 32.18 | C |

TABLE 2-continued

| | | | | | | | | | | |
|---|---|---|---|---|---|---|---|---|---|---|
| ATOM | 1567 | C | GLU | A | 197 | 76.440 | 19.746 | −57.603 | 1.00 | 34.74 | C |
| ATOM | 1568 | O | GLU | A | 197 | 76.489 | 20.485 | −58.588 | 1.00 | 34.16 | O |
| ATOM | 1569 | CB | GLU | A | 197 | 78.444 | 18.331 | −57.226 | 1.00 | 31.80 | C |
| ATOM | 1570 | CG | GLU | A | 197 | 79.095 | 16.964 | −57.014 | 1.00 | 34.42 | C |
| ATOM | 1571 | CD | GLU | A | 197 | 78.475 | 16.180 | −55.865 | 1.00 | 35.66 | C |
| ATOM | 1572 | OE1 | GLU | A | 197 | 78.111 | 16.796 | −54.841 | 1.00 | 35.30 | O |
| ATOM | 1573 | OE2 | GLU | A | 197 | 78.370 | 14.940 | −55.976 | 1.00 | 34.70 | O |
| ATOM | 1574 | N | GLU | A | 198 | 75.918 | 20.125 | −56.441 | 1.00 | 39.21 | N |
| ATOM | 1575 | CA | GLU | A | 198 | 75.415 | 21.481 | −56.253 | 1.00 | 45.49 | C |
| ATOM | 1576 | C | GLU | A | 198 | 76.606 | 22.433 | −56.207 | 1.00 | 49.36 | C |
| ATOM | 1577 | O | GLU | A | 198 | 77.685 | 22.061 | −55.748 | 1.00 | 49.39 | O |
| ATOM | 1578 | CB | GLU | A | 198 | 74.628 | 21.595 | −54.948 | 1.00 | 47.11 | C |
| ATOM | 1579 | CG | GLU | A | 198 | 73.180 | 21.179 | −55.049 | 1.00 | 48.38 | C |
| ATOM | 1580 | CD | GLU | A | 198 | 72.394 | 21.525 | −53.797 | 1.00 | 50.84 | C |
| ATOM | 1581 | OE1 | GLU | A | 198 | 72.543 | 20.820 | −52.775 | 1.00 | 51.70 | O |
| ATOM | 1582 | OE2 | GLU | A | 198 | 71.633 | 22.515 | −53.834 | 1.00 | 50.54 | O |
| ATOM | 1583 | N | SER | A | 199 | 76.404 | 23.657 | −56.683 | 1.00 | 54.65 | N |
| ATOM | 1584 | CA | SER | A | 199 | 77.455 | 24.670 | −56.709 | 1.00 | 59.93 | C |
| ATOM | 1585 | C | SER | A | 199 | 78.232 | 24.768 | −55.394 | 1.00 | 63.39 | C |
| ATOM | 1586 | O | SER | A | 199 | 77.644 | 24.798 | −54.309 | 1.00 | 64.28 | O |
| ATOM | 1587 | CB | SER | A | 199 | 76.850 | 26.033 | −57.045 | 1.00 | 60.55 | C |
| ATOM | 1588 | OG | SER | A | 199 | 77.861 | 27.016 | −57.176 | 1.00 | 63.55 | O |
| ATOM | 1589 | N | LEU | A | 200 | 79.557 | 24.827 | −55.504 | 1.00 | 66.74 | N |
| ATOM | 1590 | CA | LEU | A | 200 | 80.438 | 24.924 | −54.342 | 1.00 | 69.92 | C |
| ATOM | 1591 | C | LEU | A | 200 | 80.071 | 26.118 | −53.459 | 1.00 | 72.23 | C |
| ATOM | 1592 | O | LEU | A | 200 | 79.786 | 27.208 | −53.960 | 1.00 | 72.47 | O |
| ATOM | 1593 | CB | LEU | A | 200 | 81.890 | 25.062 | −54.804 | 0.00 | 69.55 | C |
| ATOM | 1594 | CG | LEU | A | 200 | 82.417 | 23.965 | −55.733 | 0.00 | 69.50 | C |
| ATOM | 1595 | CD1 | LEU | A | 200 | 83.796 | 24.349 | −56.240 | 0.00 | 69.39 | C |
| ATOM | 1596 | CD2 | LEU | A | 200 | 82.460 | 22.638 | −54.993 | 0.00 | 69.39 | C |
| ATOM | 1597 | N | GLU | A | 201 | 80.080 | 25.905 | −52.145 | 1.00 | 74.38 | N |
| ATOM | 1598 | CA | GLU | A | 201 | 79.755 | 26.964 | −51.193 | 1.00 | 76.04 | C |
| ATOM | 1599 | C | GLU | A | 201 | 80.923 | 27.939 | −51.062 | 1.00 | 77.48 | C |
| ATOM | 1600 | O | GLU | A | 201 | 80.902 | 28.842 | −50.224 | 1.00 | 77.93 | O |
| ATOM | 1601 | CB | GLU | A | 201 | 79.428 | 26.363 | −49.824 | 0.00 | 75.75 | C |
| ATOM | 1602 | CG | GLU | A | 201 | 78.234 | 25.421 | −49.828 | 0.00 | 75.51 | C |
| ATOM | 1603 | CD | GLU | A | 201 | 77.929 | 24.859 | −48.453 | 0.00 | 75.37 | C |
| ATOM | 1604 | OE1 | GLU | A | 201 | 78.810 | 24.189 | −47.874 | 0.00 | 75.29 | O |
| ATOM | 1605 | OE2 | GLU | A | 201 | 76.808 | 25.087 | −47.952 | 0.00 | 75.29 | O |
| ATOM | 1606 | N | VAL | A | 202 | 81.941 | 27.742 | −51.896 | 1.00 | 79.17 | N |
| ATOM | 1607 | CA | VAL | A | 202 | 83.131 | 28.590 | −51.905 | 1.00 | 80.42 | C |
| ATOM | 1608 | C | VAL | A | 202 | 83.825 | 28.606 | −50.540 | 1.00 | 81.42 | C |
| ATOM | 1609 | O | VAL | A | 202 | 84.713 | 29.424 | −50.293 | 1.00 | 81.61 | O |
| ATOM | 1610 | CB | VAL | A | 202 | 82.775 | 30.041 | −52.306 | 0.00 | 80.22 | C |
| ATOM | 1611 | CG1 | VAL | A | 202 | 84.039 | 30.812 | −52.661 | 0.00 | 80.17 | C |
| ATOM | 1612 | CG2 | VAL | A | 202 | 81.808 | 30.034 | −53.479 | 0.00 | 80.17 | C |
| ATOM | 1613 | N | ASP | A | 203 | 83.418 | 27.693 | −49.661 | 1.00 | 82.33 | N |
| ATOM | 1614 | CA | ASP | A | 203 | 83.996 | 27.597 | −48.323 | 1.00 | 82.52 | C |
| ATOM | 1615 | C | ASP | A | 203 | 83.919 | 26.173 | −47.772 | 1.00 | 82.77 | C |
| ATOM | 1616 | O | ASP | A | 203 | 82.827 | 25.637 | −47.569 | 1.00 | 83.34 | O |
| ATOM | 1617 | CB | ASP | A | 203 | 83.277 | 28.552 | −47.364 | 0.00 | 82.23 | C |
| ATOM | 1618 | CG | ASP | A | 203 | 83.486 | 30.011 | −47.724 | 0.00 | 82.05 | C |
| ATOM | 1619 | OD1 | ASP | A | 203 | 84.649 | 30.466 | −47.715 | 0.00 | 81.93 | O |
| ATOM | 1620 | OD2 | ASP | A | 203 | 82.487 | 30.702 | −48.015 | 0.00 | 81.93 | O |
| ATOM | 1621 | N | THR | A | 204 | 85.083 | 25.570 | −47.537 | 1.00 | 82.47 | N |
| ATOM | 1622 | CA | THR | A | 204 | 85.176 | 24.213 | −46.996 | 1.00 | 81.72 | C |
| ATOM | 1623 | C | THR | A | 204 | 84.354 | 23.203 | −47.798 | 1.00 | 81.25 | C |
| ATOM | 1624 | O | THR | A | 204 | 83.204 | 22.918 | −47.455 | 1.00 | 81.71 | O |
| ATOM | 1625 | CB | THR | A | 204 | 84.699 | 24.174 | −45.527 | 0.00 | 81.56 | C |
| ATOM | 1626 | OG1 | THR | A | 204 | 85.407 | 25.162 | −44.768 | 0.00 | 81.41 | O |
| ATOM | 1627 | CG2 | THR | A | 204 | 84.955 | 22.802 | −44.920 | 0.00 | 81.41 | C |
| ATOM | 1628 | N | ASN | A | 205 | 84.947 | 22.652 | −48.854 | 1.00 | 79.89 | N |
| ATOM | 1629 | CA | ASN | A | 205 | 84.247 | 21.683 | −49.692 | 1.00 | 78.05 | C |
| ATOM | 1630 | C | ASN | A | 205 | 85.202 | 20.904 | −50.602 | 1.00 | 76.98 | C |
| ATOM | 1631 | O | ASN | A | 205 | 85.421 | 21.287 | −51.753 | 1.00 | 76.69 | O |
| ATOM | 1632 | CB | ASN | A | 205 | 83.196 | 22.406 | −50.539 | 1.00 | 77.71 | C |
| ATOM | 1633 | CG | ASN | A | 205 | 82.334 | 21.454 | −51.342 | 0.00 | 77.35 | C |
| ATOM | 1634 | OD1 | ASN | A | 205 | 82.829 | 20.715 | −52.192 | 0.00 | 77.16 | O |
| ATOM | 1635 | ND2 | ASN | A | 205 | 81.033 | 21.468 | −51.075 | 0.00 | 77.16 | N |
| ATOM | 1636 | N | PRO | A | 206 | 85.780 | 19.797 | −50.093 | 1.00 | 75.69 | N |
| ATOM | 1637 | CA | PRO | A | 206 | 86.715 | 18.941 | −50.838 | 1.00 | 74.56 | C |
| ATOM | 1638 | C | PRO | A | 206 | 86.132 | 18.506 | −52.176 | 1.00 | 73.45 | C |
| ATOM | 1639 | O | PRO | A | 206 | 85.235 | 17.666 | −52.223 | 1.00 | 73.63 | O |
| ATOM | 1640 | CB | PRO | A | 206 | 86.923 | 17.758 | −49.900 | 1.00 | 74.45 | C |
| ATOM | 1641 | CG | PRO | A | 206 | 86.803 | 18.386 | −48.556 | 1.00 | 75.60 | C |
| ATOM | 1642 | CD | PRO | A | 206 | 85.600 | 19.290 | −48.721 | 1.00 | 75.39 | C |
| ATOM | 1643 | N | LEU | A | 207 | 86.653 | 19.073 | −53.259 | 1.00 | 72.11 | N |
| ATOM | 1644 | CA | LEU | A | 207 | 86.169 | 18.764 | −54.600 | 1.00 | 71.11 | C |
| ATOM | 1645 | C | LEU | A | 207 | 86.050 | 17.271 | −54.902 | 1.00 | 69.92 | C |

TABLE 2-continued

| | | | | | | | | | | |
|---|---|---|---|---|---|---|---|---|---|---|
| ATOM | 1646 | O | LEU | A | 207 | 85.486 | 16.888 | −55.927 | 1.00 | 70.59 | O |
| ATOM | 1647 | CB | LEU | A | 207 | 87.063 | 19.437 | −55.652 | 1.00 | 71.65 | C |
| ATOM | 1648 | CG | LEU | A | 207 | 87.034 | 20.971 | −55.705 | 1.00 | 71.86 | C |
| ATOM | 1649 | CD1 | LEU | A | 207 | 88.045 | 21.477 | −56.733 | 1.00 | 70.69 | C |
| ATOM | 1650 | CD2 | LEU | A | 207 | 85.624 | 21.448 | −56.052 | 1.00 | 71.51 | C |
| ATOM | 1651 | N | LEU | A | 208 | 86.571 | 16.428 | −54.016 | 1.00 | 67.91 | N |
| ATOM | 1652 | CA | LEU | A | 208 | 86.497 | 14.987 | −54.226 | 1.00 | 67.03 | C |
| ATOM | 1653 | C | LEU | A | 208 | 85.079 | 14.437 | −54.034 | 1.00 | 66.50 | C |
| ATOM | 1654 | O | LEU | A | 208 | 84.800 | 13.711 | −53.076 | 1.00 | 66.28 | O |
| ATOM | 1655 | CB | LEU | A | 208 | 87.479 | 14.268 | −53.296 | 1.00 | 66.91 | C |
| ATOM | 1656 | CG | LEU | A | 208 | 88.961 | 14.479 | −53.632 | 1.00 | 67.37 | C |
| ATOM | 1657 | CD1 | LEU | A | 208 | 89.827 | 14.031 | −52.471 | 1.00 | 67.10 | C |
| ATOM | 1658 | CD2 | LEU | A | 208 | 89.319 | 13.712 | −54.897 | 1.00 | 67.24 | C |
| ATOM | 1659 | N | GLY | A | 209 | 84.192 | 14.809 | −54.959 | 1.00 | 64.83 | N |
| ATOM | 1660 | CA | GLY | A | 209 | 82.810 | 14.355 | −54.943 | 1.00 | 61.53 | C |
| ATOM | 1661 | C | GLY | A | 209 | 82.602 | 13.492 | −56.177 | 1.00 | 59.15 | C |
| ATOM | 1662 | O | GLY | A | 209 | 83.580 | 12.975 | −56.724 | 1.00 | 60.80 | O |
| ATOM | 1663 | N | ALA | A | 210 | 81.364 | 13.328 | −56.638 | 1.00 | 54.13 | N |
| ATOM | 1664 | CA | ALA | A | 210 | 81.141 | 12.495 | −57.817 | 1.00 | 49.77 | C |
| ATOM | 1665 | C | ALA | A | 210 | 79.782 | 12.636 | −58.492 | 1.00 | 45.54 | C |
| ATOM | 1666 | O | ALA | A | 210 | 79.324 | 11.704 | −59.145 | 1.00 | 47.43 | O |
| ATOM | 1667 | CB | ALA | A | 210 | 81.385 | 11.031 | −57.463 | 1.00 | 49.38 | C |
| ATOM | 1668 | N | GLY | A | 211 | 79.138 | 13.788 | −58.340 | 1.00 | 41.07 | N |
| ATOM | 1669 | CA | GLY | A | 211 | 77.843 | 13.988 | −58.972 | 1.00 | 35.43 | C |
| ATOM | 1670 | C | GLY | A | 211 | 76.742 | 13.167 | −58.331 | 1.00 | 32.25 | C |
| ATOM | 1671 | O | GLY | A | 211 | 76.188 | 12.260 | −58.948 | 1.00 | 30.68 | O |
| ATOM | 1672 | N | LYS | A | 212 | 76.426 | 13.516 | −57.089 | 1.00 | 28.37 | N |
| ATOM | 1673 | CA | LYS | A | 212 | 75.415 | 12.844 | −56.282 | 1.00 | 28.22 | C |
| ATOM | 1674 | C | LYS | A | 212 | 73.971 | 13.001 | −56.767 | 1.00 | 25.63 | C |
| ATOM | 1675 | O | LYS | A | 212 | 73.157 | 12.087 | −56.626 | 1.00 | 25.08 | O |
| ATOM | 1676 | CB | LYS | A | 212 | 75.517 | 13.356 | −54.843 | 1.00 | 29.23 | C |
| ATOM | 1677 | CG | LYS | A | 212 | 74.549 | 12.709 | −53.882 | 1.00 | 34.33 | C |
| ATOM | 1678 | CD | LYS | A | 212 | 74.844 | 13.100 | −52.440 | 1.00 | 35.95 | C |
| ATOM | 1679 | CE | LYS | A | 212 | 74.611 | 14.573 | −52.186 | 1.00 | 37.23 | C |
| ATOM | 1680 | NZ | LYS | A | 212 | 74.779 | 14.885 | −50.739 | 1.00 | 41.07 | N |
| ATOM | 1681 | N | PHE | A | 213 | 73.653 | 14.163 | −57.325 | 1.00 | 22.50 | N |
| ATOM | 1682 | CA | PHE | A | 213 | 72.298 | 14.428 | −57.791 | 1.00 | 21.21 | C |
| ATOM | 1683 | C | PHE | A | 213 | 72.081 | 14.106 | −59.258 | 1.00 | 19.75 | C |
| ATOM | 1684 | O | PHE | A | 213 | 72.942 | 14.369 | −60.107 | 1.00 | 19.72 | O |
| ATOM | 1685 | CB | PHE | A | 213 | 71.944 | 15.885 | −57.511 | 1.00 | 20.76 | C |
| ATOM | 1686 | CG | PHE | A | 213 | 71.950 | 16.229 | −56.052 | 1.00 | 23.48 | C |
| ATOM | 1687 | CD1 | PHE | A | 213 | 70.854 | 15.934 | −55.251 | 1.00 | 24.33 | C |
| ATOM | 1688 | CD2 | PHE | A | 213 | 73.063 | 16.820 | −55.472 | 1.00 | 24.50 | C |
| ATOM | 1689 | CE1 | PHE | A | 213 | 70.866 | 16.228 | −53.883 | 1.00 | 26.65 | C |
| ATOM | 1690 | CE2 | PHE | A | 213 | 73.088 | 17.118 | −54.105 | 1.00 | 27.52 | C |
| ATOM | 1691 | CZ | PHE | A | 213 | 71.985 | 16.820 | −53.312 | 1.00 | 26.60 | C |
| ATOM | 1692 | N | ALA | A | 214 | 70.916 | 13.540 | −59.544 | 1.00 | 16.42 | N |
| ATOM | 1693 | CA | ALA | A | 214 | 70.554 | 13.169 | −60.900 | 1.00 | 16.68 | C |
| ATOM | 1694 | C | ALA | A | 214 | 69.653 | 14.214 | −61.559 | 1.00 | 16.89 | C |
| ATOM | 1695 | O | ALA | A | 214 | 68.719 | 14.731 | −60.945 | 1.00 | 15.77 | O |
| ATOM | 1696 | CB | ALA | A | 214 | 69.861 | 11.812 | −60.896 | 1.00 | 15.36 | C |
| ATOM | 1697 | N | THR | A | 215 | 69.958 | 14.524 | −62.815 | 1.00 | 15.50 | N |
| ATOM | 1698 | CA | THR | A | 215 | 69.182 | 15.481 | −63.586 | 1.00 | 16.66 | C |
| ATOM | 1699 | C | THR | A | 215 | 67.862 | 14.803 | −63.950 | 1.00 | 16.35 | C |
| ATOM | 1700 | O | THR | A | 215 | 67.840 | 13.615 | −64.255 | 1.00 | 16.49 | O |
| ATOM | 1701 | CB | THR | A | 215 | 69.931 | 15.880 | −64.886 | 1.00 | 17.41 | C |
| ATOM | 1702 | OG1 | THR | A | 215 | 71.061 | 16.698 | −64.553 | 1.00 | 16.43 | O |
| ATOM | 1703 | CG2 | THR | A | 215 | 69.005 | 16.647 | −65.850 | 1.00 | 14.24 | C |
| ATOM | 1704 | N | ASP | A | 216 | 66.768 | 15.555 | −63.902 | 1.00 | 16.75 | N |
| ATOM | 1705 | CA | ASP | A | 216 | 65.452 | 15.016 | −64.248 | 1.00 | 16.80 | C |
| ATOM | 1706 | C | ASP | A | 216 | 65.388 | 14.941 | −65.776 | 1.00 | 16.31 | C |
| ATOM | 1707 | O | ASP | A | 216 | 65.567 | 15.950 | −66.457 | 1.00 | 18.09 | O |
| ATOM | 1708 | CB | ASP | A | 216 | 64.346 | 15.948 | −63.723 | 1.00 | 16.73 | C |
| ATOM | 1709 | CG | ASP | A | 216 | 62.942 | 15.357 | −63.883 | 1.00 | 19.24 | C |
| ATOM | 1710 | OD1 | ASP | A | 216 | 62.662 | 14.748 | −64.937 | 1.00 | 21.10 | O |
| ATOM | 1711 | OD2 | ASP | A | 216 | 62.114 | 15.505 | −62.956 | 1.00 | 17.89 | O |
| ATOM | 1712 | N | PRO | A | 217 | 65.133 | 13.745 | −66.329 | 1.00 | 16.33 | N |
| ATOM | 1713 | CA | PRO | A | 217 | 65.039 | 13.497 | −67.772 | 1.00 | 15.60 | C |
| ATOM | 1714 | C | PRO | A | 217 | 64.096 | 14.471 | −68.474 | 1.00 | 15.70 | C |
| ATOM | 1715 | O | PRO | A | 217 | 64.316 | 14.827 | −69.630 | 1.00 | 15.03 | O |
| ATOM | 1716 | CB | PRO | A | 217 | 64.502 | 12.068 | −67.851 | 1.00 | 15.58 | C |
| ATOM | 1717 | CG | PRO | A | 217 | 64.951 | 11.458 | −66.595 | 1.00 | 20.06 | C |
| ATOM | 1718 | CD | PRO | A | 217 | 64.761 | 12.537 | −65.574 | 1.00 | 17.64 | C |
| ATOM | 1719 | N | ALA | A | 218 | 63.046 | 14.893 | −67.769 | 1.00 | 14.81 | N |
| ATOM | 1720 | CA | ALA | A | 218 | 62.052 | 15.809 | −68.331 | 1.00 | 16.44 | C |
| ATOM | 1721 | C | ALA | A | 218 | 62.637 | 17.171 | −68.707 | 1.00 | 16.31 | C |
| ATOM | 1722 | O | ALA | A | 218 | 62.187 | 17.802 | −69.664 | 1.00 | 13.60 | O |
| ATOM | 1723 | CB | ALA | A | 218 | 60.884 | 15.989 | −67.346 | 1.00 | 14.47 | C |
| ATOM | 1724 | N | VAL | A | 219 | 63.631 | 17.619 | −67.942 | 1.00 | 16.34 | N |

TABLE 2-continued

| | | | | | | | | | | |
|---|---|---|---|---|---|---|---|---|---|---|
| ATOM | 1725 | CA | VAL | A | 219 | 64.291 | 18.896 | −68.190 | 1.00 | 15.70 | C |
| ATOM | 1726 | C | VAL | A | 219 | 65.201 | 18.758 | −69.410 | 1.00 | 16.45 | C |
| ATOM | 1727 | O | VAL | A | 219 | 65.272 | 19.650 | −70.253 | 1.00 | 16.72 | O |
| ATOM | 1728 | CB | VAL | A | 219 | 65.148 | 19.326 | −66.970 | 1.00 | 16.80 | C |
| ATOM | 1729 | CG1 | VAL | A | 219 | 65.985 | 20.554 | −67.315 | 1.00 | 16.68 | C |
| ATOM | 1730 | CG2 | VAL | A | 219 | 64.239 | 19.628 | −65.782 | 1.00 | 19.13 | C |
| ATOM | 1731 | N | THR | A | 220 | 65.890 | 17.628 | −69.494 | 1.00 | 16.36 | N |
| ATOM | 1732 | CA | THR | A | 220 | 66.793 | 17.357 | −70.602 | 1.00 | 16.04 | C |
| ATOM | 1733 | C | THR | A | 220 | 66.013 | 17.328 | −71.915 | 1.00 | 16.80 | C |
| ATOM | 1734 | O | THR | A | 220 | 66.473 | 17.862 | −72.932 | 1.00 | 15.10 | O |
| ATOM | 1735 | CB | THR | A | 220 | 67.515 | 16.008 | −70.401 | 1.00 | 17.65 | C |
| ATOM | 1736 | OG1 | THR | A | 220 | 68.229 | 16.039 | −69.159 | 1.00 | 16.53 | O |
| ATOM | 1737 | CG2 | THR | A | 220 | 68.496 | 15.742 | −71.541 | 1.00 | 18.17 | C |
| ATOM | 1738 | N | LEU | A | 221 | 64.832 | 16.713 | −71.901 | 1.00 | 14.56 | N |
| ATOM | 1739 | CA | LEU | A | 221 | 64.015 | 16.650 | −73.113 | 1.00 | 14.73 | C |
| ATOM | 1740 | C | LEU | A | 221 | 63.472 | 18.039 | −73.443 | 1.00 | 14.66 | C |
| ATOM | 1741 | O | LEU | A | 221 | 63.474 | 18.456 | −74.600 | 1.00 | 16.14 | O |
| ATOM | 1742 | CB | LEU | A | 221 | 62.849 | 15.663 | −72.949 | 1.00 | 13.36 | C |
| ATOM | 1743 | CG | LEU | A | 221 | 61.880 | 15.597 | −74.143 | 1.00 | 17.07 | C |
| ATOM | 1744 | CD1 | LEU | A | 221 | 62.635 | 15.247 | −75.415 | 1.00 | 15.12 | C |
| ATOM | 1745 | CD2 | LEU | A | 221 | 60.792 | 14.559 | −73.877 | 1.00 | 16.19 | C |
| ATOM | 1746 | N | ALA | A | 222 | 63.015 | 18.759 | −72.425 | 1.00 | 14.93 | N |
| ATOM | 1747 | CA | ALA | A | 222 | 62.492 | 20.101 | −72.633 | 1.00 | 14.65 | C |
| ATOM | 1748 | C | ALA | A | 222 | 63.576 | 20.957 | −73.289 | 1.00 | 16.24 | C |
| ATOM | 1749 | O | ALA | A | 222 | 63.295 | 21.756 | −74.188 | 1.00 | 17.35 | O |
| ATOM | 1750 | CB | ALA | A | 222 | 62.074 | 20.709 | −71.301 | 1.00 | 13.22 | C |
| ATOM | 1751 | N | HIS | A | 223 | 64.814 | 20.780 | −72.832 | 1.00 | 16.06 | N |
| ATOM | 1752 | CA | HIS | A | 223 | 65.954 | 21.520 | −73.363 | 1.00 | 16.63 | C |
| ATOM | 1753 | C | HIS | A | 223 | 66.050 | 21.327 | −74.874 | 1.00 | 14.84 | C |
| ATOM | 1754 | O | HIS | A | 223 | 66.166 | 22.296 | −75.626 | 1.00 | 14.03 | O |
| ATOM | 1755 | CB | HIS | A | 223 | 67.255 | 21.037 | −72.713 | 1.00 | 19.72 | C |
| ATOM | 1756 | CG | HIS | A | 223 | 68.466 | 21.802 | −73.145 | 1.00 | 22.34 | C |
| ATOM | 1757 | ND1 | HIS | A | 223 | 68.951 | 22.886 | −72.444 | 1.00 | 26.25 | N |
| ATOM | 1758 | CD2 | HIS | A | 223 | 69.278 | 21.655 | −74.218 | 1.00 | 22.80 | C |
| ATOM | 1759 | CE1 | HIS | A | 223 | 70.009 | 23.373 | −73.066 | 1.00 | 26.50 | C |
| ATOM | 1760 | NE2 | HIS | A | 223 | 70.229 | 22.644 | −74.144 | 1.00 | 23.87 | N |
| ATOM | 1761 | N | GLN | A | 224 | 66.010 | 20.081 | −75.328 | 1.00 | 13.33 | N |
| ATOM | 1762 | CA | GLN | A | 224 | 66.088 | 19.839 | −76.765 | 1.00 | 15.06 | C |
| ATOM | 1763 | C | GLN | A | 224 | 64.852 | 20.373 | −77.498 | 1.00 | 15.37 | C |
| ATOM | 1764 | O | GLN | A | 224 | 64.967 | 20.874 | −78.614 | 1.00 | 15.35 | O |
| ATOM | 1765 | CB | GLN | A | 224 | 66.269 | 18.349 | −77.062 | 1.00 | 13.52 | C |
| ATOM | 1766 | CG | GLN | A | 224 | 67.546 | 17.770 | −76.447 | 1.00 | 15.32 | C |
| ATOM | 1767 | CD | GLN | A | 224 | 68.788 | 18.507 | −76.912 | 1.00 | 18.83 | C |
| ATOM | 1768 | OE1 | GLN | A | 224 | 69.788 | 18.584 | −76.192 | 1.00 | 19.18 | O |
| ATOM | 1769 | NE2 | GLN | A | 224 | 68.735 | 19.052 | −78.125 | 1.00 | 14.13 | N |
| ATOM | 1770 | N | LEU | A | 225 | 63.680 | 20.276 | −76.879 | 1.00 | 13.93 | N |
| ATOM | 1771 | CA | LEU | A | 225 | 62.458 | 20.767 | −77.518 | 1.00 | 16.55 | C |
| ATOM | 1772 | C | LEU | A | 225 | 62.508 | 22.283 | −77.728 | 1.00 | 16.56 | C |
| ATOM | 1773 | O | LEU | A | 225 | 61.930 | 22.802 | −78.680 | 1.00 | 17.04 | O |
| ATOM | 1774 | CB | LEU | A | 225 | 61.223 | 20.402 | −76.686 | 1.00 | 17.45 | C |
| ATOM | 1775 | CG | LEU | A | 225 | 60.839 | 18.919 | −76.569 | 1.00 | 18.62 | C |
| ATOM | 1776 | CD1 | LEU | A | 225 | 59.673 | 18.783 | −75.613 | 1.00 | 16.51 | C |
| ATOM | 1777 | CD2 | LEU | A | 225 | 60.471 | 18.346 | −77.942 | 1.00 | 19.54 | C |
| ATOM | 1778 | N | ILE | A | 226 | 63.189 | 22.990 | −76.829 | 1.00 | 15.15 | N |
| ATOM | 1779 | CA | ILE | A | 226 | 63.317 | 24.438 | −76.943 | 1.00 | 13.18 | C |
| ATOM | 1780 | C | ILE | A | 226 | 64.138 | 24.737 | −78.198 | 1.00 | 13.72 | C |
| ATOM | 1781 | O | ILE | A | 226 | 63.801 | 25.648 | −78.954 | 1.00 | 13.99 | O |
| ATOM | 1782 | CB | ILE | A | 226 | 63.997 | 25.037 | −75.678 | 1.00 | 13.51 | C |
| ATOM | 1783 | CG1 | ILE | A | 226 | 63.039 | 24.928 | −74.483 | 1.00 | 15.21 | C |
| ATOM | 1784 | CG2 | ILE | A | 226 | 64.390 | 26.487 | −75.927 | 1.00 | 13.21 | C |
| ATOM | 1785 | CD1 | ILE | A | 226 | 63.674 | 25.264 | −73.125 | 1.00 | 14.72 | C |
| ATOM | 1786 | N | HIS | A | 227 | 65.205 | 23.966 | −78.424 | 1.00 | 12.49 | N |
| ATOM | 1787 | CA | HIS | A | 227 | 66.035 | 24.133 | −79.626 | 1.00 | 15.07 | C |
| ATOM | 1788 | C | HIS | A | 227 | 65.157 | 23.878 | −80.850 | 1.00 | 17.56 | C |
| ATOM | 1789 | O | HIS | A | 227 | 65.197 | 24.629 | −81.838 | 1.00 | 16.28 | O |
| ATOM | 1790 | CB | HIS | A | 227 | 67.188 | 23.120 | −79.667 | 1.00 | 14.69 | C |
| ATOM | 1791 | CG | HIS | A | 227 | 68.360 | 23.496 | −78.817 | 1.00 | 18.54 | C |
| ATOM | 1792 | ND1 | HIS | A | 227 | 69.028 | 24.694 | −78.959 | 1.00 | 20.51 | N |
| ATOM | 1793 | CD2 | HIS | A | 227 | 68.976 | 22.839 | −77.806 | 1.00 | 16.02 | C |
| ATOM | 1794 | CE1 | HIS | A | 227 | 70.003 | 24.760 | −78.069 | 1.00 | 20.55 | C |
| ATOM | 1795 | NE2 | HIS | A | 227 | 69.991 | 23.648 | −77.358 | 1.00 | 17.49 | N |
| ATOM | 1796 | N | ALA | A | 228 | 64.382 | 22.797 | −80.787 | 1.00 | 15.66 | N |
| ATOM | 1797 | CA | ALA | A | 228 | 63.495 | 22.438 | −81.889 | 1.00 | 17.74 | C |
| ATOM | 1798 | C | ALA | A | 228 | 62.565 | 23.617 | −82.172 | 1.00 | 18.57 | C |
| ATOM | 1799 | O | ALA | A | 228 | 62.310 | 23.966 | −83.329 | 1.00 | 20.04 | O |
| ATOM | 1800 | CB | ALA | A | 228 | 62.680 | 21.193 | −81.525 | 1.00 | 16.91 | C |
| ATOM | 1801 | N | GLY | A | 229 | 62.067 | 24.232 | −81.107 | 1.00 | 16.77 | N |
| ATOM | 1802 | CA | GLY | A | 229 | 61.176 | 25.368 | −81.265 | 1.00 | 16.32 | C |
| ATOM | 1803 | C | GLY | A | 229 | 61.830 | 26.493 | −82.049 | 1.00 | 16.61 | C |

TABLE 2-continued

| ATOM | 1804 | O | GLY | A | 229 | 61.249 | 27.020 | −82.996 | 1.00 | 16.54 | O |
|------|------|-----|-----|---|-----|--------|--------|---------|------|-------|---|
| ATOM | 1805 | N | HIS | A | 230 | 63.043 | 26.867 | −81.653 | 1.00 | 17.06 | N |
| ATOM | 1806 | CA | HIS | A | 230 | 63.784 | 27.930 | −82.338 | 1.00 | 16.96 | C |
| ATOM | 1807 | C | HIS | A | 230 | 64.003 | 27.565 | −83.796 | 1.00 | 16.54 | C |
| ATOM | 1808 | O | HIS | A | 230 | 63.844 | 28.393 | −84.707 | 1.00 | 14.90 | O |
| ATOM | 1809 | CB | HIS | A | 230 | 65.159 | 28.137 | −81.687 | 1.00 | 15.41 | C |
| ATOM | 1810 | CG | HIS | A | 230 | 65.094 | 28.540 | −80.247 | 1.00 | 16.51 | C |
| ATOM | 1811 | ND1 | HIS | A | 230 | 66.152 | 28.372 | −79.379 | 1.00 | 14.96 | N |
| ATOM | 1812 | CD2 | HIS | A | 230 | 64.100 | 29.105 | −79.524 | 1.00 | 16.99 | C |
| ATOM | 1813 | CE1 | HIS | A | 230 | 65.809 | 28.815 | −78.183 | 1.00 | 18.04 | C |
| ATOM | 1814 | NE2 | HIS | A | 230 | 64.568 | 29.265 | −78.244 | 1.00 | 16.56 | N |
| ATOM | 1815 | N | ARG | A | 231 | 64.378 | 26.315 | −84.015 | 1.00 | 15.52 | N |
| ATOM | 1816 | CA | ARG | A | 231 | 64.668 | 25.855 | −85.355 | 1.00 | 16.61 | C |
| ATOM | 1817 | C | ARG | A | 231 | 63.436 | 25.686 | −86.262 | 1.00 | 17.68 | C |
| ATOM | 1818 | O | ARG | A | 231 | 63.538 | 25.847 | −87.476 | 1.00 | 19.47 | O |
| ATOM | 1819 | CB | ARG | A | 231 | 65.507 | 24.575 | −85.264 | 1.00 | 14.77 | C |
| ATOM | 1820 | CG | ARG | A | 231 | 66.869 | 24.819 | −84.600 | 1.00 | 14.63 | C |
| ATOM | 1821 | CD | ARG | A | 231 | 67.599 | 23.525 | −84.213 | 1.00 | 15.82 | C |
| ATOM | 1822 | NE | ARG | A | 231 | 68.010 | 22.709 | −85.358 | 1.00 | 16.29 | N |
| ATOM | 1823 | CZ | ARG | A | 231 | 69.259 | 22.610 | −85.810 | 1.00 | 19.13 | C |
| ATOM | 1824 | NH1 | ARG | A | 231 | 70.243 | 23.280 | −85.223 | 1.00 | 17.03 | N |
| ATOM | 1825 | NH2 | ARG | A | 231 | 69.534 | 21.818 | −86.839 | 1.00 | 17.80 | N |
| ATOM | 1826 | N | LEU | A | 232 | 62.276 | 25.395 | −85.685 | 1.00 | 17.64 | N |
| ATOM | 1827 | CA | LEU | A | 232 | 61.064 | 25.243 | −86.484 | 1.00 | 16.00 | C |
| ATOM | 1828 | C | LEU | A | 232 | 60.556 | 26.608 | −86.943 | 1.00 | 17.46 | C |
| ATOM | 1829 | O | LEU | A | 232 | 59.920 | 26.718 | −87.994 | 1.00 | 17.22 | O |
| ATOM | 1830 | CB | LEU | A | 232 | 59.978 | 24.505 | −85.689 | 1.00 | 15.25 | C |
| ATOM | 1831 | CG | LEU | A | 232 | 60.142 | 22.974 | −85.613 | 1.00 | 15.07 | C |
| ATOM | 1832 | CD1 | LEU | A | 232 | 59.294 | 22.386 | −84.472 | 1.00 | 11.59 | C |
| ATOM | 1833 | CD2 | LEU | A | 232 | 59.734 | 22.359 | −86.949 | 1.00 | 12.57 | C |
| ATOM | 1834 | N | TYR | A | 233 | 60.835 | 27.649 | −86.163 | 1.00 | 17.34 | N |
| ATOM | 1835 | CA | TYR | A | 233 | 60.410 | 28.988 | −86.550 | 1.00 | 18.46 | C |
| ATOM | 1836 | C | TYR | A | 233 | 61.522 | 29.731 | −87.274 | 1.00 | 17.90 | C |
| ATOM | 1837 | O | TYR | A | 233 | 61.393 | 30.917 | −87.582 | 1.00 | 19.86 | O |
| ATOM | 1838 | CB | TYR | A | 233 | 59.942 | 29.790 | −85.336 | 1.00 | 18.60 | C |
| ATOM | 1839 | CG | TYR | A | 233 | 58.601 | 29.346 | −84.826 | 1.00 | 20.21 | C |
| ATOM | 1840 | CD1 | TYR | A | 233 | 58.464 | 28.145 | −84.121 | 1.00 | 19.01 | C |
| ATOM | 1841 | CD2 | TYR | A | 233 | 57.453 | 30.088 | −85.095 | 1.00 | 18.38 | C |
| ATOM | 1842 | CE1 | TYR | A | 233 | 57.221 | 27.699 | −83.708 | 1.00 | 17.30 | C |
| ATOM | 1843 | CE2 | TYR | A | 233 | 56.203 | 29.648 | −84.680 | 1.00 | 17.82 | C |
| ATOM | 1844 | CZ | TYR | A | 233 | 56.094 | 28.451 | −83.993 | 1.00 | 17.22 | C |
| ATOM | 1845 | OH | TYR | A | 233 | 54.855 | 27.984 | −83.610 | 1.00 | 16.60 | O |
| ATOM | 1846 | N | GLY | A | 234 | 62.616 | 29.023 | −87.535 | 1.00 | 18.90 | N |
| ATOM | 1847 | CA | GLY | A | 234 | 63.743 | 29.595 | −88.250 | 1.00 | 17.89 | C |
| ATOM | 1848 | C | GLY | A | 234 | 64.449 | 30.763 | −87.584 | 1.00 | 20.21 | C |
| ATOM | 1849 | O | GLY | A | 234 | 64.993 | 31.628 | −88.280 | 1.00 | 19.12 | O |
| ATOM | 1850 | N | ILE | A | 235 | 64.457 | 30.790 | −86.253 | 1.00 | 19.18 | N |
| ATOM | 1851 | CA | ILE | A | 235 | 65.106 | 31.872 | −85.515 | 1.00 | 20.49 | C |
| ATOM | 1852 | C | ILE | A | 235 | 66.306 | 31.449 | −84.657 | 1.00 | 20.54 | C |
| ATOM | 1853 | O | ILE | A | 235 | 66.683 | 32.156 | −83.723 | 1.00 | 20.71 | O |
| ATOM | 1854 | CB | ILE | A | 235 | 64.104 | 32.609 | −84.603 | 1.00 | 20.73 | C |
| ATOM | 1855 | CG1 | ILE | A | 235 | 63.505 | 31.639 | −83.588 | 1.00 | 21.22 | C |
| ATOM | 1856 | CG2 | ILE | A | 235 | 62.996 | 33.245 | −85.446 | 1.00 | 21.52 | C |
| ATOM | 1857 | CD1 | ILE | A | 235 | 62.701 | 32.339 | −82.507 | 1.00 | 16.81 | C |
| ATOM | 1858 | N | ALA | A | 236 | 66.905 | 30.308 | −84.981 | 1.00 | 20.38 | N |
| ATOM | 1859 | CA | ALA | A | 236 | 68.067 | 29.811 | −84.246 | 1.00 | 21.64 | C |
| ATOM | 1860 | C | ALA | A | 236 | 69.258 | 30.729 | −84.504 | 1.00 | 24.04 | C |
| ATOM | 1861 | O | ALA | A | 236 | 69.480 | 31.171 | −85.636 | 1.00 | 23.91 | O |
| ATOM | 1862 | CB | ALA | A | 236 | 68.404 | 28.389 | −84.693 | 1.00 | 21.34 | C |
| ATOM | 1863 | N | ILE | A | 237 | 70.028 | 31.015 | −83.461 | 1.00 | 24.24 | N |
| ATOM | 1864 | CA | ILE | A | 237 | 71.186 | 31.889 | −83.620 | 1.00 | 25.76 | C |
| ATOM | 1865 | C | ILE | A | 237 | 72.317 | 31.182 | −84.358 | 1.00 | 26.89 | C |
| ATOM | 1866 | O | ILE | A | 237 | 72.635 | 30.030 | −84.077 | 1.00 | 27.54 | O |
| ATOM | 1867 | CB | ILE | A | 237 | 71.687 | 32.404 | −82.251 | 1.00 | 25.38 | C |
| ATOM | 1868 | CG1 | ILE | A | 237 | 70.587 | 33.254 | −81.597 | 1.00 | 26.20 | C |
| ATOM | 1869 | CG2 | ILE | A | 237 | 72.966 | 33.221 | −82.439 | 1.00 | 26.33 | C |
| ATOM | 1870 | CD1 | ILE | A | 237 | 70.823 | 33.606 | −80.128 | 1.00 | 27.48 | C |
| ATOM | 1871 | N | ASN | A | 238 | 72.914 | 31.882 | −85.317 | 1.00 | 29.80 | N |
| ATOM | 1872 | CA | ASN | A | 238 | 74.011 | 31.335 | −86.106 | 1.00 | 31.48 | C |
| ATOM | 1873 | C | ASN | A | 238 | 75.032 | 30.704 | −85.160 | 1.00 | 33.05 | C |
| ATOM | 1874 | O | ASN | A | 238 | 75.472 | 31.338 | −84.201 | 1.00 | 32.34 | O |
| ATOM | 1875 | CB | ASN | A | 238 | 74.655 | 32.460 | −86.926 | 1.00 | 32.75 | C |
| ATOM | 1876 | CG | ASN | A | 238 | 75.567 | 31.945 | −88.023 | 1.00 | 33.89 | C |
| ATOM | 1877 | OD1 | ASN | A | 238 | 75.629 | 32.526 | −89.106 | 1.00 | 38.84 | O |
| ATOM | 1878 | ND2 | ASN | A | 238 | 76.288 | 30.865 | −87.748 | 1.00 | 36.55 | N |
| ATOM | 1879 | N | PRO | A | 239 | 75.412 | 29.443 | −85.414 | 1.00 | 34.57 | N |
| ATOM | 1880 | CA | PRO | A | 239 | 76.382 | 28.747 | −84.564 | 1.00 | 37.98 | C |
| ATOM | 1881 | C | PRO | A | 239 | 77.767 | 29.383 | −84.589 | 1.00 | 39.96 | C |
| ATOM | 1882 | O | PRO | A | 239 | 78.651 | 28.997 | −83.821 | 1.00 | 38.39 | O |

TABLE 2-continued

| | | | | | | | | | | |
|---|---|---|---|---|---|---|---|---|---|---|
| ATOM | 1883 | CB | PRO | A | 239 | 76.372 | 27.327 | −85.123 | 1.00 | 37.85 | C |
| ATOM | 1884 | CG | PRO | A | 239 | 76.070 | 27.545 | −86.567 | 1.00 | 39.33 | C |
| ATOM | 1885 | CD | PRO | A | 239 | 74.969 | 28.574 | −86.517 | 1.00 | 36.40 | C |
| ATOM | 1886 | N | ASN | A | 240 | 77.950 | 30.361 | −85.472 | 1.00 | 42.28 | N |
| ATOM | 1887 | CA | ASN | A | 240 | 79.228 | 31.049 | −85.569 | 1.00 | 44.78 | C |
| ATOM | 1888 | C | ASN | A | 240 | 79.330 | 32.003 | −84.378 | 1.00 | 43.90 | C |
| ATOM | 1889 | O | ASN | A | 240 | 80.428 | 32.358 | −83.949 | 1.00 | 46.11 | O |
| ATOM | 1890 | CB | ASN | A | 240 | 79.335 | 31.815 | −86.895 | 1.00 | 47.57 | C |
| ATOM | 1891 | CG | ASN | A | 240 | 78.683 | 33.178 | −86.838 | 1.00 | 50.99 | C |
| ATOM | 1892 | OD1 | ASN | A | 240 | 77.498 | 33.303 | −86.538 | 1.00 | 54.35 | O |
| ATOM | 1893 | ND2 | ASN | A | 240 | 79.462 | 34.215 | −87.127 | 1.00 | 54.50 | N |
| ATOM | 1894 | N | ARG | A | 241 | 78.180 | 32.410 | −83.843 | 1.00 | 41.20 | N |
| ATOM | 1895 | CA | ARG | A | 241 | 78.152 | 33.294 | −82.683 | 1.00 | 38.98 | C |
| ATOM | 1896 | C | ARG | A | 241 | 78.345 | 32.440 | −81.438 | 1.00 | 38.70 | C |
| ATOM | 1897 | O | ARG | A | 241 | 77.459 | 31.672 | −81.054 | 1.00 | 35.99 | O |
| ATOM | 1898 | CB | ARG | A | 241 | 76.820 | 34.035 | −82.588 | 1.00 | 39.14 | C |
| ATOM | 1899 | CG | ARG | A | 241 | 76.542 | 34.972 | −83.737 | 1.00 | 40.47 | C |
| ATOM | 1900 | CD | ARG | A | 241 | 77.679 | 35.958 | −83.942 | 1.00 | 42.14 | C |
| ATOM | 1901 | NE | ARG | A | 241 | 77.216 | 37.117 | −84.689 | 1.00 | 47.35 | N |
| ATOM | 1902 | CZ | ARG | A | 241 | 76.516 | 38.114 | −84.156 | 1.00 | 48.73 | C |
| ATOM | 1903 | NH1 | ARG | A | 241 | 76.209 | 38.097 | −82.867 | 1.00 | 49.72 | N |
| ATOM | 1904 | NH2 | ARG | A | 241 | 76.110 | 39.119 | −84.917 | 1.00 | 51.54 | N |
| ATOM | 1905 | N | VAL | A | 242 | 79.510 | 32.579 | −80.813 | 1.00 | 37.14 | N |
| ATOM | 1906 | CA | VAL | A | 242 | 79.837 | 31.807 | −79.625 | 1.00 | 36.16 | C |
| ATOM | 1907 | C | VAL | A | 242 | 80.458 | 32.664 | −78.534 | 1.00 | 36.47 | C |
| ATOM | 1908 | O | VAL | A | 242 | 80.934 | 33.769 | −78.784 | 1.00 | 35.21 | O |
| ATOM | 1909 | CB | VAL | A | 242 | 80.816 | 30.668 | −79.962 | 1.00 | 36.54 | C |
| ATOM | 1910 | CG1 | VAL | A | 242 | 80.180 | 29.712 | −80.963 | 1.00 | 36.70 | C |
| ATOM | 1911 | CG2 | VAL | A | 242 | 82.106 | 31.243 | −80.520 | 1.00 | 36.71 | C |
| ATOM | 1912 | N | PHE | A | 243 | 80.447 | 32.135 | −77.320 | 1.00 | 36.72 | N |
| ATOM | 1913 | CA | PHE | A | 243 | 81.001 | 32.819 | −76.162 | 1.00 | 38.87 | C |
| ATOM | 1914 | C | PHE | A | 243 | 82.194 | 32.005 | −75.646 | 1.00 | 39.46 | C |
| ATOM | 1915 | O | PHE | A | 243 | 82.044 | 30.828 | −75.310 | 1.00 | 38.03 | O |
| ATOM | 1916 | CB | PHE | A | 243 | 79.913 | 32.931 | −75.089 | 1.00 | 39.61 | C |
| ATOM | 1917 | CG | PHE | A | 243 | 80.359 | 33.595 | −73.822 | 1.00 | 40.62 | C |
| ATOM | 1918 | CD1 | PHE | A | 243 | 80.887 | 34.881 | −73.839 | 1.00 | 43.63 | C |
| ATOM | 1919 | CD2 | PHE | A | 243 | 80.212 | 32.948 | −72.602 | 1.00 | 41.41 | C |
| ATOM | 1920 | CE1 | PHE | A | 243 | 81.259 | 35.516 | −72.655 | 1.00 | 44.35 | C |
| ATOM | 1921 | CE2 | PHE | A | 243 | 80.578 | 33.570 | −71.412 | 1.00 | 43.01 | C |
| ATOM | 1922 | CZ | PHE | A | 243 | 81.103 | 34.858 | −71.437 | 1.00 | 44.18 | C |
| ATOM | 1923 | N | LYS | A | 244 | 83.377 | 32.617 | −75.615 | 1.00 | 39.79 | N |
| ATOM | 1924 | CA | LYS | A | 244 | 84.576 | 31.932 | −75.125 | 1.00 | 40.45 | C |
| ATOM | 1925 | C | LYS | A | 244 | 84.669 | 32.078 | −73.613 | 1.00 | 39.14 | C |
| ATOM | 1926 | O | LYS | A | 244 | 84.521 | 33.175 | −73.079 | 1.00 | 40.80 | O |
| ATOM | 1927 | CB | LYS | A | 244 | 85.846 | 32.507 | −75.755 | 1.00 | 42.55 | C |
| ATOM | 1928 | CG | LYS | A | 244 | 86.251 | 31.896 | −77.085 | 1.00 | 46.06 | C |
| ATOM | 1929 | CD | LYS | A | 244 | 85.423 | 32.420 | −78.236 | 1.00 | 47.69 | C |
| ATOM | 1930 | CE | LYS | A | 244 | 85.954 | 31.890 | −79.557 | 1.00 | 48.24 | C |
| ATOM | 1931 | NZ | LYS | A | 244 | 85.190 | 32.439 | −80.714 | 1.00 | 50.75 | N |
| ATOM | 1932 | N | VAL | A | 245 | 84.922 | 30.971 | −72.926 | 1.00 | 38.12 | N |
| ATOM | 1933 | CA | VAL | A | 245 | 85.019 | 30.984 | −71.473 | 1.00 | 36.40 | C |
| ATOM | 1934 | C | VAL | A | 245 | 86.282 | 30.280 | −70.998 | 1.00 | 35.06 | C |
| ATOM | 1935 | O | VAL | A | 245 | 86.601 | 29.184 | −71.455 | 1.00 | 33.41 | O |
| ATOM | 1936 | CB | VAL | A | 245 | 83.823 | 30.259 | −70.831 | 1.00 | 37.53 | C |
| ATOM | 1937 | CG1 | VAL | A | 245 | 83.839 | 30.466 | −69.325 | 1.00 | 38.69 | C |
| ATOM | 1938 | CG2 | VAL | A | 245 | 82.525 | 30.755 | −71.441 | 1.00 | 39.41 | C |
| ATOM | 1939 | N | ASN | A | 246 | 87.003 | 30.908 | −70.078 | 1.00 | 33.60 | N |
| ATOM | 1940 | CA | ASN | A | 246 | 88.205 | 30.294 | −69.538 | 1.00 | 33.00 | C |
| ATOM | 1941 | C | ASN | A | 246 | 87.804 | 29.345 | −68.413 | 1.00 | 31.16 | C |
| ATOM | 1942 | O | ASN | A | 246 | 86.941 | 29.671 | −67.597 | 1.00 | 30.81 | O |
| ATOM | 1943 | CB | ASN | A | 246 | 89.158 | 31.362 | −69.000 | 1.00 | 35.61 | C |
| ATOM | 1944 | CG | ASN | A | 246 | 90.386 | 30.763 | −68.331 | 1.00 | 36.78 | C |
| ATOM | 1945 | OD1 | ASN | A | 246 | 90.394 | 30.514 | −67.123 | 1.00 | 40.13 | O |
| ATOM | 1946 | ND2 | ASN | A | 246 | 91.419 | 30.508 | −69.119 | 1.00 | 35.71 | N |
| ATOM | 1947 | N | THR | A | 247 | 88.412 | 28.165 | −68.382 | 1.00 | 29.84 | N |
| ATOM | 1948 | CA | THR | A | 247 | 88.103 | 27.197 | −67.337 | 1.00 | 29.28 | C |
| ATOM | 1949 | C | THR | A | 247 | 89.362 | 26.531 | −66.793 | 1.00 | 29.44 | C |
| ATOM | 1950 | O | THR | A | 247 | 90.321 | 26.281 | −67.532 | 1.00 | 29.55 | O |
| ATOM | 1951 | CB | THR | A | 247 | 87.132 | 26.097 | −67.839 | 1.00 | 29.03 | C |
| ATOM | 1952 | OG1 | THR | A | 247 | 86.847 | 25.194 | −66.764 | 1.00 | 29.38 | O |
| ATOM | 1953 | CG2 | THR | A | 247 | 87.737 | 25.321 | −68.990 | 1.00 | 28.23 | C |
| ATOM | 1954 | N | ASN | A | 248 | 89.345 | 26.240 | −65.496 | 1.00 | 27.96 | N |
| ATOM | 1955 | CA | ASN | A | 248 | 90.474 | 25.611 | −64.827 | 1.00 | 29.85 | C |
| ATOM | 1956 | C | ASN | A | 248 | 90.067 | 24.230 | −64.319 | 1.00 | 29.28 | C |
| ATOM | 1957 | O | ASN | A | 248 | 90.819 | 23.582 | −63.591 | 1.00 | 30.41 | O |
| ATOM | 1958 | CB | ASN | A | 248 | 90.921 | 26.470 | −63.633 | 1.00 | 31.37 | C |
| ATOM | 1959 | CG | ASN | A | 248 | 91.237 | 27.912 | −64.022 | 1.00 | 34.88 | C |
| ATOM | 1960 | OD1 | ASN | A | 248 | 92.026 | 28.160 | −64.928 | 1.00 | 37.69 | O |
| ATOM | 1961 | ND2 | ASN | A | 248 | 90.621 | 28.869 | −63.326 | 1.00 | 34.59 | N |

TABLE 2-continued

| | | | | | | | | | | |
|---|---|---|---|---|---|---|---|---|---|---|
| ATOM | 1962 | N | ALA | A | 249 | 88.880 | 23.787 | −64.721 | 1.00 | 27.23 | N |
| ATOM | 1963 | CA | ALA | A | 249 | 88.316 | 22.511 | −64.286 | 1.00 | 26.78 | C |
| ATOM | 1964 | C | ALA | A | 249 | 89.004 | 21.216 | −64.717 | 1.00 | 26.95 | C |
| ATOM | 1965 | O | ALA | A | 249 | 88.896 | 20.205 | −64.026 | 1.00 | 25.65 | O |
| ATOM | 1966 | CB | ALA | A | 249 | 86.840 | 22.457 | −64.679 | 1.00 | 25.58 | C |
| ATOM | 1967 | N | TYR | A | 250 | 89.707 | 21.225 | −65.842 | 1.00 | 25.55 | N |
| ATOM | 1968 | CA | TYR | A | 250 | 90.357 | 20.000 | −66.303 | 1.00 | 26.51 | C |
| ATOM | 1969 | C | TYR | A | 250 | 91.818 | 20.188 | −66.686 | 1.00 | 27.27 | C |
| ATOM | 1970 | O | TYR | A | 250 | 92.222 | 21.261 | −67.128 | 1.00 | 27.23 | O |
| ATOM | 1971 | CB | TYR | A | 250 | 89.605 | 19.433 | −67.512 | 1.00 | 27.09 | C |
| ATOM | 1972 | CG | TYR | A | 250 | 88.147 | 19.139 | −67.254 | 1.00 | 28.57 | C |
| ATOM | 1973 | CD1 | TYR | A | 250 | 87.757 | 17.987 | −66.576 | 1.00 | 26.24 | C |
| ATOM | 1974 | CD2 | TYR | A | 250 | 87.156 | 20.037 | −67.657 | 1.00 | 28.03 | C |
| ATOM | 1975 | CE1 | TYR | A | 250 | 86.417 | 17.734 | −66.302 | 1.00 | 27.33 | C |
| ATOM | 1976 | CE2 | TYR | A | 250 | 85.817 | 19.795 | −67.387 | 1.00 | 28.81 | C |
| ATOM | 1977 | CZ | TYR | A | 250 | 85.455 | 18.644 | −66.708 | 1.00 | 27.74 | C |
| ATOM | 1978 | OH | TYR | A | 250 | 84.132 | 18.416 | −66.424 | 1.00 | 30.22 | O |
| ATOM | 1979 | N | TYR | A | 251 | 92.605 | 19.132 | −66.524 | 1.00 | 29.64 | N |
| ATOM | 1980 | CA | TYR | A | 251 | 94.012 | 19.180 | −66.886 | 1.00 | 31.90 | C |
| ATOM | 1981 | C | TYR | A | 251 | 94.098 | 19.251 | −68.403 | 1.00 | 33.53 | C |
| ATOM | 1982 | O | TYR | A | 251 | 93.285 | 18.642 | −69.104 | 1.00 | 31.42 | O |
| ATOM | 1983 | CB | TYR | A | 251 | 94.735 | 17.925 | −66.392 | 1.00 | 31.87 | C |
| ATOM | 1984 | CG | TYR | A | 251 | 94.993 | 17.916 | −64.903 | 1.00 | 34.87 | C |
| ATOM | 1985 | CD1 | TYR | A | 251 | 95.949 | 18.764 | −64.336 | 1.00 | 35.62 | C |
| ATOM | 1986 | CD2 | TYR | A | 251 | 94.266 | 17.082 | −64.054 | 1.00 | 34.41 | C |
| ATOM | 1987 | CE1 | TYR | A | 251 | 96.171 | 18.780 | −62.960 | 1.00 | 35.90 | C |
| ATOM | 1988 | CE2 | TYR | A | 251 | 94.478 | 17.094 | −62.678 | 1.00 | 36.16 | C |
| ATOM | 1989 | CZ | TYR | A | 251 | 95.432 | 17.943 | −62.140 | 1.00 | 36.67 | C |
| ATOM | 1990 | OH | TYR | A | 251 | 95.648 | 17.951 | −60.782 | 1.00 | 38.91 | O |
| ATOM | 1991 | N | GLU | A | 252 | 95.074 | 20.005 | −68.904 | 1.00 | 35.67 | N |
| ATOM | 1992 | CA | GLU | A | 252 | 95.286 | 20.147 | −70.344 | 1.00 | 37.63 | C |
| ATOM | 1993 | C | GLU | A | 252 | 94.188 | 20.891 | −71.102 | 1.00 | 36.57 | C |
| ATOM | 1994 | O | GLU | A | 252 | 94.197 | 20.937 | −72.332 | 1.00 | 36.76 | O |
| ATOM | 1995 | CB | GLU | A | 252 | 95.504 | 18.767 | −70.970 | 1.00 | 41.34 | C |
| ATOM | 1996 | CG | GLU | A | 252 | 96.968 | 18.374 | −71.106 | 1.00 | 48.07 | C |
| ATOM | 1997 | CD | GLU | A | 252 | 97.798 | 18.750 | −69.893 | 1.00 | 50.75 | C |
| ATOM | 1998 | OE1 | GLU | A | 252 | 97.485 | 18.274 | −68.780 | 1.00 | 54.68 | O |
| ATOM | 1999 | OE2 | GLU | A | 252 | 98.764 | 19.526 | −70.058 | 1.00 | 52.61 | O |
| ATOM | 2000 | N | MET | A | 253 | 93.234 | 21.460 | −70.375 | 1.00 | 34.70 | N |
| ATOM | 2001 | CA | MET | A | 253 | 92.168 | 22.227 | −71.006 | 1.00 | 34.87 | C |
| ATOM | 2002 | C | MET | A | 253 | 92.291 | 23.621 | −70.408 | 1.00 | 34.32 | C |
| ATOM | 2003 | O | MET | A | 253 | 92.722 | 23.769 | −69.268 | 1.00 | 32.12 | O |
| ATOM | 2004 | CB | MET | A | 253 | 90.793 | 21.630 | −70.689 | 1.00 | 35.40 | C |
| ATOM | 2005 | CG | MET | A | 253 | 90.591 | 20.190 | −71.161 | 1.00 | 38.26 | C |
| ATOM | 2006 | SD | MET | A | 253 | 90.764 | 19.944 | −72.941 | 1.00 | 41.17 | S |
| ATOM | 2007 | CE | MET | A | 253 | 91.686 | 18.412 | −72.975 | 1.00 | 41.68 | C |
| ATOM | 2008 | N | SER | A | 254 | 91.938 | 24.648 | −71.169 | 1.00 | 32.96 | N |
| ATOM | 2009 | CA | SER | A | 254 | 92.052 | 25.999 | −70.647 | 1.00 | 33.60 | C |
| ATOM | 2010 | C | SER | A | 254 | 90.834 | 26.836 | −70.958 | 1.00 | 33.66 | C |
| ATOM | 2011 | O | SER | A | 254 | 90.669 | 27.927 | −70.417 | 1.00 | 33.93 | O |
| ATOM | 2012 | CB | SER | A | 254 | 93.303 | 26.682 | −71.216 | 1.00 | 35.88 | C |
| ATOM | 2013 | OG | SER | A | 254 | 93.250 | 26.743 | −72.628 | 1.00 | 39.44 | O |
| ATOM | 2014 | N | GLY | A | 255 | 89.970 | 26.323 | −71.822 | 1.00 | 34.14 | N |
| ATOM | 2015 | CA | GLY | A | 255 | 88.797 | 27.088 | −72.178 | 1.00 | 35.06 | C |
| ATOM | 2016 | C | GLY | A | 255 | 87.577 | 26.297 | −72.586 | 1.00 | 36.50 | C |
| ATOM | 2017 | O | GLY | A | 255 | 87.590 | 25.065 | −72.669 | 1.00 | 35.18 | O |
| ATOM | 2018 | N | LEU | A | 256 | 86.511 | 27.038 | −72.854 | 1.00 | 36.53 | N |
| ATOM | 2019 | CA | LEU | A | 256 | 85.248 | 26.460 | −73.249 | 1.00 | 37.60 | C |
| ATOM | 2020 | C | LEU | A | 256 | 84.581 | 27.401 | −74.233 | 1.00 | 37.65 | C |
| ATOM | 2021 | O | LEU | A | 256 | 84.684 | 28.624 | −74.111 | 1.00 | 36.91 | O |
| ATOM | 2022 | CB | LEU | A | 256 | 84.363 | 26.276 | −72.016 | 1.00 | 40.69 | C |
| ATOM | 2023 | CG | LEU | A | 256 | 82.939 | 25.750 | −72.192 | 1.00 | 42.83 | C |
| ATOM | 2024 | CD1 | LEU | A | 256 | 82.952 | 24.393 | −72.880 | 1.00 | 43.74 | C |
| ATOM | 2025 | CD2 | LEU | A | 256 | 82.287 | 25.648 | −70.824 | 1.00 | 45.10 | C |
| ATOM | 2026 | N | GLU | A | 257 | 83.902 | 26.824 | −75.215 | 1.00 | 35.01 | N |
| ATOM | 2027 | CA | GLU | A | 257 | 83.202 | 27.608 | −76.216 | 1.00 | 34.88 | C |
| ATOM | 2028 | C | GLU | A | 257 | 81.734 | 27.202 | −76.174 | 1.00 | 31.83 | C |
| ATOM | 2029 | O | GLU | A | 257 | 81.416 | 26.029 | −76.344 | 1.00 | 28.87 | O |
| ATOM | 2030 | CB | GLU | A | 257 | 83.788 | 27.317 | −77.597 | 1.00 | 38.15 | C |
| ATOM | 2031 | CG | GLU | A | 257 | 83.296 | 28.228 | −78.699 | 1.00 | 42.87 | C |
| ATOM | 2032 | CD | GLU | A | 257 | 83.987 | 27.947 | −80.022 | 1.00 | 47.89 | C |
| ATOM | 2033 | OE1 | GLU | A | 257 | 83.606 | 26.967 | −80.704 | 1.00 | 48.20 | O |
| ATOM | 2034 | OE2 | GLU | A | 257 | 84.923 | 28.703 | −80.371 | 1.00 | 50.13 | O |
| ATOM | 2035 | N | VAL | A | 258 | 80.848 | 28.167 | −75.929 | 1.00 | 29.93 | N |
| ATOM | 2036 | CA | VAL | A | 258 | 79.410 | 27.900 | −75.874 | 1.00 | 28.72 | C |
| ATOM | 2037 | C | VAL | A | 258 | 78.672 | 28.786 | −76.871 | 1.00 | 27.17 | C |
| ATOM | 2038 | O | VAL | A | 258 | 78.828 | 30.008 | −76.860 | 1.00 | 27.01 | O |
| ATOM | 2039 | CB | VAL | A | 258 | 78.844 | 28.155 | −74.456 | 1.00 | 30.26 | C |
| ATOM | 2040 | CG1 | VAL | A | 258 | 79.409 | 27.138 | −73.482 | 1.00 | 32.80 | C |

TABLE 2-continued

| | | | | | | | | | | |
|---|---|---|---|---|---|---|---|---|---|---|
| ATOM | 2041 | CG2 | VAL | A | 258 | 79.199 | 29.553 | −73.995 | 1.00 | 31.78 | C |
| ATOM | 2042 | N | SER | A | 259 | 77.861 | 28.181 | −77.733 | 1.00 | 23.95 | N |
| ATOM | 2043 | CA | SER | A | 259 | 77.134 | 28.964 | −78.726 | 1.00 | 24.53 | C |
| ATOM | 2044 | C | SER | A | 259 | 76.084 | 29.852 | −78.070 | 1.00 | 24.26 | C |
| ATOM | 2045 | O | SER | A | 259 | 75.575 | 29.537 | −76.995 | 1.00 | 23.65 | O |
| ATOM | 2046 | CB | SER | A | 259 | 76.453 | 28.042 | −79.748 | 1.00 | 26.72 | C |
| ATOM | 2047 | OG | SER | A | 259 | 75.285 | 27.450 | −79.201 | 1.00 | 26.46 | O |
| ATOM | 2048 | N | PHE | A | 260 | 75.766 | 30.968 | −78.716 | 1.00 | 23.67 | N |
| ATOM | 2049 | CA | PHE | A | 260 | 74.757 | 31.871 | −78.191 | 1.00 | 23.66 | C |
| ATOM | 2050 | C | PHE | A | 260 | 73.402 | 31.159 | −78.155 | 1.00 | 23.71 | C |
| ATOM | 2051 | O | PHE | A | 260 | 72.583 | 31.431 | −77.280 | 1.00 | 21.59 | O |
| ATOM | 2052 | CB | PHE | A | 260 | 74.683 | 33.135 | −79.054 | 1.00 | 27.45 | C |
| ATOM | 2053 | CG | PHE | A | 260 | 75.701 | 34.187 | −78.686 | 1.00 | 31.08 | C |
| ATOM | 2054 | CD1 | PHE | A | 260 | 76.910 | 33.839 | −78.085 | 1.00 | 31.13 | C |
| ATOM | 2055 | CD2 | PHE | A | 260 | 75.456 | 35.528 | −78.960 | 1.00 | 33.13 | C |
| ATOM | 2056 | CE1 | PHE | A | 260 | 77.860 | 34.812 | −77.764 | 1.00 | 34.26 | C |
| ATOM | 2057 | CE2 | PHE | A | 260 | 76.400 | 36.508 | −78.644 | 1.00 | 36.11 | C |
| ATOM | 2058 | CZ | PHE | A | 260 | 77.605 | 36.147 | −78.043 | 1.00 | 34.82 | C |
| ATOM | 2059 | N | GLU | A | 261 | 73.177 | 30.250 | −79.105 | 1.00 | 22.34 | N |
| ATOM | 2060 | CA | GLU | A | 261 | 71.930 | 29.471 | −79.170 | 1.00 | 24.71 | C |
| ATOM | 2061 | C | GLU | A | 261 | 71.765 | 28.738 | −77.837 | 1.00 | 23.03 | C |
| ATOM | 2062 | O | GLU | A | 261 | 70.687 | 28.736 | −77.239 | 1.00 | 22.15 | O |
| ATOM | 2063 | CB | GLU | A | 261 | 72.005 | 28.422 | −80.286 | 1.00 | 25.79 | C |
| ATOM | 2064 | CG | GLU | A | 261 | 70.934 | 28.504 | −81.364 | 1.00 | 33.07 | C |
| ATOM | 2065 | CD | GLU | A | 261 | 69.511 | 28.479 | −80.832 | 1.00 | 30.65 | C |
| ATOM | 2066 | OE1 | GLU | A | 261 | 69.101 | 27.481 | −80.201 | 1.00 | 33.52 | O |
| ATOM | 2067 | OE2 | GLU | A | 261 | 68.793 | 29.468 | −81.062 | 1.00 | 33.33 | O |
| ATOM | 2068 | N | GLU | A | 262 | 72.851 | 28.104 | −77.396 | 1.00 | 22.22 | N |
| ATOM | 2069 | CA | GLU | A | 262 | 72.883 | 27.369 | −76.134 | 1.00 | 21.99 | C |
| ATOM | 2070 | C | GLU | A | 262 | 72.590 | 28.289 | −74.959 | 1.00 | 21.11 | C |
| ATOM | 2071 | O | GLU | A | 262 | 71.769 | 27.972 | −74.099 | 1.00 | 21.34 | O |
| ATOM | 2072 | CB | GLU | A | 262 | 74.261 | 26.730 | −75.915 | 1.00 | 23.48 | C |
| ATOM | 2073 | CG | GLU | A | 262 | 74.322 | 25.226 | −76.138 | 1.00 | 31.10 | C |
| ATOM | 2074 | CD | GLU | A | 262 | 73.302 | 24.473 | −75.304 | 1.00 | 30.45 | C |
| ATOM | 2075 | OE1 | GLU | A | 262 | 72.100 | 24.734 | −75.485 | 1.00 | 32.76 | O |
| ATOM | 2076 | OE2 | GLU | A | 262 | 73.692 | 23.624 | −74.471 | 1.00 | 31.34 | O |
| ATOM | 2077 | N | LEU | A | 263 | 73.278 | 29.423 | −74.908 | 1.00 | 20.73 | N |
| ATOM | 2078 | CA | LEU | A | 263 | 73.072 | 30.370 | −73.815 | 1.00 | 20.46 | C |
| ATOM | 2079 | C | LEU | A | 263 | 71.623 | 30.836 | −73.782 | 1.00 | 20.97 | C |
| ATOM | 2080 | O | LEU | A | 263 | 71.025 | 30.958 | −72.719 | 1.00 | 21.74 | O |
| ATOM | 2081 | CB | LEU | A | 263 | 74.002 | 31.579 | −73.964 | 1.00 | 22.57 | C |
| ATOM | 2082 | CG | LEU | A | 263 | 75.505 | 31.303 | −73.888 | 1.00 | 22.39 | C |
| ATOM | 2083 | CD1 | LEU | A | 263 | 76.282 | 32.600 | −74.080 | 1.00 | 23.04 | C |
| ATOM | 2084 | CD2 | LEU | A | 263 | 75.835 | 30.671 | −72.550 | 1.00 | 22.42 | C |
| ATOM | 2085 | N | ARG | A | 264 | 71.060 | 31.105 | −74.952 | 1.00 | 21.34 | N |
| ATOM | 2086 | CA | ARG | A | 264 | 69.667 | 31.538 | −75.031 | 1.00 | 21.39 | C |
| ATOM | 2087 | C | ARG | A | 264 | 68.753 | 30.428 | −74.502 | 1.00 | 18.66 | C |
| ATOM | 2088 | O | ARG | A | 264 | 67.840 | 30.684 | −73.715 | 1.00 | 17.61 | O |
| ATOM | 2089 | CB | ARG | A | 264 | 69.285 | 31.852 | −76.482 | 1.00 | 21.87 | C |
| ATOM | 2090 | CG | ARG | A | 264 | 67.783 | 32.007 | −76.715 | 1.00 | 23.89 | C |
| ATOM | 2091 | CD | ARG | A | 264 | 67.408 | 31.701 | −78.160 | 1.00 | 27.07 | C |
| ATOM | 2092 | NE | ARG | A | 264 | 67.473 | 32.862 | −79.043 | 1.00 | 27.64 | N |
| ATOM | 2093 | CZ | ARG | A | 264 | 67.367 | 32.790 | −80.367 | 1.00 | 29.24 | C |
| ATOM | 2094 | NH1 | ARG | A | 264 | 67.201 | 31.609 | −80.963 | 1.00 | 23.29 | N |
| ATOM | 2095 | NH2 | ARG | A | 264 | 67.405 | 33.899 | −81.097 | 1.00 | 30.26 | N |
| ATOM | 2096 | N | THR | A | 265 | 69.007 | 29.195 | −74.933 | 1.00 | 17.61 | N |
| ATOM | 2097 | CA | THR | A | 265 | 68.185 | 28.060 | −74.513 | 1.00 | 18.67 | C |
| ATOM | 2098 | C | THR | A | 265 | 68.256 | 27.765 | −73.011 | 1.00 | 18.85 | C |
| ATOM | 2099 | O | THR | A | 265 | 67.256 | 27.374 | −72.413 | 1.00 | 18.14 | O |
| ATOM | 2100 | CB | THR | A | 265 | 68.543 | 26.809 | −75.336 | 1.00 | 19.31 | C |
| ATOM | 2101 | OG1 | THR | A | 265 | 68.291 | 27.092 | −76.720 | 1.00 | 20.55 | O |
| ATOM | 2102 | CG2 | THR | A | 265 | 67.687 | 25.600 | −74.918 | 1.00 | 17.33 | C |
| ATOM | 2103 | N | PHE | A | 266 | 69.420 | 27.971 | −72.396 | 1.00 | 20.88 | N |
| ATOM | 2104 | CA | PHE | A | 266 | 69.556 | 27.749 | −70.953 | 1.00 | 22.34 | C |
| ATOM | 2105 | C | PHE | A | 266 | 68.692 | 28.745 | −70.172 | 1.00 | 21.86 | C |
| ATOM | 2106 | O | PHE | A | 266 | 68.044 | 28.384 | −69.195 | 1.00 | 21.47 | O |
| ATOM | 2107 | CB | PHE | A | 266 | 71.010 | 27.935 | −70.489 | 1.00 | 25.42 | C |
| ATOM | 2108 | CG | PHE | A | 266 | 71.889 | 26.738 | −70.707 | 1.00 | 30.03 | C |
| ATOM | 2109 | CD1 | PHE | A | 266 | 71.511 | 25.480 | −70.240 | 1.00 | 32.92 | C |
| ATOM | 2110 | CD2 | PHE | A | 266 | 73.119 | 26.873 | −71.347 | 1.00 | 30.16 | C |
| ATOM | 2111 | CE1 | PHE | A | 266 | 72.352 | 24.371 | −70.406 | 1.00 | 33.14 | C |
| ATOM | 2112 | CE2 | PHE | A | 266 | 73.962 | 25.777 | −71.517 | 1.00 | 31.26 | C |
| ATOM | 2113 | CZ | PHE | A | 266 | 73.579 | 24.526 | −71.048 | 1.00 | 31.72 | C |
| ATOM | 2114 | N | GLY | A | 267 | 68.693 | 30.000 | −70.605 | 1.00 | 20.00 | N |
| ATOM | 2115 | CA | GLY | A | 267 | 67.934 | 31.019 | −69.902 | 1.00 | 21.24 | C |
| ATOM | 2116 | C | GLY | A | 267 | 68.659 | 31.398 | −68.615 | 1.00 | 22.52 | C |
| ATOM | 2117 | O | GLY | A | 267 | 69.875 | 31.223 | −68.510 | 1.00 | 20.45 | O |
| ATOM | 2118 | N | GLY | A | 268 | 67.915 | 31.922 | −67.644 | 1.00 | 22.92 | N |
| ATOM | 2119 | CA | GLY | A | 268 | 68.494 | 32.298 | −66.361 | 1.00 | 26.51 | C |

TABLE 2-continued

| ATOM | 2120 | C | GLY | A | 268 | 69.760 | 33.135 | −66.420 | 1.00 | 28.18 | C |
|---|---|---|---|---|---|---|---|---|---|---|---|
| ATOM | 2121 | O | GLY | A | 268 | 69.850 | 34.098 | −67.174 | 1.00 | 28.20 | O |
| ATOM | 2122 | N | HIS | A | 269 | 70.745 | 32.761 | −65.615 | 1.00 | 30.96 | N |
| ATOM | 2123 | CA | HIS | A | 269 | 72.014 | 33.478 | −65.566 | 1.00 | 33.65 | C |
| ATOM | 2124 | C | HIS | A | 269 | 72.831 | 33.434 | −66.863 | 1.00 | 32.16 | C |
| ATOM | 2125 | O | HIS | A | 269 | 73.291 | 34.466 | −67.350 | 1.00 | 32.04 | O |
| ATOM | 2126 | CB | HIS | A | 269 | 72.864 | 32.930 | −64.415 | 1.00 | 38.68 | C |
| ATOM | 2127 | CG | HIS | A | 269 | 74.278 | 33.423 | −64.422 | 1.00 | 44.57 | C |
| ATOM | 2128 | ND1 | HIS | A | 269 | 74.600 | 34.764 | −64.372 | 1.00 | 47.14 | N |
| ATOM | 2129 | CD2 | HIS | A | 269 | 75.455 | 32.756 | −64.486 | 1.00 | 46.17 | C |
| ATOM | 2130 | CE1 | HIS | A | 269 | 75.914 | 34.901 | −64.405 | 1.00 | 48.43 | C |
| ATOM | 2131 | NE2 | HIS | A | 269 | 76.457 | 33.698 | −64.474 | 1.00 | 48.21 | N |
| ATOM | 2132 | N | ASP | A | 270 | 73.010 | 32.239 | −67.415 | 1.00 | 31.36 | N |
| ATOM | 2133 | CA | ASP | A | 270 | 73.804 | 32.060 | −68.627 | 1.00 | 30.97 | C |
| ATOM | 2134 | C | ASP | A | 270 | 73.367 | 32.904 | −69.827 | 1.00 | 31.12 | C |
| ATOM | 2135 | O | ASP | A | 270 | 74.210 | 33.378 | −70.596 | 1.00 | 28.03 | O |
| ATOM | 2136 | CB | ASP | A | 270 | 73.823 | 30.584 | −69.024 | 1.00 | 31.88 | C |
| ATOM | 2137 | CG | ASP | A | 270 | 74.510 | 29.709 | −67.992 | 1.00 | 35.67 | C |
| ATOM | 2138 | OD1 | ASP | A | 270 | 75.058 | 30.252 | −67.007 | 1.00 | 35.43 | O |
| ATOM | 2139 | OD2 | ASP | A | 270 | 74.503 | 28.471 | −68.172 | 1.00 | 36.21 | O |
| ATOM | 2140 | N | ALA | A | 271 | 72.059 | 33.088 | −69.991 | 1.00 | 30.16 | N |
| ATOM | 2141 | CA | ALA | A | 271 | 71.537 | 33.869 | −71.107 | 1.00 | 30.23 | C |
| ATOM | 2142 | C | ALA | A | 271 | 71.967 | 35.331 | −71.008 | 1.00 | 30.72 | C |
| ATOM | 2143 | O | ALA | A | 271 | 72.012 | 36.039 | −72.013 | 1.00 | 29.87 | O |
| ATOM | 2144 | CB | ALA | A | 271 | 70.014 | 33.771 | −71.150 | 1.00 | 28.85 | C |
| ATOM | 2145 | N | LYS | A | 272 | 72.291 | 35.778 | −69.799 | 1.00 | 31.72 | N |
| ATOM | 2146 | CA | LYS | A | 272 | 72.712 | 37.160 | −69.596 | 1.00 | 33.93 | C |
| ATOM | 2147 | C | LYS | A | 272 | 74.103 | 37.427 | −70.168 | 1.00 | 33.20 | C |
| ATOM | 2148 | O | LYS | A | 272 | 74.535 | 38.575 | −70.245 | 1.00 | 33.80 | O |
| ATOM | 2149 | CB | LYS | A | 272 | 72.679 | 37.508 | −68.106 | 1.00 | 36.91 | C |
| ATOM | 2150 | CG | LYS | A | 272 | 71.302 | 37.342 | −67.476 | 1.00 | 40.86 | C |
| ATOM | 2151 | CD | LYS | A | 272 | 71.350 | 37.461 | −65.954 | 1.00 | 45.03 | C |
| ATOM | 2152 | CE | LYS | A | 272 | 70.018 | 37.049 | −65.327 | 1.00 | 47.39 | C |
| ATOM | 2153 | NZ | LYS | A | 272 | 70.060 | 37.056 | −63.835 | 1.00 | 49.88 | N |
| ATOM | 2154 | N | PHE | A | 273 | 74.810 | 36.374 | −70.567 | 1.00 | 33.40 | N |
| ATOM | 2155 | CA | PHE | A | 273 | 76.138 | 36.550 | −71.149 | 1.00 | 34.37 | C |
| ATOM | 2156 | C | PHE | A | 273 | 76.031 | 37.153 | −72.547 | 1.00 | 34.87 | C |
| ATOM | 2157 | O | PHE | A | 273 | 77.028 | 37.589 | −73.124 | 1.00 | 35.49 | O |
| ATOM | 2158 | CB | PHE | A | 273 | 76.891 | 35.220 | −71.217 | 1.00 | 34.29 | C |
| ATOM | 2159 | CG | PHE | A | 273 | 77.433 | 34.765 | −69.897 | 1.00 | 36.20 | C |
| ATOM | 2160 | CD1 | PHE | A | 273 | 78.236 | 35.612 | −69.136 | 1.00 | 38.26 | C |
| ATOM | 2161 | CD2 | PHE | A | 273 | 77.157 | 33.490 | −69.417 | 1.00 | 36.06 | C |
| ATOM | 2162 | CE1 | PHE | A | 273 | 78.758 | 35.193 | −67.916 | 1.00 | 38.41 | C |
| ATOM | 2163 | CE2 | PHE | A | 273 | 77.672 | 33.058 | −68.201 | 1.00 | 38.36 | C |
| ATOM | 2164 | CZ | PHE | A | 273 | 78.474 | 33.910 | −67.447 | 1.00 | 39.73 | C |
| ATOM | 2165 | N | ILE | A | 274 | 74.824 | 37.155 | −73.102 | 1.00 | 34.41 | N |
| ATOM | 2166 | CA | ILE | A | 274 | 74.607 | 37.741 | −74.418 | 1.00 | 36.72 | C |
| ATOM | 2167 | C | ILE | A | 274 | 74.324 | 39.227 | −74.206 | 1.00 | 39.97 | C |
| ATOM | 2168 | O | ILE | A | 274 | 73.423 | 39.606 | −73.454 | 1.00 | 38.89 | O |
| ATOM | 2169 | CB | ILE | A | 274 | 73.423 | 37.072 | −75.154 | 1.00 | 35.76 | C |
| ATOM | 2170 | CG1 | ILE | A | 274 | 73.780 | 35.621 | −75.483 | 1.00 | 34.46 | C |
| ATOM | 2171 | CG2 | ILE | A | 274 | 73.118 | 37.810 | −76.452 | 1.00 | 34.48 | C |
| ATOM | 2172 | CD1 | ILE | A | 274 | 72.623 | 34.818 | −76.008 | 1.00 | 34.48 | C |
| ATOM | 2173 | N | ASP | A | 275 | 75.121 | 40.059 | −74.865 | 1.00 | 43.61 | N |
| ATOM | 2174 | CA | ASP | A | 275 | 75.020 | 41.513 | −74.771 | 1.00 | 47.91 | C |
| ATOM | 2175 | C | ASP | A | 275 | 73.685 | 42.077 | −75.275 | 1.00 | 47.81 | C |
| ATOM | 2176 | O | ASP | A | 275 | 73.044 | 41.491 | −76.147 | 1.00 | 46.15 | O |
| ATOM | 2177 | CB | ASP | A | 275 | 76.182 | 42.130 | −75.557 | 1.00 | 51.93 | C |
| ATOM | 2178 | CG | ASP | A | 275 | 76.215 | 43.631 | −75.468 | 1.00 | 57.08 | C |
| ATOM | 2179 | OD1 | ASP | A | 275 | 76.184 | 44.157 | −74.335 | 1.00 | 60.62 | O |
| ATOM | 2180 | OD2 | ASP | A | 275 | 76.280 | 44.285 | −76.531 | 1.00 | 60.97 | O |
| ATOM | 2181 | N | SER | A | 276 | 73.273 | 43.219 | −74.727 | 1.00 | 47.49 | N |
| ATOM | 2182 | CA | SER | A | 276 | 72.022 | 43.853 | −75.136 | 1.00 | 48.43 | C |
| ATOM | 2183 | C | SER | A | 276 | 72.049 | 44.270 | −76.604 | 1.00 | 47.70 | C |
| ATOM | 2184 | O | SER | A | 276 | 71.052 | 44.132 | −77.317 | 1.00 | 47.17 | O |
| ATOM | 2185 | CB | SER | A | 276 | 71.729 | 45.075 | −74.265 | 1.00 | 49.09 | C |
| ATOM | 2186 | OG | SER | A | 276 | 71.412 | 44.684 | −72.944 | 1.00 | 53.28 | O |
| ATOM | 2187 | N | LEU | A | 277 | 73.187 | 44.789 | −77.052 | 1.00 | 47.10 | N |
| ATOM | 2188 | CA | LEU | A | 277 | 73.322 | 45.200 | −78.445 | 1.00 | 47.09 | C |
| ATOM | 2189 | C | LEU | A | 277 | 73.085 | 43.990 | −79.338 | 1.00 | 45.67 | C |
| ATOM | 2190 | O | LEU | A | 277 | 72.359 | 44.067 | −80.328 | 1.00 | 45.93 | O |
| ATOM | 2191 | CB | LEU | A | 277 | 74.723 | 45.758 | −78.717 | 1.00 | 46.98 | C |
| ATOM | 2192 | CG | LEU | A | 277 | 75.051 | 47.181 | −78.262 | 1.00 | 48.22 | C |
| ATOM | 2193 | CD1 | LEU | A | 277 | 76.535 | 47.444 | −78.476 | 1.00 | 48.12 | C |
| ATOM | 2194 | CD2 | LEU | A | 277 | 74.210 | 48.183 | −79.045 | 1.00 | 47.37 | C |
| ATOM | 2195 | N | GLN | A | 278 | 73.703 | 42.873 | −78.974 | 1.00 | 43.59 | N |
| ATOM | 2196 | CA | GLN | A | 278 | 73.576 | 41.641 | −79.737 | 1.00 | 43.05 | C |
| ATOM | 2197 | C | GLN | A | 278 | 72.145 | 41.132 | −79.733 | 1.00 | 41.83 | C |
| ATOM | 2198 | O | GLN | A | 278 | 71.623 | 40.714 | −80.767 | 1.00 | 40.55 | O |

TABLE 2-continued

| ATOM | 2199 | CB | GLN | A | 278 | 74.515 | 40.577 | −79.169 | 1.00 | 42.63 | C |
|---|---|---|---|---|---|---|---|---|---|---|---|
| ATOM | 2200 | CG | GLN | A | 278 | 75.981 | 40.946 | −79.302 | 1.00 | 44.93 | C |
| ATOM | 2201 | CD | GLN | A | 278 | 76.897 | 39.960 | −78.614 | 1.00 | 46.57 | C |
| ATOM | 2202 | OE1 | GLN | A | 278 | 76.800 | 39.744 | −77.402 | 1.00 | 47.27 | O |
| ATOM | 2203 | NE2 | GLN | A | 278 | 77.796 | 39.353 | −79.381 | 1.00 | 46.78 | N |
| ATOM | 2204 | N | GLU | A | 279 | 71.510 | 41.178 | −78.569 | 1.00 | 40.83 | N |
| ATOM | 2205 | CA | GLU | A | 279 | 70.138 | 40.717 | −78.439 | 1.00 | 42.10 | C |
| ATOM | 2206 | C | GLU | A | 279 | 69.187 | 41.483 | −79.359 | 1.00 | 41.42 | C |
| ATOM | 2207 | O | GLU | A | 279 | 68.354 | 40.881 | −80.041 | 1.00 | 39.32 | O |
| ATOM | 2208 | CB | GLU | A | 279 | 69.684 | 40.849 | −76.991 | 1.00 | 44.65 | C |
| ATOM | 2209 | CG | GLU | A | 279 | 68.308 | 40.289 | −76.733 | 1.00 | 51.09 | C |
| ATOM | 2210 | CD | GLU | A | 279 | 68.133 | 39.857 | −75.298 | 1.00 | 55.24 | C |
| ATOM | 2211 | OE1 | GLU | A | 279 | 68.312 | 40.708 | −74.397 | 1.00 | 57.42 | O |
| ATOM | 2212 | OE2 | GLU | A | 279 | 67.820 | 38.666 | −75.073 | 1.00 | 57.56 | O |
| ATOM | 2213 | N | ASN | A | 280 | 69.308 | 42.809 | −79.373 | 1.00 | 39.20 | N |
| ATOM | 2214 | CA | ASN | A | 280 | 68.460 | 43.624 | −80.228 | 1.00 | 38.37 | C |
| ATOM | 2215 | C | ASN | A | 280 | 68.783 | 43.337 | −81.685 | 1.00 | 36.56 | C |
| ATOM | 2216 | O | ASN | A | 280 | 67.898 | 43.331 | −82.537 | 1.00 | 36.40 | O |
| ATOM | 2217 | CB | ASN | A | 280 | 68.666 | 45.107 | −79.934 | 1.00 | 40.97 | C |
| ATOM | 2218 | CG | ASN | A | 280 | 68.222 | 45.483 | −78.541 | 1.00 | 44.31 | C |
| ATOM | 2219 | OD1 | ASN | A | 280 | 67.129 | 45.118 | −78.110 | 1.00 | 46.50 | O |
| ATOM | 2220 | ND2 | ASN | A | 280 | 69.064 | 46.223 | −77.828 | 1.00 | 46.47 | N |
| ATOM | 2221 | N | GLU | A | 281 | 70.059 | 43.097 | −81.962 | 1.00 | 33.99 | N |
| ATOM | 2222 | CA | GLU | A | 281 | 70.498 | 42.793 | −83.313 | 1.00 | 33.77 | C |
| ATOM | 2223 | C | GLU | A | 281 | 69.771 | 41.563 | −83.836 | 1.00 | 33.42 | C |
| ATOM | 2224 | O | GLU | A | 281 | 69.322 | 41.533 | −84.985 | 1.00 | 31.59 | O |
| ATOM | 2225 | CB | GLU | A | 281 | 71.996 | 42.512 | −83.338 | 1.00 | 35.05 | C |
| ATOM | 2226 | CG | GLU | A | 281 | 72.510 | 42.110 | −84.710 | 1.00 | 39.25 | C |
| ATOM | 2227 | CD | GLU | A | 281 | 73.712 | 41.189 | −84.638 | 1.00 | 41.46 | C |
| ATOM | 2228 | OE1 | GLU | A | 281 | 74.646 | 41.486 | −83.864 | 1.00 | 42.29 | O |
| ATOM | 2229 | OE2 | GLU | A | 281 | 73.721 | 40.170 | −85.361 | 1.00 | 45.18 | O |
| ATOM | 2230 | N | PHE | A | 282 | 69.677 | 40.542 | −82.988 | 1.00 | 32.35 | N |
| ATOM | 2231 | CA | PHE | A | 282 | 69.016 | 39.297 | −83.362 | 1.00 | 30.50 | C |
| ATOM | 2232 | C | PHE | A | 282 | 67.525 | 39.485 | −83.572 | 1.00 | 28.94 | C |
| ATOM | 2233 | O | PHE | A | 282 | 66.976 | 39.056 | −84.584 | 1.00 | 28.54 | O |
| ATOM | 2234 | CB | PHE | A | 282 | 69.241 | 38.226 | −82.293 | 1.00 | 30.27 | C |
| ATOM | 2235 | CG | PHE | A | 282 | 70.669 | 37.794 | −82.163 | 1.00 | 30.13 | C |
| ATOM | 2236 | CD1 | PHE | A | 282 | 71.401 | 37.429 | −83.288 | 1.00 | 28.82 | C |
| ATOM | 2237 | CD2 | PHE | A | 282 | 71.281 | 37.744 | −80.917 | 1.00 | 30.00 | C |
| ATOM | 2238 | CE1 | PHE | A | 282 | 72.720 | 37.021 | −83.176 | 1.00 | 30.62 | C |
| ATOM | 2239 | CE2 | PHE | A | 282 | 72.605 | 37.336 | −80.793 | 1.00 | 31.83 | C |
| ATOM | 2240 | CZ | PHE | A | 282 | 73.327 | 36.974 | −81.927 | 1.00 | 29.89 | C |
| ATOM | 2241 | N | ARG | A | 283 | 66.872 | 40.128 | −82.613 | 1.00 | 28.53 | N |
| ATOM | 2242 | CA | ARG | A | 283 | 65.439 | 40.351 | −82.701 | 1.00 | 31.37 | C |
| ATOM | 2243 | C | ARG | A | 283 | 65.070 | 41.096 | −83.985 | 1.00 | 32.20 | C |
| ATOM | 2244 | O | ARG | A | 283 | 64.095 | 40.750 | −84.655 | 1.00 | 31.23 | O |
| ATOM | 2245 | CB | ARG | A | 283 | 64.957 | 41.123 | −81.473 | 1.00 | 32.00 | C |
| ATOM | 2246 | CG | ARG | A | 283 | 63.459 | 41.267 | −81.396 | 1.00 | 37.02 | C |
| ATOM | 2247 | CD | ARG | A | 283 | 63.034 | 41.872 | −80.078 | 1.00 | 41.99 | C |
| ATOM | 2248 | NE | ARG | A | 283 | 63.749 | 43.110 | −79.795 | 1.00 | 49.45 | N |
| ATOM | 2249 | CZ | ARG | A | 283 | 63.407 | 43.970 | −78.840 | 1.00 | 53.09 | C |
| ATOM | 2250 | NH1 | ARG | A | 283 | 62.351 | 43.732 | −78.069 | 1.00 | 54.87 | N |
| ATOM | 2251 | NH2 | ARG | A | 283 | 64.122 | 45.071 | −78.654 | 1.00 | 54.64 | N |
| ATOM | 2252 | N | LEU | A | 284 | 65.862 | 42.103 | −84.339 | 1.00 | 32.19 | N |
| ATOM | 2253 | CA | LEU | A | 284 | 65.600 | 42.881 | −85.543 | 1.00 | 33.25 | C |
| ATOM | 2254 | C | LEU | A | 284 | 65.873 | 42.025 | −86.769 | 1.00 | 31.72 | C |
| ATOM | 2255 | O | LEU | A | 284 | 65.155 | 42.096 | −87.768 | 1.00 | 30.97 | O |
| ATOM | 2256 | CB | LEU | A | 284 | 66.487 | 44.129 | −85.570 | 1.00 | 35.94 | C |
| ATOM | 2257 | CG | LEU | A | 284 | 65.997 | 45.314 | −86.410 | 1.00 | 40.06 | C |
| ATOM | 2258 | CD1 | LEU | A | 284 | 66.029 | 44.970 | −87.887 | 1.00 | 42.39 | C |
| ATOM | 2259 | CD2 | LEU | A | 284 | 64.582 | 45.688 | −85.977 | 1.00 | 42.08 | C |
| ATOM | 2260 | N | TYR | A | 285 | 66.911 | 41.201 | −86.682 | 1.00 | 30.33 | N |
| ATOM | 2261 | CA | TYR | A | 285 | 67.283 | 40.334 | −87.789 | 1.00 | 28.58 | C |
| ATOM | 2262 | C | TYR | A | 285 | 66.143 | 39.392 | −88.184 | 1.00 | 28.51 | C |
| ATOM | 2263 | O | TYR | A | 285 | 65.742 | 39.330 | −89.352 | 1.00 | 26.89 | O |
| ATOM | 2264 | CB | TYR | A | 285 | 68.513 | 39.514 | −87.410 | 1.00 | 30.93 | C |
| ATOM | 2265 | CG | TYR | A | 285 | 69.029 | 38.635 | −88.520 | 1.00 | 31.05 | C |
| ATOM | 2266 | CD1 | TYR | A | 285 | 69.746 | 39.176 | −89.582 | 1.00 | 32.84 | C |
| ATOM | 2267 | CD2 | TYR | A | 285 | 68.808 | 37.255 | −88.504 | 1.00 | 31.84 | C |
| ATOM | 2268 | CE1 | TYR | A | 285 | 70.239 | 38.366 | −90.605 | 1.00 | 34.89 | C |
| ATOM | 2269 | CE2 | TYR | A | 285 | 69.296 | 36.437 | −89.524 | 1.00 | 33.38 | C |
| ATOM | 2270 | CZ | TYR | A | 285 | 70.010 | 37.002 | −90.572 | 1.00 | 33.34 | C |
| ATOM | 2271 | OH | TYR | A | 285 | 70.486 | 36.212 | −91.595 | 1.00 | 32.74 | O |
| ATOM | 2272 | N | TYR | A | 286 | 65.626 | 38.657 | −87.209 | 1.00 | 26.02 | N |
| ATOM | 2273 | CA | TYR | A | 286 | 64.544 | 37.719 | −87.469 | 1.00 | 26.74 | C |
| ATOM | 2274 | C | TYR | A | 286 | 63.230 | 38.412 | −87.795 | 1.00 | 27.81 | C |
| ATOM | 2275 | O | TYR | A | 286 | 62.388 | 37.855 | −88.495 | 1.00 | 27.16 | O |
| ATOM | 2276 | CB | TYR | A | 286 | 64.398 | 36.764 | −86.280 | 1.00 | 25.27 | C |
| ATOM | 2277 | CG | TYR | A | 286 | 65.626 | 35.895 | −86.147 | 1.00 | 24.69 | C |

TABLE 2-continued

| | | | | | | | | | | |
|---|---|---|---|---|---|---|---|---|---|---|
| ATOM | 2278 | CD1 | TYR | A | 286 | 65.979 | 35.012 | −87.164 | 1.00 | 21.95 | C |
| ATOM | 2279 | CD2 | TYR | A | 286 | 66.489 | 36.027 | −85.062 | 1.00 | 23.75 | C |
| ATOM | 2280 | CE1 | TYR | A | 286 | 67.159 | 34.292 | −87.111 | 1.00 | 23.66 | C |
| ATOM | 2281 | CE2 | TYR | A | 286 | 67.681 | 35.306 | −85.003 | 1.00 | 25.26 | C |
| ATOM | 2282 | CZ | TYR | A | 286 | 68.006 | 34.446 | −86.035 | 1.00 | 23.79 | C |
| ATOM | 2283 | OH | TYR | A | 286 | 69.199 | 33.760 | −86.018 | 1.00 | 28.45 | O |
| ATOM | 2284 | N | TYR | A | 287 | 63.054 | 39.625 | −87.284 | 1.00 | 29.39 | N |
| ATOM | 2285 | CA | TYR | A | 287 | 61.850 | 40.396 | −87.566 | 1.00 | 30.20 | C |
| ATOM | 2286 | C | TYR | A | 287 | 61.828 | 40.640 | −89.079 | 1.00 | 30.08 | C |
| ATOM | 2287 | O | TYR | A | 287 | 60.786 | 40.556 | −89.729 | 1.00 | 29.19 | O |
| ATOM | 2288 | CB | TYR | A | 287 | 61.900 | 41.725 | −86.812 | 1.00 | 32.54 | C |
| ATOM | 2289 | CG | TYR | A | 287 | 60.911 | 42.761 | −87.297 | 1.00 | 33.57 | C |
| ATOM | 2290 | CD1 | TYR | A | 287 | 59.544 | 42.595 | −87.105 | 1.00 | 34.23 | C |
| ATOM | 2291 | CD2 | TYR | A | 287 | 61.351 | 43.908 | −87.955 | 1.00 | 35.15 | C |
| ATOM | 2292 | CE1 | TYR | A | 287 | 58.633 | 43.550 | −87.558 | 1.00 | 36.73 | C |
| ATOM | 2293 | CE2 | TYR | A | 287 | 60.452 | 44.870 | −88.412 | 1.00 | 37.13 | C |
| ATOM | 2294 | CZ | TYR | A | 287 | 59.096 | 44.684 | −88.210 | 1.00 | 36.65 | C |
| ATOM | 2295 | OH | TYR | A | 287 | 58.209 | 45.627 | −88.663 | 1.00 | 37.62 | O |
| ATOM | 2296 | N | ASN | A | 288 | 62.998 | 40.929 | −89.630 | 1.00 | 29.96 | N |
| ATOM | 2297 | CA | ASN | A | 288 | 63.130 | 41.175 | −91.056 | 1.00 | 30.74 | C |
| ATOM | 2298 | C | ASN | A | 288 | 62.871 | 39.897 | −91.841 | 1.00 | 31.32 | C |
| ATOM | 2299 | O | ASN | A | 288 | 62.293 | 39.936 | −92.931 | 1.00 | 29.76 | O |
| ATOM | 2300 | CB | ASN | A | 288 | 64.528 | 41.718 | −91.361 | 1.00 | 30.28 | C |
| ATOM | 2301 | CG | ASN | A | 288 | 64.681 | 43.175 | −90.955 | 1.00 | 33.65 | C |
| ATOM | 2302 | OD1 | ASN | A | 288 | 65.779 | 43.631 | −90.630 | 1.00 | 36.60 | O |
| ATOM | 2303 | ND2 | ASN | A | 288 | 63.578 | 43.918 | −90.986 | 1.00 | 29.75 | N |
| ATOM | 2304 | N | LYS | A | 289 | 63.298 | 38.765 | −91.285 | 1.00 | 30.42 | N |
| ATOM | 2305 | CA | LYS | A | 289 | 63.089 | 37.475 | −91.940 | 1.00 | 30.36 | C |
| ATOM | 2306 | C | LYS | A | 289 | 61.600 | 37.173 | −92.046 | 1.00 | 28.65 | C |
| ATOM | 2307 | O | LYS | A | 289 | 61.140 | 36.646 | −93.055 | 1.00 | 30.77 | O |
| ATOM | 2308 | CB | LYS | A | 289 | 63.801 | 36.360 | −91.169 | 1.00 | 30.68 | C |
| ATOM | 2309 | CG | LYS | A | 289 | 65.291 | 36.268 | −91.451 | 1.00 | 32.31 | C |
| ATOM | 2310 | CD | LYS | A | 289 | 65.543 | 35.984 | −92.926 | 1.00 | 34.43 | C |
| ATOM | 2311 | CE | LYS | A | 289 | 66.993 | 35.610 | −93.191 | 1.00 | 36.02 | C |
| ATOM | 2312 | NZ | LYS | A | 289 | 67.929 | 36.726 | −92.934 | 1.00 | 37.96 | N |
| ATOM | 2313 | N | PHE | A | 290 | 60.851 | 37.511 | −91.002 | 1.00 | 26.90 | N |
| ATOM | 2314 | CA | PHE | A | 290 | 59.411 | 37.291 | −90.988 | 1.00 | 26.89 | C |
| ATOM | 2315 | C | PHE | A | 290 | 58.729 | 38.193 | −92.025 | 1.00 | 29.63 | C |
| ATOM | 2316 | O | PHE | A | 290 | 57.715 | 37.820 | −92.624 | 1.00 | 28.10 | O |
| ATOM | 2317 | CB | PHE | A | 290 | 58.847 | 37.579 | −89.590 | 1.00 | 24.39 | C |
| ATOM | 2318 | CG | PHE | A | 290 | 58.948 | 36.412 | −88.628 | 1.00 | 21.96 | C |
| ATOM | 2319 | CD1 | PHE | A | 290 | 60.050 | 35.563 | −88.646 | 1.00 | 20.76 | C |
| ATOM | 2320 | CD2 | PHE | A | 290 | 57.943 | 36.180 | −87.691 | 1.00 | 20.73 | C |
| ATOM | 2321 | CE1 | PHE | A | 290 | 60.150 | 34.492 | −87.741 | 1.00 | 23.59 | C |
| ATOM | 2322 | CE2 | PHE | A | 290 | 58.031 | 35.114 | −86.779 | 1.00 | 22.18 | C |
| ATOM | 2323 | CZ | PHE | A | 290 | 59.136 | 34.270 | −86.806 | 1.00 | 21.02 | C |
| ATOM | 2324 | N | LYS | A | 291 | 59.280 | 39.386 | −92.228 | 1.00 | 30.13 | N |
| ATOM | 2325 | CA | LYS | A | 291 | 58.722 | 40.314 | −93.204 | 1.00 | 31.82 | C |
| ATOM | 2326 | C | LYS | A | 291 | 58.948 | 39.765 | −94.600 | 1.00 | 31.06 | C |
| ATOM | 2327 | O | LYS | A | 291 | 58.086 | 39.890 | −95.464 | 1.00 | 33.00 | O |
| ATOM | 2328 | CB | LYS | A | 291 | 59.373 | 41.694 | −93.069 | 1.00 | 32.63 | C |
| ATOM | 2329 | CG | LYS | A | 291 | 59.023 | 42.398 | −91.767 | 1.00 | 35.95 | C |
| ATOM | 2330 | CD | LYS | A | 291 | 59.737 | 43.734 | −91.631 | 1.00 | 40.57 | C |
| ATOM | 2331 | CE | LYS | A | 291 | 59.213 | 44.760 | −92.619 | 1.00 | 41.22 | C |
| ATOM | 2332 | NZ | LYS | A | 291 | 59.953 | 46.053 | −92.500 | 1.00 | 45.62 | N |
| ATOM | 2333 | N | ASP | A | 292 | 60.103 | 39.145 | −94.819 | 1.00 | 30.63 | N |
| ATOM | 2334 | CA | ASP | A | 292 | 60.404 | 38.578 | −96.127 | 1.00 | 31.45 | C |
| ATOM | 2335 | C | ASP | A | 292 | 59.431 | 37.455 | −96.445 | 1.00 | 31.31 | C |
| ATOM | 2336 | O | ASP | A | 292 | 59.000 | 37.297 | −97.591 | 1.00 | 32.00 | O |
| ATOM | 2337 | CB | ASP | A | 292 | 61.837 | 38.051 | −96.176 | 1.00 | 32.67 | C |
| ATOM | 2338 | CG | ASP | A | 292 | 62.859 | 39.143 | −95.955 | 1.00 | 35.97 | C |
| ATOM | 2339 | OD1 | ASP | A | 292 | 62.503 | 40.325 | −96.150 | 1.00 | 36.38 | O |
| ATOM | 2340 | OD2 | ASP | A | 292 | 64.015 | 38.825 | −95.596 | 1.00 | 37.45 | O |
| ATOM | 2341 | N | ILE | A | 293 | 59.084 | 36.678 | −95.423 | 1.00 | 29.64 | N |
| ATOM | 2342 | CA | ILE | A | 293 | 58.149 | 35.583 | −95.593 | 1.00 | 27.24 | C |
| ATOM | 2343 | C | ILE | A | 293 | 56.778 | 36.123 | −95.961 | 1.00 | 27.32 | C |
| ATOM | 2344 | O | ILE | A | 293 | 56.155 | 35.641 | −96.903 | 1.00 | 27.75 | O |
| ATOM | 2345 | CB | ILE | A | 293 | 58.038 | 34.738 | −94.310 | 1.00 | 27.34 | C |
| ATOM | 2346 | CG1 | ILE | A | 293 | 59.306 | 33.896 | −94.148 | 1.00 | 26.68 | C |
| ATOM | 2347 | CG2 | ILE | A | 293 | 56.808 | 33.844 | −94.383 | 1.00 | 26.60 | C |
| ATOM | 2348 | CD1 | ILE | A | 293 | 59.384 | 33.129 | −92.846 | 1.00 | 30.16 | C |
| ATOM | 2349 | N | ALA | A | 294 | 56.311 | 37.119 | −95.216 | 1.00 | 25.01 | N |
| ATOM | 2350 | CA | ALA | A | 294 | 55.010 | 37.716 | −95.483 | 1.00 | 29.00 | C |
| ATOM | 2351 | C | ALA | A | 294 | 54.999 | 38.269 | −96.914 | 1.00 | 29.75 | C |
| ATOM | 2352 | O | ALA | A | 294 | 53.976 | 38.223 | −97.603 | 1.00 | 28.78 | O |
| ATOM | 2353 | CB | ALA | A | 294 | 54.723 | 38.831 | −94.479 | 1.00 | 25.62 | C |
| ATOM | 2354 | N | SER | A | 295 | 56.149 | 38.777 | −97.347 | 1.00 | 30.62 | N |
| ATOM | 2355 | CA | SER | A | 295 | 56.305 | 39.323 | −98.688 | 1.00 | 32.28 | C |
| ATOM | 2356 | C | SER | A | 295 | 56.171 | 38.198 | −99.706 | 1.00 | 31.38 | C |

TABLE 2-continued

| ATOM | 2357 | O | SER | A | 295 | 55.500 | 38.344 | −100.730 | 1.00 | 29.86 | O |
|---|---|---|---|---|---|---|---|---|---|---|---|
| ATOM | 2358 | CB | SER | A | 295 | 57.680 | 39.992 | −98.827 | 1.00 | 34.53 | C |
| ATOM | 2359 | OG | SER | A | 295 | 57.962 | 40.327 | −100.179 | 1.00 | 37.15 | O |
| ATOM | 2360 | N | THR | A | 296 | 56.813 | 37.072 | −99.419 | 1.00 | 29.46 | N |
| ATOM | 2361 | CA | THR | A | 296 | 56.752 | 35.923 | −100.310 | 1.00 | 28.58 | C |
| ATOM | 2362 | C | THR | A | 296 | 55.316 | 35.433 | −100.422 | 1.00 | 29.04 | C |
| ATOM | 2363 | O | THR | A | 296 | 54.852 | 35.074 | −101.508 | 1.00 | 30.49 | O |
| ATOM | 2364 | CB | THR | A | 296 | 57.648 | 34.783 | −99.795 | 1.00 | 29.02 | C |
| ATOM | 2365 | OG1 | THR | A | 296 | 59.009 | 35.223 | −99.807 | 1.00 | 26.90 | O |
| ATOM | 2366 | CG2 | THR | A | 296 | 57.517 | 33.544 | −100.674 | 1.00 | 27.10 | C |
| ATOM | 2367 | N | LEU | A | 297 | 54.608 | 35.437 | −99.297 | 1.00 | 26.76 | N |
| ATOM | 2368 | CA | LEU | A | 297 | 53.223 | 34.992 | −99.273 | 1.00 | 27.39 | C |
| ATOM | 2369 | C | LEU | A | 297 | 52.310 | 35.935 | −100.067 | 1.00 | 29.46 | C |
| ATOM | 2370 | O | LEU | A | 297 | 51.338 | 35.494 | −100.682 | 1.00 | 28.24 | O |
| ATOM | 2371 | CB | LEU | A | 297 | 52.735 | 34.865 | −97.822 | 1.00 | 23.47 | C |
| ATOM | 2372 | CG | LEU | A | 297 | 53.293 | 33.677 | −97.014 | 1.00 | 22.98 | C |
| ATOM | 2373 | CD1 | LEU | A | 297 | 52.846 | 33.776 | −95.567 | 1.00 | 23.98 | C |
| ATOM | 2374 | CD2 | LEU | A | 297 | 52.804 | 32.360 | −97.623 | 1.00 | 22.51 | C |
| ATOM | 2375 | N | ASN | A | 298 | 52.625 | 37.228 | −100.057 | 1.00 | 30.18 | N |
| ATOM | 2376 | CA | ASN | A | 298 | 51.824 | 38.202 | −100.790 | 1.00 | 32.65 | C |
| ATOM | 2377 | C | ASN | A | 298 | 52.015 | 38.066 | −102.296 | 1.00 | 32.88 | C |
| ATOM | 2378 | O | ASN | A | 298 | 51.128 | 38.418 | −103.067 | 1.00 | 35.72 | O |
| ATOM | 2379 | CB | ASN | A | 298 | 52.176 | 39.631 | −100.367 | 1.00 | 31.82 | C |
| ATOM | 2380 | CG | ASN | A | 298 | 51.737 | 39.950 | −98.951 | 1.00 | 31.82 | C |
| ATOM | 2381 | OD1 | ASN | A | 298 | 50.680 | 39.505 | −98.492 | 1.00 | 30.44 | O |
| ATOM | 2382 | ND2 | ASN | A | 298 | 52.540 | 40.749 | −98.254 | 1.00 | 32.31 | N |
| ATOM | 2383 | N | LYS | A | 299 | 53.167 | 37.550 | −102.709 | 1.00 | 33.64 | N |
| ATOM | 2384 | CA | LYS | A | 299 | 53.459 | 37.379 | −104.126 | 1.00 | 36.15 | C |
| ATOM | 2385 | C | LYS | A | 299 | 53.100 | 36.000 | −104.666 | 1.00 | 35.13 | C |
| ATOM | 2386 | O | LYS | A | 299 | 53.189 | 35.765 | −105.871 | 1.00 | 36.23 | O |
| ATOM | 2387 | CB | LYS | A | 299 | 54.939 | 37.659 | −104.392 | 1.00 | 38.68 | C |
| ATOM | 2388 | CG | LYS | A | 299 | 55.376 | 39.062 | −103.982 | 1.00 | 42.46 | C |
| ATOM | 2389 | CD | LYS | A | 299 | 56.866 | 39.273 | −104.193 | 1.00 | 44.76 | C |
| ATOM | 2390 | CE | LYS | A | 299 | 57.324 | 40.579 | −103.558 | 1.00 | 47.34 | C |
| ATOM | 2391 | NZ | LYS | A | 299 | 58.800 | 40.769 | −103.686 | 1.00 | 50.49 | N |
| ATOM | 2392 | N | ALA | A | 300 | 52.693 | 35.092 | −103.782 | 1.00 | 33.47 | N |
| ATOM | 2393 | CA | ALA | A | 300 | 52.326 | 33.741 | −104.191 | 1.00 | 32.53 | C |
| ATOM | 2394 | C | ALA | A | 300 | 51.040 | 33.766 | −105.007 | 1.00 | 32.22 | C |
| ATOM | 2395 | O | ALA | A | 300 | 50.012 | 34.264 | −104.545 | 1.00 | 30.41 | O |
| ATOM | 2396 | CB | ALA | A | 300 | 52.143 | 32.845 | −102.971 | 1.00 | 32.46 | C |
| ATOM | 2397 | N | LYS | A | 301 | 51.102 | 33.214 | −106.213 | 1.00 | 31.51 | N |
| ATOM | 2398 | CA | LYS | A | 301 | 49.940 | 33.179 | −107.090 | 1.00 | 33.43 | C |
| ATOM | 2399 | C | LYS | A | 301 | 49.450 | 31.751 | −107.266 | 1.00 | 32.00 | C |
| ATOM | 2400 | O | LYS | A | 301 | 48.282 | 31.528 | −107.578 | 1.00 | 31.97 | O |
| ATOM | 2401 | CB | LYS | A | 301 | 50.286 | 33.756 | −108.469 | 1.00 | 36.65 | C |
| ATOM | 2402 | CG | LYS | A | 301 | 51.180 | 34.992 | −108.453 | 1.00 | 40.11 | C |
| ATOM | 2403 | CD | LYS | A | 301 | 50.541 | 36.176 | −107.740 | 1.00 | 44.80 | C |
| ATOM | 2404 | CE | LYS | A | 301 | 51.481 | 37.383 | −107.759 | 1.00 | 46.20 | C |
| ATOM | 2405 | NZ | LYS | A | 301 | 50.895 | 38.578 | −107.087 | 1.00 | 50.18 | N |
| ATOM | 2406 | N | SER | A | 302 | 50.346 | 30.785 | −107.073 | 1.00 | 30.14 | N |
| ATOM | 2407 | CA | SER | A | 302 | 49.987 | 29.381 | −107.230 | 1.00 | 29.96 | C |
| ATOM | 2408 | C | SER | A | 302 | 50.650 | 28.470 | −106.196 | 1.00 | 29.47 | C |
| ATOM | 2409 | O | SER | A | 302 | 51.550 | 28.882 | −105.465 | 1.00 | 28.14 | O |
| ATOM | 2410 | CB | SER | A | 302 | 50.376 | 28.890 | −108.626 | 1.00 | 28.74 | C |
| ATOM | 2411 | OG | SER | A | 302 | 51.785 | 28.772 | −108.744 | 1.00 | 30.90 | O |
| ATOM | 2412 | N | ILE | A | 303 | 50.199 | 27.220 | −106.168 | 1.00 | 28.31 | N |
| ATOM | 2413 | CA | ILE | A | 303 | 50.724 | 26.211 | −105.255 | 1.00 | 27.42 | C |
| ATOM | 2414 | C | ILE | A | 303 | 50.691 | 24.853 | −105.960 | 1.00 | 26.70 | C |
| ATOM | 2415 | O | ILE | A | 303 | 49.774 | 24.567 | −106.731 | 1.00 | 27.01 | O |
| ATOM | 2416 | CB | ILE | A | 303 | 49.872 | 26.141 | −103.977 | 1.00 | 26.36 | C |
| ATOM | 2417 | CG1 | ILE | A | 303 | 50.511 | 25.191 | −102.964 | 1.00 | 26.40 | C |
| ATOM | 2418 | CG2 | ILE | A | 303 | 48.470 | 25.676 | −104.321 | 1.00 | 30.08 | C |
| ATOM | 2419 | CD1 | ILE | A | 303 | 49.797 | 25.171 | −101.627 | 1.00 | 22.51 | C |
| ATOM | 2420 | N | VAL | A | 304 | 51.698 | 24.025 | −105.713 | 1.00 | 25.37 | N |
| ATOM | 2421 | CA | VAL | A | 304 | 51.760 | 22.706 | −106.328 | 1.00 | 25.27 | C |
| ATOM | 2422 | C | VAL | A | 304 | 52.037 | 21.644 | −105.271 | 1.00 | 25.08 | C |
| ATOM | 2423 | O | VAL | A | 304 | 52.697 | 21.923 | −104.274 | 1.00 | 24.72 | O |
| ATOM | 2424 | CB | VAL | A | 304 | 52.894 | 22.621 | −107.370 | 1.00 | 25.46 | C |
| ATOM | 2425 | CG1 | VAL | A | 304 | 52.715 | 23.692 | −108.426 | 1.00 | 30.45 | C |
| ATOM | 2426 | CG2 | VAL | A | 304 | 54.240 | 22.770 | −106.687 | 1.00 | 27.25 | C |
| ATOM | 2427 | N | GLY | A | 305 | 51.521 | 20.436 | −105.478 | 1.00 | 22.43 | N |
| ATOM | 2428 | CA | GLY | A | 305 | 51.796 | 19.355 | −104.542 | 1.00 | 21.44 | C |
| ATOM | 2429 | C | GLY | A | 305 | 50.859 | 19.034 | −103.394 | 1.00 | 20.48 | C |
| ATOM | 2430 | O | GLY | A | 305 | 51.188 | 18.193 | −102.563 | 1.00 | 18.89 | O |
| ATOM | 2431 | N | THR | A | 306 | 49.703 | 19.681 | −103.313 | 1.00 | 20.17 | N |
| ATOM | 2432 | CA | THR | A | 306 | 48.781 | 19.371 | −102.227 | 1.00 | 19.88 | C |
| ATOM | 2433 | C | THR | A | 306 | 47.327 | 19.511 | −102.667 | 1.00 | 20.57 | C |
| ATOM | 2434 | O | THR | A | 306 | 47.013 | 20.276 | −103.580 | 1.00 | 21.92 | O |
| ATOM | 2435 | CB | THR | A | 306 | 49.028 | 20.277 | −100.987 | 1.00 | 20.84 | C |

TABLE 2-continued

| ATOM | 2436 | OG1 | THR | A | 306 | 48.202 | 19.836 | −99.894 | 1.00 | 20.64 | O |
|---|---|---|---|---|---|---|---|---|---|---|---|
| ATOM | 2437 | CG2 | THR | A | 306 | 48.698 | 21.728 | −101.305 | 1.00 | 21.88 | C |
| ATOM | 2438 | N | THR | A | 307 | 46.450 | 18.762 | −102.010 | 1.00 | 20.06 | N |
| ATOM | 2439 | CA | THR | A | 307 | 45.023 | 18.787 | −102.297 | 1.00 | 18.99 | C |
| ATOM | 2440 | C | THR | A | 307 | 44.404 | 20.084 | −101.777 | 1.00 | 19.92 | C |
| ATOM | 2441 | O | THR | A | 307 | 43.329 | 20.489 | −102.222 | 1.00 | 19.35 | O |
| ATOM | 2442 | CB | THR | A | 307 | 44.309 | 17.614 | −101.602 | 1.00 | 19.85 | C |
| ATOM | 2443 | OG1 | THR | A | 307 | 44.538 | 17.700 | −100.188 | 1.00 | 14.47 | O |
| ATOM | 2444 | CG2 | THR | A | 307 | 44.829 | 16.280 | −102.111 | 1.00 | 17.26 | C |
| ATOM | 2445 | N | ALA | A | 308 | 45.093 | 20.734 | −100.839 | 1.00 | 20.68 | N |
| ATOM | 2446 | CA | ALA | A | 308 | 44.599 | 21.967 | −100.221 | 1.00 | 18.94 | C |
| ATOM | 2447 | C | ALA | A | 308 | 44.709 | 23.201 | −101.110 | 1.00 | 19.53 | C |
| ATOM | 2448 | O | ALA | A | 308 | 45.576 | 23.287 | −101.975 | 1.00 | 18.09 | O |
| ATOM | 2449 | CB | ALA | A | 308 | 45.330 | 22.218 | −98.885 | 1.00 | 19.38 | C |
| ATOM | 2450 | N | SER | A | 309 | 43.838 | 24.173 | −100.857 | 1.00 | 20.27 | N |
| ATOM | 2451 | CA | SER | A | 309 | 43.814 | 25.407 | −101.641 | 1.00 | 21.56 | C |
| ATOM | 2452 | C | SER | A | 309 | 44.939 | 26.365 | −101.279 | 1.00 | 21.85 | C |
| ATOM | 2453 | O | SER | A | 309 | 45.508 | 26.300 | −100.182 | 1.00 | 21.14 | O |
| ATOM | 2454 | CB | SER | A | 309 | 42.483 | 26.129 | −101.440 | 1.00 | 20.37 | C |
| ATOM | 2455 | OG | SER | A | 309 | 42.432 | 26.730 | −100.155 | 1.00 | 21.25 | O |
| ATOM | 2456 | N | LEU | A | 310 | 45.240 | 27.266 | −102.210 | 1.00 | 20.16 | N |
| ATOM | 2457 | CA | LEU | A | 310 | 46.273 | 28.268 | −102.011 | 1.00 | 20.98 | C |
| ATOM | 2458 | C | LEU | A | 310 | 45.939 | 29.139 | −100.808 | 1.00 | 20.98 | C |
| ATOM | 2459 | O | LEU | A | 310 | 46.794 | 29.397 | −99.967 | 1.00 | 22.16 | O |
| ATOM | 2460 | CB | LEU | A | 310 | 46.412 | 29.144 | −103.260 | 1.00 | 21.78 | C |
| ATOM | 2461 | CG | LEU | A | 310 | 47.350 | 30.350 | −103.138 | 1.00 | 23.27 | C |
| ATOM | 2462 | CD1 | LEU | A | 310 | 48.727 | 29.891 | −102.679 | 1.00 | 23.88 | C |
| ATOM | 2463 | CD2 | LEU | A | 310 | 47.447 | 31.066 | −104.488 | 1.00 | 25.75 | C |
| ATOM | 2464 | N | GLN | A | 311 | 44.691 | 29.583 | −100.715 | 1.00 | 20.05 | N |
| ATOM | 2465 | CA | GLN | A | 311 | 44.289 | 30.437 | −99.602 | 1.00 | 20.48 | C |
| ATOM | 2466 | C | GLN | A | 311 | 44.523 | 29.767 | −98.255 | 1.00 | 20.41 | C |
| ATOM | 2467 | O | GLN | A | 311 | 44.992 | 30.401 | −97.306 | 1.00 | 19.66 | O |
| ATOM | 2468 | CB | GLN | A | 311 | 42.815 | 30.804 | −99.708 | 1.00 | 19.84 | C |
| ATOM | 2469 | CG | GLN | A | 311 | 42.412 | 31.978 | −98.817 | 1.00 | 22.09 | C |
| ATOM | 2470 | CD | GLN | A | 311 | 40.939 | 32.313 | −98.947 | 1.00 | 25.39 | C |
| ATOM | 2471 | OE1 | GLN | A | 311 | 40.311 | 31.995 | −99.955 | 1.00 | 25.80 | O |
| ATOM | 2472 | NE2 | GLN | A | 311 | 40.384 | 32.964 | −97.935 | 1.00 | 25.10 | N |
| ATOM | 2473 | N | TYR | A | 312 | 44.176 | 28.489 | −98.168 | 1.00 | 17.89 | N |
| ATOM | 2474 | CA | TYR | A | 312 | 44.339 | 27.746 | −96.923 | 1.00 | 19.08 | C |
| ATOM | 2475 | C | TYR | A | 312 | 45.798 | 27.615 | −96.500 | 1.00 | 20.83 | C |
| ATOM | 2476 | O | TYR | A | 312 | 46.132 | 27.813 | −95.327 | 1.00 | 22.94 | O |
| ATOM | 2477 | CB | TYR | A | 312 | 43.699 | 26.357 | −97.051 | 1.00 | 17.98 | C |
| ATOM | 2478 | CG | TYR | A | 312 | 44.017 | 25.408 | −95.912 | 1.00 | 20.51 | C |
| ATOM | 2479 | CD1 | TYR | A | 312 | 45.218 | 24.696 | −95.889 | 1.00 | 19.46 | C |
| ATOM | 2480 | CD2 | TYR | A | 312 | 43.118 | 25.217 | −94.862 | 1.00 | 19.84 | C |
| ATOM | 2481 | CE1 | TYR | A | 312 | 45.515 | 23.813 | −94.857 | 1.00 | 20.53 | C |
| ATOM | 2482 | CE2 | TYR | A | 312 | 43.409 | 24.333 | −93.820 | 1.00 | 22.29 | C |
| ATOM | 2483 | CZ | TYR | A | 312 | 44.607 | 23.633 | −93.828 | 1.00 | 22.21 | C |
| ATOM | 2484 | OH | TYR | A | 312 | 44.893 | 22.732 | −92.821 | 1.00 | 23.97 | O |
| ATOM | 2485 | N | MET | A | 313 | 46.661 | 27.272 | −97.449 | 1.00 | 21.18 | N |
| ATOM | 2486 | CA | MET | A | 313 | 48.074 | 27.111 | −97.159 | 1.00 | 22.54 | C |
| ATOM | 2487 | C | MET | A | 313 | 48.732 | 28.444 | −96.797 | 1.00 | 23.73 | C |
| ATOM | 2488 | O | MET | A | 313 | 49.660 | 28.476 | −95.989 | 1.00 | 20.14 | O |
| ATOM | 2489 | CB | MET | A | 313 | 48.778 | 26.453 | −98.348 | 1.00 | 22.25 | C |
| ATOM | 2490 | CG | MET | A | 313 | 48.354 | 24.999 | −98.557 | 1.00 | 22.13 | C |
| ATOM | 2491 | SD | MET | A | 313 | 48.682 | 23.966 | −97.082 | 1.00 | 22.88 | S |
| ATOM | 2492 | CE | MET | A | 313 | 50.495 | 23.854 | −97.184 | 1.00 | 23.52 | C |
| ATOM | 2493 | N | LYS | A | 314 | 48.255 | 29.543 | −97.384 | 1.00 | 23.32 | N |
| ATOM | 2494 | CA | LYS | A | 314 | 48.810 | 30.853 | −97.048 | 1.00 | 23.56 | C |
| ATOM | 2495 | C | LYS | A | 314 | 48.356 | 31.170 | −95.626 | 1.00 | 22.75 | C |
| ATOM | 2496 | O | LYS | A | 314 | 49.086 | 31.791 | −94.853 | 1.00 | 23.14 | O |
| ATOM | 2497 | CB | LYS | A | 314 | 48.287 | 31.948 | −97.993 | 1.00 | 23.70 | C |
| ATOM | 2498 | CG | LYS | A | 314 | 48.918 | 31.976 | −99.382 | 1.00 | 27.88 | C |
| ATOM | 2499 | CD | LYS | A | 314 | 48.448 | 33.211 | −100.167 | 1.00 | 32.01 | C |
| ATOM | 2500 | CE | LYS | A | 314 | 49.192 | 33.360 | −101.495 | 1.00 | 33.20 | C |
| ATOM | 2501 | NZ | LYS | A | 314 | 48.864 | 34.637 | −102.223 | 1.00 | 34.76 | N |
| ATOM | 2502 | N | ASN | A | 315 | 47.146 | 30.735 | −95.288 | 1.00 | 20.16 | N |
| ATOM | 2503 | CA | ASN | A | 315 | 46.594 | 30.985 | −93.966 | 1.00 | 20.98 | C |
| ATOM | 2504 | C | ASN | A | 315 | 47.315 | 30.211 | −92.864 | 1.00 | 20.83 | C |
| ATOM | 2505 | O | ASN | A | 315 | 47.400 | 30.673 | −91.723 | 1.00 | 20.55 | O |
| ATOM | 2506 | CB | ASN | A | 315 | 45.105 | 30.644 | −93.930 | 1.00 | 19.89 | C |
| ATOM | 2507 | CG | ASN | A | 315 | 44.468 | 31.004 | −92.613 | 1.00 | 22.07 | C |
| ATOM | 2508 | OD1 | ASN | A | 315 | 44.076 | 30.128 | −91.834 | 1.00 | 25.81 | O |
| ATOM | 2509 | ND2 | ASN | A | 315 | 44.371 | 32.299 | −92.342 | 1.00 | 20.70 | N |
| ATOM | 2510 | N | VAL | A | 316 | 47.807 | 29.023 | −93.194 | 1.00 | 19.89 | N |
| ATOM | 2511 | CA | VAL | A | 316 | 48.531 | 28.228 | −92.210 | 1.00 | 20.49 | C |
| ATOM | 2512 | C | VAL | A | 316 | 49.724 | 29.045 | −91.718 | 1.00 | 20.41 | C |
| ATOM | 2513 | O | VAL | A | 316 | 49.961 | 29.161 | −90.519 | 1.00 | 19.30 | O |
| ATOM | 2514 | CB | VAL | A | 316 | 49.058 | 26.908 | −92.815 | 1.00 | 20.52 | C |

TABLE 2-continued

| | | | | | | | | | | |
|---|---|---|---|---|---|---|---|---|---|---|
| ATOM | 2515 | CG1 | VAL | A | 316 | 50.115 | 26.297 | −91.885 | 1.00 | 23.37 | C |
| ATOM | 2516 | CG2 | VAL | A | 316 | 47.905 | 25.922 | −93.015 | 1.00 | 20.32 | C |
| ATOM | 2517 | N | PHE | A | 317 | 50.463 | 29.633 | −92.653 | 1.00 | 19.87 | N |
| ATOM | 2518 | CA | PHE | A | 317 | 51.630 | 30.417 | −92.284 | 1.00 | 20.65 | C |
| ATOM | 2519 | C | PHE | A | 317 | 51.291 | 31.776 | −91.701 | 1.00 | 21.75 | C |
| ATOM | 2520 | O | PHE | A | 317 | 52.060 | 32.323 | −90.913 | 1.00 | 23.16 | O |
| ATOM | 2521 | CB | PHE | A | 317 | 52.566 | 30.495 | −93.480 | 1.00 | 17.43 | C |
| ATOM | 2522 | CG | PHE | A | 317 | 53.075 | 29.150 | −93.884 | 1.00 | 18.38 | C |
| ATOM | 2523 | CD1 | PHE | A | 317 | 53.808 | 28.383 | −92.980 | 1.00 | 16.02 | C |
| ATOM | 2524 | CD2 | PHE | A | 317 | 52.754 | 28.603 | −95.116 | 1.00 | 17.98 | C |
| ATOM | 2525 | CE1 | PHE | A | 317 | 54.208 | 27.092 | −93.297 | 1.00 | 16.93 | C |
| ATOM | 2526 | CE2 | PHE | A | 317 | 53.150 | 27.306 | −95.444 | 1.00 | 19.19 | C |
| ATOM | 2527 | CZ | PHE | A | 317 | 53.876 | 26.549 | −94.532 | 1.00 | 17.66 | C |
| ATOM | 2528 | N | LYS | A | 318 | 50.130 | 32.312 | −92.063 | 1.00 | 21.92 | N |
| ATOM | 2529 | CA | LYS | A | 318 | 49.699 | 33.574 | −91.487 | 1.00 | 22.18 | C |
| ATOM | 2530 | C | LYS | A | 318 | 49.539 | 33.298 | −89.992 | 1.00 | 22.69 | C |
| ATOM | 2531 | O | LYS | A | 318 | 49.918 | 34.111 | −89.152 | 1.00 | 23.91 | O |
| ATOM | 2532 | CB | LYS | A | 318 | 48.346 | 34.010 | −92.042 | 1.00 | 23.37 | C |
| ATOM | 2533 | CG | LYS | A | 318 | 47.746 | 35.156 | −91.239 | 1.00 | 23.15 | C |
| ATOM | 2534 | CD | LYS | A | 318 | 46.254 | 35.263 | −91.411 | 1.00 | 26.25 | C |
| ATOM | 2535 | CE | LYS | A | 318 | 45.669 | 36.227 | −90.388 | 1.00 | 28.09 | C |
| ATOM | 2536 | NZ | LYS | A | 318 | 44.200 | 36.377 | −90.546 | 1.00 | 31.92 | N |
| ATOM | 2537 | N | GLU | A | 319 | 48.968 | 32.140 | −89.670 | 1.00 | 22.05 | N |
| ATOM | 2538 | CA | GLU | A | 319 | 48.763 | 31.751 | −88.275 | 1.00 | 23.30 | C |
| ATOM | 2539 | C | GLU | A | 319 | 50.067 | 31.357 | −87.579 | 1.00 | 20.68 | C |
| ATOM | 2540 | O | GLU | A | 319 | 50.259 | 31.667 | −86.413 | 1.00 | 22.59 | O |
| ATOM | 2541 | CB | GLU | A | 319 | 47.753 | 30.602 | −88.175 | 1.00 | 23.46 | C |
| ATOM | 2542 | CG | GLU | A | 319 | 46.362 | 30.955 | −88.717 | 1.00 | 29.09 | C |
| ATOM | 2543 | CD | GLU | A | 319 | 45.328 | 29.863 | −88.478 | 1.00 | 31.30 | C |
| ATOM | 2544 | OE1 | GLU | A | 319 | 45.678 | 28.670 | −88.603 | 1.00 | 32.87 | O |
| ATOM | 2545 | OE2 | GLU | A | 319 | 44.157 | 30.197 | −88.191 | 1.00 | 33.25 | O |
| ATOM | 2546 | N | LYS | A | 320 | 50.966 | 30.686 | −88.291 | 1.00 | 20.46 | N |
| ATOM | 2547 | CA | LYS | A | 320 | 52.231 | 30.277 | −87.683 | 1.00 | 19.53 | C |
| ATOM | 2548 | C | LYS | A | 320 | 53.059 | 31.473 | −87.223 | 1.00 | 20.70 | C |
| ATOM | 2549 | O | LYS | A | 320 | 53.570 | 31.494 | −86.109 | 1.00 | 19.46 | O |
| ATOM | 2550 | CB | LYS | A | 320 | 53.070 | 29.446 | −88.658 | 1.00 | 17.60 | C |
| ATOM | 2551 | CG | LYS | A | 320 | 54.492 | 29.155 | −88.141 | 1.00 | 18.12 | C |
| ATOM | 2552 | CD | LYS | A | 320 | 55.328 | 28.350 | −89.130 | 1.00 | 14.99 | C |
| ATOM | 2553 | CE | LYS | A | 320 | 56.766 | 28.210 | −88.653 | 1.00 | 11.63 | C |
| ATOM | 2554 | NZ | LYS | A | 320 | 57.678 | 27.630 | −89.706 | 1.00 | 11.64 | N |
| ATOM | 2555 | N | TYR | A | 321 | 53.188 | 32.469 | −88.089 | 1.00 | 20.30 | N |
| ATOM | 2556 | CA | TYR | A | 321 | 53.974 | 33.648 | −87.777 | 1.00 | 21.23 | C |
| ATOM | 2557 | C | TYR | A | 321 | 53.146 | 34.781 | −87.164 | 1.00 | 22.20 | C |
| ATOM | 2558 | O | TYR | A | 321 | 53.641 | 35.889 | −86.989 | 1.00 | 22.30 | O |
| ATOM | 2559 | CB | TYR | A | 321 | 54.682 | 34.116 | −89.053 | 1.00 | 20.53 | C |
| ATOM | 2560 | CG | TYR | A | 321 | 55.549 | 33.045 | −89.686 | 1.00 | 21.00 | C |
| ATOM | 2561 | CD1 | TYR | A | 321 | 56.773 | 32.687 | −89.114 | 1.00 | 19.59 | C |
| ATOM | 2562 | CD2 | TYR | A | 321 | 55.138 | 32.366 | −90.840 | 1.00 | 19.64 | C |
| ATOM | 2563 | CE1 | TYR | A | 321 | 57.564 | 31.687 | −89.671 | 1.00 | 16.41 | C |
| ATOM | 2564 | CE2 | TYR | A | 321 | 55.928 | 31.356 | −91.404 | 1.00 | 18.21 | C |
| ATOM | 2565 | CZ | TYR | A | 321 | 57.143 | 31.027 | −90.808 | 1.00 | 17.86 | C |
| ATOM | 2566 | OH | TYR | A | 321 | 57.951 | 30.047 | −91.347 | 1.00 | 15.87 | O |
| ATOM | 2567 | N | LEU | A | 322 | 51.896 | 34.493 | −86.821 | 1.00 | 22.15 | N |
| ATOM | 2568 | CA | LEU | A | 322 | 51.012 | 35.501 | −86.244 | 1.00 | 25.33 | C |
| ATOM | 2569 | C | LEU | A | 322 | 50.988 | 36.785 | −87.081 | 1.00 | 26.89 | C |
| ATOM | 2570 | O | LEU | A | 322 | 51.079 | 37.893 | −86.550 | 1.00 | 26.65 | O |
| ATOM | 2571 | CB | LEU | A | 322 | 51.434 | 35.821 | −84.804 | 1.00 | 25.43 | C |
| ATOM | 2572 | CG | LEU | A | 322 | 51.202 | 34.699 | −83.787 | 1.00 | 26.98 | C |
| ATOM | 2573 | CD1 | LEU | A | 322 | 51.517 | 35.206 | −82.383 | 1.00 | 27.23 | C |
| ATOM | 2574 | CD2 | LEU | A | 322 | 49.750 | 34.224 | −83.866 | 1.00 | 27.02 | C |
| ATOM | 2575 | N | LEU | A | 323 | 50.864 | 36.628 | −88.394 | 1.00 | 26.91 | N |
| ATOM | 2576 | CA | LEU | A | 323 | 50.835 | 37.775 | −89.292 | 1.00 | 29.24 | C |
| ATOM | 2577 | C | LEU | A | 323 | 49.464 | 38.453 | −89.304 | 1.00 | 29.35 | C |
| ATOM | 2578 | O | LEU | A | 323 | 48.444 | 37.837 | −88.998 | 1.00 | 28.82 | O |
| ATOM | 2579 | CB | LEU | A | 323 | 51.195 | 37.342 | −90.716 | 1.00 | 26.64 | C |
| ATOM | 2580 | CG | LEU | A | 323 | 52.544 | 36.665 | −90.968 | 1.00 | 27.17 | C |
| ATOM | 2581 | CD1 | LEU | A | 323 | 52.624 | 36.257 | −92.437 | 1.00 | 26.04 | C |
| ATOM | 2582 | CD2 | LEU | A | 323 | 53.691 | 37.600 | −90.606 | 1.00 | 25.93 | C |
| ATOM | 2583 | N | SER | A | 324 | 49.451 | 39.733 | −89.657 | 1.00 | 32.67 | N |
| ATOM | 2584 | CA | SER | A | 324 | 48.207 | 40.490 | −89.740 | 1.00 | 35.34 | C |
| ATOM | 2585 | C | SER | A | 324 | 47.725 | 40.453 | −91.188 | 1.00 | 35.47 | C |
| ATOM | 2586 | O | SER | A | 324 | 48.535 | 40.489 | −92.112 | 1.00 | 33.53 | O |
| ATOM | 2587 | CB | SER | A | 324 | 48.437 | 41.945 | −89.321 | 1.00 | 36.17 | C |
| ATOM | 2588 | OG | SER | A | 324 | 48.803 | 42.038 | −87.955 | 1.00 | 41.53 | O |
| ATOM | 2589 | N | GLU | A | 325 | 46.411 | 40.373 | −91.378 | 1.00 | 37.56 | N |
| ATOM | 2590 | CA | GLU | A | 325 | 45.825 | 40.342 | −92.718 | 1.00 | 40.83 | C |
| ATOM | 2591 | C | GLU | A | 325 | 44.769 | 41.437 | −92.859 | 1.00 | 42.19 | C |
| ATOM | 2592 | O | GLU | A | 325 | 43.753 | 41.422 | −92.164 | 1.00 | 41.80 | O |
| ATOM | 2593 | CB | GLU | A | 325 | 45.202 | 38.965 | −92.999 | 1.00 | 42.09 | C |

TABLE 2-continued

| ATOM | 2594 | CG  | GLU | A | 325 | 44.248 | 38.926 | −94.196  | 1.00 | 43.51 | C |
| ATOM | 2595 | CD  | GLU | A | 325 | 43.825 | 37.511 | −94.591  | 1.00 | 45.33 | C |
| ATOM | 2596 | OE1 | GLU | A | 325 | 43.646 | 36.658 | −93.693  | 1.00 | 43.25 | O |
| ATOM | 2597 | OE2 | GLU | A | 325 | 43.655 | 37.259 | −95.806  | 1.00 | 45.06 | O |
| ATOM | 2598 | N   | ASP | A | 326 | 45.013 | 42.385 | −93.758  | 1.00 | 45.72 | N |
| ATOM | 2599 | CA  | ASP | A | 326 | 44.075 | 43.486 | −93.972  | 1.00 | 50.29 | C |
| ATOM | 2600 | C   | ASP | A | 326 | 42.859 | 43.070 | −94.797  | 1.00 | 52.54 | C |
| ATOM | 2601 | O   | ASP | A | 326 | 42.792 | 41.947 | −95.305  | 1.00 | 52.71 | O |
| ATOM | 2602 | CB  | ASP | A | 326 | 44.775 | 44.666 | −94.654  | 1.00 | 51.77 | C |
| ATOM | 2603 | CG  | ASP | A | 326 | 45.418 | 44.284 | −95.971  | 1.00 | 54.65 | C |
| ATOM | 2604 | OD1 | ASP | A | 326 | 44.804 | 43.504 | −96.730  | 1.00 | 56.83 | O |
| ATOM | 2605 | OD2 | ASP | A | 326 | 46.533 | 44.777 | −96.255  | 1.00 | 56.47 | O |
| ATOM | 2606 | N   | THR | A | 327 | 41.902 | 43.986 | −94.931  | 1.00 | 54.65 | N |
| ATOM | 2607 | CA  | THR | A | 327 | 40.677 | 43.719 | −95.679  | 1.00 | 56.25 | C |
| ATOM | 2608 | C   | THR | A | 327 | 40.921 | 43.344 | −97.140  | 1.00 | 56.11 | C |
| ATOM | 2609 | O   | THR | A | 327 | 40.026 | 42.827 | −97.807  | 1.00 | 57.00 | O |
| ATOM | 2610 | CB  | THR | A | 327 | 39.710 | 44.930 | −95.631  | 1.00 | 57.36 | C |
| ATOM | 2611 | OG1 | THR | A | 327 | 40.399 | 46.116 | −96.047  | 1.00 | 57.63 | O |
| ATOM | 2612 | CG2 | THR | A | 327 | 39.167 | 45.125 | −94.217  | 1.00 | 58.08 | C |
| ATOM | 2613 | N   | SER | A | 328 | 42.128 | 43.601 | −97.636  | 1.00 | 55.58 | N |
| ATOM | 2614 | CA  | SER | A | 328 | 42.455 | 43.269 | −99.018  | 1.00 | 55.60 | C |
| ATOM | 2615 | C   | SER | A | 328 | 43.190 | 41.932 | −99.117  | 1.00 | 54.41 | C |
| ATOM | 2616 | O   | SER | A | 328 | 43.607 | 41.525 | −100.203 | 1.00 | 54.61 | O |
| ATOM | 2617 | CB  | SER | A | 328 | 43.303 | 44.377 | −99.645  | 1.00 | 56.21 | C |
| ATOM | 2618 | OG  | SER | A | 328 | 44.515 | 44.553 | −98.939  | 1.00 | 60.49 | O |
| ATOM | 2619 | N   | GLY | A | 329 | 43.352 | 41.259 | −97.980  | 1.00 | 52.75 | N |
| ATOM | 2620 | CA  | GLY | A | 329 | 44.016 | 39.964 | −97.964  | 1.00 | 49.73 | C |
| ATOM | 2621 | C   | GLY | A | 329 | 45.535 | 39.972 | −98.009  | 1.00 | 47.35 | C |
| ATOM | 2622 | O   | GLY | A | 329 | 46.156 | 38.948 | −98.298  | 1.00 | 47.35 | O |
| ATOM | 2623 | N   | LYS | A | 330 | 46.140 | 41.119 | −97.721  | 1.00 | 45.28 | N |
| ATOM | 2624 | CA  | LYS | A | 330 | 47.596 | 41.239 | −97.730  | 1.00 | 43.80 | C |
| ATOM | 2625 | C   | LYS | A | 330 | 48.144 | 40.950 | −96.332  | 1.00 | 40.33 | C |
| ATOM | 2626 | O   | LYS | A | 330 | 47.530 | 41.326 | −95.334  | 1.00 | 41.91 | O |
| ATOM | 2627 | CB  | LYS | A | 330 | 47.992 | 42.652 | −98.163  | 1.00 | 44.97 | C |
| ATOM | 2628 | CG  | LYS | A | 330 | 49.488 | 42.890 | −98.301  | 1.00 | 45.90 | C |
| ATOM | 2629 | CD  | LYS | A | 330 | 49.743 | 44.346 | −98.669  | 1.00 | 48.31 | C |
| ATOM | 2630 | CE  | LYS | A | 330 | 51.218 | 44.653 | −98.864  | 1.00 | 47.90 | C |
| ATOM | 2631 | NZ  | LYS | A | 330 | 51.415 | 46.111 | −99.102  | 1.00 | 47.71 | N |
| ATOM | 2632 | N   | PHE | A | 331 | 49.294 | 40.287 | −96.259  | 1.00 | 37.03 | N |
| ATOM | 2633 | CA  | PHE | A | 331 | 49.895 | 39.958 | −94.963  | 1.00 | 33.64 | C |
| ATOM | 2634 | C   | PHE | A | 331 | 50.989 | 40.938 | −94.557  | 1.00 | 32.22 | C |
| ATOM | 2635 | O   | PHE | A | 331 | 51.717 | 41.454 | −95.403  | 1.00 | 31.64 | O |
| ATOM | 2636 | CB  | PHE | A | 331 | 50.524 | 38.560 | −94.983  | 1.00 | 31.19 | C |
| ATOM | 2637 | CG  | PHE | A | 331 | 49.559 | 37.447 | −95.266  | 1.00 | 30.09 | C |
| ATOM | 2638 | CD1 | PHE | A | 331 | 48.304 | 37.423 | −94.678  | 1.00 | 27.91 | C |
| ATOM | 2639 | CD2 | PHE | A | 331 | 49.936 | 36.389 | −96.081  | 1.00 | 29.51 | C |
| ATOM | 2640 | CE1 | PHE | A | 331 | 47.438 | 36.361 | −94.896  | 1.00 | 29.19 | C |
| ATOM | 2641 | CE2 | PHE | A | 331 | 49.073 | 35.317 | −96.305  | 1.00 | 31.10 | C |
| ATOM | 2642 | CZ  | PHE | A | 331 | 47.822 | 35.304 | −95.709  | 1.00 | 28.88 | C |
| ATOM | 2643 | N   | SER | A | 332 | 51.108 | 41.176 | −93.254  | 1.00 | 32.26 | N |
| ATOM | 2644 | CA  | SER | A | 332 | 52.150 | 42.056 | −92.715  | 1.00 | 33.99 | C |
| ATOM | 2645 | C   | SER | A | 332 | 52.556 | 41.582 | −91.325  | 1.00 | 32.78 | C |
| ATOM | 2646 | O   | SER | A | 332 | 51.778 | 40.925 | −90.632  | 1.00 | 32.89 | O |
| ATOM | 2647 | CB  | SER | A | 332 | 51.661 | 43.506 | −92.618  | 1.00 | 32.69 | C |
| ATOM | 2648 | OG  | SER | A | 332 | 50.562 | 43.616 | −91.731  | 1.00 | 32.64 | O |
| ATOM | 2649 | N   | VAL | A | 333 | 53.777 | 41.913 | −90.922  | 1.00 | 33.55 | N |
| ATOM | 2650 | CA  | VAL | A | 333 | 54.256 | 41.539 | −89.599  | 1.00 | 33.53 | C |
| ATOM | 2651 | C   | VAL | A | 333 | 53.936 | 42.671 | −88.641  | 1.00 | 33.92 | C |
| ATOM | 2652 | O   | VAL | A | 333 | 54.326 | 43.813 | −88.869  | 1.00 | 34.37 | O |
| ATOM | 2653 | CB  | VAL | A | 333 | 55.777 | 41.330 | −89.576  | 1.00 | 33.83 | C |
| ATOM | 2654 | CG1 | VAL | A | 333 | 56.222 | 40.983 | −88.163  | 1.00 | 33.75 | C |
| ATOM | 2655 | CG2 | VAL | A | 333 | 56.174 | 40.238 | −90.552  | 1.00 | 31.65 | C |
| ATOM | 2656 | N   | ASP | A | 334 | 53.212 | 42.349 | −87.579  | 1.00 | 34.86 | N |
| ATOM | 2657 | CA  | ASP | A | 334 | 52.850 | 43.328 | −86.563  | 1.00 | 36.04 | C |
| ATOM | 2658 | C   | ASP | A | 334 | 53.994 | 43.367 | −85.541  | 1.00 | 37.10 | C |
| ATOM | 2659 | O   | ASP | A | 334 | 54.275 | 42.362 | −84.884  | 1.00 | 35.29 | O |
| ATOM | 2660 | CB  | ASP | A | 334 | 51.549 | 42.896 | −85.889  | 1.00 | 37.53 | C |
| ATOM | 2661 | CG  | ASP | A | 334 | 51.128 | 43.830 | −84.775  | 1.00 | 41.38 | C |
| ATOM | 2662 | OD1 | ASP | A | 334 | 51.960 | 44.116 | −83.889  | 1.00 | 44.30 | O |
| ATOM | 2663 | OD2 | ASP | A | 334 | 49.959 | 44.268 | −84.776  | 1.00 | 43.21 | O |
| ATOM | 2664 | N   | LYS | A | 335 | 54.650 | 44.519 | −85.408  | 1.00 | 36.52 | N |
| ATOM | 2665 | CA  | LYS | A | 335 | 55.768 | 44.663 | −84.476  | 1.00 | 36.08 | C |
| ATOM | 2666 | C   | LYS | A | 335 | 55.484 | 44.185 | −83.057  | 1.00 | 34.69 | C |
| ATOM | 2667 | O   | LYS | A | 335 | 56.315 | 43.514 | −82.455  | 1.00 | 32.57 | O |
| ATOM | 2668 | CB  | LYS | A | 335 | 56.248 | 46.116 | −84.442  | 1.00 | 38.07 | C |
| ATOM | 2669 | CG  | LYS | A | 335 | 56.975 | 46.544 | −85.704  | 1.00 | 41.17 | C |
| ATOM | 2670 | CD  | LYS | A | 335 | 57.361 | 48.018 | −85.664  | 1.00 | 44.51 | C |
| ATOM | 2671 | CE  | LYS | A | 335 | 58.026 | 48.440 | −86.966  | 1.00 | 45.54 | C |
| ATOM | 2672 | NZ  | LYS | A | 335 | 58.396 | 49.884 | −86.980  | 1.00 | 47.86 | N |

TABLE 2-continued

| | | | | | | | | | | |
|---|---|---|---|---|---|---|---|---|---|---|
| ATOM | 2673 | N | LEU | A | 336 | 54.319 | 44.530 | −82.521 | 1.00 | 33.95 | N |
| ATOM | 2674 | CA | LEU | A | 336 | 53.962 | 44.118 | −81.170 | 1.00 | 34.57 | C |
| ATOM | 2675 | C | LEU | A | 336 | 53.788 | 42.606 | −81.072 | 1.00 | 34.40 | C |
| ATOM | 2676 | O | LEU | A | 336 | 54.287 | 41.981 | −80.140 | 1.00 | 33.72 | O |
| ATOM | 2677 | CB | LEU | A | 336 | 52.679 | 44.820 | −80.724 | 1.00 | 37.40 | C |
| ATOM | 2678 | CG | LEU | A | 336 | 52.773 | 46.348 | −80.637 | 1.00 | 40.78 | C |
| ATOM | 2679 | CD1 | LEU | A | 336 | 51.374 | 46.952 | −80.520 | 1.00 | 42.39 | C |
| ATOM | 2680 | CD2 | LEU | A | 336 | 53.638 | 46.740 | −79.450 | 1.00 | 41.17 | C |
| ATOM | 2681 | N | LYS | A | 337 | 53.087 | 42.023 | −82.039 | 1.00 | 34.17 | N |
| ATOM | 2682 | CA | LYS | A | 337 | 52.859 | 40.580 | −82.065 | 1.00 | 33.47 | C |
| ATOM | 2683 | C | LYS | A | 337 | 54.169 | 39.820 | −82.212 | 1.00 | 31.73 | C |
| ATOM | 2684 | O | LYS | A | 337 | 54.386 | 38.810 | −81.540 | 1.00 | 30.39 | O |
| ATOM | 2685 | CB | LYS | A | 337 | 51.943 | 40.200 | −83.229 | 1.00 | 36.15 | C |
| ATOM | 2686 | CG | LYS | A | 337 | 50.501 | 40.624 | −83.057 | 1.00 | 41.18 | C |
| ATOM | 2687 | CD | LYS | A | 337 | 49.834 | 39.849 | −81.934 | 1.00 | 44.27 | C |
| ATOM | 2688 | CE | LYS | A | 337 | 48.358 | 40.201 | −81.835 | 1.00 | 47.06 | C |
| ATOM | 2689 | NZ | LYS | A | 337 | 47.668 | 39.439 | −80.757 | 1.00 | 49.99 | N |
| ATOM | 2690 | N | PHE | A | 338 | 55.032 | 40.296 | −83.105 | 1.00 | 28.80 | N |
| ATOM | 2691 | CA | PHE | A | 338 | 56.312 | 39.647 | −83.326 | 1.00 | 28.99 | C |
| ATOM | 2692 | C | PHE | A | 338 | 57.139 | 39.624 | −82.044 | 1.00 | 30.13 | C |
| ATOM | 2693 | O | PHE | A | 338 | 57.699 | 38.588 | −81.686 | 1.00 | 29.17 | O |
| ATOM | 2694 | CB | PHE | A | 338 | 57.125 | 40.356 | −84.415 | 1.00 | 27.41 | C |
| ATOM | 2695 | CG | PHE | A | 338 | 58.494 | 39.759 | −84.615 | 1.00 | 25.81 | C |
| ATOM | 2696 | CD1 | PHE | A | 338 | 58.665 | 38.626 | −85.404 | 1.00 | 25.75 | C |
| ATOM | 2697 | CD2 | PHE | A | 338 | 59.595 | 40.270 | −83.932 | 1.00 | 26.42 | C |
| ATOM | 2698 | CE1 | PHE | A | 338 | 59.909 | 38.002 | −85.506 | 1.00 | 25.61 | C |
| ATOM | 2699 | CE2 | PHE | A | 338 | 60.852 | 39.654 | −84.024 | 1.00 | 25.93 | C |
| ATOM | 2700 | CZ | PHE | A | 338 | 61.007 | 38.518 | −84.810 | 1.00 | 26.26 | C |
| ATOM | 2701 | N | ASP | A | 339 | 57.228 | 40.769 | −81.367 | 1.00 | 28.70 | N |
| ATOM | 2702 | CA | ASP | A | 339 | 58.003 | 40.857 | −80.134 | 1.00 | 29.83 | C |
| ATOM | 2703 | C | ASP | A | 339 | 57.495 | 39.898 | −79.066 | 1.00 | 28.24 | C |
| ATOM | 2704 | O | ASP | A | 339 | 58.287 | 39.274 | −78.370 | 1.00 | 28.54 | O |
| ATOM | 2705 | CB | ASP | A | 339 | 58.007 | 42.295 | −79.579 | 1.00 | 29.92 | C |
| ATOM | 2706 | CG | ASP | A | 339 | 58.924 | 43.231 | −80.362 | 1.00 | 31.88 | C |
| ATOM | 2707 | OD1 | ASP | A | 339 | 59.845 | 42.749 | −81.056 | 1.00 | 31.59 | O |
| ATOM | 2708 | OD2 | ASP | A | 339 | 58.736 | 44.460 | −80.270 | 1.00 | 34.17 | O |
| ATOM | 2709 | N | LYS | A | 340 | 56.179 | 39.779 | −78.934 | 1.00 | 28.98 | N |
| ATOM | 2710 | CA | LYS | A | 340 | 55.615 | 38.872 | −77.940 | 1.00 | 29.48 | C |
| ATOM | 2711 | C | LYS | A | 340 | 55.878 | 37.414 | −78.313 | 1.00 | 28.45 | C |
| ATOM | 2712 | O | LYS | A | 340 | 56.143 | 36.583 | −77.444 | 1.00 | 27.71 | O |
| ATOM | 2713 | CB | LYS | A | 340 | 54.113 | 39.108 | −77.782 | 1.00 | 32.51 | C |
| ATOM | 2714 | CG | LYS | A | 340 | 53.777 | 40.442 | −77.128 | 1.00 | 38.52 | C |
| ATOM | 2715 | CD | LYS | A | 340 | 52.285 | 40.565 | −76.820 | 1.00 | 42.89 | C |
| ATOM | 2716 | CE | LYS | A | 340 | 51.448 | 40.542 | −78.091 | 1.00 | 46.24 | C |
| ATOM | 2717 | NZ | LYS | A | 340 | 49.997 | 40.742 | −77.813 | 1.00 | 49.43 | N |
| ATOM | 2718 | N | LEU | A | 341 | 55.811 | 37.104 | −79.603 | 1.00 | 25.90 | N |
| ATOM | 2719 | CA | LEU | A | 341 | 56.061 | 35.742 | −80.054 | 1.00 | 24.32 | C |
| ATOM | 2720 | C | LEU | A | 341 | 57.548 | 35.423 | −79.910 | 1.00 | 23.38 | C |
| ATOM | 2721 | O | LEU | A | 341 | 57.916 | 34.368 | −79.408 | 1.00 | 23.66 | O |
| ATOM | 2722 | CB | LEU | A | 341 | 55.632 | 35.569 | −81.514 | 1.00 | 22.72 | C |
| ATOM | 2723 | CG | LEU | A | 341 | 56.002 | 34.224 | −82.149 | 1.00 | 23.57 | C |
| ATOM | 2724 | CD1 | LEU | A | 341 | 55.417 | 33.077 | −81.327 | 1.00 | 19.93 | C |
| ATOM | 2725 | CD2 | LEU | A | 341 | 55.489 | 34.185 | −83.589 | 1.00 | 24.87 | C |
| ATOM | 2726 | N | TYR | A | 342 | 58.397 | 36.348 | −80.345 | 1.00 | 22.16 | N |
| ATOM | 2727 | CA | TYR | A | 342 | 59.837 | 36.156 | −80.262 | 1.00 | 22.67 | C |
| ATOM | 2728 | C | TYR | A | 342 | 60.259 | 36.001 | −78.807 | 1.00 | 22.41 | C |
| ATOM | 2729 | O | TYR | A | 342 | 61.097 | 35.166 | −78.479 | 1.00 | 19.44 | O |
| ATOM | 2730 | CB | TYR | A | 342 | 60.570 | 37.358 | −80.865 | 1.00 | 22.20 | C |
| ATOM | 2731 | CG | TYR | A | 342 | 62.065 | 37.179 | −80.947 | 1.00 | 22.22 | C |
| ATOM | 2732 | CD1 | TYR | A | 342 | 62.634 | 36.391 | −81.945 | 1.00 | 23.38 | C |
| ATOM | 2733 | CD2 | TYR | A | 342 | 62.913 | 37.792 | −80.024 | 1.00 | 23.67 | C |
| ATOM | 2734 | CE1 | TYR | A | 342 | 64.007 | 36.217 | −82.026 | 1.00 | 24.37 | C |
| ATOM | 2735 | CE2 | TYR | A | 342 | 64.293 | 37.628 | −80.094 | 1.00 | 22.96 | C |
| ATOM | 2736 | CZ | TYR | A | 342 | 64.834 | 36.841 | −81.096 | 1.00 | 25.82 | C |
| ATOM | 2737 | OH | TYR | A | 342 | 66.196 | 36.679 | −81.181 | 1.00 | 25.77 | O |
| ATOM | 2738 | N | LYS | A | 343 | 59.670 | 36.819 | −77.941 | 1.00 | 23.01 | N |
| ATOM | 2739 | CA | LYS | A | 343 | 59.987 | 36.790 | −76.521 | 1.00 | 25.04 | C |
| ATOM | 2740 | C | LYS | A | 343 | 59.584 | 35.456 | −75.894 | 1.00 | 24.51 | C |
| ATOM | 2741 | O | LYS | A | 343 | 60.313 | 34.897 | −75.072 | 1.00 | 24.05 | O |
| ATOM | 2742 | CB | LYS | A | 343 | 59.272 | 37.939 | −75.809 | 1.00 | 27.85 | C |
| ATOM | 2743 | CG | LYS | A | 343 | 59.541 | 38.023 | −74.327 | 1.00 | 31.26 | C |
| ATOM | 2744 | CD | LYS | A | 343 | 58.766 | 39.174 | −73.712 | 1.00 | 38.45 | C |
| ATOM | 2745 | CE | LYS | A | 343 | 59.005 | 39.271 | −72.212 | 1.00 | 41.16 | C |
| ATOM | 2746 | NZ | LYS | A | 343 | 58.224 | 40.381 | −71.592 | 1.00 | 43.99 | N |
| ATOM | 2747 | N | MET | A | 344 | 58.425 | 34.943 | −76.289 | 1.00 | 21.73 | N |
| ATOM | 2748 | CA | MET | A | 344 | 57.956 | 33.678 | −75.743 | 1.00 | 21.92 | C |
| ATOM | 2749 | C | MET | A | 344 | 58.868 | 32.525 | −76.170 | 1.00 | 21.42 | C |
| ATOM | 2750 | O | MET | A | 344 | 59.237 | 31.680 | −75.352 | 1.00 | 19.71 | O |
| ATOM | 2751 | CB | MET | A | 344 | 56.512 | 33.403 | −76.183 | 1.00 | 21.97 | C |

TABLE 2-continued

| ATOM | 2752 | CG | MET | A | 344 | 55.932 | 32.146 | −75.558 | 1.00 | 26.17 | C |
| --- | --- | --- | --- | --- | --- | --- | --- | --- | --- | --- | --- |
| ATOM | 2753 | SD | MET | A | 344 | 54.182 | 31.923 | −75.856 | 1.00 | 32.42 | S |
| ATOM | 2754 | CE | MET | A | 344 | 54.209 | 31.311 | −77.527 | 1.00 | 26.53 | C |
| ATOM | 2755 | N | LEU | A | 345 | 59.254 | 32.507 | −77.443 | 1.00 | 19.46 | N |
| ATOM | 2756 | CA | LEU | A | 345 | 60.116 | 31.447 | −77.950 | 1.00 | 21.46 | C |
| ATOM | 2757 | C | LEU | A | 345 | 61.552 | 31.481 | −77.441 | 1.00 | 21.35 | C |
| ATOM | 2758 | O | LEU | A | 345 | 62.188 | 30.440 | −77.343 | 1.00 | 22.03 | O |
| ATOM | 2759 | CB | LEU | A | 345 | 60.149 | 31.473 | −79.478 | 1.00 | 20.82 | C |
| ATOM | 2760 | CG | LEU | A | 345 | 58.867 | 31.103 | −80.230 | 1.00 | 22.02 | C |
| ATOM | 2761 | CD1 | LEU | A | 345 | 59.034 | 31.455 | −81.697 | 1.00 | 20.15 | C |
| ATOM | 2762 | CD2 | LEU | A | 345 | 58.564 | 29.622 | −80.059 | 1.00 | 20.94 | C |
| ATOM | 2763 | N | THR | A | 346 | 62.069 | 32.664 | −77.117 | 1.00 | 21.44 | N |
| ATOM | 2764 | CA | THR | A | 346 | 63.460 | 32.759 | −76.674 | 1.00 | 21.82 | C |
| ATOM | 2765 | C | THR | A | 346 | 63.698 | 33.095 | −75.206 | 1.00 | 22.38 | C |
| ATOM | 2766 | O | THR | A | 346 | 64.770 | 32.798 | −74.678 | 1.00 | 23.93 | O |
| ATOM | 2767 | CB | THR | A | 346 | 64.237 | 33.796 | −77.519 | 1.00 | 23.23 | C |
| ATOM | 2768 | OG1 | THR | A | 346 | 63.685 | 35.103 | −77.299 | 1.00 | 22.83 | O |
| ATOM | 2769 | CG2 | THR | A | 346 | 64.147 | 33.451 | −78.998 | 1.00 | 25.16 | C |
| ATOM | 2770 | N | GLU | A | 347 | 62.717 | 33.708 | −74.550 | 1.00 | 24.22 | N |
| ATOM | 2771 | CA | GLU | A | 347 | 62.866 | 34.097 | −73.147 | 1.00 | 25.70 | C |
| ATOM | 2772 | C | GLU | A | 347 | 61.940 | 33.377 | −72.172 | 1.00 | 24.23 | C |
| ATOM | 2773 | O | GLU | A | 347 | 62.287 | 33.206 | −71.007 | 1.00 | 23.62 | O |
| ATOM | 2774 | CB | GLU | A | 347 | 62.663 | 35.600 | −72.995 | 1.00 | 29.25 | C |
| ATOM | 2775 | CG | GLU | A | 347 | 63.607 | 36.436 | −73.830 | 1.00 | 36.75 | C |
| ATOM | 2776 | CD | GLU | A | 347 | 63.499 | 37.907 | −73.494 | 1.00 | 40.49 | C |
| ATOM | 2777 | OE1 | GLU | A | 347 | 62.368 | 38.381 | −73.256 | 1.00 | 42.21 | O |
| ATOM | 2778 | OE2 | GLU | A | 347 | 64.543 | 38.591 | −73.478 | 1.00 | 45.19 | O |
| ATOM | 2779 | N | ILE | A | 348 | 60.758 | 32.976 | −72.622 | 1.00 | 22.34 | N |
| ATOM | 2780 | CA | ILE | A | 348 | 59.863 | 32.258 | −71.728 | 1.00 | 20.70 | C |
| ATOM | 2781 | C | ILE | A | 348 | 60.189 | 30.770 | −71.801 | 1.00 | 19.57 | C |
| ATOM | 2782 | O | ILE | A | 348 | 60.290 | 30.108 | −70.764 | 1.00 | 17.81 | O |
| ATOM | 2783 | CB | ILE | A | 348 | 58.393 | 32.502 | −72.079 | 1.00 | 23.06 | C |
| ATOM | 2784 | CG1 | ILE | A | 348 | 58.089 | 34.000 | −71.950 | 1.00 | 25.44 | C |
| ATOM | 2785 | CG2 | ILE | A | 348 | 57.493 | 31.699 | −71.141 | 1.00 | 22.04 | C |
| ATOM | 2786 | CD1 | ILE | A | 348 | 56.665 | 34.375 | −72.291 | 1.00 | 27.87 | C |
| ATOM | 2787 | N | TYR | A | 349 | 60.369 | 30.248 | −73.018 | 1.00 | 17.36 | N |
| ATOM | 2788 | CA | TYR | A | 349 | 60.716 | 28.838 | −73.187 | 1.00 | 18.71 | C |
| ATOM | 2789 | C | TYR | A | 349 | 62.224 | 28.669 | −72.969 | 1.00 | 18.71 | C |
| ATOM | 2790 | O | TYR | A | 349 | 63.009 | 28.774 | −73.914 | 1.00 | 19.31 | O |
| ATOM | 2791 | CB | TYR | A | 349 | 60.367 | 28.321 | −74.595 | 1.00 | 17.76 | C |
| ATOM | 2792 | CG | TYR | A | 349 | 58.899 | 28.385 | −75.000 | 1.00 | 18.53 | C |
| ATOM | 2793 | CD1 | TYR | A | 349 | 57.882 | 28.435 | −74.051 | 1.00 | 17.27 | C |
| ATOM | 2794 | CD2 | TYR | A | 349 | 58.540 | 28.362 | −76.346 | 1.00 | 17.72 | C |
| ATOM | 2795 | CE1 | TYR | A | 349 | 56.526 | 28.462 | −74.434 | 1.00 | 20.24 | C |
| ATOM | 2796 | CE2 | TYR | A | 349 | 57.205 | 28.386 | −76.742 | 1.00 | 18.91 | C |
| ATOM | 2797 | CZ | TYR | A | 349 | 56.203 | 28.436 | −75.785 | 1.00 | 19.49 | C |
| ATOM | 2798 | OH | TYR | A | 349 | 54.891 | 28.457 | −76.192 | 1.00 | 20.53 | O |
| ATOM | 2799 | N | THR | A | 350 | 62.631 | 28.431 | −71.725 | 1.00 | 17.17 | N |
| ATOM | 2800 | CA | THR | A | 350 | 64.051 | 28.237 | −71.412 | 1.00 | 17.88 | C |
| ATOM | 2801 | C | THR | A | 350 | 64.191 | 27.126 | −70.372 | 1.00 | 16.85 | C |
| ATOM | 2802 | O | THR | A | 350 | 63.254 | 26.847 | −69.630 | 1.00 | 15.89 | O |
| ATOM | 2803 | CB | THR | A | 350 | 64.700 | 29.511 | −70.817 | 1.00 | 18.97 | C |
| ATOM | 2804 | OG1 | THR | A | 350 | 64.162 | 29.747 | −69.514 | 1.00 | 19.67 | O |
| ATOM | 2805 | CG2 | THR | A | 350 | 64.436 | 30.732 | −71.701 | 1.00 | 18.32 | C |
| ATOM | 2806 | N | GLU | A | 351 | 65.363 | 26.502 | −70.311 | 1.00 | 18.26 | N |
| ATOM | 2807 | CA | GLU | A | 351 | 65.588 | 25.430 | −69.348 | 1.00 | 18.27 | C |
| ATOM | 2808 | C | GLU | A | 351 | 65.335 | 25.891 | −67.921 | 1.00 | 19.18 | C |
| ATOM | 2809 | O | GLU | A | 351 | 64.684 | 25.196 | −67.137 | 1.00 | 18.96 | O |
| ATOM | 2810 | CB | GLU | A | 351 | 67.019 | 24.888 | −69.450 | 1.00 | 20.36 | C |
| ATOM | 2811 | CG | GLU | A | 351 | 67.284 | 23.710 | −68.507 | 1.00 | 23.22 | C |
| ATOM | 2812 | CD | GLU | A | 351 | 68.677 | 23.109 | −68.668 | 1.00 | 27.11 | C |
| ATOM | 2813 | OE1 | GLU | A | 351 | 69.108 | 22.891 | −69.820 | 1.00 | 27.27 | O |
| ATOM | 2814 | OE2 | GLU | A | 351 | 69.338 | 22.840 | −67.640 | 1.00 | 29.82 | O |
| ATOM | 2815 | N | ASP | A | 352 | 65.853 | 27.065 | −67.578 | 1.00 | 20.93 | N |
| ATOM | 2816 | CA | ASP | A | 352 | 65.676 | 27.596 | −66.227 | 1.00 | 19.79 | C |
| ATOM | 2817 | C | ASP | A | 352 | 64.204 | 27.690 | −65.821 | 1.00 | 18.94 | C |
| ATOM | 2818 | O | ASP | A | 352 | 63.851 | 27.347 | −64.697 | 1.00 | 17.97 | O |
| ATOM | 2819 | CB | ASP | A | 352 | 66.325 | 28.973 | −66.111 | 1.00 | 22.80 | C |
| ATOM | 2820 | CG | ASP | A | 352 | 66.400 | 29.458 | −64.682 | 1.00 | 28.39 | C |
| ATOM | 2821 | OD1 | ASP | A | 352 | 67.087 | 28.800 | −63.867 | 1.00 | 31.42 | O |
| ATOM | 2822 | OD2 | ASP | A | 352 | 65.769 | 30.489 | −64.373 | 1.00 | 28.99 | O |
| ATOM | 2823 | N | ASN | A | 353 | 63.337 | 28.153 | −66.721 | 1.00 | 17.83 | N |
| ATOM | 2824 | CA | ASN | A | 353 | 61.919 | 28.249 | −66.374 | 1.00 | 17.18 | C |
| ATOM | 2825 | C | ASN | A | 353 | 61.249 | 26.888 | −66.211 | 1.00 | 16.74 | C |
| ATOM | 2826 | O | ASN | A | 353 | 60.310 | 26.749 | −65.431 | 1.00 | 17.51 | O |
| ATOM | 2827 | CB | ASN | A | 353 | 61.155 | 29.104 | −67.395 | 1.00 | 18.84 | C |
| ATOM | 2828 | CG | ASN | A | 353 | 61.393 | 30.595 | −67.191 | 1.00 | 22.31 | C |
| ATOM | 2829 | OD1 | ASN | A | 353 | 61.735 | 31.027 | −66.089 | 1.00 | 22.90 | O |
| ATOM | 2830 | ND2 | ASN | A | 353 | 61.200 | 31.386 | −68.241 | 1.00 | 22.48 | N |

TABLE 2-continued

| | | | | | | | | | | |
|---|---|---|---|---|---|---|---|---|---|---|
| ATOM | 2831 | N | PHE | A | 354 | 61.712 | 25.880 | −66.945 | 1.00 | 16.94 | N |
| ATOM | 2832 | CA | PHE | A | 354 | 61.128 | 24.550 | −66.783 | 1.00 | 17.80 | C |
| ATOM | 2833 | C | PHE | A | 354 | 61.567 | 24.011 | −65.406 | 1.00 | 18.83 | C |
| ATOM | 2834 | O | PHE | A | 354 | 60.831 | 23.271 | −64.741 | 1.00 | 17.69 | O |
| ATOM | 2835 | CB | PHE | A | 354 | 61.585 | 23.620 | −67.919 | 1.00 | 16.63 | C |
| ATOM | 2836 | CG | PHE | A | 354 | 60.661 | 23.629 | −69.117 | 1.00 | 16.98 | C |
| ATOM | 2837 | CD1 | PHE | A | 354 | 59.435 | 22.969 | −69.069 | 1.00 | 18.57 | C |
| ATOM | 2838 | CD2 | PHE | A | 354 | 61.005 | 24.311 | −70.277 | 1.00 | 16.29 | C |
| ATOM | 2839 | CE1 | PHE | A | 354 | 58.563 | 22.991 | −70.161 | 1.00 | 17.91 | C |
| ATOM | 2840 | CE2 | PHE | A | 354 | 60.142 | 24.342 | −71.378 | 1.00 | 19.03 | C |
| ATOM | 2841 | CZ | PHE | A | 354 | 58.918 | 23.680 | −71.318 | 1.00 | 16.81 | C |
| ATOM | 2842 | N | VAL | A | 355 | 62.761 | 24.402 | −64.968 | 1.00 | 18.26 | N |
| ATOM | 2843 | CA | VAL | A | 355 | 63.255 | 23.960 | −63.664 | 1.00 | 18.35 | C |
| ATOM | 2844 | C | VAL | A | 355 | 62.330 | 24.517 | −62.579 | 1.00 | 19.41 | C |
| ATOM | 2845 | O | VAL | A | 355 | 61.980 | 23.816 | −61.627 | 1.00 | 18.30 | O |
| ATOM | 2846 | CB | VAL | A | 355 | 64.712 | 24.434 | −63.429 | 1.00 | 18.83 | C |
| ATOM | 2847 | CG1 | VAL | A | 355 | 65.121 | 24.224 | −61.973 | 1.00 | 18.86 | C |
| ATOM | 2848 | CG2 | VAL | A | 355 | 65.643 | 23.654 | −64.338 | 1.00 | 17.88 | C |
| ATOM | 2849 | N | LYS | A | 356 | 61.917 | 25.770 | −62.740 | 1.00 | 17.95 | N |
| ATOM | 2850 | CA | LYS | A | 356 | 61.024 | 26.401 | −61.775 | 1.00 | 20.84 | C |
| ATOM | 2851 | C | LYS | A | 356 | 59.639 | 25.758 | −61.778 | 1.00 | 21.09 | C |
| ATOM | 2852 | O | LYS | A | 356 | 59.058 | 25.535 | −60.713 | 1.00 | 19.78 | O |
| ATOM | 2853 | CB | LYS | A | 356 | 60.881 | 27.893 | −62.072 | 1.00 | 19.86 | C |
| ATOM | 2854 | CG | LYS | A | 356 | 62.147 | 28.687 | −61.849 | 1.00 | 23.49 | C |
| ATOM | 2855 | CD | LYS | A | 356 | 61.969 | 30.135 | −62.268 | 1.00 | 25.62 | C |
| ATOM | 2856 | CE | LYS | A | 356 | 63.221 | 30.928 | −61.956 | 1.00 | 30.35 | C |
| ATOM | 2857 | NZ | LYS | A | 356 | 63.138 | 32.294 | −62.528 | 1.00 | 36.04 | N |
| ATOM | 2858 | N | PHE | A | 357 | 59.109 | 25.462 | −62.966 | 1.00 | 21.41 | N |
| ATOM | 2859 | CA | PHE | A | 357 | 57.784 | 24.850 | −63.066 | 1.00 | 21.13 | C |
| ATOM | 2860 | C | PHE | A | 357 | 57.761 | 23.426 | −62.514 | 1.00 | 22.71 | C |
| ATOM | 2861 | O | PHE | A | 357 | 56.789 | 23.024 | −61.872 | 1.00 | 22.92 | O |
| ATOM | 2862 | CB | PHE | A | 357 | 57.287 | 24.842 | −64.518 | 1.00 | 19.56 | C |
| ATOM | 2863 | CG | PHE | A | 357 | 56.550 | 26.094 | −64.926 | 1.00 | 20.14 | C |
| ATOM | 2864 | CD1 | PHE | A | 357 | 57.235 | 27.279 | −65.193 | 1.00 | 21.43 | C |
| ATOM | 2865 | CD2 | PHE | A | 357 | 55.165 | 26.081 | −65.059 | 1.00 | 17.56 | C |
| ATOM | 2866 | CE1 | PHE | A | 357 | 56.544 | 28.431 | −65.591 | 1.00 | 20.96 | C |
| ATOM | 2867 | CE2 | PHE | A | 357 | 54.471 | 27.219 | −65.453 | 1.00 | 18.83 | C |
| ATOM | 2868 | CZ | PHE | A | 357 | 55.159 | 28.396 | −65.722 | 1.00 | 20.20 | C |
| ATOM | 2869 | N | PHE | A | 358 | 58.823 | 22.662 | −62.764 | 1.00 | 22.22 | N |
| ATOM | 2870 | CA | PHE | A | 358 | 58.894 | 21.290 | −62.269 | 1.00 | 22.84 | C |
| ATOM | 2871 | C | PHE | A | 358 | 59.318 | 21.214 | −60.801 | 1.00 | 25.53 | C |
| ATOM | 2872 | O | PHE | A | 358 | 59.057 | 20.217 | −60.129 | 1.00 | 25.64 | O |
| ATOM | 2873 | CB | PHE | A | 358 | 59.878 | 20.447 | −63.093 | 1.00 | 22.26 | C |
| ATOM | 2874 | CG | PHE | A | 358 | 59.400 | 20.111 | −64.487 | 1.00 | 23.16 | C |
| ATOM | 2875 | CD1 | PHE | A | 358 | 58.091 | 19.694 | −64.715 | 1.00 | 22.06 | C |
| ATOM | 2876 | CD2 | PHE | A | 358 | 60.284 | 20.172 | −65.565 | 1.00 | 23.13 | C |
| ATOM | 2877 | CE1 | PHE | A | 358 | 57.668 | 19.338 | −66.006 | 1.00 | 23.71 | C |
| ATOM | 2878 | CE2 | PHE | A | 358 | 59.879 | 19.820 | −66.856 | 1.00 | 23.06 | C |
| ATOM | 2879 | CZ | PHE | A | 358 | 58.566 | 19.401 | −67.077 | 1.00 | 23.71 | C |
| ATOM | 2880 | N | LYS | A | 359 | 59.981 | 22.254 | −60.308 | 1.00 | 26.04 | N |
| ATOM | 2881 | CA | LYS | A | 359 | 60.446 | 22.260 | −58.922 | 1.00 | 27.67 | C |
| ATOM | 2882 | C | LYS | A | 359 | 61.448 | 21.124 | −58.707 | 1.00 | 25.62 | C |
| ATOM | 2883 | O | LYS | A | 359 | 61.244 | 20.248 | −57.868 | 1.00 | 24.68 | O |
| ATOM | 2884 | CB | LYS | A | 359 | 59.262 | 22.091 | −57.959 | 1.00 | 31.84 | C |
| ATOM | 2885 | CG | LYS | A | 359 | 59.643 | 22.110 | −56.475 | 1.00 | 37.61 | C |
| ATOM | 2886 | CD | LYS | A | 359 | 58.423 | 21.860 | −55.588 | 1.00 | 42.97 | C |
| ATOM | 2887 | CE | LYS | A | 359 | 58.807 | 21.786 | −54.113 | 1.00 | 45.26 | C |
| ATOM | 2888 | NZ | LYS | A | 359 | 57.643 | 21.443 | −53.240 | 1.00 | 47.70 | N |
| ATOM | 2889 | N | VAL | A | 360 | 62.526 | 21.128 | −59.482 | 1.00 | 22.83 | N |
| ATOM | 2890 | CA | VAL | A | 360 | 63.544 | 20.095 | −59.350 | 1.00 | 21.63 | C |
| ATOM | 2891 | C | VAL | A | 360 | 64.909 | 20.729 | −59.158 | 1.00 | 20.27 | C |
| ATOM | 2892 | O | VAL | A | 360 | 65.088 | 21.929 | −59.376 | 1.00 | 20.02 | O |
| ATOM | 2893 | CB | VAL | A | 360 | 63.627 | 19.186 | −60.609 | 1.00 | 20.29 | C |
| ATOM | 2894 | CG1 | VAL | A | 360 | 62.340 | 18.422 | −60.791 | 1.00 | 18.47 | C |
| ATOM | 2895 | CG2 | VAL | A | 360 | 63.922 | 20.027 | −61.839 | 1.00 | 19.76 | C |
| ATOM | 2896 | N | LEU | A | 361 | 65.869 | 19.917 | −58.741 | 1.00 | 18.66 | N |
| ATOM | 2897 | CA | LEU | A | 361 | 67.224 | 20.399 | −58.572 | 1.00 | 20.18 | C |
| ATOM | 2898 | C | LEU | A | 361 | 67.847 | 20.294 | −59.959 | 1.00 | 18.60 | C |
| ATOM | 2899 | O | LEU | A | 361 | 67.593 | 19.330 | −60.685 | 1.00 | 19.89 | O |
| ATOM | 2900 | CB | LEU | A | 361 | 67.985 | 19.525 | −57.580 | 1.00 | 20.24 | C |
| ATOM | 2901 | CG | LEU | A | 361 | 69.349 | 20.100 | −57.203 | 1.00 | 23.29 | C |
| ATOM | 2902 | CD1 | LEU | A | 361 | 69.150 | 21.480 | −56.569 | 1.00 | 23.00 | C |
| ATOM | 2903 | CD2 | LEU | A | 361 | 70.070 | 19.146 | −56.252 | 1.00 | 19.60 | C |
| ATOM | 2904 | N | ASN | A | 362 | 68.661 | 21.272 | −60.329 | 1.00 | 18.09 | N |
| ATOM | 2905 | CA | ASN | A | 362 | 69.276 | 21.279 | −61.653 | 1.00 | 20.44 | C |
| ATOM | 2906 | C | ASN | A | 362 | 70.485 | 22.206 | −61.586 | 1.00 | 22.03 | C |
| ATOM | 2907 | O | ASN | A | 362 | 70.566 | 23.046 | −60.698 | 1.00 | 18.71 | O |
| ATOM | 2908 | CB | ASN | A | 362 | 68.257 | 21.828 | −62.664 | 1.00 | 21.64 | C |
| ATOM | 2909 | CG | ASN | A | 362 | 68.679 | 21.630 | −64.097 | 1.00 | 22.69 | C |

TABLE 2-continued

| | | | | | | | | | | |
|---|---|---|---|---|---|---|---|---|---|---|
| ATOM | 2910 | OD1 | ASN | A | 362 | 68.554 | 20.533 | −64.646 | 1.00 | 22.91 | O |
| ATOM | 2911 | ND2 | ASN | A | 362 | 69.181 | 22.694 | −64.720 | 1.00 | 22.19 | N |
| ATOM | 2912 | N | ARG | A | 363 | 71.425 | 22.049 | −62.511 | 1.00 | 24.47 | N |
| ATOM | 2913 | CA | ARG | A | 363 | 72.594 | 22.920 | −62.541 | 1.00 | 28.03 | C |
| ATOM | 2914 | C | ARG | A | 363 | 72.116 | 24.361 | −62.728 | 1.00 | 29.13 | C |
| ATOM | 2915 | O | ARG | A | 363 | 71.091 | 24.600 | −63.365 | 1.00 | 30.16 | O |
| ATOM | 2916 | CB | ARG | A | 363 | 73.512 | 22.545 | −63.703 | 1.00 | 30.56 | C |
| ATOM | 2917 | CG | ARG | A | 363 | 72.854 | 22.681 | −65.074 | 1.00 | 35.53 | C |
| ATOM | 2918 | CD | ARG | A | 363 | 73.889 | 22.973 | −66.152 | 1.00 | 40.48 | C |
| ATOM | 2919 | NE | ARG | A | 363 | 75.021 | 22.058 | −66.065 | 1.00 | 43.30 | N |
| ATOM | 2920 | CZ | ARG | A | 363 | 74.930 | 20.746 | −66.243 | 1.00 | 45.43 | C |
| ATOM | 2921 | NH1 | ARG | A | 363 | 73.758 | 20.194 | −66.527 | 1.00 | 47.44 | N |
| ATOM | 2922 | NH2 | ARG | A | 363 | 76.006 | 19.985 | −66.117 | 1.00 | 48.36 | N |
| ATOM | 2923 | N | LYS | A | 364 | 72.866 | 25.310 | −62.182 | 1.00 | 30.52 | N |
| ATOM | 2924 | CA | LYS | A | 364 | 72.539 | 26.732 | −62.269 | 1.00 | 31.83 | C |
| ATOM | 2925 | C | LYS | A | 364 | 73.198 | 27.408 | −63.470 | 1.00 | 32.60 | C |
| ATOM | 2926 | O | LYS | A | 364 | 72.712 | 28.424 | −63.969 | 1.00 | 30.99 | O |
| ATOM | 2927 | CB | LYS | A | 364 | 73.008 | 27.445 | −60.998 | 1.00 | 35.49 | C |
| ATOM | 2928 | CG | LYS | A | 364 | 71.906 | 27.949 | −60.079 | 1.00 | 38.70 | C |
| ATOM | 2929 | CD | LYS | A | 364 | 71.100 | 26.821 | −59.469 | 1.00 | 41.67 | C |
| ATOM | 2930 | CE | LYS | A | 364 | 70.294 | 27.327 | −58.279 | 1.00 | 42.58 | C |
| ATOM | 2931 | NZ | LYS | A | 364 | 69.467 | 28.513 | −58.639 | 1.00 | 44.45 | N |
| ATOM | 2932 | N | THR | A | 365 | 74.326 | 26.859 | −63.907 | 1.00 | 32.41 | N |
| ATOM | 2933 | CA | THR | A | 365 | 75.062 | 27.412 | −65.038 | 1.00 | 34.28 | C |
| ATOM | 2934 | C | THR | A | 365 | 75.807 | 26.294 | −65.736 | 1.00 | 33.77 | C |
| ATOM | 2935 | O | THR | A | 365 | 76.105 | 25.272 | −65.121 | 1.00 | 33.25 | O |
| ATOM | 2936 | CB | THR | A | 365 | 76.097 | 28.462 | −64.585 | 1.00 | 35.79 | C |
| ATOM | 2937 | OG1 | THR | A | 365 | 76.881 | 28.878 | −65.710 | 1.00 | 37.09 | O |
| ATOM | 2938 | CG2 | THR | A | 365 | 77.024 | 27.871 | −63.526 | 1.00 | 37.01 | C |
| ATOM | 2939 | N | PHE | A | 366 | 76.118 | 26.489 | −67.015 | 1.00 | 33.62 | N |
| ATOM | 2940 | CA | PHE | A | 366 | 76.823 | 25.461 | −67.772 | 1.00 | 34.16 | C |
| ATOM | 2941 | C | PHE | A | 366 | 78.228 | 25.230 | −67.236 | 1.00 | 33.96 | C |
| ATOM | 2942 | O | PHE | A | 366 | 78.862 | 24.228 | −67.567 | 1.00 | 33.53 | O |
| ATOM | 2943 | CB | PHE | A | 366 | 76.888 | 25.821 | −69.261 | 1.00 | 34.76 | C |
| ATOM | 2944 | CG | PHE | A | 366 | 77.710 | 27.042 | −69.563 | 1.00 | 36.34 | C |
| ATOM | 2945 | CD1 | PHE | A | 366 | 77.172 | 28.314 | −69.417 | 1.00 | 37.00 | C |
| ATOM | 2946 | CD2 | PHE | A | 366 | 79.022 | 26.919 | −70.000 | 1.00 | 37.20 | C |
| ATOM | 2947 | CE1 | PHE | A | 366 | 77.930 | 29.449 | −69.703 | 1.00 | 37.88 | C |
| ATOM | 2948 | CE2 | PHE | A | 366 | 79.787 | 28.048 | −70.286 | 1.00 | 37.66 | C |
| ATOM | 2949 | CZ | PHE | A | 366 | 79.239 | 29.314 | −70.137 | 1.00 | 36.55 | C |
| ATOM | 2950 | N | LEU | A | 367 | 78.707 | 26.158 | −66.406 | 1.00 | 33.26 | N |
| ATOM | 2951 | CA | LEU | A | 367 | 80.042 | 26.054 | −65.816 | 1.00 | 33.87 | C |
| ATOM | 2952 | C | LEU | A | 367 | 80.113 | 24.994 | −64.722 | 1.00 | 33.45 | C |
| ATOM | 2953 | O | LEU | A | 367 | 81.192 | 24.668 | −64.228 | 1.00 | 33.39 | O |
| ATOM | 2954 | CB | LEU | A | 367 | 80.492 | 27.408 | −65.258 | 1.00 | 34.01 | C |
| ATOM | 2955 | CG | LEU | A | 367 | 80.929 | 28.435 | −66.310 | 1.00 | 35.45 | C |
| ATOM | 2956 | CD1 | LEU | A | 367 | 81.267 | 29.756 | −65.639 | 1.00 | 35.66 | C |
| ATOM | 2957 | CD2 | LEU | A | 367 | 82.134 | 27.897 | −67.075 | 1.00 | 33.46 | C |
| ATOM | 2958 | N | ASN | A | 368 | 78.955 | 24.473 | −64.331 | 1.00 | 33.34 | N |
| ATOM | 2959 | CA | ASN | A | 368 | 78.894 | 23.418 | −63.326 | 1.00 | 32.15 | C |
| ATOM | 2960 | C | ASN | A | 368 | 78.738 | 22.143 | −64.149 | 1.00 | 31.28 | C |
| ATOM | 2961 | O | ASN | A | 368 | 77.623 | 21.722 | −64.455 | 1.00 | 33.02 | O |
| ATOM | 2962 | CB | ASN | A | 368 | 77.689 | 23.617 | −62.408 | 1.00 | 32.78 | C |
| ATOM | 2963 | CG | ASN | A | 368 | 77.581 | 22.536 | −61.347 | 1.00 | 35.20 | C |
| ATOM | 2964 | OD1 | ASN | A | 368 | 78.466 | 21.685 | −61.215 | 1.00 | 36.19 | O |
| ATOM | 2965 | ND2 | ASN | A | 368 | 76.498 | 22.567 | −60.579 | 1.00 | 34.32 | N |
| ATOM | 2966 | N | PHE | A | 369 | 79.866 | 21.542 | −64.510 | 1.00 | 28.50 | N |
| ATOM | 2967 | CA | PHE | A | 369 | 79.882 | 20.350 | −65.355 | 1.00 | 28.34 | C |
| ATOM | 2968 | C | PHE | A | 369 | 79.371 | 19.057 | −64.740 | 1.00 | 26.42 | C |
| ATOM | 2969 | O | PHE | A | 369 | 79.580 | 18.792 | −63.559 | 1.00 | 25.67 | O |
| ATOM | 2970 | CB | PHE | A | 369 | 81.304 | 20.105 | −65.869 | 1.00 | 29.33 | C |
| ATOM | 2971 | CG | PHE | A | 369 | 81.937 | 21.311 | −66.497 | 1.00 | 29.23 | C |
| ATOM | 2972 | CD1 | PHE | A | 369 | 81.498 | 21.783 | −67.729 | 1.00 | 29.05 | C |
| ATOM | 2973 | CD2 | PHE | A | 369 | 82.964 | 21.985 | −65.844 | 1.00 | 30.06 | C |
| ATOM | 2974 | CE1 | PHE | A | 369 | 82.074 | 22.917 | −68.303 | 1.00 | 32.73 | C |
| ATOM | 2975 | CE2 | PHE | A | 369 | 83.548 | 23.119 | −66.404 | 1.00 | 31.29 | C |
| ATOM | 2976 | CZ | PHE | A | 369 | 83.101 | 23.587 | −67.638 | 1.00 | 32.71 | C |
| ATOM | 2977 | N | ASP | A | 370 | 78.711 | 18.249 | −65.567 | 1.00 | 23.85 | N |
| ATOM | 2978 | CA | ASP | A | 370 | 78.210 | 16.952 | −65.132 | 1.00 | 24.32 | C |
| ATOM | 2979 | C | ASP | A | 370 | 79.421 | 16.135 | −64.697 | 1.00 | 23.68 | C |
| ATOM | 2980 | O | ASP | A | 370 | 80.529 | 16.356 | −65.191 | 1.00 | 22.91 | O |
| ATOM | 2981 | CB | ASP | A | 370 | 77.494 | 16.236 | −66.283 | 1.00 | 24.25 | C |
| ATOM | 2982 | CG | ASP | A | 370 | 76.255 | 16.969 | −66.742 | 1.00 | 26.64 | C |
| ATOM | 2983 | OD1 | ASP | A | 370 | 75.525 | 17.496 | −65.876 | 1.00 | 27.84 | O |
| ATOM | 2984 | OD2 | ASP | A | 370 | 76.002 | 17.003 | −67.965 | 1.00 | 29.91 | O |
| ATOM | 2985 | N | LYS | A | 371 | 79.212 | 15.193 | −63.785 | 1.00 | 23.54 | N |
| ATOM | 2986 | CA | LYS | A | 371 | 80.309 | 14.372 | −63.281 | 1.00 | 23.78 | C |
| ATOM | 2987 | C | LYS | A | 371 | 80.069 | 12.873 | −63.385 | 1.00 | 23.00 | C |
| ATOM | 2988 | O | LYS | A | 371 | 80.997 | 12.083 | −63.229 | 1.00 | 23.23 | O |

TABLE 2-continued

| | | | | | | | | | | |
|---|---|---|---|---|---|---|---|---|---|---|
| ATOM | 2989 | CB | LYS | A | 371 | 80.593 | 14.733 | −61.823 | 1.00 | 25.65 | C |
| ATOM | 2990 | CG | LYS | A | 371 | 81.014 | 16.184 | −61.632 | 1.00 | 27.58 | C |
| ATOM | 2991 | CD | LYS | A | 371 | 81.088 | 16.560 | −60.167 | 1.00 | 26.61 | C |
| ATOM | 2992 | CE | LYS | A | 371 | 81.464 | 18.020 | −60.022 | 1.00 | 31.98 | C |
| ATOM | 2993 | NZ | LYS | A | 371 | 81.431 | 18.462 | −58.607 | 1.00 | 35.86 | N |
| ATOM | 2994 | N | ALA | A | 372 | 78.831 | 12.475 | −63.653 | 1.00 | 21.20 | N |
| ATOM | 2995 | CA | ALA | A | 372 | 78.525 | 11.059 | −63.752 | 1.00 | 20.03 | C |
| ATOM | 2996 | C | ALA | A | 372 | 77.348 | 10.772 | −64.669 | 1.00 | 20.47 | C |
| ATOM | 2997 | O | ALA | A | 372 | 76.626 | 11.680 | −65.074 | 1.00 | 19.53 | O |
| ATOM | 2998 | CB | ALA | A | 372 | 78.243 | 10.511 | −62.360 | 1.00 | 20.44 | C |
| ATOM | 2999 | N | VAL | A | 373 | 77.173 | 9.495 | −64.992 | 1.00 | 20.64 | N |
| ATOM | 3000 | CA | VAL | A | 373 | 76.078 | 9.032 | −65.834 | 1.00 | 20.25 | C |
| ATOM | 3001 | C | VAL | A | 373 | 75.415 | 7.852 | −65.121 | 1.00 | 20.34 | C |
| ATOM | 3002 | O | VAL | A | 373 | 76.098 | 6.969 | −64.594 | 1.00 | 21.36 | O |
| ATOM | 3003 | CB | VAL | A | 373 | 76.586 | 8.592 | −67.222 | 1.00 | 21.08 | C |
| ATOM | 3004 | CG1 | VAL | A | 373 | 77.788 | 7.696 | −67.068 | 1.00 | 22.91 | C |
| ATOM | 3005 | CG2 | VAL | A | 373 | 75.476 | 7.870 | −67.975 | 1.00 | 19.91 | C |
| ATOM | 3006 | N | PHE | A | 374 | 74.086 | 7.845 | −65.102 | 1.00 | 18.40 | N |
| ATOM | 3007 | CA | PHE | A | 374 | 73.321 | 6.799 | −64.426 | 1.00 | 17.39 | C |
| ATOM | 3008 | C | PHE | A | 374 | 72.320 | 6.121 | −65.340 | 1.00 | 18.74 | C |
| ATOM | 3009 | O | PHE | A | 374 | 71.782 | 6.741 | −66.258 | 1.00 | 19.53 | O |
| ATOM | 3010 | CB | PHE | A | 374 | 72.511 | 7.387 | −63.260 | 1.00 | 15.49 | C |
| ATOM | 3011 | CG | PHE | A | 374 | 73.342 | 8.024 | −62.183 | 1.00 | 18.22 | C |
| ATOM | 3012 | CD1 | PHE | A | 374 | 74.046 | 7.244 | −61.273 | 1.00 | 18.06 | C |
| ATOM | 3013 | CD2 | PHE | A | 374 | 73.405 | 9.410 | −62.067 | 1.00 | 17.65 | C |
| ATOM | 3014 | CE1 | PHE | A | 374 | 74.803 | 7.838 | −60.260 | 1.00 | 17.93 | C |
| ATOM | 3015 | CE2 | PHE | A | 374 | 74.157 | 10.010 | −61.059 | 1.00 | 19.63 | C |
| ATOM | 3016 | CZ | PHE | A | 374 | 74.857 | 9.220 | −60.154 | 1.00 | 18.54 | C |
| ATOM | 3017 | N | LYS | A | 375 | 72.073 | 4.844 | −65.074 | 1.00 | 18.70 | N |
| ATOM | 3018 | CA | LYS | A | 375 | 71.071 | 4.091 | −65.812 | 1.00 | 20.64 | C |
| ATOM | 3019 | C | LYS | A | 375 | 69.839 | 4.269 | −64.938 | 1.00 | 20.55 | C |
| ATOM | 3020 | O | LYS | A | 375 | 69.923 | 4.123 | −63.719 | 1.00 | 19.78 | O |
| ATOM | 3021 | CB | LYS | A | 375 | 71.410 | 2.608 | −65.863 | 1.00 | 19.89 | C |
| ATOM | 3022 | CG | LYS | A | 375 | 70.376 | 1.775 | −66.607 | 1.00 | 20.96 | C |
| ATOM | 3023 | CD | LYS | A | 375 | 70.521 | 1.971 | −68.104 | 1.00 | 22.72 | C |
| ATOM | 3024 | CE | LYS | A | 375 | 69.565 | 1.098 | −68.901 | 1.00 | 22.87 | C |
| ATOM | 3025 | NZ | LYS | A | 375 | 68.173 | 1.590 | −68.834 | 1.00 | 26.23 | N |
| ATOM | 3026 | N | ILE | A | 376 | 68.711 | 4.600 | −65.554 | 1.00 | 19.32 | N |
| ATOM | 3027 | CA | ILE | A | 376 | 67.472 | 4.791 | −64.820 | 1.00 | 16.38 | C |
| ATOM | 3028 | C | ILE | A | 376 | 66.355 | 4.028 | −65.504 | 1.00 | 16.61 | C |
| ATOM | 3029 | O | ILE | A | 376 | 66.539 | 3.470 | −66.587 | 1.00 | 17.37 | O |
| ATOM | 3030 | CB | ILE | A | 376 | 67.071 | 6.282 | −64.749 | 1.00 | 16.71 | C |
| ATOM | 3031 | CG1 | ILE | A | 376 | 66.937 | 6.866 | −66.166 | 1.00 | 15.35 | C |
| ATOM | 3032 | CG2 | ILE | A | 376 | 68.091 | 7.039 | −63.941 | 1.00 | 17.34 | C |
| ATOM | 3033 | CD1 | ILE | A | 376 | 66.342 | 8.264 | −66.224 | 1.00 | 16.39 | C |
| ATOM | 3034 | N | ASN | A | 377 | 65.198 | 4.000 | −64.858 | 1.00 | 16.56 | N |
| ATOM | 3035 | CA | ASN | A | 377 | 64.029 | 3.319 | −65.389 | 1.00 | 17.78 | C |
| ATOM | 3036 | C | ASN | A | 377 | 62.819 | 4.076 | −64.859 | 1.00 | 17.41 | C |
| ATOM | 3037 | O | ASN | A | 377 | 62.333 | 3.796 | −63.768 | 1.00 | 16.36 | O |
| ATOM | 3038 | CB | ASN | A | 377 | 64.016 | 1.866 | −64.916 | 1.00 | 19.96 | C |
| ATOM | 3039 | CG | ASN | A | 377 | 62.810 | 1.096 | −65.421 | 1.00 | 24.59 | C |
| ATOM | 3040 | OD1 | ASN | A | 377 | 62.149 | 1.502 | −66.380 | 1.00 | 25.32 | O |
| ATOM | 3041 | ND2 | ASN | A | 377 | 62.522 | −0.027 | −64.777 | 1.00 | 26.30 | N |
| ATOM | 3042 | N | ILE | A | 378 | 62.336 | 5.034 | −65.645 | 1.00 | 17.86 | N |
| ATOM | 3043 | CA | ILE | A | 378 | 61.210 | 5.877 | −65.243 | 1.00 | 17.18 | C |
| ATOM | 3044 | C | ILE | A | 378 | 59.813 | 5.369 | −65.564 | 1.00 | 16.17 | C |
| ATOM | 3045 | O | ILE | A | 378 | 58.834 | 6.007 | −65.177 | 1.00 | 14.33 | O |
| ATOM | 3046 | CB | ILE | A | 378 | 61.307 | 7.271 | −65.881 | 1.00 | 19.04 | C |
| ATOM | 3047 | CG1 | ILE | A | 378 | 61.051 | 7.159 | −67.395 | 1.00 | 19.38 | C |
| ATOM | 3048 | CG2 | ILE | A | 378 | 62.665 | 7.877 | −65.593 | 1.00 | 19.88 | C |
| ATOM | 3049 | CD1 | ILE | A | 378 | 61.010 | 8.496 | −68.125 | 1.00 | 22.93 | C |
| ATOM | 3050 | N | VAL | A | 379 | 59.703 | 4.255 | −66.279 | 1.00 | 15.96 | N |
| ATOM | 3051 | CA | VAL | A | 379 | 58.384 | 3.742 | −66.627 | 1.00 | 19.34 | C |
| ATOM | 3052 | C | VAL | A | 379 | 57.550 | 3.322 | −65.407 | 1.00 | 19.85 | C |
| ATOM | 3053 | O | VAL | A | 379 | 56.374 | 3.678 | −65.305 | 1.00 | 19.96 | O |
| ATOM | 3054 | CB | VAL | A | 379 | 58.479 | 2.569 | −67.631 | 1.00 | 20.18 | C |
| ATOM | 3055 | CG1 | VAL | A | 379 | 57.110 | 1.904 | −67.785 | 1.00 | 21.74 | C |
| ATOM | 3056 | CG2 | VAL | A | 379 | 58.942 | 3.094 | −68.985 | 1.00 | 22.86 | C |
| ATOM | 3057 | N | PRO | A | 380 | 58.140 | 2.561 | −64.467 | 1.00 | 19.25 | N |
| ATOM | 3058 | CA | PRO | A | 380 | 57.368 | 2.151 | −63.284 | 1.00 | 18.59 | C |
| ATOM | 3059 | C | PRO | A | 380 | 56.949 | 3.346 | −62.416 | 1.00 | 17.56 | C |
| ATOM | 3060 | O | PRO | A | 380 | 57.769 | 4.208 | −62.104 | 1.00 | 17.68 | O |
| ATOM | 3061 | CB | PRO | A | 380 | 58.336 | 1.227 | −62.542 | 1.00 | 18.56 | C |
| ATOM | 3062 | CG | PRO | A | 380 | 59.156 | 0.634 | −63.646 | 1.00 | 19.50 | C |
| ATOM | 3063 | CD | PRO | A | 380 | 59.427 | 1.845 | −64.523 | 1.00 | 20.28 | C |
| ATOM | 3064 | N | LYS | A | 381 | 55.681 | 3.393 | −62.011 | 1.00 | 18.53 | N |
| ATOM | 3065 | CA | LYS | A | 381 | 55.193 | 4.498 | −61.185 | 1.00 | 18.76 | C |
| ATOM | 3066 | C | LYS | A | 381 | 55.834 | 4.595 | −59.804 | 1.00 | 19.82 | C |
| ATOM | 3067 | O | LYS | A | 381 | 55.854 | 5.669 | −59.200 | 1.00 | 19.42 | O |

TABLE 2-continued

| | | | | | | | | | | |
|---|---|---|---|---|---|---|---|---|---|---|
| ATOM | 3068 | CB | LYS | A | 381 | 53.668 | 4.429 | −61.064 | 1.00 | 21.31 | C |
| ATOM | 3069 | CG | LYS | A | 381 | 52.975 | 4.753 | −62.381 | 1.00 | 25.94 | C |
| ATOM | 3070 | CD | LYS | A | 381 | 51.465 | 4.635 | −62.311 | 1.00 | 29.76 | C |
| ATOM | 3071 | CE | LYS | A | 381 | 50.851 | 4.964 | −63.667 | 1.00 | 32.21 | C |
| ATOM | 3072 | NZ | LYS | A | 381 | 49.375 | 4.780 | −63.679 | 1.00 | 38.66 | N |
| ATOM | 3073 | N | VAL | A | 382 | 56.360 | 3.484 | −59.297 | 1.00 | 20.69 | N |
| ATOM | 3074 | CA | VAL | A | 382 | 57.015 | 3.514 | −57.993 | 1.00 | 19.52 | C |
| ATOM | 3075 | C | VAL | A | 382 | 58.361 | 4.236 | −58.096 | 1.00 | 19.95 | C |
| ATOM | 3076 | O | VAL | A | 382 | 58.936 | 4.651 | −57.084 | 1.00 | 17.90 | O |
| ATOM | 3077 | CB | VAL | A | 382 | 57.242 | 2.079 | −57.427 | 1.00 | 21.21 | C |
| ATOM | 3078 | CG1 | VAL | A | 382 | 55.902 | 1.451 | −57.067 | 1.00 | 18.26 | C |
| ATOM | 3079 | CG2 | VAL | A | 382 | 57.978 | 1.217 | −58.434 | 1.00 | 18.81 | C |
| ATOM | 3080 | N | ASN | A | 383 | 58.842 | 4.402 | −59.329 | 1.00 | 16.79 | N |
| ATOM | 3081 | CA | ASN | A | 383 | 60.123 | 5.058 | −59.590 | 1.00 | 17.42 | C |
| ATOM | 3082 | C | ASN | A | 383 | 60.008 | 6.523 | −59.971 | 1.00 | 17.83 | C |
| ATOM | 3083 | O | ASN | A | 383 | 60.726 | 7.369 | −59.449 | 1.00 | 19.97 | O |
| ATOM | 3084 | CB | ASN | A | 383 | 60.867 | 4.352 | −60.739 | 1.00 | 15.62 | C |
| ATOM | 3085 | CG | ASN | A | 383 | 61.502 | 3.047 | −60.321 | 1.00 | 16.74 | C |
| ATOM | 3086 | OD1 | ASN | A | 383 | 62.086 | 2.327 | −61.149 | 1.00 | 19.86 | O |
| ATOM | 3087 | ND2 | ASN | A | 383 | 61.399 | 2.727 | −59.040 | 1.00 | 13.84 | N |
| ATOM | 3088 | N | TYR | A | 384 | 59.079 | 6.826 | −60.868 | 1.00 | 17.51 | N |
| ATOM | 3089 | CA | TYR | A | 384 | 58.965 | 8.178 | −61.386 | 1.00 | 17.00 | C |
| ATOM | 3090 | C | TYR | A | 384 | 57.540 | 8.443 | −61.847 | 1.00 | 17.18 | C |
| ATOM | 3091 | O | TYR | A | 384 | 56.893 | 7.562 | −62.408 | 1.00 | 19.81 | O |
| ATOM | 3092 | CB | TYR | A | 384 | 59.964 | 8.271 | −62.556 | 1.00 | 15.03 | C |
| ATOM | 3093 | CG | TYR | A | 384 | 60.129 | 9.596 | −63.271 | 1.00 | 17.38 | C |
| ATOM | 3094 | CD1 | TYR | A | 384 | 59.198 | 10.029 | −64.217 | 1.00 | 16.04 | C |
| ATOM | 3095 | CD2 | TYR | A | 384 | 61.269 | 10.379 | −63.058 | 1.00 | 17.85 | C |
| ATOM | 3096 | CE1 | TYR | A | 384 | 59.402 | 11.208 | −64.938 | 1.00 | 16.64 | C |
| ATOM | 3097 | CE2 | TYR | A | 384 | 61.483 | 11.555 | −63.770 | 1.00 | 17.75 | C |
| ATOM | 3098 | CZ | TYR | A | 384 | 60.547 | 11.966 | −64.709 | 1.00 | 17.57 | C |
| ATOM | 3099 | OH | TYR | A | 384 | 60.766 | 13.135 | −65.401 | 1.00 | 15.33 | O |
| ATOM | 3100 | N | THR | A | 385 | 57.039 | 9.648 | −61.609 | 1.00 | 17.98 | N |
| ATOM | 3101 | CA | THR | A | 385 | 55.681 | 9.962 | −62.048 | 1.00 | 19.85 | C |
| ATOM | 3102 | C | THR | A | 385 | 55.620 | 11.229 | −62.897 | 1.00 | 19.49 | C |
| ATOM | 3103 | O | THR | A | 385 | 56.475 | 12.114 | −62.797 | 1.00 | 18.17 | O |
| ATOM | 3104 | CB | THR | A | 385 | 54.699 | 10.139 | −60.855 | 1.00 | 19.39 | C |
| ATOM | 3105 | OG1 | THR | A | 385 | 55.086 | 11.276 | −60.079 | 1.00 | 21.14 | O |
| ATOM | 3106 | CG2 | THR | A | 385 | 54.679 | 8.899 | −59.971 | 1.00 | 19.88 | C |
| ATOM | 3107 | N | ILE | A | 386 | 54.592 | 11.294 | −63.733 | 1.00 | 18.65 | N |
| ATOM | 3108 | CA | ILE | A | 386 | 54.350 | 12.426 | −64.615 | 1.00 | 20.37 | C |
| ATOM | 3109 | C | ILE | A | 386 | 54.355 | 13.742 | −63.844 | 1.00 | 19.77 | C |
| ATOM | 3110 | O | ILE | A | 386 | 54.962 | 14.728 | −64.261 | 1.00 | 18.14 | O |
| ATOM | 3111 | CB | ILE | A | 386 | 52.975 | 12.268 | −65.311 | 1.00 | 20.59 | C |
| ATOM | 3112 | CG1 | ILE | A | 386 | 53.038 | 11.097 | −66.296 | 1.00 | 24.62 | C |
| ATOM | 3113 | CG2 | ILE | A | 386 | 52.563 | 13.580 | −65.971 | 1.00 | 20.73 | C |
| ATOM | 3114 | CD1 | ILE | A | 386 | 51.676 | 10.638 | −66.832 | 1.00 | 25.11 | C |
| ATOM | 3115 | N | TYR | A | 387 | 53.688 | 13.744 | −62.702 | 1.00 | 20.44 | N |
| ATOM | 3116 | CA | TYR | A | 387 | 53.577 | 14.947 | −61.902 | 1.00 | 23.36 | C |
| ATOM | 3117 | C | TYR | A | 387 | 54.707 | 15.318 | −60.954 | 1.00 | 22.96 | C |
| ATOM | 3118 | O | TYR | A | 387 | 54.918 | 16.505 | −60.697 | 1.00 | 22.27 | O |
| ATOM | 3119 | CB | TYR | A | 387 | 52.237 | 14.918 | −61.157 | 1.00 | 28.88 | C |
| ATOM | 3120 | CG | TYR | A | 387 | 51.101 | 15.405 | −62.036 | 1.00 | 35.48 | C |
| ATOM | 3121 | CD1 | TYR | A | 387 | 50.938 | 16.771 | −62.292 | 1.00 | 37.16 | C |
| ATOM | 3122 | CD2 | TYR | A | 387 | 50.249 | 14.508 | −62.683 | 1.00 | 37.32 | C |
| ATOM | 3123 | CE1 | TYR | A | 387 | 49.964 | 17.235 | −63.173 | 1.00 | 40.63 | C |
| ATOM | 3124 | CE2 | TYR | A | 387 | 49.264 | 14.966 | −63.573 | 1.00 | 39.81 | C |
| ATOM | 3125 | CZ | TYR | A | 387 | 49.132 | 16.332 | −63.813 | 1.00 | 41.73 | C |
| ATOM | 3126 | OH | TYR | A | 387 | 48.184 | 16.810 | −64.697 | 1.00 | 44.90 | O |
| ATOM | 3127 | N | ASP | A | 388 | 55.448 | 14.338 | −60.446 | 1.00 | 21.10 | N |
| ATOM | 3128 | CA | ASP | A | 388 | 56.528 | 14.649 | −59.510 | 1.00 | 19.84 | C |
| ATOM | 3129 | C | ASP | A | 388 | 57.924 | 14.219 | −59.952 | 1.00 | 18.60 | C |
| ATOM | 3130 | O | ASP | A | 388 | 58.910 | 14.563 | −59.296 | 1.00 | 16.72 | O |
| ATOM | 3131 | CB | ASP | A | 388 | 56.269 | 14.003 | −58.140 | 1.00 | 21.92 | C |
| ATOM | 3132 | CG | ASP | A | 388 | 54.983 | 14.468 | −57.490 | 1.00 | 23.09 | C |
| ATOM | 3133 | OD1 | ASP | A | 388 | 54.544 | 15.614 | −57.735 | 1.00 | 22.68 | O |
| ATOM | 3134 | OD2 | ASP | A | 388 | 54.421 | 13.675 | −56.705 | 1.00 | 24.08 | O |
| ATOM | 3135 | N | GLY | A | 389 | 58.020 | 13.460 | −61.038 | 1.00 | 16.45 | N |
| ATOM | 3136 | CA | GLY | A | 389 | 59.329 | 13.001 | −61.465 | 1.00 | 18.41 | C |
| ATOM | 3137 | C | GLY | A | 389 | 59.853 | 12.014 | −60.428 | 1.00 | 18.51 | C |
| ATOM | 3138 | O | GLY | A | 389 | 59.156 | 11.057 | −60.076 | 1.00 | 18.33 | O |
| ATOM | 3139 | N | PHE | A | 390 | 61.061 | 12.245 | −59.919 | 1.00 | 18.04 | N |
| ATOM | 3140 | CA | PHE | A | 390 | 61.650 | 11.347 | −58.919 | 1.00 | 19.24 | C |
| ATOM | 3141 | C | PHE | A | 390 | 61.227 | 11.669 | −57.479 | 1.00 | 19.18 | C |
| ATOM | 3142 | O | PHE | A | 390 | 61.224 | 10.786 | −56.617 | 1.00 | 21.03 | O |
| ATOM | 3143 | CB | PHE | A | 390 | 63.185 | 11.406 | −58.973 | 1.00 | 17.18 | C |
| ATOM | 3144 | CG | PHE | A | 390 | 63.795 | 10.773 | −60.204 | 1.00 | 17.26 | C |
| ATOM | 3145 | CD1 | PHE | A | 390 | 63.710 | 9.404 | −60.419 | 1.00 | 14.96 | C |
| ATOM | 3146 | CD2 | PHE | A | 390 | 64.521 | 11.547 | −61.104 | 1.00 | 13.62 | C |

TABLE 2-continued

| ATOM | 3147 | CE1 | PHE | A | 390 | 64.348 | 8.811 | −61.509 | 1.00 | 17.70 | C |
|---|---|---|---|---|---|---|---|---|---|---|---|
| ATOM | 3148 | CE2 | PHE | A | 390 | 65.163 | 10.964 | −62.198 | 1.00 | 17.48 | C |
| ATOM | 3149 | CZ | PHE | A | 390 | 65.080 | 9.594 | −62.401 | 1.00 | 14.84 | C |
| ATOM | 3150 | N | ASN | A | 391 | 60.889 | 12.931 | −57.228 | 1.00 | 18.97 | N |
| ATOM | 3151 | CA | ASN | A | 391 | 60.522 | 13.401 | −55.890 | 1.00 | 21.44 | C |
| ATOM | 3152 | C | ASN | A | 391 | 59.068 | 13.131 | −55.512 | 1.00 | 20.80 | C |
| ATOM | 3153 | O | ASN | A | 391 | 58.264 | 14.051 | −55.354 | 1.00 | 20.63 | O |
| ATOM | 3154 | CB | ASN | A | 391 | 60.845 | 14.897 | −55.790 | 1.00 | 18.27 | C |
| ATOM | 3155 | CG | ASN | A | 391 | 62.271 | 15.213 | −56.233 | 1.00 | 22.28 | C |
| ATOM | 3156 | OD1 | ASN | A | 391 | 63.224 | 14.541 | −55.821 | 1.00 | 21.99 | O |
| ATOM | 3157 | ND2 | ASN | A | 391 | 62.427 | 16.237 | −57.071 | 1.00 | 16.94 | N |
| ATOM | 3158 | N | LEU | A | 392 | 58.748 | 11.854 | −55.363 | 1.00 | 22.01 | N |
| ATOM | 3159 | CA | LEU | A | 392 | 57.400 | 11.416 | −55.032 | 1.00 | 23.59 | C |
| ATOM | 3160 | C | LEU | A | 392 | 56.766 | 12.079 | −53.808 | 1.00 | 24.43 | C |
| ATOM | 3161 | O | LEU | A | 392 | 57.360 | 12.144 | −52.734 | 1.00 | 25.67 | O |
| ATOM | 3162 | CB | LEU | A | 392 | 57.400 | 9.893 | −54.860 | 1.00 | 23.80 | C |
| ATOM | 3163 | CG | LEU | A | 392 | 57.996 | 9.145 | −56.060 | 1.00 | 22.28 | C |
| ATOM | 3164 | CD1 | LEU | A | 392 | 57.797 | 7.645 | −55.892 | 1.00 | 16.63 | C |
| ATOM | 3165 | CD2 | LEU | A | 392 | 57.322 | 9.628 | −57.342 | 1.00 | 20.79 | C |
| ATOM | 3166 | N | ARG | A | 393 | 55.546 | 12.571 | −53.986 | 1.00 | 25.46 | N |
| ATOM | 3167 | CA | ARG | A | 393 | 54.810 | 13.216 | −52.905 | 1.00 | 26.96 | C |
| ATOM | 3168 | C | ARG | A | 393 | 54.468 | 12.222 | −51.794 | 1.00 | 27.59 | C |
| ATOM | 3169 | O | ARG | A | 393 | 54.329 | 11.024 | −52.040 | 1.00 | 27.08 | O |
| ATOM | 3170 | CB | ARG | A | 393 | 53.509 | 13.802 | −53.447 | 1.00 | 25.99 | C |
| ATOM | 3171 | CG | ARG | A | 393 | 52.575 | 12.755 | −54.021 | 1.00 | 27.10 | C |
| ATOM | 3172 | CD | ARG | A | 393 | 51.411 | 13.409 | −54.747 | 1.00 | 27.86 | C |
| ATOM | 3173 | NE | ARG | A | 393 | 51.876 | 14.277 | −55.826 | 1.00 | 27.31 | N |
| ATOM | 3174 | CZ | ARG | A | 393 | 51.089 | 15.081 | −56.535 | 1.00 | 28.24 | C |
| ATOM | 3175 | NH1 | ARG | A | 393 | 49.787 | 15.134 | −56.283 | 1.00 | 27.64 | N |
| ATOM | 3176 | NH2 | ARG | A | 393 | 51.606 | 15.837 | −57.495 | 1.00 | 26.07 | N |
| ATOM | 3177 | N | ASN | A | 394 | 54.320 | 12.741 | −50.581 | 1.00 | 30.06 | N |
| ATOM | 3178 | CA | ASN | A | 394 | 53.967 | 11.943 | −49.414 | 1.00 | 32.98 | C |
| ATOM | 3179 | C | ASN | A | 394 | 55.014 | 10.910 | −49.018 | 1.00 | 33.55 | C |
| ATOM | 3180 | O | ASN | A | 394 | 54.692 | 9.933 | −48.349 | 1.00 | 35.68 | O |
| ATOM | 3181 | CB | ASN | A | 394 | 52.622 | 11.235 | −49.631 | 1.00 | 34.77 | C |
| ATOM | 3182 | CG | ASN | A | 394 | 51.499 | 12.198 | −50.002 | 1.00 | 36.82 | C |
| ATOM | 3183 | OD1 | ASN | A | 394 | 51.383 | 13.290 | −49.439 | 1.00 | 38.98 | O |
| ATOM | 3184 | ND2 | ASN | A | 394 | 50.658 | 11.787 | −50.948 | 1.00 | 35.68 | N |
| ATOM | 3185 | N | THR | A | 395 | 56.261 | 11.116 | −49.433 | 1.00 | 33.40 | N |
| ATOM | 3186 | CA | THR | A | 395 | 57.335 | 10.192 | −49.082 | 1.00 | 32.35 | C |
| ATOM | 3187 | C | THR | A | 395 | 58.569 | 10.986 | −48.671 | 1.00 | 32.40 | C |
| ATOM | 3188 | O | THR | A | 395 | 58.565 | 12.219 | −48.698 | 1.00 | 31.96 | O |
| ATOM | 3189 | CB | THR | A | 395 | 57.742 | 9.277 | −50.265 | 1.00 | 33.02 | C |
| ATOM | 3190 | OG1 | THR | A | 395 | 58.494 | 10.037 | −51.220 | 1.00 | 31.87 | O |
| ATOM | 3191 | CG2 | THR | A | 395 | 56.512 | 8.687 | −50.944 | 1.00 | 34.10 | C |
| ATOM | 3192 | N | ASN | A | 396 | 59.626 | 10.271 | −48.302 | 1.00 | 31.20 | N |
| ATOM | 3193 | CA | ASN | A | 396 | 60.871 | 10.909 | −47.906 | 1.00 | 31.68 | C |
| ATOM | 3194 | C | ASN | A | 396 | 61.489 | 11.606 | −49.120 | 1.00 | 29.61 | C |
| ATOM | 3195 | O | ASN | A | 396 | 62.289 | 12.531 | −48.978 | 1.00 | 28.52 | O |
| ATOM | 3196 | CB | ASN | A | 396 | 61.846 | 9.864 | −47.328 | 1.00 | 33.05 | C |
| ATOM | 3197 | CG | ASN | A | 396 | 62.167 | 8.729 | −48.311 | 1.00 | 37.51 | C |
| ATOM | 3198 | OD1 | ASN | A | 396 | 61.265 | 8.091 | −48.867 | 1.00 | 40.07 | O |
| ATOM | 3199 | ND2 | ASN | A | 396 | 63.460 | 8.463 | −48.512 | 1.00 | 33.90 | N |
| ATOM | 3200 | N | LEU | A | 397 | 61.084 | 11.171 | −50.309 | 1.00 | 27.52 | N |
| ATOM | 3201 | CA | LEU | A | 397 | 61.594 | 11.721 | −51.566 | 1.00 | 27.06 | C |
| ATOM | 3202 | C | LEU | A | 397 | 61.008 | 13.073 | −51.979 | 1.00 | 26.30 | C |
| ATOM | 3203 | O | LEU | A | 397 | 61.517 | 13.721 | −52.893 | 1.00 | 24.49 | O |
| ATOM | 3204 | CB | LEU | A | 397 | 61.364 | 10.710 | −52.691 | 1.00 | 26.88 | C |
| ATOM | 3205 | CG | LEU | A | 397 | 62.401 | 9.604 | −52.924 | 1.00 | 26.95 | C |
| ATOM | 3206 | CD1 | LEU | A | 397 | 63.105 | 9.222 | −51.647 | 1.00 | 23.27 | C |
| ATOM | 3207 | CD2 | LEU | A | 397 | 61.704 | 8.418 | −53.559 | 1.00 | 22.08 | C |
| ATOM | 3208 | N | ALA | A | 398 | 59.947 | 13.508 | −51.311 | 1.00 | 25.41 | N |
| ATOM | 3209 | CA | ALA | A | 398 | 59.315 | 14.775 | −51.661 | 1.00 | 25.79 | C |
| ATOM | 3210 | C | ALA | A | 398 | 60.086 | 15.996 | −51.182 | 1.00 | 26.27 | C |
| ATOM | 3211 | O | ALA | A | 398 | 60.034 | 17.049 | −51.814 | 1.00 | 28.57 | O |
| ATOM | 3212 | CB | ALA | A | 398 | 57.889 | 14.821 | −51.106 | 1.00 | 24.53 | C |
| ATOM | 3213 | N | ALA | A | 399 | 60.802 | 15.857 | −50.074 | 1.00 | 25.66 | N |
| ATOM | 3214 | CA | ALA | A | 399 | 61.548 | 16.977 | −49.512 | 1.00 | 27.30 | C |
| ATOM | 3215 | C | ALA | A | 399 | 62.998 | 17.098 | −49.976 | 1.00 | 27.88 | C |
| ATOM | 3216 | O | ALA | A | 399 | 63.665 | 16.100 | −50.240 | 1.00 | 26.66 | O |
| ATOM | 3217 | CB | ALA | A | 399 | 61.507 | 16.901 | −47.990 | 1.00 | 27.39 | C |
| ATOM | 3218 | N | ASN | A | 400 | 63.468 | 18.343 | −50.056 | 1.00 | 29.40 | N |
| ATOM | 3219 | CA | ASN | A | 400 | 64.839 | 18.677 | −50.450 | 1.00 | 30.30 | C |
| ATOM | 3220 | C | ASN | A | 400 | 65.357 | 17.940 | −51.681 | 1.00 | 27.36 | C |
| ATOM | 3221 | O | ASN | A | 400 | 66.540 | 17.617 | −51.750 | 1.00 | 26.47 | O |
| ATOM | 3222 | CB | ASN | A | 400 | 65.799 | 18.413 | −49.285 | 1.00 | 34.05 | C |
| ATOM | 3223 | CG | ASN | A | 400 | 65.329 | 19.040 | −47.991 | 1.00 | 38.75 | C |
| ATOM | 3224 | OD1 | ASN | A | 400 | 65.187 | 20.261 | −47.895 | 1.00 | 42.86 | O |
| ATOM | 3225 | ND2 | ASN | A | 400 | 65.078 | 18.206 | −46.985 | 1.00 | 38.93 | N |

TABLE 2-continued

| | | | | | | | | | | |
|---|---|---|---|---|---|---|---|---|---|---|
| ATOM | 3226 | N | PHE | A | 401 | 64.474 | 17.688 | −52.645 | 1.00 | 25.59 | N |
| ATOM | 3227 | CA | PHE | A | 401 | 64.837 | 16.993 | −53.878 | 1.00 | 24.50 | C |
| ATOM | 3228 | C | PHE | A | 401 | 65.486 | 15.644 | −53.593 | 1.00 | 22.95 | C |
| ATOM | 3229 | O | PHE | A | 401 | 66.321 | 15.184 | −54.374 | 1.00 | 19.44 | O |
| ATOM | 3230 | CB | PHE | A | 401 | 65.813 | 17.843 | −54.693 | 1.00 | 25.55 | C |
| ATOM | 3231 | CG | PHE | A | 401 | 65.371 | 19.259 | −54.881 | 1.00 | 28.43 | C |
| ATOM | 3232 | CD1 | PHE | A | 401 | 64.216 | 19.553 | −55.600 | 1.00 | 28.41 | C |
| ATOM | 3233 | CD2 | PHE | A | 401 | 66.111 | 20.303 | −54.338 | 1.00 | 29.06 | C |
| ATOM | 3234 | CE1 | PHE | A | 401 | 63.801 | 20.876 | −55.778 | 1.00 | 29.05 | C |
| ATOM | 3235 | CE2 | PHE | A | 401 | 65.707 | 21.629 | −54.507 | 1.00 | 31.74 | C |
| ATOM | 3236 | CZ | PHE | A | 401 | 64.547 | 21.915 | −55.231 | 1.00 | 30.65 | C |
| ATOM | 3237 | N | ASN | A | 402 | 65.107 | 15.012 | −52.481 | 1.00 | 21.66 | N |
| ATOM | 3238 | CA | ASN | A | 402 | 65.683 | 13.717 | −52.110 | 1.00 | 21.80 | C |
| ATOM | 3239 | C | ASN | A | 402 | 65.529 | 12.663 | −53.203 | 1.00 | 20.15 | C |
| ATOM | 3240 | O | ASN | A | 402 | 66.357 | 11.760 | −53.320 | 1.00 | 22.24 | O |
| ATOM | 3241 | CB | ASN | A | 402 | 65.064 | 13.183 | −50.804 | 1.00 | 22.58 | C |
| ATOM | 3242 | CG | ASN | A | 402 | 65.586 | 13.902 | −49.566 | 1.00 | 24.70 | C |
| ATOM | 3243 | OD1 | ASN | A | 402 | 66.729 | 14.365 | −49.532 | 1.00 | 23.70 | O |
| ATOM | 3244 | ND2 | ASN | A | 402 | 64.756 | 13.972 | −48.532 | 1.00 | 24.18 | N |
| ATOM | 3245 | N | GLY | A | 403 | 64.473 | 12.761 | −54.001 | 1.00 | 16.17 | N |
| ATOM | 3246 | CA | GLY | A | 403 | 64.295 | 11.784 | −55.065 | 1.00 | 13.95 | C |
| ATOM | 3247 | C | GLY | A | 403 | 65.413 | 11.856 | −56.100 | 1.00 | 15.09 | C |
| ATOM | 3248 | O | GLY | A | 403 | 65.724 | 10.864 | −56.764 | 1.00 | 14.30 | O |
| ATOM | 3249 | N | GLN | A | 404 | 66.021 | 13.030 | −56.254 | 1.00 | 14.23 | N |
| ATOM | 3250 | CA | GLN | A | 404 | 67.114 | 13.181 | −57.212 | 1.00 | 16.72 | C |
| ATOM | 3251 | C | GLN | A | 404 | 68.473 | 12.895 | −56.567 | 1.00 | 17.71 | C |
| ATOM | 3252 | O | GLN | A | 404 | 69.510 | 12.908 | −57.239 | 1.00 | 19.01 | O |
| ATOM | 3253 | CB | GLN | A | 404 | 67.117 | 14.592 | −57.799 | 1.00 | 14.44 | C |
| ATOM | 3254 | CG | GLN | A | 404 | 65.840 | 14.963 | −58.535 | 1.00 | 15.87 | C |
| ATOM | 3255 | CD | GLN | A | 404 | 65.859 | 16.396 | −59.021 | 1.00 | 16.23 | C |
| ATOM | 3256 | OE1 | GLN | A | 404 | 66.574 | 16.739 | −59.970 | 1.00 | 20.14 | O |
| ATOM | 3257 | NE2 | GLN | A | 404 | 65.090 | 17.245 | −58.365 | 1.00 | 14.70 | N |
| ATOM | 3258 | N | ASN | A | 405 | 68.471 | 12.661 | −55.259 | 1.00 | 18.49 | N |
| ATOM | 3259 | CA | ASN | A | 405 | 69.710 | 12.348 | −54.540 | 1.00 | 17.74 | C |
| ATOM | 3260 | C | ASN | A | 405 | 69.928 | 10.851 | −54.768 | 1.00 | 17.93 | C |
| ATOM | 3261 | O | ASN | A | 405 | 69.218 | 10.017 | −54.198 | 1.00 | 18.00 | O |
| ATOM | 3262 | CB | ASN | A | 405 | 69.549 | 12.637 | −53.041 | 1.00 | 18.78 | C |
| ATOM | 3263 | CG | ASN | A | 405 | 70.853 | 12.482 | −52.272 | 1.00 | 20.64 | C |
| ATOM | 3264 | OD1 | ASN | A | 405 | 71.597 | 11.526 | −52.480 | 1.00 | 22.33 | O |
| ATOM | 3265 | ND2 | ASN | A | 405 | 71.135 | 13.429 | −51.381 | 1.00 | 19.96 | N |
| ATOM | 3266 | N | THR | A | 406 | 70.892 | 10.507 | −55.615 | 1.00 | 19.27 | N |
| ATOM | 3267 | CA | THR | A | 406 | 71.143 | 9.111 | −55.919 | 1.00 | 19.85 | C |
| ATOM | 3268 | C | THR | A | 406 | 71.616 | 8.312 | −54.710 | 1.00 | 22.72 | C |
| ATOM | 3269 | O | THR | A | 406 | 71.598 | 7.079 | −54.742 | 1.00 | 22.13 | O |
| ATOM | 3270 | CB | THR | A | 406 | 72.164 | 8.948 | −57.070 | 1.00 | 21.57 | C |
| ATOM | 3271 | OG1 | THR | A | 406 | 73.412 | 9.545 | −56.700 | 1.00 | 19.21 | O |
| ATOM | 3272 | CG2 | THR | A | 406 | 71.640 | 9.614 | −58.340 | 1.00 | 20.46 | C |
| ATOM | 3273 | N | GLU | A | 407 | 72.024 | 8.997 | −53.642 | 1.00 | 23.34 | N |
| ATOM | 3274 | CA | GLU | A | 407 | 72.471 | 8.283 | −52.445 | 1.00 | 27.84 | C |
| ATOM | 3275 | C | GLU | A | 407 | 71.303 | 7.955 | −51.512 | 1.00 | 27.49 | C |
| ATOM | 3276 | O | GLU | A | 407 | 71.396 | 7.026 | −50.714 | 1.00 | 30.45 | O |
| ATOM | 3277 | CB | GLU | A | 407 | 73.536 | 9.085 | −51.683 | 1.00 | 28.71 | C |
| ATOM | 3278 | CG | GLU | A | 407 | 74.761 | 9.422 | −52.524 | 1.00 | 35.66 | C |
| ATOM | 3279 | CD | GLU | A | 407 | 75.903 | 10.006 | −51.710 | 1.00 | 38.36 | C |
| ATOM | 3280 | OE1 | GLU | A | 407 | 75.632 | 10.698 | −50.705 | 1.00 | 39.50 | O |
| ATOM | 3281 | OE2 | GLU | A | 407 | 77.075 | 9.783 | −52.089 | 1.00 | 39.20 | O |
| ATOM | 3282 | N | ILE | A | 408 | 70.212 | 8.710 | −51.613 | 1.00 | 24.50 | N |
| ATOM | 3283 | CA | ILE | A | 408 | 69.031 | 8.468 | −50.781 | 1.00 | 22.28 | C |
| ATOM | 3284 | C | ILE | A | 408 | 68.055 | 7.559 | −51.525 | 1.00 | 22.66 | C |
| ATOM | 3285 | O | ILE | A | 408 | 67.559 | 6.571 | −50.979 | 1.00 | 22.15 | O |
| ATOM | 3286 | CB | ILE | A | 408 | 68.308 | 9.792 | −50.429 | 1.00 | 22.99 | C |
| ATOM | 3287 | CG1 | ILE | A | 408 | 69.224 | 10.656 | −49.567 | 1.00 | 23.91 | C |
| ATOM | 3288 | CG2 | ILE | A | 408 | 66.979 | 9.506 | −49.703 | 1.00 | 23.10 | C |
| ATOM | 3289 | CD1 | ILE | A | 408 | 68.601 | 11.967 | −49.127 | 1.00 | 27.87 | C |
| ATOM | 3290 | N | ASN | A | 409 | 67.802 | 7.894 | −52.784 | 1.00 | 20.56 | N |
| ATOM | 3291 | CA | ASN | A | 409 | 66.886 | 7.142 | −53.632 | 1.00 | 20.69 | C |
| ATOM | 3292 | C | ASN | A | 409 | 67.706 | 6.232 | −54.546 | 1.00 | 21.35 | C |
| ATOM | 3293 | O | ASN | A | 409 | 67.493 | 6.195 | −55.760 | 1.00 | 19.99 | O |
| ATOM | 3294 | CB | ASN | A | 409 | 66.046 | 8.141 | −54.451 | 1.00 | 19.86 | C |
| ATOM | 3295 | CG | ASN | A | 409 | 65.005 | 7.469 | −55.329 | 1.00 | 19.74 | C |
| ATOM | 3296 | OD1 | ASN | A | 409 | 64.628 | 6.319 | −55.104 | 1.00 | 18.96 | O |
| ATOM | 3297 | ND2 | ASN | A | 409 | 64.520 | 8.200 | −56.332 | 1.00 | 15.67 | N |
| ATOM | 3298 | N | ASN | A | 410 | 68.623 | 5.466 | −53.958 | 1.00 | 21.31 | N |
| ATOM | 3299 | CA | ASN | A | 410 | 69.492 | 4.611 | −54.762 | 1.00 | 22.82 | C |
| ATOM | 3300 | C | ASN | A | 410 | 68.888 | 3.463 | −55.577 | 1.00 | 20.53 | C |
| ATOM | 3301 | O | ASN | A | 410 | 69.533 | 2.980 | −56.499 | 1.00 | 20.79 | O |
| ATOM | 3302 | CB | ASN | A | 410 | 70.681 | 4.102 | −53.918 | 1.00 | 26.30 | C |
| ATOM | 3303 | CG | ASN | A | 410 | 70.261 | 3.461 | −52.607 | 1.00 | 30.01 | C |
| ATOM | 3304 | OD1 | ASN | A | 410 | 69.687 | 4.117 | −51.731 | 1.00 | 31.67 | O |

TABLE 2-continued

| ATOM | 3305 | ND2 | ASN | A | 410 | 70.564 | 2.170 | −52.458 | 1.00 | 31.70 | N |
|---|---|---|---|---|---|---|---|---|---|---|---|
| ATOM | 3306 | N | MET | A | 411 | 67.667 | 3.029 | −55.280 | 1.00 | 19.39 | N |
| ATOM | 3307 | CA | MET | A | 411 | 67.074 | 1.945 | −56.069 | 1.00 | 18.71 | C |
| ATOM | 3308 | C | MET | A | 411 | 66.743 | 2.425 | −57.489 | 1.00 | 17.84 | C |
| ATOM | 3309 | O | MET | A | 411 | 66.473 | 1.623 | −58.385 | 1.00 | 18.78 | O |
| ATOM | 3310 | CB | MET | A | 411 | 65.790 | 1.409 | −55.409 | 1.00 | 19.68 | C |
| ATOM | 3311 | CG | MET | A | 411 | 64.553 | 2.289 | −55.579 | 1.00 | 21.83 | C |
| ATOM | 3312 | SD | MET | A | 411 | 63.019 | 1.553 | −54.906 | 1.00 | 23.22 | S |
| ATOM | 3313 | CE | MET | A | 411 | 61.781 | 2.699 | −55.583 | 1.00 | 21.23 | C |
| ATOM | 3314 | N | ASN | A | 412 | 66.765 | 3.736 | −57.696 | 1.00 | 16.76 | N |
| ATOM | 3315 | CA | ASN | A | 412 | 66.451 | 4.288 | −59.011 | 1.00 | 18.56 | C |
| ATOM | 3316 | C | ASN | A | 412 | 67.660 | 4.529 | −59.903 | 1.00 | 18.06 | C |
| ATOM | 3317 | O | ASN | A | 412 | 67.515 | 5.023 | −61.018 | 1.00 | 18.18 | O |
| ATOM | 3318 | CB | ASN | A | 412 | 65.680 | 5.601 | −58.847 | 1.00 | 17.60 | C |
| ATOM | 3319 | CG | ASN | A | 412 | 64.187 | 5.387 | −58.785 | 1.00 | 19.26 | C |
| ATOM | 3320 | OD1 | ASN | A | 412 | 63.529 | 5.213 | −59.817 | 1.00 | 18.85 | O |
| ATOM | 3321 | ND2 | ASN | A | 412 | 63.639 | 5.384 | −57.574 | 1.00 | 20.23 | N |
| ATOM | 3322 | N | PHE | A | 413 | 68.852 | 4.182 | −59.428 | 1.00 | 17.66 | N |
| ATOM | 3323 | CA | PHE | A | 413 | 70.042 | 4.436 | −60.231 | 1.00 | 18.46 | C |
| ATOM | 3324 | C | PHE | A | 413 | 71.141 | 3.391 | −60.141 | 1.00 | 19.31 | C |
| ATOM | 3325 | O | PHE | A | 413 | 71.323 | 2.730 | −59.112 | 1.00 | 19.37 | O |
| ATOM | 3326 | CB | PHE | A | 413 | 70.666 | 5.791 | −59.846 | 1.00 | 17.17 | C |
| ATOM | 3327 | CG | PHE | A | 413 | 69.670 | 6.912 | −59.676 | 1.00 | 18.01 | C |
| ATOM | 3328 | CD1 | PHE | A | 413 | 69.036 | 7.121 | −58.454 | 1.00 | 16.11 | C |
| ATOM | 3329 | CD2 | PHE | A | 413 | 69.364 | 7.758 | −60.741 | 1.00 | 15.32 | C |
| ATOM | 3330 | CE1 | PHE | A | 413 | 68.110 | 8.160 | −58.296 | 1.00 | 17.47 | C |
| ATOM | 3331 | CE2 | PHE | A | 413 | 68.436 | 8.799 | −60.592 | 1.00 | 15.98 | C |
| ATOM | 3332 | CZ | PHE | A | 413 | 67.811 | 9.002 | −59.373 | 1.00 | 14.87 | C |
| ATOM | 3333 | N | THR | A | 414 | 71.868 | 3.263 | −61.246 | 1.00 | 19.44 | N |
| ATOM | 3334 | CA | THR | A | 414 | 73.027 | 2.389 | −61.349 | 1.00 | 18.64 | C |
| ATOM | 3335 | C | THR | A | 414 | 74.094 | 3.307 | −61.946 | 1.00 | 20.15 | C |
| ATOM | 3336 | O | THR | A | 414 | 73.931 | 3.831 | −63.056 | 1.00 | 16.75 | O |
| ATOM | 3337 | CB | THR | A | 414 | 72.798 | 1.207 | −62.307 | 1.00 | 20.82 | C |
| ATOM | 3338 | OG1 | THR | A | 414 | 71.933 | 0.246 | −61.689 | 1.00 | 19.37 | O |
| ATOM | 3339 | CG2 | THR | A | 414 | 74.133 | 0.542 | −62.665 | 1.00 | 20.10 | C |
| ATOM | 3340 | N | LYS | A | 415 | 75.166 | 3.538 | −61.200 | 1.00 | 18.83 | N |
| ATOM | 3341 | CA | LYS | A | 415 | 76.235 | 4.393 | −61.689 | 1.00 | 19.63 | C |
| ATOM | 3342 | C | LYS | A | 415 | 76.967 | 3.644 | −62.790 | 1.00 | 18.38 | C |
| ATOM | 3343 | O | LYS | A | 415 | 77.330 | 2.483 | −62.623 | 1.00 | 19.62 | O |
| ATOM | 3344 | CB | LYS | A | 415 | 77.186 | 4.746 | −60.545 | 1.00 | 22.30 | C |
| ATOM | 3345 | CG | LYS | A | 415 | 78.213 | 5.796 | −60.894 | 1.00 | 25.37 | C |
| ATOM | 3346 | CD | LYS | A | 415 | 78.992 | 6.191 | −59.656 | 1.00 | 30.63 | C |
| ATOM | 3347 | CE | LYS | A | 415 | 80.147 | 7.116 | −59.999 | 1.00 | 32.79 | C |
| ATOM | 3348 | NZ | LYS | A | 415 | 79.653 | 8.367 | −60.613 | 1.00 | 35.93 | N |
| ATOM | 3349 | N | LEU | A | 416 | 77.163 | 4.297 | −63.930 | 1.00 | 18.75 | N |
| ATOM | 3350 | CA | LEU | A | 416 | 77.838 | 3.662 | −65.049 | 1.00 | 20.46 | C |
| ATOM | 3351 | C | LEU | A | 416 | 79.252 | 4.194 | −65.246 | 1.00 | 23.26 | C |
| ATOM | 3352 | O | LEU | A | 416 | 79.642 | 5.202 | −64.652 | 1.00 | 23.26 | O |
| ATOM | 3353 | CB | LEU | A | 416 | 77.031 | 3.882 | −66.327 | 1.00 | 22.02 | C |
| ATOM | 3354 | CG | LEU | A | 416 | 75.565 | 3.435 | −66.266 | 1.00 | 24.30 | C |
| ATOM | 3355 | CD1 | LEU | A | 416 | 74.817 | 3.975 | −67.468 | 1.00 | 24.07 | C |
| ATOM | 3356 | CD2 | LEU | A | 416 | 75.485 | 1.916 | −66.213 | 1.00 | 23.40 | C |
| ATOM | 3357 | N | LYS | A | 417 | 80.015 | 3.499 | −66.081 | 1.00 | 23.29 | N |
| ATOM | 3358 | CA | LYS | A | 417 | 81.377 | 3.904 | −66.395 | 1.00 | 23.88 | C |
| ATOM | 3359 | C | LYS | A | 417 | 81.305 | 5.140 | −67.287 | 1.00 | 22.49 | C |
| ATOM | 3360 | O | LYS | A | 417 | 80.520 | 5.186 | −68.235 | 1.00 | 21.71 | O |
| ATOM | 3361 | CB | LYS | A | 417 | 82.111 | 2.779 | −67.145 | 1.00 | 25.86 | C |
| ATOM | 3362 | CG | LYS | A | 417 | 83.361 | 3.243 | −67.892 | 1.00 | 28.31 | C |
| ATOM | 3363 | CD | LYS | A | 417 | 84.011 | 2.113 | −68.693 | 1.00 | 30.23 | C |
| ATOM | 3364 | CE | LYS | A | 417 | 85.192 | 2.625 | −69.509 | 1.00 | 32.27 | C |
| ATOM | 3365 | NZ | LYS | A | 417 | 85.790 | 1.557 | −70.361 | 1.00 | 34.82 | N |
| ATOM | 3366 | N | ASN | A | 418 | 82.118 | 6.138 | −66.969 | 1.00 | 20.89 | N |
| ATOM | 3367 | CA | ASN | A | 418 | 82.184 | 7.372 | −67.744 | 1.00 | 22.55 | C |
| ATOM | 3368 | C | ASN | A | 418 | 83.366 | 7.169 | −68.697 | 1.00 | 23.41 | C |
| ATOM | 3369 | O | ASN | A | 418 | 84.481 | 6.912 | −68.248 | 1.00 | 23.60 | O |
| ATOM | 3370 | CB | ASN | A | 418 | 82.451 | 8.549 | −66.799 | 1.00 | 21.37 | C |
| ATOM | 3371 | CG | ASN | A | 418 | 82.506 | 9.888 | −67.516 | 1.00 | 23.33 | C |
| ATOM | 3372 | OD1 | ASN | A | 418 | 82.456 | 9.963 | −68.748 | 1.00 | 21.52 | O |
| ATOM | 3373 | ND2 | ASN | A | 418 | 82.623 | 10.961 | −66.739 | 1.00 | 21.79 | N |
| ATOM | 3374 | N | PHE | A | 419 | 83.131 | 7.270 | −70.001 | 1.00 | 23.30 | N |
| ATOM | 3375 | CA | PHE | A | 419 | 84.204 | 7.062 | −70.976 | 1.00 | 24.49 | C |
| ATOM | 3376 | C | PHE | A | 419 | 85.079 | 8.282 | −71.246 | 1.00 | 25.67 | C |
| ATOM | 3377 | O | PHE | A | 419 | 85.948 | 8.244 | −72.112 | 1.00 | 26.27 | O |
| ATOM | 3378 | CB | PHE | A | 419 | 83.630 | 6.563 | −72.301 | 1.00 | 23.67 | C |
| ATOM | 3379 | CG | PHE | A | 419 | 83.162 | 5.132 | −72.268 | 1.00 | 23.66 | C |
| ATOM | 3380 | CD1 | PHE | A | 419 | 82.124 | 4.740 | −71.430 | 1.00 | 23.40 | C |
| ATOM | 3381 | CD2 | PHE | A | 419 | 83.758 | 4.177 | −73.089 | 1.00 | 24.83 | C |
| ATOM | 3382 | CE1 | PHE | A | 419 | 81.682 | 3.415 | −71.406 | 1.00 | 25.14 | C |
| ATOM | 3383 | CE2 | PHE | A | 419 | 83.326 | 2.842 | −73.076 | 1.00 | 25.13 | C |

TABLE 2-continued

| | | | | | | | | | | |
|---|---|---|---|---|---|---|---|---|---|---|
| ATOM | 3384 | CZ | PHE | A | 419 | 82.285 | 2.463 | −72.231 | 1.00 | 25.95 C |
| ATOM | 3385 | N | THR | A | 420 | 84.864 | 9.353 | −70.494 | 1.00 | 24.62 N |
| ATOM | 3386 | CA | THR | A | 420 | 85.626 | 10.583 | −70.680 | 1.00 | 26.40 C |
| ATOM | 3387 | C | THR | A | 420 | 87.139 | 10.427 | −70.581 | 1.00 | 27.09 C |
| ATOM | 3388 | O | THR | A | 420 | 87.644 | 9.617 | −69.808 | 1.00 | 26.60 O |
| ATOM | 3389 | CB | THR | A | 420 | 85.226 | 11.655 | −69.637 | 1.00 | 26.15 C |
| ATOM | 3390 | OG1 | THR | A | 420 | 85.965 | 12.860 | −69.875 | 1.00 | 26.91 O |
| ATOM | 3391 | CG2 | THR | A | 420 | 85.536 | 11.165 | −68.227 | 1.00 | 27.07 C |
| ATOM | 3392 | N | PRO | A | 421 | 87.881 | 11.201 | −71.384 | 1.00 | 26.63 N |
| ATOM | 3393 | CA | PRO | A | 421 | 89.343 | 11.142 | −71.349 | 1.00 | 27.52 C |
| ATOM | 3394 | C | PRO | A | 421 | 89.835 | 12.291 | −70.467 | 1.00 | 26.60 C |
| ATOM | 3395 | O | PRO | A | 421 | 91.006 | 12.356 | −70.121 | 1.00 | 27.88 O |
| ATOM | 3396 | CB | PRO | A | 421 | 89.726 | 11.349 | −72.807 | 1.00 | 28.59 C |
| ATOM | 3397 | CG | PRO | A | 421 | 88.716 | 12.368 | −73.241 | 1.00 | 27.78 C |
| ATOM | 3398 | CD | PRO | A | 421 | 87.420 | 11.837 | −72.632 | 1.00 | 27.74 C |
| ATOM | 3399 | N | LEU | A | 422 | 88.929 | 13.199 | −70.107 | 1.00 | 25.61 N |
| ATOM | 3400 | CA | LEU | A | 422 | 89.293 | 14.350 | −69.277 | 1.00 | 26.42 C |
| ATOM | 3401 | C | LEU | A | 422 | 89.598 | 13.974 | −67.829 | 1.00 | 28.04 C |
| ATOM | 3402 | O | LEU | A | 422 | 88.998 | 13.053 | −67.282 | 1.00 | 26.88 O |
| ATOM | 3403 | CB | LEU | A | 422 | 88.179 | 15.394 | −69.290 | 1.00 | 23.47 C |
| ATOM | 3404 | CG | LEU | A | 422 | 87.698 | 15.905 | −70.652 | 1.00 | 24.44 C |
| ATOM | 3405 | CD1 | LEU | A | 422 | 86.665 | 16.998 | −70.433 | 1.00 | 19.69 C |
| ATOM | 3406 | CD2 | LEU | A | 422 | 88.878 | 16.428 | −71.471 | 1.00 | 22.94 C |
| ATOM | 3407 | N | VAL | A | 423 | 90.527 | 14.705 | −67.215 | 1.00 | 28.13 N |
| ATOM | 3408 | CA | VAL | A | 423 | 90.915 | 14.468 | −65.828 | 1.00 | 29.46 C |
| ATOM | 3409 | C | VAL | A | 423 | 90.647 | 15.743 | −65.035 | 1.00 | 29.72 C |
| ATOM | 3410 | O | VAL | A | 423 | 91.305 | 16.759 | −65.251 | 1.00 | 29.60 O |
| ATOM | 3411 | CB | VAL | A | 423 | 92.422 | 14.117 | −65.720 | 1.00 | 31.70 C |
| ATOM | 3412 | CG1 | VAL | A | 423 | 92.816 | 13.908 | −64.261 | 1.00 | 31.77 C |
| ATOM | 3413 | CG2 | VAL | A | 423 | 92.720 | 12.868 | −66.534 | 1.00 | 31.54 C |
| ATOM | 3414 | N | PRO | A | 424 | 89.667 | 15.711 | −64.113 | 1.00 | 29.70 N |
| ATOM | 3415 | CA | PRO | A | 424 | 89.320 | 16.879 | −63.295 | 1.00 | 30.56 C |
| ATOM | 3416 | C | PRO | A | 424 | 90.498 | 17.375 | −62.460 | 1.00 | 30.26 C |
| ATOM | 3417 | O | PRO | A | 424 | 91.190 | 16.579 | −61.839 | 1.00 | 29.19 O |
| ATOM | 3418 | CB | PRO | A | 424 | 88.182 | 16.360 | −62.410 | 1.00 | 29.50 C |
| ATOM | 3419 | CG | PRO | A | 424 | 87.557 | 15.295 | −63.248 | 1.00 | 32.20 C |
| ATOM | 3420 | CD | PRO | A | 424 | 88.774 | 14.583 | −63.802 | 1.00 | 30.63 C |
| ATOM | 3421 | N | ARG | A | 425 | 90.717 | 18.688 | −62.454 | 1.00 | 32.19 N |
| ATOM | 3422 | CA | ARG | A | 425 | 91.799 | 19.287 | −61.678 | 1.00 | 34.18 C |
| ATOM | 3423 | C | ARG | A | 425 | 91.268 | 19.769 | −60.333 | 1.00 | 36.14 C |
| ATOM | 3424 | O | ARG | A | 425 | 91.873 | 19.509 | −59.286 | 1.00 | 38.32 O |
| ATOM | 3425 | CB | ARG | A | 425 | 92.426 | 20.466 | −62.435 | 1.00 | 34.62 C |
| ATOM | 3426 | CG | ARG | A | 425 | 93.481 | 21.233 | −61.633 | 1.00 | 35.24 C |
| ATOM | 3427 | CD | ARG | A | 425 | 94.340 | 22.156 | −62.500 | 1.00 | 35.14 C |
| ATOM | 3428 | NE | ARG | A | 425 | 95.270 | 22.934 | −61.676 | 1.00 | 39.67 N |
| ATOM | 3429 | CZ | ARG | A | 425 | 96.219 | 23.740 | −62.151 | 1.00 | 39.70 C |
| ATOM | 3430 | NH1 | ARG | A | 425 | 96.381 | 23.887 | −63.463 | 1.00 | 39.21 N |
| ATOM | 3431 | NH2 | ARG | A | 425 | 97.006 | 24.406 | −61.313 | 1.00 | 34.95 N |
| TER | 3432 | | ARG | A | 425 | | | | | |
| ATOM | 3433 | N | MET | B | 146 | 62.203 | 30.824 | −50.991 | 1.00 | 71.78 N |
| ATOM | 3434 | CA | MET | B | 146 | 61.509 | 29.568 | −50.577 | 1.00 | 71.61 C |
| ATOM | 3435 | C | MET | B | 146 | 60.137 | 29.453 | −51.245 | 1.00 | 70.59 C |
| ATOM | 3436 | O | MET | B | 146 | 59.746 | 28.378 | −51.704 | 1.00 | 70.70 O |
| ATOM | 3437 | CB | MET | B | 146 | 61.361 | 29.537 | −49.050 | 1.00 | 72.41 C |
| ATOM | 3438 | CG | MET | B | 146 | 62.692 | 29.621 | −48.305 | 1.00 | 73.09 C |
| ATOM | 3439 | SD | MET | B | 146 | 62.542 | 29.566 | −46.503 | 1.00 | 74.22 S |
| ATOM | 3440 | CE | MET | B | 146 | 62.818 | 27.816 | −46.189 | 1.00 | 73.80 C |
| ATOM | 3441 | N | ASP | B | 147 | 59.414 | 30.569 | −51.299 | 1.00 | 69.34 N |
| ATOM | 3442 | CA | ASP | B | 147 | 58.089 | 30.613 | −51.915 | 1.00 | 66.55 C |
| ATOM | 3443 | C | ASP | B | 147 | 58.115 | 31.593 | −53.083 | 1.00 | 63.96 C |
| ATOM | 3444 | O | ASP | B | 147 | 57.087 | 31.875 | −53.702 | 1.00 | 62.79 O |
| ATOM | 3445 | CB | ASP | B | 147 | 57.043 | 31.068 | −50.896 | 1.00 | 68.46 C |
| ATOM | 3446 | CG | ASP | B | 147 | 57.076 | 30.250 | −49.621 | 1.00 | 70.05 C |
| ATOM | 3447 | OD1 | ASP | B | 147 | 56.869 | 29.018 | −49.697 | 1.00 | 70.31 O |
| ATOM | 3448 | OD2 | ASP | B | 147 | 57.311 | 30.841 | −48.544 | 1.00 | 70.38 O |
| ATOM | 3449 | N | GLU | B | 148 | 59.303 | 32.116 | −53.367 | 1.00 | 60.49 N |
| ATOM | 3450 | CA | GLU | B | 148 | 59.491 | 33.066 | −54.454 | 1.00 | 57.12 C |
| ATOM | 3451 | C | GLU | B | 148 | 59.375 | 32.362 | −55.797 | 1.00 | 52.76 C |
| ATOM | 3452 | O | GLU | B | 148 | 59.025 | 32.976 | −56.803 | 1.00 | 51.05 O |
| ATOM | 3453 | CB | GLU | B | 148 | 60.863 | 33.734 | −54.330 | 1.00 | 59.63 C |
| ATOM | 3454 | CG | GLU | B | 148 | 60.964 | 34.715 | −53.170 | 1.00 | 63.83 C |
| ATOM | 3455 | CD | GLU | B | 148 | 62.384 | 35.182 | −52.913 | 1.00 | 65.92 C |
| ATOM | 3456 | OE1 | GLU | B | 148 | 63.204 | 34.353 | −52.459 | 1.00 | 68.17 O |
| ATOM | 3457 | OE2 | GLU | B | 148 | 62.680 | 36.372 | −53.165 | 1.00 | 66.61 O |
| ATOM | 3458 | N | ASN | B | 149 | 59.671 | 31.067 | −55.804 | 1.00 | 48.74 N |
| ATOM | 3459 | CA | ASN | B | 149 | 59.598 | 30.282 | −57.027 | 1.00 | 46.06 C |
| ATOM | 3460 | C | ASN | B | 149 | 58.162 | 30.285 | −57.548 | 1.00 | 44.07 C |
| ATOM | 3461 | O | ASN | B | 149 | 57.912 | 30.636 | −58.699 | 1.00 | 43.07 O |
| ATOM | 3462 | CB | ASN | B | 149 | 60.057 | 28.843 | −56.766 | 1.00 | 44.53 C |

TABLE 2-continued

| | | | | | | | | | | |
|---|---|---|---|---|---|---|---|---|---|---|
| ATOM | 3463 | CG | ASN | B | 149 | 60.234 | 28.045 | −58.048 | 1.00 | 44.35 | C |
| ATOM | 3464 | OD1 | ASN | B | 149 | 61.088 | 28.366 | −58.877 | 1.00 | 42.40 | O |
| ATOM | 3465 | ND2 | ASN | B | 149 | 59.422 | 27.004 | −58.219 | 1.00 | 42.19 | N |
| ATOM | 3466 | N | LEU | B | 150 | 57.220 | 29.904 | −56.691 | 1.00 | 43.01 | N |
| ATOM | 3467 | CA | LEU | B | 150 | 55.814 | 29.862 | −57.076 | 1.00 | 42.39 | C |
| ATOM | 3468 | C | LEU | B | 150 | 55.342 | 31.215 | −57.597 | 1.00 | 42.49 | C |
| ATOM | 3469 | O | LEU | B | 150 | 54.550 | 31.288 | −58.536 | 1.00 | 41.41 | O |
| ATOM | 3470 | CB | LEU | B | 150 | 54.948 | 29.437 | −55.888 | 1.00 | 42.83 | C |
| ATOM | 3471 | CG | LEU | B | 150 | 53.443 | 29.323 | −56.151 | 1.00 | 43.40 | C |
| ATOM | 3472 | CD1 | LEU | B | 150 | 53.186 | 28.367 | −57.311 | 1.00 | 41.48 | C |
| ATOM | 3473 | CD2 | LEU | B | 150 | 52.745 | 28.837 | −54.888 | 1.00 | 44.38 | C |
| ATOM | 3474 | N | GLU | B | 151 | 55.832 | 32.289 | −56.989 | 1.00 | 42.21 | N |
| ATOM | 3475 | CA | GLU | B | 151 | 55.442 | 33.623 | −57.418 | 1.00 | 42.29 | C |
| ATOM | 3476 | C | GLU | B | 151 | 55.923 | 33.851 | −58.846 | 1.00 | 39.62 | C |
| ATOM | 3477 | O | GLU | B | 151 | 55.220 | 34.448 | −59.659 | 1.00 | 38.76 | O |
| ATOM | 3478 | CB | GLU | B | 151 | 56.036 | 34.681 | −56.487 | 1.00 | 44.85 | C |
| ATOM | 3479 | CG | GLU | B | 151 | 55.368 | 36.042 | −56.612 | 1.00 | 50.09 | C |
| ATOM | 3480 | CD | GLU | B | 151 | 55.876 | 37.042 | −55.583 | 1.00 | 52.86 | C |
| ATOM | 3481 | OE1 | GLU | B | 151 | 55.912 | 36.694 | −54.381 | 1.00 | 53.71 | O |
| ATOM | 3482 | OE2 | GLU | B | 151 | 56.228 | 38.177 | −55.974 | 1.00 | 54.29 | O |
| ATOM | 3483 | N | GLN | B | 152 | 57.122 | 33.369 | −59.152 | 1.00 | 38.02 | N |
| ATOM | 3484 | CA | GLN | B | 152 | 57.674 | 33.518 | −60.494 | 1.00 | 35.90 | C |
| ATOM | 3485 | C | GLN | B | 152 | 56.858 | 32.669 | −61.465 | 1.00 | 32.33 | C |
| ATOM | 3486 | O | GLN | B | 152 | 56.575 | 33.091 | −62.584 | 1.00 | 30.13 | O |
| ATOM | 3487 | CB | GLN | B | 152 | 59.138 | 33.081 | −60.520 | 1.00 | 39.29 | C |
| ATOM | 3488 | CG | GLN | B | 152 | 60.030 | 33.877 | −59.589 | 1.00 | 43.02 | C |
| ATOM | 3489 | CD | GLN | B | 152 | 61.492 | 33.546 | −59.777 | 1.00 | 46.04 | C |
| ATOM | 3490 | OE1 | GLN | B | 152 | 62.054 | 33.772 | −60.849 | 1.00 | 48.06 | O |
| ATOM | 3491 | NE2 | GLN | B | 152 | 62.118 | 33.005 | −58.738 | 1.00 | 48.33 | N |
| ATOM | 3492 | N | VAL | B | 153 | 56.481 | 31.472 | −61.026 | 1.00 | 30.23 | N |
| ATOM | 3493 | CA | VAL | B | 153 | 55.675 | 30.575 | −61.843 | 1.00 | 28.27 | C |
| ATOM | 3494 | C | VAL | B | 153 | 54.347 | 31.245 | −62.218 | 1.00 | 29.55 | C |
| ATOM | 3495 | O | VAL | B | 153 | 54.004 | 31.327 | −63.402 | 1.00 | 27.56 | O |
| ATOM | 3496 | CB | VAL | B | 153 | 55.389 | 29.243 | −61.097 | 1.00 | 28.81 | C |
| ATOM | 3497 | CG1 | VAL | B | 153 | 54.313 | 28.455 | −61.825 | 1.00 | 27.72 | C |
| ATOM | 3498 | CG2 | VAL | B | 153 | 56.669 | 28.416 | −60.997 | 1.00 | 27.25 | C |
| ATOM | 3499 | N | SER | B | 154 | 53.603 | 31.736 | −61.224 | 1.00 | 28.40 | N |
| ATOM | 3500 | CA | SER | B | 154 | 52.325 | 32.385 | −61.516 | 1.00 | 30.27 | C |
| ATOM | 3501 | C | SER | B | 154 | 52.519 | 33.581 | −62.446 | 1.00 | 28.76 | C |
| ATOM | 3502 | O | SER | B | 154 | 51.671 | 33.866 | −63.291 | 1.00 | 28.55 | O |
| ATOM | 3503 | CB | SER | B | 154 | 51.618 | 32.814 | −60.218 | 1.00 | 31.75 | C |
| ATOM | 3504 | OG | SER | B | 154 | 52.426 | 33.675 | −59.440 | 1.00 | 38.09 | O |
| ATOM | 3505 | N | GLY | B | 155 | 53.646 | 34.267 | −62.303 | 1.00 | 29.43 | N |
| ATOM | 3506 | CA | GLY | B | 155 | 53.927 | 35.406 | −63.158 | 1.00 | 30.14 | C |
| ATOM | 3507 | C | GLY | B | 155 | 54.095 | 34.978 | −64.607 | 1.00 | 31.69 | C |
| ATOM | 3508 | O | GLY | B | 155 | 53.512 | 35.574 | −65.520 | 1.00 | 31.53 | O |
| ATOM | 3509 | N | ILE | B | 156 | 54.900 | 33.941 | −64.824 | 1.00 | 29.41 | N |
| ATOM | 3510 | CA | ILE | B | 156 | 55.129 | 33.423 | −66.168 | 1.00 | 27.50 | C |
| ATOM | 3511 | C | ILE | B | 156 | 53.820 | 32.904 | −66.758 | 1.00 | 27.81 | C |
| ATOM | 3512 | O | ILE | B | 156 | 53.576 | 33.033 | −67.954 | 1.00 | 28.17 | O |
| ATOM | 3513 | CB | ILE | B | 156 | 56.177 | 32.283 | −66.150 | 1.00 | 26.41 | C |
| ATOM | 3514 | CG1 | ILE | B | 156 | 57.551 | 32.861 | −65.796 | 1.00 | 25.61 | C |
| ATOM | 3515 | CG2 | ILE | B | 156 | 56.204 | 31.573 | −67.487 | 1.00 | 23.40 | C |
| ATOM | 3516 | CD1 | ILE | B | 156 | 58.622 | 31.828 | −65.588 | 1.00 | 24.73 | C |
| ATOM | 3517 | N | ILE | B | 157 | 52.987 | 32.306 | −65.914 | 1.00 | 28.03 | N |
| ATOM | 3518 | CA | ILE | B | 157 | 51.700 | 31.789 | −66.352 | 1.00 | 29.82 | C |
| ATOM | 3519 | C | ILE | B | 157 | 50.870 | 32.944 | −66.910 | 1.00 | 32.58 | C |
| ATOM | 3520 | O | ILE | B | 157 | 50.137 | 32.781 | −67.889 | 1.00 | 34.44 | O |
| ATOM | 3521 | CB | ILE | B | 157 | 50.949 | 31.116 | −65.175 | 1.00 | 28.24 | C |
| ATOM | 3522 | CG1 | ILE | B | 157 | 51.638 | 29.795 | −64.822 | 1.00 | 25.84 | C |
| ATOM | 3523 | CG2 | ILE | B | 157 | 49.490 | 30.879 | −65.536 | 1.00 | 29.93 | C |
| ATOM | 3524 | CD1 | ILE | B | 157 | 50.986 | 29.029 | −63.694 | 1.00 | 26.01 | C |
| ATOM | 3525 | N | GLY | B | 158 | 50.999 | 34.112 | −66.289 | 1.00 | 34.03 | N |
| ATOM | 3526 | CA | GLY | B | 158 | 50.261 | 35.275 | −66.744 | 1.00 | 35.98 | C |
| ATOM | 3527 | C | GLY | B | 158 | 50.581 | 35.598 | −68.192 | 1.00 | 38.15 | C |
| ATOM | 3528 | O | GLY | B | 158 | 49.679 | 35.781 | −69.015 | 1.00 | 37.93 | O |
| ATOM | 3529 | N | ASN | B | 159 | 51.871 | 35.663 | −68.506 | 1.00 | 37.07 | N |
| ATOM | 3530 | CA | ASN | B | 159 | 52.318 | 35.967 | −69.858 | 1.00 | 38.71 | C |
| ATOM | 3531 | C | ASN | B | 159 | 51.857 | 34.915 | −70.865 | 1.00 | 38.58 | C |
| ATOM | 3532 | O | ASN | B | 159 | 51.529 | 35.240 | −72.008 | 1.00 | 38.35 | O |
| ATOM | 3533 | CB | ASN | B | 159 | 53.841 | 36.079 | −69.890 | 1.00 | 40.79 | C |
| ATOM | 3534 | CG | ASN | B | 159 | 54.363 | 37.107 | −68.910 | 1.00 | 44.13 | C |
| ATOM | 3535 | OD1 | ASN | B | 159 | 53.982 | 38.274 | −68.963 | 1.00 | 47.14 | O |
| ATOM | 3536 | ND2 | ASN | B | 159 | 55.236 | 36.679 | −68.005 | 1.00 | 47.17 | N |
| ATOM | 3537 | N | LEU | B | 160 | 51.842 | 33.655 | −70.444 | 1.00 | 36.91 | N |
| ATOM | 3538 | CA | LEU | B | 160 | 51.415 | 32.579 | −71.327 | 1.00 | 37.11 | C |
| ATOM | 3539 | C | LEU | B | 160 | 49.924 | 32.715 | −71.620 | 1.00 | 38.83 | C |
| ATOM | 3540 | O | LEU | B | 160 | 49.472 | 32.456 | −72.738 | 1.00 | 36.45 | O |
| ATOM | 3541 | CB | LEU | B | 160 | 51.699 | 31.219 | −70.686 | 1.00 | 34.04 | C |

TABLE 2-continued

| | | | | | | | | | | |
|---|---|---|---|---|---|---|---|---|---|---|
| ATOM | 3542 | CG | LEU | B | 160 | 53.172 | 30.835 | −70.520 | 1.00 | 31.74 | C |
| ATOM | 3543 | CD1 | LEU | B | 160 | 53.289 | 29.567 | −69.691 | 1.00 | 31.54 | C |
| ATOM | 3544 | CD2 | LEU | B | 160 | 53.800 | 30.643 | −71.891 | 1.00 | 31.70 | C |
| ATOM | 3545 | N | ARG | B | 161 | 49.162 | 33.125 | −70.608 | 1.00 | 40.26 | N |
| ATOM | 3546 | CA | ARG | B | 161 | 47.724 | 33.289 | −70.766 | 1.00 | 42.34 | C |
| ATOM | 3547 | C | ARG | B | 161 | 47.432 | 34.333 | −71.839 | 1.00 | 42.87 | C |
| ATOM | 3548 | O | ARG | B | 161 | 46.477 | 34.194 | −72.602 | 1.00 | 42.13 | O |
| ATOM | 3549 | CB | ARG | B | 161 | 47.082 | 33.700 | −69.435 | 1.00 | 43.13 | C |
| ATOM | 3550 | CG | ARG | B | 161 | 45.564 | 33.812 | −69.490 | 1.00 | 44.65 | C |
| ATOM | 3551 | CD | ARG | B | 161 | 44.958 | 33.963 | −68.097 | 1.00 | 46.89 | C |
| ATOM | 3552 | NE | ARG | B | 161 | 44.997 | 32.717 | −67.331 | 1.00 | 48.13 | N |
| ATOM | 3553 | CZ | ARG | B | 161 | 45.676 | 32.546 | −66.199 | 1.00 | 49.73 | C |
| ATOM | 3554 | NH1 | ARG | B | 161 | 46.390 | 33.542 | −65.685 | 1.00 | 48.02 | N |
| ATOM | 3555 | NH2 | ARG | B | 161 | 45.635 | 31.377 | −65.572 | 1.00 | 50.63 | N |
| ATOM | 3556 | N | HIS | B | 162 | 48.267 | 35.368 | −71.902 | 1.00 | 44.07 | N |
| ATOM | 3557 | CA | HIS | B | 162 | 48.099 | 36.426 | −72.889 | 1.00 | 45.38 | C |
| ATOM | 3558 | C | HIS | B | 162 | 48.369 | 35.925 | −74.309 | 1.00 | 45.20 | C |
| ATOM | 3559 | O | HIS | B | 162 | 47.752 | 36.393 | −75.270 | 1.00 | 45.39 | O |
| ATOM | 3560 | CB | HIS | B | 162 | 49.029 | 37.600 | −72.582 | 1.00 | 48.56 | C |
| ATOM | 3561 | CG | HIS | B | 162 | 48.986 | 38.680 | −73.617 | 1.00 | 53.25 | C |
| ATOM | 3562 | ND1 | HIS | B | 162 | 47.835 | 39.380 | −73.913 | 1.00 | 55.19 | N |
| ATOM | 3563 | CD2 | HIS | B | 162 | 49.936 | 39.143 | −74.466 | 1.00 | 54.71 | C |
| ATOM | 3564 | CE1 | HIS | B | 162 | 48.076 | 40.223 | −74.902 | 1.00 | 56.44 | C |
| ATOM | 3565 | NE2 | HIS | B | 162 | 49.343 | 40.099 | −75.256 | 1.00 | 56.18 | N |
| ATOM | 3566 | N | MET | B | 163 | 49.291 | 34.976 | −74.438 | 1.00 | 42.15 | N |
| ATOM | 3567 | CA | MET | B | 163 | 49.632 | 34.418 | −75.741 | 1.00 | 40.81 | C |
| ATOM | 3568 | C | MET | B | 163 | 48.675 | 33.299 | −76.138 | 1.00 | 39.32 | C |
| ATOM | 3569 | O | MET | B | 163 | 48.533 | 32.976 | −77.318 | 1.00 | 38.23 | O |
| ATOM | 3570 | CB | MET | B | 163 | 51.067 | 33.885 | −75.726 | 1.00 | 40.39 | C |
| ATOM | 3571 | CG | MET | B | 163 | 52.125 | 34.964 | −75.626 | 1.00 | 42.11 | C |
| ATOM | 3572 | SD | MET | B | 163 | 52.302 | 35.903 | −77.155 | 1.00 | 45.96 | S |
| ATOM | 3573 | CE | MET | B | 163 | 50.973 | 37.065 | −77.022 | 1.00 | 46.46 | C |
| ATOM | 3574 | N | ALA | B | 164 | 48.012 | 32.726 | −75.142 | 1.00 | 37.52 | N |
| ATOM | 3575 | CA | ALA | B | 164 | 47.080 | 31.631 | −75.361 | 1.00 | 39.91 | C |
| ATOM | 3576 | C | ALA | B | 164 | 46.002 | 31.913 | −76.398 | 1.00 | 40.49 | C |
| ATOM | 3577 | O | ALA | B | 164 | 45.593 | 31.011 | −77.123 | 1.00 | 39.17 | O |
| ATOM | 3578 | CB | ALA | B | 164 | 46.428 | 31.244 | −74.045 | 1.00 | 38.36 | C |
| ATOM | 3579 | N | LEU | B | 165 | 45.538 | 33.157 | −76.466 | 1.00 | 43.68 | N |
| ATOM | 3580 | CA | LEU | B | 165 | 44.481 | 33.516 | −77.410 | 1.00 | 46.75 | C |
| ATOM | 3581 | C | LEU | B | 165 | 44.923 | 33.460 | −78.864 | 1.00 | 47.31 | C |
| ATOM | 3582 | O | LEU | B | 165 | 44.099 | 33.320 | −79.766 | 1.00 | 50.02 | O |
| ATOM | 3583 | CB | LEU | B | 165 | 43.933 | 34.911 | −77.094 | 1.00 | 49.29 | C |
| ATOM | 3584 | CG | LEU | B | 165 | 42.756 | 35.395 | −77.954 | 1.00 | 51.46 | C |
| ATOM | 3585 | CD1 | LEU | B | 165 | 41.646 | 34.347 | −77.976 | 1.00 | 51.44 | C |
| ATOM | 3586 | CD2 | LEU | B | 165 | 42.233 | 36.712 | −77.394 | 1.00 | 52.19 | C |
| ATOM | 3587 | N | ASP | B | 166 | 46.225 | 33.561 | −79.093 | 1.00 | 46.97 | N |
| ATOM | 3588 | CA | ASP | B | 166 | 46.753 | 33.519 | −80.448 | 1.00 | 46.15 | C |
| ATOM | 3589 | C | ASP | B | 166 | 47.567 | 32.257 | −80.716 | 1.00 | 44.13 | C |
| ATOM | 3590 | O | ASP | B | 166 | 47.665 | 31.807 | −81.854 | 1.00 | 43.35 | O |
| ATOM | 3591 | CB | ASP | B | 166 | 47.636 | 34.746 | −80.702 | 1.00 | 47.43 | C |
| ATOM | 3592 | CG | ASP | B | 166 | 46.859 | 36.046 | −80.655 | 1.00 | 50.48 | C |
| ATOM | 3593 | OD1 | ASP | B | 166 | 45.895 | 36.193 | −81.438 | 1.00 | 51.87 | O |
| ATOM | 3594 | OD2 | ASP | B | 166 | 47.214 | 36.924 | −79.840 | 1.00 | 52.04 | O |
| ATOM | 3595 | N | MET | B | 167 | 48.143 | 31.690 | −79.661 | 1.00 | 42.53 | N |
| ATOM | 3596 | CA | MET | B | 167 | 48.995 | 30.508 | −79.775 | 1.00 | 40.82 | C |
| ATOM | 3597 | C | MET | B | 167 | 48.454 | 29.273 | −79.064 | 1.00 | 38.32 | C |
| ATOM | 3598 | O | MET | B | 167 | 49.121 | 28.240 | −79.033 | 1.00 | 38.32 | O |
| ATOM | 3599 | CB | MET | B | 167 | 50.369 | 30.824 | −79.177 | 1.00 | 43.13 | C |
| ATOM | 3600 | CG | MET | B | 167 | 51.121 | 31.948 | −79.855 | 1.00 | 46.34 | C |
| ATOM | 3601 | SD | MET | B | 167 | 52.044 | 31.377 | −81.291 | 1.00 | 51.72 | S |
| ATOM | 3602 | CE | MET | B | 167 | 50.834 | 31.515 | −82.534 | 1.00 | 52.01 | C |
| ATOM | 3603 | N | GLY | B | 168 | 47.259 | 29.375 | −78.494 | 1.00 | 34.73 | N |
| ATOM | 3604 | CA | GLY | B | 168 | 46.706 | 28.260 | −77.743 | 1.00 | 32.69 | C |
| ATOM | 3605 | C | GLY | B | 168 | 46.251 | 27.009 | −78.469 | 1.00 | 31.81 | C |
| ATOM | 3606 | O | GLY | B | 168 | 46.196 | 25.938 | −77.865 | 1.00 | 30.15 | O |
| ATOM | 3607 | N | ASN | B | 169 | 45.918 | 27.133 | −79.751 | 1.00 | 30.52 | N |
| ATOM | 3608 | CA | ASN | B | 169 | 45.449 | 25.990 | −80.525 | 1.00 | 31.24 | C |
| ATOM | 3609 | C | ASN | B | 169 | 46.386 | 25.616 | −81.660 | 1.00 | 28.50 | C |
| ATOM | 3610 | O | ASN | B | 169 | 47.141 | 26.450 | −82.151 | 1.00 | 28.50 | O |
| ATOM | 3611 | CB | ASN | B | 169 | 44.061 | 26.281 | −81.105 | 1.00 | 35.37 | C |
| ATOM | 3612 | CG | ASN | B | 169 | 43.019 | 26.503 | −80.032 | 1.00 | 39.19 | C |
| ATOM | 3613 | OD1 | ASN | B | 169 | 42.801 | 25.645 | −79.174 | 1.00 | 41.14 | O |
| ATOM | 3614 | ND2 | ASN | B | 169 | 42.365 | 27.660 | −80.072 | 1.00 | 41.41 | N |
| ATOM | 3615 | N | GLU | B | 170 | 46.316 | 24.358 | −82.081 | 1.00 | 27.05 | N |
| ATOM | 3616 | CA | GLU | B | 170 | 47.145 | 23.865 | −83.172 | 1.00 | 25.65 | C |
| ATOM | 3617 | C | GLU | B | 170 | 46.513 | 24.326 | −84.480 | 1.00 | 24.89 | C |
| ATOM | 3618 | O | GLU | B | 170 | 45.339 | 24.695 | −84.509 | 1.00 | 24.46 | O |
| ATOM | 3619 | CB | GLU | B | 170 | 47.236 | 22.334 | −83.104 | 1.00 | 24.78 | C |
| ATOM | 3620 | CG | GLU | B | 170 | 47.485 | 21.836 | −81.683 | 1.00 | 28.53 | C |

TABLE 2-continued

| | | | | | | | | | | |
|---|---|---|---|---|---|---|---|---|---|---|
| ATOM | 3621 | CD | GLU | B | 170 | 47.906 | 20.375 | −81.593 | 1.00 | 29.17 | C |
| ATOM | 3622 | OE1 | GLU | B | 170 | 47.496 | 19.560 | −82.446 | 1.00 | 30.11 | O |
| ATOM | 3623 | OE2 | GLU | B | 170 | 48.641 | 20.041 | −80.642 | 1.00 | 30.31 | O |
| ATOM | 3624 | N | ILE | B | 171 | 47.292 | 24.313 | −85.557 | 1.00 | 22.89 | N |
| ATOM | 3625 | CA | ILE | B | 171 | 46.810 | 24.753 | −86.860 | 1.00 | 21.22 | C |
| ATOM | 3626 | C | ILE | B | 171 | 47.046 | 23.685 | −87.932 | 1.00 | 22.41 | C |
| ATOM | 3627 | O | ILE | B | 171 | 47.561 | 22.607 | −87.629 | 1.00 | 20.92 | O |
| ATOM | 3628 | CB | ILE | B | 171 | 47.516 | 26.051 | −87.278 | 1.00 | 21.76 | C |
| ATOM | 3629 | CG1 | ILE | B | 171 | 49.034 | 25.857 | −87.210 | 1.00 | 20.86 | C |
| ATOM | 3630 | CG2 | ILE | B | 171 | 47.079 | 27.190 | −86.370 | 1.00 | 22.41 | C |
| ATOM | 3631 | CD1 | ILE | B | 171 | 49.841 | 27.067 | −87.665 | 1.00 | 24.76 | C |
| ATOM | 3632 | N | ASP | B | 172 | 46.689 | 23.997 | −89.181 | 1.00 | 22.16 | N |
| ATOM | 3633 | CA | ASP | B | 172 | 46.835 | 23.052 | −90.299 | 1.00 | 22.79 | C |
| ATOM | 3634 | C | ASP | B | 172 | 46.218 | 21.713 | −89.881 | 1.00 | 22.46 | C |
| ATOM | 3635 | O | ASP | B | 172 | 46.830 | 20.652 | −90.017 | 1.00 | 22.58 | O |
| ATOM | 3636 | CB | ASP | B | 172 | 48.315 | 22.874 | −90.657 | 1.00 | 23.08 | C |
| ATOM | 3637 | CG | ASP | B | 172 | 48.525 | 21.959 | −91.859 | 1.00 | 27.63 | C |
| ATOM | 3638 | OD1 | ASP | B | 172 | 47.661 | 21.952 | −92.763 | 1.00 | 26.75 | O |
| ATOM | 3639 | OD2 | ASP | B | 172 | 49.564 | 21.259 | −91.912 | 1.00 | 27.32 | O |
| ATOM | 3640 | N | THR | B | 173 | 44.991 | 21.794 | −89.378 | 1.00 | 21.88 | N |
| ATOM | 3641 | CA | THR | B | 173 | 44.244 | 20.644 | −88.875 | 1.00 | 23.33 | C |
| ATOM | 3642 | C | THR | B | 173 | 43.329 | 19.936 | −89.872 | 1.00 | 23.95 | C |
| ATOM | 3643 | O | THR | B | 173 | 42.859 | 18.835 | −89.591 | 1.00 | 22.75 | O |
| ATOM | 3644 | CB | THR | B | 173 | 43.350 | 21.060 | −87.709 | 1.00 | 24.81 | C |
| ATOM | 3645 | OG1 | THR | B | 173 | 42.417 | 22.045 | −88.172 | 1.00 | 29.78 | O |
| ATOM | 3646 | CG2 | THR | B | 173 | 44.175 | 21.659 | −86.573 | 1.00 | 28.42 | C |
| ATOM | 3647 | N | GLN | B | 174 | 43.051 | 20.559 | −91.016 | 1.00 | 23.47 | N |
| ATOM | 3648 | CA | GLN | B | 174 | 42.164 | 19.943 | −91.997 | 1.00 | 23.33 | C |
| ATOM | 3649 | C | GLN | B | 174 | 42.823 | 18.801 | −92.775 | 1.00 | 22.86 | C |
| ATOM | 3650 | O | GLN | B | 174 | 44.032 | 18.782 | −92.976 | 1.00 | 21.99 | O |
| ATOM | 3651 | CB | GLN | B | 174 | 41.579 | 21.032 | −92.910 | 1.00 | 23.49 | C |
| ATOM | 3652 | CG | GLN | B | 174 | 40.558 | 21.892 | −92.152 | 1.00 | 24.60 | C |
| ATOM | 3653 | CD | GLN | B | 174 | 40.031 | 23.084 | −92.937 | 1.00 | 25.67 | C |
| ATOM | 3654 | OE1 | GLN | B | 174 | 39.722 | 22.979 | −94.121 | 1.00 | 27.20 | O |
| ATOM | 3655 | NE2 | GLN | B | 174 | 39.905 | 24.221 | −92.264 | 1.00 | 26.14 | N |
| ATOM | 3656 | N | ASN | B | 175 | 42.006 | 17.851 | −93.213 | 1.00 | 22.83 | N |
| ATOM | 3657 | CA | ASN | B | 175 | 42.476 | 16.641 | −93.889 | 1.00 | 22.80 | C |
| ATOM | 3658 | C | ASN | B | 175 | 43.075 | 16.704 | −95.303 | 1.00 | 22.90 | C |
| ATOM | 3659 | O | ASN | B | 175 | 42.592 | 16.039 | −96.207 | 1.00 | 24.94 | O |
| ATOM | 3660 | CB | ASN | B | 175 | 41.332 | 15.621 | −93.851 | 1.00 | 24.91 | C |
| ATOM | 3661 | CG | ASN | B | 175 | 41.805 | 14.200 | −94.052 | 1.00 | 25.96 | C |
| ATOM | 3662 | OD1 | ASN | B | 175 | 42.838 | 13.796 | −93.518 | 1.00 | 26.70 | O |
| ATOM | 3663 | ND2 | ASN | B | 175 | 41.038 | 13.425 | −94.809 | 1.00 | 24.93 | N |
| ATOM | 3664 | N | ARG | B | 176 | 44.148 | 17.463 | −95.493 | 1.00 | 22.15 | N |
| ATOM | 3665 | CA | ARG | B | 176 | 44.770 | 17.562 | −96.813 | 1.00 | 21.35 | C |
| ATOM | 3666 | C | ARG | B | 176 | 45.841 | 16.491 | −97.000 | 1.00 | 20.91 | C |
| ATOM | 3667 | O | ARG | B | 176 | 46.297 | 15.883 | −96.033 | 1.00 | 20.34 | O |
| ATOM | 3668 | CB | ARG | B | 176 | 45.416 | 18.936 | −96.991 | 1.00 | 19.52 | C |
| ATOM | 3669 | CG | ARG | B | 176 | 46.632 | 19.171 | −96.071 | 1.00 | 18.45 | C |
| ATOM | 3670 | CD | ARG | B | 176 | 47.072 | 20.642 | −96.053 | 1.00 | 19.16 | C |
| ATOM | 3671 | NE | ARG | B | 176 | 48.249 | 20.844 | −95.210 | 1.00 | 19.28 | N |
| ATOM | 3672 | CZ | ARG | B | 176 | 49.491 | 20.548 | −95.582 | 1.00 | 21.75 | C |
| ATOM | 3673 | NH1 | ARG | B | 176 | 49.721 | 20.047 | −96.786 | 1.00 | 21.34 | N |
| ATOM | 3674 | NH2 | ARG | B | 176 | 50.502 | 20.725 | −94.743 | 1.00 | 22.77 | N |
| ATOM | 3675 | N | GLN | B | 177 | 46.239 | 16.267 | −98.248 | 1.00 | 19.37 | N |
| ATOM | 3676 | CA | GLN | B | 177 | 47.284 | 15.292 | −98.564 | 1.00 | 20.82 | C |
| ATOM | 3677 | C | GLN | B | 177 | 48.272 | 15.975 | −99.507 | 1.00 | 20.68 | C |
| ATOM | 3678 | O | GLN | B | 177 | 47.985 | 17.050 | −100.052 | 1.00 | 21.08 | O |
| ATOM | 3679 | CB | GLN | B | 177 | 46.697 | 14.055 | −99.264 | 1.00 | 21.82 | C |
| ATOM | 3680 | CG | GLN | B | 177 | 45.537 | 13.388 | −98.534 | 1.00 | 21.40 | C |
| ATOM | 3681 | CD | GLN | B | 177 | 44.952 | 12.216 | −99.320 | 1.00 | 25.69 | C |
| ATOM | 3682 | OE1 | GLN | B | 177 | 44.697 | 12.320 | −100.524 | 1.00 | 25.86 | O |
| ATOM | 3683 | NE2 | GLN | B | 177 | 44.714 | 11.105 | −98.635 | 1.00 | 25.23 | N |
| ATOM | 3684 | N | ILE | B | 178 | 49.431 | 15.356 | −99.700 | 1.00 | 20.27 | N |
| ATOM | 3685 | CA | ILE | B | 178 | 50.448 | 15.898 | −100.597 | 1.00 | 21.49 | C |
| ATOM | 3686 | C | ILE | B | 178 | 50.892 | 14.820 | −101.573 | 1.00 | 23.03 | C |
| ATOM | 3687 | O | ILE | B | 178 | 50.673 | 13.631 | −101.336 | 1.00 | 21.97 | O |
| ATOM | 3688 | CB | ILE | B | 178 | 51.689 | 16.395 | −99.825 | 1.00 | 22.08 | C |
| ATOM | 3689 | CG1 | ILE | B | 178 | 52.242 | 15.261 | −98.955 | 1.00 | 20.72 | C |
| ATOM | 3690 | CG2 | ILE | B | 178 | 51.331 | 17.633 | −98.994 | 1.00 | 17.64 | C |
| ATOM | 3691 | CD1 | ILE | B | 178 | 53.560 | 15.595 | −98.280 | 1.00 | 21.25 | C |
| ATOM | 3692 | N | ASP | B | 179 | 51.515 | 15.232 | −102.672 | 1.00 | 23.80 | N |
| ATOM | 3693 | CA | ASP | B | 179 | 51.972 | 14.269 | −103.659 | 1.00 | 27.51 | C |
| ATOM | 3694 | C | ASP | B | 179 | 53.081 | 13.415 | −103.074 | 1.00 | 29.07 | C |
| ATOM | 3695 | O | ASP | B | 179 | 53.873 | 13.891 | −102.257 | 1.00 | 27.29 | O |
| ATOM | 3696 | CB | ASP | B | 179 | 52.496 | 14.970 | −104.914 | 1.00 | 27.35 | C |
| ATOM | 3697 | CG | ASP | B | 179 | 51.415 | 15.737 | −105.656 | 1.00 | 31.49 | C |
| ATOM | 3698 | OD1 | ASP | B | 179 | 50.213 | 15.491 | −105.416 | 1.00 | 31.37 | O |
| ATOM | 3699 | OD2 | ASP | B | 179 | 51.776 | 16.583 | −106.497 | 1.00 | 33.44 | O |

TABLE 2-continued

| ATOM | 3700 | N | ARG | B | 180 | 53.138 | 12.158 | −103.497 | 1.00 | 31.58 | N |
| --- | --- | --- | --- | --- | --- | --- | --- | --- | --- | --- | --- |
| ATOM | 3701 | CA | ARG | B | 180 | 54.172 | 11.251 | −103.019 | 1.00 | 36.24 | C |
| ATOM | 3702 | C | ARG | B | 180 | 55.523 | 11.778 | −103.451 | 1.00 | 38.11 | C |
| ATOM | 3703 | O | ARG | B | 180 | 55.691 | 12.226 | −104.589 | 1.00 | 37.53 | O |
| ATOM | 3704 | CB | ARG | B | 180 | 53.988 | 9.855 | −103.604 | 1.00 | 37.92 | C |
| ATOM | 3705 | CG | ARG | B | 180 | 52.672 | 9.220 | −103.265 | 1.00 | 43.68 | C |
| ATOM | 3706 | CD | ARG | B | 180 | 52.626 | 7.788 | −103.755 | 1.00 | 48.22 | C |
| ATOM | 3707 | NE | ARG | B | 180 | 51.361 | 7.162 | −103.400 | 1.00 | 51.45 | N |
| ATOM | 3708 | CZ | ARG | B | 180 | 51.071 | 5.887 | −103.628 | 1.00 | 55.02 | C |
| ATOM | 3709 | NH1 | ARG | B | 180 | 51.962 | 5.097 | −104.215 | 1.00 | 55.83 | N |
| ATOM | 3710 | NH2 | ARG | B | 180 | 49.890 | 5.404 | −103.265 | 1.00 | 56.28 | N |
| ATOM | 3711 | N | ILE | B | 181 | 56.486 | 11.724 | −102.543 | 1.00 | 40.27 | N |
| ATOM | 3712 | CA | ILE | B | 181 | 57.827 | 12.181 | −102.849 | 1.00 | 43.26 | C |
| ATOM | 3713 | C | ILE | B | 181 | 58.612 | 11.019 | −103.440 | 1.00 | 47.06 | C |
| ATOM | 3714 | O | ILE | B | 181 | 58.873 | 10.025 | −102.762 | 1.00 | 46.40 | O |
| ATOM | 3715 | CB | ILE | B | 181 | 58.537 | 12.684 | −101.588 | 1.00 | 42.67 | C |
| ATOM | 3716 | CG1 | ILE | B | 181 | 57.763 | 13.870 | −101.005 | 1.00 | 41.48 | C |
| ATOM | 3717 | CG2 | ILE | B | 181 | 59.971 | 13.078 | −101.921 | 1.00 | 42.25 | C |
| ATOM | 3718 | CD1 | ILE | B | 181 | 58.383 | 14.450 | −99.758 | 1.00 | 40.23 | C |
| ATOM | 3719 | N | MET | B | 182 | 58.979 | 11.148 | −104.710 | 1.00 | 51.90 | N |
| ATOM | 3720 | CA | MET | B | 182 | 59.728 | 10.106 | −105.397 | 1.00 | 57.74 | C |
| ATOM | 3721 | C | MET | B | 182 | 61.131 | 9.987 | −104.813 | 1.00 | 60.35 | C |
| ATOM | 3722 | O | MET | B | 182 | 61.883 | 10.961 | −104.773 | 1.00 | 60.30 | O |
| ATOM | 3723 | CB | MET | B | 182 | 59.802 | 10.413 | −106.893 | 1.00 | 60.14 | C |
| ATOM | 3724 | CG | MET | B | 182 | 58.437 | 10.624 | −107.541 | 1.00 | 64.62 | C |
| ATOM | 3725 | SD | MET | B | 182 | 57.294 | 9.240 | −107.273 | 1.00 | 69.48 | S |
| ATOM | 3726 | CE | MET | B | 182 | 57.734 | 8.169 | −108.652 | 1.00 | 69.10 | C |
| ATOM | 3727 | N | GLU | B | 183 | 61.472 | 8.786 | −104.359 | 1.00 | 63.83 | N |
| ATOM | 3728 | CA | GLU | B | 183 | 62.777 | 8.529 | −103.763 | 1.00 | 67.06 | C |
| ATOM | 3729 | C | GLU | B | 183 | 63.827 | 8.312 | −104.849 | 1.00 | 69.30 | C |
| ATOM | 3730 | O | GLU | B | 183 | 63.995 | 7.197 | −105.346 | 1.00 | 69.78 | O |
| ATOM | 3731 | CB | GLU | B | 183 | 62.701 | 7.296 | −102.861 | 0.00 | 66.80 | C |
| ATOM | 3732 | CG | GLU | B | 183 | 63.826 | 7.195 | −101.850 | 0.00 | 66.84 | C |
| ATOM | 3733 | CD | GLU | B | 183 | 63.796 | 8.324 | −100.839 | 0.00 | 66.79 | C |
| ATOM | 3734 | OE1 | GLU | B | 183 | 62.785 | 8.448 | −100.116 | 0.00 | 66.79 | O |
| ATOM | 3735 | OE2 | GLU | B | 183 | 64.781 | 9.089 | −100.766 | 0.00 | 66.79 | O |
| ATOM | 3736 | N | LYS | B | 184 | 64.528 | 9.383 | −105.213 | 1.00 | 71.56 | N |
| ATOM | 3737 | CA | LYS | B | 184 | 65.564 | 9.315 | −106.242 | 1.00 | 74.15 | C |
| ATOM | 3738 | C | LYS | B | 184 | 66.902 | 8.845 | −105.666 | 1.00 | 75.69 | C |
| ATOM | 3739 | O | LYS | B | 184 | 67.084 | 8.796 | −104.447 | 1.00 | 76.32 | O |
| ATOM | 3740 | CB | LYS | B | 184 | 65.749 | 10.686 | −106.897 | 0.00 | 73.73 | C |
| ATOM | 3741 | CG | LYS | B | 184 | 64.502 | 11.232 | −107.573 | 0.00 | 73.64 | C |
| ATOM | 3742 | CD | LYS | B | 184 | 64.769 | 12.596 | −108.190 | 0.00 | 73.46 | C |
| ATOM | 3743 | CE | LYS | B | 184 | 63.526 | 13.155 | −108.862 | 0.00 | 73.40 | C |
| ATOM | 3744 | NZ | LYS | B | 184 | 63.782 | 14.492 | −109.466 | 0.00 | 73.34 | N |
| ATOM | 3745 | N | ALA | B | 185 | 67.835 | 8.502 | −106.552 | 1.00 | 77.15 | N |
| ATOM | 3746 | CA | ALA | B | 185 | 69.159 | 8.038 | −106.142 | 1.00 | 78.43 | C |
| ATOM | 3747 | C | ALA | B | 185 | 69.875 | 9.114 | −105.330 | 1.00 | 79.43 | C |
| ATOM | 3748 | O | ALA | B | 185 | 70.406 | 10.077 | −105.885 | 1.00 | 79.34 | O |
| ATOM | 3749 | CB | ALA | B | 185 | 69.986 | 7.672 | −107.369 | 0.00 | 78.23 | C |
| ATOM | 3750 | N | ASP | B | 186 | 69.888 | 8.938 | −104.013 | 1.00 | 80.80 | N |
| ATOM | 3751 | CA | ASP | B | 186 | 70.522 | 9.897 | −103.116 | 1.00 | 81.80 | C |
| ATOM | 3752 | C | ASP | B | 186 | 72.041 | 9.751 | −103.042 | 1.00 | 82.76 | C |
| ATOM | 3753 | O | ASP | B | 186 | 72.587 | 9.409 | −101.991 | 1.00 | 83.12 | O |
| ATOM | 3754 | CB | ASP | B | 186 | 69.924 | 9.768 | −101.714 | 0.00 | 81.33 | C |
| ATOM | 3755 | CG | ASP | B | 186 | 68.451 | 10.123 | −101.674 | 0.00 | 81.07 | C |
| ATOM | 3756 | OD1 | ASP | B | 186 | 67.831 | 9.978 | −100.600 | 0.00 | 80.89 | O |
| ATOM | 3757 | OD2 | ASP | B | 186 | 67.912 | 10.552 | −102.717 | 0.00 | 80.89 | O |
| ATOM | 3758 | N | SER | B | 187 | 72.718 | 10.011 | −104.158 | 1.00 | 83.43 | N |
| ATOM | 3759 | CA | SER | B | 187 | 74.176 | 9.929 | −104.203 | 1.00 | 83.44 | C |
| ATOM | 3760 | C | SER | B | 187 | 74.717 | 11.069 | −103.347 | 1.00 | 83.58 | C |
| ATOM | 3761 | O | SER | B | 187 | 75.664 | 10.898 | −102.576 | 1.00 | 83.46 | O |
| ATOM | 3762 | CB | SER | B | 187 | 74.673 | 10.075 | −105.643 | 0.00 | 83.23 | C |
| ATOM | 3763 | OG | SER | B | 187 | 74.282 | 11.321 | −106.193 | 0.00 | 83.02 | O |
| ATOM | 3764 | N | ASN | B | 188 | 74.091 | 12.232 | −103.500 | 1.00 | 83.37 | N |
| ATOM | 3765 | CA | ASN | B | 188 | 74.442 | 13.436 | −102.754 | 1.00 | 82.77 | C |
| ATOM | 3766 | C | ASN | B | 188 | 73.155 | 14.244 | −102.601 | 1.00 | 82.38 | C |
| ATOM | 3767 | O | ASN | B | 188 | 73.086 | 15.410 | −102.995 | 1.00 | 82.68 | O |
| ATOM | 3768 | CB | ASN | B | 188 | 75.490 | 14.251 | −103.517 | 0.00 | 82.29 | C |
| ATOM | 3769 | CG | ASN | B | 188 | 76.792 | 13.496 | −103.704 | 0.00 | 81.95 | C |
| ATOM | 3770 | OD1 | ASN | B | 188 | 77.445 | 13.112 | −102.733 | 0.00 | 81.74 | O |
| ATOM | 3771 | ND2 | ASN | B | 188 | 77.176 | 13.280 | −104.956 | 0.00 | 81.74 | N |
| ATOM | 3772 | N | LYS | B | 189 | 72.138 | 13.606 | −102.026 | 1.00 | 81.50 | N |
| ATOM | 3773 | CA | LYS | B | 189 | 70.832 | 14.228 | −101.835 | 1.00 | 80.66 | C |
| ATOM | 3774 | C | LYS | B | 189 | 70.836 | 15.395 | −100.847 | 1.00 | 80.09 | C |
| ATOM | 3775 | O | LYS | B | 189 | 71.324 | 16.482 | −101.161 | 1.00 | 80.18 | O |
| ATOM | 3776 | CB | LYS | B | 189 | 69.816 | 13.176 | −101.382 | 0.00 | 80.08 | C |
| ATOM | 3777 | CG | LYS | B | 189 | 68.366 | 13.608 | −101.533 | 0.00 | 79.44 | C |
| ATOM | 3778 | CD | LYS | B | 189 | 68.010 | 13.821 | −102.997 | 0.00 | 78.93 | C |

TABLE 2-continued

| | | | | | | | | | | |
|---|---|---|---|---|---|---|---|---|---|---|
| ATOM | 3779 | CE | LYS | B | 189 | 66.554 | 14.217 | −103.166 | 0.00 | 78.62 | C |
| ATOM | 3780 | NZ | LYS | B | 189 | 66.191 | 14.390 | −104.600 | 0.00 | 78.38 | N |
| ATOM | 3781 | N | THR | B | 190 | 70.291 | 15.166 | −99.654 | 1.00 | 78.78 | N |
| ATOM | 3782 | CA | THR | B | 190 | 70.213 | 16.210 | −98.638 | 1.00 | 76.78 | C |
| ATOM | 3783 | C | THR | B | 190 | 71.413 | 16.260 | −97.697 | 1.00 | 75.46 | C |
| ATOM | 3784 | O | THR | B | 190 | 72.095 | 15.260 | −97.475 | 1.00 | 75.79 | O |
| ATOM | 3785 | CB | THR | B | 190 | 68.945 | 16.056 | −97.781 | 0.00 | 76.63 | C |
| ATOM | 3786 | OG1 | THR | B | 190 | 69.020 | 14.838 | −97.031 | 0.00 | 76.38 | O |
| ATOM | 3787 | CG2 | THR | B | 190 | 67.708 | 16.026 | −98.667 | 0.00 | 76.38 | C |
| ATOM | 3788 | N | ARG | B | 191 | 71.652 | 17.445 | −97.146 | 1.00 | 73.46 | N |
| ATOM | 3789 | CA | ARG | B | 191 | 72.751 | 17.680 | −96.218 | 1.00 | 70.71 | C |
| ATOM | 3790 | C | ARG | B | 191 | 72.166 | 17.854 | −94.821 | 1.00 | 67.71 | C |
| ATOM | 3791 | O | ARG | B | 191 | 70.949 | 17.809 | −94.645 | 1.00 | 67.17 | O |
| ATOM | 3792 | CB | ARG | B | 191 | 73.502 | 18.947 | −96.626 | 1.00 | 72.30 | C |
| ATOM | 3793 | CG | ARG | B | 191 | 73.873 | 18.976 | −98.097 | 1.00 | 73.74 | C |
| ATOM | 3794 | CD | ARG | B | 191 | 74.351 | 20.349 | −98.523 | 1.00 | 74.50 | C |
| ATOM | 3795 | NE | ARG | B | 191 | 74.614 | 20.399 | −99.957 | 1.00 | 74.89 | N |
| ATOM | 3796 | CZ | ARG | B | 191 | 74.974 | 21.497 | −100.612 | 1.00 | 74.92 | C |
| ATOM | 3797 | NH1 | ARG | B | 191 | 75.115 | 22.645 | −99.961 | 1.00 | 74.06 | N |
| ATOM | 3798 | NH2 | ARG | B | 191 | 75.191 | 21.448 | −101.920 | 1.00 | 74.62 | N |
| ATOM | 3799 | N | ILE | B | 192 | 73.026 | 18.061 | −93.831 | 1.00 | 64.32 | N |
| ATOM | 3800 | CA | ILE | B | 192 | 72.558 | 18.236 | −92.462 | 1.00 | 61.68 | C |
| ATOM | 3801 | C | ILE | B | 192 | 72.993 | 19.561 | −91.846 | 1.00 | 60.52 | C |
| ATOM | 3802 | O | ILE | B | 192 | 74.149 | 19.971 | −91.980 | 1.00 | 60.43 | O |
| ATOM | 3803 | CB | ILE | B | 192 | 73.068 | 17.103 | −91.541 | 1.00 | 60.97 | C |
| ATOM | 3804 | CG1 | ILE | B | 192 | 72.563 | 15.750 | −92.041 | 1.00 | 60.78 | C |
| ATOM | 3805 | CG2 | ILE | B | 192 | 72.594 | 17.342 | −90.110 | 1.00 | 61.17 | C |
| ATOM | 3806 | CD1 | ILE | B | 192 | 72.991 | 14.582 | −91.177 | 1.00 | 59.87 | C |
| ATOM | 3807 | N | ASP | B | 193 | 72.057 | 20.232 | −91.180 | 1.00 | 58.56 | N |
| ATOM | 3808 | CA | ASP | B | 193 | 72.360 | 21.485 | −90.503 | 1.00 | 57.37 | C |
| ATOM | 3809 | C | ASP | B | 193 | 72.804 | 21.137 | −89.082 | 1.00 | 58.24 | C |
| ATOM | 3810 | O | ASP | B | 193 | 72.013 | 20.639 | −88.277 | 1.00 | 56.46 | O |
| ATOM | 3811 | CB | ASP | B | 193 | 71.134 | 22.405 | −90.468 | 1.00 | 54.38 | C |
| ATOM | 3812 | CG | ASP | B | 193 | 70.890 | 23.106 | −91.797 | 1.00 | 53.24 | C |
| ATOM | 3813 | OD1 | ASP | B | 193 | 71.821 | 23.143 | −92.626 | 1.00 | 52.44 | O |
| ATOM | 3814 | OD2 | ASP | B | 193 | 69.776 | 23.636 | −92.008 | 1.00 | 49.34 | O |
| ATOM | 3815 | N | GLU | B | 194 | 74.081 | 21.389 | −88.800 | 1.00 | 60.07 | N |
| ATOM | 3816 | CA | GLU | B | 194 | 74.692 | 21.108 | −87.503 | 1.00 | 62.13 | C |
| ATOM | 3817 | C | GLU | B | 194 | 73.795 | 21.407 | −86.311 | 1.00 | 62.78 | C |
| ATOM | 3818 | O | GLU | B | 194 | 73.105 | 22.426 | −86.277 | 1.00 | 60.78 | O |
| ATOM | 3819 | CB | GLU | B | 194 | 75.995 | 21.900 | −87.352 | 1.00 | 63.73 | C |
| ATOM | 3820 | CG | GLU | B | 194 | 76.699 | 21.690 | −86.016 | 1.00 | 66.16 | C |
| ATOM | 3821 | CD | GLU | B | 194 | 77.933 | 22.565 | −85.854 | 1.00 | 67.84 | C |
| ATOM | 3822 | OE1 | GLU | B | 194 | 78.865 | 22.443 | −86.678 | 1.00 | 69.10 | O |
| ATOM | 3823 | OE2 | GLU | B | 194 | 77.970 | 23.374 | −84.902 | 1.00 | 68.26 | O |
| ATOM | 3824 | N | ALA | B | 195 | 73.834 | 20.512 | −85.327 | 1.00 | 64.87 | N |
| ATOM | 3825 | CA | ALA | B | 195 | 73.042 | 20.644 | −84.110 | 1.00 | 66.84 | C |
| ATOM | 3826 | C | ALA | B | 195 | 73.829 | 21.345 | −83.003 | 1.00 | 68.55 | C |
| ATOM | 3827 | O | ALA | B | 195 | 74.828 | 22.017 | −83.265 | 1.00 | 68.72 | O |
| ATOM | 3828 | CB | ALA | B | 195 | 72.590 | 19.266 | −83.637 | 1.00 | 66.35 | C |
| ATOM | 3829 | N | ASN | B | 196 | 73.374 | 21.174 | −81.764 | 1.00 | 70.97 | N |
| ATOM | 3830 | CA | ASN | B | 196 | 74.014 | 21.786 | −80.602 | 1.00 | 73.49 | C |
| ATOM | 3831 | C | ASN | B | 196 | 74.528 | 20.724 | −79.623 | 1.00 | 74.93 | C |
| ATOM | 3832 | O | ASN | B | 196 | 73.760 | 20.158 | −78.844 | 1.00 | 75.70 | O |
| ATOM | 3833 | CB | ASN | B | 196 | 73.012 | 22.706 | −79.896 | 1.00 | 74.09 | C |
| ATOM | 3834 | CG | ASN | B | 196 | 72.365 | 23.695 | −80.847 | 1.00 | 74.59 | C |
| ATOM | 3835 | OD1 | ASN | B | 196 | 73.027 | 24.587 | −81.379 | 1.00 | 74.96 | O |
| ATOM | 3836 | ND2 | ASN | B | 196 | 71.064 | 23.535 | −81.075 | 1.00 | 74.64 | N |
| ATOM | 3837 | N | GLN | B | 197 | 75.833 | 20.464 | −79.668 | 1.00 | 76.26 | N |
| ATOM | 3838 | CA | GLN | B | 197 | 76.470 | 19.470 | −78.801 | 1.00 | 77.30 | C |
| ATOM | 3839 | C | GLN | B | 197 | 76.699 | 19.974 | −77.375 | 1.00 | 77.91 | C |
| ATOM | 3840 | O | GLN | B | 197 | 77.634 | 20.734 | −77.132 | 1.00 | 78.24 | O |
| ATOM | 3841 | CB | GLN | B | 197 | 77.816 | 19.050 | −79.401 | 1.00 | 77.50 | C |
| ATOM | 3842 | CG | GLN | B | 197 | 77.716 | 18.195 | −80.650 | 1.00 | 77.91 | C |
| ATOM | 3843 | CD | GLN | B | 197 | 77.239 | 16.788 | −80.348 | 1.00 | 78.41 | C |
| ATOM | 3844 | OE1 | GLN | B | 197 | 76.118 | 16.588 | −79.875 | 1.00 | 78.73 | O |
| ATOM | 3845 | NE2 | GLN | B | 197 | 78.094 | 15.802 | −80.614 | 1.00 | 77.78 | N |
| ATOM | 3846 | N | ARG | B | 198 | 75.860 | 19.534 | −76.438 | 1.00 | 78.32 | N |
| ATOM | 3847 | CA | ARG | B | 198 | 75.966 | 19.935 | −75.029 | 1.00 | 78.45 | C |
| ATOM | 3848 | C | ARG | B | 198 | 76.512 | 21.354 | −74.827 | 1.00 | 78.58 | C |
| ATOM | 3849 | O | ARG | B | 198 | 76.077 | 22.297 | −75.495 | 1.00 | 78.77 | O |
| ATOM | 3850 | CB | ARG | B | 198 | 76.837 | 18.934 | −74.252 | 1.00 | 77.79 | C |
| ATOM | 3851 | CG | ARG | B | 198 | 78.215 | 18.680 | −74.856 | 1.00 | 77.10 | C |
| ATOM | 3852 | CD | ARG | B | 198 | 79.106 | 17.854 | −73.930 | 1.00 | 76.02 | C |
| ATOM | 3853 | NE | ARG | B | 198 | 80.048 | 18.683 | −73.177 | 1.00 | 75.94 | N |
| ATOM | 3854 | CZ | ARG | B | 198 | 79.717 | 19.483 | −72.166 | 1.00 | 75.99 | C |
| ATOM | 3855 | NH1 | ARG | B | 198 | 78.456 | 19.571 | −71.767 | 1.00 | 76.93 | N |
| ATOM | 3856 | NH2 | ARG | B | 198 | 80.651 | 20.201 | −71.554 | 1.00 | 74.62 | N |
| ATOM | 3857 | N | ALA | B | 199 | 77.458 | 21.498 | −73.899 | 1.00 | 78.62 | N |

TABLE 2-continued

| | | | | | | | | | | |
|---|---|---|---|---|---|---|---|---|---|---|
| ATOM | 3858 | CA | ALA | B | 199 | 78.073 | 22.792 | −73.606 | 1.00 | 77.71 | C |
| ATOM | 3859 | C | ALA | B | 199 | 78.949 | 23.212 | −74.781 | 1.00 | 76.60 | C |
| ATOM | 3860 | O | ALA | B | 199 | 79.440 | 24.339 | −74.834 | 1.00 | 76.89 | O |
| ATOM | 3861 | CB | ALA | B | 199 | 78.908 | 22.735 | −72.330 | 1.00 | 78.18 | C |
| ATOM | 3862 | N | THR | B | 200 | 79.143 | 22.316 | −75.713 | 1.00 | 75.48 | N |
| ATOM | 3863 | CA | THR | B | 200 | 79.932 | 22.551 | −76.916 | 1.00 | 73.92 | C |
| ATOM | 3864 | C | THR | B | 200 | 81.428 | 22.595 | −76.640 | 1.00 | 72.71 | C |
| ATOM | 3865 | O | THR | B | 200 | 81.876 | 22.254 | −75.540 | 1.00 | 72.57 | O |
| ATOM | 3866 | CB | TER | B | 200 | 79.402 | 23.762 | −77.691 | 1.00 | 74.14 | C |
| ATOM | 3867 | OG1 | THR | B | 200 | 77.973 | 23.695 | −77.759 | 1.00 | 73.12 | O |
| ATOM | 3868 | CG2 | THR | B | 200 | 79.983 | 23.774 | −79.102 | 1.00 | 73.83 | C |
| ATOM | 3869 | N | LYS | B | 201 | 82.212 | 22.972 | −77.635 | 1.00 | 70.96 | N |
| ATOM | 3870 | CA | LYS | B | 201 | 83.668 | 22.914 | −77.668 | 1.00 | 68.39 | C |
| ATOM | 3871 | C | LYS | B | 201 | 84.527 | 23.227 | −76.406 | 1.00 | 66.94 | C |
| ATOM | 3872 | O | LYS | B | 201 | 84.630 | 24.361 | −75.948 | 1.00 | 65.66 | O |
| ATOM | 3873 | CB | LYS | B | 201 | 84.128 | 23.808 | −78.793 | 1.00 | 67.59 | C |
| ATOM | 3874 | CG | LYS | B | 201 | 85.389 | 23.298 | −79.476 | 1.00 | 67.36 | C |
| ATOM | 3875 | CD | LYS | B | 201 | 85.754 | 24.242 | −80.597 | 1.00 | 67.91 | C |
| ATOM | 3876 | CE | LYS | B | 201 | 86.712 | 23.605 | −81.583 | 1.00 | 68.42 | C |
| ATOM | 3877 | NZ | LYS | B | 201 | 86.907 | 24.448 | −82.796 | 1.00 | 69.60 | N |
| ATOM | 3878 | N | MET | B | 202 | 85.125 | 22.139 | −75.862 | 1.00 | 65.45 | N |
| ATOM | 3879 | CA | MET | B | 202 | 86.016 | 22.107 | −74.703 | 1.00 | 64.39 | C |
| ATOM | 3880 | C | MET | B | 202 | 87.422 | 22.198 | −75.235 | 1.00 | 64.39 | C |
| ATOM | 3881 | O | MET | B | 202 | 88.098 | 21.192 | −75.403 | 1.00 | 64.41 | O |
| ATOM | 3882 | CB | MET | B | 202 | 85.856 | 20.824 | −73.901 | 1.00 | 62.90 | C |
| ATOM | 3883 | CG | MET | B | 202 | 86.627 | 20.792 | −72.596 | 1.00 | 61.80 | C |
| ATOM | 3884 | SD | MET | B | 202 | 85.849 | 21.797 | −71.309 | 1.00 | 59.98 | S |
| ATOM | 3885 | CE | MET | B | 202 | 84.611 | 20.658 | −70.699 | 1.00 | 59.70 | C |
| ATOM | 3886 | N | LEU | B | 203 | 87.847 | 23.409 | −75.515 | 1.00 | 64.54 | N |
| ATOM | 3887 | CA | LEU | B | 203 | 89.141 | 23.654 | −76.155 | 1.00 | 64.56 | C |
| ATOM | 3888 | C | LEU | B | 203 | 90.358 | 23.299 | −75.295 | 1.00 | 65.09 | C |
| ATOM | 3889 | O | LEU | B | 203 | 90.345 | 23.544 | −74.092 | 1.00 | 65.15 | O |
| ATOM | 3890 | CB | LEU | B | 203 | 89.148 | 25.107 | −76.618 | 1.00 | 63.64 | C |
| ATOM | 3891 | CG | LEU | B | 203 | 87.903 | 25.571 | −77.376 | 1.00 | 63.09 | C |
| ATOM | 3892 | CD1 | LEU | B | 203 | 87.946 | 27.063 | −77.657 | 1.00 | 62.58 | C |
| ATOM | 3893 | CD2 | LEU | B | 203 | 87.746 | 24.780 | −78.667 | 1.00 | 61.84 | C |
| ATOM | 3894 | N | GLY | B | 204 | 91.404 | 22.712 | −75.911 | 1.00 | 65.26 | N |
| ATOM | 3895 | CA | GLY | B | 204 | 92.618 | 22.339 | −75.211 | 1.00 | 65.34 | C |
| ATOM | 3896 | C | GLY | B | 204 | 93.541 | 23.556 | −75.070 | 1.00 | 65.58 | C |
| ATOM | 3897 | O | GLY | B | 204 | 93.112 | 24.702 | −75.229 | 1.00 | 65.57 | O |
| ATOM | 3898 | OXT | GLY | B | 204 | 94.615 | 23.257 | −74.240 | 1.00 | 65.78 | O |

TABLE 1

| | | | | | | | | | | |
|---|---|---|---|---|---|---|---|---|---|---|
| ATOM | 1 | N | PRO | A | 2 | 13.663 | −19.877 | 76.282 | 1.00 | 34.74 | N |
| ATOM | 2 | CA | PRO | A | 2 | 14.273 | −21.069 | 75.680 | 1.00 | 52.96 | C |
| ATOM | 3 | C | PRO | A | 2 | 13.389 | −22.204 | 76.054 | 1.00 | 41.78 | C |
| ATOM | 4 | O | PRO | A | 2 | 12.221 | −21.985 | 76.370 | 1.00 | 67.10 | O |
| ATOM | 5 | CB | PRO | A | 2 | 15.638 | −21.253 | 76.307 | 1.00 | 26.43 | C |
| ATOM | 6 | CG | PRO | A | 2 | 15.993 | −19.841 | 76.612 | 1.00 | 42.98 | C |
| ATOM | 7 | CD | PRO | A | 2 | 14.686 | −19.157 | 77.051 | 1.00 | 48.21 | C |
| ATOM | 8 | N | PHE | A | 3 | 13.954 | −23.407 | 76.007 | 1.00 | 47.22 | N |
| ATOM | 9 | CA | PHE | A | 3 | 13.260 | −24.626 | 76.404 | 1.00 | 43.68 | C |
| ATOM | 10 | C | PHE | A | 3 | 12.594 | −24.286 | 77.726 | 1.00 | 36.19 | C |
| ATOM | 11 | O | PHE | A | 3 | 13.212 | −23.702 | 78.620 | 1.00 | 29.99 | O |
| ATOM | 12 | CB | PHE | A | 3 | 14.262 | −25.749 | 76.637 | 1.00 | 51.22 | C |
| ATOM | 13 | CG | PHE | A | 3 | 13.639 | −27.079 | 76.856 | 1.00 | 41.04 | C |
| ATOM | 14 | CD1 | PHE | A | 3 | 13.367 | −27.916 | 75.783 | 1.00 | 55.79 | C |
| ATOM | 15 | CD2 | PHE | A | 3 | 13.329 | −27.513 | 78.141 | 1.00 | 71.37 | C |
| ATOM | 16 | CE1 | PHE | A | 3 | 12.795 | −29.182 | 75.983 | 1.00 | 54.16 | C |
| ATOM | 17 | CE2 | PHE | A | 3 | 12.752 | −28.781 | 78.357 | 1.00 | 65.29 | C |
| ATOM | 18 | CZ | PHE | A | 3 | 12.487 | −29.610 | 77.271 | 1.00 | 54.73 | C |
| ATOM | 19 | N | VAL | A | 4 | 11.319 | −24.625 | 77.806 | 1.00 | 31.97 | N |
| ATOM | 20 | CA | VAL | A | 4 | 10.491 | −24.379 | 78.972 | 1.00 | 55.08 | C |
| ATOM | 21 | C | VAL | A | 4 | 10.330 | −25.738 | 79.636 | 1.00 | 50.35 | C |
| ATOM | 22 | O | VAL | A | 4 | 9.642 | −26.609 | 79.119 | 1.00 | 46.10 | O |
| ATOM | 23 | CB | VAL | A | 4 | 9.107 | −23.819 | 78.529 | 1.00 | 40.26 | C |
| ATOM | 24 | CG1 | VAL | A | 4 | 8.264 | −23.470 | 79.714 | 1.00 | 40.98 | C |
| ATOM | 25 | CG2 | VAL | A | 4 | 9.322 | −22.594 | 77.645 | 1.00 | 47.66 | C |
| ATOM | 26 | N | ASN | A | 5 | 10.974 | −25.916 | 80.781 | 1.00 | 57.10 | N |
| ATOM | 27 | CA | ASN | A | 5 | 10.911 | −27.189 | 81.472 | 1.00 | 65.28 | C |
| ATOM | 28 | C | ASN | A | 5 | 9.557 | −27.619 | 82.022 | 1.00 | 69.95 | C |
| ATOM | 29 | O | ASN | A | 5 | 9.221 | −28.800 | 81.946 | 1.00 | 80.84 | O |
| ATOM | 30 | CB | ASN | A | 5 | 11.966 | −27.224 | 82.566 | 1.00 | 69.31 | C |
| ATOM | 31 | CG | ASN | A | 5 | 13.364 | −27.283 | 81.996 | 1.00 | 81.39 | C |
| ATOM | 32 | OD1 | ASN | A | 5 | 13.646 | −28.090 | 81.103 | 1.00 | 77.72 | O |

TABLE 1-continued

| | | | | | | | | | | |
|---|---|---|---|---|---|---|---|---|---|---|
| ATOM | 33 | ND2 | ASN | A | 5 | 14.251 | −26.426 | 82.497 | 1.00 | 91.76 N |
| ATOM | 34 | N | LYS | A | 6 | 8.767 | −26.693 | 82.557 | 1.00 | 58.24 N |
| ATOM | 35 | CA | LYS | A | 6 | 7.461 | −27.075 | 83.089 | 1.00 | 61.72 C |
| ATOM | 36 | C | LYS | A | 6 | 6.274 | −26.559 | 82.265 | 1.00 | 67.62 C |
| ATOM | 37 | O | LYS | A | 6 | 6.358 | −25.497 | 81.642 | 1.00 | 72.93 O |
| ATOM | 38 | CB | LYS | A | 6 | 7.330 | −26.608 | 84.540 | 1.00 | 65.31 C |
| ATOM | 39 | CG | LYS | A | 6 | 7.552 | −25.109 | 84.729 | 1.00 | 50.46 C |
| ATOM | 40 | CD | LYS | A | 6 | 7.178 | −24.685 | 86.148 | 1.00 | 69.06 C |
| ATOM | 41 | CE | LYS | A | 6 | 8.177 | −25.203 | 87.162 | 1.00 | 72.87 C |
| ATOM | 42 | NZ | LYS | A | 6 | 7.944 | −24.635 | 88.519 | 1.00 | 73.14 N |
| ATOM | 43 | N | GLN | A | 7 | 5.176 | −27.318 | 82.262 | 1.00 | 57.01 N |
| ATOM | 44 | CA | GLN | A | 7 | 3.968 | −26.943 | 81.519 | 1.00 | 65.35 C |
| ATOM | 45 | C | GLN | A | 7 | 3.124 | −26.007 | 82.385 | 1.00 | 67.57 C |
| ATOM | 46 | O | GLN | A | 7 | 2.593 | −26.407 | 83.418 | 1.00 | 81.02 O |
| ATOM | 47 | CB | GLN | A | 7 | 3.156 | −28.187 | 81.126 | 1.00 | 69.91 C |
| ATOM | 48 | CG | GLN | A | 7 | 4.005 | −29.409 | 80.796 | 1.00 | 72.98 C |
| ATOM | 49 | CD | GLN | A | 7 | 4.756 | −29.245 | 79.504 | 1.00 | 76.85 C |
| ATOM | 50 | OE1 | GLN | A | 7 | 5.421 | −28.229 | 79.298 | 1.00 | 75.54 O |
| ATOM | 51 | NE2 | GLN | A | 7 | 4.808 | −30.113 | 78.490 | 1.00 | 74.11 N |
| ATOM | 52 | N | PHE | A | 8 | 3.012 | −24.757 | 81.954 | 1.00 | 53.98 N |
| ATOM | 53 | CA | PHE | A | 8 | 2.271 | −23.741 | 82.685 | 1.00 | 51.76 C |
| ATOM | 54 | C | PHE | A | 8 | 0.822 | −23.629 | 82.221 | 1.00 | 56.93 C |
| ATOM | 55 | O | PHE | A | 8 | 0.538 | −23.740 | 81.031 | 1.00 | 55.35 O |
| ATOM | 56 | CB | PHE | A | 8 | 2.925 | −22.367 | 82.506 | 1.00 | 59.57 C |
| ATOM | 57 | CG | PHE | A | 8 | 4.232 | −22.171 | 83.198 | 1.00 | 54.76 C |
| ATOM | 58 | CD1 | PHE | A | 8 | 4.251 | −21.802 | 84.539 | 1.00 | 59.88 C |
| ATOM | 59 | CD2 | PHE | A | 8 | 5.442 | −22.315 | 82.526 | 1.00 | 55.42 C |
| ATOM | 60 | CE1 | PHE | A | 8 | 5.451 | −21.580 | 85.199 | 1.00 | 58.82 C |
| ATOM | 61 | CE2 | PHE | A | 8 | 6.652 | −22.097 | 83.178 | 1.00 | 42.22 C |
| ATOM | 62 | CZ | PHE | A | 8 | 6.656 | −21.727 | 84.514 | 1.00 | 59.95 C |
| ATOM | 63 | N | ASN | A | 9 | −0.085 | −23.423 | 83.135 | 1.00 | 38.79 N |
| ATOM | 64 | CA | ASN | A | 9 | −1.489 | −23.224 | 82.850 | 1.00 | 49.19 C |
| ATOM | 65 | C | ASN | A | 9 | −1.818 | −21.864 | 83.468 | 1.00 | 30.80 C |
| ATOM | 66 | O | ASN | A | 9 | −1.368 | −21.574 | 84.572 | 1.00 | 38.66 O |
| ATOM | 67 | CB | ASN | A | 9 | −2.346 | −24.321 | 83.485 | 1.00 | 43.11 C |
| ATOM | 68 | CG | ASN | A | 9 | −2.013 | −25.686 | 82.954 | 1.00 | 55.82 C |
| ATOM | 69 | OD1 | ASN | A | 9 | −2.223 | −25.972 | 81.769 | 1.00 | 67.21 O |
| ATOM | 70 | ND2 | ASN | A | 9 | −1.484 | −26.547 | 83.820 | 1.00 | 60.70 N |
| ATOM | 71 | N | TYR | A | 10 | −2.575 | −21.033 | 82.776 | 1.00 | 31.03 N |
| ATOM | 72 | CA | TYR | A | 10 | −2.879 | −19.730 | 83.317 | 1.00 | 28.21 C |
| ATOM | 73 | C | TYR | A | 10 | −3.532 | −19.805 | 84.703 | 1.00 | 50.93 C |
| ATOM | 74 | O | TYR | A | 10 | −3.419 | −18.863 | 85.500 | 1.00 | 41.37 O |
| ATOM | 75 | CB | TYR | A | 10 | −3.779 | −18.957 | 82.347 | 1.00 | 31.68 C |
| ATOM | 76 | CG | TYR | A | 10 | −3.996 | −17.531 | 82.781 | 1.00 | 34.20 C |
| ATOM | 77 | CD1 | TYR | A | 10 | −2.988 | −16.579 | 82.619 | 1.00 | 37.28 C |
| ATOM | 78 | CD2 | TYR | A | 10 | −5.166 | −17.147 | 83.451 | 1.00 | 34.57 C |
| ATOM | 79 | CE1 | TYR | A | 10 | −3.129 | −15.284 | 83.118 | 1.00 | 25.01 C |
| ATOM | 80 | CE2 | TYR | A | 10 | −5.308 | −15.842 | 83.961 | 1.00 | 37.39 C |
| ATOM | 81 | CZ | TYR | A | 10 | −4.273 | −14.925 | 83.787 | 1.00 | 32.45 C |
| ATOM | 82 | OH | TYR | A | 10 | −4.344 | −13.648 | 84.301 | 1.00 | 46.85 O |
| ATOM | 83 | N | LYS | A | 11 | −4.192 | −20.937 | 84.981 | 1.00 | 60.25 N |
| ATOM | 84 | CA | LYS | A | 11 | −4.909 | −21.191 | 86.242 | 1.00 | 52.46 C |
| ATOM | 85 | C | LYS | A | 11 | −4.011 | −21.533 | 87.428 | 1.00 | 60.68 C |
| ATOM | 86 | O | LYS | A | 11 | −4.360 | −21.220 | 88.572 | 1.00 | 44.07 O |
| ATOM | 87 | CB | LYS | A | 11 | −5.904 | −22.342 | 86.075 | 1.00 | 58.97 C |
| ATOM | 88 | CG | LYS | A | 11 | −7.007 | −22.123 | 85.052 | 1.00 | 70.60 C |
| ATOM | 89 | CD | LYS | A | 11 | −7.993 | −21.050 | 85.479 | 1.00 | 73.95 C |
| ATOM | 90 | CE | LYS | A | 11 | −9.290 | −21.184 | 84.685 | 1.00 | 68.03 C |
| ATOM | 91 | NZ | LYS | A | 11 | −10.290 | −20.145 | 85.060 | 1.00 | 84.78 N |
| ATOM | 92 | N | ASP | A | 12 | −2.890 | −22.209 | 87.156 | 1.00 | 54.95 N |
| ATOM | 93 | CA | ASP | A | 12 | −1.920 | −22.585 | 88.187 | 1.00 | 25.58 C |
| ATOM | 94 | C | ASP | A | 12 | −1.804 | −21.473 | 89.250 | 1.00 | 51.42 C |
| ATOM | 95 | O | ASP | A | 12 | −1.841 | −20.278 | 88.941 | 1.00 | 36.27 O |
| ATOM | 96 | CB | ASP | A | 12 | −0.555 | −22.854 | 87.552 | 1.00 | 26.45 C |
| ATOM | 97 | CG | ASP | A | 12 | −0.571 | −24.021 | 86.550 | 1.00 | 54.62 C |
| ATOM | 98 | OD1 | ASP | A | 12 | −1.553 | −24.799 | 86.524 | 1.00 | 55.46 O |
| ATOM | 99 | OD2 | ASP | A | 12 | 0.420 | −24.171 | 85.787 | 1.00 | 58.06 O |
| ATOM | 100 | N | PRO | A | 13 | −1.679 | −21.858 | 90.529 | 1.00 | 55.63 N |
| ATOM | 101 | CA | PRO | A | 13 | −1.567 | −20.884 | 91.622 | 1.00 | 55.49 C |
| ATOM | 102 | C | PRO | A | 13 | −0.221 | −20.161 | 91.700 | 1.00 | 41.31 C |
| ATOM | 103 | O | PRO | A | 13 | 0.798 | −20.700 | 91.309 | 1.00 | 38.38 O |
| ATOM | 104 | CB | PRO | A | 13 | −1.810 | −21.740 | 92.858 | 1.00 | 50.61 C |
| ATOM | 105 | CG | PRO | A | 13 | −1.093 | −23.022 | 92.472 | 1.00 | 51.15 C |
| ATOM | 106 | CD | PRO | A | 13 | −1.579 | −23.239 | 91.040 | 1.00 | 60.12 C |
| ATOM | 107 | N | VAL | A | 14 | −0.247 | −18.939 | 92.230 | 1.00 | 50.47 N |
| ATOM | 108 | CA | VAL | A | 14 | 0.951 | −18.130 | 92.407 | 1.00 | 51.88 C |
| ATOM | 109 | C | VAL | A | 14 | 1.888 | −18.822 | 93.392 | 1.00 | 50.70 C |
| ATOM | 110 | O | VAL | A | 14 | 1.436 | −19.396 | 94.368 | 1.00 | 51.55 O |
| ATOM | 111 | CB | VAL | A | 14 | 0.581 | −16.725 | 92.939 | 1.00 | 48.46 C |

TABLE 1-continued

| | | | | | | | | | | |
|---|---|---|---|---|---|---|---|---|---|---|
| ATOM | 112 | CG1 | VAL | A | 14 | 1.796 | −16.046 | 93.561 | 1.00 | 69.42 C |
| ATOM | 113 | CG2 | VAL | A | 14 | 0.050 | −15.873 | 91.794 | 1.00 | 51.42 C |
| ATOM | 114 | N | ASN | A | 15 | 3.189 | −18.784 | 93.115 | 1.00 | 57.76 N |
| ATOM | 115 | CA | ASN | A | 15 | 4.176 | −19.407 | 93.986 | 1.00 | 47.65 C |
| ATOM | 116 | C | ASN | A | 15 | 5.322 | −18.440 | 94.222 | 1.00 | 51.25 C |
| ATOM | 117 | O | ASN | A | 15 | 6.371 | −18.813 | 94.746 | 1.00 | 60.86 O |
| ATOM | 118 | CB | ASN | A | 15 | 4.700 | −20.717 | 93.379 | 1.00 | 48.92 C |
| ATOM | 119 | CG | ASN | A | 15 | 5.350 | −20.521 | 92.014 | 1.00 | 58.38 C |
| ATOM | 120 | OD1 | ASN | A | 15 | 6.092 | −19.560 | 91.792 | 1.00 | 56.17 O |
| ATOM | 121 | ND2 | ASN | A | 15 | 5.095 | −21.451 | 91.103 | 1.00 | 43.88 N |
| ATOM | 122 | N | GLY | A | 16 | 5.111 | −17.191 | 93.820 | 1.00 | 52.31 N |
| ATOM | 123 | CA | GLY | A | 16 | 6.112 | −16.159 | 94.011 | 1.00 | 56.36 C |
| ATOM | 124 | C | GLY | A | 16 | 7.448 | −16.391 | 93.330 | 1.00 | 57.62 C |
| ATOM | 125 | O | GLY | A | 16 | 8.309 | −15.507 | 93.335 | 1.00 | 39.06 O |
| ATOM | 126 | N | VAL | A | 17 | 7.621 | −17.574 | 92.748 | 1.00 | 42.18 N |
| ATOM | 127 | CA | VAL | A | 17 | 8.855 | −17.916 | 92.059 | 1.00 | 56.96 C |
| ATOM | 128 | C | VAL | A | 17 | 8.706 | −17.713 | 90.554 | 1.00 | 57.74 C |
| ATOM | 129 | O | VAL | A | 17 | 9.131 | −16.684 | 90.014 | 1.00 | 50.50 O |
| ATOM | 130 | CB | VAL | A | 17 | 9.239 | −19.376 | 92.305 | 1.00 | 57.95 C |
| ATOM | 131 | CG1 | VAL | A | 17 | 10.680 | −19.608 | 91.874 | 1.00 | 44.39 C |
| ATOM | 132 | CG2 | VAL | A | 17 | 9.043 | −19.712 | 93.775 | 1.00 | 70.86 C |
| ATOM | 133 | N | ASP | A | 18 | 8.104 | −18.695 | 89.885 | 1.00 | 40.22 N |
| ATOM | 134 | CA | ASP | A | 18 | 7.906 | −18.601 | 88.449 | 1.00 | 46.40 C |
| ATOM | 135 | C | ASP | A | 18 | 6.459 | −18.328 | 88.001 | 1.00 | 35.24 C |
| ATOM | 136 | O | ASP | A | 18 | 6.159 | −18.378 | 86.810 | 1.00 | 42.59 O |
| ATOM | 137 | CB | ASP | A | 18 | 8.451 | −19.852 | 87.761 | 1.00 | 39.92 C |
| ATOM | 138 | CG | ASP | A | 18 | 7.844 | −21.111 | 88.301 | 1.00 | 52.46 C |
| ATOM | 139 | OD1 | ASP | A | 18 | 6.800 | −20.993 | 88.975 | 1.00 | 53.92 O |
| ATOM | 140 | OD2 | ASP | A | 18 | 8.393 | −22.206 | 88.037 | 1.00 | 46.12 O |
| ATOM | 141 | N | ILE | A | 19 | 5.573 | −18.045 | 88.954 | 1.00 | 35.53 N |
| ATOM | 142 | CA | ILE | A | 19 | 4.178 | −17.709 | 88.668 | 1.00 | 25.77 C |
| ATOM | 143 | C | ILE | A | 19 | 3.771 | −16.699 | 89.723 | 1.00 | 28.75 C |
| ATOM | 144 | O | ILE | A | 19 | 3.659 | −17.033 | 90.893 | 1.00 | 38.34 O |
| ATOM | 145 | CB | ILE | A | 19 | 3.229 | −18.903 | 88.779 | 1.00 | 41.11 C |
| ATOM | 146 | CG1 | ILE | A | 19 | 3.605 | −19.985 | 87.784 | 1.00 | 42.66 C |
| ATOM | 147 | CG2 | ILE | A | 19 | 1.803 | −18.459 | 88.456 | 1.00 | 54.22 C |
| ATOM | 148 | CD1 | ILE | A | 19 | 2.674 | −21.147 | 87.843 | 1.00 | 39.93 C |
| ATOM | 149 | N | ALA | A | 20 | 3.532 | −15.460 | 89.317 | 1.00 | 40.75 N |
| ATOM | 150 | CA | ALA | A | 20 | 3.210 | −14.443 | 90.283 | 1.00 | 24.25 C |
| ATOM | 151 | C | ALA | A | 20 | 2.530 | −13.226 | 89.699 | 1.00 | 45.44 C |
| ATOM | 152 | O | ALA | A | 20 | 2.393 | −13.077 | 88.487 | 1.00 | 46.72 C |
| ATOM | 153 | CB | ALA | A | 20 | 4.506 | −13.999 | 90.979 | 1.00 | 31.00 C |
| ATOM | 154 | N | TYR | A | 21 | 2.116 | −12.345 | 90.601 | 1.00 | 34.72 N |
| ATOM | 155 | CA | TYR | A | 21 | 1.520 | −11.094 | 90.229 | 1.00 | 27.28 C |
| ATOM | 156 | C | TYR | A | 21 | 2.644 | −10.082 | 90.326 | 1.00 | 45.71 C |
| ATOM | 157 | O | TYR | A | 21 | 3.431 | −10.089 | 91.287 | 1.00 | 38.30 O |
| ATOM | 158 | CB | TYR | A | 21 | 0.370 | −10.751 | 91.164 | 1.00 | 40.69 C |
| ATOM | 159 | CG | TYR | A | 21 | −0.901 | −11.439 | 90.724 | 1.00 | 51.93 C |
| ATOM | 160 | CD1 | TYR | A | 21 | −1.218 | −12.726 | 91.168 | 1.00 | 30.40 C |
| ATOM | 161 | CD2 | TYR | A | 21 | −1.768 | −10.814 | 89.822 | 1.00 | 38.16 C |
| ATOM | 162 | CE1 | TYR | A | 21 | −2.368 | −13.365 | 90.722 | 1.00 | 53.56 C |
| ATOM | 163 | CE2 | TYR | A | 21 | −2.922 | −11.444 | 89.374 | 1.00 | 48.29 C |
| ATOM | 164 | CZ | TYR | A | 21 | −3.219 | −12.717 | 89.826 | 1.00 | 42.22 C |
| ATOM | 165 | OH | TYR | A | 21 | −4.376 | −13.330 | 89.404 | 1.00 | 57.12 O |
| ATOM | 166 | N | ILE | A | 22 | 2.728 | −9.218 | 89.326 | 1.00 | 33.20 N |
| ATOM | 167 | CA | ILE | A | 22 | 3.804 | −8.252 | 89.272 | 1.00 | 38.94 C |
| ATOM | 168 | C | ILE | A | 22 | 3.326 | −6.906 | 88.794 | 1.00 | 35.60 C |
| ATOM | 169 | O | ILE | A | 22 | 2.217 | −6.772 | 88.262 | 1.00 | 37.96 O |
| ATOM | 170 | CB | ILE | A | 22 | 4.865 | −8.702 | 88.278 | 1.00 | 26.40 C |
| ATOM | 171 | CG1 | ILE | A | 22 | 4.291 | −8.558 | 86.857 | 1.00 | 31.16 C |
| ATOM | 172 | CG2 | ILE | A | 22 | 5.245 | −10.181 | 88.536 | 1.00 | 23.23 C |
| ATOM | 173 | CD1 | ILE | A | 22 | 5.313 | −8.575 | 85.779 | 1.00 | 49.51 C |
| ATOM | 174 | N | LYS | A | 23 | 4.194 | −5.924 | 88.978 | 1.00 | 37.16 N |
| ATOM | 175 | CA | LYS | A | 23 | 3.957 | −4.562 | 88.535 | 1.00 | 35.03 C |
| ATOM | 176 | C | LYS | A | 23 | 5.189 | −4.157 | 87.748 | 1.00 | 47.46 C |
| ATOM | 177 | O | LYS | A | 23 | 6.319 | −4.436 | 88.153 | 1.00 | 39.54 O |
| ATOM | 178 | CB | LYS | A | 23 | 3.767 | −3.618 | 89.716 | 1.00 | 46.09 C |
| ATOM | 179 | CG | LYS | A | 23 | 2.482 | −3.849 | 90.496 | 1.00 | 46.00 C |
| ATOM | 180 | CD | LYS | A | 23 | 2.247 | −2.732 | 91.510 | 1.00 | 64.45 C |
| ATOM | 181 | CE | LYS | A | 23 | 2.100 | −1.365 | 90.836 | 1.00 | 69.72 C |
| ATOM | 182 | NZ | LYS | A | 23 | 1.941 | −0.226 | 91.805 | 1.00 | 76.85 N |
| ATOM | 183 | N | ILE | A | 24 | 4.955 | −3.526 | 86.609 | 1.00 | 33.54 N |
| ATOM | 184 | CA | ILE | A | 24 | 6.021 | −3.069 | 85.743 | 1.00 | 50.53 C |
| ATOM | 185 | C | ILE | A | 24 | 6.535 | −1.723 | 86.258 | 1.00 | 47.76 C |
| ATOM | 186 | O | ILE | A | 24 | 5.754 | −0.794 | 86.502 | 1.00 | 41.52 O |
| ATOM | 187 | CB | ILE | A | 24 | 5.497 | −2.949 | 84.292 | 1.00 | 51.71 C |
| ATOM | 188 | CG1 | ILE | A | 24 | 5.119 | −4.344 | 83.790 | 1.00 | 50.64 C |
| ATOM | 189 | CG2 | ILE | A | 24 | 6.532 | −2.282 | 83.404 | 1.00 | 50.83 C |
| ATOM | 190 | CD1 | ILE | A | 24 | 4.234 | −4.343 | 82.549 | 1.00 | 61.20 C |

TABLE 1-continued

| | | | | | | | | | | |
|---|---|---|---|---|---|---|---|---|---|---|
| ATOM | 191 | N | PRO | A | 25 | 7.863 | −1.607 | 86.459 | 1.00 | 68.54 N |
| ATOM | 192 | CA | PRO | A | 25 | 8.514 | −0.388 | 86.923 | 1.00 | 67.90 C |
| ATOM | 193 | C | PRO | A | 25 | 8.329 | 0.691 | 85.890 | 1.00 | 70.22 C |
| ATOM | 194 | O | PRO | A | 25 | 9.140 | 0.798 | 84.971 | 1.00 | 81.75 O |
| ATOM | 195 | CB | PRO | A | 25 | 10.001 | −0.783 | 87.001 | 1.00 | 85.01 C |
| ATOM | 196 | CG | PRO | A | 25 | 10.154 | −1.821 | 85.938 | 1.00 | 72.53 C |
| ATOM | 197 | CD | PRO | A | 25 | 8.864 | −2.592 | 85.972 | 1.00 | 73.41 C |
| ATOM | 198 | N | ASN | A | 26 | 7.263 | 1.513 | 86.021 | 1.00 | 72.97 N |
| ATOM | 199 | CA | ASN | A | 26 | 7.101 | 2.496 | 84.948 | 1.00 | 75.29 C |
| ATOM | 200 | C | ASN | A | 26 | 6.614 | 3.908 | 85.256 | 1.00 | 80.51 C |
| ATOM | 201 | O | ASN | A | 26 | 7.341 | 4.860 | 85.010 | 1.00 | 91.30 O |
| ATOM | 202 | CB | ASN | A | 26 | 6.222 | 1.872 | 83.868 | 1.00 | 81.53 C |
| ATOM | 203 | CG | ASN | A | 26 | 4.857 | 2.522 | 83.800 | 1.00 | 87.13 C |
| ATOM | 204 | OD1 | ASN | A | 26 | 4.105 | 2.524 | 84.759 | 1.00 | 86.48 O |
| ATOM | 205 | ND2 | ASN | A | 26 | 4.532 | 3.084 | 82.630 | 1.00 | 87.51 N |
| ATOM | 206 | N | ALA | A | 27 | 5.402 | 4.058 | 85.783 | 1.00 | 78.63 N |
| ATOM | 207 | CA | ALA | A | 27 | 4.850 | 5.395 | 85.993 | 1.00 | 91.46 C |
| ATOM | 208 | C | ALA | A | 27 | 3.761 | 5.514 | 87.062 | 1.00 | 91.70 C |
| ATOM | 209 | O | ALA | A | 27 | 4.012 | 5.957 | 88.179 | 1.00 | 86.76 O |
| ATOM | 210 | CB | ALA | A | 27 | 4.337 | 5.926 | 84.656 | 1.00 | 80.22 C |
| ATOM | 211 | N | GLY | A | 28 | 2.548 | 5.103 | 86.695 | 1.00 | 93.34 N |
| ATOM | 212 | CA | GLY | A | 28 | 1.426 | 5.173 | 87.611 | 1.00 | 90.33 C |
| ATOM | 213 | C | GLY | A | 28 | 1.341 | 4.021 | 88.593 | 1.00 | 87.32 C |
| ATOM | 214 | O | GLY | A | 28 | 2.290 | 3.250 | 88.763 | 1.00 | 81.15 O |
| ATOM | 215 | N | GLN | A | 29 | 0.184 | 3.914 | 89.241 | 1.00 | 86.11 N |
| ATOM | 216 | CA | GLN | A | 29 | −0.067 | 2.872 | 90.226 | 1.00 | 87.93 C |
| ATOM | 217 | C | GLN | A | 29 | −0.889 | 1.756 | 89.581 | 1.00 | 88.01 C |
| ATOM | 218 | O | GLN | A | 29 | −1.994 | 1.453 | 90.033 | 1.00 | 89.41 O |
| ATOM | 219 | CB | GLN | A | 29 | −0.791 | 3.473 | 91.460 | 1.00 | 93.27 C |
| ATOM | 220 | CG | GLN | A | 29 | −0.093 | 4.700 | 92.100 | 1.00 | 88.94 C |
| ATOM | 221 | CD | GLN | A | 29 | −0.904 | 5.321 | 93.237 | 1.00 | 93.43 C |
| ATOM | 222 | OE1 | GLN | A | 29 | −1.974 | 5.872 | 93.022 | 1.00 | 85.90 O |
| ATOM | 223 | NE2 | GLN | A | 29 | −0.567 | 5.325 | 94.530 | 1.00 | 76.10 N |
| ATOM | 224 | N | MET | A | 30 | −0.349 | 1.156 | 88.519 | 1.00 | 79.49 N |
| ATOM | 225 | CA | MET | A | 30 | −1.038 | 0.074 | 87.819 | 1.00 | 70.45 C |
| ATOM | 226 | C | MET | A | 30 | −1.393 | −1.036 | 88.797 | 1.00 | 67.65 C |
| ATOM | 227 | O | MET | A | 30 | −0.769 | −1.180 | 89.844 | 1.00 | 71.10 O |
| ATOM | 228 | CB | MET | A | 30 | −0.154 | −0.490 | 86.701 | 1.00 | 76.59 C |
| ATOM | 229 | CG | MET | A | 30 | 0.814 | −1.580 | 87.128 | 1.00 | 61.39 C |
| ATOM | 230 | SD | MET | A | 30 | 1.753 | −2.241 | 85.734 | 1.00 | 55.45 S |
| ATOM | 231 | CE | MET | A | 30 | 1.260 | −3.961 | 85.790 | 1.00 | 48.66 C |
| ATOM | 232 | N | GLN | A | 31 | −2.407 | −1.818 | 88.462 | 1.00 | 65.32 N |
| ATOM | 233 | CA | GLN | A | 31 | −2.778 | −2.935 | 89.282 | 1.00 | 63.54 C |
| ATOM | 234 | C | GLN | A | 31 | −1.958 | −4.112 | 88.788 | 1.00 | 55.69 C |
| ATOM | 235 | O | GLN | A | 31 | −1.768 | −4.266 | 87.578 | 1.00 | 47.96 O |
| ATOM | 236 | CB | GLN | A | 31 | −4.286 | −3.215 | 89.227 | 1.00 | 66.34 C |
| ATOM | 237 | CG | GLN | A | 31 | −4.838 | −3.357 | 87.824 | 1.00 | 81.15 C |
| ATOM | 238 | CD | GLN | A | 31 | −6.313 | −3.684 | 87.793 | 1.00 | 86.15 C |
| ATOM | 239 | OE1 | GLN | A | 31 | −6.786 | −4.557 | 88.507 | 1.00 | 91.57 O |
| ATOM | 240 | NE2 | GLN | A | 31 | −7.222 | −3.093 | 87.035 | 1.00 | 82.30 N |
| ATOM | 241 | N | PRO | A | 32 | −1.458 | −4.957 | 89.693 | 1.00 | 60.31 N |
| ATOM | 242 | CA | PRO | A | 32 | −0.649 | −6.106 | 89.293 | 1.00 | 52.60 C |
| ATOM | 243 | C | PRO | A | 32 | −1.333 | −6.968 | 88.257 | 1.00 | 50.82 C |
| ATOM | 244 | O | PRO | A | 32 | −2.529 | −6.861 | 88.027 | 1.00 | 67.88 O |
| ATOM | 245 | CB | PRO | A | 32 | −0.453 | −6.866 | 90.583 | 1.00 | 64.28 C |
| ATOM | 246 | CG | PRO | A | 32 | −1.672 | −6.528 | 91.368 | 1.00 | 59.70 C |
| ATOM | 247 | CD | PRO | A | 32 | −1.992 | −5.092 | 91.050 | 1.00 | 55.55 C |
| ATOM | 248 | N | VAL | A | 33 | −0.554 | −7.832 | 87.615 | 1.00 | 47.29 N |
| ATOM | 249 | CA | VAL | A | 33 | −1.063 | −8.753 | 86.606 | 1.00 | 48.41 C |
| ATOM | 250 | C | VAL | A | 33 | −0.274 | −10.028 | 86.764 | 1.00 | 39.92 C |
| ATOM | 251 | O | VAL | A | 33 | 0.881 | −10.004 | 87.167 | 1.00 | 42.83 O |
| ATOM | 252 | CB | VAL | A | 33 | −0.908 | −8.226 | 85.169 | 1.00 | 42.14 C |
| ATOM | 253 | CG1 | VAL | A | 33 | −1.811 | −7.013 | 84.951 | 1.00 | 35.77 C |
| ATOM | 254 | CG2 | VAL | A | 33 | 0.551 | −7.868 | 84.876 | 1.00 | 39.45 C |
| ATOM | 255 | N | LYS | A | 34 | −0.920 | −11.136 | 86.432 | 1.00 | 37.41 N |
| ATOM | 256 | CA | LYS | A | 34 | −0.329 | −12.452 | 86.562 | 1.00 | 34.66 C |
| ATOM | 257 | C | LYS | A | 34 | 0.741 | −12.711 | 85.500 | 1.00 | 36.31 C |
| ATOM | 258 | O | LYS | A | 34 | 0.531 | −12.483 | 84.319 | 1.00 | 32.42 O |
| ATOM | 259 | CB | LYS | A | 34 | −1.443 | −13.487 | 86.503 | 1.00 | 25.15 C |
| ATOM | 260 | CG | LYS | A | 34 | −1.007 | −14.876 | 86.921 | 1.00 | 57.36 C |
| ATOM | 261 | CD | LYS | A | 34 | −2.200 | −15.758 | 87.292 | 1.00 | 37.59 C |
| ATOM | 262 | CE | LYS | A | 34 | −1.745 | −17.146 | 87.683 | 1.00 | 40.16 C |
| ATOM | 263 | NZ | LYS | A | 34 | −2.838 | −18.045 | 88.147 | 1.00 | 35.34 N |
| ATOM | 264 | N | ALA | A | 35 | 1.897 | −13.194 | 85.927 | 1.00 | 38.54 N |
| ATOM | 265 | CA | ALA | A | 35 | 2.980 | −13.427 | 84.992 | 1.00 | 33.10 C |
| ATOM | 266 | C | ALA | A | 35 | 3.663 | −14.765 | 85.216 | 1.00 | 33.93 C |
| ATOM | 267 | O | ALA | A | 35 | 3.647 | −15.297 | 86.327 | 1.00 | 41.78 O |
| ATOM | 268 | CB | ALA | A | 35 | 3.962 | −12.275 | 85.086 | 1.00 | 28.79 C |
| ATOM | 269 | N | PHE | A | 36 | 4.246 | −15.319 | 84.154 | 1.00 | 34.16 N |

TABLE 1-continued

| | | | | | | | | | | |
|---|---|---|---|---|---|---|---|---|---|---|
| ATOM | 270 | CA | PHE | A | 36 | 4.897 | −16.624 | 84.231 | 1.00 | 27.12 C |
| ATOM | 271 | C | PHE | A | 36 | 6.345 | −16.597 | 83.782 | 1.00 | 45.27 C |
| ATOM | 272 | O | PHE | A | 36 | 6.656 | −16.135 | 82.674 | 1.00 | 32.60 O |
| ATOM | 273 | CB | PHE | A | 36 | 4.125 | −17.637 | 83.389 | 1.00 | 27.03 C |
| ATOM | 274 | CG | PHE | A | 36 | 2.644 | −17.607 | 83.639 | 1.00 | 37.59 C |
| ATOM | 275 | CD1 | PHE | A | 36 | 1.888 | −16.484 | 83.282 | 1.00 | 20.81 C |
| ATOM | 276 | CD2 | PHE | A | 36 | 2.013 | −18.660 | 84.316 | 1.00 | 54.14 C |
| ATOM | 277 | CE1 | PHE | A | 36 | 0.517 | −16.398 | 83.604 | 1.00 | 42.06 C |
| ATOM | 278 | CE2 | PHE | A | 36 | 0.631 | −18.593 | 84.650 | 1.00 | 33.24 C |
| ATOM | 279 | CZ | PHE | A | 36 | −0.113 | −17.457 | 84.295 | 1.00 | 31.91 C |
| ATOM | 280 | N | LYS | A | 37 | 7.234 | −17.096 | 84.645 | 1.00 | 30.30 N |
| ATOM | 281 | CA | LYS | A | 37 | 8.646 | −17.119 | 84.325 | 1.00 | 26.03 C |
| ATOM | 282 | C | LYS | A | 37 | 8.922 | −18.448 | 83.621 | 1.00 | 37.81 C |
| ATOM | 283 | O | LYS | A | 37 | 9.019 | −19.499 | 84.261 | 1.00 | 42.79 O |
| ATOM | 284 | CB | LYS | A | 37 | 9.448 | −16.937 | 85.608 | 1.00 | 29.71 C |
| ATOM | 285 | CG | LYS | A | 37 | 10.966 | −17.005 | 85.453 | 1.00 | 51.08 C |
| ATOM | 286 | CD | LYS | A | 37 | 11.661 | −16.606 | 86.757 | 1.00 | 34.54 C |
| ATOM | 287 | CE | LYS | A | 37 | 13.090 | −17.064 | 86.776 | 1.00 | 56.11 C |
| ATOM | 288 | NZ | LYS | A | 37 | 13.761 | −16.774 | 88.086 | 1.00 | 73.27 N |
| ATOM | 289 | N | ILE | A | 38 | 9.036 | −18.411 | 82.297 | 1.00 | 25.61 N |
| ATOM | 290 | CA | ILE | A | 38 | 9.228 | −19.644 | 81.535 | 1.00 | 27.68 C |
| ATOM | 291 | C | ILE | A | 38 | 10.669 | −20.121 | 81.362 | 1.00 | 25.50 C |
| ATOM | 292 | O | ILE | A | 38 | 10.923 | −21.228 | 80.865 | 1.00 | 26.57 O |
| ATOM | 293 | CB | ILE | A | 38 | 8.568 | −19.507 | 80.134 | 1.00 | 39.90 C |
| ATOM | 294 | CG1 | ILE | A | 38 | 9.350 | −18.497 | 79.266 | 1.00 | 30.80 C |
| ATOM | 295 | CG2 | ILE | A | 38 | 7.115 | −19.016 | 80.302 | 1.00 | 32.77 C |
| ATOM | 296 | CD1 | ILE | A | 38 | 8.950 | −18.502 | 77.779 | 1.00 | 28.27 C |
| ATOM | 297 | N | HIS | A | 39 | 11.614 | −19.319 | 81.796 | 1.00 | 33.26 N |
| ATOM | 298 | CA | HIS | A | 39 | 13.034 | −19.590 | 81.658 | 1.00 | 21.86 C |
| ATOM | 299 | C | HIS | A | 39 | 13.754 | −18.528 | 82.420 | 1.00 | 27.03 C |
| ATOM | 300 | O | HIS | A | 39 | 13.235 | −17.414 | 82.579 | 1.00 | 28.90 O |
| ATOM | 301 | CB | HIS | A | 39 | 13.425 | −19.600 | 80.188 | 1.00 | 29.01 C |
| ATOM | 302 | CG | HIS | A | 39 | 14.788 | −20.271 | 79.943 | 1.00 | 34.78 C |
| ATOM | 303 | ND1 | HIS | A | 39 | 15.988 | −19.627 | 80.181 | 1.00 | 39.71 N |
| ATOM | 304 | CD2 | HIS | A | 39 | 15.109 | −21.513 | 79.511 | 1.00 | 32.90 C |
| ATOM | 305 | CE1 | HIS | A | 39 | 16.989 | −20.445 | 79.911 | 1.00 | 26.33 C |
| ATOM | 306 | NE2 | HIS | A | 39 | 16.484 | −21.597 | 79.503 | 1.00 | 37.26 N |
| ATOM | 307 | N | ASN | A | 40 | 14.960 | −18.821 | 82.892 | 1.00 | 34.09 N |
| ATOM | 308 | CA | ASN | A | 40 | 15.752 | −17.853 | 83.610 | 1.00 | 41.59 C |
| ATOM | 309 | C | ASN | A | 40 | 15.716 | −16.472 | 82.937 | 1.00 | 23.69 C |
| ATOM | 310 | O | ASN | A | 40 | 15.950 | −16.387 | 81.735 | 1.00 | 24.34 O |
| ATOM | 311 | CB | ASN | A | 40 | 17.209 | −18.357 | 83.733 | 1.00 | 37.49 C |
| ATOM | 312 | CG | ASN | A | 40 | 18.063 | −17.526 | 84.675 | 1.00 | 48.80 C |
| ATOM | 313 | OD1 | ASN | A | 40 | 19.291 | −17.500 | 84.555 | 1.00 | 70.33 O |
| ATOM | 314 | ND2 | ASN | A | 40 | 17.422 | −16.851 | 85.625 | 1.00 | 56.88 N |
| ATOM | 315 | N | LYS | A | 41 | 15.389 | −15.414 | 83.680 | 1.00 | 26.11 N |
| ATOM | 316 | CA | LYS | A | 41 | 15.396 | −14.035 | 83.096 | 1.00 | 37.13 C |
| ATOM | 317 | C | LYS | A | 41 | 14.311 | −13.744 | 82.042 | 1.00 | 29.19 C |
| ATOM | 318 | O | LYS | A | 41 | 14.258 | −12.625 | 81.544 | 1.00 | 27.78 O |
| ATOM | 319 | CB | LYS | A | 41 | 16.788 | −13.755 | 82.489 | 1.00 | 39.18 C |
| ATOM | 320 | CG | LYS | A | 41 | 17.929 | −13.754 | 83.482 | 1.00 | 30.28 C |
| ATOM | 321 | CD | LYS | A | 41 | 17.667 | −12.738 | 84.599 | 1.00 | 28.66 C |
| ATOM | 322 | CE | LYS | A | 41 | 18.961 | −12.346 | 85.296 | 1.00 | 49.73 C |
| ATOM | 323 | NZ | LYS | A | 41 | 19.691 | −13.534 | 85.817 | 1.00 | 41.82 N |
| ATOM | 324 | N | ILE | A | 42 | 13.452 | −14.700 | 81.702 | 1.00 | 24.32 N |
| ATOM | 325 | CA | ILE | A | 42 | 12.428 | −14.455 | 80.679 | 1.00 | 30.36 C |
| ATOM | 326 | C | ILE | A | 42 | 10.991 | −14.660 | 81.178 | 1.00 | 33.74 C |
| ATOM | 327 | O | ILE | A | 42 | 10.619 | −15.749 | 81.616 | 1.00 | 23.51 O |
| ATOM | 328 | CB | ILE | A | 42 | 12.704 | −15.377 | 79.473 | 1.00 | 31.54 C |
| ATOM | 329 | CG1 | ILE | A | 42 | 14.082 | −15.065 | 78.902 | 1.00 | 26.01 C |
| ATOM | 330 | CG2 | ILE | A | 42 | 11.620 | −15.230 | 78.411 | 1.00 | 23.47 C |
| ATOM | 331 | CD1 | ILE | A | 42 | 14.407 | −15.809 | 77.622 | 1.00 | 26.39 C |
| ATOM | 332 | N | TRP | A | 43 | 10.187 | −13.610 | 81.090 | 1.00 | 24.05 N |
| ATOM | 333 | CA | TRP | A | 43 | 8.798 | −13.690 | 81.575 | 1.00 | 24.13 C |
| ATOM | 334 | C | TRP | A | 43 | 7.741 | −13.443 | 80.476 | 1.00 | 23.71 C |
| ATOM | 335 | O | TRP | A | 43 | 7.988 | −12.765 | 79.472 | 1.00 | 34.53 O |
| ATOM | 336 | CB | TRP | A | 43 | 8.534 | −12.677 | 82.692 | 1.00 | 17.84 C |
| ATOM | 337 | CG | TRP | A | 43 | 9.266 | −12.898 | 83.972 | 1.00 | 37.45 C |
| ATOM | 338 | CD1 | TRP | A | 43 | 10.612 | −12.756 | 84.184 | 1.00 | 51.31 C |
| ATOM | 339 | CD2 | TRP | A | 43 | 8.707 | −13.301 | 85.231 | 1.00 | 43.55 C |
| ATOM | 340 | NE1 | TRP | A | 43 | 10.924 | −13.043 | 85.490 | 1.00 | 32.27 N |
| ATOM | 341 | CE2 | TRP | A | 43 | 9.774 | −13.383 | 86.157 | 1.00 | 56.09 C |
| ATOM | 342 | CE3 | TRP | A | 43 | 7.403 | −13.605 | 85.673 | 1.00 | 32.60 C |
| ATOM | 343 | CZ2 | TRP | A | 43 | 9.584 | −13.763 | 87.494 | 1.00 | 47.11 C |
| ATOM | 344 | CZ3 | TRP | A | 43 | 7.212 | −13.981 | 86.991 | 1.00 | 41.98 C |
| ATOM | 345 | CH2 | TRP | A | 43 | 8.299 | −14.055 | 87.893 | 1.00 | 38.85 C |
| ATOM | 346 | N | VAL | A | 44 | 6.557 | −14.013 | 80.674 | 1.00 | 32.98 N |
| ATOM | 347 | CA | VAL | A | 44 | 5.416 | −13.859 | 79.770 | 1.00 | 27.08 C |
| ATOM | 348 | C | VAL | A | 44 | 4.224 | −13.309 | 80.568 | 1.00 | 30.53 C |

TABLE 1-continued

| | | | | | | | | | | | |
|---|---|---|---|---|---|---|---|---|---|---|---|
| ATOM | 349 | O | VAL | A | 44 | 3.824 | −13.887 | 81.575 | 1.00 | 37.81 | O |
| ATOM | 350 | CB | VAL | A | 44 | 4.987 | −15.204 | 79.147 | 1.00 | 30.21 | C |
| ATOM | 351 | CG1 | VAL | A | 44 | 3.768 | −14.999 | 78.251 | 1.00 | 29.70 | C |
| ATOM | 352 | CG2 | VAL | A | 44 | 6.113 | −15.777 | 78.334 | 1.00 | 23.73 | C |
| ATOM | 353 | N | ILE | A | 45 | 3.688 | −12.178 | 80.134 | 1.00 | 29.45 | N |
| ATOM | 354 | CA | ILE | A | 45 | 2.549 | −11.543 | 80.786 | 1.00 | 26.10 | C |
| ATOM | 355 | C | ILE | A | 45 | 1.424 | −11.611 | 79.750 | 1.00 | 43.62 | C |
| ATOM | 356 | O | ILE | A | 45 | 1.381 | −10.797 | 78.815 | 1.00 | 30.33 | O |
| ATOM | 357 | CB | ILE | A | 45 | 2.837 | −10.056 | 81.103 | 1.00 | 26.50 | C |
| ATOM | 358 | CG1 | ILE | A | 45 | 4.075 | −9.945 | 82.004 | 1.00 | 23.40 | C |
| ATOM | 359 | CG2 | ILE | A | 45 | 1.614 | −9.411 | 81.748 | 1.00 | 24.64 | C |
| ATOM | 360 | CD1 | ILE | A | 45 | 4.381 | −8.516 | 82.456 | 1.00 | 26.81 | C |
| ATOM | 361 | N | PRO | A | 46 | 0.513 | −12.596 | 79.885 | 1.00 | 43.30 | N |
| ATOM | 362 | CA | PRO | A | 46 | −0.584 | −12.713 | 78.913 | 1.00 | 38.54 | C |
| ATOM | 363 | C | PRO | A | 46 | −1.702 | −11.718 | 79.196 | 1.00 | 29.57 | C |
| ATOM | 364 | O | PRO | A | 46 | −2.781 | −12.078 | 79.653 | 1.00 | 38.89 | O |
| ATOM | 365 | CB | PRO | A | 46 | −1.016 | −14.181 | 79.054 | 1.00 | 33.01 | C |
| ATOM | 366 | CG | PRO | A | 46 | −0.770 | −14.454 | 80.474 | 1.00 | 43.79 | C |
| ATOM | 367 | CD | PRO | A | 46 | 0.514 | −13.738 | 80.818 | 1.00 | 33.31 | C |
| ATOM | 368 | N | GLU | A | 47 | −1.404 | −10.460 | 78.917 | 1.00 | 27.41 | N |
| ATOM | 369 | CA | GLU | A | 47 | −2.308 | −9.347 | 79.116 | 1.00 | 35.78 | C |
| ATOM | 370 | C | GLU | A | 47 | −2.054 | −8.384 | 77.963 | 1.00 | 46.28 | C |
| ATOM | 371 | O | GLU | A | 47 | −1.008 | −8.470 | 77.305 | 1.00 | 48.25 | O |
| ATOM | 372 | CB | GLU | A | 47 | −1.967 | −8.607 | 80.410 | 1.00 | 36.19 | C |
| ATOM | 373 | CG | GLU | A | 47 | −2.141 | −9.405 | 81.684 | 1.00 | 64.81 | C |
| ATOM | 374 | CD | GLU | A | 47 | −3.590 | −9.558 | 82.099 | 1.00 | 57.26 | C |
| ATOM | 375 | OE1 | GLU | A | 47 | −4.340 | −8.561 | 82.004 | 1.00 | 44.78 | O |
| ATOM | 376 | OE2 | GLU | A | 47 | −3.965 | −10.668 | 82.539 | 1.00 | 57.00 | O |
| ATOM | 377 | N | ARG | A | 48 | −2.999 | −7.474 | 77.735 | 1.00 | 26.54 | N |
| ATOM | 378 | CA | ARG | A | 48 | −2.860 | −6.459 | 76.699 | 1.00 | 43.89 | C |
| ATOM | 379 | C | ARG | A | 48 | −1.942 | −5.380 | 77.304 | 1.00 | 34.35 | C |
| ATOM | 380 | O | ARG | A | 48 | −2.033 | −5.084 | 78.487 | 1.00 | 34.04 | O |
| ATOM | 381 | CB | ARG | A | 48 | −4.228 | −5.861 | 76.341 | 1.00 | 30.85 | C |
| ATOM | 382 | CG | ARG | A | 48 | −5.190 | −6.816 | 75.621 | 1.00 | 22.95 | C |
| ATOM | 383 | CD | ARG | A | 48 | −4.741 | −7.165 | 74.223 | 1.00 | 27.43 | C |
| ATOM | 384 | NE | ARG | A | 48 | −4.873 | −6.063 | 73.268 | 1.00 | 39.46 | N |
| ATOM | 385 | CZ | ARG | A | 48 | −6.026 | −5.660 | 72.729 | 1.00 | 48.43 | C |
| ATOM | 386 | NH1 | ARG | A | 48 | −7.173 | −6.260 | 73.046 | 1.00 | 36.99 | N |
| ATOM | 387 | NH2 | ARG | A | 48 | −6.032 | −4.669 | 71.855 | 1.00 | 31.60 | N |
| ATOM | 388 | N | ASP | A | 49 | −1.072 | −4.774 | 76.505 | 1.00 | 33.04 | N |
| ATOM | 389 | CA | ASP | A | 49 | −0.165 | −3.796 | 77.068 | 1.00 | 30.22 | C |
| ATOM | 390 | C | ASP | A | 49 | −0.675 | −2.365 | 77.159 | 1.00 | 45.85 | C |
| ATOM | 391 | O | ASP | A | 49 | −0.624 | −1.594 | 76.201 | 1.00 | 38.57 | O |
| ATOM | 392 | CB | ASP | A | 49 | 1.193 | −3.824 | 76.343 | 1.00 | 35.44 | C |
| ATOM | 393 | CG | ASP | A | 49 | 2.193 | −2.793 | 76.918 | 1.00 | 40.69 | C |
| ATOM | 394 | OD1 | ASP | A | 49 | 1.986 | −2.312 | 78.054 | 1.00 | 38.84 | O |
| ATOM | 395 | OD2 | ASP | A | 49 | 3.196 | −2.461 | 76.244 | 1.00 | 35.91 | O |
| ATOM | 396 | N | THR | A | 50 | −1.154 | −2.022 | 78.346 | 1.00 | 36.50 | N |
| ATOM | 397 | CA | THR | A | 50 | −1.645 | −0.689 | 78.627 | 1.00 | 48.93 | C |
| ATOM | 398 | C | THR | A | 50 | −0.783 | −0.159 | 79.783 | 1.00 | 46.35 | C |
| ATOM | 399 | O | THR | A | 50 | −1.180 | 0.752 | 80.496 | 1.00 | 56.69 | O |
| ATOM | 400 | CB | THR | A | 50 | −3.125 | −0.733 | 79.061 | 1.00 | 44.10 | C |
| ATOM | 401 | OG1 | THR | A | 50 | −3.267 | −1.670 | 80.130 | 1.00 | 45.90 | O |
| ATOM | 402 | CG2 | THR | A | 50 | −4.031 | −1.174 | 77.886 | 1.00 | 39.80 | C |
| ATOM | 403 | N | PHE | A | 51 | 0.408 | −0.733 | 79.933 | 1.00 | 45.47 | N |
| ATOM | 404 | CA | PHE | A | 51 | 1.344 | −0.379 | 81.008 | 1.00 | 58.08 | C |
| ATOM | 405 | C | PHE | A | 51 | 2.660 | 0.227 | 80.554 | 1.00 | 39.81 | C |
| ATOM | 406 | O | PHE | A | 51 | 3.162 | 1.164 | 81.153 | 1.00 | 54.65 | O |
| ATOM | 407 | CB | PHE | A | 51 | 1.687 | −1.619 | 81.843 | 1.00 | 41.93 | C |
| ATOM | 408 | CG | PHE | A | 51 | 0.536 | −2.536 | 82.052 | 1.00 | 43.77 | C |
| ATOM | 409 | CD1 | PHE | A | 51 | −0.583 | −2.115 | 82.749 | 1.00 | 50.80 | C |
| ATOM | 410 | CD2 | PHE | A | 51 | 0.562 | −3.823 | 81.544 | 1.00 | 49.18 | C |
| ATOM | 411 | CE1 | PHE | A | 51 | −1.666 | −2.967 | 82.941 | 1.00 | 45.75 | C |
| ATOM | 412 | CE2 | PHE | A | 51 | −0.521 | −4.685 | 81.733 | 1.00 | 48.44 | C |
| ATOM | 413 | CZ | PHE | A | 51 | −1.636 | −4.255 | 82.432 | 1.00 | 44.00 | C |
| ATOM | 414 | N | THR | A | 52 | 3.237 | −0.317 | 79.502 | 1.00 | 51.39 | N |
| ATOM | 415 | CA | THR | A | 52 | 4.520 | 0.188 | 79.047 | 1.00 | 54.59 | C |
| ATOM | 416 | C | THR | A | 52 | 4.541 | 1.637 | 78.580 | 1.00 | 61.95 | C |
| ATOM | 417 | O | THR | A | 52 | 5.588 | 2.279 | 78.594 | 1.00 | 62.13 | O |
| ATOM | 418 | CB | THR | A | 52 | 5.061 | −0.717 | 77.958 | 1.00 | 51.75 | C |
| ATOM | 419 | OG1 | THR | A | 52 | 5.417 | −1.969 | 78.553 | 1.00 | 66.44 | O |
| ATOM | 420 | CG2 | THR | A | 52 | 6.279 | −0.117 | 77.307 | 1.00 | 79.60 | C |
| ATOM | 421 | N | ASN | A | 53 | 3.387 | 2.162 | 78.194 | 1.00 | 53.03 | N |
| ATOM | 422 | CA | ASN | A | 53 | 3.302 | 3.529 | 77.703 | 1.00 | 48.07 | C |
| ATOM | 423 | C | ASN | A | 53 | 2.072 | 4.244 | 78.272 | 1.00 | 73.96 | C |
| ATOM | 424 | O | ASN | A | 53 | 0.941 | 3.783 | 78.087 | 1.00 | 68.82 | O |
| ATOM | 425 | CB | ASN | A | 53 | 3.230 | 3.509 | 76.179 | 1.00 | 46.69 | C |
| ATOM | 426 | CG | ASN | A | 53 | 3.273 | 4.888 | 75.576 | 1.00 | 62.81 | C |
| ATOM | 427 | OD1 | ASN | A | 53 | 3.208 | 5.890 | 76.286 | 1.00 | 60.61 | O |

TABLE 1-continued

| | | | | | | | | | | |
|---|---|---|---|---|---|---|---|---|---|---|
| ATOM | 428 | ND2 | ASN | A | 53 | 3.382 | 4.949 | 74.252 | 1.00 | 61.70 N |
| ATOM | 429 | N | PRO | A | 54 | 2.281 | 5.381 | 78.973 | 1.00 | 76.82 N |
| ATOM | 430 | CA | PRO | A | 54 | 1.206 | 6.175 | 79.579 | 1.00 | 75.69 C |
| ATOM | 431 | C | PRO | A | 54 | 0.263 | 6.770 | 78.535 | 1.00 | 70.32 C |
| ATOM | 432 | O | PRO | A | 54 | −0.874 | 7.111 | 78.839 | 1.00 | 66.10 O |
| ATOM | 433 | CB | PRO | A | 54 | 1.973 | 7.246 | 80.358 | 1.00 | 73.56 C |
| ATOM | 434 | CG | PRO | A | 54 | 3.183 | 7.466 | 79.503 | 1.00 | 57.44 C |
| ATOM | 435 | CD | PRO | A | 54 | 3.584 | 6.043 | 79.179 | 1.00 | 79.45 C |
| ATOM | 436 | N | GLU | A | 55 | 0.751 | 6.890 | 77.303 | 1.00 | 74.37 N |
| ATOM | 437 | CA | GLU | A | 55 | −0.045 | 7.425 | 76.203 | 1.00 | 80.05 C |
| ATOM | 438 | C | GLU | A | 55 | −0.915 | 6.323 | 75.589 | 1.00 | 74.99 C |
| ATOM | 439 | O | GLU | A | 55 | −1.563 | 6.528 | 74.560 | 1.00 | 75.03 O |
| ATOM | 440 | CB | GLU | A | 55 | 0.867 | 7.997 | 75.109 | 1.00 | 88.18 C |
| ATOM | 441 | CG | GLU | A | 55 | 1.719 | 9.189 | 75.504 | 1.00 | 79.22 C |
| ATOM | 442 | CD | GLU | A | 55 | 2.574 | 9.675 | 74.345 | 1.00 | 89.45 C |
| ATOM | 443 | OE1 | GLU | A | 55 | 3.414 | 8.889 | 73.850 | 1.00 | 84.15 O |
| ATOM | 444 | OE2 | GLU | A | 55 | 2.402 | 10.840 | 73.920 | 1.00 | 98.81 O |
| ATOM | 445 | N | GLU | A | 56 | −0.907 | 5.149 | 76.213 | 1.00 | 76.34 N |
| ATOM | 446 | CA | GLU | A | 56 | −1.689 | 4.022 | 75.728 | 1.00 | 63.79 C |
| ATOM | 447 | C | GLU | A | 56 | −2.246 | 3.259 | 76.913 | 1.00 | 64.58 C |
| ATOM | 448 | O | GLU | A | 56 | −2.055 | 2.054 | 77.042 | 1.00 | 69.70 O |
| ATOM | 449 | CB | GLU | A | 56 | −0.819 | 3.103 | 74.867 | 1.00 | 60.71 C |
| ATOM | 450 | CG | GLU | A | 56 | −0.213 | 3.802 | 73.657 | 1.00 | 73.91 C |
| ATOM | 451 | CD | GLU | A | 56 | 0.523 | 2.856 | 72.722 | 1.00 | 79.92 C |
| ATOM | 452 | OE1 | GLU | A | 56 | −0.110 | 1.903 | 72.220 | 1.00 | 86.08 O |
| ATOM | 453 | OE2 | GLU | A | 56 | 1.731 | 3.067 | 72.483 | 1.00 | 84.27 O |
| ATOM | 454 | N | GLY | A | 57 | −2.945 | 3.976 | 77.780 | 1.00 | 71.51 N |
| ATOM | 455 | CA | GLY | A | 57 | −3.521 | 3.356 | 78.957 | 1.00 | 70.85 C |
| ATOM | 456 | C | GLY | A | 57 | −4.801 | 2.578 | 78.720 | 1.00 | 74.18 C |
| ATOM | 457 | O | GLY | A | 57 | −5.257 | 1.866 | 79.621 | 1.00 | 66.47 O |
| ATOM | 458 | N | ASP | A | 58 | −5.386 | 2.705 | 77.528 | 1.00 | 65.37 N |
| ATOM | 459 | CA | ASP | A | 58 | −6.622 | 1.986 | 77.222 | 1.00 | 59.75 C |
| ATOM | 460 | C | ASP | A | 58 | −6.578 | 1.359 | 75.838 | 1.00 | 67.23 C |
| ATOM | 461 | O | ASP | A | 58 | −5.612 | 1.552 | 75.103 | 1.00 | 58.17 O |
| ATOM | 462 | CB | ASP | A | 58 | −7.824 | 2.918 | 77.332 | 1.00 | 62.20 C |
| ATOM | 463 | CG | ASP | A | 58 | −7.707 | 4.120 | 76.430 | 1.00 | 72.93 C |
| ATOM | 464 | OD1 | ASP | A | 58 | −7.677 | 3.926 | 75.189 | 1.00 | 75.47 O |
| ATOM | 465 | OD2 | ASP | A | 58 | −7.645 | 5.254 | 76.967 | 1.00 | 67.97 O |
| ATOM | 466 | N | LEU | A | 59 | −7.634 | 0.627 | 75.484 | 1.00 | 58.86 N |
| ATOM | 467 | CA | LEU | A | 59 | −7.698 | −0.062 | 74.198 | 1.00 | 44.90 C |
| ATOM | 468 | C | LEU | A | 59 | −8.692 | 0.552 | 73.221 | 1.00 | 55.68 C |
| ATOM | 469 | O | LEU | A | 59 | −9.169 | −0.098 | 72.282 | 1.00 | 45.55 O |
| ATOM | 470 | CB | LEU | A | 59 | −8.014 | −1.534 | 74.441 | 1.00 | 33.38 C |
| ATOM | 471 | CG | LEU | A | 59 | −7.027 | −2.133 | 75.453 | 1.00 | 35.86 C |
| ATOM | 472 | CD1 | LEU | A | 59 | −7.393 | −3.570 | 75.800 | 1.00 | 33.37 C |
| ATOM | 473 | CD2 | LEU | A | 59 | −5.617 | −2.055 | 74.859 | 1.00 | 32.93 C |
| ATOM | 474 | N | ASN | A | 60 | −8.983 | 1.826 | 73.444 | 1.00 | 64.18 N |
| ATOM | 475 | CA | ASN | A | 60 | −9.893 | 2.560 | 72.595 | 1.00 | 63.91 C |
| ATOM | 476 | C | ASN | A | 60 | −9.248 | 2.776 | 71.237 | 1.00 | 60.63 C |
| ATOM | 477 | O | ASN | A | 60 | −8.199 | 3.406 | 71.131 | 1.00 | 58.83 O |
| ATOM | 478 | CB | ASN | A | 60 | −10.228 | 3.897 | 73.242 | 1.00 | 63.05 C |
| ATOM | 479 | CG | ASN | A | 60 | −11.078 | 3.731 | 74.461 | 1.00 | 65.79 C |
| ATOM | 480 | OD1 | ASN | A | 60 | −12.126 | 3.087 | 74.410 | 1.00 | 70.87 O |
| ATOM | 481 | ND2 | ASN | A | 60 | −10.641 | 4.301 | 75.573 | 1.00 | 82.50 N |
| ATOM | 482 | N | PRO | A | 61 | −9.874 | 2.243 | 70.178 | 1.00 | 60.90 N |
| ATOM | 483 | CA | PRO | A | 61 | −9.401 | 2.349 | 68.800 | 1.00 | 64.24 C |
| ATOM | 484 | C | PRO | A | 61 | −9.660 | 3.737 | 68.225 | 1.00 | 50.16 C |
| ATOM | 485 | O | PRO | A | 61 | −10.668 | 4.357 | 68.521 | 1.00 | 51.42 O |
| ATOM | 486 | CB | PRO | A | 61 | −10.213 | 1.273 | 68.088 | 1.00 | 55.69 C |
| ATOM | 487 | CG | PRO | A | 61 | −11.529 | 1.406 | 68.752 | 1.00 | 53.59 C |
| ATOM | 488 | CD | PRO | A | 61 | −11.164 | 1.529 | 70.222 | 1.00 | 66.01 C |
| ATOM | 489 | N | PRO | A | 62 | −8.748 | 4.242 | 67.395 | 1.00 | 43.63 N |
| ATOM | 490 | CA | PRO | A | 62 | −8.956 | 5.572 | 66.809 | 1.00 | 56.39 C |
| ATOM | 491 | C | PRO | A | 62 | −10.132 | 5.564 | 65.832 | 1.00 | 32.92 C |
| ATOM | 492 | O | PRO | A | 62 | −10.588 | 4.501 | 65.417 | 1.00 | 47.88 O |
| ATOM | 493 | CB | PRO | A | 62 | −7.624 | 5.850 | 66.104 | 1.00 | 32.49 C |
| ATOM | 494 | CG | PRO | A | 62 | −7.212 | 4.489 | 65.658 | 1.00 | 59.60 C |
| ATOM | 495 | CD | PRO | A | 62 | −7.523 | 3.618 | 66.872 | 1.00 | 47.95 C |
| ATOM | 496 | N | PRO | A | 63 | −10.654 | 6.744 | 65.471 | 1.00 | 60.80 N |
| ATOM | 497 | CA | PRO | A | 63 | −11.782 | 6.759 | 64.521 | 1.00 | 48.03 C |
| ATOM | 498 | C | PRO | A | 63 | −11.334 | 6.035 | 63.250 | 1.00 | 62.32 C |
| ATOM | 499 | O | PRO | A | 63 | −10.127 | 6.000 | 62.952 | 1.00 | 59.93 O |
| ATOM | 500 | CB | PRO | A | 63 | −12.023 | 8.246 | 64.292 | 1.00 | 33.45 C |
| ATOM | 501 | CG | PRO | A | 63 | −11.626 | 8.854 | 65.610 | 1.00 | 55.88 C |
| ATOM | 502 | CD | PRO | A | 63 | −10.363 | 8.099 | 65.982 | 1.00 | 47.15 C |
| ATOM | 503 | N | GLU | A | 64 | −12.287 | 5.465 | 62.509 | 1.00 | 58.36 N |
| ATOM | 504 | CA | GLU | A | 64 | −11.970 | 4.704 | 61.300 | 1.00 | 53.39 C |
| ATOM | 505 | C | GLU | A | 64 | −11.143 | 5.464 | 60.284 | 1.00 | 53.45 C |
| ATOM | 506 | O | GLU | A | 64 | −10.194 | 4.921 | 59.712 | 1.00 | 43.74 O |

TABLE 1-continued

| | | | | | | | | | | |
|---|---|---|---|---|---|---|---|---|---|---|
| ATOM | 507 | CB | GLU | A | 64 | −13.248 | 4.192 | 60.628 | 1.00 | 54.74 C |
| ATOM | 508 | CG | GLU | A | 64 | −14.017 | 3.171 | 61.455 | 1.00 | 63.99 C |
| ATOM | 509 | CD | GLU | A | 64 | −14.957 | 2.331 | 60.607 | 1.00 | 78.77 C |
| ATOM | 510 | OE1 | GLU | A | 64 | −14.481 | 1.738 | 59.611 | 1.00 | 82.22 O |
| ATOM | 511 | OE2 | GLU | A | 64 | −16.165 | 2.256 | 60.934 | 1.00 | 77.24 O |
| ATOM | 512 | N | ALA | A | 65 | −11.495 | 6.723 | 60.061 | 1.00 | 55.03 N |
| ATOM | 513 | CA | ALA | A | 65 | −10.770 | 7.535 | 59.098 | 1.00 | 49.83 C |
| ATOM | 514 | C | ALA | A | 65 | −9.324 | 7.740 | 59.525 | 1.00 | 50.17 C |
| ATOM | 515 | O | ALA | A | 65 | −8.456 | 7.981 | 58.683 | 1.00 | 48.20 O |
| ATOM | 516 | CB | ALA | A | 65 | −11.452 | 8.869 | 58.932 | 1.00 | 57.13 C |
| ATOM | 517 | N | LYS | A | 66 | −9.051 | 7.621 | 60.822 | 1.00 | 38.23 N |
| ATOM | 518 | CA | LYS | A | 66 | −7.687 | 7.826 | 61.314 | 1.00 | 48.94 C |
| ATOM | 519 | C | LYS | A | 66 | −6.842 | 6.561 | 61.463 | 1.00 | 47.54 C |
| ATOM | 520 | O | LYS | A | 66 | −5.668 | 6.644 | 61.812 | 1.00 | 50.42 O |
| ATOM | 521 | CB | LYS | A | 66 | −7.726 | 8.551 | 62.669 | 1.00 | 60.92 C |
| ATOM | 522 | CG | LYS | A | 66 | −7.289 | 10.011 | 62.639 | 1.00 | 56.33 C |
| ATOM | 523 | CD | LYS | A | 66 | −8.170 | 10.866 | 61.742 | 1.00 | 58.25 C |
| ATOM | 524 | CE | LYS | A | 66 | −7.850 | 12.372 | 61.875 | 1.00 | 56.56 C |
| ATOM | 525 | NZ | LYS | A | 66 | −8.122 | 12.912 | 63.248 | 1.00 | 62.33 N |
| ATOM | 526 | N | GLN | A | 67 | −7.427 | 5.396 | 61.202 | 1.00 | 48.35 N |
| ATOM | 527 | CA | GLN | A | 67 | −6.706 | 4.131 | 61.351 | 1.00 | 26.18 C |
| ATOM | 528 | C | GLN | A | 67 | −5.771 | 3.756 | 60.203 | 1.00 | 30.53 C |
| ATOM | 529 | O | GLN | A | 67 | −6.138 | 3.821 | 59.045 | 1.00 | 42.94 O |
| ATOM | 530 | CB | GLN | A | 67 | −7.713 | 2.998 | 61.577 | 1.00 | 39.78 C |
| ATOM | 531 | CG | GLN | A | 67 | −8.619 | 3.206 | 62.806 | 1.00 | 38.22 C |
| ATOM | 532 | CD | GLN | A | 67 | −9.588 | 2.051 | 63.024 | 1.00 | 42.07 C |
| ATOM | 533 | OE1 | GLN | A | 67 | −9.559 | 1.054 | 62.303 | 1.00 | 44.67 O |
| ATOM | 534 | NE2 | GLN | A | 67 | −10.433 | 2.174 | 64.033 | 1.00 | 32.39 N |
| ATOM | 535 | N | VAL | A | 68 | −4.554 | 3.363 | 60.533 | 1.00 | 30.74 N |
| ATOM | 536 | CA | VAL | A | 68 | −3.580 | 2.945 | 59.529 | 1.00 | 41.90 C |
| ATOM | 537 | C | VAL | A | 68 | −4.176 | 1.770 | 58.754 | 1.00 | 31.55 C |
| ATOM | 538 | O | VAL | A | 68 | −4.824 | 0.919 | 59.334 | 1.00 | 40.45 O |
| ATOM | 539 | CB | VAL | A | 68 | −2.284 | 2.462 | 60.202 | 1.00 | 41.58 C |
| ATOM | 540 | CG1 | VAL | A | 68 | −1.374 | 1.829 | 59.174 | 1.00 | 61.70 C |
| ATOM | 541 | CG2 | VAL | A | 68 | −1.585 | 3.622 | 60.865 | 1.00 | 47.89 C |
| ATOM | 542 | N | PRO | A | 69 | −3.963 | 1.714 | 57.434 | 1.00 | 48.77 N |
| ATOM | 543 | CA | PRO | A | 69 | −4.504 | 0.613 | 56.612 | 1.00 | 42.95 C |
| ATOM | 544 | C | PRO | A | 69 | −4.137 | −0.764 | 57.175 | 1.00 | 51.17 C |
| ATOM | 545 | O | PRO | A | 69 | −4.973 | −1.663 | 57.249 | 1.00 | 38.61 O |
| ATOM | 546 | CB | PRO | A | 69 | −3.889 | 0.868 | 55.240 | 1.00 | 39.04 C |
| ATOM | 547 | CG | PRO | A | 69 | −3.803 | 2.373 | 55.200 | 1.00 | 53.46 C |
| ATOM | 548 | CD | PRO | A | 69 | −3.278 | 2.720 | 56.601 | 1.00 | 45.78 C |
| ATOM | 549 | N | VAL | A | 70 | −2.882 | −0.918 | 57.580 | 1.00 | 45.85 N |
| ATOM | 550 | CA | VAL | A | 70 | −2.407 | −2.170 | 58.163 | 1.00 | 41.03 C |
| ATOM | 551 | C | VAL | A | 70 | −2.480 | −2.081 | 59.691 | 1.00 | 30.06 C |
| ATOM | 552 | O | VAL | A | 70 | −1.492 | −1.779 | 60.350 | 1.00 | 39.45 O |
| ATOM | 553 | CB | VAL | A | 70 | −0.932 | −2.468 | 57.731 | 1.00 | 33.80 C |
| ATOM | 554 | CG1 | VAL | A | 70 | −0.402 | −3.677 | 58.467 | 1.00 | 32.86 C |
| ATOM | 555 | CG2 | VAL | A | 70 | −0.867 | −2.713 | 56.220 | 1.00 | 36.07 C |
| ATOM | 556 | N | SER | A | 71 | −3.658 | −2.338 | 60.241 | 1.00 | 34.56 N |
| ATOM | 557 | CA | SER | A | 71 | −3.884 | −2.306 | 61.683 | 1.00 | 31.51 C |
| ATOM | 558 | C | SER | A | 71 | −5.107 | −3.174 | 61.975 | 1.00 | 30.56 C |
| ATOM | 559 | O | SER | A | 71 | −5.879 | −3.469 | 61.068 | 1.00 | 43.78 O |
| ATOM | 560 | CB | SER | A | 71 | −4.190 | −0.878 | 62.129 | 1.00 | 32.96 C |
| ATOM | 561 | OG | SER | A | 71 | −5.408 | −0.419 | 61.543 | 1.00 | 31.35 O |
| ATOM | 562 | N | TYR | A | 72 | −5.289 | −3.581 | 63.226 | 1.00 | 36.09 N |
| ATOM | 563 | CA | TYR | A | 72 | −6.469 | −4.364 | 63.609 | 1.00 | 32.36 C |
| ATOM | 564 | C | TYR | A | 72 | −6.818 | −4.066 | 65.051 | 1.00 | 28.58 C |
| ATOM | 565 | O | TYR | A | 72 | −5.947 | −4.136 | 65.917 | 1.00 | 37.80 O |
| ATOM | 566 | CB | TYR | A | 72 | −6.239 | −5.868 | 63.449 | 1.00 | 27.59 C |
| ATOM | 567 | CG | TYR | A | 72 | −7.502 | −6.682 | 63.677 | 1.00 | 53.69 C |
| ATOM | 568 | CD1 | TYR | A | 72 | −8.516 | −6.709 | 62.721 | 1.00 | 38.72 C |
| ATOM | 569 | CD2 | TYR | A | 72 | −7.687 | −7.423 | 64.852 | 1.00 | 50.52 C |
| ATOM | 570 | CE1 | TYR | A | 72 | −9.670 | −7.447 | 62.917 | 1.00 | 37.21 C |
| ATOM | 571 | CE2 | TYR | A | 72 | −8.844 | −8.167 | 65.056 | 1.00 | 52.55 C |
| ATOM | 572 | CZ | TYR | A | 72 | −9.834 | −8.172 | 64.080 | 1.00 | 54.15 C |
| ATOM | 573 | OH | TYR | A | 72 | −10.998 | −8.887 | 64.267 | 1.00 | 51.19 O |
| ATOM | 574 | N | TYR | A | 73 | −8.079 | −3.725 | 65.300 | 1.00 | 30.32 N |
| ATOM | 575 | CA | TYR | A | 73 | −8.563 | −3.409 | 66.641 | 1.00 | 32.30 C |
| ATOM | 576 | C | TYR | A | 73 | −9.712 | −4.288 | 67.131 | 1.00 | 47.36 C |
| ATOM | 577 | O | TYR | A | 73 | −10.600 | −4.680 | 66.378 | 1.00 | 53.18 O |
| ATOM | 578 | CB | TYR | A | 73 | −9.026 | −1.959 | 66.735 | 1.00 | 39.41 C |
| ATOM | 579 | CG | TYR | A | 73 | −7.945 | −0.952 | 66.437 | 1.00 | 41.73 C |
| ATOM | 580 | CD1 | TYR | A | 73 | −7.627 | −0.616 | 65.116 | 1.00 | 42.75 C |
| ATOM | 581 | CD2 | TYR | A | 73 | −7.201 | −0.366 | 67.469 | 1.00 | 33.14 C |
| ATOM | 582 | CE1 | TYR | A | 73 | −6.594 | 0.274 | 64.829 | 1.00 | 44.92 C |
| ATOM | 583 | CE2 | TYR | A | 73 | −6.163 | 0.524 | 67.193 | 1.00 | 30.59 C |
| ATOM | 584 | CZ | TYR | A | 73 | −5.858 | 0.836 | 65.872 | 1.00 | 42.42 C |
| ATOM | 585 | OH | TYR | A | 73 | −4.775 | 1.644 | 65.577 | 1.00 | 36.43 O |

TABLE 1-continued

| | | | | | | | | | | |
|---|---|---|---|---|---|---|---|---|---|---|
| ATOM | 586 | N | ASP | A | 74 | −9.664 | −4.591 | 68.417 | 1.00 | 41.76 N |
| ATOM | 587 | CA | ASP | A | 74 | −10.666 | −5.379 | 69.100 | 1.00 | 33.82 C |
| ATOM | 588 | C | ASP | A | 74 | −10.288 | −5.302 | 70.564 | 1.00 | 36.65 C |
| ATOM | 589 | O | ASP | A | 74 | −9.451 | −6.052 | 71.049 | 1.00 | 39.17 O |
| ATOM | 590 | CB | ASP | A | 74 | −10.672 | −6.831 | 68.638 | 1.00 | 31.41 C |
| ATOM | 591 | CG | ASP | A | 74 | −11.665 | −7.690 | 69.451 | 1.00 | 58.01 C |
| ATOM | 592 | OD1 | ASP | A | 74 | −12.379 | −7.119 | 70.319 | 1.00 | 44.62 O |
| ATOM | 593 | OD2 | ASP | A | 74 | −11.722 | −8.926 | 69.239 | 1.00 | 37.46 O |
| ATOM | 594 | N | SER | A | 75 | −10.896 | −4.355 | 71.252 | 1.00 | 42.51 N |
| ATOM | 595 | CA | SER | A | 75 | −10.653 | −4.135 | 72.666 | 1.00 | 45.99 C |
| ATOM | 596 | C | SER | A | 75 | −10.857 | −5.405 | 73.486 | 1.00 | 49.16 C |
| ATOM | 597 | O | SER | A | 75 | −10.352 | −5.519 | 74.593 | 1.00 | 37.12 O |
| ATOM | 598 | CB | SER | A | 75 | −11.612 | −3.054 | 73.185 | 1.00 | 59.81 C |
| ATOM | 599 | OG | SER | A | 75 | −12.975 | −3.457 | 73.042 | 1.00 | 60.08 O |
| ATOM | 600 | N | THR | A | 76 | −11.585 | −6.361 | 72.917 | 1.00 | 57.79 N |
| ATOM | 601 | CA | THR | A | 76 | −11.921 | −7.615 | 73.590 | 1.00 | 49.91 C |
| ATOM | 602 | C | THR | A | 76 | −10.907 | −8.770 | 73.547 | 1.00 | 42.18 C |
| ATOM | 603 | O | THR | A | 76 | −10.967 | −9.679 | 74.381 | 1.00 | 37.21 O |
| ATOM | 604 | CB | THR | A | 76 | −13.294 | −8.107 | 73.054 | 1.00 | 53.64 C |
| ATOM | 605 | OG1 | THR | A | 76 | −14.322 | −7.265 | 73.593 | 1.00 | 59.29 O |
| ATOM | 606 | CG2 | THR | A | 76 | −13.575 | −9.542 | 73.443 | 1.00 | 63.82 C |
| ATOM | 607 | N | TYR | A | 77 | −9.990 | −8.763 | 72.584 | 1.00 | 29.26 N |
| ATOM | 608 | CA | TYR | A | 77 | −9.017 | −9.861 | 72.492 | 1.00 | 41.48 C |
| ATOM | 609 | C | TYR | A | 77 | −8.145 | −9.961 | 73.752 | 1.00 | 42.02 C |
| ATOM | 610 | O | TYR | A | 77 | −7.769 | −8.945 | 74.328 | 1.00 | 37.32 O |
| ATOM | 611 | CB | TYR | A | 77 | −8.141 | −9.670 | 71.265 | 1.00 | 41.83 C |
| ATOM | 612 | CG | TYR | A | 77 | −6.896 | −10.505 | 71.274 | 1.00 | 36.42 C |
| ATOM | 613 | CD1 | TYR | A | 77 | −6.961 | −11.903 | 71.207 | 1.00 | 34.47 C |
| ATOM | 614 | CD2 | TYR | A | 77 | −5.638 | −9.896 | 71.368 | 1.00 | 35.59 C |
| ATOM | 615 | CE1 | TYR | A | 77 | −5.806 | −12.675 | 71.232 | 1.00 | 26.16 C |
| ATOM | 616 | CE2 | TYR | A | 77 | −4.474 | −10.646 | 71.398 | 1.00 | 23.57 C |
| ATOM | 617 | CZ | TYR | A | 77 | −4.558 | −12.032 | 71.332 | 1.00 | 41.07 C |
| ATOM | 618 | OH | TYR | A | 77 | −3.386 | −12.744 | 71.389 | 1.00 | 34.58 O |
| ATOM | 619 | N | LEU | A | 78 | −7.861 | −11.186 | 74.189 | 1.00 | 39.55 N |
| ATOM | 620 | CA | LEU | A | 78 | −7.057 | −11.434 | 75.388 | 1.00 | 35.10 C |
| ATOM | 621 | C | LEU | A | 78 | −7.619 | −10.862 | 76.681 | 1.00 | 53.83 C |
| ATOM | 622 | O | LEU | A | 78 | −6.844 | −10.400 | 77.518 | 1.00 | 61.71 O |
| ATOM | 623 | CB | LEU | A | 78 | −5.634 | −10.880 | 75.237 | 1.00 | 42.47 C |
| ATOM | 624 | CG | LEU | A | 78 | −4.443 | −11.821 | 75.008 | 1.00 | 53.52 C |
| ATOM | 625 | CD1 | LEU | A | 78 | −3.163 | −11.027 | 75.233 | 1.00 | 46.05 C |
| ATOM | 626 | CD2 | LEU | A | 78 | −4.454 | −12.985 | 75.952 | 1.00 | 28.91 C |
| ATOM | 627 | N | SER | A | 79 | −8.939 | −10.863 | 76.870 | 1.00 | 64.71 N |
| ATOM | 628 | CA | SER | A | 79 | −9.475 | −10.334 | 78.130 | 1.00 | 57.49 C |
| ATOM | 629 | C | SER | A | 79 | −10.033 | −11.419 | 79.054 | 1.00 | 41.65 C |
| ATOM | 630 | O | SER | A | 79 | −10.365 | −11.135 | 80.200 | 1.00 | 53.46 O |
| ATOM | 631 | CB | SER | A | 79 | −10.537 | −9.250 | 77.889 | 1.00 | 37.67 C |
| ATOM | 632 | OG | SER | A | 79 | −11.662 | −9.755 | 77.211 | 1.00 | 36.13 O |
| ATOM | 633 | N | THR | A | 80 | −10.117 | −12.655 | 78.568 | 1.00 | 38.30 N |
| ATOM | 634 | CA | THR | A | 80 | −10.619 | −13.760 | 79.380 | 1.00 | 34.18 C |
| ATOM | 635 | C | THR | A | 80 | −9.522 | −14.779 | 79.710 | 1.00 | 51.76 C |
| ATOM | 636 | O | THR | A | 80 | −8.556 | −14.946 | 78.950 | 1.00 | 58.36 O |
| ATOM | 637 | CB | THR | A | 80 | −11.743 | −14.514 | 78.659 | 1.00 | 47.81 C |
| ATOM | 638 | OG1 | THR | A | 80 | −11.195 | −15.251 | 77.564 | 1.00 | 41.95 O |
| ATOM | 639 | CG2 | THR | A | 80 | −12.794 | −13.540 | 78.144 | 1.00 | 49.23 C |
| ATOM | 640 | N | ASP | A | 81 | −9.689 | −15.481 | 80.826 | 1.00 | 44.25 N |
| ATOM | 641 | CA | ASP | A | 81 | −8.713 | −16.473 | 81.261 | 1.00 | 53.01 C |
| ATOM | 642 | C | ASP | A | 81 | −8.439 | −17.522 | 80.210 | 1.00 | 45.32 C |
| ATOM | 643 | O | ASP | A | 81 | −7.316 | −18.019 | 80.094 | 1.00 | 48.37 O |
| ATOM | 644 | CB | ASP | A | 81 | −9.164 | −17.178 | 82.548 | 1.00 | 54.83 C |
| ATOM | 645 | CG | ASP | A | 81 | −9.248 | −16.233 | 83.737 | 1.00 | 65.57 C |
| ATOM | 646 | OD1 | ASP | A | 81 | −8.603 | −15.160 | 83.701 | 1.00 | 72.90 O |
| ATOM | 647 | OD2 | ASP | A | 81 | −9.951 | −16.563 | 84.718 | 1.00 | 69.22 O |
| ATOM | 648 | N | ASN | A | 82 | −9.455 | −17.861 | 79.434 | 1.00 | 38.93 N |
| ATOM | 649 | CA | ASN | A | 82 | −9.271 | −18.877 | 78.416 | 1.00 | 44.55 C |
| ATOM | 650 | C | ASN | A | 82 | −8.361 | −18.399 | 77.291 | 1.00 | 46.16 C |
| ATOM | 651 | O | ASN | A | 82 | −7.580 | −19.183 | 76.746 | 1.00 | 34.88 O |
| ATOM | 652 | CB | ASN | A | 82 | −10.622 | −19.324 | 77.883 | 1.00 | 36.55 C |
| ATOM | 653 | CG | ASN | A | 82 | −11.428 | −20.054 | 78.943 | 1.00 | 73.56 C |
| ATOM | 654 | OD1 | ASN | A | 82 | −11.216 | −21.249 | 79.197 | 1.00 | 64.18 O |
| ATOM | 655 | ND2 | ASN | A | 82 | −12.332 | −19.325 | 79.599 | 1.00 | 60.50 N |
| ATOM | 656 | N | GLU | A | 83 | −8.474 | −17.121 | 76.944 | 1.00 | 35.41 N |
| ATOM | 657 | CA | GLU | A | 83 | −7.627 | −16.563 | 75.904 | 1.00 | 40.85 C |
| ATOM | 658 | C | GLU | A | 83 | −6.192 | −16.488 | 76.443 | 1.00 | 20.95 C |
| ATOM | 659 | O | GLU | A | 83 | −5.260 | −16.906 | 75.763 | 1.00 | 44.32 O |
| ATOM | 660 | CB | GLU | A | 83 | −8.084 | −15.157 | 75.531 | 1.00 | 40.04 C |
| ATOM | 661 | CG | GLU | A | 83 | −9.413 | −15.046 | 74.825 | 1.00 | 45.78 C |
| ATOM | 662 | CD | GLU | A | 83 | −9.766 | −13.587 | 74.574 | 1.00 | 42.93 C |
| ATOM | 663 | OE1 | GLU | A | 83 | −10.175 | −12.880 | 75.531 | 1.00 | 45.17 O |
| ATOM | 664 | OE2 | GLU | A | 83 | −9.602 | −13.144 | 73.414 | 1.00 | 62.21 O |

TABLE 1-continued

| | | | | | | | | | | | |
|---|---|---|---|---|---|---|---|---|---|---|---|
| ATOM | 665 | N | LYS | A | 84 | −6.038 | −15.962 | 77.665 | 1.00 | 32.63 | N |
| ATOM | 666 | CA | LYS | A | 84 | −4.727 | −15.813 | 78.314 | 1.00 | 26.50 | C |
| ATOM | 667 | C | LYS | A | 84 | −4.001 | −17.145 | 78.376 | 1.00 | 42.18 | C |
| ATOM | 668 | O | LYS | A | 84 | −2.794 | −17.231 | 78.107 | 1.00 | 32.26 | O |
| ATOM | 669 | CB | LYS | A | 84 | −4.878 | −15.220 | 79.712 | 1.00 | 23.97 | C |
| ATOM | 670 | CG | LYS | A | 84 | −5.478 | −13.835 | 79.664 | 1.00 | 23.75 | C |
| ATOM | 671 | CD | LYS | A | 84 | −5.661 | −13.177 | 81.002 | 1.00 | 26.32 | C |
| ATOM | 672 | CE | LYS | A | 84 | −6.237 | −11.785 | 80.744 | 1.00 | 54.26 | C |
| ATOM | 673 | NZ | LYS | A | 84 | −6.597 | −10.996 | 81.951 | 1.00 | 59.91 | N |
| ATOM | 674 | N | ASP | A | 85 | −4.748 | −18.195 | 78.677 | 1.00 | 30.48 | N |
| ATOM | 675 | CA | ASP | A | 85 | −4.159 | −19.513 | 78.735 | 1.00 | 29.25 | C |
| ATOM | 676 | C | ASP | A | 85 | −3.700 | −19.976 | 77.372 | 1.00 | 30.40 | C |
| ATOM | 677 | O | ASP | A | 85 | −2.719 | −20.704 | 77.251 | 1.00 | 41.81 | O |
| ATOM | 678 | CB | ASP | A | 85 | −5.151 | −20.532 | 79.271 | 1.00 | 30.79 | C |
| ATOM | 679 | CG | ASP | A | 85 | −4.517 | −21.887 | 79.453 | 1.00 | 35.14 | C |
| ATOM | 680 | OD1 | ASP | A | 85 | −3.602 | −22.006 | 80.306 | 1.00 | 54.46 | O |
| ATOM | 681 | OD2 | ASP | A | 85 | −4.908 | −22.823 | 78.733 | 1.00 | 45.39 | O |
| ATOM | 682 | N | ASN | A | 86 | −4.428 | −19.587 | 76.334 | 1.00 | 37.38 | N |
| ATOM | 683 | CA | ASN | A | 86 | −4.034 | −20.006 | 74.996 | 1.00 | 41.95 | C |
| ATOM | 684 | C | ASN | A | 86 | −2.844 | −19.128 | 74.522 | 1.00 | 20.96 | C |
| ATOM | 685 | O | ASN | A | 86 | −1.972 | −19.573 | 73.779 | 1.00 | 29.50 | O |
| ATOM | 686 | CB | ASN | A | 86 | −5.259 | −19.933 | 74.068 | 1.00 | 31.63 | C |
| ATOM | 687 | CG | ASN | A | 86 | −5.004 | −20.544 | 72.721 | 1.00 | 42.73 | C |
| ATOM | 688 | OD1 | ASN | A | 86 | −4.792 | −19.822 | 71.747 | 1.00 | 51.61 | O |
| ATOM | 689 | ND2 | ASN | A | 86 | −5.013 | −21.885 | 72.646 | 1.00 | 31.51 | N |
| ATOM | 690 | N | TYR | A | 87 | −2.812 | −17.895 | 74.998 | 1.00 | 26.35 | N |
| ATOM | 691 | CA | TYR | A | 87 | −1.730 | −16.961 | 74.684 | 1.00 | 27.39 | C |
| ATOM | 692 | C | TYR | A | 87 | −0.419 | −17.541 | 75.227 | 1.00 | 31.52 | C |
| ATOM | 693 | O | TYR | A | 87 | 0.570 | −17.711 | 74.499 | 1.00 | 35.34 | O |
| ATOM | 694 | CB | TYR | A | 87 | −2.019 | −15.617 | 75.356 | 1.00 | 26.91 | C |
| ATOM | 695 | CG | TYR | A | 87 | −0.969 | −14.569 | 75.088 | 1.00 | 35.92 | C |
| ATOM | 696 | CD1 | TYR | A | 87 | −1.005 | −13.789 | 73.923 | 1.00 | 29.53 | C |
| ATOM | 697 | CD2 | TYR | A | 87 | 0.110 | −14.404 | 75.968 | 1.00 | 35.25 | C |
| ATOM | 698 | CE1 | TYR | A | 87 | 0.015 | −12.862 | 73.637 | 1.00 | 32.04 | C |
| ATOM | 699 | CE2 | TYR | A | 87 | 1.133 | −13.495 | 75.696 | 1.00 | 42.23 | C |
| ATOM | 700 | CZ | TYR | A | 87 | 1.079 | −12.722 | 74.536 | 1.00 | 39.56 | C |
| ATOM | 701 | OH | TYR | A | 87 | 2.052 | −11.784 | 74.338 | 1.00 | 32.40 | O |
| ATOM | 702 | N | LEU | A | 88 | −0.439 | −17.862 | 76.521 | 1.00 | 39.01 | N |
| ATOM | 703 | CA | LEU | A | 88 | 0.700 | −18.429 | 77.222 | 1.00 | 29.15 | C |
| ATOM | 704 | C | LEU | A | 88 | 1.234 | −19.680 | 76.536 | 1.00 | 31.77 | C |
| ATOM | 705 | O | LEU | A | 88 | 2.433 | −19.782 | 76.277 | 1.00 | 31.17 | O |
| ATOM | 706 | CB | LEU | A | 88 | 0.300 | −18.728 | 78.672 | 1.00 | 41.13 | C |
| ATOM | 707 | CG | LEU | A | 88 | 1.328 | −19.148 | 79.730 | 1.00 | 47.42 | C |
| ATOM | 708 | CD1 | LEU | A | 88 | 2.553 | −18.209 | 79.775 | 1.00 | 21.34 | C |
| ATOM | 709 | CD2 | LEU | A | 88 | 0.600 | −19.158 | 81.064 | 1.00 | 42.42 | C |
| ATOM | 710 | N | LYS | A | 89 | 0.351 | −20.625 | 76.221 | 1.00 | 27.49 | N |
| ATOM | 711 | CA | LYS | A | 89 | 0.798 | −21.852 | 75.557 | 1.00 | 27.93 | C |
| ATOM | 712 | C | LYS | A | 89 | 1.243 | −21.541 | 74.131 | 1.00 | 21.97 | C |
| ATOM | 713 | O | LYS | A | 89 | 2.107 | −22.210 | 73.579 | 1.00 | 38.44 | O |
| ATOM | 714 | CB | LYS | A | 89 | −0.324 | −22.907 | 75.535 | 1.00 | 39.42 | C |
| ATOM | 715 | CG | LYS | A | 89 | −0.747 | −23.418 | 76.924 | 1.00 | 53.94 | C |
| ATOM | 716 | CD | LYS | A | 89 | −1.882 | −24.450 | 76.811 | 1.00 | 67.52 | C |
| ATOM | 717 | CE | LYS | A | 89 | −2.183 | −25.158 | 78.126 | 1.00 | 56.18 | C |
| ATOM | 718 | NZ | LYS | A | 89 | −2.684 | −24.225 | 79.169 | 1.00 | 55.01 | N |
| ATOM | 719 | N | GLY | A | 90 | 0.630 | −20.542 | 73.515 | 1.00 | 27.37 | N |
| ATOM | 720 | CA | GLY | A | 90 | 1.058 | −20.204 | 72.174 | 1.00 | 29.41 | C |
| ATOM | 721 | C | GLY | A | 90 | 2.493 | −19.685 | 72.197 | 1.00 | 25.63 | C |
| ATOM | 722 | O | GLY | A | 90 | 3.325 | −20.157 | 71.451 | 1.00 | 23.29 | O |
| ATOM | 723 | N | VAL | A | 91 | 2.783 | −18.727 | 73.075 | 1.00 | 29.48 | N |
| ATOM | 724 | CA | VAL | A | 91 | 4.119 | −18.163 | 73.152 | 1.00 | 26.05 | C |
| ATOM | 725 | C | VAL | A | 91 | 5.176 | −19.209 | 73.500 | 1.00 | 39.92 | C |
| ATOM | 726 | O | VAL | A | 91 | 6.266 | −19.252 | 72.911 | 1.00 | 34.97 | O |
| ATOM | 727 | CB | VAL | A | 91 | 4.144 | −17.032 | 74.166 | 1.00 | 30.44 | C |
| ATOM | 728 | CG1 | VAL | A | 91 | 5.609 | −16.528 | 74.398 | 1.00 | 28.68 | C |
| ATOM | 729 | CG2 | VAL | A | 91 | 3.258 | −15.931 | 73.673 | 1.00 | 15.47 | C |
| ATOM | 730 | N | THR | A | 92 | 4.839 | −20.060 | 74.457 | 1.00 | 34.71 | N |
| ATOM | 731 | CA | THR | A | 92 | 5.730 | −21.115 | 74.895 | 1.00 | 22.98 | C |
| ATOM | 732 | C | THR | A | 92 | 6.072 | −22.048 | 73.749 | 1.00 | 24.80 | C |
| ATOM | 733 | O | THR | A | 92 | 7.226 | −22.437 | 73.568 | 1.00 | 31.57 | O |
| ATOM | 734 | CB | THR | A | 92 | 5.092 | −21.906 | 76.032 | 1.00 | 44.80 | C |
| ATOM | 735 | OG1 | THR | A | 92 | 5.058 | −21.096 | 77.217 | 1.00 | 31.65 | O |
| ATOM | 736 | CG2 | THR | A | 92 | 5.875 | −23.173 | 76.297 | 1.00 | 51.08 | C |
| ATOM | 737 | N | LYS | A | 93 | 5.072 | −22.407 | 72.961 | 1.00 | 27.94 | N |
| ATOM | 738 | CA | LYS | A | 93 | 5.325 | −23.274 | 71.839 | 1.00 | 27.02 | C |
| ATOM | 739 | C | LYS | A | 93 | 6.200 | −22.576 | 70.799 | 1.00 | 23.24 | C |
| ATOM | 740 | O | LYS | A | 93 | 7.008 | −23.207 | 70.130 | 1.00 | 25.34 | O |
| ATOM | 741 | CB | LYS | A | 93 | 4.016 | −23.680 | 71.205 | 1.00 | 26.90 | C |
| ATOM | 742 | CG | LYS | A | 93 | 4.126 | −24.869 | 70.283 | 1.00 | 33.89 | C |
| ATOM | 743 | CD | LYS | A | 93 | 2.718 | −25.218 | 69.807 | 1.00 | 41.68 | C |

TABLE 1-continued

| | | | | | | | | | | |
|---|---|---|---|---|---|---|---|---|---|---|
| ATOM | 744 | CE | LYS | A | 93 | 2.647 | −26.601 | 69.271 | 1.00 | 36.01 C |
| ATOM | 745 | NZ | LYS | A | 93 | 1.255 | −26.942 | 68.982 | 1.00 | 30.44 N |
| ATOM | 746 | N | LEU | A | 94 | 6.069 | −21.266 | 70.639 | 1.00 | 33.24 N |
| ATOM | 747 | CA | LEU | A | 94 | 6.931 | −20.629 | 69.626 | 1.00 | 38.84 C |
| ATOM | 748 | C | LEU | A | 94 | 8.380 | −20.603 | 70.136 | 1.00 | 21.17 C |
| ATOM | 749 | O | LEU | A | 94 | 9.325 | −20.793 | 69.377 | 1.00 | 29.62 O |
| ATOM | 750 | CB | LEU | A | 94 | 6.411 | −19.224 | 69.253 | 1.00 | 25.23 C |
| ATOM | 751 | CG | LEU | A | 94 | 5.036 | −19.186 | 68.566 | 1.00 | 27.77 C |
| ATOM | 752 | CD1 | LEU | A | 94 | 4.560 | −17.742 | 68.419 | 1.00 | 31.21 C |
| ATOM | 753 | CD2 | LEU | A | 94 | 5.096 | −19.858 | 67.223 | 1.00 | 28.58 C |
| ATOM | 754 | N | PHE | A | 95 | 8.553 | −20.406 | 71.433 | 1.00 | 20.92 N |
| ATOM | 755 | CA | PHE | A | 95 | 9.903 | −20.410 | 71.988 | 1.00 | 28.31 C |
| ATOM | 756 | C | PHE | A | 95 | 10.549 | −21.767 | 71.737 | 1.00 | 41.25 C |
| ATOM | 757 | O | PHE | A | 95 | 11.721 | −21.856 | 71.357 | 1.00 | 38.68 O |
| ATOM | 758 | CB | PHE | A | 95 | 9.868 | −20.104 | 73.487 | 1.00 | 36.34 C |
| ATOM | 759 | CG | PHE | A | 95 | 10.101 | −18.664 | 73.808 | 1.00 | 25.05 C |
| ATOM | 760 | CD1 | PHE | A | 95 | 11.391 | −18.152 | 73.815 | 1.00 | 29.43 C |
| ATOM | 761 | CD2 | PHE | A | 95 | 9.033 | −17.816 | 74.092 | 1.00 | 28.90 C |
| ATOM | 762 | CE1 | PHE | A | 95 | 11.632 | −16.821 | 74.103 | 1.00 | 19.70 C |
| ATOM | 763 | CE2 | PHE | A | 95 | 9.245 | −16.477 | 74.380 | 1.00 | 23.48 C |
| ATOM | 764 | CZ | PHE | A | 95 | 10.564 | −15.970 | 74.386 | 1.00 | 31.85 C |
| ATOM | 765 | N | GLU | A | 96 | 9.777 | −22.830 | 71.926 | 1.00 | 30.26 N |
| ATOM | 766 | CA | GLU | A | 96 | 10.309 | −24.170 | 71.702 | 1.00 | 28.55 C |
| ATOM | 767 | C | GLU | A | 96 | 10.657 | −24.400 | 70.237 | 1.00 | 27.64 C |
| ATOM | 768 | O | GLU | A | 96 | 11.645 | −25.079 | 69.922 | 1.00 | 29.61 O |
| ATOM | 769 | CB | GLU | A | 96 | 9.296 | −25.218 | 72.151 | 1.00 | 44.19 C |
| ATOM | 770 | CG | GLU | A | 96 | 8.940 | −25.135 | 73.628 | 1.00 | 37.86 C |
| ATOM | 771 | CD | GLU | A | 96 | 10.151 | −25.301 | 74.555 | 1.00 | 65.15 C |
| ATOM | 772 | OE1 | GLU | A | 96 | 11.243 | −25.744 | 74.094 | 1.00 | 52.22 O |
| ATOM | 773 | OE2 | GLU | A | 96 | 9.987 | −24.998 | 75.758 | 1.00 | 49.28 O |
| ATOM | 774 | N | ARG | A | 97 | 9.850 | −23.835 | 69.339 | 1.00 | 30.20 N |
| ATOM | 775 | CA | ARG | A | 97 | 10.113 | −23.985 | 67.911 | 1.00 | 31.23 C |
| ATOM | 776 | C | ARG | A | 97 | 11.420 | −23.249 | 67.584 | 1.00 | 30.99 C |
| ATOM | 777 | O | ARG | A | 97 | 12.254 | −23.756 | 66.844 | 1.00 | 36.37 O |
| ATOM | 778 | CB | ARG | A | 97 | 8.955 | −23.409 | 67.090 | 1.00 | 27.63 C |
| ATOM | 779 | CG | ARG | A | 97 | 9.116 | −23.558 | 65.576 | 1.00 | 21.53 C |
| ATOM | 780 | CD | ARG | A | 97 | 7.723 | −23.505 | 64.938 | 1.00 | 39.81 C |
| ATOM | 781 | NE | ARG | A | 97 | 7.735 | −23.261 | 63.495 | 1.00 | 33.07 N |
| ATOM | 782 | CZ | ARG | A | 97 | 8.329 | −24.054 | 62.614 | 1.00 | 30.90 C |
| ATOM | 783 | NH1 | ARG | A | 97 | 8.955 | −25.147 | 63.028 | 1.00 | 36.23 N |
| ATOM | 784 | NH2 | ARG | A | 97 | 8.316 | −23.746 | 61.329 | 1.00 | 30.30 N |
| ATOM | 785 | N | ILE | A | 98 | 11.591 | −22.050 | 68.138 | 1.00 | 28.40 N |
| ATOM | 786 | CA | ILE | A | 98 | 12.810 | −21.284 | 67.923 | 1.00 | 22.56 C |
| ATOM | 787 | C | ILE | A | 98 | 13.985 | −22.048 | 68.543 | 1.00 | 31.84 C |
| ATOM | 788 | O | ILE | A | 98 | 15.008 | −22.296 | 67.888 | 1.00 | 31.91 O |
| ATOM | 789 | CB | ILE | A | 98 | 12.688 | −19.873 | 68.568 | 1.00 | 32.23 C |
| ATOM | 790 | CG1 | ILE | A | 98 | 11.729 | −19.034 | 67.724 | 1.00 | 25.30 C |
| ATOM | 791 | CG2 | ILE | A | 98 | 14.084 | −19.194 | 68.688 | 1.00 | 25.64 C |
| ATOM | 792 | CD1 | ILE | A | 98 | 11.054 | −17.958 | 68.443 | 1.00 | 29.64 C |
| ATOM | 793 | N | TYR | A | 99 | 13.825 | −22.435 | 69.803 | 1.00 | 34.71 N |
| ATOM | 794 | CA | TYR | A | 99 | 14.871 | −23.160 | 70.529 | 1.00 | 37.48 C |
| ATOM | 795 | C | TYR | A | 99 | 15.270 | −24.465 | 69.859 | 1.00 | 48.27 C |
| ATOM | 796 | O | TYR | A | 99 | 16.398 | −24.931 | 70.030 | 1.00 | 35.43 O |
| ATOM | 797 | CB | TYR | A | 99 | 14.408 | −23.482 | 71.937 | 1.00 | 35.65 C |
| ATOM | 798 | CG | TYR | A | 99 | 15.483 | −24.087 | 72.809 | 1.00 | 43.02 C |
| ATOM | 799 | CD1 | TYR | A | 99 | 16.536 | −23.312 | 73.277 | 1.00 | 44.51 C |
| ATOM | 800 | CD2 | TYR | A | 99 | 15.438 | −25.425 | 73.181 | 1.00 | 53.18 C |
| ATOM | 801 | CE1 | TYR | A | 99 | 17.511 | −23.844 | 74.092 | 1.00 | 54.14 C |
| ATOM | 802 | CE2 | TYR | A | 99 | 16.424 | −25.978 | 74.002 | 1.00 | 56.74 C |
| ATOM | 803 | CZ | TYR | A | 99 | 17.454 | −25.178 | 74.452 | 1.00 | 57.16 C |
| ATOM | 804 | OH | TYR | A | 99 | 18.451 | −25.706 | 75.245 | 1.00 | 75.88 O |
| ATOM | 805 | N | SER | A | 100 | 14.348 | −25.039 | 69.089 | 1.00 | 36.53 N |
| ATOM | 806 | CA | SER | A | 100 | 14.603 | −26.309 | 68.417 | 1.00 | 40.19 C |
| ATOM | 807 | C | SER | A | 100 | 15.550 | −26.238 | 67.234 | 1.00 | 42.56 C |
| ATOM | 808 | O | SER | A | 100 | 15.890 | −27.270 | 66.677 | 1.00 | 39.84 O |
| ATOM | 809 | CB | SER | A | 100 | 13.284 | −26.956 | 67.961 | 1.00 | 40.26 C |
| ATOM | 810 | OG | SER | A | 100 | 12.848 | −26.419 | 66.723 | 1.00 | 50.88 O |
| ATOM | 811 | N | THR | A | 101 | 15.943 | −25.036 | 66.817 | 1.00 | 33.60 N |
| ATOM | 812 | CA | THR | A | 101 | 16.887 | −24.907 | 65.704 | 1.00 | 27.62 C |
| ATOM | 813 | C | THR | A | 101 | 18.225 | −24.546 | 66.330 | 1.00 | 27.05 C |
| ATOM | 814 | O | THR | A | 101 | 18.256 | −23.997 | 67.433 | 1.00 | 33.64 O |
| ATOM | 815 | CB | THR | A | 101 | 16.466 | −23.777 | 64.708 | 1.00 | 39.06 C |
| ATOM | 816 | OG1 | THR | A | 101 | 16.402 | −22.513 | 65.398 | 1.00 | 37.73 O |
| ATOM | 817 | CG2 | THR | A | 101 | 15.094 | −24.085 | 64.071 | 1.00 | 30.86 C |
| ATOM | 818 | N | ASP | A | 102 | 19.330 | −24.848 | 65.654 | 1.00 | 36.17 N |
| ATOM | 819 | CA | ASP | A | 102 | 20.658 | −24.490 | 66.182 | 1.00 | 25.04 C |
| ATOM | 820 | C | ASP | A | 102 | 20.770 | −22.960 | 66.325 | 1.00 | 46.04 C |
| ATOM | 821 | O | ASP | A | 102 | 21.341 | −22.453 | 67.286 | 1.00 | 39.05 O |
| ATOM | 822 | CB | ASP | A | 102 | 21.752 | −24.982 | 65.239 | 1.00 | 30.53 C |

TABLE 1-continued

| | | | | | | | | | | |
|---|---|---|---|---|---|---|---|---|---|---|
| ATOM | 823 | CG | ASP | A | 102 | 21.885 | −26.503 | 65.236 | 1.00 | 62.81 C |
| ATOM | 824 | OD1 | ASP | A | 102 | 22.180 | −27.077 | 66.296 | 1.00 | 46.52 O |
| ATOM | 825 | OD2 | ASP | A | 102 | 21.694 | −27.135 | 64.171 | 1.00 | 83.82 O |
| ATOM | 826 | N | LEU | A | 103 | 20.208 | −22.229 | 65.362 | 1.00 | 37.62 N |
| ATOM | 827 | CA | LEU | A | 103 | 20.258 | −20.773 | 65.367 | 1.00 | 39.54 C |
| ATOM | 828 | C | LEU | A | 103 | 19.481 | −20.156 | 66.545 | 1.00 | 30.73 C |
| ATOM | 829 | O | LEU | A | 103 | 19.975 | −19.268 | 67.232 | 1.00 | 29.16 O |
| ATOM | 830 | CB | LEU | A | 103 | 19.690 | −20.248 | 64.041 | 1.00 | 31.51 C |
| ATOM | 831 | CG | LEU | A | 103 | 19.818 | −18.746 | 63.845 | 1.00 | 34.27 C |
| ATOM | 832 | CD1 | LEU | A | 103 | 21.297 | −18.427 | 63.596 | 1.00 | 21.66 C |
| ATOM | 833 | CD2 | LEU | A | 103 | 18.926 | −18.283 | 62.663 | 1.00 | 25.33 C |
| ATOM | 834 | N | GLY | A | 104 | 18.271 | −20.658 | 66.770 | 1.00 | 36.50 N |
| ATOM | 835 | CA | GLY | A | 104 | 17.426 | −20.164 | 67.848 | 1.00 | 29.10 C |
| ATOM | 836 | C | GLY | A | 104 | 17.944 | −20.471 | 69.249 | 1.00 | 29.12 C |
| ATOM | 837 | O | GLY | A | 104 | 17.756 | −19.677 | 70.178 | 1.00 | 25.14 O |
| ATOM | 838 | N | ARG | A | 105 | 18.596 | −21.619 | 69.403 | 1.00 | 35.23 N |
| ATOM | 839 | CA | ARG | A | 105 | 19.163 | −22.030 | 70.688 | 1.00 | 36.89 C |
| ATOM | 840 | C | ARG | A | 105 | 20.282 | −21.048 | 71.044 | 1.00 | 33.66 C |
| ATOM | 841 | O | ARG | A | 105 | 20.419 | −20.630 | 72.190 | 1.00 | 39.90 O |
| ATOM | 842 | CB | ARG | A | 105 | 19.716 | −23.462 | 70.579 | 1.00 | 38.06 C |
| ATOM | 843 | CG | ARG | A | 105 | 20.394 | −23.993 | 71.845 | 1.00 | 49.12 C |
| ATOM | 844 | CD | ARG | A | 105 | 21.028 | −25.377 | 71.615 | 1.00 | 44.24 C |
| ATOM | 845 | NE | ARG | A | 105 | 21.705 | −25.879 | 72.818 | 1.00 | 75.03 N |
| ATOM | 846 | CZ | ARG | A | 105 | 21.168 | −26.707 | 73.719 | 1.00 | 71.87 C |
| ATOM | 847 | NH1 | ARG | A | 105 | 19.925 | −27.156 | 73.569 | 1.00 | 64.80 N |
| ATOM | 848 | NH2 | ARG | A | 105 | 21.881 | −27.085 | 74.780 | 1.00 | 70.46 N |
| ATOM | 849 | N | MET | A | 106 | 21.067 | −20.675 | 70.042 | 1.00 | 34.69 N |
| ATOM | 850 | CA | MET | A | 106 | 22.165 | −19.736 | 70.224 | 1.00 | 38.75 C |
| ATOM | 851 | C | MET | A | 106 | 21.654 | −18.339 | 70.589 | 1.00 | 37.93 C |
| ATOM | 852 | O | MET | A | 106 | 22.171 | −17.699 | 71.526 | 1.00 | 29.91 O |
| ATOM | 853 | CB | MET | A | 106 | 23.023 | −19.668 | 68.947 | 1.00 | 28.07 C |
| ATOM | 854 | CG | MET | A | 106 | 23.965 | −20.844 | 68.779 | 1.00 | 43.37 C |
| ATOM | 855 | SD | MET | A | 106 | 25.088 | −20.932 | 70.224 | 1.00 | 72.48 S |
| ATOM | 856 | CE | MET | A | 106 | 24.224 | −22.119 | 71.300 | 1.00 | 69.46 C |
| ATOM | 857 | N | LEU | A | 107 | 20.646 | −17.867 | 69.855 | 1.00 | 26.53 N |
| ATOM | 858 | CA | LEU | A | 107 | 20.077 | −16.548 | 70.120 | 1.00 | 24.82 C |
| ATOM | 859 | C | LEU | A | 107 | 19.502 | −16.493 | 71.531 | 1.00 | 40.04 C |
| ATOM | 860 | O | LEU | A | 107 | 19.774 | −15.547 | 72.287 | 1.00 | 38.44 O |
| ATOM | 861 | CB | LEU | A | 107 | 18.960 | −16.217 | 69.127 | 1.00 | 23.70 C |
| ATOM | 862 | CG | LEU | A | 107 | 18.096 | −14.978 | 69.414 | 1.00 | 21.55 C |
| ATOM | 863 | CD1 | LEU | A | 107 | 19.005 | −13.759 | 69.498 | 1.00 | 28.55 C |
| ATOM | 864 | CD2 | LEU | A | 107 | 17.065 | −14.760 | 68.274 | 1.00 | 24.38 C |
| ATOM | 865 | N | LEU | A | 108 | 18.707 | −17.498 | 71.896 | 1.00 | 22.91 N |
| ATOM | 866 | CA | LEU | A | 108 | 18.120 | −17.482 | 73.225 | 1.00 | 24.79 C |
| ATOM | 867 | C | LEU | A | 108 | 19.198 | −17.537 | 74.304 | 1.00 | 21.16 C |
| ATOM | 868 | O | LEU | A | 108 | 19.046 | −16.923 | 75.349 | 1.00 | 30.46 O |
| ATOM | 869 | CB | LEU | A | 108 | 17.080 | −18.605 | 73.364 | 1.00 | 25.39 C |
| ATOM | 870 | CG | LEU | A | 108 | 15.838 | −18.392 | 72.466 | 1.00 | 28.83 C |
| ATOM | 871 | CD1 | LEU | A | 108 | 15.003 | −19.666 | 72.478 | 1.00 | 21.42 C |
| ATOM | 872 | CD2 | LEU | A | 108 | 14.994 | −17.190 | 72.923 | 1.00 | 21.50 C |
| ATOM | 873 | N | THR | A | 109 | 20.305 | −18.226 | 74.038 | 1.00 | 28.89 N |
| ATOM | 874 | CA | THR | A | 109 | 21.403 | −18.289 | 75.016 | 1.00 | 27.21 C |
| ATOM | 875 | C | THR | A | 109 | 22.023 | −16.905 | 75.129 | 1.00 | 22.15 C |
| ATOM | 876 | O | THR | A | 109 | 22.310 | −16.442 | 76.219 | 1.00 | 37.28 O |
| ATOM | 877 | CB | THR | A | 109 | 22.526 | −19.262 | 74.586 | 1.00 | 40.28 C |
| ATOM | 878 | OG1 | THR | A | 109 | 21.989 | −20.572 | 74.388 | 1.00 | 40.55 O |
| ATOM | 879 | CG2 | THR | A | 109 | 23.615 | −19.333 | 75.651 | 1.00 | 29.86 C |
| ATOM | 880 | N | SER | A | 110 | 22.205 | −16.224 | 74.000 | 1.00 | 32.87 N |
| ATOM | 881 | CA | SER | A | 110 | 22.789 | −14.882 | 74.034 | 1.00 | 30.71 C |
| ATOM | 882 | C | SER | A | 110 | 21.850 | −13.934 | 74.783 | 1.00 | 27.28 C |
| ATOM | 883 | O | SER | A | 110 | 22.293 | −13.072 | 75.530 | 1.00 | 34.18 O |
| ATOM | 884 | CB | SER | A | 110 | 23.032 | −14.355 | 72.614 | 1.00 | 28.15 C |
| ATOM | 885 | OG | SER | A | 110 | 23.831 | −15.237 | 71.840 | 1.00 | 36.40 O |
| ATOM | 886 | N | ILE | A | 111 | 20.545 | −14.109 | 74.593 | 1.00 | 29.15 N |
| ATOM | 887 | CA | ILE | A | 111 | 19.577 | −13.248 | 75.266 | 1.00 | 33.28 C |
| ATOM | 888 | C | ILE | A | 111 | 19.588 | −13.490 | 76.774 | 1.00 | 18.12 C |
| ATOM | 889 | O | ILE | A | 111 | 19.513 | −12.555 | 77.549 | 1.00 | 20.06 O |
| ATOM | 890 | CB | ILE | A | 111 | 18.132 | −13.457 | 74.665 | 1.00 | 35.82 C |
| ATOM | 891 | CG1 | ILE | A | 111 | 18.016 | −12.689 | 73.345 | 1.00 | 26.91 C |
| ATOM | 892 | CG2 | ILE | A | 111 | 17.048 | −12.967 | 75.611 | 1.00 | 18.63 C |
| ATOM | 893 | CD1 | ILE | A | 111 | 16.737 | −13.010 | 72.576 | 1.00 | 31.51 C |
| ATOM | 894 | N | VAL | A | 112 | 19.689 | −14.746 | 77.192 | 1.00 | 17.67 N |
| ATOM | 895 | CA | VAL | A | 112 | 19.681 | −15.024 | 78.635 | 1.00 | 25.83 C |
| ATOM | 896 | C | VAL | A | 112 | 20.956 | −14.523 | 79.344 | 1.00 | 32.33 C |
| ATOM | 897 | O | VAL | A | 112 | 20.907 | −14.116 | 80.494 | 1.00 | 33.49 O |
| ATOM | 898 | CB | VAL | A | 112 | 19.491 | −16.528 | 78.914 | 1.00 | 40.06 C |
| ATOM | 899 | CG1 | VAL | A | 112 | 19.718 | −16.818 | 80.415 | 1.00 | 29.20 C |
| ATOM | 900 | CG2 | VAL | A | 112 | 18.080 | −16.956 | 78.503 | 1.00 | 22.58 C |
| ATOM | 901 | N | ARG | A | 113 | 22.089 | −14.561 | 78.657 | 1.00 | 25.46 N |

TABLE 1-continued

| | | | | | | | | | | |
|---|---|---|---|---|---|---|---|---|---|---|
| ATOM | 902 | CA | ARG | A | 113 | 23.339 | −14.063 | 79.227 | 1.00 | 36.77 C |
| ATOM | 903 | C | ARG | A | 113 | 23.398 | −12.537 | 79.158 | 1.00 | 32.81 C |
| ATOM | 904 | O | ARG | A | 113 | 24.211 | −11.918 | 79.832 | 1.00 | 33.53 O |
| ATOM | 905 | CB | ARG | A | 113 | 24.531 | −14.654 | 78.475 | 1.00 | 39.99 C |
| ATOM | 906 | CG | ARG | A | 113 | 24.611 | −16.170 | 78.574 | 1.00 | 47.00 C |
| ATOM | 907 | CD | ARG | A | 113 | 25.463 | −16.794 | 77.460 | 1.00 | 51.93 C |
| ATOM | 908 | NE | ARG | A | 113 | 26.866 | −17.016 | 77.826 | 1.00 | 69.79 N |
| ATOM | 909 | CZ | ARG | A | 113 | 27.811 | −16.079 | 77.788 | 1.00 | 79.05 C |
| ATOM | 910 | NH1 | ARG | A | 113 | 27.500 | −14.845 | 77.396 | 1.00 | 72.22 N |
| ATOM | 911 | NH2 | ARG | A | 113 | 29.066 | −16.373 | 78.138 | 1.00 | 53.28 N |
| ATOM | 912 | N | GLY | A | 114 | 22.511 | −11.941 | 78.358 | 1.00 | 38.83 N |
| ATOM | 913 | CA | GLY | A | 114 | 22.485 | −10.489 | 78.179 | 1.00 | 19.69 C |
| ATOM | 914 | C | GLY | A | 114 | 21.931 | −9.615 | 79.297 | 1.00 | 27.74 C |
| ATOM | 915 | O | GLY | A | 114 | 21.173 | −8.681 | 79.036 | 1.00 | 31.31 O |
| ATOM | 916 | N | ILE | A | 115 | 22.329 | −9.879 | 80.538 | 1.00 | 23.42 N |
| ATOM | 917 | CA | ILE | A | 115 | 21.882 | −9.072 | 81.666 | 1.00 | 28.03 C |
| ATOM | 918 | C | ILE | A | 115 | 22.182 | −7.575 | 81.474 | 1.00 | 27.13 C |
| ATOM | 919 | O | ILE | A | 115 | 23.305 | −7.191 | 81.181 | 1.00 | 22.92 O |
| ATOM | 920 | CB | ILE | A | 115 | 22.584 | −9.493 | 82.982 | 1.00 | 40.85 C |
| ATOM | 921 | CG1 | ILE | A | 115 | 22.422 | −10.997 | 83.222 | 1.00 | 30.96 C |
| ATOM | 922 | CG2 | ILE | A | 115 | 22.038 | −8.668 | 84.141 | 1.00 | 25.98 C |
| ATOM | 923 | CD1 | ILE | A | 115 | 21.002 | −11.451 | 83.206 | 1.00 | 57.86 C |
| ATOM | 924 | N | PRO | A | 116 | 21.170 | −6.716 | 81.635 | 1.00 | 25.27 N |
| ATOM | 925 | CA | PRO | A | 116 | 21.403 | −5.280 | 81.477 | 1.00 | 29.83 C |
| ATOM | 926 | C | PRO | A | 116 | 22.465 | −4.827 | 82.476 | 1.00 | 35.27 C |
| ATOM | 927 | O | PRO | A | 116 | 22.425 | −5.207 | 83.640 | 1.00 | 33.77 O |
| ATOM | 928 | CB | PRO | A | 116 | 20.036 | −4.672 | 81.785 | 1.00 | 30.16 C |
| ATOM | 929 | CG | PRO | A | 116 | 19.100 | −5.718 | 81.259 | 1.00 | 31.54 C |
| ATOM | 930 | CD | PRO | A | 116 | 19.737 | −6.997 | 81.808 | 1.00 | 23.12 C |
| ATOM | 931 | N | PHE | A | 117 | 23.386 | −3.987 | 82.026 | 1.00 | 32.82 N |
| ATOM | 932 | CA | PHE | A | 117 | 24.453 | −3.525 | 82.888 | 1.00 | 38.63 C |
| ATOM | 933 | C | PHE | A | 117 | 24.005 | −2.791 | 84.160 | 1.00 | 49.97 C |
| ATOM | 934 | O | PHE | A | 117 | 22.939 | −2.180 | 84.199 | 1.00 | 30.05 O |
| ATOM | 935 | CB | PHE | A | 117 | 25.424 | −2.664 | 82.096 | 1.00 | 28.77 C |
| ATOM | 936 | CG | PHE | A | 117 | 26.678 | −2.341 | 82.863 | 1.00 | 40.48 C |
| ATOM | 937 | CD1 | PHE | A | 117 | 27.523 | −3.353 | 83.285 | 1.00 | 30.06 C |
| ATOM | 938 | CD2 | PHE | A | 117 | 26.973 | −1.031 | 83.221 | 1.00 | 25.04 C |
| ATOM | 939 | CE1 | PHE | A | 117 | 28.651 | −3.057 | 84.069 | 1.00 | 46.05 C |
| ATOM | 940 | CE2 | PHE | A | 117 | 28.090 | −0.727 | 83.998 | 1.00 | 31.49 C |
| ATOM | 941 | CZ | PHE | A | 117 | 28.927 | −1.740 | 84.422 | 1.00 | 28.02 C |
| ATOM | 942 | N | TRP | A | 118 | 24.826 | −2.879 | 85.211 | 1.00 | 43.83 N |
| ATOM | 943 | CA | TRP | A | 118 | 24.512 | −2.236 | 86.488 | 1.00 | 23.84 C |
| ATOM | 944 | C | TRP | A | 118 | 25.117 | −0.846 | 86.534 | 1.00 | 34.39 C |
| ATOM | 945 | O | TRP | A | 118 | 26.028 | −0.566 | 87.305 | 1.00 | 35.76 O |
| ATOM | 946 | CB | TRP | A | 118 | 25.043 | −3.066 | 87.638 | 1.00 | 23.42 C |
| ATOM | 947 | CG | TRP | A | 118 | 24.132 | −4.181 | 88.055 | 1.00 | 29.89 C |
| ATOM | 948 | CD1 | TRP | A | 118 | 23.277 | −4.902 | 87.254 | 1.00 | 26.59 C |
| ATOM | 949 | CD2 | TRP | A | 118 | 23.934 | −4.659 | 89.386 | 1.00 | 24.32 C |
| ATOM | 950 | NE1 | TRP | A | 118 | 22.557 | −5.783 | 88.013 | 1.00 | 34.25 N |
| ATOM | 951 | CE2 | TRP | A | 118 | 22.939 | −5.658 | 89.326 | 1.00 | 31.02 C |
| ATOM | 952 | CE3 | TRP | A | 118 | 24.507 | −4.339 | 90.633 | 1.00 | 35.38 C |
| ATOM | 953 | CZ2 | TRP | A | 118 | 22.487 | −6.334 | 90.469 | 1.00 | 22.27 C |
| ATOM | 954 | CZ3 | TRP | A | 118 | 24.062 | −5.011 | 91.767 | 1.00 | 22.99 C |
| ATOM | 955 | CH2 | TRP | A | 118 | 23.063 | −5.998 | 91.677 | 1.00 | 38.21 C |
| ATOM | 956 | N | GLY | A | 119 | 24.590 | 0.037 | 85.710 | 1.00 | 23.08 N |
| ATOM | 957 | CA | GLY | A | 119 | 25.133 | 1.375 | 85.672 | 1.00 | 39.00 C |
| ATOM | 958 | C | GLY | A | 119 | 24.179 | 2.424 | 86.185 | 1.00 | 36.33 C |
| ATOM | 959 | O | GLY | A | 119 | 24.083 | 3.503 | 85.621 | 1.00 | 47.94 O |
| ATOM | 960 | N | GLY | A | 120 | 23.475 | 2.129 | 87.264 | 1.00 | 33.85 N |
| ATOM | 961 | CA | GLY | A | 120 | 22.556 | 3.114 | 87.770 | 1.00 | 34.37 C |
| ATOM | 962 | C | GLY | A | 120 | 23.021 | 3.979 | 88.929 | 1.00 | 49.67 C |
| ATOM | 963 | O | GLY | A | 120 | 22.182 | 4.626 | 89.542 | 1.00 | 41.64 O |
| ATOM | 964 | N | SER | A | 121 | 24.315 | 4.013 | 89.251 | 1.00 | 40.84 N |
| ATOM | 965 | CA | SER | A | 121 | 24.754 | 4.852 | 90.372 | 1.00 | 48.00 C |
| ATOM | 966 | C | SER | A | 121 | 25.350 | 6.178 | 89.921 | 1.00 | 42.94 C |
| ATOM | 967 | O | SER | A | 121 | 25.907 | 6.283 | 88.840 | 1.00 | 37.52 O |
| ATOM | 968 | CB | SER | A | 121 | 25.794 | 4.121 | 91.226 | 1.00 | 54.40 C |
| ATOM | 969 | OG | SER | A | 121 | 26.312 | 4.983 | 92.227 | 1.00 | 54.16 O |
| ATOM | 970 | N | THR | A | 122 | 25.249 | 7.193 | 90.762 | 1.00 | 48.98 N |
| ATOM | 971 | CA | THR | A | 122 | 25.836 | 8.488 | 90.421 | 1.00 | 54.82 C |
| ATOM | 972 | C | THR | A | 122 | 27.345 | 8.464 | 90.759 | 1.00 | 61.51 C |
| ATOM | 973 | O | THR | A | 122 | 28.141 | 9.199 | 90.171 | 1.00 | 62.61 O |
| ATOM | 974 | CB | THR | A | 122 | 25.157 | 9.606 | 91.199 | 1.00 | 50.35 C |
| ATOM | 975 | OG1 | THR | A | 122 | 25.235 | 9.311 | 92.597 | 1.00 | 72.48 O |
| ATOM | 976 | CG2 | THR | A | 122 | 23.697 | 9.710 | 90.806 | 1.00 | 49.55 C |
| ATOM | 977 | N | ILE | A | 123 | 27.728 | 7.599 | 91.697 | 1.00 | 54.72 N |
| ATOM | 978 | CA | ILE | A | 123 | 29.123 | 7.460 | 92.108 | 1.00 | 41.59 C |
| ATOM | 979 | C | ILE | A | 123 | 29.800 | 6.579 | 91.078 | 1.00 | 44.06 C |
| ATOM | 980 | O | ILE | A | 123 | 29.432 | 5.422 | 90.925 | 1.00 | 46.11 O |

TABLE 1-continued

| | | | | | | | | | | |
|---|---|---|---|---|---|---|---|---|---|---|
| ATOM | 981 | CB | ILE | A | 123 | 29.220 | 6.780 | 93.482 | 1.00 | 45.74 | C |
| ATOM | 982 | CG1 | ILE | A | 123 | 28.418 | 7.593 | 94.504 | 1.00 | 51.29 | C |
| ATOM | 983 | CG2 | ILE | A | 123 | 30.689 | 6.615 | 93.888 | 1.00 | 47.32 | C |
| ATOM | 984 | CD1 | ILE | A | 123 | 28.003 | 6.807 | 95.742 | 1.00 | 55.36 | C |
| ATOM | 985 | N | ASP | A | 124 | 30.811 | 7.105 | 90.397 | 1.00 | 53.60 | N |
| ATOM | 986 | CA | ASP | A | 124 | 31.476 | 6.334 | 89.357 | 1.00 | 54.29 | C |
| ATOM | 987 | C | ASP | A | 124 | 32.178 | 5.033 | 89.750 | 1.00 | 55.37 | C |
| ATOM | 988 | O | ASP | A | 124 | 32.540 | 4.257 | 88.864 | 1.00 | 60.28 | O |
| ATOM | 989 | CB | ASP | A | 124 | 32.434 | 7.235 | 88.550 | 1.00 | 62.63 | C |
| ATOM | 990 | CG | ASP | A | 124 | 33.772 | 7.455 | 89.236 | 1.00 | 78.28 | C |
| ATOM | 991 | OD1 | ASP | A | 124 | 33.775 | 7.825 | 90.428 | 1.00 | 86.20 | O |
| ATOM | 992 | OD2 | ASP | A | 124 | 34.822 | 7.267 | 88.575 | 1.00 | 75.63 | O |
| ATOM | 993 | N | THR | A | 125 | 32.361 | 4.759 | 91.042 | 1.00 | 39.33 | N |
| ATOM | 994 | CA | THR | A | 125 | 33.031 | 3.505 | 91.422 | 1.00 | 43.56 | C |
| ATOM | 995 | C | THR | A | 125 | 32.093 | 2.498 | 92.099 | 1.00 | 43.17 | C |
| ATOM | 996 | O | THR | A | 125 | 32.539 | 1.538 | 92.731 | 1.00 | 46.53 | O |
| ATOM | 997 | CB | THR | A | 125 | 34.220 | 3.757 | 92.362 | 1.00 | 49.65 | C |
| ATOM | 998 | OG1 | THR | A | 125 | 33.778 | 4.530 | 93.480 | 1.00 | 49.40 | O |
| ATOM | 999 | CG2 | THR | A | 125 | 35.336 | 4.504 | 91.636 | 1.00 | 52.11 | C |
| ATOM | 1000 | N | GLU | A | 126 | 30.794 | 2.718 | 91.933 | 1.00 | 43.54 | N |
| ATOM | 1001 | CA | GLU | A | 126 | 29.753 | 1.878 | 92.519 | 1.00 | 42.24 | C |
| ATOM | 1002 | C | GLU | A | 126 | 28.840 | 1.243 | 91.458 | 1.00 | 38.02 | C |
| ATOM | 1003 | O | GLU | A | 126 | 28.365 | 1.925 | 90.560 | 1.00 | 47.66 | O |
| ATOM | 1004 | CB | GLU | A | 126 | 28.903 | 2.741 | 93.447 | 1.00 | 32.33 | C |
| ATOM | 1005 | CG | GLU | A | 126 | 27.754 | 2.049 | 94.136 | 1.00 | 46.21 | C |
| ATOM | 1006 | CD | GLU | A | 126 | 27.021 | 3.003 | 95.077 | 1.00 | 67.14 | C |
| ATOM | 1007 | OE1 | GLU | A | 126 | 26.406 | 3.983 | 94.589 | 1.00 | 63.51 | O |
| ATOM | 1008 | OE2 | GLU | A | 126 | 27.076 | 2.788 | 96.311 | 1.00 | 79.04 | O |
| ATOM | 1009 | N | LEU | A | 127 | 28.621 | −0.062 | 91.559 | 1.00 | 33.13 | N |
| ATOM | 1010 | CA | LEU | A | 127 | 27.739 | −0.775 | 90.651 | 1.00 | 40.49 | C |
| ATOM | 1011 | C | LEU | A | 127 | 26.398 | −0.839 | 91.344 | 1.00 | 45.77 | C |
| ATOM | 1012 | O | LEU | A | 127 | 26.320 | −1.239 | 92.508 | 1.00 | 41.34 | O |
| ATOM | 1013 | CB | LEU | A | 127 | 28.199 | −2.212 | 90.400 | 1.00 | 37.13 | C |
| ATOM | 1014 | CG | LEU | A | 127 | 29.448 | −2.482 | 89.585 | 1.00 | 36.49 | C |
| ATOM | 1015 | CD1 | LEU | A | 127 | 29.461 | −3.967 | 89.220 | 1.00 | 42.25 | C |
| ATOM | 1016 | CD2 | LEU | A | 127 | 29.455 | −1.621 | 88.337 | 1.00 | 36.50 | C |
| ATOM | 1017 | N | LYS | A | 128 | 25.353 | −0.454 | 90.615 | 1.00 | 48.17 | N |
| ATOM | 1018 | CA | LYS | A | 128 | 23.990 | −0.440 | 91.125 | 1.00 | 28.94 | C |
| ATOM | 1019 | C | LYS | A | 128 | 23.002 | −0.683 | 89.982 | 1.00 | 46.94 | C |
| ATOM | 1020 | O | LYS | A | 128 | 23.080 | −0.050 | 88.914 | 1.00 | 31.45 | O |
| ATOM | 1021 | CB | LYS | A | 128 | 23.687 | 0.910 | 91.758 | 1.00 | 30.51 | C |
| ATOM | 1022 | CG | LYS | A | 128 | 22.303 | 1.011 | 92.340 | 1.00 | 26.45 | C |
| ATOM | 1023 | CD | LYS | A | 128 | 21.953 | 2.455 | 92.652 | 1.00 | 39.99 | C |
| ATOM | 1024 | CE | LYS | A | 128 | 20.568 | 2.571 | 93.267 | 1.00 | 32.96 | C |
| ATOM | 1025 | NZ | LYS | A | 128 | 20.341 | 3.931 | 93.837 | 1.00 | 58.25 | N |
| ATOM | 1026 | N | VAL | A | 129 | 22.057 | −1.587 | 90.217 | 1.00 | 29.75 | N |
| ATOM | 1027 | CA | VAL | A | 129 | 21.083 | −1.906 | 89.195 | 1.00 | 34.87 | C |
| ATOM | 1028 | C | VAL | A | 129 | 20.268 | −0.665 | 88.821 | 1.00 | 35.65 | C |
| ATOM | 1029 | O | VAL | A | 129 | 20.174 | 0.275 | 89.598 | 1.00 | 34.00 | O |
| ATOM | 1030 | CB | VAL | A | 129 | 20.113 | −3.037 | 89.661 | 1.00 | 47.35 | C |
| ATOM | 1031 | CG1 | VAL | A | 129 | 19.182 | −2.537 | 90.784 | 1.00 | 29.85 | C |
| ATOM | 1032 | CG2 | VAL | A | 129 | 19.297 | −3.532 | 88.483 | 1.00 | 44.18 | C |
| ATOM | 1033 | N | ILE | A | 130 | 19.737 | −0.645 | 87.599 | 1.00 | 30.37 | N |
| ATOM | 1034 | CA | ILE | A | 130 | 18.871 | 0.445 | 87.175 | 1.00 | 35.36 | C |
| ATOM | 1035 | C | ILE | A | 130 | 17.447 | −0.099 | 87.393 | 1.00 | 22.90 | C |
| ATOM | 1036 | O | ILE | A | 130 | 17.099 | −1.172 | 86.901 | 1.00 | 41.64 | O |
| ATOM | 1037 | CB | ILE | A | 130 | 19.121 | 0.809 | 85.683 | 1.00 | 46.21 | C |
| ATOM | 1038 | CG1 | ILE | A | 130 | 20.438 | 1.589 | 85.569 | 1.00 | 35.86 | C |
| ATOM | 1039 | CG2 | ILE | A | 130 | 17.935 | 1.622 | 85.117 | 1.00 | 36.32 | C |
| ATOM | 1040 | CD1 | ILE | A | 130 | 20.967 | 1.758 | 84.135 | 1.00 | 26.54 | C |
| ATOM | 1041 | N | ASP | A | 131 | 16.637 | 0.621 | 88.157 | 1.00 | 39.64 | N |
| ATOM | 1042 | CA | ASP | A | 131 | 15.259 | 0.194 | 88.479 | 1.00 | 31.04 | C |
| ATOM | 1043 | C | ASP | A | 131 | 14.354 | −0.287 | 87.323 | 1.00 | 48.83 | C |
| ATOM | 1044 | O | ASP | A | 131 | 13.596 | −1.248 | 87.481 | 1.00 | 40.92 | O |
| ATOM | 1045 | CB | ASP | A | 131 | 14.553 | 1.312 | 89.232 | 1.00 | 37.26 | C |
| ATOM | 1046 | CG | ASP | A | 131 | 14.237 | 2.517 | 88.341 | 1.00 | 74.30 | C |
| ATOM | 1047 | OD1 | ASP | A | 131 | 15.003 | 2.798 | 87.388 | 1.00 | 68.31 | O |
| ATOM | 1048 | OD2 | ASP | A | 131 | 13.219 | 3.200 | 88.604 | 1.00 | 87.93 | O |
| ATOM | 1049 | N | THR | A | 132 | 14.446 | 0.347 | 86.159 | 1.00 | 36.75 | N |
| ATOM | 1050 | CA | THR | A | 132 | 13.606 | −0.040 | 85.034 | 1.00 | 38.57 | C |
| ATOM | 1051 | C | THR | A | 132 | 14.028 | −1.323 | 84.316 | 1.00 | 47.65 | C |
| ATOM | 1052 | O | THR | A | 132 | 13.450 | −1.697 | 83.291 | 1.00 | 37.49 | O |
| ATOM | 1053 | CB | THR | A | 132 | 13.483 | 1.117 | 84.054 | 1.00 | 43.30 | C |
| ATOM | 1054 | OG1 | THR | A | 132 | 14.795 | 1.581 | 83.676 | 1.00 | 35.27 | O |
| ATOM | 1055 | CG2 | THR | A | 132 | 12.705 | 2.274 | 84.735 | 1.00 | 29.94 | C |
| ATOM | 1056 | N | ASN | A | 133 | 15.038 | −1.991 | 84.866 | 1.00 | 28.71 | N |
| ATOM | 1057 | CA | ASN | A | 133 | 15.497 | −3.266 | 84.332 | 1.00 | 27.72 | C |
| ATOM | 1058 | C | ASN | A | 133 | 15.001 | −4.410 | 85.266 | 1.00 | 24.25 | C |
| ATOM | 1059 | O | ASN | A | 133 | 15.463 | −5.548 | 85.211 | 1.00 | 31.93 | O |

TABLE 1-continued

| ATOM | 1060 | CB | ASN | A | 133 | 17.015 | −3.280 | 84.228 | 1.00 | 25.12 | C |
|---|---|---|---|---|---|---|---|---|---|---|---|
| ATOM | 1061 | CG | ASN | A | 133 | 17.535 | −2.418 | 83.106 | 1.00 | 32.07 | C |
| ATOM | 1062 | OD1 | ASN | A | 133 | 18.670 | −1.944 | 83.160 | 1.00 | 33.18 | O |
| ATOM | 1063 | ND2 | ASN | A | 133 | 16.731 | −2.227 | 82.073 | 1.00 | 25.89 | N |
| ATOM | 1064 | N | CYS | A | 134 | 14.032 | −4.091 | 86.105 | 1.00 | 27.93 | N |
| ATOM | 1065 | CA | CYS | A | 134 | 13.472 | −5.067 | 87.027 | 1.00 | 40.51 | C |
| ATOM | 1066 | C | CYS | A | 134 | 11.955 | −5.019 | 86.968 | 1.00 | 33.72 | C |
| ATOM | 1067 | O | CYS | A | 134 | 11.375 | −4.166 | 86.303 | 1.00 | 31.77 | O |
| ATOM | 1068 | CB | CYS | A | 134 | 13.876 | −4.730 | 88.478 | 1.00 | 47.63 | C |
| ATOM | 1069 | SG | CYS | A | 134 | 15.657 | −4.493 | 88.786 | 1.00 | 37.78 | S |
| ATOM | 1070 | N | ILE | A | 135 | 11.333 | −5.951 | 87.676 | 1.00 | 34.29 | N |
| ATOM | 1071 | CA | ILE | A | 135 | 9.891 | −5.966 | 87.844 | 1.00 | 40.14 | C |
| ATOM | 1072 | C | ILE | A | 135 | 9.687 | −6.193 | 89.347 | 1.00 | 45.47 | C |
| ATOM | 1073 | O | ILE | A | 135 | 10.564 | −6.734 | 90.031 | 1.00 | 39.75 | O |
| ATOM | 1074 | CB | ILE | A | 135 | 9.174 | −7.101 | 87.080 | 1.00 | 35.79 | C |
| ATOM | 1075 | CG1 | ILE | A | 135 | 9.813 | −8.452 | 87.421 | 1.00 | 43.15 | C |
| ATOM | 1076 | CG2 | ILE | A | 135 | 9.140 | −6.794 | 85.575 | 1.00 | 29.98 | C |
| ATOM | 1077 | CD1 | ILE | A | 135 | 9.017 | −9.639 | 86.887 | 1.00 | 36.33 | C |
| ATOM | 1078 | N | ASN | A | 136 | 8.550 | −5.747 | 89.867 | 1.00 | 42.67 | N |
| ATOM | 1079 | CA | ASN | A | 136 | 8.234 | −5.951 | 91.266 | 1.00 | 27.13 | C |
| ATOM | 1080 | C | ASN | A | 136 | 7.297 | −7.137 | 91.437 | 1.00 | 38.06 | C |
| ATOM | 1081 | O | ASN | A | 136 | 6.120 | −7.074 | 91.063 | 1.00 | 40.26 | O |
| ATOM | 1082 | CB | ASN | A | 136 | 7.583 | −4.704 | 91.854 | 1.00 | 51.50 | C |
| ATOM | 1083 | CG | ASN | A | 136 | 8.575 | −3.594 | 92.078 | 1.00 | 53.19 | C |
| ATOM | 1084 | OD1 | ASN | A | 136 | 9.702 | −3.847 | 92.497 | 1.00 | 44.15 | O |
| ATOM | 1085 | ND2 | ASN | A | 136 | 8.161 | −2.355 | 91.820 | 1.00 | 52.23 | N |
| ATOM | 1086 | N | VAL | A | 137 | 7.836 | −8.226 | 91.972 | 1.00 | 36.09 | N |
| ATOM | 1087 | CA | VAL | A | 137 | 7.061 | −9.433 | 92.236 | 1.00 | 33.34 | C |
| ATOM | 1088 | C | VAL | A | 137 | 6.337 | −9.331 | 93.585 | 1.00 | 44.04 | C |
| ATOM | 1089 | O | VAL | A | 137 | 6.958 | −9.141 | 94.629 | 1.00 | 46.23 | O |
| ATOM | 1090 | CB | VAL | A | 137 | 7.962 | −10.660 | 92.279 | 1.00 | 46.56 | C |
| ATOM | 1091 | CG1 | VAL | A | 137 | 7.152 | −11.884 | 92.695 | 1.00 | 36.57 | C |
| ATOM | 1092 | CG2 | VAL | A | 137 | 8.623 | −10.870 | 90.914 | 1.00 | 35.64 | C |
| ATOM | 1093 | N | ILE | A | 138 | 5.019 | −9.457 | 93.566 | 1.00 | 46.76 | N |
| ATOM | 1094 | CA | ILE | A | 138 | 4.238 | −9.369 | 94.792 | 1.00 | 40.44 | C |
| ATOM | 1095 | C | ILE | A | 138 | 4.416 | −10.561 | 95.702 | 1.00 | 37.63 | C |
| ATOM | 1096 | O | ILE | A | 138 | 4.240 | −11.702 | 95.289 | 1.00 | 39.17 | O |
| ATOM | 1097 | CB | ILE | A | 138 | 2.732 | −9.222 | 94.496 | 1.00 | 49.07 | C |
| ATOM | 1098 | CG1 | ILE | A | 138 | 2.404 | −7.769 | 94.170 | 1.00 | 50.03 | C |
| ATOM | 1099 | CG2 | ILE | A | 138 | 1.915 | −9.646 | 95.691 | 1.00 | 64.62 | C |
| ATOM | 1100 | CD1 | ILE | A | 138 | 0.931 | −7.532 | 93.865 | 1.00 | 69.81 | C |
| ATOM | 1101 | N | GLN | A | 139 | 4.739 | −10.272 | 96.960 | 1.00 | 48.58 | N |
| ATOM | 1102 | CA | GLN | A | 139 | 4.940 | −11.298 | 97.979 | 1.00 | 44.77 | C |
| ATOM | 1103 | C | GLN | A | 139 | 3.618 | −11.682 | 98.659 | 1.00 | 65.81 | C |
| ATOM | 1104 | O | GLN | A | 139 | 2.617 | −10.961 | 98.554 | 1.00 | 47.36 | O |
| ATOM | 1105 | CB | GLN | A | 139 | 5.942 | −10.789 | 99.012 | 1.00 | 43.95 | C |
| ATOM | 1106 | CG | GLN | A | 139 | 7.300 | −10.544 | 98.395 | 1.00 | 60.23 | C |
| ATOM | 1107 | CD | GLN | A | 139 | 7.821 | −11.795 | 97.724 | 1.00 | 60.78 | C |
| ATOM | 1108 | OE1 | GLN | A | 139 | 8.172 | −12.766 | 98.395 | 1.00 | 72.77 | O |
| ATOM | 1109 | NE2 | GLN | A | 139 | 7.849 | −11.793 | 96.393 | 1.00 | 57.04 | N |
| ATOM | 1110 | N | PRO | A | 140 | 3.593 | −12.834 | 99.352 | 1.00 | 63.13 | N |
| ATOM | 1111 | CA | PRO | A | 140 | 2.371 | −13.285 | 100.035 | 1.00 | 66.50 | C |
| ATOM | 1112 | C | PRO | A | 140 | 1.773 | −12.224 | 100.949 | 1.00 | 66.01 | C |
| ATOM | 1113 | O | PRO | A | 140 | 0.551 | −12.112 | 101.085 | 1.00 | 55.80 | O |
| ATOM | 1114 | CB | PRO | A | 140 | 2.846 | −14.512 | 100.811 | 1.00 | 52.92 | C |
| ATOM | 1115 | CG | PRO | A | 140 | 3.886 | −15.093 | 99.877 | 1.00 | 61.36 | C |
| ATOM | 1116 | CD | PRO | A | 140 | 4.663 | −13.845 | 99.461 | 1.00 | 55.34 | C |
| ATOM | 1117 | N | ASP | A | 141 | 2.651 | −11.439 | 101.559 | 1.00 | 59.10 | N |
| ATOM | 1118 | CA | ASP | A | 141 | 2.249 | −10.391 | 102.481 | 1.00 | 54.80 | C |
| ATOM | 1119 | C | ASP | A | 141 | 2.026 | −9.063 | 101.783 | 1.00 | 58.16 | C |
| ATOM | 1120 | O | ASP | A | 141 | 2.163 | −8.009 | 102.400 | 1.00 | 54.58 | O |
| ATOM | 1121 | CB | ASP | A | 141 | 3.323 | −10.227 | 103.550 | 1.00 | 69.98 | C |
| ATOM | 1122 | CG | ASP | A | 141 | 4.710 | −10.020 | 102.946 | 1.00 | 83.36 | C |
| ATOM | 1123 | OD1 | ASP | A | 141 | 5.171 | −10.915 | 102.191 | 1.00 | 70.32 | O |
| ATOM | 1124 | OD2 | ASP | A | 141 | 5.329 | −8.965 | 103.229 | 1.00 | 75.14 | O |
| ATOM | 1125 | N | GLY | A | 142 | 1.700 | −9.108 | 100.496 | 1.00 | 49.11 | N |
| ATOM | 1126 | CA | GLY | A | 142 | 1.451 | −7.882 | 99.762 | 1.00 | 46.00 | C |
| ATOM | 1127 | C | GLY | A | 142 | 2.645 | −6.991 | 99.451 | 1.00 | 56.21 | C |
| ATOM | 1128 | O | GLY | A | 142 | 2.516 | −6.048 | 98.664 | 1.00 | 58.80 | O |
| ATOM | 1129 | N | SER | A | 143 | 3.804 | −7.262 | 100.047 | 1.00 | 59.10 | N |
| ATOM | 1130 | CA | SER | A | 143 | 4.986 | −6.441 | 99.768 | 1.00 | 62.26 | C |
| ATOM | 1131 | C | SER | A | 143 | 5.588 | −6.818 | 98.409 | 1.00 | 62.56 | C |
| ATOM | 1132 | O | SER | A | 143 | 5.382 | −7.935 | 97.903 | 1.00 | 55.97 | O |
| ATOM | 1133 | CB | SER | A | 143 | 6.049 | −6.608 | 100.862 | 1.00 | 52.81 | C |
| ATOM | 1134 | OG | SER | A | 143 | 6.639 | −7.901 | 100.839 | 1.00 | 56.60 | O |
| ATOM | 1135 | N | TYR | A | 144 | 6.327 | −5.879 | 97.826 | 1.00 | 60.09 | N |
| ATOM | 1136 | CA | TYR | A | 144 | 6.950 | −6.091 | 96.529 | 1.00 | 56.04 | C |
| ATOM | 1137 | C | TYR | A | 144 | 8.408 | −6.493 | 96.651 | 1.00 | 54.70 | C |
| ATOM | 1138 | O | TYR | A | 144 | 9.169 | −5.873 | 97.385 | 1.00 | 50.72 | O |

TABLE 1-continued

| | | | | | | | | | | |
|---|---|---|---|---|---|---|---|---|---|---|
| ATOM | 1139 | CB | TYR | A | 144 | 6.854 | −4.819 | 95.676 | 1.00 | 59.69 C |
| ATOM | 1140 | CG | TYR | A | 144 | 5.438 | −4.390 | 95.345 | 1.00 | 67.32 C |
| ATOM | 1141 | CD1 | TYR | A | 144 | 4.635 | −5.146 | 94.492 | 1.00 | 64.37 C |
| ATOM | 1142 | CD2 | TYR | A | 144 | 4.899 | −3.233 | 95.898 | 1.00 | 75.31 C |
| ATOM | 1143 | CE1 | TYR | A | 144 | 3.327 | −4.757 | 94.201 | 1.00 | 76.43 C |
| ATOM | 1144 | CE2 | TYR | A | 144 | 3.593 | −2.835 | 95.618 | 1.00 | 79.53 C |
| ATOM | 1145 | CZ | TYR | A | 144 | 2.812 | −3.599 | 94.772 | 1.00 | 82.11 C |
| ATOM | 1146 | OH | TYR | A | 144 | 1.517 | −3.199 | 94.510 | 1.00 | 85.43 O |
| ATOM | 1147 | N | ARG | A | 145 | 8.774 | −7.554 | 95.941 | 1.00 | 58.78 N |
| ATOM | 1148 | CA | ARG | A | 145 | 10.147 | −8.029 | 95.893 | 1.00 | 49.34 C |
| ATOM | 1149 | C | ARG | A | 145 | 10.653 | −7.740 | 94.474 | 1.00 | 57.67 C |
| ATOM | 1150 | O | ARG | A | 145 | 10.155 | −8.298 | 93.491 | 1.00 | 44.74 O |
| ATOM | 1151 | CB | ARG | A | 145 | 10.232 | −9.534 | 96.158 | 1.00 | 52.18 C |
| ATOM | 1152 | CG | ARG | A | 145 | 11.622 | −10.126 | 95.860 | 1.00 | 62.80 C |
| ATOM | 1153 | CD | ARG | A | 145 | 11.720 | −11.630 | 96.162 | 1.00 | 66.23 C |
| ATOM | 1154 | NE | ARG | A | 145 | 10.920 | −12.468 | 95.267 | 1.00 | 71.19 N |
| ATOM | 1155 | CZ | ARG | A | 145 | 11.208 | −12.683 | 93.987 | 1.00 | 76.08 C |
| ATOM | 1156 | NH1 | ARG | A | 145 | 12.281 | −12.116 | 93.445 | 1.00 | 77.61 N |
| ATOM | 1157 | NH2 | ARG | A | 145 | 10.434 | −13.472 | 93.253 | 1.00 | 62.68 N |
| ATOM | 1158 | N | SER | A | 146 | 11.635 | −6.855 | 94.380 | 1.00 | 45.05 N |
| ATOM | 1159 | CA | SER | A | 146 | 12.229 | −6.483 | 93.111 | 1.00 | 48.62 C |
| ATOM | 1160 | C | SER | A | 146 | 13.070 | −7.605 | 92.488 | 1.00 | 44.88 C |
| ATOM | 1161 | O | SER | A | 146 | 13.895 | −8.216 | 93.153 | 1.00 | 39.93 O |
| ATOM | 1162 | CB | SER | A | 146 | 13.092 | −5.248 | 93.313 | 1.00 | 38.79 C |
| ATOM | 1163 | OG | SER | A | 146 | 13.989 | −5.105 | 92.236 | 1.00 | 54.81 O |
| ATOM | 1164 | N | GLU | A | 147 | 12.847 | −7.884 | 91.206 | 1.00 | 43.70 N |
| ATOM | 1165 | CA | GLU | A | 147 | 13.607 | −8.915 | 90.525 | 1.00 | 26.39 C |
| ATOM | 1166 | C | GLU | A | 147 | 14.065 | −8.464 | 89.126 | 1.00 | 46.96 C |
| ATOM | 1167 | O | GLU | A | 147 | 13.300 | −7.825 | 88.372 | 1.00 | 30.61 O |
| ATOM | 1168 | CB | GLU | A | 147 | 12.788 | −10.198 | 90.400 | 1.00 | 26.90 C |
| ATOM | 1169 | CG | GLU | A | 147 | 13.562 | −11.312 | 89.743 | 1.00 | 31.91 C |
| ATOM | 1170 | CD | GLU | A | 147 | 12.779 | −12.618 | 89.654 | 1.00 | 55.11 C |
| ATOM | 1171 | OE1 | GLU | A | 147 | 12.138 | −13.006 | 90.654 | 1.00 | 68.16 O |
| ATOM | 1172 | OE2 | GLU | A | 147 | 12.815 | −13.277 | 88.592 | 1.00 | 59.34 O |
| ATOM | 1173 | N | GLU | A | 148 | 15.311 | −8.818 | 88.789 | 1.00 | 31.60 N |
| ATOM | 1174 | CA | GLU | A | 148 | 15.918 | −8.483 | 87.501 | 1.00 | 34.63 C |
| ATOM | 1175 | C | GLU | A | 148 | 15.514 | −9.466 | 86.439 | 1.00 | 26.01 C |
| ATOM | 1176 | O | GLU | A | 148 | 15.399 | −10.651 | 86.705 | 1.00 | 35.85 O |
| ATOM | 1177 | CB | GLU | A | 148 | 17.448 | −8.527 | 87.592 | 1.00 | 36.94 C |
| ATOM | 1178 | CG | GLU | A | 148 | 18.098 | −7.313 | 88.176 | 1.00 | 36.63 C |
| ATOM | 1179 | CD | GLU | A | 148 | 19.566 | −7.569 | 88.427 | 1.00 | 57.06 C |
| ATOM | 1180 | OE1 | GLU | A | 148 | 20.368 | −7.594 | 87.454 | 1.00 | 41.80 O |
| ATOM | 1181 | OE2 | GLU | A | 148 | 19.897 | −7.771 | 89.615 | 1.00 | 68.74 O |
| ATOM | 1182 | N | LEU | A | 149 | 15.334 | −8.987 | 85.224 | 1.00 | 28.80 N |
| ATOM | 1183 | CA | LEU | A | 149 | 14.963 | −9.893 | 84.142 | 1.00 | 36.85 C |
| ATOM | 1184 | C | LEU | A | 149 | 15.442 | −9.276 | 82.850 | 1.00 | 19.64 C |
| ATOM | 1185 | O | LEU | A | 149 | 15.618 | −8.065 | 82.774 | 1.00 | 19.96 O |
| ATOM | 1186 | CB | LEU | A | 149 | 13.430 | −10.104 | 84.092 | 1.00 | 24.94 C |
| ATOM | 1187 | CG | LEU | A | 149 | 12.537 | −8.915 | 83.701 | 1.00 | 27.98 C |
| ATOM | 1188 | CD1 | LEU | A | 149 | 11.040 | −9.374 | 83.783 | 1.00 | 27.69 C |
| ATOM | 1189 | CD2 | LEU | A | 149 | 12.752 | −7.726 | 84.643 | 1.00 | 21.47 C |
| ATOM | 1190 | N | ASN | A | 150 | 15.627 | −10.109 | 81.827 | 1.00 | 23.98 N |
| ATOM | 1191 | CA | ASN | A | 150 | 16.099 | −9.623 | 80.535 | 1.00 | 20.71 C |
| ATOM | 1192 | C | ASN | A | 150 | 14.978 | −9.347 | 79.531 | 1.00 | 26.59 C |
| ATOM | 1193 | O | ASN | A | 150 | 15.005 | −8.368 | 78.806 | 1.00 | 27.95 O |
| ATOM | 1194 | CB | ASN | A | 150 | 17.035 | −10.655 | 79.912 | 1.00 | 24.67 C |
| ATOM | 1195 | CG | ASN | A | 150 | 18.307 | −10.849 | 80.712 | 1.00 | 31.13 C |
| ATOM | 1196 | OD1 | ASN | A | 150 | 18.551 | −10.139 | 81.692 | 1.00 | 24.90 O |
| ATOM | 1197 | ND2 | ASN | A | 150 | 19.128 | −11.805 | 80.291 | 1.00 | 23.67 N |
| ATOM | 1198 | N | LEU | A | 151 | 13.998 | −10.237 | 79.499 | 1.00 | 27.64 N |
| ATOM | 1199 | CA | LEU | A | 151 | 12.924 | −10.161 | 78.532 | 1.00 | 18.79 C |
| ATOM | 1200 | C | LEU | A | 151 | 11.531 | −10.441 | 79.081 | 1.00 | 29.72 C |
| ATOM | 1201 | O | LEU | A | 151 | 11.350 | −11.259 | 79.988 | 1.00 | 27.65 O |
| ATOM | 1202 | CB | LEU | A | 151 | 13.236 | −11.152 | 77.423 | 1.00 | 27.50 C |
| ATOM | 1203 | CG | LEU | A | 151 | 12.302 | −11.354 | 76.231 | 1.00 | 23.30 C |
| ATOM | 1204 | CD1 | LEU | A | 151 | 12.391 | −10.191 | 75.282 | 1.00 | 33.20 C |
| ATOM | 1205 | CD2 | LEU | A | 151 | 12.724 | −12.596 | 75.552 | 1.00 | 21.01 C |
| ATOM | 1206 | N | VAL | A | 152 | 10.555 | −9.733 | 78.529 | 1.00 | 29.02 N |
| ATOM | 1207 | CA | VAL | A | 152 | 9.163 | −9.925 | 78.884 | 1.00 | 23.89 C |
| ATOM | 1208 | C | VAL | A | 152 | 8.387 | −10.022 | 77.573 | 1.00 | 33.76 C |
| ATOM | 1209 | O | VAL | A | 152 | 8.610 | −9.224 | 76.649 | 1.00 | 23.83 O |
| ATOM | 1210 | CB | VAL | A | 152 | 8.584 | −8.744 | 79.692 | 1.00 | 25.77 C |
| ATOM | 1211 | CG1 | VAL | A | 152 | 7.106 | −8.978 | 79.942 | 1.00 | 23.82 C |
| ATOM | 1212 | CG2 | VAL | A | 152 | 9.319 | −8.579 | 81.005 | 1.00 | 21.02 C |
| ATOM | 1213 | N | ILE | A | 153 | 7.524 | −11.032 | 77.470 | 1.00 | 30.35 N |
| ATOM | 1214 | CA | ILE | A | 153 | 6.684 | −11.180 | 76.300 | 1.00 | 27.40 C |
| ATOM | 1215 | C | ILE | A | 153 | 5.291 | −10.776 | 76.779 | 1.00 | 30.39 C |
| ATOM | 1216 | O | ILE | A | 153 | 4.746 | −11.363 | 77.698 | 1.00 | 29.95 O |
| ATOM | 1217 | CB | ILE | A | 153 | 6.635 | −12.620 | 75.778 | 1.00 | 29.52 C |

TABLE 1-continued

| ATOM | 1218 | CG1 | ILE | A | 153 | 8.048 | −13.108 | 75.425 | 1.00 | 25.49 | C |
|---|---|---|---|---|---|---|---|---|---|---|---|
| ATOM | 1219 | CG2 | ILE | A | 153 | 5.718 | −12.674 | 74.577 | 1.00 | 23.78 | C |
| ATOM | 1220 | CD1 | ILE | A | 153 | 8.772 | −12.227 | 74.384 | 1.00 | 19.96 | C |
| ATOM | 1221 | N | ILE | A | 154 | 4.735 | −9.741 | 76.174 | 1.00 | 29.30 | N |
| ATOM | 1222 | CA | ILE | A | 154 | 3.443 | −9.241 | 76.590 | 1.00 | 32.65 | C |
| ATOM | 1223 | C | ILE | A | 154 | 2.506 | −9.051 | 75.391 | 1.00 | 35.01 | C |
| ATOM | 1224 | O | ILE | A | 154 | 2.973 | −8.920 | 74.259 | 1.00 | 20.78 | O |
| ATOM | 1225 | CB | ILE | A | 154 | 3.622 | −7.898 | 77.333 | 1.00 | 26.26 | C |
| ATOM | 1226 | CG1 | ILE | A | 154 | 2.335 | −7.519 | 78.052 | 1.00 | 31.10 | C |
| ATOM | 1227 | CG2 | ILE | A | 154 | 4.022 | −6.804 | 76.342 | 1.00 | 29.87 | C |
| ATOM | 1228 | CD1 | ILE | A | 154 | 2.480 | −6.349 | 78.997 | 1.00 | 41.54 | C |
| ATOM | 1229 | N | GLY | A | 155 | 1.192 | −9.052 | 75.654 | 1.00 | 31.45 | N |
| ATOM | 1230 | CA | GLY | A | 155 | 0.204 | −8.870 | 74.597 | 1.00 | 23.53 | C |
| ATOM | 1231 | C | GLY | A | 155 | 0.241 | −7.494 | 73.951 | 1.00 | 28.05 | C |
| ATOM | 1232 | O | GLY | A | 155 | 0.744 | −6.532 | 74.542 | 1.00 | 19.87 | O |
| ATOM | 1233 | N | PRO | A | 156 | −0.300 | −7.362 | 72.725 | 1.00 | 42.77 | N |
| ATOM | 1234 | CA | PRO | A | 156 | −0.292 | −6.059 | 72.053 | 1.00 | 23.90 | C |
| ATOM | 1235 | C | PRO | A | 156 | −1.179 | −4.986 | 72.712 | 1.00 | 41.79 | C |
| ATOM | 1236 | O | PRO | A | 156 | −2.018 | −5.277 | 73.586 | 1.00 | 31.28 | O |
| ATOM | 1237 | CB | PRO | A | 156 | −0.741 | −6.407 | 70.630 | 1.00 | 36.82 | C |
| ATOM | 1238 | CG | PRO | A | 156 | −1.684 | −7.567 | 70.854 | 1.00 | 32.21 | C |
| ATOM | 1239 | CD | PRO | A | 156 | −0.939 | −8.395 | 71.882 | 1.00 | 25.02 | C |
| ATOM | 1240 | N | SER | A | 157 | −0.960 | −3.746 | 72.288 | 1.00 | 22.72 | N |
| ATOM | 1241 | CA | SER | A | 157 | −1.714 | −2.605 | 72.765 | 1.00 | 42.23 | C |
| ATOM | 1242 | C | SER | A | 157 | −2.993 | −2.497 | 71.889 | 1.00 | 30.04 | C |
| ATOM | 1243 | O | SER | A | 157 | −3.398 | −3.472 | 71.284 | 1.00 | 29.52 | O |
| ATOM | 1244 | CB | SER | A | 157 | −0.839 | −1.346 | 72.647 | 1.00 | 35.50 | C |
| ATOM | 1245 | OG | SER | A | 157 | −1.394 | −0.281 | 73.394 | 1.00 | 59.20 | O |
| ATOM | 1246 | N | ALA | A | 158 | −3.625 | −1.331 | 71.820 | 1.00 | 39.92 | N |
| ATOM | 1247 | CA | ALA | A | 158 | −4.861 | −1.186 | 71.015 | 1.00 | 48.84 | C |
| ATOM | 1248 | C | ALA | A | 158 | −4.785 | −1.842 | 69.638 | 1.00 | 28.31 | C |
| ATOM | 1249 | O | ALA | A | 158 | −5.663 | −2.592 | 69.267 | 1.00 | 41.94 | O |
| ATOM | 1250 | CB | ALA | A | 158 | −5.232 | 0.285 | 70.861 | 1.00 | 25.06 | C |
| ATOM | 1251 | N | ASP | A | 159 | −3.753 | −1.539 | 68.865 | 1.00 | 34.19 | N |
| ATOM | 1252 | CA | ASP | A | 159 | −3.624 | −2.158 | 67.567 | 1.00 | 22.79 | C |
| ATOM | 1253 | C | ASP | A | 159 | −3.000 | −3.533 | 67.844 | 1.00 | 33.50 | C |
| ATOM | 1254 | O | ASP | A | 159 | −1.856 | −3.660 | 68.270 | 1.00 | 31.55 | O |
| ATOM | 1255 | CB | ASP | A | 159 | −2.727 | −1.322 | 66.649 | 1.00 | 40.04 | C |
| ATOM | 1256 | CG | ASP | A | 159 | −2.507 | −1.980 | 65.278 | 1.00 | 35.66 | C |
| ATOM | 1257 | OD1 | ASP | A | 159 | −2.989 | −3.124 | 65.051 | 1.00 | 33.87 | O |
| ATOM | 1258 | OD2 | ASP | A | 159 | −1.839 | −1.344 | 64.433 | 1.00 | 39.29 | O |
| ATOM | 1259 | N | ILE | A | 160 | −3.785 | −4.562 | 67.599 | 1.00 | 28.91 | N |
| ATOM | 1260 | CA | ILE | A | 160 | −3.368 | −5.915 | 67.841 | 1.00 | 27.87 | C |
| ATOM | 1261 | C | ILE | A | 160 | −2.166 | −6.445 | 67.071 | 1.00 | 29.69 | C |
| ATOM | 1262 | O | ILE | A | 160 | −1.391 | −7.219 | 67.620 | 1.00 | 41.03 | O |
| ATOM | 1263 | CB | ILE | A | 160 | −4.572 | −6.838 | 67.644 | 1.00 | 22.11 | C |
| ATOM | 1264 | CG1 | ILE | A | 160 | −5.584 | −6.562 | 68.761 | 1.00 | 26.42 | C |
| ATOM | 1265 | CG2 | ILE | A | 160 | −4.133 | −8.291 | 67.607 | 1.00 | 43.42 | C |
| ATOM | 1266 | CD1 | ILE | A | 160 | −6.857 | −7.318 | 68.610 | 1.00 | 37.75 | C |
| ATOM | 1267 | N | ILE | A | 161 | −1.991 | −6.039 | 65.820 | 1.00 | 30.83 | N |
| ATOM | 1268 | CA | ILE | A | 161 | −0.872 | −6.554 | 65.037 | 1.00 | 32.52 | C |
| ATOM | 1269 | C | ILE | A | 161 | 0.336 | −5.652 | 64.998 | 1.00 | 35.35 | C |
| ATOM | 1270 | O | ILE | A | 161 | 1.188 | −5.818 | 64.138 | 1.00 | 35.19 | O |
| ATOM | 1271 | CB | ILE | A | 161 | −1.271 | −6.883 | 63.566 | 1.00 | 30.95 | C |
| ATOM | 1272 | CG1 | ILE | A | 161 | −2.000 | −5.692 | 62.946 | 1.00 | 32.47 | C |
| ATOM | 1273 | CG2 | ILE | A | 161 | −2.123 | −8.150 | 63.539 | 1.00 | 39.58 | C |
| ATOM | 1274 | CD1 | ILE | A | 161 | −2.561 | −5.951 | 61.588 | 1.00 | 36.95 | C |
| ATOM | 1275 | N | GLN | A | 162 | 0.411 | −4.678 | 65.895 | 1.00 | 29.97 | N |
| ATOM | 1276 | CA | GLN | A | 162 | 1.596 | −3.841 | 65.923 | 1.00 | 35.99 | C |
| ATOM | 1277 | C | GLN | A | 162 | 2.596 | −4.476 | 66.914 | 1.00 | 30.49 | C |
| ATOM | 1278 | O | GLN | A | 162 | 2.543 | −4.227 | 68.115 | 1.00 | 41.18 | O |
| ATOM | 1279 | CB | GLN | A | 162 | 1.244 | −2.435 | 66.364 | 1.00 | 27.32 | C |
| ATOM | 1280 | CG | GLN | A | 162 | 2.455 | −1.572 | 66.632 | 1.00 | 37.01 | C |
| ATOM | 1281 | CD | GLN | A | 162 | 2.080 | −0.117 | 66.754 | 1.00 | 59.46 | C |
| ATOM | 1282 | OE1 | GLN | A | 162 | 1.944 | 0.583 | 65.746 | 1.00 | 71.60 | O |
| ATOM | 1283 | NE2 | GLN | A | 162 | 1.877 | 0.347 | 67.986 | 1.00 | 59.88 | N |
| ATOM | 1284 | N | PHE | A | 163 | 3.484 | −5.322 | 66.405 | 1.00 | 31.71 | N |
| ATOM | 1285 | CA | PHE | A | 163 | 4.459 | −5.980 | 67.258 | 1.00 | 30.87 | C |
| ATOM | 1286 | C | PHE | A | 163 | 5.750 | −5.184 | 67.290 | 1.00 | 43.50 | C |
| ATOM | 1287 | O | PHE | A | 163 | 6.166 | −4.616 | 66.277 | 1.00 | 36.56 | O |
| ATOM | 1288 | CB | PHE | A | 163 | 4.777 | −7.386 | 66.752 | 1.00 | 22.38 | C |
| ATOM | 1289 | CG | PHE | A | 163 | 3.561 | −8.255 | 66.514 | 1.00 | 26.76 | C |
| ATOM | 1290 | CD1 | PHE | A | 163 | 2.410 | −8.126 | 67.297 | 1.00 | 30.98 | C |
| ATOM | 1291 | CD2 | PHE | A | 163 | 3.602 | −9.248 | 65.542 | 1.00 | 29.43 | C |
| ATOM | 1292 | CE1 | PHE | A | 163 | 1.310 | −8.997 | 67.102 | 1.00 | 35.91 | C |
| ATOM | 1293 | CE2 | PHE | A | 163 | 2.522 | −10.125 | 65.338 | 1.00 | 32.21 | C |
| ATOM | 1294 | CZ | PHE | A | 163 | 1.373 | −10.002 | 66.117 | 1.00 | 24.61 | C |
| ATOM | 1295 | N | GLU | A | 164 | 6.400 | −5.152 | 68.448 | 1.00 | 37.10 | N |
| ATOM | 1296 | CA | GLU | A | 164 | 7.648 | −4.429 | 68.544 | 1.00 | 37.02 | C |

TABLE 1-continued

| ATOM | 1297 | C | GLU | A | 164 | 8.358 | -4.710 | 69.842 | 1.00 | 39.17 | C |
|---|---|---|---|---|---|---|---|---|---|---|---|
| ATOM | 1298 | O | GLU | A | 164 | 7.789 | -5.213 | 70.801 | 1.00 | 29.51 | O |
| ATOM | 1299 | CB | GLU | A | 164 | 7.417 | -2.920 | 68.417 | 1.00 | 50.30 | C |
| ATOM | 1300 | CG | GLU | A | 164 | 6.597 | -2.318 | 69.553 | 1.00 | 46.23 | C |
| ATOM | 1301 | CD | GLU | A | 164 | 6.158 | -0.883 | 69.260 | 1.00 | 79.82 | C |
| ATOM | 1302 | OE1 | GLU | A | 164 | 7.032 | -0.009 | 69.025 | 1.00 | 73.79 | O |
| ATOM | 1303 | OE2 | GLU | A | 164 | 4.928 | -0.635 | 69.263 | 1.00 | 82.04 | O |
| ATOM | 1304 | N | CYS | A | 165 | 9.616 | -4.316 | 69.856 | 1.00 | 40.04 | N |
| ATOM | 1305 | CA | CYS | A | 165 | 10.485 | -4.510 | 70.983 | 1.00 | 36.00 | C |
| ATOM | 1306 | C | CYS | A | 165 | 10.740 | -3.148 | 71.615 | 1.00 | 40.81 | C |
| ATOM | 1307 | O | CYS | A | 165 | 11.391 | -2.303 | 71.020 | 1.00 | 33.85 | O |
| ATOM | 1308 | CB | CYS | A | 165 | 11.770 | -5.140 | 70.463 | 1.00 | 37.19 | C |
| ATOM | 1309 | SG | CYS | A | 165 | 12.811 | -5.756 | 71.734 | 1.00 | 40.85 | S |
| ATOM | 1310 | N | LYS | A | 166 | 10.214 | -2.935 | 72.821 | 1.00 | 45.76 | N |
| ATOM | 1311 | CA | LYS | A | 166 | 10.368 | -1.654 | 73.505 | 1.00 | 43.27 | C |
| ATOM | 1312 | C | LYS | A | 166 | 11.012 | -1.819 | 74.885 | 1.00 | 50.06 | C |
| ATOM | 1313 | O | LYS | A | 166 | 11.106 | -2.934 | 75.411 | 1.00 | 30.74 | O |
| ATOM | 1314 | CB | LYS | A | 166 | 9.010 | -0.998 | 73.650 | 1.00 | 37.26 | C |
| ATOM | 1315 | CG | LYS | A | 166 | 8.076 | -1.809 | 74.512 | 1.00 | 30.06 | C |
| ATOM | 1316 | CD | LYS | A | 166 | 6.639 | -1.769 | 73.987 | 1.00 | 53.02 | C |
| ATOM | 1317 | CE | LYS | A | 166 | 6.024 | -0.380 | 74.096 | 1.00 | 55.97 | C |
| ATOM | 1318 | NZ | LYS | A | 166 | 6.620 | 0.581 | 73.136 | 1.00 | 57.98 | N |
| ATOM | 1319 | N | SER | A | 167 | 11.431 | -0.699 | 75.474 | 1.00 | 26.75 | N |
| ATOM | 1320 | CA | SER | A | 167 | 12.105 | -0.718 | 76.760 | 1.00 | 27.36 | C |
| ATOM | 1321 | C | SER | A | 167 | 12.090 | 0.657 | 77.409 | 1.00 | 32.98 | C |
| ATOM | 1322 | O | SER | A | 167 | 11.893 | 1.665 | 76.733 | 1.00 | 27.25 | O |
| ATOM | 1323 | CB | SER | A | 167 | 13.551 | -1.196 | 76.589 | 1.00 | 26.39 | C |
| ATOM | 1324 | OG | SER | A | 167 | 14.286 | -0.350 | 75.728 | 1.00 | 30.71 | O |
| ATOM | 1325 | N | PHE | A | 168 | 12.291 | 0.691 | 78.719 | 1.00 | 30.02 | N |
| ATOM | 1326 | CA | PHE | A | 168 | 12.289 | 1.948 | 79.467 | 1.00 | 28.46 | C |
| ATOM | 1327 | C | PHE | A | 168 | 13.615 | 2.665 | 79.315 | 1.00 | 40.56 | C |
| ATOM | 1328 | O | PHE | A | 168 | 14.682 | 2.049 | 79.301 | 1.00 | 36.03 | O |
| ATOM | 1329 | CB | PHE | A | 168 | 11.984 | 1.668 | 80.941 | 1.00 | 27.42 | C |
| ATOM | 1330 | CG | PHE | A | 168 | 10.593 | 1.122 | 81.157 | 1.00 | 37.34 | C |
| ATOM | 1331 | CD1 | PHE | A | 168 | 9.477 | 1.962 | 81.057 | 1.00 | 43.95 | C |
| ATOM | 1332 | CD2 | PHE | A | 168 | 10.388 | -0.233 | 81.367 | 1.00 | 28.97 | C |
| ATOM | 1333 | CE1 | PHE | A | 168 | 8.175 | 1.454 | 81.152 | 1.00 | 43.40 | C |
| ATOM | 1334 | CE2 | PHE | A | 168 | 9.085 | -0.760 | 81.465 | 1.00 | 48.63 | C |
| ATOM | 1335 | CZ | PHE | A | 168 | 7.977 | 0.086 | 81.357 | 1.00 | 26.70 | C |
| ATOM | 1336 | N | GLY | A | 169 | 13.540 | 3.980 | 79.191 | 1.00 | 35.33 | N |
| ATOM | 1337 | CA | GLY | A | 169 | 14.746 | 4.753 | 79.033 | 1.00 | 34.88 | C |
| ATOM | 1338 | C | GLY | A | 169 | 15.290 | 5.257 | 80.349 | 1.00 | 30.56 | C |
| ATOM | 1339 | O | GLY | A | 169 | 14.686 | 5.079 | 81.404 | 1.00 | 32.36 | O |
| ATOM | 1340 | N | HIS | A | 170 | 16.447 | 5.894 | 80.262 | 1.00 | 37.93 | N |
| ATOM | 1341 | CA | HIS | A | 170 | 17.112 | 6.473 | 81.416 | 1.00 | 52.44 | C |
| ATOM | 1342 | C | HIS | A | 170 | 17.050 | 7.992 | 81.210 | 1.00 | 59.02 | C |
| ATOM | 1343 | O | HIS | A | 170 | 16.749 | 8.454 | 80.114 | 1.00 | 51.95 | O |
| ATOM | 1344 | CB | HIS | A | 170 | 18.558 | 6.015 | 81.452 | 1.00 | 38.34 | C |
| ATOM | 1345 | CG | HIS | A | 170 | 19.241 | 6.313 | 82.737 | 1.00 | 50.20 | C |
| ATOM | 1346 | ND1 | HIS | A | 170 | 19.093 | 5.517 | 83.851 | 1.00 | 48.69 | N |
| ATOM | 1347 | CD2 | HIS | A | 170 | 20.055 | 7.332 | 83.099 | 1.00 | 51.09 | C |
| ATOM | 1348 | CE1 | HIS | A | 170 | 19.791 | 6.033 | 84.847 | 1.00 | 57.33 | C |
| ATOM | 1349 | NE2 | HIS | A | 170 | 20.384 | 7.133 | 84.417 | 1.00 | 44.07 | N |
| ATOM | 1350 | N | GLU | A | 171 | 17.349 | 8.777 | 82.236 | 1.00 | 56.68 | N |
| ATOM | 1351 | CA | GLU | A | 171 | 17.266 | 10.220 | 82.069 | 1.00 | 48.47 | C |
| ATOM | 1352 | C | GLU | A | 171 | 18.463 | 10.787 | 81.312 | 1.00 | 55.68 | C |
| ATOM | 1353 | O | GLU | A | 171 | 18.387 | 11.884 | 80.757 | 1.00 | 64.04 | O |
| ATOM | 1354 | CB | GLU | A | 171 | 17.123 | 10.914 | 83.429 | 1.00 | 67.18 | C |
| ATOM | 1355 | CG | GLU | A | 171 | 16.231 | 10.166 | 84.425 | 1.00 | 78.54 | C |
| ATOM | 1356 | CD | GLU | A | 171 | 16.921 | 8.934 | 85.023 | 1.00 | 85.35 | C |
| ATOM | 1357 | OE1 | GLU | A | 171 | 17.897 | 9.127 | 85.793 | 1.00 | 82.46 | O |
| ATOM | 1358 | OE2 | GLU | A | 171 | 16.498 | 7.786 | 84.722 | 1.00 | 57.29 | O |
| ATOM | 1359 | N | VAL | A | 172 | 19.564 | 10.049 | 81.272 | 1.00 | 39.51 | N |
| ATOM | 1360 | CA | VAL | A | 172 | 20.736 | 10.531 | 80.561 | 1.00 | 43.59 | C |
| ATOM | 1361 | C | VAL | A | 172 | 21.407 | 9.448 | 79.711 | 1.00 | 51.27 | C |
| ATOM | 1362 | O | VAL | A | 172 | 21.899 | 9.723 | 78.620 | 1.00 | 63.34 | O |
| ATOM | 1363 | CB | VAL | A | 172 | 21.764 | 11.151 | 81.550 | 1.00 | 60.62 | C |
| ATOM | 1364 | CG1 | VAL | A | 172 | 22.187 | 10.133 | 82.575 | 1.00 | 57.76 | C |
| ATOM | 1365 | CG2 | VAL | A | 172 | 22.971 | 11.674 | 80.800 | 1.00 | 61.93 | C |
| ATOM | 1366 | N | LEU | A | 173 | 21.417 | 8.219 | 80.208 | 1.00 | 51.43 | N |
| ATOM | 1367 | CA | LEU | A | 173 | 22.016 | 7.097 | 79.494 | 1.00 | 41.89 | C |
| ATOM | 1368 | C | LEU | A | 173 | 21.109 | 6.571 | 78.360 | 1.00 | 47.05 | C |
| ATOM | 1369 | O | LEU | A | 173 | 19.896 | 6.483 | 78.522 | 1.00 | 52.65 | O |
| ATOM | 1370 | CB | LEU | A | 173 | 22.287 | 5.962 | 80.484 | 1.00 | 32.50 | C |
| ATOM | 1371 | CG | LEU | A | 173 | 23.280 | 6.242 | 81.612 | 1.00 | 50.36 | C |
| ATOM | 1372 | CD1 | LEU | A | 173 | 23.076 | 5.269 | 82.763 | 1.00 | 31.75 | C |
| ATOM | 1373 | CD2 | LEU | A | 173 | 24.690 | 6.141 | 81.054 | 1.00 | 36.98 | C |
| ATOM | 1374 | N | ASN | A | 174 | 21.698 | 6.245 | 77.215 | 1.00 | 37.08 | N |
| ATOM | 1375 | CA | ASN | A | 174 | 20.953 | 5.666 | 76.087 | 1.00 | 37.76 | C |

TABLE 1-continued

| | | | | | | | | | | |
|---|---|---|---|---|---|---|---|---|---|---|
| ATOM | 1376 | C | ASN | A | 174 | 21.288 | 4.185 | 76.188 | 1.00 | 26.30 C |
| ATOM | 1377 | O | ASN | A | 174 | 22.171 | 3.685 | 75.479 | 1.00 | 38.84 O |
| ATOM | 1378 | CB | ASN | A | 174 | 21.465 | 6.200 | 74.751 | 1.00 | 38.84 C |
| ATOM | 1379 | CG | ASN | A | 174 | 21.373 | 7.704 | 74.656 | 1.00 | 67.21 C |
| ATOM | 1380 | OD1 | ASN | A | 174 | 22.149 | 8.429 | 75.288 | 1.00 | 80.01 O |
| ATOM | 1381 | ND2 | ASN | A | 174 | 20.415 | 8.190 | 73.876 | 1.00 | 68.70 N |
| ATOM | 1382 | N | LEU | A | 175 | 20.578 | 3.495 | 77.067 | 1.00 | 22.80 N |
| ATOM | 1383 | CA | LEU | A | 175 | 20.846 | 2.088 | 77.366 | 1.00 | 22.23 C |
| ATOM | 1384 | C | LEU | A | 175 | 20.919 | 1.116 | 76.209 | 1.00 | 18.80 C |
| ATOM | 1385 | O | LEU | A | 175 | 21.709 | 0.185 | 76.227 | 1.00 | 27.38 O |
| ATOM | 1386 | CB | LEU | A | 175 | 19.820 | 1.585 | 78.397 | 1.00 | 25.53 C |
| ATOM | 1387 | CG | LEU | A | 175 | 19.689 | 2.460 | 79.647 | 1.00 | 38.11 C |
| ATOM | 1388 | CD1 | LEU | A | 175 | 18.571 | 1.894 | 80.548 | 1.00 | 25.68 C |
| ATOM | 1389 | CD2 | LEU | A | 175 | 21.063 | 2.536 | 80.390 | 1.00 | 23.35 C |
| ATOM | 1390 | N | THR | A | 176 | 20.085 | 1.314 | 75.202 | 1.00 | 29.71 N |
| ATOM | 1391 | CA | THR | A | 176 | 20.085 | 0.410 | 74.061 | 1.00 | 26.53 C |
| ATOM | 1392 | C | THR | A | 176 | 21.233 | 0.662 | 73.113 | 1.00 | 30.40 C |
| ATOM | 1393 | O | THR | A | 176 | 21.480 | −0.139 | 72.230 | 1.00 | 27.19 O |
| ATOM | 1394 | CB | THR | A | 176 | 18.758 | 0.522 | 73.236 | 1.00 | 43.28 C |
| ATOM | 1395 | OG1 | THR | A | 176 | 18.620 | 1.847 | 72.721 | 1.00 | 38.69 O |
| ATOM | 1396 | CG2 | THR | A | 176 | 17.530 | 0.224 | 74.114 | 1.00 | 33.26 C |
| ATOM | 1397 | N | ARG | A | 177 | 21.949 | 1.763 | 73.311 | 1.00 | 34.23 N |
| ATOM | 1398 | CA | ARG | A | 177 | 23.018 | 2.126 | 72.397 | 1.00 | 36.94 C |
| ATOM | 1399 | C | ARG | A | 177 | 24.374 | 2.484 | 72.995 | 1.00 | 43.07 C |
| ATOM | 1400 | O | ARG | A | 177 | 25.194 | 3.063 | 72.303 | 1.00 | 37.60 O |
| ATOM | 1401 | CB | ARG | A | 177 | 22.551 | 3.294 | 71.530 | 1.00 | 32.08 C |
| ATOM | 1402 | CG | ARG | A | 177 | 21.567 | 2.942 | 70.440 | 1.00 | 42.12 C |
| ATOM | 1403 | CD | ARG | A | 177 | 21.126 | 4.190 | 69.666 | 1.00 | 38.80 C |
| ATOM | 1404 | NE | ARG | A | 177 | 19.782 | 4.588 | 70.061 | 1.00 | 60.55 N |
| ATOM | 1405 | CZ | ARG | A | 177 | 19.427 | 5.822 | 70.385 | 1.00 | 60.12 C |
| ATOM | 1406 | NH1 | ARG | A | 177 | 20.325 | 6.792 | 70.358 | 1.00 | 68.23 N |
| ATOM | 1407 | NH2 | ARG | A | 177 | 18.181 | 6.078 | 70.760 | 1.00 | 63.96 N |
| ATOM | 1408 | N | ASN | A | 178 | 24.617 | 2.171 | 74.264 | 1.00 | 36.12 N |
| ATOM | 1409 | CA | ASN | A | 178 | 25.918 | 2.492 | 74.867 | 1.00 | 42.68 C |
| ATOM | 1410 | C | ASN | A | 178 | 26.560 | 1.220 | 75.409 | 1.00 | 38.64 C |
| ATOM | 1411 | O | ASN | A | 178 | 27.460 | 1.275 | 76.235 | 1.00 | 38.08 O |
| ATOM | 1412 | CB | ASN | A | 178 | 25.749 | 3.506 | 76.003 | 1.00 | 27.21 C |
| ATOM | 1413 | CG | ASN | A | 178 | 24.916 | 2.962 | 77.170 | 1.00 | 38.83 C |
| ATOM | 1414 | OD1 | ASN | A | 178 | 24.521 | 1.785 | 77.186 | 1.00 | 39.07 O |
| ATOM | 1415 | ND2 | ASN | A | 178 | 24.662 | 3.818 | 78.164 | 1.00 | 30.54 N |
| ATOM | 1416 | N | GLY | A | 179 | 26.061 | 0.077 | 74.950 | 1.00 | 39.04 N |
| ATOM | 1417 | CA | GLY | A | 179 | 26.565 | −1.217 | 75.386 | 1.00 | 24.91 C |
| ATOM | 1418 | C | GLY | A | 179 | 25.985 | −1.739 | 76.705 | 1.00 | 27.06 C |
| ATOM | 1419 | O | GLY | A | 179 | 26.269 | −2.873 | 77.091 | 1.00 | 29.51 O |
| ATOM | 1420 | N | TYR | A | 180 | 25.185 | −0.923 | 77.392 | 1.00 | 22.07 N |
| ATOM | 1421 | CA | TYR | A | 180 | 24.604 | −1.321 | 78.685 | 1.00 | 31.90 C |
| ATOM | 1422 | C | TYR | A | 180 | 23.478 | −2.325 | 78.579 | 1.00 | 27.16 C |
| ATOM | 1423 | O | TYR | A | 180 | 23.477 | −3.339 | 79.279 | 1.00 | 37.14 O |
| ATOM | 1424 | CB | TYR | A | 180 | 24.049 | −0.100 | 79.422 | 1.00 | 27.98 C |
| ATOM | 1425 | CG | TYR | A | 180 | 25.062 | 0.712 | 80.182 | 1.00 | 32.39 C |
| ATOM | 1426 | CD1 | TYR | A | 180 | 26.399 | 0.749 | 79.790 | 1.00 | 32.11 C |
| ATOM | 1427 | CD2 | TYR | A | 180 | 24.667 | 1.493 | 81.267 | 1.00 | 35.56 C |
| ATOM | 1428 | CE1 | TYR | A | 180 | 27.324 | 1.549 | 80.463 | 1.00 | 38.05 C |
| ATOM | 1429 | CE2 | TYR | A | 180 | 25.563 | 2.292 | 81.936 | 1.00 | 35.19 C |
| ATOM | 1430 | CZ | TYR | A | 180 | 26.893 | 2.319 | 81.533 | 1.00 | 44.97 C |
| ATOM | 1431 | OH | TYR | A | 180 | 27.772 | 3.135 | 82.199 | 1.00 | 54.45 O |
| ATOM | 1432 | N | GLY | A | 181 | 22.514 | −2.004 | 77.707 | 1.00 | 33.00 N |
| ATOM | 1433 | CA | GLY | A | 181 | 21.349 | −2.837 | 77.505 | 1.00 | 29.05 C |
| ATOM | 1434 | C | GLY | A | 181 | 20.270 | −2.550 | 78.538 | 1.00 | 30.97 C |
| ATOM | 1435 | O | GLY | A | 181 | 20.532 | −1.932 | 79.561 | 1.00 | 29.65 O |
| ATOM | 1436 | N | SER | A | 182 | 19.050 | −2.998 | 78.269 | 1.00 | 29.39 N |
| ATOM | 1437 | CA | SER | A | 182 | 17.932 | −2.786 | 79.180 | 1.00 | 29.89 C |
| ATOM | 1438 | C | SER | A | 182 | 16.887 | −3.867 | 78.954 | 1.00 | 17.65 C |
| ATOM | 1439 | O | SER | A | 182 | 16.817 | −4.448 | 77.881 | 1.00 | 30.65 O |
| ATOM | 1440 | CB | SER | A | 182 | 17.300 | −1.411 | 78.962 | 1.00 | 18.97 C |
| ATOM | 1441 | OG | SER | A | 182 | 16.911 | −1.253 | 77.607 | 1.00 | 33.07 O |
| ATOM | 1442 | N | THR | A | 183 | 16.105 | −4.148 | 79.988 | 1.00 | 26.48 N |
| ATOM | 1443 | CA | THR | A | 183 | 15.059 | −5.151 | 79.920 | 1.00 | 23.34 C |
| ATOM | 1444 | C | THR | A | 183 | 14.163 | −4.846 | 78.714 | 1.00 | 23.56 C |
| ATOM | 1445 | O | THR | A | 183 | 13.730 | −3.711 | 78.527 | 1.00 | 25.24 O |
| ATOM | 1446 | CB | THR | A | 183 | 14.269 | −5.122 | 81.197 | 1.00 | 20.50 C |
| ATOM | 1447 | OG1 | THR | A | 183 | 15.162 | −5.431 | 82.272 | 1.00 | 19.00 O |
| ATOM | 1448 | CG2 | THR | A | 183 | 13.112 | −6.131 | 81.145 | 1.00 | 21.63 C |
| ATOM | 1449 | N | GLN | A | 184 | 13.950 | −5.844 | 77.872 | 1.00 | 20.68 N |
| ATOM | 1450 | CA | GLN | A | 184 | 13.130 | −5.686 | 76.662 | 1.00 | 27.68 C |
| ATOM | 1451 | C | GLN | A | 184 | 11.711 | −6.251 | 76.816 | 1.00 | 26.21 C |
| ATOM | 1452 | O | GLN | A | 184 | 11.527 | −7.373 | 77.296 | 1.00 | 28.54 O |
| ATOM | 1453 | CB | GLN | A | 184 | 13.821 | −6.375 | 75.455 | 1.00 | 23.86 C |
| ATOM | 1454 | CG | GLN | A | 184 | 15.151 | −5.755 | 75.057 | 1.00 | 22.80 C |

TABLE 1-continued

| ATOM | 1455 | CD | GLN | A | 184 | 15.021 | −4.252 | 74.822 | 1.00 | 37.95 | C |
|---|---|---|---|---|---|---|---|---|---|---|---|
| ATOM | 1456 | OE1 | GLN | A | 184 | 14.301 | −3.826 | 73.922 | 1.00 | 22.47 | O |
| ATOM | 1457 | NE2 | GLN | A | 184 | 15.699 | −3.449 | 75.642 | 1.00 | 27.87 | N |
| ATOM | 1458 | N | TYR | A | 185 | 10.731 | −5.452 | 76.405 | 1.00 | 25.44 | N |
| ATOM | 1459 | CA | TYR | A | 185 | 9.299 | −5.813 | 76.420 | 1.00 | 28.93 | C |
| ATOM | 1460 | C | TYR | A | 185 | 8.823 | −5.951 | 74.967 | 1.00 | 31.20 | C |
| ATOM | 1461 | O | TYR | A | 185 | 8.753 | −4.964 | 74.234 | 1.00 | 21.02 | O |
| ATOM | 1462 | CB | TYR | A | 185 | 8.464 | −4.721 | 77.094 | 1.00 | 25.81 | C |
| ATOM | 1463 | CG | TYR | A | 185 | 8.670 | −4.605 | 78.586 | 1.00 | 21.11 | C |
| ATOM | 1464 | CD1 | TYR | A | 185 | 9.887 | −4.162 | 79.118 | 1.00 | 19.53 | C |
| ATOM | 1465 | CD2 | TYR | A | 185 | 7.668 | −4.983 | 79.461 | 1.00 | 29.44 | C |
| ATOM | 1466 | CE1 | TYR | A | 185 | 10.095 | −4.104 | 80.499 | 1.00 | 25.00 | C |
| ATOM | 1467 | CE2 | TYR | A | 185 | 7.858 | −4.928 | 80.843 | 1.00 | 34.36 | C |
| ATOM | 1468 | CZ | TYR | A | 185 | 9.074 | −4.489 | 81.353 | 1.00 | 33.72 | C |
| ATOM | 1469 | OH | TYR | A | 185 | 9.257 | −4.440 | 82.713 | 1.00 | 36.88 | O |
| ATOM | 1470 | N | ILE | A | 186 | 8.535 | −7.176 | 74.549 | 1.00 | 21.02 | N |
| ATOM | 1471 | CA | ILE | A | 186 | 8.085 | −7.423 | 73.202 | 1.00 | 23.41 | C |
| ATOM | 1472 | C | ILE | A | 186 | 6.572 | −7.557 | 73.173 | 1.00 | 21.90 | C |
| ATOM | 1473 | O | ILE | A | 186 | 6.019 | −8.446 | 73.807 | 1.00 | 26.60 | O |
| ATOM | 1474 | CB | ILE | A | 186 | 8.700 | −8.726 | 72.646 | 1.00 | 24.78 | C |
| ATOM | 1475 | CG1 | ILE | A | 186 | 10.232 | −8.607 | 72.589 | 1.00 | 23.12 | C |
| ATOM | 1476 | CG2 | ILE | A | 186 | 8.079 | −9.032 | 71.304 | 1.00 | 21.41 | C |
| ATOM | 1477 | CD1 | ILE | A | 186 | 10.974 | −9.897 | 72.191 | 1.00 | 19.26 | C |
| ATOM | 1478 | N | ARG | A | 187 | 5.917 | −6.638 | 72.478 | 1.00 | 24.39 | N |
| ATOM | 1479 | CA | ARG | A | 187 | 4.471 | −6.661 | 72.302 | 1.00 | 24.16 | C |
| ATOM | 1480 | C | ARG | A | 187 | 4.310 | −7.690 | 71.170 | 1.00 | 26.94 | C |
| ATOM | 1481 | O | ARG | A | 187 | 4.866 | −7.505 | 70.096 | 1.00 | 21.41 | O |
| ATOM | 1482 | CB | ARG | A | 187 | 3.988 | −5.297 | 71.849 | 1.00 | 25.79 | C |
| ATOM | 1483 | CG | ARG | A | 187 | 3.655 | −4.336 | 72.984 | 1.00 | 27.55 | C |
| ATOM | 1484 | CD | ARG | A | 187 | 3.223 | −2.982 | 72.428 | 1.00 | 28.95 | C |
| ATOM | 1485 | NE | ARG | A | 187 | 2.955 | −1.994 | 73.465 | 1.00 | 26.15 | N |
| ATOM | 1486 | CZ | ARG | A | 187 | 2.642 | −0.736 | 73.188 | 1.00 | 47.70 | C |
| ATOM | 1487 | NH1 | ARG | A | 187 | 2.565 | −0.348 | 71.917 | 1.00 | 42.33 | N |
| ATOM | 1488 | NH2 | ARG | A | 187 | 2.409 | 0.138 | 74.161 | 1.00 | 28.11 | N |
| ATOM | 1489 | N | PHE | A | 188 | 3.543 | −8.749 | 71.403 | 1.00 | 21.81 | N |
| ATOM | 1490 | CA | PHE | A | 188 | 3.424 | −9.819 | 70.412 | 1.00 | 27.86 | C |
| ATOM | 1491 | C | PHE | A | 188 | 2.209 | −10.676 | 70.648 | 1.00 | 30.81 | C |
| ATOM | 1492 | O | PHE | A | 188 | 1.768 | −10.804 | 71.787 | 1.00 | 27.89 | O |
| ATOM | 1493 | CB | PHE | A | 188 | 4.651 | −10.740 | 70.521 | 1.00 | 37.56 | C |
| ATOM | 1494 | CG | PHE | A | 188 | 4.585 | −11.969 | 69.646 | 1.00 | 30.97 | C |
| ATOM | 1495 | CD1 | PHE | A | 188 | 4.834 | −11.880 | 68.279 | 1.00 | 25.15 | C |
| ATOM | 1496 | CD2 | PHE | A | 188 | 4.229 | −13.196 | 70.184 | 1.00 | 24.31 | C |
| ATOM | 1497 | CE1 | PHE | A | 188 | 4.728 | −13.004 | 67.450 | 1.00 | 34.59 | C |
| ATOM | 1498 | CE2 | PHE | A | 188 | 4.116 | −14.334 | 69.383 | 1.00 | 37.66 | C |
| ATOM | 1499 | CZ | PHE | A | 188 | 4.364 | −14.247 | 68.005 | 1.00 | 30.82 | C |
| ATOM | 1500 | N | SER | A | 189 | 1.676 | −11.275 | 69.581 | 1.00 | 35.72 | N |
| ATOM | 1501 | CA | SER | A | 189 | 0.545 | −12.195 | 69.727 | 1.00 | 30.78 | C |
| ATOM | 1502 | C | SER | A | 189 | 0.687 | −13.446 | 68.874 | 1.00 | 33.44 | C |
| ATOM | 1503 | O | SER | A | 189 | 0.909 | −13.378 | 67.668 | 1.00 | 34.68 | O |
| ATOM | 1504 | CB | SER | A | 189 | −0.805 | −11.532 | 69.403 | 1.00 | 49.08 | C |
| ATOM | 1505 | OG | SER | A | 189 | −1.852 | −12.507 | 69.418 | 1.00 | 37.51 | O |
| ATOM | 1506 | N | PRO | A | 190 | 0.581 | −14.621 | 69.498 | 1.00 | 25.24 | N |
| ATOM | 1507 | CA | PRO | A | 190 | 0.692 | −15.851 | 68.722 | 1.00 | 37.56 | C |
| ATOM | 1508 | C | PRO | A | 190 | −0.682 | −16.224 | 68.106 | 1.00 | 36.78 | C |
| ATOM | 1509 | O | PRO | A | 190 | −0.785 | −17.193 | 67.368 | 1.00 | 27.66 | O |
| ATOM | 1510 | CB | PRO | A | 190 | 1.142 | −16.859 | 69.767 | 1.00 | 32.05 | C |
| ATOM | 1511 | CG | PRO | A | 190 | 0.398 | −16.411 | 70.962 | 1.00 | 39.05 | C |
| ATOM | 1512 | CD | PRO | A | 190 | 0.521 | −14.913 | 70.937 | 1.00 | 32.44 | C |
| ATOM | 1513 | N | ASP | A | 191 | −1.718 | −15.431 | 68.397 | 1.00 | 23.83 | N |
| ATOM | 1514 | CA | ASP | A | 191 | −3.064 | −15.713 | 67.910 | 1.00 | 27.83 | C |
| ATOM | 1515 | C | ASP | A | 191 | −3.470 | −15.157 | 66.528 | 1.00 | 43.01 | C |
| ATOM | 1516 | O | ASP | A | 191 | −4.565 | −15.445 | 66.059 | 1.00 | 34.85 | O |
| ATOM | 1517 | CB | ASP | A | 191 | −4.062 | −15.269 | 68.977 | 1.00 | 19.36 | C |
| ATOM | 1518 | CG | ASP | A | 191 | −3.741 | −15.872 | 70.343 | 1.00 | 33.13 | C |
| ATOM | 1519 | OD1 | ASP | A | 191 | −3.554 | −17.115 | 70.406 | 1.00 | 43.94 | O |
| ATOM | 1520 | OD2 | ASP | A | 191 | −3.666 | −15.126 | 71.349 | 1.00 | 33.85 | O |
| ATOM | 1521 | N | PHE | A | 192 | −2.600 | −14.376 | 65.885 | 1.00 | 30.20 | N |
| ATOM | 1522 | CA | PHE | A | 192 | −2.883 | −13.816 | 64.562 | 1.00 | 25.08 | C |
| ATOM | 1523 | C | PHE | A | 192 | −1.644 | −13.921 | 63.698 | 1.00 | 25.54 | C |
| ATOM | 1524 | O | PHE | A | 192 | −0.551 | −14.100 | 64.213 | 1.00 | 33.26 | O |
| ATOM | 1525 | CB | PHE | A | 192 | −3.253 | −12.337 | 64.648 | 1.00 | 30.51 | C |
| ATOM | 1526 | CG | PHE | A | 192 | −4.344 | −12.036 | 65.628 | 1.00 | 40.20 | C |
| ATOM | 1527 | CD1 | PHE | A | 192 | −4.062 | −11.904 | 66.979 | 1.00 | 25.28 | C |
| ATOM | 1528 | CD2 | PHE | A | 192 | −5.659 | −11.870 | 65.195 | 1.00 | 27.85 | C |
| ATOM | 1529 | CE1 | PHE | A | 192 | −5.074 | −11.605 | 67.889 | 1.00 | 24.58 | C |
| ATOM | 1530 | CE2 | PHE | A | 192 | −6.690 | −11.567 | 66.108 | 1.00 | 26.54 | C |
| ATOM | 1531 | CZ | PHE | A | 192 | −6.406 | −11.434 | 67.438 | 1.00 | 20.89 | C |
| ATOM | 1532 | N | THR | A | 193 | −1.810 | −13.844 | 62.387 | 1.00 | 26.65 | N |
| ATOM | 1533 | CA | THR | A | 193 | −0.653 | −13.859 | 61.502 | 1.00 | 31.95 | C |

TABLE 1-continued

| | | | | | | | | | |
|---|---|---|---|---|---|---|---|---|---|
| ATOM | 1534 | C | THR | A | 193 | −1.042 | −13.095 | 60.235 | 1.00 | 36.86 | C |
| ATOM | 1535 | O | THR | A | 193 | −2.222 | −12.823 | 60.025 | 1.00 | 31.09 | O |
| ATOM | 1536 | CB | THR | A | 193 | −0.203 | −15.271 | 61.165 | 1.00 | 45.13 | C |
| ATOM | 1537 | OG1 | THR | A | 193 | 1.141 | −15.225 | 60.679 | 1.00 | 27.91 | O |
| ATOM | 1538 | CG2 | THR | A | 193 | −1.110 | −15.893 | 60.124 | 1.00 | 28.41 | C |
| ATOM | 1539 | N | PHE | A | 194 | −0.060 | −12.754 | 59.410 | 1.00 | 30.04 | N |
| ATOM | 1540 | CA | PHE | A | 194 | −0.297 | −11.973 | 58.204 | 1.00 | 30.99 | C |
| ATOM | 1541 | C | PHE | A | 194 | −0.266 | −12.792 | 56.938 | 1.00 | 22.12 | C |
| ATOM | 1542 | O | PHE | A | 194 | 0.547 | −13.699 | 56.787 | 1.00 | 33.98 | O |
| ATOM | 1543 | CB | PHE | A | 194 | 0.779 | −10.887 | 58.025 | 1.00 | 29.59 | C |
| ATOM | 1544 | CG | PHE | A | 194 | 1.021 | −10.043 | 59.232 | 1.00 | 52.30 | C |
| ATOM | 1545 | CD1 | PHE | A | 194 | 1.667 | −10.574 | 60.351 | 1.00 | 44.77 | C |
| ATOM | 1546 | CD2 | PHE | A | 194 | 0.623 | −8.704 | 59.251 | 1.00 | 46.80 | C |
| ATOM | 1547 | CE1 | PHE | A | 194 | 1.918 | −9.784 | 61.474 | 1.00 | 59.73 | C |
| ATOM | 1548 | CE2 | PHE | A | 194 | 0.867 | −7.904 | 60.365 | 1.00 | 44.11 | C |
| ATOM | 1549 | CZ | PHE | A | 194 | 1.518 | −8.445 | 61.485 | 1.00 | 43.49 | C |
| ATOM | 1550 | N | GLY | A | 195 | −1.127 | −12.430 | 55.999 | 1.00 | 32.59 | N |
| ATOM | 1551 | CA | GLY | A | 195 | −1.135 | −13.139 | 54.740 | 1.00 | 27.08 | C |
| ATOM | 1552 | C | GLY | A | 195 | −0.375 | −12.338 | 53.690 | 1.00 | 49.76 | C |
| ATOM | 1553 | O | GLY | A | 195 | −0.420 | −11.107 | 53.699 | 1.00 | 36.49 | O |
| ATOM | 1554 | N | PHE | A | 196 | 0.343 | −13.034 | 52.810 | 1.00 | 36.23 | N |
| ATOM | 1555 | CA | PHE | A | 196 | 1.053 | −12.400 | 51.725 | 1.00 | 47.22 | C |
| ATOM | 1556 | C | PHE | A | 196 | 0.877 | −13.222 | 50.439 | 1.00 | 53.71 | C |
| ATOM | 1557 | O | PHE | A | 196 | 0.263 | −14.291 | 50.457 | 1.00 | 44.34 | O |
| ATOM | 1558 | CB | PHE | A | 196 | 2.531 | −12.237 | 52.069 | 1.00 | 31.68 | C |
| ATOM | 1559 | CG | PHE | A | 196 | 3.244 | −13.521 | 52.328 | 1.00 | 48.37 | C |
| ATOM | 1560 | CD1 | PHE | A | 196 | 3.193 | −14.120 | 53.585 | 1.00 | 30.85 | C |
| ATOM | 1561 | CD2 | PHE | A | 196 | 4.003 | −14.127 | 51.320 | 1.00 | 39.39 | C |
| ATOM | 1562 | CE1 | PHE | A | 196 | 3.888 | −15.298 | 53.839 | 1.00 | 32.40 | C |
| ATOM | 1563 | CE2 | PHE | A | 196 | 4.700 | −15.307 | 51.569 | 1.00 | 41.15 | C |
| ATOM | 1564 | CZ | PHE | A | 196 | 4.638 | −15.893 | 52.843 | 1.00 | 29.08 | C |
| ATOM | 1565 | N | GLU | A | 197 | 1.386 | −12.703 | 49.326 | 1.00 | 40.79 | N |
| ATOM | 1566 | CA | GLU | A | 197 | 1.294 | −13.384 | 48.040 | 1.00 | 48.23 | C |
| ATOM | 1567 | C | GLU | A | 197 | 2.684 | −13.741 | 47.580 | 1.00 | 47.44 | C |
| ATOM | 1568 | O | GLU | A | 197 | 3.647 | −13.072 | 47.929 | 1.00 | 50.83 | O |
| ATOM | 1569 | CB | GLU | A | 197 | 0.656 | −12.487 | 46.991 | 1.00 | 35.17 | C |
| ATOM | 1570 | CG | GLU | A | 197 | −0.842 | −12.425 | 47.037 | 1.00 | 44.27 | C |
| ATOM | 1571 | CD | GLU | A | 197 | −1.397 | −11.387 | 46.065 | 1.00 | 67.09 | C |
| ATOM | 1572 | OE1 | GLU | A | 197 | −0.921 | −11.331 | 44.905 | 1.00 | 66.96 | O |
| ATOM | 1573 | OE2 | GLU | A | 197 | −2.311 | −10.627 | 46.456 | 1.00 | 63.96 | O |
| ATOM | 1574 | N | GLU | A | 198 | 2.783 | −14.770 | 46.764 | 1.00 | 60.85 | N |
| ATOM | 1575 | CA | GLU | A | 198 | 4.058 | −15.249 | 46.265 | 1.00 | 65.72 | C |
| ATOM | 1576 | C | GLU | A | 198 | 3.822 | −16.577 | 45.573 | 1.00 | 73.64 | C |
| ATOM | 1577 | O | GLU | A | 198 | 2.701 | −17.084 | 45.568 | 1.00 | 82.37 | O |
| ATOM | 1578 | CB | GLU | A | 198 | 5.072 | −15.418 | 47.391 | 1.00 | 62.67 | C |
| ATOM | 1579 | CG | GLU | A | 198 | 6.491 | −15.658 | 46.922 | 1.00 | 71.33 | C |
| ATOM | 1580 | CD | GLU | A | 198 | 6.907 | −14.697 | 45.820 | 1.00 | 83.94 | C |
| ATOM | 1581 | OE1 | GLU | A | 198 | 6.722 | −13.472 | 45.981 | 1.00 | 91.15 | O |
| ATOM | 1582 | OE2 | GLU | A | 198 | 7.424 | −15.167 | 44.785 | 1.00 | 93.29 | O |
| ATOM | 1583 | N | SER | A | 199 | 4.872 | −17.130 | 44.977 | 1.00 | 81.35 | N |
| ATOM | 1584 | CA | SER | A | 199 | 4.789 | −18.416 | 44.292 | 1.00 | 78.80 | C |
| ATOM | 1585 | C | SER | A | 199 | 6.022 | −18.592 | 43.426 | 1.00 | 84.33 | C |
| ATOM | 1586 | O | SER | A | 199 | 6.069 | −18.104 | 42.292 | 1.00 | 92.07 | O |
| ATOM | 1587 | CB | SER | A | 199 | 3.532 | −18.492 | 43.418 | 1.00 | 87.05 | C |
| ATOM | 1588 | OG | SER | A | 199 | 3.321 | −19.808 | 42.929 | 1.00 | 85.72 | O |
| ATOM | 1589 | N | LEU | A | 200 | 7.019 | −19.288 | 43.968 | 1.00 | 88.70 | N |
| ATOM | 1590 | CA | LEU | A | 200 | 8.266 | −19.538 | 43.248 | 1.00 | 92.19 | C |
| ATOM | 1591 | C | LEU | A | 200 | 7.983 | −20.363 | 41.979 | 1.00 | 89.24 | C |
| ATOM | 1592 | O | LEU | A | 200 | 7.472 | −21.479 | 42.047 | 1.00 | 79.41 | O |
| ATOM | 1593 | CB | LEU | A | 200 | 9.276 | −20.245 | 44.169 | 1.00 | 86.65 | C |
| ATOM | 1594 | CG | LEU | A | 200 | 9.713 | −19.497 | 45.446 | 1.00 | 91.81 | C |
| ATOM | 1595 | CD1 | LEU | A | 200 | 10.577 | −20.385 | 46.339 | 1.00 | 74.58 | C |
| ATOM | 1596 | CD2 | LEU | A | 200 | 10.444 | −18.217 | 45.089 | 1.00 | 88.75 | C |
| ATOM | 1597 | N | GLU | A | 201 | 8.327 | −19.758 | 40.834 | 1.00 | 89.05 | N |
| ATOM | 1598 | CA | GLU | A | 201 | 8.130 | −20.319 | 39.491 | 1.00 | 83.19 | C |
| ATOM | 1599 | C | GLU | A | 201 | 9.449 | −20.425 | 38.733 | 1.00 | 82.12 | C |
| ATOM | 1600 | O | GLU | A | 201 | 10.520 | −20.442 | 39.334 | 1.00 | 95.54 | O |
| ATOM | 1601 | CB | GLU | A | 201 | 7.181 | −19.428 | 38.680 | 1.00 | 86.08 | C |
| ATOM | 1602 | CG | GLU | A | 201 | 5.870 | −19.119 | 39.373 | 1.00 | 87.02 | C |
| ATOM | 1603 | CD | GLU | A | 201 | 5.081 | −20.369 | 39.676 | 1.00 | 90.98 | C |
| ATOM | 1604 | OE1 | GLU | A | 201 | 4.395 | −20.901 | 38.775 | 1.00 | 94.97 | O |
| ATOM | 1605 | OE2 | GLU | A | 201 | 5.136 | −20.820 | 40.843 | 1.00 | 80.70 | O |
| ATOM | 1606 | N | VAL | A | 202 | 9.368 | −20.507 | 37.407 | 0.00 | 75.22 | N |
| ATOM | 1607 | CA | VAL | A | 202 | 10.568 | −20.618 | 36.586 | 0.00 | 69.86 | C |
| ATOM | 1608 | C | VAL | A | 202 | 10.652 | −19.614 | 35.436 | 0.00 | 67.47 | C |
| ATOM | 1609 | O | VAL | A | 202 | 11.422 | −18.655 | 35.502 | 0.00 | 66.78 | O |
| ATOM | 1610 | CB | VAL | A | 202 | 10.710 | −22.040 | 36.002 | 0.00 | 68.90 | C |
| ATOM | 1611 | CG1 | VAL | A | 202 | 11.984 | −22.187 | 35.197 | 0.00 | 68.06 | C |
| ATOM | 1612 | CG2 | VAL | A | 202 | 10.663 | −23.067 | 37.121 | 0.00 | 68.06 | C |

TABLE 1-continued

| | | | | | | | | | | |
|---|---|---|---|---|---|---|---|---|---|---|
| ATOM | 1613 | N | ASP | A | 203 | 9.866 | −19.829 | 34.384 | 0.00 | 65.09 | N |
| ATOM | 1614 | CA | ASP | A | 203 | 9.908 | −18.934 | 33.232 | 0.00 | 63.13 | C |
| ATOM | 1615 | C | ASP | A | 203 | 8.592 | −18.278 | 32.816 | 0.00 | 62.34 | C |
| ATOM | 1616 | O | ASP | A | 203 | 8.449 | −17.060 | 32.916 | 0.00 | 62.07 | O |
| ATOM | 1617 | CB | ASP | A | 203 | 10.509 | −19.668 | 32.029 | 0.00 | 62.25 | C |
| ATOM | 1618 | CG | ASP | A | 203 | 11.977 | −20.002 | 32.224 | 0.00 | 61.54 | C |
| ATOM | 1619 | OD1 | ASP | A | 203 | 12.784 | −19.063 | 32.392 | 0.00 | 61.12 | O |
| ATOM | 1620 | OD2 | ASP | A | 203 | 12.324 | −21.202 | 32.210 | 0.00 | 61.12 | O |
| ATOM | 1621 | N | THR | A | 204 | 7.634 | −19.072 | 32.348 | 0.00 | 61.67 | N |
| ATOM | 1622 | CA | THR | A | 204 | 6.359 | −18.518 | 31.896 | 0.00 | 61.20 | C |
| ATOM | 1623 | C | THR | A | 204 | 5.132 | −19.292 | 32.369 | 0.00 | 61.43 | C |
| ATOM | 1624 | O | THR | A | 204 | 4.754 | −20.280 | 31.738 | 0.00 | 61.15 | O |
| ATOM | 1625 | CB | THR | A | 204 | 6.309 | −18.464 | 30.352 | 0.00 | 60.74 | C |
| ATOM | 1626 | OG1 | THR | A | 204 | 6.427 | −19.788 | 29.822 | 0.00 | 60.36 | O |
| ATOM | 1627 | CG2 | THR | A | 204 | 7.425 | −17.585 | 29.810 | 0.00 | 60.36 | C |
| ATOM | 1628 | N | ASN | A | 205 | 4.494 | −18.852 | 33.487 | 0.00 | 62.01 | N |
| ATOM | 1629 | CA | ASN | A | 205 | 3.309 | −19.571 | 33.886 | 0.00 | 63.12 | C |
| ATOM | 1630 | C | ASN | A | 205 | 2.530 | −19.045 | 35.104 | 0.00 | 64.83 | C |
| ATOM | 1631 | O | ASN | A | 205 | 2.310 | −19.825 | 36.017 | 0.00 | 64.36 | O |
| ATOM | 1632 | CB | ASN | A | 205 | 3.677 | −21.039 | 34.143 | 0.00 | 61.87 | C |
| ATOM | 1633 | CG | ASN | A | 205 | 2.461 | −21.910 | 34.431 | 0.00 | 61.16 | C |
| ATOM | 1634 | OD1 | ASN | A | 205 | 1.553 | −21.988 | 33.603 | 0.00 | 60.75 | O |
| ATOM | 1635 | ND2 | ASN | A | 205 | 2.437 | −22.568 | 35.584 | 0.00 | 60.75 | N |
| ATOM | 1636 | N | PRO | A | 206 | 2.046 | −17.818 | 35.175 | 1.00 | 72.72 | N |
| ATOM | 1637 | CA | PRO | A | 206 | 1.248 | −17.600 | 36.402 | 1.00 | 65.86 | C |
| ATOM | 1638 | C | PRO | A | 206 | −0.225 | −17.481 | 36.065 | 1.00 | 60.89 | C |
| ATOM | 1639 | O | PRO | A | 206 | −0.865 | −16.557 | 36.551 | 1.00 | 49.06 | O |
| ATOM | 1640 | CB | PRO | A | 206 | 1.745 | −16.283 | 37.004 | 1.00 | 68.26 | C |
| ATOM | 1641 | CG | PRO | A | 206 | 2.120 | −15.507 | 35.791 | 1.00 | 75.59 | C |
| ATOM | 1642 | CD | PRO | A | 206 | 2.740 | −16.521 | 34.876 | 1.00 | 77.17 | C |
| ATOM | 1643 | N | LEU | A | 207 | −0.780 | −18.392 | 35.265 | 1.00 | 71.10 | N |
| ATOM | 1644 | CA | LEU | A | 207 | −2.206 | −18.341 | 34.894 | 1.00 | 64.94 | C |
| ATOM | 1645 | C | LEU | A | 207 | −3.167 | −18.222 | 36.080 | 1.00 | 58.65 | C |
| ATOM | 1646 | O | LEU | A | 207 | −4.131 | −17.463 | 36.023 | 1.00 | 52.01 | O |
| ATOM | 1647 | CB | LEU | A | 207 | −2.596 | −19.576 | 34.065 | 1.00 | 67.79 | C |
| ATOM | 1648 | CG | LEU | A | 207 | −4.013 | −19.611 | 33.465 | 1.00 | 75.77 | C |
| ATOM | 1649 | CD1 | LEU | A | 207 | −4.137 | −18.592 | 32.337 | 1.00 | 77.06 | C |
| ATOM | 1650 | CD2 | LEU | A | 207 | −4.303 | −20.996 | 32.928 | 1.00 | 75.39 | C |
| ATOM | 1651 | N | LEU | A | 208 | −2.906 | −18.964 | 37.153 | 1.00 | 52.92 | N |
| ATOM | 1652 | CA | LEU | A | 208 | −3.777 | −18.926 | 38.325 | 1.00 | 55.70 | C |
| ATOM | 1653 | C | LEU | A | 208 | −3.492 | −17.796 | 39.301 | 1.00 | 53.26 | C |
| ATOM | 1654 | O | LEU | A | 208 | −4.180 | −17.678 | 40.308 | 1.00 | 62.02 | O |
| ATOM | 1655 | CB | LEU | A | 208 | −3.690 | −20.244 | 39.994 | 1.00 | 59.46 | C |
| ATOM | 1656 | CG | LEU | A | 208 | −4.188 | −21.500 | 38.403 | 1.00 | 49.09 | C |
| ATOM | 1657 | CD1 | LEU | A | 208 | −3.958 | −22.690 | 39.320 | 1.00 | 37.65 | C |
| ATOM | 1658 | CD2 | LEU | A | 208 | −5.673 | −21.329 | 38.050 | 1.00 | 48.93 | C |
| ATOM | 1659 | N | GLY | A | 209 | −2.482 | −16.977 | 39.015 | 1.00 | 63.39 | N |
| ATOM | 1660 | CA | GLY | A | 209 | −2.139 | −15.886 | 39.912 | 1.00 | 57.26 | C |
| ATOM | 1661 | C | GLY | A | 209 | −1.248 | −16.384 | 41.037 | 1.00 | 58.32 | C |
| ATOM | 1662 | O | GLY | A | 209 | −1.039 | −17.591 | 41.185 | 1.00 | 53.84 | O |
| ATOM | 1663 | N | ALA | A | 210 | −0.723 | −15.465 | 41.840 | 1.00 | 52.43 | N |
| ATOM | 1664 | CA | ALA | A | 210 | 0.154 | −15.847 | 42.944 | 1.00 | 48.98 | C |
| ATOM | 1665 | C | ALA | A | 210 | −0.615 | −16.549 | 44.046 | 1.00 | 38.89 | C |
| ATOM | 1666 | O | ALA | A | 210 | −1.803 | −16.318 | 44.251 | 1.00 | 46.07 | O |
| ATOM | 1667 | CB | ALA | A | 210 | 0.857 | −14.630 | 43.512 | 1.00 | 56.75 | C |
| ATOM | 1668 | N | GLY | A | 211 | 0.080 | −17.428 | 44.747 | 1.00 | 56.44 | N |
| ATOM | 1669 | CA | GLY | A | 211 | −0.538 | −18.153 | 45.835 | 1.00 | 51.28 | C |
| ATOM | 1670 | C | GLY | A | 211 | −0.696 | −17.206 | 47.000 | 1.00 | 51.99 | C |
| ATOM | 1671 | O | GLY | A | 211 | 0.002 | −16.191 | 47.095 | 1.00 | 57.95 | O |
| ATOM | 1672 | N | LYS | A | 212 | −1.638 | −17.526 | 47.871 | 1.00 | 40.22 | N |
| ATOM | 1673 | CA | LYS | A | 212 | −1.909 | −16.731 | 49.057 | 1.00 | 49.88 | C |
| ATOM | 1674 | C | LYS | A | 212 | −1.418 | −17.536 | 50.261 | 1.00 | 53.77 | C |
| ATOM | 1675 | O | LYS | A | 212 | −1.955 | −18.611 | 50.561 | 1.00 | 41.99 | O |
| ATOM | 1676 | CB | LYS | A | 212 | −3.412 | −16.461 | 49.169 | 1.00 | 47.53 | C |
| ATOM | 1677 | CG | LYS | A | 212 | −4.037 | −15.913 | 47.880 | 1.00 | 51.03 | C |
| ATOM | 1678 | CD | LYS | A | 212 | −5.553 | −15.869 | 47.980 | 1.00 | 66.40 | C |
| ATOM | 1679 | CE | LYS | A | 212 | −6.201 | −15.537 | 46.643 | 1.00 | 70.80 | C |
| ATOM | 1680 | NZ | LYS | A | 212 | −5.850 | −14.174 | 46.165 | 1.00 | 67.99 | N |
| ATOM | 1681 | N | PHE | A | 213 | −0.399 | −17.012 | 50.943 | 1.00 | 45.18 | N |
| ATOM | 1682 | CA | PHE | A | 213 | 0.179 | −17.688 | 52.093 | 1.00 | 30.32 | C |
| ATOM | 1683 | C | PHE | A | 213 | 0.144 | −16.899 | 53.398 | 1.00 | 45.88 | C |
| ATOM | 1684 | O | PHE | A | 213 | −0.198 | −15.719 | 53.426 | 1.00 | 36.58 | O |
| ATOM | 1685 | CB | PHE | A | 213 | 1.630 | −18.098 | 51.815 | 1.00 | 26.52 | C |
| ATOM | 1686 | CG | PHE | A | 213 | 1.807 | −18.946 | 50.598 | 1.00 | 24.41 | C |
| ATOM | 1687 | CD1 | PHE | A | 213 | 1.925 | −18.354 | 49.329 | 1.00 | 35.38 | C |
| ATOM | 1688 | CD2 | PHE | A | 213 | 1.898 | −20.339 | 50.707 | 1.00 | 42.02 | C |
| ATOM | 1689 | CE1 | PHE | A | 213 | 2.139 | −19.136 | 48.179 | 1.00 | 40.61 | C |
| ATOM | 1690 | CE2 | PHE | A | 213 | 2.110 | −21.151 | 49.567 | 1.00 | 37.42 | C |
| ATOM | 1691 | CZ | PHE | A | 213 | 2.232 | −20.554 | 48.301 | 1.00 | 43.25 | C |

TABLE 1-continued

| | | | | | | | | | | |
|---|---|---|---|---|---|---|---|---|---|---|
| ATOM | 1692 | N | ALA | A | 214 | 0.496 | −17.576 | 54.490 | 1.00 | 35.13 | N |
| ATOM | 1693 | CA | ALA | A | 214 | 0.510 | −16.943 | 55.793 | 1.00 | 46.86 | C |
| ATOM | 1694 | C | ALA | A | 214 | 1.916 | −17.056 | 56.386 | 1.00 | 36.79 | C |
| ATOM | 1695 | O | ALA | A | 214 | 2.633 | −18.019 | 56.173 | 1.00 | 30.73 | O |
| ATOM | 1696 | CB | ALA | A | 214 | −0.540 | −17.591 | 56.737 | 1.00 | 24.94 | C |
| ATOM | 1697 | N | THR | A | 215 | 2.294 | −16.035 | 57.125 | 1.00 | 31.38 | N |
| ATOM | 1698 | CA | THR | A | 215 | 3.592 | −15.987 | 57.753 | 1.00 | 34.59 | C |
| ATOM | 1699 | C | THR | A | 215 | 3.627 | −16.862 | 58.991 | 1.00 | 31.69 | C |
| ATOM | 1700 | O | THR | A | 215 | 2.741 | −16.794 | 59.830 | 1.00 | 28.57 | O |
| ATOM | 1701 | CB | THR | A | 215 | 3.933 | −14.537 | 58.183 | 1.00 | 30.92 | C |
| ATOM | 1702 | OG1 | THR | A | 215 | 4.181 | −13.757 | 57.019 | 1.00 | 30.86 | O |
| ATOM | 1703 | CG2 | THR | A | 215 | 5.174 | −14.509 | 59.101 | 1.00 | 29.49 | C |
| ATOM | 1704 | N | ASP | A | 216 | 4.660 | −17.667 | 59.113 | 1.00 | 23.29 | N |
| ATOM | 1705 | CA | ASP | A | 216 | 4.792 | −18.481 | 60.305 | 1.00 | 32.91 | C |
| ATOM | 1706 | C | ASP | A | 216 | 5.122 | −17.569 | 61.507 | 1.00 | 26.35 | C |
| ATOM | 1707 | O | ASP | A | 216 | 6.113 | −16.853 | 61.490 | 1.00 | 30.62 | O |
| ATOM | 1708 | CB | ASP | A | 216 | 5.925 | −19.479 | 60.133 | 1.00 | 25.07 | C |
| ATOM | 1709 | CG | ASP | A | 216 | 6.017 | −20.458 | 61.304 | 1.00 | 34.92 | C |
| ATOM | 1710 | OD1 | ASP | A | 216 | 5.613 | −20.098 | 62.433 | 1.00 | 31.92 | O |
| ATOM | 1711 | OD2 | ASP | A | 216 | 6.509 | −21.581 | 61.096 | 1.00 | 26.35 | O |
| ATOM | 1712 | N | PRO | A | 217 | 4.318 | −17.627 | 62.575 | 1.00 | 22.54 | N |
| ATOM | 1713 | CA | PRO | A | 217 | 4.486 | −16.831 | 63.798 | 1.00 | 34.24 | C |
| ATOM | 1714 | C | PRO | A | 217 | 5.863 | −16.949 | 64.457 | 1.00 | 29.48 | C |
| ATOM | 1715 | O | PRO | A | 217 | 6.303 | −16.040 | 65.156 | 1.00 | 24.59 | O |
| ATOM | 1716 | CB | PRO | A | 217 | 3.407 | −17.383 | 64.726 | 1.00 | 30.46 | C |
| ATOM | 1717 | CG | PRO | A | 217 | 2.395 | −17.922 | 63.801 | 1.00 | 38.93 | C |
| ATOM | 1718 | CD | PRO | A | 217 | 3.205 | −18.573 | 62.729 | 1.00 | 30.40 | C |
| ATOM | 1719 | N | ALA | A | 218 | 6.520 | −18.082 | 64.261 | 1.00 | 22.34 | N |
| ATOM | 1720 | CA | ALA | A | 218 | 7.844 | −18.304 | 64.860 | 1.00 | 23.35 | C |
| ATOM | 1721 | C | ALA | A | 218 | 8.879 | −17.357 | 64.251 | 1.00 | 38.08 | C |
| ATOM | 1722 | O | ALA | A | 218 | 9.856 | −16.996 | 64.913 | 1.00 | 26.73 | O |
| ATOM | 1723 | CB | ALA | A | 218 | 8.285 | −19.759 | 64.646 | 1.00 | 33.53 | C |
| ATOM | 1724 | N | VAL | A | 219 | 8.661 | −16.983 | 62.982 | 1.00 | 27.36 | N |
| ATOM | 1725 | CA | VAL | A | 219 | 9.545 | −16.065 | 62.282 | 1.00 | 33.14 | C |
| ATOM | 1726 | C | VAL | A | 219 | 9.280 | −14.667 | 62.841 | 1.00 | 28.23 | C |
| ATOM | 1727 | O | VAL | A | 219 | 10.208 | −13.941 | 63.152 | 1.00 | 34.21 | O |
| ATOM | 1728 | CB | VAL | A | 219 | 9.297 | −16.097 | 60.740 | 1.00 | 34.75 | C |
| ATOM | 1729 | CG1 | VAL | A | 219 | 10.173 | −15.081 | 60.049 | 1.00 | 29.14 | C |
| ATOM | 1730 | CG2 | VAL | A | 219 | 9.644 | −17.491 | 60.185 | 1.00 | 33.96 | C |
| ATOM | 1731 | N | THR | A | 220 | 8.006 | −14.324 | 63.002 | 1.00 | 34.70 | N |
| ATOM | 1732 | CA | THR | A | 220 | 7.605 | −13.035 | 63.538 | 1.00 | 27.42 | C |
| ATOM | 1733 | C | THR | A | 220 | 8.137 | −12.886 | 64.959 | 1.00 | 30.41 | C |
| ATOM | 1734 | O | THR | A | 220 | 8.521 | −11.809 | 65.356 | 1.00 | 31.54 | O |
| ATOM | 1735 | CB | THR | A | 220 | 6.045 | −12.894 | 63.564 | 1.00 | 24.00 | C |
| ATOM | 1736 | OG1 | THR | A | 220 | 5.541 | −13.069 | 62.250 | 1.00 | 30.41 | O |
| ATOM | 1737 | CG2 | THR | A | 220 | 5.622 | −11.527 | 64.017 | 1.00 | 22.46 | C |
| ATOM | 1738 | N | LEU | A | 221 | 8.156 | −13.959 | 65.746 | 1.00 | 25.36 | N |
| ATOM | 1739 | CA | LEU | A | 221 | 8.701 | −13.819 | 67.090 | 1.00 | 31.72 | C |
| ATOM | 1740 | C | LEU | A | 221 | 10.231 | −13.732 | 67.001 | 1.00 | 21.17 | C |
| ATOM | 1741 | O | LEU | A | 221 | 10.844 | −12.895 | 67.666 | 1.00 | 24.64 | O |
| ATOM | 1742 | CB | LEU | A | 221 | 8.287 | −14.986 | 67.992 | 1.00 | 30.59 | C |
| ATOM | 1743 | CG | LEU | A | 221 | 8.766 | −14.985 | 69.456 | 1.00 | 34.36 | C |
| ATOM | 1744 | CD1 | LEU | A | 221 | 8.289 | −13.703 | 70.181 | 1.00 | 19.38 | C |
| ATOM | 1745 | CD2 | LEU | A | 221 | 8.201 | −16.216 | 70.177 | 1.00 | 19.68 | C |
| ATOM | 1746 | N | ALA | A | 222 | 10.845 | −14.551 | 66.151 | 1.00 | 17.66 | N |
| ATOM | 1747 | CA | ALA | A | 222 | 12.307 | −14.523 | 66.056 | 1.00 | 27.17 | C |
| ATOM | 1748 | C | ALA | A | 222 | 12.784 | −13.109 | 65.675 | 1.00 | 36.47 | C |
| ATOM | 1749 | O | ALA | A | 222 | 13.789 | −12.608 | 66.203 | 1.00 | 24.67 | O |
| ATOM | 1750 | CB | ALA | A | 222 | 12.806 | −15.540 | 65.045 | 1.00 | 17.21 | C |
| ATOM | 1751 | N | HIS | A | 223 | 12.047 | −12.480 | 64.765 | 1.00 | 23.59 | N |
| ATOM | 1752 | CA | HIS | A | 223 | 12.357 | −11.126 | 64.351 | 1.00 | 39.65 | C |
| ATOM | 1753 | C | HIS | A | 223 | 12.470 | −10.195 | 65.580 | 1.00 | 33.46 | C |
| ATOM | 1754 | O | HIS | A | 223 | 13.487 | −9.527 | 65.770 | 1.00 | 23.09 | O |
| ATOM | 1755 | CB | HIS | A | 223 | 11.270 | −10.606 | 63.419 | 1.00 | 22.00 | C |
| ATOM | 1756 | CG | HIS | A | 223 | 11.561 | −9.255 | 62.863 | 1.00 | 26.90 | C |
| ATOM | 1757 | ND1 | HIS | A | 223 | 12.193 | −9.067 | 61.654 | 1.00 | 28.19 | N |
| ATOM | 1758 | CD2 | HIS | A | 223 | 11.273 | −8.022 | 63.340 | 1.00 | 20.94 | C |
| ATOM | 1759 | CE1 | HIS | A | 223 | 12.274 | −7.773 | 61.404 | 1.00 | 31.61 | C |
| ATOM | 1760 | NE2 | HIS | A | 223 | 11.724 | −7.121 | 62.410 | 1.00 | 26.33 | N |
| ATOM | 1761 | N | GLN | A | 224 | 11.426 | −10.155 | 66.402 | 1.00 | 16.78 | N |
| ATOM | 1762 | CA | GLN | A | 224 | 11.431 | −9.325 | 67.604 | 1.00 | 20.88 | C |
| ATOM | 1763 | C | GLN | A | 224 | 12.553 | −9.682 | 68.593 | 1.00 | 29.53 | C |
| ATOM | 1764 | O | GLN | A | 224 | 13.123 | −8.802 | 69.249 | 1.00 | 22.55 | O |
| ATOM | 1765 | CB | GLN | A | 224 | 10.086 | −9.437 | 68.325 | 1.00 | 22.12 | C |
| ATOM | 1766 | CG | GLN | A | 224 | 8.943 | −8.985 | 67.460 | 1.00 | 24.88 | C |
| ATOM | 1767 | CD | GLN | A | 224 | 9.115 | −7.536 | 67.076 | 1.00 | 42.15 | C |
| ATOM | 1768 | OE1 | GLN | A | 224 | 8.661 | −7.093 | 66.037 | 1.00 | 43.54 | O |
| ATOM | 1769 | NE2 | GLN | A | 224 | 9.780 | −6.783 | 67.936 | 1.00 | 47.31 | N |
| ATOM | 1770 | N | LEU | A | 225 | 12.868 | −10.964 | 68.705 | 1.00 | 19.20 | N |

TABLE 1-continued

| | | | | | | | | | | |
|---|---|---|---|---|---|---|---|---|---|---|
| ATOM | 1771 | CA | LEU | A | 225 | 13.901 | −11.402 | 69.623 | 1.00 | 28.27 C |
| ATOM | 1772 | C | LEU | A | 225 | 15.291 | −10.949 | 69.140 | 1.00 | 28.29 C |
| ATOM | 1773 | O | LEU | A | 225 | 16.202 | −10.725 | 69.944 | 1.00 | 23.99 O |
| ATOM | 1774 | CB | LEU | A | 225 | 13.862 | −12.939 | 69.764 | 1.00 | 20.34 C |
| ATOM | 1775 | CG | LEU | A | 225 | 12.673 | −13.568 | 70.532 | 1.00 | 30.87 C |
| ATOM | 1776 | CD1 | LEU | A | 225 | 12.749 | −15.113 | 70.408 | 1.00 | 23.35 C |
| ATOM | 1777 | CD2 | LEU | A | 225 | 12.721 | −13.175 | 72.005 | 1.00 | 20.79 C |
| ATOM | 1778 | N | ILE | A | 226 | 15.448 | −10.831 | 67.827 | 1.00 | 27.25 N |
| ATOM | 1779 | CA | ILE | A | 226 | 16.713 | −10.403 | 67.270 | 1.00 | 15.14 C |
| ATOM | 1780 | C | ILE | A | 226 | 16.877 | −8.947 | 67.700 | 1.00 | 23.61 C |
| ATOM | 1781 | O | ILE | A | 226 | 17.962 | −8.551 | 68.086 | 1.00 | 23.29 O |
| ATOM | 1782 | CB | ILE | A | 226 | 16.719 | −10.548 | 65.742 | 1.00 | 23.50 C |
| ATOM | 1783 | CG1 | ILE | A | 226 | 16.740 | −12.036 | 65.363 | 1.00 | 28.66 C |
| ATOM | 1784 | CG2 | ILE | A | 226 | 17.935 | −9.832 | 65.131 | 1.00 | 25.41 C |
| ATOM | 1785 | CD1 | ILE | A | 226 | 16.533 | −12.324 | 63.811 | 1.00 | 20.03 C |
| ATOM | 1786 | N | HIS | A | 227 | 15.802 | −8.160 | 67.654 | 1.00 | 18.00 N |
| ATOM | 1787 | CA | HIS | A | 227 | 15.892 | −6.777 | 68.090 | 1.00 | 21.42 C |
| ATOM | 1788 | C | HIS | A | 227 | 16.302 | −6.755 | 69.533 | 1.00 | 27.30 C |
| ATOM | 1789 | O | HIS | A | 227 | 17.080 | −5.903 | 69.941 | 1.00 | 23.00 O |
| ATOM | 1790 | CB | HIS | A | 227 | 14.541 | −6.062 | 68.001 | 1.00 | 16.28 C |
| ATOM | 1791 | CG | HIS | A | 227 | 14.232 | −5.556 | 66.638 | 1.00 | 34.52 C |
| ATOM | 1792 | ND1 | HIS | A | 227 | 15.081 | −4.709 | 65.957 | 1.00 | 25.39 N |
| ATOM | 1793 | CD2 | HIS | A | 227 | 13.226 | −5.848 | 65.785 | 1.00 | 25.21 C |
| ATOM | 1794 | CE1 | HIS | A | 227 | 14.620 | −4.513 | 64.741 | 1.00 | 22.18 C |
| ATOM | 1795 | NE2 | HIS | A | 227 | 13.498 | −5.196 | 64.609 | 1.00 | 33.46 N |
| ATOM | 1796 | N | ALA | A | 228 | 15.736 | −7.685 | 70.309 | 1.00 | 26.68 N |
| ATOM | 1797 | CA | ALA | A | 228 | 15.997 | −7.759 | 71.731 | 1.00 | 32.76 C |
| ATOM | 1798 | C | ALA | A | 228 | 17.482 | −8.068 | 71.964 | 1.00 | 25.45 C |
| ATOM | 1799 | O | ALA | A | 228 | 18.096 | −7.486 | 72.844 | 1.00 | 21.15 O |
| ATOM | 1800 | CB | ALA | A | 228 | 15.097 | −8.806 | 72.380 | 1.00 | 17.99 C |
| ATOM | 1801 | N | GLY | A | 229 | 18.027 | −8.989 | 71.182 | 1.00 | 20.75 N |
| ATOM | 1802 | CA | GLY | A | 229 | 19.441 | −9.295 | 71.278 | 1.00 | 32.02 C |
| ATOM | 1803 | C | GLY | A | 229 | 20.288 | −8.014 | 71.159 | 1.00 | 48.17 C |
| ATOM | 1804 | O | GLY | A | 229 | 21.124 | −7.735 | 72.024 | 1.00 | 31.61 O |
| ATOM | 1805 | N | HIS | A | 230 | 20.067 | −7.234 | 70.100 | 1.00 | 28.20 N |
| ATOM | 1806 | CA | HIS | A | 230 | 20.800 | −5.988 | 69.902 | 1.00 | 39.03 C |
| ATOM | 1807 | C | HIS | A | 230 | 20.698 | −5.045 | 71.097 | 1.00 | 32.34 C |
| ATOM | 1808 | O | HIS | A | 230 | 21.671 | −4.414 | 71.499 | 1.00 | 29.51 O |
| ATOM | 1809 | CB | HIS | A | 230 | 20.242 | −5.212 | 68.700 | 1.00 | 21.73 C |
| ATOM | 1810 | CG | HIS | A | 230 | 20.335 | −5.947 | 67.404 | 1.00 | 24.07 C |
| ATOM | 1811 | ND1 | HIS | A | 230 | 19.531 | −5.649 | 66.325 | 1.00 | 26.05 N |
| ATOM | 1812 | CD2 | HIS | A | 230 | 21.118 | −6.983 | 67.017 | 1.00 | 32.19 C |
| ATOM | 1813 | CE1 | HIS | A | 230 | 19.809 | −6.474 | 65.332 | 1.00 | 25.52 C |
| ATOM | 1814 | NE2 | HIS | A | 230 | 20.766 | −7.294 | 65.725 | 1.00 | 32.81 N |
| ATOM | 1815 | N | ARG | A | 231 | 19.484 | −4.906 | 71.611 | 1.00 | 23.46 N |
| ATOM | 1816 | CA | ARG | A | 231 | 19.223 | −3.992 | 72.690 | 1.00 | 18.28 C |
| ATOM | 1817 | C | ARG | A | 231 | 19.688 | −4.428 | 74.067 | 1.00 | 29.38 C |
| ATOM | 1818 | O | ARG | A | 231 | 20.025 | −3.579 | 74.893 | 1.00 | 23.41 O |
| ATOM | 1819 | CB | ARG | A | 231 | 17.735 | −3.655 | 72.729 | 1.00 | 18.04 C |
| ATOM | 1820 | CG | ARG | A | 231 | 17.229 | −3.001 | 71.454 | 1.00 | 29.44 C |
| ATOM | 1821 | CD | ARG | A | 231 | 15.680 | −2.954 | 71.390 | 1.00 | 20.13 C |
| ATOM | 1822 | NE | ARG | A | 231 | 15.287 | −1.677 | 70.829 | 1.00 | 55.63 N |
| ATOM | 1823 | CZ | ARG | A | 231 | 14.608 | −0.728 | 71.469 | 1.00 | 43.29 C |
| ATOM | 1824 | NH1 | ARG | A | 231 | 14.205 | −0.902 | 72.716 | 1.00 | 27.88 N |
| ATOM | 1825 | NH2 | ARG | A | 231 | 14.384 | 0.433 | 70.865 | 1.00 | 48.35 N |
| ATOM | 1826 | N | LEU | A | 232 | 19.685 | −5.734 | 74.330 | 1.00 | 24.36 N |
| ATOM | 1827 | CA | LEU | A | 232 | 20.120 | −6.231 | 75.622 | 1.00 | 23.28 C |
| ATOM | 1828 | C | LEU | A | 232 | 21.633 | −5.967 | 75.720 | 1.00 | 26.70 C |
| ATOM | 1829 | O | LEU | A | 232 | 22.152 | −5.717 | 76.800 | 1.00 | 26.02 O |
| ATOM | 1830 | CB | LEU | A | 232 | 19.813 | −7.738 | 75.766 | 1.00 | 17.48 C |
| ATOM | 1831 | CG | LEU | A | 232 | 18.344 | −8.090 | 76.105 | 1.00 | 22.11 C |
| ATOM | 1832 | CD1 | LEU | A | 232 | 18.122 | −9.553 | 75.957 | 1.00 | 19.23 C |
| ATOM | 1833 | CD2 | LEU | A | 232 | 18.027 | −7.654 | 77.522 | 1.00 | 23.99 C |
| ATOM | 1834 | N | TYR | A | 233 | 22.314 | −5.997 | 74.576 | 1.00 | 26.72 N |
| ATOM | 1835 | CA | TYR | A | 233 | 23.753 | −5.757 | 74.515 | 1.00 | 28.58 C |
| ATOM | 1836 | C | TYR | A | 233 | 24.122 | −4.305 | 74.198 | 1.00 | 25.97 C |
| ATOM | 1837 | O | TYR | A | 233 | 25.291 | −3.994 | 73.968 | 1.00 | 31.90 O |
| ATOM | 1838 | CB | TYR | A | 233 | 24.404 | −6.695 | 73.501 | 1.00 | 21.88 C |
| ATOM | 1839 | CG | TYR | A | 233 | 24.525 | −8.122 | 73.998 | 1.00 | 38.99 C |
| ATOM | 1840 | CD1 | TYR | A | 233 | 23.423 | −8.982 | 73.980 | 1.00 | 27.45 C |
| ATOM | 1841 | CD2 | TYR | A | 233 | 25.723 | −8.592 | 74.557 | 1.00 | 20.50 C |
| ATOM | 1842 | CE1 | TYR | A | 233 | 23.502 | −10.262 | 74.502 | 1.00 | 26.41 C |
| ATOM | 1843 | CE2 | TYR | A | 233 | 25.808 | −9.877 | 75.095 | 1.00 | 30.26 C |
| ATOM | 1844 | CZ | TYR | A | 233 | 24.691 | −10.704 | 75.064 | 1.00 | 29.09 C |
| ATOM | 1845 | OH | TYR | A | 233 | 24.753 | −11.951 | 75.616 | 1.00 | 29.59 O |
| ATOM | 1846 | N | GLY | A | 234 | 23.123 | −3.422 | 74.192 | 1.00 | 29.70 N |
| ATOM | 1847 | CA | GLY | A | 234 | 23.369 | −2.004 | 73.936 | 1.00 | 21.87 C |
| ATOM | 1848 | C | GLY | A | 234 | 24.059 | −1.680 | 72.620 | 1.00 | 30.58 C |
| ATOM | 1849 | O | GLY | A | 234 | 24.848 | −0.771 | 72.566 | 1.00 | 36.73 O |

TABLE 1-continued

| | | | | | | | | | | |
|---|---|---|---|---|---|---|---|---|---|---|
| ATOM | 1850 | N | ILE | A | 235 | 23.761 | −2.407 | 71.552 | 1.00 | 30.01 N |
| ATOM | 1851 | CA | ILE | A | 235 | 24.406 | −2.126 | 70.283 | 1.00 | 36.06 C |
| ATOM | 1852 | C | ILE | A | 235 | 23.413 | −1.844 | 69.182 | 1.00 | 36.43 C |
| ATOM | 1853 | O | ILE | A | 235 | 23.709 | −2.051 | 68.015 | 1.00 | 39.74 O |
| ATOM | 1854 | CB | ILE | A | 235 | 25.322 | −3.273 | 69.822 | 1.00 | 24.19 C |
| ATOM | 1855 | CG1 | ILE | A | 235 | 24.536 | −4.565 | 69.665 | 1.00 | 25.80 C |
| ATOM | 1856 | CG2 | ILE | A | 235 | 26.462 | −3.486 | 70.838 | 1.00 | 31.85 C |
| ATOM | 1857 | CD1 | ILE | A | 235 | 25.361 | −5.695 | 68.988 | 1.00 | 30.91 C |
| ATOM | 1858 | N | ALA | A | 236 | 22.235 | −1.367 | 69.563 | 1.00 | 37.22 N |
| ATOM | 1859 | CA | ALA | A | 236 | 21.189 | −1.049 | 68.600 | 1.00 | 31.94 C |
| ATOM | 1860 | C | ALA | A | 236 | 21.606 | 0.216 | 67.870 | 1.00 | 44.83 C |
| ATOM | 1861 | O | ALA | A | 236 | 22.424 | 0.974 | 68.374 | 1.00 | 36.62 O |
| ATOM | 1862 | CB | ALA | A | 236 | 19.848 | −0.821 | 69.311 | 1.00 | 28.06 C |
| ATOM | 1863 | N | ILE | A | 237 | 21.041 | 0.439 | 66.687 | 1.00 | 38.94 N |
| ATOM | 1864 | CA | ILE | A | 237 | 21.364 | 1.616 | 65.905 | 1.00 | 38.52 C |
| ATOM | 1865 | C | ILE | A | 237 | 20.220 | 2.573 | 66.009 | 1.00 | 40.66 C |
| ATOM | 1866 | O | ILE | A | 237 | 19.068 | 2.171 | 65.909 | 1.00 | 41.33 O |
| ATOM | 1867 | CB | ILE | A | 237 | 21.553 | 1.297 | 64.399 | 1.00 | 44.62 C |
| ATOM | 1868 | CG1 | ILE | A | 237 | 22.636 | 0.235 | 64.202 | 1.00 | 46.38 C |
| ATOM | 1869 | CG2 | ILE | A | 237 | 21.946 | 2.573 | 63.647 | 1.00 | 48.66 C |
| ATOM | 1870 | CD1 | ILE | A | 237 | 23.956 | 0.598 | 64.825 | 1.00 | 46.87 C |
| ATOM | 1871 | N | ASN | A | 238 | 20.525 | 3.846 | 66.199 | 1.00 | 40.97 N |
| ATOM | 1872 | CA | ASN | A | 238 | 19.478 | 4.856 | 66.285 | 1.00 | 44.69 C |
| ATOM | 1873 | C | ASN | A | 238 | 18.573 | 4.725 | 65.048 | 1.00 | 44.17 C |
| ATOM | 1874 | O | ASN | A | 238 | 19.060 | 4.651 | 63.931 | 1.00 | 36.05 O |
| ATOM | 1875 | CB | ASN | A | 238 | 20.114 | 6.243 | 66.300 | 1.00 | 43.86 C |
| ATOM | 1876 | CG | ASN | A | 238 | 19.142 | 7.317 | 66.698 | 1.00 | 53.90 C |
| ATOM | 1877 | OD1 | ASN | A | 238 | 18.011 | 7.373 | 66.204 | 1.00 | 64.25 O |
| ATOM | 1878 | ND2 | ASN | A | 238 | 19.571 | 8.187 | 67.601 | 1.00 | 64.46 N |
| ATOM | 1879 | N | PRO | A | 239 | 17.248 | 4.682 | 65.237 | 1.00 | 54.14 N |
| ATOM | 1880 | CA | PRO | A | 239 | 16.377 | 4.556 | 64.062 | 1.00 | 58.31 C |
| ATOM | 1881 | C | PRO | A | 239 | 16.364 | 5.735 | 63.070 | 1.00 | 64.57 C |
| ATOM | 1882 | O | PRO | A | 239 | 15.796 | 5.620 | 61.975 | 1.00 | 45.18 O |
| ATOM | 1883 | CB | PRO | A | 239 | 15.001 | 4.270 | 64.675 | 1.00 | 58.53 C |
| ATOM | 1884 | CG | PRO | A | 239 | 15.089 | 4.873 | 66.036 | 1.00 | 60.75 C |
| ATOM | 1885 | CD | PRO | A | 239 | 16.477 | 4.528 | 66.484 | 1.00 | 48.65 C |
| ATOM | 1886 | N | ASN | A | 240 | 16.989 | 6.857 | 63.425 | 1.00 | 65.89 N |
| ATOM | 1887 | CA | ASN | A | 240 | 17.017 | 7.976 | 62.486 | 1.00 | 67.05 C |
| ATOM | 1888 | C | ASN | A | 240 | 18.057 | 7.692 | 61.410 | 1.00 | 60.82 C |
| ATOM | 1889 | O | ASN | A | 240 | 18.104 | 8.357 | 60.376 | 1.00 | 69.60 O |
| ATOM | 1890 | CB | ASN | A | 240 | 17.300 | 9.328 | 63.176 | 1.00 | 41.51 C |
| ATOM | 1891 | CG | ASN | A | 240 | 18.694 | 9.428 | 63.782 | 1.00 | 68.48 C |
| ATOM | 1892 | OD1 | ASN | A | 240 | 19.681 | 8.881 | 63.268 | 1.00 | 64.20 O |
| ATOM | 1893 | ND2 | ASN | A | 240 | 18.782 | 10.173 | 64.879 | 1.00 | 73.14 N |
| ATOM | 1894 | N | ARG | A | 241 | 18.884 | 6.687 | 61.654 | 1.00 | 48.52 N |
| ATOM | 1895 | CA | ARG | A | 241 | 19.896 | 6.302 | 60.692 | 1.00 | 47.24 C |
| ATOM | 1896 | C | ARG | A | 241 | 19.217 | 5.352 | 59.702 | 1.00 | 57.27 C |
| ATOM | 1897 | O | ARG | A | 241 | 18.855 | 4.223 | 60.047 | 1.00 | 54.73 O |
| ATOM | 1898 | CB | ARG | A | 241 | 21.058 | 5.635 | 61.420 | 1.00 | 39.07 C |
| ATOM | 1899 | CG | ARG | A | 241 | 21.694 | 6.548 | 62.459 | 1.00 | 55.13 C |
| ATOM | 1900 | CD | ARG | A | 241 | 22.385 | 7.722 | 61.774 | 1.00 | 61.27 C |
| ATOM | 1901 | NE | ARG | A | 241 | 23.388 | 7.206 | 60.856 | 1.00 | 57.03 N |
| ATOM | 1902 | CZ | ARG | A | 241 | 24.607 | 6.841 | 61.224 | 1.00 | 65.64 C |
| ATOM | 1903 | NH1 | ARG | A | 241 | 24.983 | 6.960 | 62.492 | 1.00 | 63.61 N |
| ATOM | 1904 | NH2 | ARG | A | 241 | 25.431 | 6.306 | 60.337 | 1.00 | 59.66 N |
| ATOM | 1905 | N | VAL | A | 242 | 19.026 | 5.825 | 58.476 | 1.00 | 49.90 N |
| ATOM | 1906 | CA | VAL | A | 242 | 18.351 | 5.039 | 57.451 | 1.00 | 43.41 C |
| ATOM | 1907 | C | VAL | A | 242 | 19.108 | 4.995 | 56.124 | 1.00 | 59.30 C |
| ATOM | 1908 | O | VAL | A | 242 | 19.982 | 5.826 | 55.873 | 1.00 | 59.30 O |
| ATOM | 1909 | CB | VAL | A | 242 | 16.955 | 5.610 | 57.191 | 1.00 | 52.88 C |
| ATOM | 1910 | CG1 | VAL | A | 242 | 16.280 | 5.941 | 58.511 | 1.00 | 45.49 C |
| ATOM | 1911 | CG2 | VAL | A | 242 | 17.060 | 6.863 | 56.348 | 1.00 | 64.30 C |
| ATOM | 1912 | N | PHE | A | 243 | 18.777 | 4.010 | 55.289 | 1.00 | 53.85 N |
| ATOM | 1913 | CA | PHE | A | 243 | 19.393 | 3.856 | 53.977 | 1.00 | 39.61 C |
| ATOM | 1914 | C | PHE | A | 243 | 18.296 | 3.823 | 52.929 | 1.00 | 53.35 C |
| ATOM | 1915 | O | PHE | A | 243 | 17.220 | 3.277 | 53.159 | 1.00 | 47.53 O |
| ATOM | 1916 | CB | PHE | A | 243 | 20.202 | 2.562 | 53.872 | 1.00 | 47.05 C |
| ATOM | 1917 | CG | PHE | A | 243 | 21.367 | 2.483 | 54.813 | 1.00 | 46.17 C |
| ATOM | 1918 | CD1 | PHE | A | 243 | 22.506 | 3.247 | 54.600 | 1.00 | 58.44 C |
| ATOM | 1919 | CD2 | PHE | A | 243 | 21.333 | 1.622 | 55.905 | 1.00 | 44.50 C |
| ATOM | 1920 | CE1 | PHE | A | 243 | 23.608 | 3.154 | 55.466 | 1.00 | 67.68 C |
| ATOM | 1921 | CE2 | PHE | A | 243 | 22.425 | 1.520 | 56.775 | 1.00 | 66.53 C |
| ATOM | 1922 | CZ | PHE | A | 243 | 23.565 | 2.287 | 56.555 | 1.00 | 58.98 C |
| ATOM | 1923 | N | LYS | A | 244 | 18.577 | 4.450 | 51.778 | 1.00 | 62.34 N |
| ATOM | 1924 | CA | LYS | A | 244 | 17.628 | 4.455 | 50.675 | 1.00 | 71.69 C |
| ATOM | 1925 | C | LYS | A | 244 | 17.698 | 3.089 | 50.017 | 1.00 | 62.67 C |
| ATOM | 1926 | O | LYS | A | 244 | 18.787 | 2.551 | 49.810 | 1.00 | 64.71 O |
| ATOM | 1927 | CB | LYS | A | 244 | 17.959 | 5.593 | 49.683 | 1.00 | 69.20 C |
| ATOM | 1928 | CG | LYS | A | 244 | 17.450 | 5.387 | 48.264 | 1.00 | 85.67 C |

TABLE 1-continued

| | | | | | | | | | | |
|---|---|---|---|---|---|---|---|---|---|---|
| ATOM | 1929 | CD | LYS | A | 244 | 15.921 | 5.500 | 48.201 | 1.00 | 87.46 | C |
| ATOM | 1930 | CE | LYS | A | 244 | 15.452 | 6.931 | 48.369 | 1.00 | 84.11 | C |
| ATOM | 1931 | NZ | LYS | A | 244 | 14.007 | 7.086 | 48.053 | 1.00 | 76.30 | N |
| ATOM | 1932 | N | VAL | A | 245 | 16.545 | 2.515 | 49.665 | 1.00 | 62.20 | N |
| ATOM | 1933 | CA | VAL | A | 245 | 16.563 | 1.161 | 49.082 | 1.00 | 80.89 | C |
| ATOM | 1934 | C | VAL | A | 245 | 16.050 | 1.073 | 47.644 | 1.00 | 81.07 | C |
| ATOM | 1935 | O | VAL | A | 245 | 15.319 | 0.126 | 47.358 | 1.00 | 86.19 | O |
| ATOM | 1936 | CB | VAL | A | 245 | 15.680 | 0.184 | 49.891 | 1.00 | 68.92 | C |
| ATOM | 1937 | CG1 | VAL | A | 245 | 16.353 | −0.196 | 51.196 | 1.00 | 71.72 | C |
| ATOM | 1938 | CG2 | VAL | A | 245 | 14.316 | 0.807 | 50.147 | 1.00 | 68.80 | C |
| ATOM | 1939 | N | ASN | A | 246 | 16.347 | 1.976 | 46.720 | 1.00 | 79.02 | N |
| ATOM | 1940 | CA | ASN | A | 246 | 15.792 | 1.688 | 45.399 | 1.00 | 83.42 | C |
| ATOM | 1941 | C | ASN | A | 246 | 16.791 | 1.676 | 44.242 | 1.00 | 77.33 | C |
| ATOM | 1942 | O | ASN | A | 246 | 17.629 | 0.799 | 44.044 | 1.00 | 95.47 | O |
| ATOM | 1943 | CB | ASN | A | 246 | 14.708 | 2.663 | 44.951 | 1.00 | 84.27 | C |
| ATOM | 1944 | CG | ASN | A | 246 | 14.487 | 2.445 | 43.437 | 1.00 | 93.10 | C |
| ATOM | 1945 | OD1 | ASN | A | 246 | 14.081 | 3.366 | 42.710 | 1.00 | 89.97 | O |
| ATOM | 1946 | ND2 | ASN | A | 246 | 14.744 | 1.226 | 42.988 | 1.00 | 94.59 | N |
| ATOM | 1947 | N | THR | A | 247 | 16.566 | 2.757 | 43.493 | 0.00 | 70.64 | N |
| ATOM | 1948 | CA | THR | A | 247 | 17.117 | 3.286 | 42.231 | 0.00 | 64.16 | C |
| ATOM | 1949 | C | THR | A | 247 | 16.097 | 4.375 | 41.957 | 0.00 | 61.41 | C |
| ATOM | 1950 | O | THR | A | 247 | 15.583 | 4.955 | 42.908 | 0.00 | 60.56 | O |
| ATOM | 1951 | CB | THR | A | 247 | 17.142 | 2.281 | 41.055 | 0.00 | 63.06 | C |
| ATOM | 1952 | OG1 | THR | A | 247 | 15.809 | 1.789 | 40.841 | 0.00 | 62.08 | O |
| ATOM | 1953 | CG2 | THR | A | 247 | 18.094 | 1.136 | 41.363 | 0.00 | 62.08 | C |
| ATOM | 1954 | N | ASN | A | 248 | 15.761 | 4.666 | 40.697 | 0.00 | 58.61 | N |
| ATOM | 1955 | CA | ASN | A | 248 | 14.765 | 5.707 | 40.351 | 0.00 | 56.26 | C |
| ATOM | 1956 | C | ASN | A | 248 | 14.061 | 6.432 | 41.508 | 0.00 | 54.92 | C |
| ATOM | 1957 | O | ASN | A | 248 | 12.839 | 6.348 | 41.652 | 0.00 | 54.71 | O |
| ATOM | 1958 | CB | ASN | A | 248 | 13.678 | 5.082 | 39.462 | 0.00 | 55.82 | C |
| ATOM | 1959 | CG | ASN | A | 248 | 14.091 | 4.982 | 38.009 | 0.00 | 55.43 | C |
| ATOM | 1960 | OD1 | ASN | A | 248 | 15.079 | 4.330 | 37.677 | 0.00 | 55.22 | O |
| ATOM | 1961 | ND2 | ASN | A | 248 | 13.331 | 5.629 | 37.131 | 0.00 | 55.22 | N |
| ATOM | 1962 | N | ALA | A | 249 | 14.829 | 7.152 | 42.318 | 0.00 | 53.45 | N |
| ATOM | 1963 | CA | ALA | A | 249 | 14.285 | 7.891 | 43.454 | 0.00 | 52.03 | C |
| ATOM | 1964 | C | ALA | A | 249 | 15.368 | 8.820 | 43.989 | 0.00 | 51.09 | C |
| ATOM | 1965 | O | ALA | A | 249 | 16.549 | 8.609 | 43.723 | 0.00 | 50.93 | O |
| ATOM | 1966 | CB | ALA | A | 249 | 13.800 | 6.956 | 44.544 | 0.00 | 51.99 | C |
| ATOM | 1967 | N | TYR | A | 250 | 14.971 | 9.842 | 44.741 | 0.00 | 50.03 | N |
| ATOM | 1968 | CA | TYR | A | 250 | 15.930 | 10.797 | 45.287 | 0.00 | 49.04 | C |
| ATOM | 1969 | C | TYR | A | 250 | 16.027 | 10.686 | 46.806 | 0.00 | 48.75 | C |
| ATOM | 1970 | O | TYR | A | 250 | 15.133 | 10.170 | 47.457 | 0.00 | 48.63 | O |
| ATOM | 1971 | CB | TYR | A | 250 | 15.559 | 12.213 | 44.871 | 0.00 | 48.40 | C |
| ATOM | 1972 | CG | TYR | A | 250 | 15.130 | 12.296 | 43.413 | 0.00 | 47.71 | C |
| ATOM | 1973 | CD1 | TYR | A | 250 | 15.972 | 11.807 | 42.414 | 0.00 | 47.42 | C |
| ATOM | 1974 | CD2 | TYR | A | 250 | 13.900 | 12.830 | 43.033 | 0.00 | 47.42 | C |
| ATOM | 1975 | CE1 | TYR | A | 250 | 15.598 | 11.842 | 41.074 | 0.00 | 47.15 | C |
| ATOM | 1976 | CE2 | TYR | A | 250 | 13.515 | 12.871 | 41.694 | 0.00 | 47.15 | C |
| ATOM | 1977 | CZ | TYR | A | 250 | 14.369 | 12.374 | 40.721 | 0.00 | 47.09 | C |
| ATOM | 1978 | OH | TYR | A | 250 | 13.992 | 12.403 | 39.398 | 0.00 | 46.94 | O |
| ATOM | 1979 | N | TYR | A | 251 | 17.117 | 11.168 | 47.366 | 0.00 | 48.49 | N |
| ATOM | 1980 | CA | TYR | A | 251 | 17.364 | 11.052 | 48.807 | 0.00 | 48.34 | C |
| ATOM | 1981 | C | TYR | A | 251 | 16.386 | 11.819 | 49.694 | 0.00 | 48.64 | C |
| ATOM | 1982 | O | TYR | A | 251 | 15.171 | 11.676 | 49.558 | 0.00 | 48.5.7 | O |
| ATOM | 1983 | CB | TYR | A | 251 | 18.805 | 11.450 | 49.136 | 0.00 | 47.73 | C |
| ATOM | 1984 | CG | TYR | A | 251 | 19.315 | 12.726 | 48.532 | 0.00 | 47.13 | C |
| ATOM | 1985 | CD1 | TYR | A | 251 | 18.472 | 13.816 | 48.317 | 0.00 | 46.87 | C |
| ATOM | 1986 | CD2 | TYR | A | 251 | 20.659 | 12.858 | 48.185 | 0.00 | 46.87 | C |
| ATOM | 1987 | CE1 | TYR | A | 251 | 18.955 | 15.004 | 47.772 | 0.00 | 46.63 | C |
| ATOM | 1988 | CE2 | TYR | A | 251 | 21.153 | 14.041 | 47.643 | 0.00 | 46.63 | C |
| ATOM | 1989 | CZ | TYR | A | 251 | 20.296 | 15.109 | 47.439 | 0.00 | 46.57 | C |
| ATOM | 1990 | OH | TYR | A | 251 | 20.778 | 16.282 | 46.904 | 0.00 | 46.44 | O |
| ATOM | 1991 | N | GLU | A | 252 | 16.923 | 12.626 | 50.607 | 0.00 | 49.14 | N |
| ATOM | 1992 | CA | GLU | A | 252 | 16.108 | 13.384 | 51.554 | 0.00 | 49.78 | C |
| ATOM | 1993 | C | GLU | A | 252 | 15.466 | 12.383 | 52.498 | 0.00 | 50.62 | C |
| ATOM | 1994 | O | GLU | A | 252 | 14.837 | 12.751 | 53.489 | 0.00 | 50.57 | O |
| ATOM | 1995 | CB | GLU | A | 252 | 15.007 | 14.179 | 50.846 | 0.00 | 49.26 | C |
| ATOM | 1996 | CG | GLU | A | 252 | 15.297 | 15.660 | 50.702 | 0.00 | 48.67 | C |
| ATOM | 1997 | CD | GLU | A | 252 | 16.362 | 15.945 | 49.670 | 0.00 | 48.36 | C |
| ATOM | 1998 | OE1 | GLU | A | 252 | 16.121 | 15.656 | 48.479 | 0.00 | 48.17 | O |
| ATOM | 1999 | OE2 | GLU | A | 252 | 17.437 | 16.455 | 50.047 | 0.00 | 48.17 | O |
| ATOM | 2000 | N | MET | A | 253 | 15.633 | 11.108 | 52.167 | 0.00 | 51.80 | N |
| ATOM | 2001 | CA | MET | A | 253 | 15.079 | 10.026 | 52.958 | 0.00 | 53.16 | C |
| ATOM | 2002 | C | MET | A | 253 | 13.529 | 10.066 | 52.933 | 0.00 | 54.49 | C |
| ATOM | 2003 | O | MET | A | 253 | 12.892 | 10.363 | 53.942 | 0.00 | 54.51 | O |
| ATOM | 2004 | CB | MET | A | 253 | 15.652 | 10.077 | 54.391 | 0.00 | 52.65 | C |
| ATOM | 2005 | CG | MET | A | 253 | 17.171 | 9.977 | 54.461 | 0.00 | 52.20 | C |
| ATOM | 2006 | SD | MET | A | 253 | 17.821 | 10.244 | 56.117 | 0.00 | 51.89 | S |
| ATOM | 2007 | CE | MET | A | 253 | 19.235 | 9.145 | 56.111 | 0.00 | 51.65 | C |

TABLE 1-continued

| | | | | | | | | | | |
|---|---|---|---|---|---|---|---|---|---|---|
| ATOM | 2008 | N | SER | A | 254 | 12.955 | 9.767 | 51.756 | 0.00 | 56.26 | N |
| ATOM | 2009 | CA | SER | A | 254 | 11.524 | 9.717 | 51.444 | 0.00 | 58.20 | C |
| ATOM | 2010 | C | SER | A | 254 | 11.380 | 8.531 | 50.484 | 0.00 | 59.82 | C |
| ATOM | 2011 | O | SER | A | 254 | 11.814 | 7.439 | 50.854 | 0.00 | 59.80 | O |
| ATOM | 2012 | CB | SER | A | 254 | 11.036 | 11.063 | 50.891 | 0.00 | 58.00 | C |
| ATOM | 2013 | OG | SER | A | 254 | 11.228 | 12.103 | 51.833 | 0.00 | 57.93 | O |
| ATOM | 2014 | N | GLY | A | 255 | 10.807 | 8.679 | 49.301 | 0.00 | 61.79 | N |
| ATOM | 2015 | CA | GLY | A | 255 | 10.704 | 7.516 | 48.469 | 0.00 | 65.13 | C |
| ATOM | 2016 | C | GLY | A | 255 | 10.913 | 6.298 | 49.365 | 0.00 | 67.90 | C |
| ATOM | 2017 | O | GLY | A | 255 | 9.994 | 5.870 | 50.058 | 0.00 | 67.32 | O |
| ATOM | 2018 | N | LEU | A | 256 | 12.137 | 5.759 | 49.363 | 1.00 | 73.74 | N |
| ATOM | 2019 | CA | LEU | A | 256 | 12.327 | 4.555 | 50.169 | 1.00 | 79.55 | C |
| ATOM | 2020 | C | LEU | A | 256 | 13.620 | 4.477 | 50.959 | 1.00 | 73.32 | C |
| ATOM | 2021 | O | LEU | A | 256 | 14.695 | 4.227 | 50.414 | 1.00 | 68.52 | O |
| ATOM | 2022 | CB | LEU | A | 256 | 12.146 | 3.349 | 49.287 | 1.00 | 77.27 | C |
| ATOM | 2023 | CG | LEU | A | 256 | 10.743 | 2.782 | 49.288 | 1.00 | 83.48 | C |
| ATOM | 2024 | CD1 | LEU | A | 256 | 10.674 | 1.527 | 48.430 | 1.00 | 69.09 | C |
| ATOM | 2025 | CD2 | LEU | A | 256 | 10.295 | 2.497 | 50.717 | 1.00 | 73.58 | C |
| ATOM | 2026 | N | GLU | A | 257 | 13.497 | 4.701 | 52.259 | 1.00 | 78.45 | N |
| ATOM | 2027 | CA | GLU | A | 257 | 14.634 | 4.605 | 53.154 | 1.00 | 75.12 | C |
| ATOM | 2028 | C | GLU | A | 257 | 14.237 | 3.785 | 54.368 | 1.00 | 75.68 | C |
| ATOM | 2029 | O | GLU | A | 257 | 13.446 | 4.220 | 55.195 | 1.00 | 72.12 | O |
| ATOM | 2030 | CB | GLU | A | 257 | 15.150 | 5.985 | 53.576 | 1.00 | 73.85 | C |
| ATOM | 2031 | CG | GLU | A | 257 | 14.203 | 7.139 | 53.318 | 1.00 | 91.24 | C |
| ATOM | 2032 | CD | GLU | A | 257 | 13.088 | 7.244 | 54.345 | 1.00 | 100.75 | C |
| ATOM | 2033 | OE1 | GLU | A | 257 | 12.241 | 6.322 | 54.400 | 1.00 | 99.11 | O |
| ATOM | 2034 | OE2 | GLU | A | 257 | 13.064 | 8.251 | 55.095 | 1.00 | 102.89 | O |
| ATOM | 2035 | N | VAL | A | 258 | 14.788 | 2.598 | 54.436 | 1.00 | 71.66 | N |
| ATOM | 2036 | CA | VAL | A | 258 | 14.578 | 1.684 | 55.527 | 1.00 | 56.80 | C |
| ATOM | 2037 | C | VAL | A | 258 | 15.662 | 1.926 | 56.568 | 1.00 | 49.80 | C |
| ATOM | 2038 | O | VAL | A | 258 | 16.814 | 2.184 | 56.227 | 1.00 | 37.46 | O |
| ATOM | 2039 | CB | VAL | A | 258 | 14.647 | 0.243 | 55.021 | 1.00 | 53.82 | C |
| ATOM | 2040 | CG1 | VAL | A | 258 | 14.397 | −0.727 | 56.158 | 1.00 | 46.37 | C |
| ATOM | 2041 | CG2 | VAL | A | 258 | 13.642 | 0.003 | 53.913 | 1.00 | 43.19 | C |
| ATOM | 2042 | N | SER | A | 259 | 15.303 | 1.844 | 57.841 | 1.00 | 49.83 | N |
| ATOM | 2043 | CA | SER | A | 259 | 16.286 | 2.075 | 58.873 | 1.00 | 29.40 | C |
| ATOM | 2044 | C | SER | A | 259 | 17.336 | 0.979 | 58.864 | 1.00 | 40.49 | C |
| ATOM | 2045 | O | SER | A | 259 | 17.069 | −0.166 | 58.472 | 1.00 | 43.04 | O |
| ATOM | 2046 | CB | SER | A | 259 | 15.622 | 2.139 | 60.238 | 1.00 | 54.77 | C |
| ATOM | 2047 | OG | SER | A | 259 | 15.101 | 0.878 | 60.594 | 1.00 | 53.41 | O |
| ATOM | 2048 | N | PHE | A | 260 | 18.538 | 1.369 | 59.261 | 1.00 | 30.09 | N |
| ATOM | 2049 | CA | PHE | A | 260 | 19.693 | 0.482 | 59.363 | 1.00 | 41.84 | C |
| ATOM | 2050 | C | PHE | A | 260 | 19.306 | −0.705 | 60.281 | 1.00 | 37.61 | C |
| ATOM | 2051 | O | PHE | A | 260 | 19.598 | −1.866 | 59.974 | 1.00 | 37.50 | O |
| ATOM | 2052 | CB | PHE | A | 260 | 20.849 | 1.300 | 59.957 | 1.00 | 45.36 | C |
| ATOM | 2053 | CG | PHE | A | 260 | 22.194 | 0.624 | 59.939 | 1.00 | 51.06 | C |
| ATOM | 2054 | CD1 | PHE | A | 260 | 22.331 | −0.740 | 59.719 | 1.00 | 48.68 | C |
| ATOM | 2055 | CD2 | PHE | A | 260 | 23.337 | 1.368 | 60.226 | 1.00 | 43.13 | C |
| ATOM | 2056 | CE1 | PHE | A | 260 | 23.589 | −1.354 | 59.793 | 1.00 | 57.63 | C |
| ATOM | 2057 | CE2 | PHE | A | 260 | 24.589 | 0.767 | 60.302 | 1.00 | 48.71 | C |
| ATOM | 2058 | CZ | PHE | A | 260 | 24.717 | −0.595 | 60.088 | 1.00 | 43.96 | C |
| ATOM | 2059 | N | GLU | A | 261 | 18.645 | −0.406 | 61.398 | 1.00 | 39.27 | N |
| ATOM | 2060 | CA | GLU | A | 261 | 18.215 | −1.449 | 62.344 | 1.00 | 56.79 | C |
| ATOM | 2061 | C | GLU | A | 261 | 17.431 | −2.583 | 61.666 | 1.00 | 37.52 | C |
| ATOM | 2062 | O | GLU | A | 261 | 17.741 | −3.754 | 61.884 | 1.00 | 41.85 | O |
| ATOM | 2063 | CB | GLU | A | 261 | 17.358 | −0.854 | 63.477 | 1.00 | 43.41 | C |
| ATOM | 2064 | CG | GLU | A | 261 | 18.052 | −0.761 | 64.840 | 1.00 | 60.06 | C |
| ATOM | 2065 | CD | GLU | A | 261 | 18.548 | −2.102 | 65.385 | 1.00 | 60.06 | C |
| ATOM | 2066 | OE1 | GLU | A | 261 | 17.713 | −2.964 | 65.752 | 1.00 | 59.55 | O |
| ATOM | 2067 | OE2 | GLU | A | 261 | 19.788 | −2.288 | 65.457 | 1.00 | 46.91 | O |
| ATOM | 2068 | N | GLU | A | 262 | 16.435 | −2.226 | 60.849 | 1.00 | 38.65 | N |
| ATOM | 2069 | CA | GLU | A | 262 | 15.600 | −3.199 | 60.134 | 1.00 | 27.26 | C |
| ATOM | 2070 | C | GLU | A | 262 | 16.301 | −4.001 | 59.073 | 1.00 | 49.26 | C |
| ATOM | 2071 | O | GLU | A | 262 | 16.081 | −5.222 | 58.944 | 1.00 | 36.06 | O |
| ATOM | 2072 | CB | GLU | A | 262 | 14.425 | −2.539 | 59.430 | 1.00 | 30.01 | C |
| ATOM | 2073 | CG | GLU | A | 262 | 13.329 | −2.070 | 60.314 | 1.00 | 37.65 | C |
| ATOM | 2074 | CD | GLU | A | 262 | 12.896 | −3.114 | 61.289 | 1.00 | 30.01 | C |
| ATOM | 2075 | OE1 | GLU | A | 262 | 12.496 | −4.199 | 60.861 | 1.00 | 39.88 | O |
| ATOM | 2076 | OE2 | GLU | A | 262 | 12.948 | −2.835 | 62.490 | 1.00 | 53.12 | O |
| ATOM | 2077 | N | LEU | A | 263 | 17.096 | −3.317 | 58.260 | 1.00 | 34.65 | N |
| ATOM | 2078 | CA | LEU | A | 263 | 17.785 | −4.020 | 57.196 | 1.00 | 32.10 | C |
| ATOM | 2079 | C | LEU | A | 263 | 18.698 | −5.084 | 57.778 | 1.00 | 34.92 | C |
| ATOM | 2080 | O | LEU | A | 263 | 18.812 | −6.189 | 57.248 | 1.00 | 38.45 | O |
| ATOM | 2081 | CB | LEU | A | 263 | 18.575 | −3.034 | 56.326 | 1.00 | 32.20 | C |
| ATOM | 2082 | CG | LEU | A | 263 | 17.694 | −2.057 | 55.522 | 1.00 | 51.26 | C |
| ATOM | 2083 | CD1 | LEU | A | 263 | 18.591 | −0.942 | 54.910 | 1.00 | 53.44 | C |
| ATOM | 2084 | CD2 | LEU | A | 263 | 16.923 | −2.824 | 54.416 | 1.00 | 26.68 | C |
| ATOM | 2085 | N | ARG | A | 264 | 19.345 | −4.749 | 58.881 | 1.00 | 24.75 | N |
| ATOM | 2086 | CA | ARG | A | 264 | 20.235 | −5.688 | 59.508 | 1.00 | 27.65 | C |

TABLE 1-continued

| | | | | | | | | | | |
|---|---|---|---|---|---|---|---|---|---|---|
| ATOM | 2087 | C | ARG | A | 264 | 19.455 | −6.831 | 60.179 | 1.00 | 28.60 | C |
| ATOM | 2088 | O | ARG | A | 264 | 19.887 | −7.978 | 60.169 | 1.00 | 39.46 | O |
| ATOM | 2089 | CB | ARG | A | 264 | 21.093 | −4.961 | 60.540 | 1.00 | 29.95 | C |
| ATOM | 2090 | CG | ARG | A | 264 | 21.299 | −5.741 | 61.824 | 1.00 | 43.92 | C |
| ATOM | 2091 | CD | ARG | A | 264 | 21.956 | −4.894 | 62.895 | 1.00 | 48.75 | C |
| ATOM | 2092 | NE | ARG | A | 264 | 23.256 | −4.400 | 62.460 | 1.00 | 61.85 | N |
| ATOM | 2093 | CZ | ARG | A | 264 | 24.099 | −3.741 | 63.251 | 1.00 | 64.72 | C |
| ATOM | 2094 | NH1 | ARG | A | 264 | 23.766 | −3.511 | 64.517 | 1.00 | 36.34 | N |
| ATOM | 2095 | NH2 | ARG | A | 264 | 25.260 | −3.297 | 62.771 | 1.00 | 56.73 | N |
| ATOM | 2096 | N | THR | A | 265 | 18.309 | −6.522 | 60.763 | 1.00 | 33.92 | N |
| ATOM | 2097 | CA | THR | A | 265 | 17.512 | −7.549 | 61.433 | 1.00 | 25.89 | C |
| ATOM | 2098 | C | THR | A | 265 | 16.956 | −8.550 | 60.428 | 1.00 | 23.36 | C |
| ATOM | 2099 | O | THR | A | 265 | 16.999 | −9.744 | 60.664 | 1.00 | 26.76 | O |
| ATOM | 2100 | CB | THR | A | 265 | 16.388 | −6.887 | 62.240 | 1.00 | 32.90 | C |
| ATOM | 2101 | OG1 | THR | A | 265 | 16.986 | −6.143 | 63.296 | 1.00 | 33.07 | O |
| ATOM | 2102 | CG2 | THR | A | 265 | 15.403 | −7.926 | 62.839 | 1.00 | 29.25 | C |
| ATOM | 2103 | N | PHE | A | 266 | 16.452 | −8.074 | 59.297 | 1.00 | 28.28 | N |
| ATOM | 2104 | CA | PHE | A | 266 | 15.916 | −8.982 | 58.279 | 1.00 | 26.68 | C |
| ATOM | 2105 | C | PHE | A | 266 | 17.037 | −9.730 | 57.571 | 1.00 | 34.24 | C |
| ATOM | 2106 | O | PHE | A | 266 | 16.907 | −10.916 | 57.241 | 1.00 | 35.23 | O |
| ATOM | 2107 | CB | PHE | A | 266 | 15.120 | −8.228 | 57.220 | 1.00 | 40.07 | C |
| ATOM | 2108 | CG | PHE | A | 266 | 14.524 | −9.135 | 56.172 | 1.00 | 57.42 | C |
| ATOM | 2109 | CD1 | PHE | A | 266 | 13.224 | −9.632 | 56.315 | 1.00 | 59.28 | C |
| ATOM | 2110 | CD2 | PHE | A | 266 | 15.280 | −9.534 | 55.067 | 1.00 | 57.18 | C |
| ATOM | 2111 | CE1 | PHE | A | 266 | 12.688 | −10.512 | 55.371 | 1.00 | 61.68 | C |
| ATOM | 2112 | CE2 | PHE | A | 266 | 14.758 | −10.414 | 54.118 | 1.00 | 60.12 | C |
| ATOM | 2113 | CZ | PHE | A | 266 | 13.458 | −10.905 | 54.271 | 1.00 | 60.00 | C |
| ATOM | 2114 | N | GLY | A | 267 | 18.138 | −9.027 | 57.321 | 1.00 | 31.64 | N |
| ATOM | 2115 | CA | GLY | A | 267 | 19.290 | −9.639 | 56.667 | 1.00 | 29.00 | C |
| ATOM | 2116 | C | GLY | A | 267 | 19.074 | −10.070 | 55.234 | 1.00 | 27.40 | C |
| ATOM | 2117 | O | GLY | A | 267 | 18.336 | −9.445 | 54.484 | 1.00 | 38.37 | O |
| ATOM | 2118 | N | GLY | A | 268 | 19.732 | −11.148 | 54.845 | 1.00 | 42.12 | N |
| ATOM | 2119 | CA | GLY | A | 268 | 19.574 | −11.651 | 53.495 | 1.00 | 37.74 | C |
| ATOM | 2120 | C | GLY | A | 268 | 19.851 | −10.624 | 52.405 | 1.00 | 53.03 | C |
| ATOM | 2121 | O | GLY | A | 268 | 20.674 | −9.721 | 52.562 | 1.00 | 44.93 | O |
| ATOM | 2122 | N | HIS | A | 269 | 19.151 | −10.769 | 51.290 | 1.00 | 40.03 | N |
| ATOM | 2123 | CA | HIS | A | 269 | 19.330 | −9.866 | 50.177 | 1.00 | 56.46 | C |
| ATOM | 2124 | C | HIS | A | 269 | 19.125 | −8.393 | 50.515 | 1.00 | 55.06 | C |
| ATOM | 2125 | O | HIS | A | 269 | 19.562 | −7.528 | 49.770 | 1.00 | 50.80 | O |
| ATOM | 2126 | CB | HIS | A | 269 | 18.414 | −10.290 | 49.033 | 1.00 | 57.76 | C |
| ATOM | 2127 | CG | HIS | A | 269 | 18.929 | −11.472 | 48.271 | 1.00 | 67.85 | C |
| ATOM | 2128 | ND1 | HIS | A | 269 | 20.137 | −11.456 | 47.606 | 1.00 | 74.17 | N |
| ATOM | 2129 | CD2 | HIS | A | 269 | 18.412 | −12.709 | 48.083 | 1.00 | 69.71 | C |
| ATOM | 2130 | CE1 | HIS | A | 269 | 20.343 | −12.632 | 47.041 | 1.00 | 62.32 | C |
| ATOM | 2131 | NE2 | HIS | A | 269 | 19.312 | −13.411 | 47.316 | 1.00 | 71.65 | N |
| ATOM | 2132 | N | ASP | A | 270 | 18.477 | −8.105 | 51.638 | 1.00 | 54.55 | N |
| ATOM | 2133 | CA | ASP | A | 270 | 18.253 | −6.721 | 52.026 | 1.00 | 43.57 | C |
| ATOM | 2134 | C | ASP | A | 270 | 19.399 | −6.139 | 52.851 | 1.00 | 45.29 | C |
| ATOM | 2135 | O | ASP | A | 270 | 19.444 | −4.943 | 53.077 | 1.00 | 59.37 | O |
| ATOM | 2136 | CB | ASP | A | 270 | 16.945 | −6.591 | 52.803 | 1.00 | 57.96 | C |
| ATOM | 2137 | CG | ASP | A | 270 | 15.750 | −7.028 | 51.993 | 1.00 | 67.88 | C |
| ATOM | 2138 | OD1 | ASP | A | 270 | 15.601 | −6.533 | 50.858 | 1.00 | 72.65 | O |
| ATOM | 2139 | OD2 | ASP | A | 270 | 14.964 | −7.863 | 52.486 | 1.00 | 77.44 | O |
| ATOM | 2140 | N | ALA | A | 271 | 20.328 | −6.972 | 53.304 | 1.00 | 47.23 | N |
| ATOM | 2141 | CA | ALA | A | 271 | 21.446 | −6.456 | 54.090 | 1.00 | 68.18 | C |
| ATOM | 2142 | C | ALA | A | 271 | 22.582 | −5.960 | 53.188 | 1.00 | 65.95 | C |
| ATOM | 2143 | O | ALA | A | 271 | 23.663 | −5.607 | 53.661 | 1.00 | 63.53 | O |
| ATOM | 2144 | CB | ALA | A | 271 | 21.965 | −7.528 | 55.046 | 1.00 | 55.40 | C |
| ATOM | 2145 | N | LYS | A | 272 | 22.333 | −5.930 | 51.883 | 1.00 | 68.77 | N |
| ATOM | 2146 | CA | LYS | A | 272 | 23.348 | −5.470 | 50.945 | 1.00 | 62.56 | C |
| ATOM | 2147 | C | LYS | A | 272 | 23.208 | −3.994 | 50.625 | 1.00 | 71.83 | C |
| ATOM | 2148 | O | LYS | A | 272 | 24.058 | −3.409 | 49.950 | 1.00 | 68.61 | O |
| ATOM | 2149 | CB | LYS | A | 272 | 23.307 | −6.298 | 49.661 | 1.00 | 63.37 | C |
| ATOM | 2150 | CG | LYS | A | 272 | 24.267 | −7.492 | 49.711 | 1.00 | 78.01 | C |
| ATOM | 2151 | CD | LYS | A | 272 | 25.713 | −7.042 | 49.991 | 1.00 | 76.23 | C |
| ATOM | 2152 | CE | LYS | A | 272 | 26.676 | −8.226 | 50.107 | 1.00 | 85.31 | C |
| ATOM | 2153 | NZ | LYS | A | 272 | 26.354 | −9.117 | 51.256 | 1.00 | 74.68 | N |
| ATOM | 2154 | N | PHE | A | 273 | 22.139 | −3.395 | 51.132 | 1.00 | 57.71 | N |
| ATOM | 2155 | CA | PHE | A | 273 | 21.876 | −1.991 | 50.921 | 1.00 | 34.28 | C |
| ATOM | 2156 | C | PHE | A | 273 | 22.461 | −1.180 | 52.068 | 1.00 | 56.44 | C |
| ATOM | 2157 | O | PHE | A | 273 | 22.325 | 0.040 | 52.121 | 1.00 | 54.31 | O |
| ATOM | 2158 | CB | PHE | A | 273 | 20.375 | −1.783 | 50.838 | 1.00 | 39.40 | C |
| ATOM | 2159 | CG | PHE | A | 273 | 19.735 | −2.532 | 49.708 | 1.00 | 62.66 | C |
| ATOM | 2160 | CD1 | PHE | A | 273 | 20.172 | −2.336 | 48.400 | 1.00 | 57.41 | C |
| ATOM | 2161 | CD2 | PHE | A | 273 | 18.688 | −3.419 | 49.940 | 1.00 | 62.97 | C |
| ATOM | 2162 | CE1 | PHE | A | 273 | 19.581 | −3.004 | 47.332 | 1.00 | 58.30 | C |
| ATOM | 2163 | CE2 | PHE | A | 273 | 18.087 | −4.096 | 48.880 | 1.00 | 64.58 | C |
| ATOM | 2164 | CZ | PHE | A | 273 | 18.536 | −3.886 | 47.568 | 1.00 | 61.22 | C |
| ATOM | 2165 | N | ILE | A | 274 | 23.115 | −1.862 | 52.995 | 1.00 | 52.89 | N |

TABLE 1-continued

| | | | | | | | | | | |
|---|---|---|---|---|---|---|---|---|---|---|
| ATOM | 2166 | CA | ILE | A | 274 | 23.698 | −1.179 | 54.138 | 1.00 | 58.30 | C |
| ATOM | 2167 | C | ILE | A | 274 | 25.135 | −0.763 | 53.878 | 1.00 | 47.68 | C |
| ATOM | 2168 | O | ILE | A | 274 | 25.988 | −1.607 | 53.634 | 1.00 | 46.63 | O |
| ATOM | 2169 | CB | ILE | A | 274 | 23.665 | −2.071 | 55.393 | 1.00 | 58.58 | C |
| ATOM | 2170 | CG1 | ILE | A | 274 | 22.216 | −2.199 | 55.890 | 1.00 | 62.53 | C |
| ATOM | 2171 | CG2 | ILE | A | 274 | 24.595 | −1.488 | 56.462 | 1.00 | 57.77 | C |
| ATOM | 2172 | CD1 | ILE | A | 274 | 22.039 | −3.010 | 57.155 | 1.00 | 48.27 | C |
| ATOM | 2173 | N | ASP | A | 275 | 25.394 | 0.540 | 53.946 | 1.00 | 55.60 | N |
| ATOM | 2174 | CA | ASP | A | 275 | 26.735 | 1.086 | 53.729 | 1.00 | 48.24 | C |
| ATOM | 2175 | C | ASP | A | 275 | 27.772 | 0.333 | 54.553 | 1.00 | 55.64 | C |
| ATOM | 2176 | O | ASP | A | 275 | 27.687 | 0.291 | 55.781 | 1.00 | 55.59 | O |
| ATOM | 2177 | CB | ASP | A | 275 | 26.756 | 2.569 | 54.109 | 1.00 | 69.05 | C |
| ATOM | 2178 | CG | ASP | A | 275 | 28.100 | 3.231 | 53.827 | 1.00 | 70.55 | C |
| ATOM | 2179 | OD1 | ASP | A | 275 | 29.098 | 2.910 | 54.514 | 1.00 | 74.65 | O |
| ATOM | 2180 | OD2 | ASP | A | 275 | 28.156 | 4.076 | 52.910 | 1.00 | 81.46 | O |
| ATOM | 2181 | N | SER | A | 276 | 28.755 | −0.253 | 53.883 | 1.00 | 45.02 | N |
| ATOM | 2182 | CA | SER | A | 276 | 29.791 | −1.002 | 54.581 | 1.00 | 69.09 | C |
| ATOM | 2183 | C | SER | A | 276 | 30.577 | −0.155 | 55.580 | 1.00 | 58.37 | C |
| ATOM | 2184 | O | SER | A | 276 | 30.778 | −0.559 | 56.718 | 1.00 | 71.32 | O |
| ATOM | 2185 | CB | SER | A | 276 | 30.756 | −1.640 | 53.576 | 1.00 | 68.87 | C |
| ATOM | 2186 | OG | SER | A | 276 | 30.110 | −2.661 | 52.834 | 1.00 | 67.59 | O |
| ATOM | 2187 | N | LEU | A | 277 | 31.017 | 1.021 | 55.165 | 1.00 | 64.15 | N |
| ATOM | 2188 | CA | LEU | A | 277 | 31.783 | 1.872 | 56.061 | 1.00 | 74.56 | C |
| ATOM | 2189 | C | LEU | A | 277 | 30.998 | 2.203 | 57.322 | 1.00 | 75.36 | C |
| ATOM | 2190 | O | LEU | A | 277 | 31.457 | 1.923 | 58.431 | 1.00 | 62.10 | O |
| ATOM | 2191 | CB | LEU | A | 277 | 32.205 | 3.151 | 55.346 | 1.00 | 68.21 | C |
| ATOM | 2192 | CG | LEU | A | 277 | 33.262 | 2.895 | 54.268 | 1.00 | 77.45 | C |
| ATOM | 2193 | CD1 | LEU | A | 277 | 33.635 | 4.213 | 53.589 | 1.00 | 74.39 | C |
| ATOM | 2194 | CD2 | LEU | A | 277 | 34.488 | 2.240 | 54.899 | 1.00 | 72.20 | C |
| ATOM | 2195 | N | GLN | A | 278 | 29.822 | 2.802 | 57.151 | 1.00 | 68.95 | N |
| ATOM | 2196 | CA | GLN | A | 278 | 28.974 | 3.131 | 58.291 | 1.00 | 61.52 | C |
| ATOM | 2197 | C | GLN | A | 278 | 28.831 | 1.910 | 59.190 | 1.00 | 60.08 | C |
| ATOM | 2198 | O | GLN | A | 278 | 28.809 | 2.022 | 60.413 | 1.00 | 74.46 | O |
| ATOM | 2199 | CB | GLN | A | 28 | 27.595 | 3.557 | 57.821 | 1.00 | 55.80 | C |
| ATOM | 2200 | CG | GLN | A | 278 | 27.554 | 4.919 | 57.220 | 1.00 | 55.37 | C |
| ATOM | 2201 | CD | GLN | A | 278 | 26.151 | 5.319 | 56.868 | 1.00 | 76.92 | C |
| ATOM | 2202 | OE1 | GLN | A | 278 | 25.260 | 5.293 | 57.720 | 1.00 | 77.74 | O |
| ATOM | 2203 | NE2 | GLN | A | 278 | 25.933 | 5.687 | 55.606 | 1.00 | 78.33 | N |
| ATOM | 2204 | N | GLU | A | 279 | 28.735 | 0.740 | 58.573 | 1.00 | 59.77 | N |
| ATOM | 2205 | CA | GLU | A | 279 | 28.605 | −0.499 | 59.313 | 1.00 | 59.42 | C |
| ATOM | 2206 | C | GLU | A | 279 | 29.880 | −0.702 | 60.118 | 1.00 | 53.18 | C |
| ATOM | 2207 | O | GLU | A | 279 | 29.847 | −1.085 | 61.286 | 1.00 | 55.57 | O |
| ATOM | 2208 | CB | GLU | A | 279 | 28.403 | −1.654 | 58.337 | 1.00 | 55.86 | C |
| ATOM | 2209 | CG | GLU | A | 279 | 28.028 | −2.972 | 58.981 | 1.00 | 68.13 | C |
| ATOM | 2210 | CD | GLU | A | 279 | 27.671 | −4.032 | 57.946 | 1.00 | 82.49 | C |
| ATOM | 2211 | OE1 | GLU | A | 279 | 28.580 | −4.515 | 57.228 | 1.00 | 78.31 | O |
| ATOM | 2212 | OE2 | GLU | A | 279 | 26.473 | −4.374 | 57.843 | 1.00 | 83.47 | O |
| ATOM | 2213 | N | ASN | A | 280 | 31.008 | −0.424 | 59.478 | 1.00 | 61.84 | N |
| ATOM | 2214 | CA | ASN | A | 280 | 32.313 | −0.582 | 60.108 | 1.00 | 51.76 | C |
| ATOM | 2215 | C | ASN | A | 280 | 32.480 | 0.403 | 61.266 | 1.00 | 52.31 | C |
| ATOM | 2216 | O | ASN | A | 280 | 33.014 | 0.057 | 62.319 | 1.00 | 52.99 | O |
| ATOM | 2217 | CB | ASN | A | 280 | 33.414 | −0.362 | 59.071 | 1.00 | 62.74 | C |
| ATOM | 2218 | CG | ASN | A | 280 | 34.745 | −0.958 | 59.497 | 1.00 | 76.43 | C |
| ATOM | 2219 | OD1 | ASN | A | 280 | 35.806 | −0.511 | 59.050 | 1.00 | 73.41 | O |
| ATOM | 2220 | ND2 | ASN | A | 280 | 34.698 | −1.980 | 60.356 | 1.00 | 69.65 | N |
| ATOM | 2221 | N | GLU | A | 281 | 32.015 | 1.629 | 61.073 | 1.00 | 40.01 | N |
| ATOM | 2222 | CA | GLU | A | 281 | 32.113 | 2.627 | 62.116 | 1.00 | 46.62 | C |
| ATOM | 2223 | C | GLU | A | 281 | 31.364 | 2.217 | 63.378 | 1.00 | 60.94 | C |
| ATOM | 2224 | O | GLU | A | 281 | 31.886 | 2.374 | 64.489 | 1.00 | 57.82 | O |
| ATOM | 2225 | CB | GLU | A | 281 | 31.597 | 3.964 | 61.605 | 1.00 | 48.89 | C |
| ATOM | 2226 | CG | GLU | A | 281 | 32.644 | 4.734 | 60.805 | 1.00 | 71.37 | C |
| ATOM | 2227 | CD | GLU | A | 281 | 32.031 | 5.675 | 59.788 | 1.00 | 80.14 | C |
| ATOM | 2228 | OE1 | GLU | A | 281 | 31.147 | 6.475 | 60.170 | 1.00 | 80.74 | O |
| ATOM | 2229 | OE2 | GLU | A | 281 | 32.437 | 5.610 | 58.605 | 1.00 | 87.84 | O |
| ATOM | 2230 | N | PHE | A | 282 | 30.150 | 1.688 | 63.218 | 1.00 | 52.39 | N |
| ATOM | 2231 | CA | PHE | A | 282 | 29.366 | 1.265 | 64.374 | 1.00 | 35.61 | C |
| ATOM | 2232 | C | PHE | A | 282 | 30.045 | 0.143 | 65.156 | 1.00 | 23.96 | C |
| ATOM | 2233 | O | PHE | A | 282 | 30.070 | 0.159 | 66.377 | 1.00 | 32.97 | O |
| ATOM | 2234 | CB | PHE | A | 282 | 27.959 | 0.864 | 63.936 | 1.00 | 33.08 | C |
| ATOM | 2235 | CG | PHE | A | 282 | 27.026 | 2.030 | 63.848 | 1.00 | 31.47 | C |
| ATOM | 2236 | CD1 | PHE | A | 282 | 26.673 | 2.722 | 64.991 | 1.00 | 33.73 | C |
| ATOM | 2237 | CD2 | PHE | A | 282 | 26.520 | 2.448 | 62.632 | 1.00 | 33.05 | C |
| ATOM | 2238 | CE1 | PHE | A | 282 | 25.833 | 3.827 | 64.926 | 1.00 | 56.94 | C |
| ATOM | 2239 | CE2 | PHE | A | 282 | 25.684 | 3.544 | 62.555 | 1.00 | 43.15 | C |
| ATOM | 2240 | CZ | PHE | A | 282 | 25.333 | 4.238 | 63.712 | 1.00 | 41.99 | C |
| ATOM | 2241 | N | ARG | A | 283 | 30.618 | −0.821 | 64.456 | 1.00 | 32.37 | N |
| ATOM | 2242 | CA | ARG | A | 283 | 31.308 | −1.893 | 65.156 | 1.00 | 43.56 | C |
| ATOM | 2243 | C | ARG | A | 283 | 32.448 | −1.340 | 66.028 | 1.00 | 45.56 | C |
| ATOM | 2244 | O | ARG | A | 283 | 32.703 | −1.853 | 67.123 | 1.00 | 47.49 | O |

TABLE 1-continued

| | | | | | | | | | | |
|---|---|---|---|---|---|---|---|---|---|---|
| ATOM | 2245 | CB | ARG | A | 283 | 31.873 | −2.901 | 64.154 | 1.00 | 28.27 | C |
| ATOM | 2246 | CG | ARG | A | 283 | 32.718 | −3.985 | 64.788 | 1.00 | 38.15 | C |
| ATOM | 2247 | CD | ARG | A | 283 | 32.989 | −5.131 | 63.825 | 1.00 | 46.18 | C |
| ATOM | 2248 | NE | ARG | A | 283 | 34.413 | −5.448 | 63.750 | 1.00 | 76.82 | N |
| ATOM | 2249 | CZ | ARG | A | 283 | 35.337 | −4.631 | 63.242 | 1.00 | 88.44 | C |
| ATOM | 2250 | NH1 | ARG | A | 283 | 34.985 | −3.443 | 62.759 | 1.00 | 85.10 | N |
| ATOM | 2251 | NH2 | ARG | A | 283 | 36.616 | −4.998 | 63.212 | 1.00 | 86.33 | N |
| ATOM | 2252 | N | LEU | A | 284 | 33.118 | −0.291 | 65.543 | 1.00 | 41.40 | N |
| ATOM | 2253 | CA | LEU | A | 284 | 34.248 | 0.313 | 66.252 | 1.00 | 43.76 | C |
| ATOM | 2254 | C | LEU | A | 284 | 33.704 | 1.102 | 67.432 | 1.00 | 25.34 | C |
| ATOM | 2255 | O | LEU | A | 284 | 34.208 | 1.033 | 68.538 | 1.00 | 44.26 | O |
| ATOM | 2256 | CB | LEU | A | 284 | 35.023 | 1.249 | 65.309 | 1.00 | 52.77 | C |
| ATOM | 2257 | CG | LEU | A | 284 | 36.542 | 1.361 | 65.517 | 1.00 | 67.49 | C |
| ATOM | 2258 | CD1 | LEU | A | 284 | 36.876 | 1.975 | 66.889 | 1.00 | 42.76 | C |
| ATOM | 2259 | CD2 | LEU | A | 284 | 37.152 | −0.039 | 65.360 | 1.00 | 58.73 | C |
| ATOM | 2260 | N | TYR | A | 285 | 32.661 | 1.859 | 67.169 | 1.00 | 36.61 | N |
| ATOM | 2261 | CA | TYR | A | 285 | 32.008 | 2.640 | 68.197 | 1.00 | 39.34 | C |
| ATOM | 2262 | C | TYR | A | 285 | 31.522 | 1.685 | 69.323 | 1.00 | 43.83 | C |
| ATOM | 2263 | O | TYR | A | 285 | 31.757 | 1.941 | 70.497 | 1.00 | 53.51 | O |
| ATOM | 2264 | CB | TYR | A | 285 | 30.829 | 3.375 | 67.559 | 1.00 | 34.34 | C |
| ATOM | 2265 | CG | TYR | A | 285 | 29.954 | 4.169 | 68.508 | 1.00 | 45.46 | C |
| ATOM | 2266 | CD1 | TYR | A | 285 | 30.235 | 5.502 | 68.787 | 1.00 | 46.30 | C |
| ATOM | 2267 | CD2 | TYR | A | 285 | 28.839 | 3.588 | 69.122 | 1.00 | 43.24 | C |
| ATOM | 2268 | CE1 | TYR | A | 285 | 29.442 | 6.245 | 69.650 | 1.00 | 38.16 | C |
| ATOM | 2269 | CE2 | TYR | A | 285 | 28.022 | 4.329 | 69.992 | 1.00 | 35.18 | C |
| ATOM | 2270 | CZ | TYR | A | 285 | 28.339 | 5.654 | 70.250 | 1.00 | 41.41 | C |
| ATOM | 2271 | OH | TYR | A | 285 | 27.599 | 6.388 | 71.127 | 1.00 | 40.61 | O |
| ATOM | 2272 | N | TYR | A | 286 | 30.879 | 0.568 | 68.989 | 1.00 | 31.48 | N |
| ATOM | 2273 | CA | TYR | A | 286 | 30.412 | −0.297 | 70.078 | 1.00 | 43.57 | C |
| ATOM | 2274 | C | TYR | A | 286 | 31.539 | −1.030 | 70.774 | 1.00 | 24.57 | C |
| ATOM | 2275 | O | TYR | A | 286 | 31.444 | −1.301 | 71.964 | 1.00 | 30.40 | O |
| ATOM | 2276 | CB | TYR | A | 286 | 29.316 | −1.275 | 69.601 | 1.00 | 26.72 | C |
| ATOM | 2277 | CG | TYR | A | 286 | 27.994 | −0.553 | 69.401 | 1.00 | 28.57 | C |
| ATOM | 2278 | CD1 | TYR | A | 286 | 27.417 | 0.153 | 70.451 | 1.00 | 26.03 | C |
| ATOM | 2279 | CD2 | TYR | A | 286 | 27.407 | −0.443 | 68.133 | 1.00 | 26.61 | C |
| ATOM | 2280 | CE1 | TYR | A | 286 | 26.312 | 0.964 | 70.244 | 1.00 | 28.10 | C |
| ATOM | 2281 | CE2 | TYR | A | 286 | 26.291 | 0.373 | 67.925 | 1.00 | 26.82 | C |
| ATOM | 2282 | CZ | TYR | A | 286 | 25.766 | 1.071 | 68.985 | 1.00 | 33.32 | C |
| ATOM | 2283 | OH | TYR | A | 286 | 24.724 | 1.928 | 68.784 | 1.00 | 50.06 | O |
| ATOM | 2284 | N | TYR | A | 287 | 32.588 | −1.370 | 70.028 | 1.00 | 32.89 | N |
| ATOM | 2285 | CA | TYR | A | 287 | 33.764 | −2.033 | 70.606 | 1.00 | 34.78 | C |
| ATOM | 2286 | C | TYR | A | 287 | 34.296 | −1.117 | 71.716 | 1.00 | 43.43 | C |
| ATOM | 2287 | O | TYR | A | 287 | 34.744 | −1.580 | 72.758 | 1.00 | 33.13 | O |
| ATOM | 2288 | CB | TYR | A | 287 | 34.867 | −2.199 | 69.561 | 1.00 | 34.08 | C |
| ATOM | 2289 | CG | TYR | A | 287 | 36.255 | −2.491 | 70.138 | 1.00 | 32.52 | C |
| ATOM | 2290 | CD1 | TYR | A | 287 | 36.587 | −3.752 | 70.635 | 1.00 | 43.75 | C |
| ATOM | 2291 | CD2 | TYR | A | 287 | 37.253 | −1.515 | 70.126 | 1.00 | 57.77 | C |
| ATOM | 2292 | CE1 | TYR | A | 287 | 37.884 | −4.041 | 71.100 | 1.00 | 39.97 | C |
| ATOM | 2293 | CE2 | TYR | A | 287 | 38.556 | −1.789 | 70.586 | 1.00 | 42.47 | C |
| ATOM | 2294 | CZ | TYR | A | 287 | 38.866 | −3.050 | 71.067 | 1.00 | 50.02 | C |
| ATOM | 2295 | OH | TYR | A | 287 | 40.158 | −3.320 | 71.481 | 1.00 | 38.42 | O |
| ATOM | 2296 | N | ASN | A | 288 | 34.240 | 0.188 | 71.468 | 1.00 | 31.25 | N |
| ATOM | 2297 | CA | ASN | A | 288 | 34.708 | 1.143 | 72.440 | 1.00 | 31.00 | C |
| ATOM | 2298 | C | ASN | A | 288 | 33.789 | 1.199 | 73.636 | 1.00 | 36.53 | C |
| ATOM | 2299 | O | ASN | A | 288 | 34.254 | 1.295 | 74.781 | 1.00 | 47.71 | O |
| ATOM | 2300 | CB | ASN | A | 288 | 34.842 | 2.526 | 71.790 | 1.00 | 45.99 | C |
| ATOM | 2301 | CG | ASN | A | 288 | 36.163 | 2.687 | 71.034 | 1.00 | 55.94 | C |
| ATOM | 2302 | OD1 | ASN | A | 288 | 36.329 | 3.612 | 70.242 | 1.00 | 54.82 | O |
| ATOM | 2303 | ND2 | ASN | A | 288 | 37.104 | 1.779 | 71.282 | 1.00 | 56.31 | N |
| ATOM | 2304 | N | LYS | A | 289 | 32.482 | 1.154 | 73.386 | 1.00 | 37.74 | N |
| ATOM | 2305 | CA | LYS | A | 289 | 31.530 | 1.171 | 74.480 | 1.00 | 31.87 | C |
| ATOM | 2306 | C | LYS | A | 289 | 31.823 | −0.008 | 75.398 | 1.00 | 22.81 | C |
| ATOM | 2307 | O | LYS | A | 289 | 31.737 | 0.109 | 76.616 | 1.00 | 42.64 | O |
| ATOM | 2308 | CB | LYS | A | 289 | 30.096 | 1.084 | 73.948 | 1.00 | 51.98 | C |
| ATOM | 2309 | CG | LYS | A | 289 | 29.588 | 2.369 | 73.303 | 1.00 | 40.83 | C |
| ATOM | 2310 | CD | LYS | A | 289 | 29.685 | 3.523 | 74.280 | 1.00 | 54.01 | C |
| ATOM | 2311 | CE | LYS | A | 289 | 29.438 | 4.878 | 73.621 | 1.00 | 48.29 | C |
| ATOM | 2312 | NZ | LYS | A | 289 | 29.424 | 5.988 | 74.636 | 1.00 | 52.67 | N |
| ATOM | 2313 | N | PHE | A | 290 | 32.188 | −1.146 | 74.817 | 1.00 | 33.46 | N |
| ATOM | 2314 | CA | PHE | A | 290 | 32.503 | −2.332 | 75.618 | 1.00 | 39.69 | C |
| ATOM | 2315 | C | PHE | A | 290 | 33.783 | −2.129 | 76.444 | 1.00 | 45.92 | C |
| ATOM | 2316 | O | PHE | A | 290 | 33.937 | −2.689 | 77.543 | 1.00 | 38.02 | O |
| ATOM | 2317 | CB | PHE | A | 290 | 32.663 | −3.561 | 74.714 | 1.00 | 32.57 | C |
| ATOM | 2318 | CG | PHE | A | 290 | 31.345 | −4.210 | 74.309 | 1.00 | 39.42 | C |
| ATOM | 2319 | CD1 | PHE | A | 290 | 30.195 | −3.451 | 74.150 | 1.00 | 22.67 | C |
| ATOM | 2320 | CD2 | PHE | A | 290 | 31.282 | −5.580 | 74.038 | 1.00 | 30.05 | C |
| ATOM | 2321 | CE1 | PHE | A | 290 | 28.999 | −4.031 | 73.726 | 1.00 | 29.53 | C |
| ATOM | 2322 | CE2 | PHE | A | 290 | 30.096 | −6.167 | 73.610 | 1.00 | 39.96 | C |
| ATOM | 2323 | CZ | PHE | A | 290 | 28.952 | −5.390 | 73.455 | 1.00 | 27.60 | C |

TABLE 1-continued

| | | | | | | | | | | |
|---|---|---|---|---|---|---|---|---|---|---|
| ATOM | 2324 | N | LYS | A | 291 | 34.697 | −1.330 | 75.901 | 1.00 | 44.70 N |
| ATOM | 2325 | CA | LYS | A | 291 | 35.960 | −1.040 | 76.564 | 1.00 | 33.69 C |
| ATOM | 2326 | C | LYS | A | 291 | 35.699 | −0.149 | 77.739 | 1.00 | 30.24 C |
| ATOM | 2327 | O | LYS | A | 291 | 36.333 | −0.305 | 78.779 | 1.00 | 27.75 O |
| ATOM | 2328 | CB | LYS | A | 291 | 36.935 | −0.379 | 75.591 | 1.00 | 39.25 C |
| ATOM | 2329 | CG | LYS | A | 291 | 37.609 | −1.393 | 74.675 | 1.00 | 46.54 C |
| ATOM | 2330 | CD | LYS | A | 291 | 38.446 | −0.736 | 73.576 | 1.00 | 62.11 C |
| ATOM | 2331 | CE | LYS | A | 291 | 39.482 | 0.232 | 74.115 | 1.00 | 56.37 C |
| ATOM | 2332 | NZ | LYS | A | 291 | 40.344 | 0.807 | 73.022 | 1.00 | 70.65 N |
| ATOM | 2333 | N | ASP | A | 292 | 34.754 | 0.776 | 77.579 | 1.00 | 28.21 N |
| ATOM | 2334 | CA | ASP | A | 292 | 34.396 | 1.669 | 78.664 | 1.00 | 28.66 C |
| ATOM | 2335 | C | ASP | A | 292 | 33.793 | 0.847 | 79.795 | 1.00 | 57.70 C |
| ATOM | 2336 | O | ASP | A | 292 | 34.070 | 1.089 | 80.977 | 1.00 | 59.97 O |
| ATOM | 2337 | CB | ASP | A | 292 | 33.373 | 2.691 | 78.211 | 1.00 | 40.66 C |
| ATOM | 2338 | CG | ASP | A | 292 | 33.895 | 3.579 | 77.106 | 1.00 | 70.09 C |
| ATOM | 2339 | OD1 | ASP | A | 292 | 34.990 | 4.172 | 77.264 | 1.00 | 78.13 O |
| ATOM | 2340 | OD2 | ASP | A | 292 | 33.207 | 3.687 | 76.070 | 1.00 | 91.47 O |
| ATOM | 2341 | N | ILE | A | 293 | 32.960 | −0.125 | 79.436 | 1.00 | 48.12 N |
| ATOM | 2342 | CA | ILE | A | 293 | 32.352 | −0.963 | 80.452 | 1.00 | 46.06 C |
| ATOM | 2343 | C | ILE | A | 293 | 33.441 | −1.715 | 81.184 | 1.00 | 32.16 C |
| ATOM | 2344 | O | ILE | A | 293 | 33.404 | −1.799 | 82.412 | 1.00 | 51.38 O |
| ATOM | 2345 | CB | ILE | A | 293 | 31.306 | −1.920 | 79.835 | 1.00 | 31.89 C |
| ATOM | 2346 | CG1 | ILE | A | 293 | 30.094 | −1.099 | 79.405 | 1.00 | 31.93 C |
| ATOM | 2347 | CG2 | ILE | A | 293 | 30.873 | −2.976 | 80.832 | 1.00 | 32.86 C |
| ATOM | 2348 | CD1 | ILE | A | 293 | 28.996 | −1.927 | 78.757 | 1.00 | 55.11 C |
| ATOM | 2349 | N | ALA | A | 294 | 34.410 | −2.254 | 80.448 | 1.00 | 33.04 N |
| ATOM | 2350 | CA | ALA | A | 294 | 35.525 | −2.967 | 81.089 | 1.00 | 38.15 C |
| ATOM | 2351 | C | ALA | A | 294 | 36.261 | −2.062 | 82.117 | 1.00 | 50.88 C |
| ATOM | 2352 | O | ALA | A | 294 | 36.626 | −2.516 | 83.201 | 1.00 | 37.93 O |
| ATOM | 2353 | CB | ALA | A | 294 | 36.508 | −3.469 | 80.042 | 1.00 | 36.23 C |
| ATOM | 2354 | N | SER | A | 295 | 36.460 | −0.782 | 81.790 | 1.00 | 39.46 N |
| ATOM | 2355 | CA | SER | A | 295 | 37.131 | 0.120 | 82.729 | 1.00 | 51.26 C |
| ATOM | 2356 | C | SER | A | 295 | 36.237 | 0.388 | 83.950 | 1.00 | 49.11 C |
| ATOM | 2357 | O | SER | A | 295 | 36.717 | 0.445 | 85.092 | 1.00 | 42.88 O |
| ATOM | 2358 | CB | SER | A | 295 | 37.521 | 1.444 | 82.043 | 1.00 | 38.90 C |
| ATOM | 2359 | OG | SER | A | 295 | 36.388 | 2.238 | 81.771 | 1.00 | 70.81 O |
| ATOM | 2360 | N | THR | A | 296 | 34.938 | 0.548 | 83.717 | 1.00 | 42.17 N |
| ATOM | 2361 | CA | THR | A | 296 | 34.008 | 0.779 | 84.825 | 1.00 | 39.46 C |
| ATOM | 2362 | C | THR | A | 296 | 34.119 | −0.417 | 85.786 | 1.00 | 35.44 C |
| ATOM | 2363 | O | THR | A | 296 | 34.232 | −0.256 | 86.992 | 1.00 | 32.58 O |
| ATOM | 2364 | CB | THR | A | 296 | 32.562 | 0.912 | 84.293 | 1.00 | 42.44 C |
| ATOM | 2365 | OG1 | THR | A | 296 | 32.503 | 2.026 | 83.403 | 1.00 | 49.42 O |
| ATOM | 2366 | CG2 | THR | A | 296 | 31.548 | 1.132 | 85.419 | 1.00 | 25.20 C |
| ATOM | 2367 | N | LEU | A | 297 | 34.117 | −1.624 | 85.244 | 1.00 | 29.99 N |
| ATOM | 2368 | CA | LEU | A | 297 | 34.223 | −2.785 | 86.101 | 1.00 | 31.56 C |
| ATOM | 2369 | C | LEU | A | 297 | 35.565 | −2.782 | 86.833 | 1.00 | 54.98 C |
| ATOM | 2370 | O | LEU | A | 297 | 35.629 | −3.110 | 88.014 | 1.00 | 38.04 O |
| ATOM | 2371 | CB | LEU | A | 297 | 34.077 | −4.069 | 85.279 | 1.00 | 40.57 C |
| ATOM | 2372 | CG | LEU | A | 297 | 32.681 | −4.271 | 84.675 | 1.00 | 41.84 C |
| ATOM | 2373 | CD1 | LEU | A | 297 | 32.681 | −5.437 | 83.710 | 1.00 | 31.31 C |
| ATOM | 2374 | CD2 | LEU | A | 297 | 31.702 | −4.500 | 85.805 | 1.00 | 23.11 C |
| ATOM | 2375 | N | ASN | A | 298 | 36.626 | −2.405 | 86.121 | 1.00 | 40.66 N |
| ATOM | 2376 | CA | ASN | A | 298 | 37.972 | −2.377 | 86.685 | 1.00 | 46.02 C |
| ATOM | 2377 | C | ASN | A | 298 | 38.096 | −1.371 | 87.830 | 1.00 | 49.77 C |
| ATOM | 2378 | O | ASN | A | 298 | 38.794 | −1.619 | 88.806 | 1.00 | 51.79 O |
| ATOM | 2379 | CB | ASN | A | 298 | 38.986 | −2.050 | 85.580 | 1.00 | 34.71 C |
| ATOM | 2380 | CG | ASN | A | 298 | 39.277 | −3.244 | 84.664 | 1.00 | 36.88 C |
| ATOM | 2381 | OD1 | ASN | A | 298 | 39.850 | −3.079 | 83.589 | 1.00 | 48.64 O |
| ATOM | 2382 | ND2 | ASN | A | 298 | 38.898 | −4.443 | 85.094 | 1.00 | 37.72 N |
| ATOM | 2383 | N | LYS | A | 299 | 37.398 | −0.247 | 87.717 | 1.00 | 42.77 N |
| ATOM | 2384 | CA | LYS | A | 299 | 37.435 | 0.780 | 88.736 | 1.00 | 29.77 C |
| ATOM | 2385 | C | LYS | A | 299 | 36.376 | 0.649 | 89.820 | 1.00 | 36.02 C |
| ATOM | 2386 | O | LYS | A | 299 | 36.295 | 1.496 | 90.704 | 1.00 | 43.44 O |
| ATOM | 2387 | CB | LYS | A | 299 | 37.314 | 2.153 | 88.071 | 1.00 | 34.96 C |
| ATOM | 2388 | CG | LYS | A | 299 | 38.605 | 2.564 | 87.381 | 1.00 | 54.22 C |
| ATOM | 2389 | CD | LYS | A | 299 | 38.403 | 3.602 | 86.274 | 1.00 | 64.33 C |
| ATOM | 2390 | CE | LYS | A | 299 | 39.740 | 3.861 | 85.551 | 1.00 | 74.99 C |
| ATOM | 2391 | NZ | LYS | A | 299 | 39.657 | 4.763 | 84.352 | 1.00 | 69.67 N |
| ATOM | 2392 | N | ALA | A | 300 | 35.566 | −0.401 | 89.774 | 1.00 | 35.71 N |
| ATOM | 2393 | CA | ALA | A | 300 | 34.502 | −0.565 | 90.769 | 1.00 | 38.77 C |
| ATOM | 2394 | C | ALA | A | 300 | 35.039 | −0.902 | 92.150 | 1.00 | 45.15 C |
| ATOM | 2395 | O | ALA | A | 300 | 35.789 | −1.861 | 92.303 | 1.00 | 53.99 O |
| ATOM | 2396 | CB | ALA | A | 300 | 33.557 | −1.634 | 90.337 | 1.00 | 20.24 C |
| ATOM | 2397 | N | LYS | A | 301 | 34.639 | −0.125 | 93.150 | 1.00 | 43.21 N |
| ATOM | 2398 | CA | LYS | A | 301 | 35.084 | −0.354 | 94.516 | 1.00 | 30.23 C |
| ATOM | 2399 | C | LYS | A | 301 | 33.938 | −0.824 | 95.408 | 1.00 | 45.63 C |
| ATOM | 2400 | O | LYS | A | 301 | 34.157 | −1.499 | 96.407 | 1.00 | 41.68 O |
| ATOM | 2401 | CB | LYS | A | 301 | 35.683 | 0.929 | 95.067 | 1.00 | 42.16 C |
| ATOM | 2402 | CG | LYS | A | 301 | 36.945 | 1.348 | 94.334 | 1.00 | 40.41 C |

TABLE 1-continued

| ATOM | 2403 | CD | LYS | A | 301 | 38.009 | 0.263 | 94.469 | 1.00 | 51.01 | C |
|---|---|---|---|---|---|---|---|---|---|---|---|
| ATOM | 2404 | CE | LYS | A | 301 | 39.210 | 0.540 | 93.576 | 1.00 | 72.45 | C |
| ATOM | 2405 | NZ | LYS | A | 301 | 40.242 | −0.545 | 93.696 | 1.00 | 72.79 | N |
| ATOM | 2406 | N | SER | A | 302 | 32.706 | −0.488 | 95.044 | 1.00 | 45.61 | N |
| ATOM | 2407 | CA | SER | A | 302 | 31.568 | −0.915 | 95.866 | 1.00 | 45.77 | C |
| ATOM | 2408 | C | SER | A | 302 | 30.324 | −1.368 | 95.070 | 1.00 | 44.12 | C |
| ATOM | 2409 | O | SER | A | 302 | 30.280 | −1.255 | 93.850 | 1.00 | 37.27 | O |
| ATOM | 2410 | CB | SER | A | 302 | 31.191 | 0.218 | 96.810 | 1.00 | 31.92 | C |
| ATOM | 2411 | OG | SER | A | 302 | 30.834 | 1.366 | 96.061 | 1.00 | 41.85 | O |
| ATOM | 2412 | N | ILE | A | 303 | 29.307 | −1.854 | 95.778 | 1.00 | 35.67 | N |
| ATOM | 2413 | CA | ILE | A | 303 | 28.093 | −2.309 | 95.149 | 1.00 | 26.25 | C |
| ATOM | 2414 | C | ILE | A | 303 | 26.816 | −2.135 | 96.024 | 1.00 | 45.17 | C |
| ATOM | 2415 | O | ILE | A | 303 | 26.842 | −2.280 | 97.256 | 1.00 | 37.95 | O |
| ATOM | 2416 | CB | ILE | A | 303 | 28.261 | −3.805 | 94.737 | 1.00 | 32.56 | C |
| ATOM | 2417 | CG1 | ILE | A | 303 | 27.064 | −4.266 | 93.896 | 1.00 | 27.06 | C |
| ATOM | 2418 | CG2 | ILE | A | 303 | 28.356 | −4.661 | 95.968 | 1.00 | 25.45 | C |
| ATOM | 2419 | CD1 | ILE | A | 303 | 27.174 | −5.669 | 93.413 | 1.00 | 34.48 | C |
| ATOM | 2420 | N | VAL | A | 304 | 25.698 | −1.820 | 95.378 | 1.00 | 31.58 | N |
| ATOM | 2421 | CA | VAL | A | 304 | 24.417 | −1.636 | 96.078 | 1.00 | 28.57 | C |
| ATOM | 2422 | C | VAL | A | 304 | 23.580 | −2.909 | 95.916 | 1.00 | 41.86 | C |
| ATOM | 2423 | O | VAL | A | 304 | 23.552 | −3.518 | 94.855 | 1.00 | 33.62 | O |
| ATOM | 2424 | CB | VAL | A | 304 | 23.636 | −0.433 | 95.509 | 1.00 | 27.92 | C |
| ATOM | 2425 | CG1 | VAL | A | 304 | 22.286 | −0.271 | 96.209 | 1.00 | 28.15 | C |
| ATOM | 2426 | CG2 | VAL | A | 304 | 24.451 | 0.820 | 95.645 | 1.00 | 29.16 | C |
| ATOM | 2427 | N | GLY | A | 305 | 22.895 | −3.310 | 96.975 | 1.00 | 40.05 | N |
| ATOM | 2428 | CA | GLY | A | 305 | 22.104 | −4.523 | 96.903 | 1.00 | 48.50 | C |
| ATOM | 2429 | C | GLY | A | 305 | 22.462 | −5.401 | 98.084 | 1.00 | 50.22 | C |
| ATOM | 2430 | O | GLY | A | 305 | 23.493 | −5.189 | 98.714 | 1.00 | 63.91 | O |
| ATOM | 2431 | N | THR | A | 306 | 21.648 | −6.406 | 98.373 | 1.00 | 54.25 | N |
| ATOM | 2432 | CA | THR | A | 306 | 21.920 | −7.246 | 99.525 | 1.00 | 53.92 | C |
| ATOM | 2433 | C | THR | A | 306 | 22.461 | −8.638 | 99.264 | 1.00 | 51.34 | C |
| ATOM | 2434 | O | THR | A | 306 | 23.318 | −9.124 | 100.005 | 1.00 | 39.43 | O |
| ATOM | 2435 | CB | THR | A | 306 | 20.675 | −7.354 | 100.402 | 1.00 | 57.80 | C |
| ATOM | 2436 | OG1 | THR | A | 306 | 19.639 | −8.033 | 99.690 | 1.00 | 70.18 | O |
| ATOM | 2437 | CG2 | THR | A | 306 | 20.196 | −5.972 | 100.770 | 1.00 | 63.46 | C |
| ATOM | 2438 | N | THR | A | 307 | 21.976 | −9.284 | 98.214 | 1.00 | 57.29 | N |
| ATOM | 2439 | CA | THR | A | 307 | 22.445 | −10.629 | 97.887 | 1.00 | 46.74 | C |
| ATOM | 2440 | C | THR | A | 307 | 23.733 | −10.699 | 97.078 | 1.00 | 50.79 | C |
| ATOM | 2441 | O | THR | A | 307 | 24.636 | −11.455 | 97.427 | 1.00 | 64.74 | O |
| ATOM | 2442 | CB | THR | A | 307 | 21.369 | −11.428 | 97.117 | 1.00 | 64.42 | C |
| ATOM | 2443 | OG1 | THR | A | 307 | 20.364 | −11.868 | 98.039 | 1.00 | 77.89 | O |
| ATOM | 2444 | CG2 | THR | A | 307 | 21.984 | −12.649 | 96.405 | 1.00 | 56.20 | C |
| ATOM | 2445 | N | ALA | A | 308 | 23.821 | −9.920 | 96.005 | 1.00 | 53.74 | N |
| ATOM | 2446 | CA | ALA | A | 308 | 24.991 | −9.968 | 95.135 | 1.00 | 54.41 | C |
| ATOM | 2447 | C | ALA | A | 308 | 26.236 | −9.209 | 95.575 | 1.00 | 42.08 | C |
| ATOM | 2448 | O | ALA | A | 308 | 26.156 | −8.041 | 95.963 | 1.00 | 41.01 | O |
| ATOM | 2449 | CB | ALA | A | 308 | 24.594 | −9.517 | 93.735 | 1.00 | 53.48 | C |
| ATOM | 2450 | N | SER | A | 309 | 27.383 | −9.887 | 95.483 | 1.00 | 37.50 | N |
| ATOM | 2451 | CA | SER | A | 309 | 28.677 | −9.304 | 95.826 | 1.00 | 38.18 | C |
| ATOM | 2452 | C | SER | A | 309 | 29.272 | −8.716 | 94.561 | 1.00 | 34.97 | C |
| ATOM | 2453 | O | SER | A | 309 | 28.970 | −9.161 | 93.457 | 1.00 | 35.62 | O |
| ATOM | 2454 | CB | SER | A | 309 | 29.635 | −10.360 | 96.354 | 1.00 | 41.05 | C |
| ATOM | 2455 | OG | SER | A | 309 | 30.304 | −10.999 | 95.278 | 1.00 | 46.37 | O |
| ATOM | 2456 | N | LEU | A | 310 | 30.149 | −7.737 | 94.740 | 1.00 | 39.72 | N |
| ATOM | 2457 | CA | LEU | A | 310 | 30.791 | −7.067 | 93.629 | 1.00 | 40.72 | C |
| ATOM | 2458 | C | LEU | A | 310 | 31.487 | −8.042 | 92.694 | 1.00 | 54.44 | C |
| ATOM | 2459 | O | LEU | A | 310 | 31.219 | −8.053 | 91.485 | 1.00 | 54.61 | O |
| ATOM | 2460 | CB | LEU | A | 310 | 31.778 | −6.038 | 94.162 | 1.00 | 38.57 | C |
| ATOM | 2461 | CG | LEU | A | 310 | 32.611 | −5.314 | 93.112 | 1.00 | 32.77 | C |
| ATOM | 2462 | CD1 | LEU | A | 310 | 31.739 | −4.687 | 92.029 | 1.00 | 38.92 | C |
| ATOM | 2463 | CD2 | LEU | A | 310 | 33.475 | −4.260 | 93.771 | 1.00 | 33.38 | C |
| ATOM | 2464 | N | GLN | A | 311 | 32.398 | −8.842 | 93.246 | 1.00 | 39.62 | N |
| ATOM | 2465 | CA | GLN | A | 311 | 33.099 | −9.830 | 92.433 | 1.00 | 28.35 | C |
| ATOM | 2466 | C | GLN | A | 311 | 32.110 | −10.683 | 91.641 | 1.00 | 46.04 | C |
| ATOM | 2467 | O | GLN | A | 311 | 32.345 | −11.024 | 90.478 | 1.00 | 38.58 | O |
| ATOM | 2468 | CB | GLN | A | 311 | 33.962 | −10.719 | 93.313 | 1.00 | 41.19 | C |
| ATOM | 2469 | CG | GLN | A | 311 | 34.895 | −11.640 | 92.536 | 1.00 | 54.66 | C |
| ATOM | 2470 | CD | GLN | A | 311 | 35.950 | −12.261 | 93.424 | 1.00 | 79.91 | C |
| ATOM | 2471 | OE1 | GLN | A | 311 | 35.703 | −13.250 | 94.098 | 1.00 | 82.04 | O |
| ATOM | 2472 | NE2 | GLN | A | 311 | 37.204 | −11.841 | 93.568 | 1.00 | 60.87 | N |
| ATOM | 2473 | N | TYR | A | 312 | 31.003 | −11.030 | 92.284 | 1.00 | 44.83 | N |
| ATOM | 2474 | CA | TYR | A | 312 | 29.973 | −11.815 | 91.634 | 1.00 | 36.62 | C |
| ATOM | 2475 | C | TYR | A | 312 | 29.449 | −11.074 | 90.388 | 1.00 | 42.36 | C |
| ATOM | 2476 | O | TYR | A | 312 | 29.436 | −11.619 | 89.282 | 1.00 | 33.63 | O |
| ATOM | 2477 | CB | TYR | A | 312 | 28.822 | −12.087 | 92.623 | 1.00 | 26.84 | C |
| ATOM | 2478 | CG | TYR | A | 312 | 27.742 | −12.888 | 91.974 | 1.00 | 35.34 | C |
| ATOM | 2479 | CD1 | TYR | A | 312 | 27.846 | −14.275 | 91.915 | 1.00 | 42.18 | C |
| ATOM | 2480 | CD2 | TYR | A | 312 | 26.634 | −12.287 | 91.396 | 1.00 | 45.17 | C |
| ATOM | 2481 | CE1 | TYR | A | 312 | 26.855 | −15.045 | 91.284 | 1.00 | 51.04 | C |

TABLE 1-continued

| | | | | | | | | | | |
|---|---|---|---|---|---|---|---|---|---|---|
| ATOM | 2482 | CE2 | TYR | A | 312 | 25.642 | −13.038 | 90.766 | 1.00 | 41.79 | C |
| ATOM | 2483 | CZ | TYR | A | 312 | 25.756 | −14.413 | 90.711 | 1.00 | 51.20 | C |
| ATOM | 2484 | OH | TYR | A | 312 | 24.780 | −15.172 | 90.104 | 1.00 | 48.07 | O |
| ATOM | 2485 | N | MET | A | 313 | 29.039 | −9.821 | 90.566 | 1.00 | 39.04 | N |
| ATOM | 2486 | CA | MET | A | 313 | 28.519 | −9.057 | 89.448 | 1.00 | 35.72 | C |
| ATOM | 2487 | C | MET | A | 313 | 29.578 | −8.837 | 88.373 | 1.00 | 41.87 | C |
| ATOM | 2488 | O | MET | A | 313 | 29.279 | −8.943 | 87.176 | 1.00 | 34.56 | O |
| ATOM | 2489 | CB | MET | A | 313 | 27.977 | −7.714 | 89.923 | 1.00 | 32.57 | C |
| ATOM | 2490 | CG | MET | A | 313 | 26.567 | −7.794 | 90.449 | 1.00 | 52.32 | C |
| ATOM | 2491 | SD | MET | A | 313 | 25.426 | −8.502 | 89.242 | 1.00 | 54.62 | S |
| ATOM | 2492 | CE | MET | A | 313 | 25.171 | −10.141 | 89.918 | 1.00 | 18.86 | C |
| ATOM | 2493 | N | LYS | A | 314 | 30.812 | −8.541 | 88.780 | 1.00 | 29.35 | N |
| ATOM | 2494 | CA | LYS | A | 314 | 31.866 | −8.337 | 87.780 | 1.00 | 34.48 | C |
| ATOM | 2495 | C | LYS | A | 314 | 31.994 | −9.607 | 86.953 | 1.00 | 35.25 | C |
| ATOM | 2496 | O | LYS | A | 314 | 32.206 | −9.554 | 85.750 | 1.00 | 36.36 | O |
| ATOM | 2497 | CB | LYS | A | 314 | 33.218 | −8.020 | 88.427 | 1.00 | 26.91 | C |
| ATOM | 2498 | CG | LYS | A | 314 | 33.283 | −6.635 | 89.042 | 1.00 | 44.76 | C |
| ATOM | 2499 | CD | LYS | A | 314 | 34.570 | −6.458 | 89.834 | 1.00 | 48.64 | C |
| ATOM | 2500 | CE | LYS | A | 314 | 35.802 | −6.511 | 88.932 | 1.00 | 59.15 | C |
| ATOM | 2501 | NZ | LYS | A | 314 | 37.049 | −6.134 | 89.651 | 1.00 | 68.05 | N |
| ATOM | 2502 | N | ASN | A | 315 | 31.861 | −10.761 | 87.593 | 1.00 | 43.27 | N |
| ATOM | 2503 | CA | ASN | A | 315 | 31.980 | −11.988 | 86.828 | 1.00 | 38.69 | C |
| ATOM | 2504 | C | ASN | A | 315 | 30.772 | −12.159 | 85.889 | 1.00 | 43.63 | C |
| ATOM | 2505 | O | ASN | A | 315 | 30.914 | −12.692 | 84.797 | 1.00 | 37.92 | O |
| ATOM | 2506 | CB | ASN | A | 315 | 32.117 | −13.196 | 87.750 | 1.00 | 38.49 | C |
| ATOM | 2507 | CG | ASN | A | 315 | 32.316 | −14.485 | 86.975 | 1.00 | 49.39 | C |
| ATOM | 2508 | OD1 | ASN | A | 315 | 31.481 | −15.391 | 87.052 | 1.00 | 56.24 | O |
| ATOM | 2509 | ND2 | ASN | A | 315 | 33.418 | −14.565 | 86.238 | 1.00 | 62.62 | N |
| ATOM | 2510 | N | VAL | A | 316 | 29.593 | −11.710 | 86.311 | 1.00 | 30.36 | N |
| ATOM | 2511 | CA | VAL | A | 316 | 28.415 | −11.791 | 85.473 | 1.00 | 34.82 | C |
| ATOM | 2512 | C | VAL | A | 316 | 28.676 | −11.043 | 84.188 | 1.00 | 34.96 | C |
| ATOM | 2513 | O | VAL | A | 316 | 28.435 | −11.545 | 83.085 | 1.00 | 33.64 | O |
| ATOM | 2514 | CB | VAL | A | 316 | 27.146 | −11.246 | 86.161 | 1.00 | 28.12 | C |
| ATOM | 2515 | CG1 | VAL | A | 316 | 26.046 | −11.028 | 85.150 | 1.00 | 21.33 | C |
| ATOM | 2516 | CG2 | VAL | A | 316 | 26.695 | −12.209 | 87.258 | 1.00 | 45.20 | C |
| ATOM | 2517 | N | PHE | A | 317 | 29.187 | −9.825 | 84.330 | 1.00 | 30.09 | N |
| ATOM | 2518 | CA | PHE | A | 317 | 29.455 | −9.017 | 83.168 | 1.00 | 27.93 | C |
| ATOM | 2519 | C | PHE | A | 317 | 30.665 | −9.485 | 82.378 | 1.00 | 34.67 | C |
| ATOM | 2520 | O | PHE | A | 317 | 30.719 | −9.314 | 81.152 | 1.00 | 30.27 | O |
| ATOM | 2521 | CB | PHE | A | 317 | 29.532 | −7.558 | 83.584 | 1.00 | 27.89 | C |
| ATOM | 2522 | CG | PHE | A | 317 | 28.215 | −7.046 | 84.082 | 1.00 | 31.19 | C |
| ATOM | 2523 | CD1 | PHE | A | 317 | 27.105 | −7.077 | 83.243 | 1.00 | 37.16 | C |
| ATOM | 2524 | CD2 | PHE | A | 317 | 28.038 | −6.673 | 85.412 | 1.00 | 25.32 | C |
| ATOM | 2525 | CE1 | PHE | A | 317 | 25.824 | −6.750 | 83.731 | 1.00 | 35.47 | C |
| ATOM | 2526 | CE2 | PHE | A | 317 | 26.765 | −6.354 | 85.903 | 1.00 | 25.19 | C |
| ATOM | 2527 | CZ | PHE | A | 317 | 25.660 | −6.393 | 85.065 | 1.00 | 21.92 | C |
| ATOM | 2528 | N | LYS | A | 318 | 31.620 | −10.098 | 83.064 | 1.00 | 24.09 | N |
| ATOM | 2529 | CA | LYS | A | 318 | 32.781 | −10.614 | 82.364 | 1.00 | 33.12 | C |
| ATOM | 2530 | C | LYS | A | 318 | 32.275 | −11.689 | 81.372 | 1.00 | 37.35 | C |
| ATOM | 2531 | O | LYS | A | 318 | 32.749 | −11.762 | 80.236 | 1.00 | 42.72 | O |
| ATOM | 2532 | CB | LYS | A | 318 | 33.779 | −11.204 | 83.366 | 1.00 | 30.84 | C |
| ATOM | 2533 | CG | LYS | A | 318 | 34.865 | −12.054 | 82.756 | 1.00 | 49.03 | C |
| ATOM | 2534 | CD | LYS | A | 318 | 35.624 | −12.797 | 83.851 | 1.00 | 52.34 | C |
| ATOM | 2535 | CE | LYS | A | 318 | 36.504 | −13.879 | 83.272 | 1.00 | 49.95 | C |
| ATOM | 2536 | NZ | LYS | A | 318 | 37.316 | −13.333 | 82.160 | 1.00 | 66.09 | N |
| ATOM | 2537 | N | GLU | A | 319 | 31.303 | −12.505 | 81.790 | 1.00 | 33.08 | N |
| ATOM | 2538 | CA | GLU | A | 319 | 30.758 | −13.547 | 80.909 | 1.00 | 28.72 | C |
| ATOM | 2539 | C | GLU | A | 319 | 29.887 | −12.925 | 79.813 | 1.00 | 39.14 | C |
| ATOM | 2540 | O | GLU | A | 319 | 29.882 | −13.382 | 78.672 | 1.00 | 42.13 | O |
| ATOM | 2541 | CB | GLU | A | 319 | 29.923 | −14.556 | 81.703 | 1.00 | 29.43 | C |
| ATOM | 2542 | CG | GLU | A | 319 | 30.695 | −15.231 | 82.836 | 1.00 | 61.10 | C |
| ATOM | 2543 | CD | GLU | A | 319 | 29.818 | −16.137 | 83.694 | 1.00 | 84.59 | C |
| ATOM | 2544 | OE1 | GLU | A | 319 | 28.750 | −15.666 | 84.153 | 1.00 | 85.91 | O |
| ATOM | 2545 | OE2 | GLU | A | 319 | 30.198 | −17.316 | 83.918 | 1.00 | 81.51 | O |
| ATOM | 2546 | N | LYS | A | 320 | 29.156 | −11.874 | 80.153 | 1.00 | 33.61 | N |
| ATOM | 2547 | CA | LYS | A | 320 | 28.308 | −11.242 | 79.159 | 1.00 | 38.32 | C |
| ATOM | 2548 | C | LYS | A | 320 | 29.101 | −10.659 | 78.001 | 1.00 | 43.83 | C |
| ATOM | 2549 | O | LYS | A | 320 | 28.849 | −10.995 | 76.837 | 1.00 | 31.82 | O |
| ATOM | 2550 | CB | LYS | A | 320 | 27.462 | −10.111 | 79.763 | 1.00 | 23.20 | C |
| ATOM | 2551 | CG | LYS | A | 320 | 26.595 | −9.421 | 78.713 | 1.00 | 21.58 | C |
| ATOM | 2552 | CD | LYS | A | 320 | 25.731 | −8.321 | 79.282 | 1.00 | 25.65 | C |
| ATOM | 2553 | CE | LYS | A | 320 | 25.015 | −7.566 | 78.161 | 1.00 | 20.65 | C |
| ATOM | 2554 | NZ | LYS | A | 320 | 24.267 | −6.369 | 78.668 | 1.00 | 21.80 | N |
| ATOM | 2555 | N | TYR | A | 321 | 30.029 | −9.754 | 78.321 | 1.00 | 37.92 | N |
| ATOM | 2556 | CA | TYR | A | 321 | 30.817 | −9.091 | 77.292 | 1.00 | 42.84 | C |
| ATOM | 2557 | C | TYR | A | 321 | 32.070 | −9.860 | 76.879 | 1.00 | 40.34 | C |
| ATOM | 2558 | O | TYR | A | 321 | 32.906 | −9.325 | 76.162 | 1.00 | 48.11 | O |
| ATOM | 2559 | CB | TYR | A | 321 | 31.176 | −7.684 | 77.757 | 1.00 | 39.77 | C |
| ATOM | 2560 | CG | TYR | A | 321 | 29.978 | −6.819 | 78.099 | 1.00 | 42.79 | C |

TABLE 1-continued

| | | | | | | | | | | |
|---|---|---|---|---|---|---|---|---|---|---|
| ATOM | 2561 | CD1 | TYR | A | 321 | 29.219 | −6.202 | 77.099 | 1.00 | 35.20 | C |
| ATOM | 2562 | CD2 | TYR | A | 321 | 29.592 | −6.632 | 79.429 | 1.00 | 34.65 | C |
| ATOM | 2563 | CE1 | TYR | A | 321 | 28.101 | −5.426 | 77.423 | 1.00 | 25.65 | C |
| ATOM | 2564 | CE2 | TYR | A | 321 | 28.495 | −5.859 | 79.757 | 1.00 | 23.91 | C |
| ATOM | 2565 | CZ | TYR | A | 321 | 27.750 | −5.261 | 78.750 | 1.00 | 36.51 | C |
| ATOM | 2566 | OH | TYR | A | 321 | 26.656 | −4.499 | 79.079 | 1.00 | 23.23 | O |
| ATOM | 2567 | N | LEU | A | 322 | 32.182 | −11.111 | 77.334 | 1.00 | 37.22 | N |
| ATOM | 2568 | CA | LEU | A | 322 | 33.309 | −11.992 | 77.013 | 1.00 | 49.07 | C |
| ATOM | 2569 | C | LEU | A | 322 | 34.685 | −11.329 | 77.188 | 1.00 | 49.08 | C |
| ATOM | 2570 | O | LEU | A | 322 | 35.533 | −11.398 | 76.298 | 1.00 | 43.05 | O |
| ATOM | 2571 | CB | LEU | A | 322 | 33.162 | −12.497 | 75.565 | 1.00 | 46.23 | C |
| ATOM | 2572 | CG | LEU | A | 322 | 31.796 | −13.083 | 75.176 | 1.00 | 41.02 | C |
| ATOM | 2573 | CD1 | LEU | A | 322 | 31.740 | −13.285 | 73.690 | 1.00 | 43.67 | C |
| ATOM | 2574 | CD2 | LEU | A | 322 | 31.550 | −14.400 | 75.899 | 1.00 | 45.69 | C |
| ATOM | 2575 | N | LEU | A | 323 | 34.903 | −10.698 | 78.339 | 1.00 | 48.83 | N |
| ATOM | 2576 | CA | LEU | A | 323 | 36.160 | −10.006 | 78.615 | 1.00 | 38.98 | C |
| ATOM | 2577 | C | LEU | A | 323 | 37.311 | −10.909 | 79.016 | 1.00 | 42.04 | C |
| ATOM | 2578 | O | LEU | A | 323 | 37.107 | −12.043 | 79.465 | 1.00 | 44.07 | O |
| ATOM | 2579 | CB | LEU | A | 323 | 35.960 | −8.979 | 79.735 | 1.00 | 42.34 | C |
| ATOM | 2580 | CG | LEU | A | 323 | 34.732 | −8.094 | 79.597 | 1.00 | 34.95 | C |
| ATOM | 2581 | CD1 | LEU | A | 323 | 34.583 | −7.225 | 80.855 | 1.00 | 26.41 | C |
| ATOM | 2582 | CD2 | LEU | A | 323 | 34.864 | −7.260 | 78.339 | 1.00 | 30.44 | C |
| ATOM | 2583 | N | SER | A | 324 | 38.528 | −10.396 | 78.846 | 1.00 | 41.80 | N |
| ATOM | 2584 | CA | SER | A | 324 | 39.716 | −11.131 | 79.260 | 1.00 | 61.71 | C |
| ATOM | 2585 | C | SER | A | 324 | 40.064 | −10.609 | 80.662 | 1.00 | 49.10 | C |
| ATOM | 2586 | O | SER | A | 324 | 39.918 | −9.413 | 80.956 | 1.00 | 44.34 | O |
| ATOM | 2587 | CB | SER | A | 324 | 40.893 | −10.872 | 78.308 | 1.00 | 56.52 | C |
| ATOM | 2588 | OG | SER | A | 324 | 40.538 | −11.100 | 76.959 | 1.00 | 58.74 | O |
| ATOM | 2589 | N | GLU | A | 325 | 40.495 | −11.511 | 81.529 | 1.00 | 47.18 | N |
| ATOM | 2590 | CA | GLU | A | 325 | 40.882 | −11.141 | 82.886 | 1.00 | 68.56 | C |
| ATOM | 2591 | C | GLU | A | 325 | 42.392 | −11.380 | 82.954 | 1.00 | 74.16 | C |
| ATOM | 2592 | O | GLU | A | 325 | 42.840 | −12.506 | 83.167 | 1.00 | 77.90 | O |
| ATOM | 2593 | CB | GLU | A | 325 | 40.147 | −12.025 | 83.894 | 1.00 | 64.62 | C |
| ATOM | 2594 | CG | GLU | A | 325 | 40.251 | −11.566 | 85.343 | 1.00 | 75.42 | C |
| ATOM | 2595 | CD | GLU | A | 325 | 39.564 | −12.527 | 86.308 | 1.00 | 80.88 | C |
| ATOM | 2596 | OE1 | GLU | A | 325 | 38.323 | −12.681 | 86.239 | 1.00 | 76.26 | O |
| ATOM | 2597 | OE2 | GLU | A | 325 | 40.272 | −13.137 | 87.140 | 1.00 | 94.09 | O |
| ATOM | 2598 | N | ASP | A | 326 | 43.169 | −10.316 | 82.759 | 1.00 | 74.51 | N |
| ATOM | 2599 | CA | ASP | A | 326 | 44.629 | −10.406 | 82.743 | 1.00 | 72.27 | C |
| ATOM | 2600 | C | ASP | A | 326 | 45.254 | −11.047 | 83.975 | 1.00 | 57.65 | C |
| ATOM | 2601 | O | ASP | A | 326 | 44.568 | −11.412 | 84.919 | 1.00 | 46.70 | O |
| ATOM | 2602 | CB | ASP | A | 326 | 45.234 | −9.015 | 82.536 | 1.00 | 60.60 | C |
| ATOM | 2603 | CG | ASP | A | 326 | 45.562 | −8.323 | 83.845 | 1.00 | 80.75 | C |
| ATOM | 2604 | OD1 | ASP | A | 326 | 44.802 | −8.506 | 84.825 | 1.00 | 79.53 | O |
| ATOM | 2605 | OD2 | ASP | A | 326 | 46.575 | −7.589 | 83.892 | 1.00 | 85.39 | O |
| ATOM | 2606 | N | THR | A | 327 | 46.578 | −11.169 | 83.943 | 1.00 | 73.89 | N |
| ATOM | 2607 | CA | THR | A | 327 | 47.343 | −11.765 | 85.036 | 1.00 | 76.65 | C |
| ATOM | 2608 | C | THR | A | 327 | 47.133 | −11.045 | 86.371 | 1.00 | 71.97 | C |
| ATOM | 2609 | O | THR | A | 327 | 47.373 | −11.620 | 87.434 | 1.00 | 75.50 | O |
| ATOM | 2610 | CB | THR | A | 327 | 48.856 | −11.771 | 84.700 | 1.00 | 81.59 | C |
| ATOM | 2611 | OG1 | THR | A | 327 | 49.060 | −12.445 | 83.452 | 1.00 | 86.49 | O |
| ATOM | 2612 | CG2 | THR | A | 327 | 49.652 | −12.494 | 85.783 | 1.00 | 85.36 | C |
| ATOM | 2613 | N | SER | A | 328 | 46.678 | −9.794 | 86.309 | 1.00 | 76.39 | N |
| ATOM | 2614 | CA | SER | A | 328 | 46.445 | −8.996 | 87.512 | 1.00 | 67.96 | C |
| ATOM | 2615 | C | SER | A | 328 | 44.982 | −8.892 | 87.944 | 1.00 | 68.19 | C |
| ATOM | 2616 | O | SER | A | 328 | 44.695 | −8.329 | 88.996 | 1.00 | 74.31 | O |
| ATOM | 2617 | CB | SER | A | 328 | 47.025 | −7.581 | 87.333 | 1.00 | 72.65 | C |
| ATOM | 2618 | OG | SER | A | 328 | 46.382 | −6.862 | 86.290 | 1.00 | 76.35 | O |
| ATOM | 2619 | N | GLY | A | 329 | 44.057 | −9.431 | 87.153 | 1.00 | 53.84 | N |
| ATOM | 2620 | CA | GLY | A | 329 | 42.655 | −9.352 | 87.531 | 1.00 | 53.91 | C |
| ATOM | 2621 | C | GLY | A | 329 | 41.897 | −8.239 | 86.827 | 1.00 | 57.30 | C |
| ATOM | 2622 | O | GLY | A | 329 | 40.693 | −8.080 | 86.998 | 1.00 | 56.75 | O |
| ATOM | 2623 | N | LYS | A | 330 | 42.620 | −7.467 | 86.028 | 1.00 | 59.62 | N |
| ATOM | 2624 | CA | LYS | A | 330 | 42.057 | −6.368 | 85.262 | 1.00 | 65.06 | C |
| ATOM | 2625 | C | LYS | A | 330 | 41.339 | −6.917 | 84.006 | 1.00 | 70.38 | C |
| ATOM | 2626 | O | LYS | A | 330 | 41.891 | −7.745 | 83.267 | 1.00 | 50.09 | O |
| ATOM | 2627 | CB | LYS | A | 330 | 43.195 | −5.420 | 84.865 | 1.00 | 60.78 | C |
| ATOM | 2628 | CG | LYS | A | 330 | 42.779 | −4.204 | 84.072 | 1.00 | 73.26 | C |
| ATOM | 2629 | CD | LYS | A | 330 | 43.998 | −3.457 | 83.542 | 1.00 | 70.28 | C |
| ATOM | 2630 | CE | LYS | A | 330 | 43.577 | −2.287 | 82.654 | 1.00 | 81.19 | C |
| ATOM | 2631 | NZ | LYS | A | 330 | 44.729 | −1.646 | 81.956 | 1.00 | 75.43 | N |
| ATOM | 2632 | N | PHE | A | 331 | 40.113 | −6.453 | 83.766 | 1.00 | 64.54 | N |
| ATOM | 2633 | CA | PHE | A | 331 | 39.338 | −6.911 | 82.612 | 1.00 | 53.87 | C |
| ATOM | 2634 | C | PHE | A | 331 | 39.697 | −6.170 | 81.339 | 1.00 | 35.78 | C |
| ATOM | 2635 | O | PHE | A | 331 | 39.949 | −4.969 | 81.344 | 1.00 | 39.57 | O |
| ATOM | 2636 | CB | PHE | A | 331 | 37.820 | −6.722 | 82.825 | 1.00 | 49.73 | C |
| ATOM | 2637 | CG | PHE | A | 331 | 37.218 | −7.604 | 83.879 | 1.00 | 29.02 | C |
| ATOM | 2638 | CD1 | PHE | A | 331 | 37.709 | −8.886 | 84.112 | 1.00 | 54.89 | C |
| ATOM | 2639 | CD2 | PHE | A | 331 | 36.138 | −7.160 | 84.622 | 1.00 | 40.75 | C |

TABLE 1-continued

| | | | | | | | | | | |
|---|---|---|---|---|---|---|---|---|---|---|
| ATOM | 2640 | CE1 | PHE | A | 331 | 37.127 | −9.715 | 85.076 | 1.00 | 36.76 | C |
| ATOM | 2641 | CE2 | PHE | A | 331 | 35.549 | −7.982 | 85.591 | 1.00 | 43.89 | C |
| ATOM | 2642 | CZ | PHE | A | 331 | 36.047 | −9.257 | 85.815 | 1.00 | 46.36 | C |
| ATOM | 2643 | N | SER | A | 332 | 39.681 | −6.894 | 80.237 | 1.00 | 31.84 | N |
| ATOM | 2644 | CA | SER | A | 332 | 39.953 | −6.286 | 78.948 | 1.00 | 44.88 | C |
| ATOM | 2645 | C | SER | A | 332 | 39.057 | −6.914 | 77.868 | 1.00 | 31.71 | C |
| ATOM | 2646 | O | SER | A | 332 | 38.643 | −8.069 | 77.993 | 1.00 | 37.82 | O |
| ATOM | 2647 | CB | SER | A | 332 | 41.419 | −6.490 | 78.577 | 1.00 | 55.70 | C |
| ATOM | 2648 | OG | SER | A | 332 | 41.632 | −6.131 | 77.225 | 1.00 | 58.43 | O |
| ATOM | 2649 | N | VAL | A | 333 | 38.795 | −6.167 | 76.804 | 1.00 | 33.44 | N |
| ATOM | 2650 | CA | VAL | A | 333 | 37.968 | −6.656 | 75.698 | 1.00 | 49.17 | C |
| ATOM | 2651 | C | VAL | A | 333 | 38.715 | −7.549 | 74.709 | 1.00 | 50.39 | C |
| ATOM | 2652 | O | VAL | A | 333 | 39.572 | −7.094 | 73.954 | 1.00 | 44.92 | O |
| ATOM | 2653 | CB | VAL | A | 333 | 37.349 | −5.498 | 74.908 | 1.00 | 49.19 | C |
| ATOM | 2654 | CG1 | VAL | A | 333 | 36.621 | −6.034 | 73.683 | 1.00 | 49.18 | C |
| ATOM | 2655 | CG2 | VAL | A | 333 | 36.393 | −4.735 | 75.792 | 1.00 | 55.23 | C |
| ATOM | 2656 | N | ASP | A | 334 | 38.362 | −8.828 | 74.727 | 1.00 | 59.24 | N |
| ATOM | 2657 | CA | ASP | A | 334 | 38.949 | −9.843 | 73.854 | 1.00 | 61.34 | C |
| ATOM | 2658 | C | ASP | A | 334 | 38.477 | −9.572 | 72.410 | 1.00 | 65.70 | C |
| ATOM | 2659 | O | ASP | A | 334 | 37.333 | −9.874 | 72.049 | 1.00 | 49.07 | O |
| ATOM | 2660 | CB | ASP | A | 334 | 38.466 | −11.220 | 74.335 | 1.00 | 65.68 | C |
| ATOM | 2661 | CG | ASP | A | 334 | 39.126 | −12.378 | 73.609 | 1.00 | 68.83 | C |
| ATOM | 2662 | OD1 | ASP | A | 334 | 39.375 | −12.288 | 72.382 | 1.00 | 68.14 | O |
| ATOM | 2663 | OD2 | ASP | A | 334 | 39.372 | −13.399 | 74.285 | 1.00 | 67.77 | O |
| ATOM | 2664 | N | LYS | A | 335 | 39.352 | −8.997 | 71.592 | 1.00 | 55.29 | N |
| ATOM | 2665 | CA | LYS | A | 335 | 38.998 | −8.675 | 70.209 | 1.00 | 65.30 | C |
| ATOM | 2666 | C | LYS | A | 335 | 38.495 | −9.883 | 69.423 | 1.00 | 54.95 | C |
| ATOM | 2667 | O | LYS | A | 335 | 37.593 | −9.781 | 68.598 | 1.00 | 42.22 | O |
| ATOM | 2668 | CB | LYS | A | 335 | 40.198 | −8.060 | 69.501 | 1.00 | 44.11 | C |
| ATOM | 2669 | CG | LYS | A | 335 | 40.588 | −6.710 | 70.072 | 1.00 | 63.96 | C |
| ATOM | 2670 | CD | LYS | A | 335 | 41.997 | −6.273 | 69.646 | 1.00 | 63.71 | C |
| ATOM | 2671 | CE | LYS | A | 335 | 42.450 | −5.106 | 70.512 | 1.00 | 66.98 | C |
| ATOM | 2672 | NZ | LYS | A | 335 | 43.791 | −4.594 | 70.174 | 1.00 | 68.89 | N |
| ATOM | 2673 | N | LEU | A | 336 | 39.082 | −11.034 | 69.695 | 1.00 | 52.78 | N |
| ATOM | 2674 | CA | LEU | A | 336 | 38.687 | −12.244 | 69.006 | 1.00 | 56.05 | C |
| ATOM | 2675 | C | LEU | A | 336 | 37.252 | −12.593 | 69.380 | 1.00 | 64.18 | C |
| ATOM | 2676 | O | LEU | A | 336 | 36.395 | −12.780 | 68.515 | 1.00 | 58.69 | O |
| ATOM | 2677 | CB | LEU | A | 336 | 39.622 | −13.381 | 69.398 | 1.00 | 68.16 | C |
| ATOM | 2678 | CG | LEU | A | 336 | 40.015 | −14.300 | 68.242 | 1.00 | 68.99 | C |
| ATOM | 2679 | CD1 | LEU | A | 336 | 38.812 | −15.117 | 67.797 | 1.00 | 68.85 | C |
| ATOM | 2680 | CD2 | LEU | A | 336 | 40.570 | −13.456 | 67.098 | 1.00 | 57.35 | C |
| ATOM | 2681 | N | LYS | A | 337 | 37.000 | −12.678 | 70.680 | 1.00 | 62.56 | N |
| ATOM | 2682 | CA | LYS | A | 337 | 35.677 | −12.987 | 71.185 | 1.00 | 55.00 | C |
| ATOM | 2683 | C | LYS | A | 337 | 34.656 | −11.891 | 70.882 | 1.00 | 44.09 | C |
| ATOM | 2684 | O | LYS | A | 337 | 33.495 | −12.183 | 70.595 | 1.00 | 41.84 | O |
| ATOM | 2685 | CB | LYS | A | 337 | 35.758 | −13.264 | 72.676 | 1.00 | 55.70 | C |
| ATOM | 2686 | CG | LYS | A | 337 | 36.470 | −14.578 | 72.977 | 1.00 | 46.63 | C |
| ATOM | 2687 | CD | LYS | A | 337 | 36.569 | −14.840 | 74.475 | 1.00 | 61.80 | C |
| ATOM | 2688 | CE | LYS | A | 337 | 36.882 | −16.301 | 74.750 | 1.00 | 60.18 | C |
| ATOM | 2689 | NZ | LYS | A | 337 | 36.842 | −16.612 | 76.207 | 1.00 | 77.72 | N |
| ATOM | 2690 | N | PHE | A | 338 | 35.079 | −10.638 | 70.925 | 1.00 | 32.19 | N |
| ATOM | 2691 | CA | PHE | A | 338 | 34.166 | −9.554 | 70.620 | 1.00 | 31.35 | C |
| ATOM | 2692 | C | PHE | A | 338 | 33.651 | −9.659 | 69.187 | 1.00 | 50.28 | C |
| ATOM | 2693 | O | PHE | A | 338 | 32.439 | −9.732 | 68.960 | 1.00 | 46.83 | O |
| ATOM | 2694 | CB | PHE | A | 338 | 34.843 | −8.201 | 70.772 | 1.00 | 29.80 | C |
| ATOM | 2695 | CG | PHE | A | 338 | 34.013 | −7.070 | 70.267 | 1.00 | 29.63 | C |
| ATOM | 2696 | CD1 | PHE | A | 338 | 32.937 | −6.592 | 71.010 | 1.00 | 34.03 | C |
| ATOM | 2697 | CD2 | PHE | A | 338 | 34.264 | −6.520 | 69.014 | 1.00 | 44.95 | C |
| ATOM | 2698 | CE1 | PHE | A | 338 | 32.107 | −5.570 | 70.516 | 1.00 | 45.45 | C |
| ATOM | 2699 | CE2 | PHE | A | 338 | 33.443 | −5.493 | 68.498 | 1.00 | 53.53 | C |
| ATOM | 2700 | CZ | PHE | A | 338 | 32.361 | −5.015 | 69.250 | 1.00 | 42.77 | C |
| ATOM | 2701 | N | ASP | A | 339 | 34.576 | −9.651 | 68.223 | 1.00 | 47.84 | N |
| ATOM | 2702 | CA | ASP | A | 339 | 34.216 | −9.736 | 66.805 | 1.00 | 44.53 | C |
| ATOM | 2703 | C | ASP | A | 339 | 33.175 | −10.823 | 66.529 | 1.00 | 53.61 | C |
| ATOM | 2704 | O | ASP | A | 339 | 32.189 | −10.591 | 65.817 | 1.00 | 40.63 | O |
| ATOM | 2705 | CB | ASP | A | 339 | 35.445 | −10.017 | 65.929 | 1.00 | 53.73 | C |
| ATOM | 2706 | CG | ASP | A | 339 | 36.289 | −8.775 | 65.674 | 1.00 | 65.28 | C |
| ATOM | 2707 | OD1 | ASP | A | 339 | 35.736 | −7.653 | 65.720 | 1.00 | 78.76 | O |
| ATOM | 2708 | OD2 | ASP | A | 339 | 37.504 | −8.925 | 65.405 | 1.00 | 75.48 | O |
| ATOM | 2709 | N | LYS | A | 340 | 33.414 | −12.004 | 67.084 | 1.00 | 28.96 | N |
| ATOM | 2710 | CA | LYS | A | 340 | 32.522 | −13.130 | 66.911 | 1.00 | 38.28 | C |
| ATOM | 2711 | C | LYS | A | 340 | 31.130 | −12.837 | 67.475 | 1.00 | 59.51 | C |
| ATOM | 2712 | O | LYS | A | 340 | 30.122 | −13.100 | 66.808 | 1.00 | 45.33 | O |
| ATOM | 2713 | CB | LYS | A | 340 | 33.101 | −14.346 | 67.614 | 1.00 | 38.33 | C |
| ATOM | 2714 | CG | LYS | A | 340 | 32.725 | −15.675 | 66.978 | 1.00 | 55.99 | C |
| ATOM | 2715 | CD | LYS | A | 340 | 33.896 | −16.651 | 67.126 | 1.00 | 77.87 | C |
| ATOM | 2716 | CE | LYS | A | 340 | 35.156 | −16.112 | 66.433 | 1.00 | 73.91 | C |
| ATOM | 2717 | NZ | LYS | A | 340 | 36.388 | −16.833 | 66.847 | 1.00 | 72.30 | N |
| ATOM | 2718 | N | LEU | A | 341 | 31.092 | −12.289 | 68.696 | 1.00 | 39.97 | N |

TABLE 1-continued

| | | | | | | | | | | |
|---|---|---|---|---|---|---|---|---|---|---|
| ATOM | 2719 | CA | LEU | A | 341 | 29.845 | −11.965 | 69.379 | 1.00 | 39.58 C |
| ATOM | 2720 | C | LEU | A | 341 | 29.038 | −10.949 | 68.588 | 1.00 | 40.66 C |
| ATOM | 2721 | O | LEU | A | 341 | 27.830 | −11.122 | 68.370 | 1.00 | 32.13 O |
| ATOM | 2722 | CB | LEU | A | 341 | 30.118 | −11.401 | 70.780 | 1.00 | 46.18 C |
| ATOM | 2723 | CG | LEU | A | 341 | 28.862 | −10.877 | 71.497 | 1.00 | 47.79 C |
| ATOM | 2724 | CD1 | LEU | A | 341 | 27.857 | −12.026 | 71.748 | 1.00 | 36.26 C |
| ATOM | 2725 | CD2 | LEU | A | 341 | 29.274 | −10.212 | 72.806 | 1.00 | 45.74 C |
| ATOM | 2726 | N | TYR | A | 342 | 29.723 | −9.888 | 68.181 | 1.00 | 25.68 N |
| ATOM | 2727 | CA | TYR | A | 342 | 29.117 | −8.818 | 67.405 | 1.00 | 29.12 C |
| ATOM | 2728 | C | TYR | A | 342 | 28.540 | −9.377 | 66.103 | 1.00 | 47.92 C |
| ATOM | 2729 | O | TYR | A | 342 | 27.378 | −9.128 | 65.751 | 1.00 | 38.52 O |
| ATOM | 2730 | CB | TYR | A | 342 | 30.164 | −7.779 | 67.051 | 1.00 | 38.24 C |
| ATOM | 2731 | CG | TYR | A | 342 | 29.591 | −6.489 | 66.548 | 1.00 | 31.96 C |
| ATOM | 2732 | CD1 | TYR | A | 342 | 29.028 | −5.567 | 67.429 | 1.00 | 41.45 C |
| ATOM | 2733 | CD2 | TYR | A | 342 | 29.580 | −6.194 | 65.190 | 1.00 | 29.72 C |
| ATOM | 2734 | CE1 | TYR | A | 342 | 28.470 | −4.378 | 66.966 | 1.00 | 26.51 C |
| ATOM | 2735 | CE2 | TYR | A | 342 | 29.013 | −5.008 | 64.723 | 1.00 | 30.56 C |
| ATOM | 2736 | CZ | TYR | A | 342 | 28.466 | −4.112 | 65.620 | 1.00 | 23.67 C |
| ATOM | 2737 | OH | TYR | A | 342 | 27.918 | −2.936 | 65.160 | 1.00 | 33.76 O |
| ATOM | 2738 | N | LYS | A | 343 | 29.370 | −10.130 | 65.387 | 1.00 | 40.51 N |
| ATOM | 2739 | CA | LYS | A | 343 | 28.951 | −10.723 | 64.127 | 1.00 | 40.90 C |
| ATOM | 2740 | C | LYS | A | 343 | 27.705 | −11.581 | 64.341 | 1.00 | 28.98 C |
| ATOM | 2741 | O | LYS | A | 343 | 26.740 | −11.467 | 63.611 | 1.00 | 38.51 O |
| ATOM | 2742 | CB | LYS | A | 343 | 30.058 | −11.596 | 63.536 | 1.00 | 37.71 C |
| ATOM | 2743 | CG | LYS | A | 343 | 29.736 | −12.106 | 62.127 | 1.00 | 44.58 C |
| ATOM | 2744 | CD | LYS | A | 343 | 30.811 | −13.055 | 61.612 | 1.00 | 50.81 C |
| ATOM | 2745 | CE | LYS | A | 343 | 30.529 | −13.494 | 60.185 | 1.00 | 56.54 C |
| ATOM | 2746 | NZ | LYS | A | 343 | 30.510 | −12.323 | 59.265 | 1.00 | 62.75 N |
| ATOM | 2747 | N | MET | A | 344 | 27.751 | −12.452 | 65.331 | 1.00 | 38.68 N |
| ATOM | 2748 | CA | MET | A | 344 | 26.622 | −13.322 | 65.648 | 1.00 | 42.02 C |
| ATOM | 2749 | C | MET | A | 344 | 25.347 | −12.475 | 65.889 | 1.00 | 38.99 C |
| ATOM | 2750 | O | MET | A | 344 | 24.291 | −12.731 | 65.297 | 1.00 | 33.59 O |
| ATOM | 2751 | CB | MET | A | 344 | 26.961 | −14.117 | 66.900 | 1.00 | 31.73 C |
| ATOM | 2752 | CG | MET | A | 344 | 26.007 | −15.219 | 67.233 | 1.00 | 60.05 C |
| ATOM | 2753 | SD | MET | A | 344 | 26.422 | −16.695 | 66.322 | 1.00 | 58.23 S |
| ATOM | 2754 | CE | MET | A | 344 | 28.104 | −16.914 | 66.849 | 1.00 | 63.97 C |
| ATOM | 2755 | N | LEU | A | 345 | 25.465 | −11.447 | 66.731 | 1.00 | 34.71 N |
| ATOM | 2756 | CA | LEU | A | 345 | 24.318 | −10.604 | 67.056 | 1.00 | 43.27 C |
| ATOM | 2757 | C | LEU | A | 345 | 23.779 | −9.781 | 65.904 | 1.00 | 44.08 C |
| ATOM | 2758 | O | LEU | A | 345 | 22.557 | −9.598 | 65.783 | 1.00 | 26.18 O |
| ATOM | 2759 | CB | LEU | A | 345 | 24.644 | −9.655 | 68.216 | 1.00 | 32.74 C |
| ATOM | 2760 | CG | LEU | A | 345 | 24.758 | −10.243 | 69.643 | 1.00 | 40.31 C |
| ATOM | 2761 | CD1 | LEU | A | 345 | 25.439 | −9.215 | 70.557 | 1.00 | 26.81 C |
| ATOM | 2762 | CD2 | LEU | A | 345 | 23.379 | −10.617 | 70.187 | 1.00 | 31.49 C |
| ATOM | 2763 | N | THR | A | 346 | 24.676 | −9.312 | 65.042 | 1.00 | 31.36 N |
| ATOM | 2764 | CA | THR | A | 346 | 24.254 | −8.466 | 63.954 | 1.00 | 28.79 C |
| ATOM | 2765 | C | THR | A | 346 | 24.116 | −9.082 | 62.579 | 1.00 | 37.33 C |
| ATOM | 2766 | O | THR | A | 346 | 23.453 | −8.488 | 61.737 | 1.00 | 41.92 O |
| ATOM | 2767 | CB | THR | A | 346 | 25.163 | −7.226 | 63.797 | 1.00 | 36.45 C |
| ATOM | 2768 | OG1 | THR | A | 346 | 26.472 | −7.650 | 63.393 | 1.00 | 35.73 O |
| ATOM | 2769 | CG2 | THR | A | 346 | 25.254 | −6.453 | 65.115 | 1.00 | 47.83 C |
| ATOM | 2770 | N | GLU | A | 347 | 24.738 | −10.227 | 62.310 | 1.00 | 35.84 N |
| ATOM | 2771 | CA | GLU | A | 347 | 24.585 | −10.808 | 60.971 | 1.00 | 35.39 C |
| ATOM | 2772 | C | GLU | A | 347 | 24.268 | −12.308 | 60.878 | 1.00 | 36.46 C |
| ATOM | 2773 | O | GLU | A | 347 | 23.897 | −12.804 | 59.810 | 1.00 | 31.35 O |
| ATOM | 2774 | CB | GLU | A | 347 | 25.777 | −10.453 | 60.059 | 1.00 | 32.13 C |
| ATOM | 2775 | CG | GLU | A | 347 | 27.146 | −10.866 | 60.514 | 1.00 | 60.87 C |
| ATOM | 2776 | CD | GLU | A | 347 | 28.231 | −10.434 | 59.505 | 1.00 | 79.20 C |
| ATOM | 2777 | OE1 | GLU | A | 347 | 28.348 | −11.065 | 58.427 | 1.00 | 58.33 O |
| ATOM | 2778 | OE2 | GLU | A | 347 | 28.959 | −9.453 | 59.787 | 1.00 | 64.82 O |
| ATOM | 2779 | N | ILE | A | 348 | 24.408 | −13.039 | 61.974 | 1.00 | 27.96 N |
| ATOM | 2780 | CA | ILE | A | 348 | 24.040 | −14.447 | 61.930 | 1.00 | 30.31 C |
| ATOM | 2781 | C | ILE | A | 348 | 22.591 | −14.536 | 62.385 | 1.00 | 27.01 C |
| ATOM | 2782 | O | ILE | A | 348 | 21.810 | −15.280 | 61.809 | 1.00 | 32.31 O |
| ATOM | 2783 | CB | ILE | A | 348 | 24.961 | −15.293 | 62.821 | 1.00 | 28.33 C |
| ATOM | 2784 | CG1 | ILE | A | 348 | 26.398 | −15.160 | 62.289 | 1.00 | 47.92 C |
| ATOM | 2785 | CG2 | ILE | A | 348 | 24.555 | −16.771 | 62.781 | 1.00 | 32.83 C |
| ATOM | 2786 | CD1 | ILE | A | 348 | 27.437 | −15.931 | 63.101 | 1.00 | 47.56 C |
| ATOM | 2787 | N | TYR | A | 349 | 22.227 | −13.744 | 63.395 | 1.00 | 27.08 N |
| ATOM | 2788 | CA | TYR | A | 349 | 20.861 | −13.749 | 63.907 | 1.00 | 23.99 C |
| ATOM | 2789 | C | TYR | A | 349 | 20.014 | −12.826 | 63.040 | 1.00 | 23.11 C |
| ATOM | 2790 | O | TYR | A | 349 | 19.918 | −11.635 | 63.328 | 1.00 | 27.75 O |
| ATOM | 2791 | CB | TYR | A | 349 | 20.781 | −13.241 | 65.353 | 1.00 | 26.83 C |
| ATOM | 2792 | CG | TYR | A | 349 | 21.518 | −14.055 | 66.384 | 1.00 | 26.90 C |
| ATOM | 2793 | CD1 | TYR | A | 349 | 21.778 | −15.402 | 66.183 | 1.00 | 34.23 C |
| ATOM | 2794 | CD2 | TYR | A | 349 | 21.984 | −13.465 | 67.551 | 1.00 | 17.64 C |
| ATOM | 2795 | CE1 | TYR | A | 349 | 22.501 | −16.136 | 67.109 | 1.00 | 35.12 C |
| ATOM | 2796 | CE2 | TYR | A | 349 | 22.706 | −14.195 | 68.489 | 1.00 | 22.30 C |
| ATOM | 2797 | CZ | TYR | A | 349 | 22.966 | −15.528 | 68.252 | 1.00 | 24.36 C |

TABLE 1-continued

| | | | | | | | | | | |
|---|---|---|---|---|---|---|---|---|---|---|
| ATOM | 2798 | OH | TYR | A | 349 | 23.726 | −16.248 | 69.124 | 1.00 | 32.23 O |
| ATOM | 2799 | N | THR | A | 350 | 19.433 | −13.360 | 61.971 | 1.00 | 22.31 N |
| ATOM | 2800 | CA | THR | A | 350 | 18.571 | −12.567 | 61.095 | 1.00 | 26.17 C |
| ATOM | 2801 | C | THR | A | 350 | 17.290 | −13.330 | 60.720 | 1.00 | 27.58 C |
| ATOM | 2802 | O | THR | A | 350 | 17.237 | −14.567 | 60.777 | 1.00 | 27.38 O |
| ATOM | 2803 | CB | THR | A | 350 | 19.281 | −12.226 | 59.773 | 1.00 | 36.13 C |
| ATOM | 2804 | OG1 | THR | A | 350 | 19.539 | −13.441 | 59.054 | 1.00 | 32.98 O |
| ATOM | 2805 | CG2 | THR | A | 350 | 20.591 | −11.502 | 60.034 | 1.00 | 29.73 C |
| ATOM | 2806 | N | GLU | A | 351 | 16.261 | −12.589 | 60.332 | 1.00 | 22.05 N |
| ATOM | 2807 | CA | GLU | A | 351 | 15.021 | −13.207 | 59.902 | 1.00 | 25.50 C |
| ATOM | 2808 | C | GLU | A | 351 | 15.338 | −14.154 | 58.735 | 1.00 | 30.65 C |
| ATOM | 2809 | O | GLU | A | 351 | 14.851 | −15.278 | 58.686 | 1.00 | 48.13 O |
| ATOM | 2810 | CB | GLU | A | 351 | 14.017 | −12.153 | 59.446 | 1.00 | 29.42 C |
| ATOM | 2811 | CG | GLU | A | 351 | 12.669 | −12.759 | 59.036 | 1.00 | 30.20 C |
| ATOM | 2812 | CD | GLU | A | 351 | 11.562 | −11.714 | 58.867 | 1.00 | 46.35 C |
| ATOM | 2813 | OE1 | GLU | A | 351 | 11.449 | −10.826 | 59.749 | 1.00 | 31.98 O |
| ATOM | 2814 | OE2 | GLU | A | 351 | 10.790 | −11.794 | 57.867 | 1.00 | 33.58 O |
| ATOM | 2815 | N | ASP | A | 352 | 16.155 | −13.689 | 57.795 | 1.00 | 31.12 N |
| ATOM | 2816 | CA | ASP | A | 352 | 16.535 | −14.492 | 56.632 | 1.00 | 26.55 C |
| ATOM | 2817 | C | ASP | A | 352 | 17.133 | −15.825 | 57.040 | 1.00 | 31.13 C |
| ATOM | 2818 | O | ASP | A | 352 | 16.795 | −16.855 | 56.480 | 1.00 | 31.13 O |
| ATOM | 2819 | CB | ASP | A | 352 | 17.568 | −13.764 | 55.772 | 1.00 | 43.57 C |
| ATOM | 2820 | CG | ASP | A | 352 | 18.045 | −14.613 | 54.584 | 1.00 | 44.49 C |
| ATOM | 2821 | OD1 | ASP | A | 352 | 17.237 | −14.895 | 53.676 | 1.00 | 49.69 O |
| ATOM | 2822 | OD2 | ASP | A | 352 | 19.234 | −15.001 | 54.561 | 1.00 | 69.66 O |
| ATOM | 2823 | N | ASN | A | 353 | 18.046 | −15.814 | 58.004 | 1.00 | 31.46 N |
| ATOM | 2824 | CA | ASN | A | 353 | 18.630 | −17.072 | 58.432 | 1.00 | 28.65 C |
| ATOM | 2825 | C | ASN | A | 353 | 17.621 | −17.975 | 59.135 | 1.00 | 28.17 C |
| ATOM | 2826 | O | ASN | A | 353 | 17.644 | −19.185 | 58.933 | 1.00 | 35.63 O |
| ATOM | 2827 | CB | ASN | A | 353 | 19.873 | −16.819 | 59.287 | 1.00 | 37.40 C |
| ATOM | 2828 | CG | ASN | A | 353 | 21.053 | −16.431 | 58.431 | 1.00 | 45.64 C |
| ATOM | 2829 | OD1 | ASN | A | 353 | 21.149 | −16.916 | 57.323 | 1.00 | 45.47 O |
| ATOM | 2830 | ND2 | ASN | A | 353 | 21.940 | −15.561 | 58.919 | 1.00 | 36.59 N |
| ATOM | 2831 | N | PHE | A | 354 | 16.719 | −17.402 | 59.928 | 1.00 | 20.86 N |
| ATOM | 2832 | CA | PHE | A | 354 | 15.711 | −18.204 | 60.614 | 1.00 | 29.83 C |
| ATOM | 2833 | C | PHE | A | 354 | 14.790 | −18.868 | 59.598 | 1.00 | 32.69 C |
| ATOM | 2834 | O | PHE | A | 354 | 14.374 | −20.006 | 59.777 | 1.00 | 33.65 O |
| ATOM | 2835 | CB | PHE | A | 354 | 14.870 | −17.350 | 61.583 | 1.00 | 24.81 C |
| ATOM | 2836 | CG | PHE | A | 354 | 15.434 | −17.305 | 62.970 | 1.00 | 48.44 C |
| ATOM | 2837 | CD1 | PHE | A | 354 | 15.324 | −18.406 | 63.807 | 1.00 | 42.54 C |
| ATOM | 2838 | CD2 | PHE | A | 354 | 16.182 | −16.204 | 63.399 | 1.00 | 36.86 C |
| ATOM | 2839 | CE1 | PHE | A | 354 | 15.960 | −18.423 | 65.049 | 1.00 | 30.75 C |
| ATOM | 2840 | CE2 | PHE | A | 354 | 16.816 | −16.214 | 64.622 | 1.00 | 32.95 C |
| ATOM | 2841 | CZ | PHE | A | 354 | 16.705 | −17.334 | 65.451 | 1.00 | 29.29 C |
| ATOM | 2842 | N | VAL | A | 355 | 14.456 | −18.139 | 58.539 | 1.00 | 42.17 N |
| ATOM | 2843 | CA | VAL | A | 355 | 13.598 | −18.676 | 57.497 | 1.00 | 31.53 C |
| ATOM | 2844 | C | VAL | A | 355 | 14.239 | −19.931 | 56.916 | 1.00 | 42.82 C |
| ATOM | 2845 | O | VAL | A | 355 | 13.558 | −20.909 | 56.599 | 1.00 | 40.86 O |
| ATOM | 2846 | CB | VAL | A | 355 | 13.368 | −17.637 | 56.394 | 1.00 | 45.73 C |
| ATOM | 2847 | CG1 | VAL | A | 355 | 12.860 | −18.332 | 55.147 | 1.00 | 32.42 C |
| ATOM | 2848 | CG2 | VAL | A | 355 | 12.348 | −16.545 | 56.886 | 1.00 | 19.76 C |
| ATOM | 2849 | N | LYS | A | 356 | 15.560 | −19.931 | 56.794 | 1.00 | 35.23 N |
| ATOM | 2850 | CA | LYS | A | 356 | 16.214 | −21.121 | 56.269 | 1.00 | 35.41 C |
| ATOM | 2851 | C | LYS | A | 356 | 16.071 | −22.292 | 57.233 | 1.00 | 41.47 C |
| ATOM | 2852 | O | LYS | A | 356 | 15.638 | −23.369 | 56.847 | 1.00 | 50.46 O |
| ATOM | 2853 | CB | LYS | A | 356 | 17.692 | −20.854 | 55.997 | 1.00 | 46.92 C |
| ATOM | 2854 | CG | LYS | A | 356 | 17.935 | −19.969 | 54.802 | 1.00 | 42.37 C |
| ATOM | 2855 | CD | LYS | A | 356 | 19.383 | −19.517 | 54.745 | 1.00 | 34.69 C |
| ATOM | 2856 | CE | LYS | A | 356 | 19.561 | −18.477 | 53.639 | 1.00 | 45.51 C |
| ATOM | 2857 | NZ | LYS | A | 356 | 20.942 | −17.885 | 53.614 | 1.00 | 52.22 N |
| ATOM | 2858 | N | PHE | A | 357 | 16.429 | −22.088 | 58.490 | 1.00 | 33.53 N |
| ATOM | 2859 | CA | PHE | A | 357 | 16.333 | −23.161 | 59.463 | 1.00 | 45.62 C |
| ATOM | 2860 | C | PHE | A | 357 | 14.928 | −23.709 | 59.594 | 1.00 | 53.87 C |
| ATOM | 2861 | O | PHE | A | 357 | 14.757 | −24.917 | 59.722 | 1.00 | 52.46 O |
| ATOM | 2862 | CB | PHE | A | 357 | 16.816 | −22.701 | 60.832 | 1.00 | 40.16 C |
| ATOM | 2863 | CG | PHE | A | 357 | 18.285 | −22.783 | 60.996 | 1.00 | 39.10 C |
| ATOM | 2864 | CD1 | PHE | A | 357 | 19.122 | −21.909 | 60.312 | 1.00 | 54.21 C |
| ATOM | 2865 | CD2 | PHE | A | 357 | 18.848 | −23.757 | 61.823 | 1.00 | 47.01 C |
| ATOM | 2866 | CE1 | PHE | A | 357 | 20.491 | −21.995 | 60.441 | 1.00 | 37.38 C |
| ATOM | 2867 | CE2 | PHE | A | 357 | 20.225 | −23.860 | 61.961 | 1.00 | 42.07 C |
| ATOM | 2868 | CZ | PHE | A | 357 | 21.052 | −22.973 | 61.267 | 1.00 | 49.77 C |
| ATOM | 2869 | N | PHE | A | 358 | 13.925 | −22.828 | 59.565 | 1.00 | 45.28 N |
| ATOM | 2870 | CA | PHE | A | 358 | 12.536 | −23.254 | 59.688 | 1.00 | 26.43 C |
| ATOM | 2871 | C | PHE | A | 358 | 11.982 | −23.935 | 58.431 | 1.00 | 38.29 C |
| ATOM | 2872 | O | PHE | A | 358 | 10.977 | −24.643 | 58.499 | 1.00 | 42.58 O |
| ATOM | 2873 | CB | PHE | A | 358 | 11.629 | −22.074 | 60.040 | 1.00 | 28.58 C |
| ATOM | 2874 | CG | PHE | A | 358 | 11.807 | −21.557 | 61.425 | 1.00 | 31.21 C |
| ATOM | 2875 | CD1 | PHE | A | 358 | 12.040 | −22.424 | 62.491 | 1.00 | 29.34 C |
| ATOM | 2876 | CD2 | PHE | A | 358 | 11.713 | −20.202 | 61.679 | 1.00 | 26.23 C |

TABLE 1-continued

| | | | | | | | | | | |
|---|---|---|---|---|---|---|---|---|---|---|
| ATOM | 2877 | CE1 | PHE | A | 358 | 12.184 | −21.935 | 63.804 | 1.00 | 34.43 C |
| ATOM | 2878 | CE2 | PHE | A | 358 | 11.853 | −19.693 | 62.986 | 1.00 | 32.01 C |
| ATOM | 2879 | CZ | PHE | A | 358 | 12.090 | −20.560 | 64.048 | 1.00 | 29.95 C |
| ATOM | 2880 | N | LYS | A | 359 | 12.627 | −23.730 | 57.289 | 1.00 | 42.63 N |
| ATOM | 2881 | CA | LYS | A | 359 | 12.137 | −24.318 | 56.052 | 1.00 | 45.65 C |
| ATOM | 2882 | C | LYS | A | 359 | 10.710 | −23.826 | 55.799 | 1.00 | 39.32 C |
| ATOM | 2883 | O | LYS | A | 359 | 9.815 | −24.608 | 55.508 | 1.00 | 38.22 O |
| ATOM | 2884 | CB | LYS | A | 359 | 12.155 | −25.857 | 56.131 | 1.00 | 49.51 C |
| ATOM | 2885 | CG | LYS | A | 359 | 13.498 | −26.511 | 55.829 | 1.00 | 50.46 C |
| ATOM | 2886 | CD | LYS | A | 359 | 14.460 | −26.483 | 57.004 | 1.00 | 60.87 C |
| ATOM | 2887 | CE | LYS | A | 359 | 14.043 | −27.454 | 58.117 | 1.00 | 75.03 C |
| ATOM | 2888 | NZ | LYS | A | 359 | 14.046 | −28.878 | 57.675 | 1.00 | 65.67 N |
| ATOM | 2889 | N | VAL | A | 360 | 10.496 | −22.521 | 55.927 | 1.00 | 36.73 N |
| ATOM | 2890 | CA | VAL | A | 360 | 9.170 | −21.952 | 55.688 | 1.00 | 35.39 C |
| ATOM | 2891 | C | VAL | A | 360 | 9.190 | −20.956 | 54.530 | 1.00 | 38.32 C |
| ATOM | 2892 | O | VAL | A | 360 | 10.243 | −20.514 | 54.068 | 1.00 | 37.41 O |
| ATOM | 2893 | CB | VAL | A | 360 | 8.604 | −21.200 | 56.931 | 1.00 | 46.66 C |
| ATOM | 2894 | CG1 | VAL | A | 360 | 8.163 | −22.191 | 58.000 | 1.00 | 40.63 C |
| ATOM | 2895 | CG2 | VAL | A | 360 | 9.660 | −20.251 | 57.481 | 1.00 | 25.52 C |
| ATOM | 2896 | N | LEU | A | 361 | 8.013 | −20.619 | 54.049 | 1.00 | 25.11 N |
| ATOM | 2897 | CA | LEU | A | 361 | 7.922 | −19.657 | 52.980 | 1.00 | 35.04 C |
| ATOM | 2898 | C | LEU | A | 361 | 7.780 | −18.363 | 53.749 | 1.00 | 27.14 C |
| ATOM | 2899 | O | LEU | A | 361 | 7.035 | −18.302 | 54.728 | 1.00 | 44.89 O |
| ATOM | 2900 | CB | LEU | A | 361 | 6.671 | −19.904 | 52.123 | 1.00 | 26.48 C |
| ATOM | 2901 | CG | LEU | A | 361 | 6.548 | −18.980 | 50.904 | 1.00 | 51.44 C |
| ATOM | 2902 | CD1 | LEU | A | 361 | 7.785 | −19.157 | 50.035 | 1.00 | 32.36 C |
| ATOM | 2903 | CD2 | LEU | A | 361 | 5.283 | −19.302 | 50.095 | 1.00 | 37.88 C |
| ATOM | 2904 | N | ASN | A | 362 | 8.505 | −17.335 | 53.335 | 1.00 | 35.37 N |
| ATOM | 2905 | CA | ASN | A | 362 | 8.435 | −16.049 | 54.015 | 1.00 | 37.78 C |
| ATOM | 2906 | C | ASN | A | 362 | 8.686 | −14.999 | 52.943 | 1.00 | 41.67 C |
| ATOM | 2907 | O | ASN | A | 362 | 9.235 | −15.325 | 51.891 | 1.00 | 33.58 O |
| ATOM | 2908 | CB | ASN | A | 362 | 9.525 | −15.974 | 55.108 | 1.00 | 30.92 C |
| ATOM | 2909 | CG | ASN | A | 362 | 9.377 | −14.755 | 56.022 | 1.00 | 44.50 C |
| ATOM | 2910 | OD1 | ASN | A | 362 | 8.506 | −14.697 | 56.917 | 1.00 | 28.00 O |
| ATOM | 2911 | ND2 | ASN | A | 362 | 10.239 | −13.765 | 55.799 | 1.00 | 41.13 N |
| ATOM | 2912 | N | ARG | A | 363 | 8.266 | −13.758 | 53.196 | 1.00 | 34.46 N |
| ATOM | 2913 | CA | ARG | A | 363 | 8.500 | −12.664 | 52.250 | 1.00 | 47.74 C |
| ATOM | 2914 | C | ARG | A | 363 | 9.979 | −12.737 | 51.859 | 1.00 | 47.04 C |
| ATOM | 2915 | O | ARG | A | 363 | 10.839 | −13.001 | 52.707 | 1.00 | 40.68 O |
| ATOM | 2916 | CB | ARG | A | 363 | 8.235 | −11.323 | 52.927 | 1.00 | 46.58 C |
| ATOM | 2917 | CG | ARG | A | 363 | 9.094 | −11.141 | 54.190 | 1.00 | 49.62 C |
| ATOM | 2918 | CD | ARG | A | 363 | 8.714 | −9.899 | 55.000 | 1.00 | 55.03 C |
| ATOM | 2919 | NE | ARG | A | 363 | 9.455 | −9.837 | 56.261 | 1.00 | 58.91 N |
| ATOM | 2920 | CZ | ARG | A | 363 | 9.318 | −8.880 | 57.173 | 1.00 | 62.48 C |
| ATOM | 2921 | NH1 | ARG | A | 363 | 8.461 | −7.883 | 56.976 | 1.00 | 59.03 N |
| ATOM | 2922 | NH2 | ARG | A | 363 | 10.044 | −8.916 | 58.284 | 1.00 | 51.74 N |
| ATOM | 2923 | N | LYS | A | 364 | 10.283 | −12.509 | 50.587 | 1.00 | 56.81 N |
| ATOM | 2924 | CA | LYS | A | 364 | 11.675 | −12.559 | 50.139 | 1.00 | 65.64 C |
| ATOM | 2925 | C | LYS | A | 364 | 12.435 | −11.300 | 50.560 | 1.00 | 52.10 C |
| ATOM | 2926 | O | LYS | A | 364 | 13.587 | −11.359 | 50.976 | 1.00 | 64.67 O |
| ATOM | 2927 | CB | LYS | A | 364 | 11.736 | −12.715 | 48.621 | 1.00 | 60.63 C |
| ATOM | 2928 | CG | LYS | A | 364 | 10.812 | −13.793 | 48.085 | 1.00 | 69.86 C |
| ATOM | 2929 | CD | LYS | A | 364 | 11.118 | −15.176 | 48.663 | 1.00 | 69.72 C |
| ATOM | 2930 | CE | LYS | A | 364 | 9.939 | −16.129 | 48.379 | 1.00 | 76.86 C |
| ATOM | 2931 | NZ | LYS | A | 364 | 10.149 | −17.528 | 48.854 | 1.00 | 73.19 N |
| ATOM | 2932 | N | THR | A | 365 | 11.780 | −10.159 | 50.448 | 1.00 | 54.54 N |
| ATOM | 2933 | CA | THR | A | 365 | 12.394 | −8.898 | 50.821 | 1.00 | 60.31 C |
| ATOM | 2934 | C | THR | A | 365 | 11.578 | −8.282 | 51.928 | 1.00 | 59.29 C |
| ATOM | 2935 | O | THR | A | 365 | 10.345 | −8.326 | 51.888 | 1.00 | 58.33 O |
| ATOM | 2936 | CB | THR | A | 365 | 12.379 | −7.858 | 49.665 | 1.00 | 63.83 C |
| ATOM | 2937 | OG1 | THR | A | 365 | 13.106 | −8.351 | 48.536 | 1.00 | 66.81 O |
| ATOM | 2938 | CG2 | THR | A | 365 | 13.009 | −6.560 | 50.132 | 1.00 | 70.44 C |
| ATOM | 2939 | N | PHE | A | 366 | 12.266 | −7.692 | 52.898 | 1.00 | 50.51 N |
| ATOM | 2940 | CA | PHE | A | 366 | 11.607 | −7.010 | 53.994 | 1.00 | 60.37 C |
| ATOM | 2941 | C | PHE | A | 366 | 10.617 | −6.018 | 53.376 | 1.00 | 66.02 C |
| ATOM | 2942 | O | PHE | A | 366 | 9.668 | −5.578 | 54.023 | 1.00 | 57.51 O |
| ATOM | 2943 | CB | PHE | A | 366 | 12.645 | −6.247 | 54.814 | 1.00 | 72.50 C |
| ATOM | 2944 | CG | PHE | A | 366 | 12.057 | −5.416 | 55.910 | 1.00 | 67.83 C |
| ATOM | 2945 | CD1 | PHE | A | 366 | 11.592 | −6.016 | 57.079 | 1.00 | 56.62 C |
| ATOM | 2946 | CD2 | PHE | A | 366 | 11.935 | −4.035 | 55.758 | 1.00 | 66.17 C |
| ATOM | 2947 | CE1 | PHE | A | 366 | 11.006 | −5.255 | 58.085 | 1.00 | 67.15 C |
| ATOM | 2948 | CE2 | PHE | A | 366 | 11.351 | −3.260 | 56.757 | 1.00 | 72.98 C |
| ATOM | 2949 | CZ | PHE | A | 366 | 10.883 | −3.872 | 57.927 | 1.00 | 69.62 C |
| ATOM | 2950 | N | LEU | A | 367 | 10.855 | −5.684 | 52.108 | 1.00 | 72.11 N |
| ATOM | 2951 | CA | LEU | A | 367 | 10.024 | −4.742 | 51.370 | 1.00 | 73.36 C |
| ATOM | 2952 | C | LEU | A | 367 | 8.823 | −5.349 | 50.664 | 1.00 | 74.10 C |
| ATOM | 2953 | O | LEU | A | 367 | 8.447 | −4.890 | 49.585 | 1.00 | 76.16 O |
| ATOM | 2954 | CB | LEU | A | 367 | 10.876 | −3.994 | 50.343 | 1.00 | 73.97 C |
| ATOM | 2955 | CG | LEU | A | 367 | 12.015 | −3.162 | 50.936 | 1.00 | 72.78 C |

TABLE 1-continued

| | | | | | | | | | | |
|---|---|---|---|---|---|---|---|---|---|---|
| ATOM | 2956 | CD1 | LEU | A | 367 | 12.796 | −2.527 | 49.810 | 1.00 | 81.49 C |
| ATOM | 2957 | CD2 | LEU | A | 367 | 11.459 | −2.098 | 51.870 | 1.00 | 67.01 C |
| ATOM | 2958 | N | ASN | A | 368 | 8.226 | −6.377 | 51.265 | 1.00 | 80.85 N |
| ATOM | 2959 | CA | ASN | A | 368 | 7.044 | −7.019 | 50.686 | 1.00 | 73.65 C |
| ATOM | 2960 | C | ASN | A | 368 | 5.806 | −6.504 | 51.386 | 1.00 | 63.60 C |
| ATOM | 2961 | O | ASN | A | 368 | 5.895 | −6.005 | 52.511 | 1.00 | 78.09 O |
| ATOM | 2962 | CB | ASN | A | 368 | 7.116 | −8.540 | 50.827 | 1.00 | 76.03 C |
| ATOM | 2963 | CG | ASN | A | 368 | 7.935 | −9.183 | 49.726 | 1.00 | 81.41 C |
| ATOM | 2964 | OD1 | ASN | A | 368 | 7.693 | −8.940 | 48.542 | 1.00 | 75.34 O |
| ATOM | 2965 | ND2 | ASN | A | 368 | 8.908 | −10.009 | 50.107 | 1.00 | 80.57 N |
| ATOM | 2966 | N | PHE | A | 369 | 4.653 | −6.626 | 50.734 | 1.00 | 45.81 N |
| ATOM | 2967 | CA | PHE | A | 369 | 3.415 | −6.135 | 51.331 | 1.00 | 61.45 C |
| ATOM | 2968 | C | PHE | A | 369 | 2.479 | −7.230 | 51.786 | 1.00 | 45.67 C |
| ATOM | 2969 | O | PHE | A | 369 | 2.211 | −8.173 | 51.050 | 1.00 | 64.00 O |
| ATOM | 2970 | CB | PHE | A | 369 | 2.656 | −5.235 | 50.351 | 1.00 | 62.30 C |
| ATOM | 2971 | CG | PHE | A | 369 | 3.511 | −4.188 | 49.709 | 1.00 | 69.45 C |
| ATOM | 2972 | CD1 | PHE | A | 369 | 4.319 | −3.361 | 50.483 | 1.00 | 77.57 C |
| ATOM | 2973 | CD2 | PHE | A | 369 | 3.509 | −4.024 | 48.334 | 1.00 | 69.05 C |
| ATOM | 2974 | CE1 | PHE | A | 369 | 5.118 | −2.380 | 49.891 | 1.00 | 78.51 C |
| ATOM | 2975 | CE2 | PHE | A | 369 | 4.299 | −3.051 | 47.734 | 1.00 | 74.53 C |
| ATOM | 2976 | CZ | PHE | A | 369 | 5.105 | −2.227 | 48.515 | 1.00 | 77.48 C |
| ATOM | 2977 | N | ASP | A | 370 | 1.979 | −7.093 | 53.005 | 1.00 | 36.32 N |
| ATOM | 2978 | CA | ASP | A | 370 | 1.029 | −8.048 | 53.548 | 1.00 | 47.10 C |
| ATOM | 2979 | C | ASP | A | 370 | −0.343 | −7.719 | 52.952 | 1.00 | 40.51 C |
| ATOM | 2980 | O | ASP | A | 370 | −0.643 | −6.560 | 52.706 | 1.00 | 44.76 O |
| ATOM | 2981 | CB | ASP | A | 370 | 0.982 | −7.919 | 55.068 | 1.00 | 42.57 C |
| ATOM | 2982 | CG | ASP | A | 370 | 2.288 | −8.332 | 55.733 | 1.00 | 71.61 C |
| ATOM | 2983 | OD1 | ASP | A | 370 | 2.813 | −9.427 | 55.394 | 1.00 | 58.41 O |
| ATOM | 2984 | OD2 | ASP | A | 370 | 2.776 | −7.571 | 56.603 | 1.00 | 63.79 O |
| ATOM | 2985 | N | LYS | A | 371 | −1.171 | −8.729 | 52.724 | 1.00 | 40.49 N |
| ATOM | 2986 | CA | LYS | A | 371 | −2.500 | −8.516 | 52.156 | 1.00 | 52.01 C |
| ATOM | 2987 | C | LYS | A | 371 | −3.649 | −8.591 | 53.168 | 1.00 | 47.62 C |
| ATOM | 2988 | O | LYS | A | 371 | −4.678 | −7.937 | 52.988 | 1.00 | 33.25 O |
| ATOM | 2989 | CB | LYS | A | 371 | −2.757 | −9.532 | 51.049 | 1.00 | 54.28 C |
| ATOM | 2990 | CG | LYS | A | 371 | −1.730 | −9.503 | 49.935 | 1.00 | 61.46 C |
| ATOM | 2991 | CD | LYS | A | 371 | −2.044 | −8.417 | 48.938 | 1.00 | 58.66 C |
| ATOM | 2992 | CE | LYS | A | 371 | −0.878 | −8.204 | 47.991 | 1.00 | 71.29 C |
| ATOM | 2993 | NZ | LYS | A | 371 | 0.332 | −7.727 | 48.719 | 1.00 | 73.58 N |
| ATOM | 2994 | N | ALA | A | 372 | −3.487 | −9.387 | 54.226 | 1.00 | 34.20 N |
| ATOM | 2995 | CA | ALA | A | 372 | −4.558 | −9.505 | 55.218 | 1.00 | 37.81 C |
| ATOM | 2996 | C | ALA | A | 372 | −4.118 | −10.068 | 56.567 | 1.00 | 24.71 C |
| ATOM | 2997 | O | ALA | A | 372 | −2.987 | −10.527 | 56.731 | 1.00 | 31.45 O |
| ATOM | 2998 | CB | ALA | A | 372 | −5.711 | −10.360 | 54.653 | 1.00 | 44.56 C |
| ATOM | 2999 | N | VAL | A | 373 | −5.030 | −9.986 | 57.529 | 1.00 | 30.90 N |
| ATOM | 3000 | CA | VAL | A | 373 | −4.817 | −10.516 | 58.858 | 1.00 | 43.64 C |
| ATOM | 3001 | C | VAL | A | 373 | −5.658 | −11.799 | 58.967 | 1.00 | 31.25 C |
| ATOM | 3002 | O | VAL | A | 373 | −6.818 | −11.819 | 58.546 | 1.00 | 34.16 O |
| ATOM | 3003 | CB | VAL | A | 373 | −5.334 | −9.567 | 59.964 | 1.00 | 41.76 C |
| ATOM | 3004 | CG1 | VAL | A | 373 | −4.869 | −10.063 | 61.325 | 1.00 | 41.35 C |
| ATOM | 3005 | CG2 | VAL | A | 373 | −4.872 | −8.201 | 59.746 | 1.00 | 49.47 C |
| ATOM | 3006 | N | PHE | A | 374 | −5.085 | −12.828 | 59.583 | 1.00 | 30.81 N |
| ATOM | 3007 | CA | PHE | A | 374 | −5.754 | −14.122 | 59.782 | 1.00 | 39.45 C |
| ATOM | 3008 | C | PHE | A | 374 | −5.791 | −14.555 | 61.244 | 1.00 | 28.06 C |
| ATOM | 3009 | O | PHE | A | 374 | −4.786 | −14.460 | 61.929 | 1.00 | 41.73 O |
| ATOM | 3010 | CB | PHE | A | 374 | −5.025 | −15.210 | 59.002 | 1.00 | 34.27 C |
| ATOM | 3011 | CG | PHE | A | 374 | −5.292 | −15.190 | 57.535 | 1.00 | 34.50 C |
| ATOM | 3012 | CD1 | PHE | A | 374 | −6.547 | −15.562 | 57.040 | 1.00 | 56.10 C |
| ATOM | 3013 | CD2 | PHE | A | 374 | −4.294 | −14.814 | 56.638 | 1.00 | 36.43 C |
| ATOM | 3014 | CE1 | PHE | A | 374 | −6.805 | −15.565 | 55.670 | 1.00 | 35.48 C |
| ATOM | 3015 | CE2 | PHE | A | 374 | −4.543 | −14.812 | 55.258 | 1.00 | 53.64 C |
| ATOM | 3016 | CZ | PHE | A | 374 | −5.800 | −15.188 | 54.777 | 1.00 | 41.96 C |
| ATOM | 3017 | N | LYS | A | 375 | −6.944 | −15.019 | 61.730 | 1.00 | 35.46 N |
| ATOM | 3018 | CA | LYS | A | 375 | −7.003 | −15.511 | 63.105 | 1.00 | 27.49 C |
| ATOM | 3019 | C | LYS | A | 375 | −6.480 | −16.929 | 63.014 | 1.00 | 34.35 C |
| ATOM | 3020 | O | LYS | A | 375 | −6.829 | −17.648 | 62.079 | 1.00 | 34.11 O |
| ATOM | 3021 | CB | LYS | A | 375 | −8.426 | −15.544 | 63.660 | 1.00 | 40.29 C |
| ATOM | 3022 | CG | LYS | A | 375 | −8.515 | −16.020 | 65.127 | 1.00 | 26.38 C |
| ATOM | 3023 | CD | LYS | A | 375 | −8.244 | −14.883 | 66.093 | 1.00 | 40.22 C |
| ATOM | 3024 | CE | LYS | A | 375 | −8.204 | −15.332 | 67.568 | 1.00 | 32.83 C |
| ATOM | 3025 | NZ | LYS | A | 375 | −7.043 | −16.240 | 67.810 | 1.00 | 50.34 N |
| ATOM | 3026 | N | ILE | A | 376 | −5.620 | −17.324 | 63.950 | 1.00 | 28.43 N |
| ATOM | 3027 | CA | ILE | A | 376 | −5.090 | −18.675 | 63.933 | 1.00 | 24.61 C |
| ATOM | 3028 | C | ILE | A | 376 | −5.074 | −19.242 | 65.351 | 1.00 | 38.66 C |
| ATOM | 3029 | O | ILE | A | 376 | −5.308 | −18.518 | 66.337 | 1.00 | 22.20 O |
| ATOM | 3030 | CB | ILE | A | 376 | −3.638 | −18.725 | 63.362 | 1.00 | 35.98 C |
| ATOM | 3031 | CG1 | ILE | A | 376 | −2.640 | −18.118 | 64.370 | 1.00 | 24.91 C |
| ATOM | 3032 | CG2 | ILE | A | 376 | −3.587 | −17.990 | 62.050 | 1.00 | 35.59 C |
| ATOM | 3033 | CD1 | ILE | A | 376 | −1.212 | −17.952 | 63.840 | 1.00 | 28.37 C |
| ATOM | 3034 | N | ASN | A | 377 | −4.815 | −20.544 | 65.450 | 1.00 | 36.10 N |

TABLE 1-continued

| | | | | | | | | | | |
|---|---|---|---|---|---|---|---|---|---|---|
| ATOM | 3035 | CA | ASN | A | 377 | −4.713 | −21.192 | 66.758 | 1.00 | 37.79 C |
| ATOM | 3036 | C | ASN | A | 377 | −3.657 | −22.248 | 66.654 | 1.00 | 29.89 C |
| ATOM | 3037 | O | ASN | A | 377 | −3.901 | −23.316 | 66.158 | 1.00 | 39.69 O |
| ATOM | 3038 | CB | ASN | A | 377 | −6.018 | −21.845 | 67.214 | 1.00 | 47.92 C |
| ATOM | 3039 | CG | ASN | A | 377 | −5.911 | −22.378 | 68.647 | 1.00 | 54.48 C |
| ATOM | 3040 | OD1 | ASN | A | 377 | −4.828 | −22.367 | 69.248 | 1.00 | 41.90 O |
| ATOM | 3041 | ND2 | ASN | A | 377 | −7.016 | −22.840 | 69.189 | 1.00 | 39.03 N |
| ATOM | 3042 | N | ILE | A | 378 | −2.480 | −21.921 | 67.161 | 1.00 | 33.96 N |
| ATOM | 3043 | CA | ILE | A | 378 | −1.311 | −22.768 | 67.102 | 1.00 | 31.54 C |
| ATOM | 3044 | C | ILE | A | 378 | −1.145 | −23.783 | 68.231 | 1.00 | 36.71 C |
| ATOM | 3045 | O | ILE | A | 378 | −0.300 | −24.660 | 68.154 | 1.00 | 31.14 O |
| ATOM | 3046 | CB | ILE | A | 378 | −0.074 | −21.839 | 67.028 | 1.00 | 45.74 C |
| ATOM | 3047 | CG1 | ILE | A | 378 | 0.078 | −21.339 | 65.594 | 1.00 | 43.01 C |
| ATOM | 3048 | CG2 | ILE | A | 378 | 1.160 | −22.498 | 67.553 | 1.00 | 59.72 C |
| ATOM | 3049 | CD1 | ILE | A | 378 | 1.315 | −20.513 | 65.392 | 1.00 | 62.22 C |
| ATOM | 3050 | N | VAL | A | 379 | −1.953 | −23.682 | 69.276 | 1.00 | 32.13 N |
| ATOM | 3051 | CA | VAL | A | 379 | −1.779 | −24.589 | 70.389 | 1.00 | 36.57 C |
| ATOM | 3052 | C | VAL | A | 379 | −2.013 | −26.056 | 70.028 | 1.00 | 49.26 C |
| ATOM | 3053 | O | VAL | A | 379 | −1.130 | −26.879 | 70.240 | 1.00 | 30.90 O |
| ATOM | 3054 | CB | VAL | A | 379 | −2.626 | −24.111 | 71.584 | 1.00 | 52.74 C |
| ATOM | 3055 | CG1 | VAL | A | 379 | −2.636 | −25.163 | 72.708 | 1.00 | 39.17 C |
| ATOM | 3056 | CG2 | VAL | A | 379 | −2.031 | −22.770 | 72.092 | 1.00 | 26.21 C |
| ATOM | 3057 | N | PRO | A | 380 | −3.179 | −26.395 | 69.435 | 1.00 | 50.93 N |
| ATOM | 3058 | CA | PRO | A | 380 | −3.455 | −27.785 | 69.060 | 1.00 | 21.05 C |
| ATOM | 3059 | C | PRO | A | 380 | −2.337 | −28.379 | 68.216 | 1.00 | 38.86 C |
| ATOM | 3060 | O | PRO | A | 380 | −1.922 | −27.801 | 67.217 | 1.00 | 37.88 O |
| ATOM | 3061 | CB | PRO | A | 380 | −4.754 | −27.677 | 68.260 | 1.00 | 21.89 C |
| ATOM | 3062 | CG | PRO | A | 380 | −5.440 | −26.519 | 68.878 | 1.00 | 32.43 C |
| ATOM | 3063 | CD | PRO | A | 380 | −4.317 | −25.523 | 69.080 | 1.00 | 35.86 C |
| ATOM | 3064 | N | LYS | A | 381 | −1.859 | −29.553 | 68.587 | 1.00 | 37.22 N |
| ATOM | 3065 | CA | LYS | A | 381 | −0.788 | −30.177 | 67.825 | 1.00 | 32.94 C |
| ATOM | 3066 | C | LYS | A | 381 | −1.233 | −30.591 | 66.427 | 1.00 | 43.63 C |
| ATOM | 3067 | O | LYS | A | 381 | −0.394 | −30.860 | 65.560 | 1.00 | 47.69 O |
| ATOM | 3068 | CB | LYS | A | 381 | −0.257 | −31.393 | 68.566 | 1.00 | 31.43 C |
| ATOM | 3069 | CG | LYS | A | 381 | 0.991 | −31.958 | 67.933 | 1.00 | 47.11 C |
| ATOM | 3070 | CD | LYS | A | 381 | 1.810 | −32.796 | 68.918 | 1.00 | 45.89 C |
| ATOM | 3071 | CE | LYS | A | 381 | 3.095 | −33.282 | 68.240 | 1.00 | 64.96 C |
| ATOM | 3072 | NZ | LYS | A | 381 | 3.912 | −34.211 | 69.075 | 1.00 | 73.28 N |
| ATOM | 3073 | N | VAL | A | 382 | −2.544 | −30.676 | 66.203 | 1.00 | 38.43 N |
| ATOM | 3074 | CA | VAL | A | 382 | −3.036 | −31.040 | 64.873 | 1.00 | 45.26 C |
| ATOM | 3075 | C | VAL | A | 382 | −3.027 | −29.843 | 63.900 | 1.00 | 43.36 C |
| ATOM | 3076 | O | VAL | A | 382 | −3.141 | −30.020 | 62.696 | 1.00 | 37.20 O |
| ATOM | 3077 | CB | VAL | A | 382 | −4.446 | −31.649 | 64.948 | 1.00 | 44.13 C |
| ATOM | 3078 | CG1 | VAL | A | 382 | −4.368 | −32.972 | 65.695 | 1.00 | 44.16 C |
| ATOM | 3079 | CG2 | VAL | A | 382 | −5.410 | −30.695 | 65.650 | 1.00 | 36.65 C |
| ATOM | 3080 | N | ASN | A | 383 | −2.856 | −28.634 | 64.438 | 1.00 | 40.05 N |
| ATOM | 3081 | CA | ASN | A | 383 | −2.794 | −27.401 | 63.643 | 1.00 | 35.88 C |
| ATOM | 3082 | C | ASN | A | 383 | −1.359 | −26.930 | 63.391 | 1.00 | 37.93 C |
| ATOM | 3083 | O | ASN | A | 383 | −1.037 | −26.442 | 62.307 | 1.00 | 35.45 O |
| ATOM | 3084 | CB | ASN | A | 383 | −3.509 | −26.247 | 64.365 | 1.00 | 32.62 C |
| ATOM | 3085 | CG | ASN | A | 383 | −5.007 | −26.448 | 64.476 | 1.00 | 35.76 C |
| ATOM | 3086 | OD1 | ASN | A | 383 | −5.551 | −27.429 | 63.964 | 1.00 | 38.93 O |
| ATOM | 3087 | ND2 | ASN | A | 383 | −5.689 | −25.504 | 65.142 | 1.00 | 25.48 N |
| ATOM | 3088 | N | TYR | A | 384 | −0.496 | −27.087 | 64.393 | 1.00 | 40.05 N |
| ATOM | 3089 | CA | TYR | A | 384 | 0.876 | −26.573 | 64.313 | 1.00 | 37.56 C |
| ATOM | 3090 | C | TYR | A | 384 | 1.876 | −27.307 | 65.235 | 1.00 | 45.27 C |
| ATOM | 3091 | O | TYR | A | 384 | 1.570 | −27.591 | 66.394 | 1.00 | 31.39 O |
| ATOM | 3092 | CB | TYR | A | 384 | 0.788 | −25.073 | 64.683 | 1.00 | 36.66 C |
| ATOM | 3093 | CG | TYR | A | 384 | 2.044 | −24.221 | 64.588 | 1.00 | 42.35 C |
| ATOM | 3094 | CD1 | TYR | A | 384 | 2.975 | −24.197 | 65.626 | 1.00 | 35.89 C |
| ATOM | 3095 | CD2 | TYR | A | 384 | 2.281 | −23.403 | 63.461 | 1.00 | 55.00 C |
| ATOM | 3096 | CE1 | TYR | A | 384 | 4.116 | −23.386 | 65.558 | 1.00 | 46.83 C |
| ATOM | 3097 | CE2 | TYR | A | 384 | 3.425 | −22.588 | 63.376 | 1.00 | 37.83 C |
| ATOM | 3098 | CZ | TYR | A | 384 | 4.337 | −22.589 | 64.433 | 1.00 | 37.42 C |
| ATOM | 3099 | OH | TYR | A | 384 | 5.468 | −21.832 | 64.371 | 1.00 | 31.12 O |
| ATOM | 3100 | N | THR | A | 385 | 3.070 | −27.609 | 64.738 | 1.00 | 34.69 N |
| ATOM | 3101 | CA | THR | A | 385 | 4.037 | −28.260 | 65.604 | 1.00 | 35.44 C |
| ATOM | 3102 | C | THR | A | 385 | 5.362 | −27.525 | 65.684 | 1.00 | 39.18 C |
| ATOM | 3103 | O | THR | A | 385 | 5.703 | −26.721 | 64.813 | 1.00 | 39.55 O |
| ATOM | 3104 | CB | THR | A | 385 | 4.346 | −29.706 | 65.166 | 1.00 | 42.20 C |
| ATOM | 3105 | OG1 | THR | A | 385 | 5.175 | −29.692 | 63.999 | 1.00 | 45.50 O |
| ATOM | 3106 | CG2 | THR | A | 385 | 3.042 | −30.471 | 64.883 | 1.00 | 47.13 C |
| ATOM | 3107 | N | ILE | A | 386 | 6.106 | −27.858 | 66.735 | 1.00 | 34.75 N |
| ATOM | 3108 | CA | ILE | A | 386 | 7.419 | −27.311 | 67.040 | 1.00 | 31.44 C |
| ATOM | 3109 | C | ILE | A | 386 | 8.398 | −27.564 | 65.915 | 1.00 | 33.76 C |
| ATOM | 3110 | O | ILE | A | 386 | 9.225 | −26.714 | 65.617 | 1.00 | 47.86 O |
| ATOM | 3111 | CB | ILE | A | 386 | 7.979 | −27.934 | 68.343 | 1.00 | 45.84 C |
| ATOM | 3112 | CG1 | ILE | A | 386 | 7.173 | −27.430 | 69.527 | 1.00 | 39.07 C |
| ATOM | 3113 | CG2 | ILE | A | 386 | 9.458 | −27.568 | 68.562 | 1.00 | 37.58 C |

TABLE 1-continued

| | | | | | | | | | | |
|---|---|---|---|---|---|---|---|---|---|---|
| ATOM | 3114 | CD1 | ILE | A | 386 | 7.629 | −28.006 | 70.854 | 1.00 | 59.40 C |
| ATOM | 3115 | N | TYR | A | 387 | 8.299 | −28.720 | 65.276 | 1.00 | 28.41 N |
| ATOM | 3116 | CA | TYR | A | 387 | 9.203 | −29.044 | 64.186 | 1.00 | 25.00 C |
| ATOM | 3117 | C | TYR | A | 387 | 8.753 | −28.683 | 62.787 | 1.00 | 35.02 C |
| ATOM | 3118 | O | TYR | A | 387 | 9.582 | −28.476 | 61.934 | 1.00 | 36.46 O |
| ATOM | 3119 | CB | TYR | A | 387 | 9.558 | −30.534 | 64.212 | 1.00 | 52.72 C |
| ATOM | 3120 | CG | TYR | A | 387 | 10.730 | −30.868 | 65.111 | 1.00 | 63.83 C |
| ATOM | 3121 | CD1 | TYR | A | 387 | 10.604 | −30.843 | 66.502 | 1.00 | 55.20 C |
| ATOM | 3122 | CD2 | TYR | A | 387 | 11.986 | −31.152 | 64.565 | 1.00 | 75.24 C |
| ATOM | 3123 | CE1 | TYR | A | 387 | 11.704 | −31.091 | 67.332 | 1.00 | 64.10 C |
| ATOM | 3124 | CE2 | TYR | A | 387 | 13.099 | −31.398 | 65.383 | 1.00 | 71.46 C |
| ATOM | 3125 | CZ | TYR | A | 387 | 12.948 | −31.364 | 66.766 | 1.00 | 76.90 C |
| ATOM | 3126 | OH | TYR | A | 387 | 14.041 | −31.592 | 67.575 | 1.00 | 83.08 O |
| ATOM | 3127 | N | ASP | A | 388 | 7.453 | −28.616 | 62.526 | 1.00 | 31.91 N |
| ATOM | 3128 | CA | ASP | A | 388 | 7.022 | −28.311 | 61.168 | 1.00 | 37.90 C |
| ATOM | 3129 | C | ASP | A | 388 | 6.202 | −27.052 | 61.018 | 1.00 | 26.79 C |
| ATOM | 3130 | O | ASP | A | 388 | 5.888 | −26.675 | 59.908 | 1.00 | 38.16 O |
| ATOM | 3131 | CB | ASP | A | 388 | 6.186 | −29.460 | 60.590 | 1.00 | 60.42 C |
| ATOM | 3132 | CG | ASP | A | 388 | 6.942 | −30.769 | 60.519 | 1.00 | 54.28 C |
| ATOM | 3133 | OD1 | ASP | A | 388 | 8.080 | −30.796 | 59.987 | 1.00 | 51.54 O |
| ATOM | 3134 | OD2 | ASP | A | 388 | 6.372 | −31.772 | 60.988 | 1.00 | 63.60 O |
| ATOM | 3135 | N | GLY | A | 389 | 5.831 | −26.432 | 62.129 | 1.00 | 30.31 N |
| ATOM | 3136 | CA | GLY | A | 389 | 5.015 | −25.246 | 62.057 | 1.00 | 36.04 C |
| ATOM | 3137 | C | GLY | A | 389 | 3.649 | −25.638 | 61.528 | 1.00 | 50.08 C |
| ATOM | 3138 | O | GLY | A | 389 | 2.967 | −26.465 | 62.137 | 1.00 | 43.82 O |
| ATOM | 3139 | N | PHE | A | 390 | 3.257 | −25.054 | 60.398 | 1.00 | 32.03 N |
| ATOM | 3140 | CA | PHE | A | 390 | 1.970 | −25.348 | 59.774 | 1.00 | 37.59 C |
| ATOM | 3141 | C | PHE | A | 390 | 2.052 | −26.464 | 58.750 | 1.00 | 30.51 C |
| ATOM | 3142 | O | PHE | A | 390 | 1.046 | −27.082 | 58.440 | 1.00 | 29.37 O |
| ATOM | 3143 | CB | PHE | A | 390 | 1.412 | −24.125 | 59.046 | 1.00 | 29.72 C |
| ATOM | 3144 | CG | PHE | A | 390 | 0.836 | −23.100 | 59.943 | 1.00 | 31.66 C |
| ATOM | 3145 | CD1 | PHE | A | 390 | −0.322 | −23.359 | 60.648 | 1.00 | 21.78 C |
| ATOM | 3146 | CD2 | PHE | A | 390 | 1.432 | −21.836 | 60.041 | 1.00 | 37.74 C |
| ATOM | 3147 | CE1 | PHE | A | 390 | −0.899 | −22.373 | 61.448 | 1.00 | 23.62 C |
| ATOM | 3148 | CE2 | PHE | A | 390 | 0.868 | −20.832 | 60.835 | 1.00 | 26.58 C |
| ATOM | 3149 | CZ | PHE | A | 390 | −0.295 | −21.093 | 61.536 | 1.00 | 35.31 C |
| ATOM | 3150 | N | ASN | A | 391 | 3.246 | −26.686 | 58.209 | 1.00 | 37.39 N |
| ATOM | 3151 | CA | ASN | A | 391 | 3.458 | −27.688 | 57.173 | 1.00 | 35.10 C |
| ATOM | 3152 | C | ASN | A | 391 | 3.655 | −29.080 | 57.752 | 1.00 | 34.20 C |
| ATOM | 3153 | O | ASN | A | 391 | 4.690 | −29.698 | 57.572 | 1.00 | 35.24 O |
| ATOM | 3154 | CB | ASN | A | 391 | 4.666 | −27.295 | 56.322 | 1.00 | 31.86 C |
| ATOM | 3155 | CG | ASN | A | 391 | 4.530 | −25.882 | 55.726 | 1.00 | 33.83 C |
| ATOM | 3156 | OD1 | ASN | A | 391 | 3.453 | −25.490 | 55.258 | 1.00 | 43.73 O |
| ATOM | 3157 | ND2 | ASN | A | 391 | 5.623 | −25.128 | 55.726 | 1.00 | 30.89 N |
| ATOM | 3158 | N | LEU | A | 392 | 2.627 | −29.561 | 58.437 | 1.00 | 39.18 N |
| ATOM | 3159 | CA | LEU | A | 392 | 2.650 | −30.859 | 59.093 | 1.00 | 35.20 C |
| ATOM | 3160 | C | LEU | A | 392 | 3.131 | −32.027 | 58.223 | 1.00 | 37.35 C |
| ATOM | 3161 | O | LEU | A | 392 | 2.678 | −32.208 | 57.092 | 1.00 | 39.58 O |
| ATOM | 3162 | CB | LEU | A | 392 | 1.258 | −31.129 | 59.644 | 1.00 | 40.67 C |
| ATOM | 3163 | CG | LEU | A | 392 | 0.727 | −30.048 | 60.585 | 1.00 | 41.60 C |
| ATOM | 3164 | CD1 | LEU | A | 392 | −0.684 | −30.394 | 61.003 | 1.00 | 35.73 C |
| ATOM | 3165 | CD2 | LEU | A | 392 | 1.632 | −29.932 | 61.828 | 1.00 | 36.32 C |
| ATOM | 3166 | N | ARG | A | 393 | 4.079 | −32.807 | 58.744 | 1.00 | 39.82 N |
| ATOM | 3167 | CA | ARG | A | 393 | 4.573 | −33.966 | 58.001 | 1.00 | 55.31 C |
| ATOM | 3168 | C | ARG | A | 393 | 3.485 | −35.057 | 57.875 | 1.00 | 35.81 C |
| ATOM | 3169 | O | ARG | A | 393 | 2.543 | −35.119 | 58.670 | 1.00 | 38.94 O |
| ATOM | 3170 | CB | ARG | A | 393 | 5.829 | −34.541 | 58.669 | 1.00 | 43.73 C |
| ATOM | 3171 | CG | ARG | A | 393 | 5.598 | −35.140 | 60.048 | 1.00 | 49.91 C |
| ATOM | 3172 | CD | ARG | A | 393 | 6.927 | −35.441 | 60.726 | 1.00 | 63.93 C |
| ATOM | 3173 | NE | ARG | A | 393 | 7.636 | −34.213 | 61.082 | 1.00 | 49.05 N |
| ATOM | 3174 | CZ | ARG | A | 393 | 8.864 | −34.167 | 61.589 | 1.00 | 61.26 C |
| ATOM | 3175 | NH1 | ARG | A | 393 | 9.554 | −35.281 | 61.804 | 1.00 | 63.42 N |
| ATOM | 3176 | NH2 | ARG | A | 393 | 9.397 | −33.000 | 61.909 | 1.00 | 66.82 N |
| ATOM | 3177 | N | ASN | A | 394 | 3.610 | −35.890 | 56.849 | 1.00 | 40.26 N |
| ATOM | 3178 | CA | ASN | A | 394 | 2.662 | −36.979 | 56.591 | 1.00 | 51.31 C |
| ATOM | 3179 | C | ASN | A | 394 | 1.219 | −36.560 | 56.356 | 1.00 | 53.04 C |
| ATOM | 3180 | O | ASN | A | 394 | 0.285 | −37.296 | 56.673 | 1.00 | 39.24 O |
| ATOM | 3181 | CB | ASN | A | 394 | 2.723 | −38.007 | 57.722 | 1.00 | 38.63 C |
| ATOM | 3182 | CG | ASN | A | 394 | 4.136 | −38.484 | 57.978 | 1.00 | 31.28 C |
| ATOM | 3183 | OD1 | ASN | A | 394 | 4.911 | −38.669 | 57.043 | 1.00 | 42.79 O |
| ATOM | 3184 | ND2 | ASN | A | 394 | 4.478 | −38.681 | 59.239 | 1.00 | 41.56 N |
| ATOM | 3185 | N | THR | A | 395 | 1.045 | −35.355 | 55.836 | 1.00 | 45.01 N |
| ATOM | 3186 | CA | THR | A | 395 | −0.275 | −34.855 | 55.491 | 1.00 | 46.63 C |
| ATOM | 3187 | C | THR | A | 395 | 0.004 | −34.162 | 54.164 | 1.00 | 40.12 C |
| ATOM | 3188 | O | THR | A | 395 | 1.176 | −34.056 | 53.755 | 1.00 | 38.00 O |
| ATOM | 3189 | CB | THR | A | 395 | −0.816 | −33.824 | 56.523 | 1.00 | 54.42 C |
| ATOM | 3190 | OG1 | THR | A | 395 | −0.102 | −32.592 | 56.397 | 1.00 | 63.42 O |
| ATOM | 3191 | CG2 | THR | A | 395 | −0.648 | −34.342 | 57.942 | 1.00 | 51.62 C |
| ATOM | 3192 | N | ASN | A | 396 | −1.033 | −33.697 | 53.472 | 1.00 | 43.94 N |

TABLE 1-continued

| ATOM | 3193 | CA | ASN | A | 396 | −0.789 | −33.015 | 52.204 | 1.00 | 46.46 | C |
|------|------|-----|-----|---|-----|--------|---------|--------|------|-------|---|
| ATOM | 3194 | C | ASN | A | 396 | −0.418 | −31.548 | 52.475 | 1.00 | 47.91 | C |
| ATOM | 3195 | O | ASN | A | 396 | −0.505 | −30.706 | 51.594 | 1.00 | 50.96 | O |
| ATOM | 3196 | CB | ASN | A | 396 | −2.014 | −33.084 | 51.291 | 1.00 | 43.49 | C |
| ATOM | 3197 | CG | ASN | A | 396 | −2.995 | −31.975 | 51.557 | 1.00 | 53.82 | C |
| ATOM | 3198 | OD1 | ASN | A | 396 | −3.453 | −31.797 | 52.685 | 1.00 | 65.78 | O |
| ATOM | 3199 | ND2 | ASN | A | 396 | −3.328 | −31.215 | 50.517 | 1.00 | 42.18 | N |
| ATOM | 3200 | N | LEU | A | 397 | 0.021 | −31.271 | 53.699 | 1.00 | 49.83 | N |
| ATOM | 3201 | CA | LEU | A | 397 | 0.409 | −29.934 | 54.128 | 1.00 | 49.53 | C |
| ATOM | 3202 | C | LEU | A | 397 | 1.915 | −29.766 | 54.164 | 1.00 | 55.85 | C |
| ATOM | 3203 | O | LEU | A | 397 | 2.411 | −28.645 | 54.344 | 1.00 | 44.89 | O |
| ATOM | 3204 | CB | LEU | A | 397 | −0.148 | −29.663 | 55.523 | 1.00 | 31.77 | C |
| ATOM | 3205 | CG | LEU | A | 397 | −1.421 | −28.813 | 55.562 | 1.00 | 61.96 | C |
| ATOM | 3206 | CD1 | LEU | A | 397 | −2.410 | −29.206 | 54.465 | 1.00 | 37.41 | C |
| ATOM | 3207 | CD2 | LEU | A | 397 | −2.029 | −28.921 | 56.944 | 1.00 | 31.95 | C |
| ATOM | 3208 | N | ALA | A | 398 | 2.646 | −30.862 | 53.967 | 1.00 | 38.52 | N |
| ATOM | 3209 | CA | ALA | A | 398 | 4.105 | −30.801 | 54.046 | 1.00 | 38.77 | C |
| ATOM | 3210 | C | ALA | A | 398 | 4.839 | −30.406 | 52.774 | 1.00 | 51.91 | C |
| ATOM | 3211 | O | ALA | A | 398 | 6.030 | −30.065 | 52.813 | 1.00 | 44.58 | O |
| ATOM | 3212 | CB | ALA | A | 398 | 4.637 | −32.122 | 54.547 | 1.00 | 46.51 | C |
| ATOM | 3213 | N | ALA | A | 399 | 4.143 | −30.450 | 51.648 | 1.00 | 37.99 | N |
| ATOM | 3214 | CA | ALA | A | 399 | 4.771 | −30.106 | 50.381 | 1.00 | 49.97 | C |
| ATOM | 3215 | C | ALA | A | 399 | 4.364 | −28.719 | 49.898 | 1.00 | 57.65 | C |
| ATOM | 3216 | O | ALA | A | 399 | 3.230 | −28.276 | 50.140 | 1.00 | 38.87 | O |
| ATOM | 3217 | CB | ALA | A | 399 | 4.401 | −31.136 | 49.321 | 1.00 | 61.82 | C |
| ATOM | 3218 | N | ASN | A | 400 | 5.302 | −28.045 | 49.229 | 1.00 | 40.67 | N |
| ATOM | 3219 | CA | ASN | A | 400 | 5.057 | −26.719 | 48.669 | 1.00 | 49.94 | C |
| ATOM | 3220 | C | ASN | A | 400 | 4.436 | −25.763 | 49.682 | 1.00 | 40.32 | C |
| ATOM | 3221 | O | ASN | A | 400 | 3.581 | −24.951 | 49.337 | 1.00 | 43.19 | O |
| ATOM | 3222 | CB | ASN | A | 400 | 4.133 | −26.856 | 47.460 | 1.00 | 43.59 | C |
| ATOM | 3223 | CG | ASN | A | 400 | 4.635 | −27.878 | 46.461 | 1.00 | 51.15 | C |
| ATOM | 3224 | OD1 | ASN | A | 400 | 3.863 | −28.380 | 45.640 | 1.00 | 61.63 | O |
| ATOM | 3225 | ND2 | ASN | A | 400 | 5.936 | −28.191 | 46.519 | 1.00 | 34.51 | N |
| ATOM | 3226 | N | PHE | A | 401 | 4.874 | −25.906 | 50.929 | 1.00 | 33.17 | N |
| ATOM | 3227 | CA | PHE | A | 401 | 4.372 | −25.040 | 52.000 | 1.00 | 36.44 | C |
| ATOM | 3228 | C | PHE | A | 401 | 2.854 | −24.980 | 51.954 | 1.00 | 39.33 | C |
| ATOM | 3229 | O | PHE | A | 401 | 2.272 | −23.917 | 52.171 | 1.00 | 34.77 | O |
| ATOM | 3230 | CB | PHE | A | 401 | 4.954 | −23.645 | 51.862 | 1.00 | 39.50 | C |
| ATOM | 3231 | CG | PHE | A | 401 | 6.414 | −23.637 | 51.533 | 1.00 | 44.40 | C |
| ATOM | 3232 | CD1 | PHE | A | 401 | 7.365 | −23.880 | 52.515 | 1.00 | 38.42 | C |
| ATOM | 3233 | CD2 | PHE | A | 401 | 6.841 | −23.375 | 50.231 | 1.00 | 34.87 | C |
| ATOM | 3234 | CE1 | PHE | A | 401 | 8.729 | −23.862 | 52.204 | 1.00 | 48.82 | C |
| ATOM | 3235 | CE2 | PHE | A | 401 | 8.195 | −23.358 | 49.914 | 1.00 | 42.97 | C |
| ATOM | 3236 | CZ | PHE | A | 401 | 9.140 | −23.598 | 50.895 | 1.00 | 35.88 | C |
| ATOM | 3237 | N | ASN | A | 402 | 2.237 | −26.126 | 51.679 | 1.00 | 31.46 | N |
| ATOM | 3238 | CA | ASN | A | 402 | 0.787 | −26.170 | 51.618 | 1.00 | 29.65 | C |
| ATOM | 3239 | C | ASN | A | 402 | 0.170 | −25.763 | 52.951 | 1.00 | 38.26 | C |
| ATOM | 3240 | O | ASN | A | 402 | −0.934 | −25.198 | 52.995 | 1.00 | 35.73 | O |
| ATOM | 3241 | CB | ASN | A | 402 | 0.302 | −27.561 | 51.212 | 1.00 | 37.13 | C |
| ATOM | 3242 | CG | ASN | A | 402 | 0.308 | −27.773 | 49.702 | 1.00 | 49.08 | C |
| ATOM | 3243 | OD1 | ASN | A | 402 | 0.379 | −26.819 | 48.916 | 1.00 | 37.22 | O |
| ATOM | 3244 | ND2 | ASN | A | 402 | 0.218 | −29.034 | 49.292 | 1.00 | 41.95 | N |
| ATOM | 3245 | N | GLY | A | 403 | 0.878 | −26.021 | 54.044 | 1.00 | 31.91 | N |
| ATOM | 3246 | CA | GLY | A | 403 | 0.370 | −25.678 | 55.361 | 1.00 | 35.27 | C |
| ATOM | 3247 | C | GLY | A | 403 | 0.268 | −24.165 | 55.534 | 1.00 | 25.85 | C |
| ATOM | 3248 | O | GLY | A | 403 | −0.577 | −23.661 | 56.285 | 1.00 | 24.94 | O |
| ATOM | 3249 | N | GLN | A | 404 | 1.134 | −23.431 | 54.847 | 1.00 | 25.96 | N |
| ATOM | 3250 | CA | GLN | A | 404 | 1.072 | −21.981 | 54.922 | 1.00 | 43.28 | C |
| ATOM | 3251 | C | GLN | A | 404 | 0.089 | −21.419 | 53.922 | 1.00 | 31.71 | C |
| ATOM | 3252 | O | GLN | A | 404 | −0.316 | −20.254 | 54.004 | 1.00 | 32.38 | O |
| ATOM | 3253 | CB | GLN | A | 404 | 2.446 | −21.365 | 54.702 | 1.00 | 24.26 | C |
| ATOM | 3254 | CG | GLN | A | 404 | 3.454 | −21.828 | 55.742 | 1.00 | 25.75 | C |
| ATOM | 3255 | CD | GLN | A | 404 | 4.767 | −21.077 | 55.658 | 1.00 | 30.08 | C |
| ATOM | 3256 | OE1 | GLN | A | 404 | 4.821 | −19.850 | 55.844 | 1.00 | 30.28 | O |
| ATOM | 3257 | NE2 | GLN | A | 404 | 5.954 | −21.604 | 55.402 | 1.00 | 29.49 | N |
| ATOM | 3258 | N | ASN | A | 405 | −0.312 | −22.242 | 52.951 | 1.00 | 34.07 | N |
| ATOM | 3259 | CA | ASN | A | 405 | −1.256 | −21.788 | 51.922 | 1.00 | 24.56 | C |
| ATOM | 3260 | C | ASN | A | 405 | −2.619 | −21.595 | 52.525 | 1.00 | 33.05 | C |
| ATOM | 3261 | O | ASN | A | 405 | −3.222 | −22.518 | 53.071 | 1.00 | 45.47 | O |
| ATOM | 3262 | CB | ASN | A | 405 | −1.369 | −22.780 | 50.793 | 1.00 | 23.00 | C |
| ATOM | 3263 | CG | ASN | A | 405 | −2.221 | −22.257 | 49.662 | 1.00 | 24.95 | C |
| ATOM | 3264 | OD1 | ASN | A | 405 | −3.339 | −21.771 | 49.874 | 1.00 | 25.71 | O |
| ATOM | 3265 | ND2 | ASN | A | 405 | −1.693 | −22.346 | 48.447 | 1.00 | 34.85 | N |
| ATOM | 3266 | N | THR | A | 406 | −3.112 | −20.383 | 52.408 | 1.00 | 34.25 | N |
| ATOM | 3267 | CA | THR | A | 406 | −4.397 | −20.036 | 53.012 | 1.00 | 36.81 | C |
| ATOM | 3268 | C | THR | A | 406 | −5.651 | −20.536 | 52.270 | 1.00 | 37.98 | C |
| ATOM | 3269 | O | THR | A | 406 | −6.766 | −20.454 | 52.787 | 1.00 | 34.64 | O |
| ATOM | 3270 | CB | THR | A | 406 | −4.433 | −18.515 | 53.225 | 1.00 | 38.97 | C |
| ATOM | 3271 | OG1 | THR | A | 406 | −3.525 | −18.165 | 54.261 | 1.00 | 53.99 | O |

TABLE 1-continued

| ATOM | 3272 | CG2 | THR | A | 406 | −5.840 | −18.076 | 53.586 | 1.00 | 51.83 | C |
|---|---|---|---|---|---|---|---|---|---|---|---|
| ATOM | 3273 | N | GLU | A | 407 | −5.480 | −21.052 | 51.064 | 1.00 | 31.04 | N |
| ATOM | 3274 | CA | GLU | A | 407 | −6.635 | −21.571 | 50.331 | 1.00 | 52.24 | C |
| ATOM | 3275 | C | GLU | A | 407 | −6.722 | −23.035 | 50.729 | 1.00 | 33.65 | C |
| ATOM | 3276 | O | GLU | A | 407 | −7.744 | −23.500 | 51.220 | 1.00 | 53.84 | O |
| ATOM | 3277 | CB | GLU | A | 407 | −6.429 | −21.499 | 48.816 | 1.00 | 34.13 | C |
| ATOM | 3278 | CG | GLU | A | 407 | −5.759 | −20.231 | 48.301 | 1.00 | 63.62 | C |
| ATOM | 3279 | CD | GLU | A | 407 | −6.754 | −19.189 | 47.824 | 1.00 | 75.82 | C |
| ATOM | 3280 | OE1 | GLU | A | 407 | −7.434 | −18.571 | 48.674 | 1.00 | 82.11 | O |
| ATOM | 3281 | OE2 | GLU | A | 407 | −6.859 | −18.997 | 46.591 | 1.00 | 58.91 | O |
| ATOM | 3282 | N | ILE | A | 408 | −5.619 | −23.738 | 50.516 | 1.00 | 31.37 | N |
| ATOM | 3283 | CA | ILE | A | 408 | −5.511 | −25.145 | 50.822 | 1.00 | 38.78 | C |
| ATOM | 3284 | C | ILE | A | 408 | −5.821 | −25.433 | 52.287 | 1.00 | 49.73 | C |
| ATOM | 3285 | O | ILE | A | 408 | −6.856 | −26.013 | 52.600 | 1.00 | 59.24 | O |
| ATOM | 3286 | CB | ILE | A | 408 | −4.099 | −25.651 | 50.466 | 1.00 | 42.47 | C |
| ATOM | 3287 | CG1 | ILE | A | 408 | −3.895 | −25.548 | 48.955 | 1.00 | 36.15 | C |
| ATOM | 3288 | CG2 | ILE | A | 408 | −3.896 | −27.076 | 50.948 | 1.00 | 33.63 | C |
| ATOM | 3289 | CD1 | ILE | A | 408 | −2.602 | −26.139 | 48.483 | 1.00 | 46.45 | C |
| ATOM | 3290 | N | ASN | A | 409 | −4.941 | −24.997 | 53.181 | 1.00 | 46.02 | N |
| ATOM | 3291 | CA | ASN | A | 409 | −5.105 | −25.219 | 54.619 | 1.00 | 29.32 | C |
| ATOM | 3292 | C | ASN | A | 409 | −6.049 | −24.182 | 55.212 | 1.00 | 36.86 | C |
| ATOM | 3293 | O | ASN | A | 409 | −5.799 | −23.650 | 56.287 | 1.00 | 39.79 | O |
| ATOM | 3294 | CB | ASN | A | 409 | −3.725 | −25.148 | 55.285 | 1.00 | 33.24 | C |
| ATOM | 3295 | CG | ASN | A | 409 | −3.753 | −25.514 | 56.752 | 1.00 | 41.77 | C |
| ATOM | 3296 | OD1 | ASN | A | 409 | −4.731 | −26.078 | 57.251 | 1.00 | 46.25 | O |
| ATOM | 3297 | ND2 | ASN | A | 409 | −2.664 | −25.207 | 57.456 | 1.00 | 36.57 | N |
| ATOM | 3298 | N | ASN | A | 410 | −7.151 | −23.911 | 54.516 | 1.00 | 36.76 | N |
| ATOM | 3299 | CA | ASN | A | 410 | −8.117 | −22.904 | 54.955 | 1.00 | 30.63 | C |
| ATOM | 3300 | C | ASN | A | 410 | −8.717 | −23.045 | 56.346 | 1.00 | 39.46 | C |
| ATOM | 3301 | O | ASN | A | 410 | −9.208 | −22.060 | 56.911 | 1.00 | 36.82 | O |
| ATOM | 3302 | CB | ASN | A | 410 | −9.260 | −22.805 | 53.942 | 1.00 | 39.32 | C |
| ATOM | 3303 | CG | ASN | A | 410 | −9.928 | −24.135 | 53.711 | 1.00 | 53.61 | C |
| ATOM | 3304 | OD1 | ASN | A | 410 | −9.466 | −24.941 | 52.908 | 1.00 | 50.19 | O |
| ATOM | 3305 | ND2 | ASN | A | 410 | −10.999 | −24.391 | 54.447 | 1.00 | 38.68 | N |
| ATOM | 3306 | N | MET | A | 411 | −8.703 | −24.252 | 56.898 | 1.00 | 43.46 | N |
| ATOM | 3307 | CA | MET | A | 411 | −9.262 | −24.471 | 58.231 | 1.00 | 43.96 | C |
| ATOM | 3308 | C | MET | A | 411 | −8.347 | −23.947 | 59.335 | 1.00 | 50.70 | C |
| ATOM | 3309 | O | MET | A | 411 | −8.743 | −23.830 | 60.493 | 1.00 | 43.26 | O |
| ATOM | 3310 | CB | MET | A | 411 | −9.542 | −25.960 | 58.448 | 1.00 | 63.74 | C |
| ATOM | 3311 | CG | MET | A | 411 | −10.765 | −26.475 | 57.677 | 1.00 | 76.60 | C |
| ATOM | 3312 | SD | MET | A | 411 | −12.374 | −25.773 | 58.232 | 1.00 | 98.40 | S |
| ATOM | 3313 | CE | MET | A | 411 | −12.551 | −24.259 | 57.188 | 1.00 | 67.31 | C |
| ATOM | 3314 | N | ASN | A | 412 | −7.116 | −23.620 | 58.971 | 1.00 | 47.98 | N |
| ATOM | 3315 | CA | ASN | A | 412 | −6.191 | −23.094 | 59.949 | 1.00 | 44.65 | C |
| ATOM | 3316 | C | ASN | A | 412 | −6.071 | −21.573 | 59.949 | 1.00 | 54.91 | C |
| ATOM | 3317 | O | ASN | A | 412 | −5.465 | −20.983 | 60.858 | 1.00 | 45.71 | O |
| ATOM | 3318 | CB | ASN | A | 412 | −4.826 | −23.744 | 59.765 | 1.00 | 39.76 | C |
| ATOM | 3319 | CG | ASN | A | 412 | −4.679 | −24.979 | 60.618 | 1.00 | 30.19 | C |
| ATOM | 3320 | OD1 | ASN | A | 412 | −4.847 | −24.913 | 61.826 | 1.00 | 43.43 | O |
| ATOM | 3321 | ND2 | ASN | A | 412 | −4.381 | −26.103 | 60.004 | 1.00 | 40.14 | N |
| ATOM | 3322 | N | PHE | A | 413 | −6.686 | −20.929 | 58.963 | 1.00 | 34.02 | N |
| ATOM | 3323 | CA | PHE | A | 413 | −6.609 | −19.474 | 58.862 | 1.00 | 31.35 | C |
| ATOM | 3324 | C | PHE | A | 413 | −7.973 | −18.862 | 58.644 | 1.00 | 28.16 | C |
| ATOM | 3325 | O | PHE | A | 413 | −8.630 | −19.184 | 57.667 | 1.00 | 51.12 | O |
| ATOM | 3326 | CB | PHE | A | 413 | −5.695 | −19.100 | 57.682 | 1.00 | 28.17 | C |
| ATOM | 3327 | CG | PHE | A | 413 | −4.316 | −19.699 | 57.776 | 1.00 | 33.05 | C |
| ATOM | 3328 | CD1 | PHE | A | 413 | −3.336 | −19.110 | 58.576 | 1.00 | 26.15 | C |
| ATOM | 3329 | CD2 | PHE | A | 413 | −4.008 | −20.886 | 57.111 | 1.00 | 26.12 | C |
| ATOM | 3330 | CE1 | PHE | A | 413 | −2.076 | −19.695 | 58.716 | 1.00 | 28.35 | C |
| ATOM | 3331 | CE2 | PHE | A | 413 | −2.756 | −21.471 | 57.249 | 1.00 | 31.56 | C |
| ATOM | 3332 | CZ | PHE | A | 413 | −1.785 | −20.876 | 58.058 | 1.00 | 26.21 | C |
| ATOM | 3333 | N | THR | A | 414 | −8.395 | −17.963 | 59.522 | 1.00 | 42.85 | N |
| ATOM | 3334 | CA | THR | A | 414 | −9.697 | −17.309 | 59.376 | 1.00 | 30.86 | C |
| ATOM | 3335 | C | THR | A | 414 | −9.453 | −15.825 | 59.109 | 1.00 | 45.66 | C |
| ATOM | 3336 | O | THR | A | 414 | −9.015 | −15.109 | 60.018 | 1.00 | 37.33 | O |
| ATOM | 3337 | CB | THR | A | 414 | −10.533 | −17.422 | 60.666 | 1.00 | 41.55 | C |
| ATOM | 3338 | OG1 | THR | A | 414 | −10.588 | −18.793 | 61.079 | 1.00 | 49.94 | O |
| ATOM | 3339 | CG2 | THR | A | 414 | −11.954 | −16.881 | 60.440 | 1.00 | 40.34 | C |
| ATOM | 3340 | N | LYS | A | 415 | −9.751 | −15.358 | 57.890 | 1.00 | 37.99 | N |
| ATOM | 3341 | CA | LYS | A | 415 | −9.518 | −13.961 | 57.540 | 1.00 | 29.24 | C |
| ATOM | 3342 | C | LYS | A | 415 | −10.387 | −13.035 | 58.361 | 1.00 | 36.48 | C |
| ATOM | 3343 | O | LYS | A | 415 | −11.578 | −13.260 | 58.537 | 1.00 | 52.70 | O |
| ATOM | 3344 | CB | LYS | A | 415 | −9.750 | −13.700 | 56.050 | 1.00 | 43.36 | C |
| ATOM | 3345 | CG | LYS | A | 415 | −9.297 | −12.299 | 55.629 | 1.00 | 42.79 | C |
| ATOM | 3346 | CD | LYS | A | 415 | −9.767 | −11.877 | 54.234 | 1.00 | 43.92 | C |
| ATOM | 3347 | CE | LYS | A | 415 | −9.283 | −12.800 | 53.124 | 1.00 | 49.87 | C |
| ATOM | 3348 | NZ | LYS | A | 415 | −7.810 | −12.869 | 53.013 | 1.00 | 55.37 | N |
| ATOM | 3349 | N | LEU | A | 416 | −9.773 | −11.993 | 58.886 | 1.00 | 35.53 | N |
| ATOM | 3350 | CA | LEU | A | 416 | −10.477 | −11.020 | 59.706 | 1.00 | 48.39 | C |

TABLE 1-continued

| ATOM | 3351 | C | LEU | A | 416 | −10.593 | −9.695 | 58.992 | 1.00 | 28.22 | C |
|---|---|---|---|---|---|---|---|---|---|---|---|
| ATOM | 3352 | O | LEU | A | 416 | −11.469 | −8.892 | 59.298 | 1.00 | 45.95 | O |
| ATOM | 3353 | CB | LEU | A | 416 | −9.718 | −10.785 | 61.017 | 1.00 | 41.50 | C |
| ATOM | 3354 | CG | LEU | A | 416 | −9.777 | −11.929 | 62.019 | 1.00 | 50.34 | C |
| ATOM | 3355 | CD1 | LEU | A | 416 | −8.744 | −11.684 | 63.139 | 1.00 | 39.53 | C |
| ATOM | 3356 | CD2 | LEU | A | 416 | −11.220 | −12.018 | 62.572 | 1.00 | 34.19 | C |
| ATOM | 3357 | N | LYS | A | 417 | −9.688 | −9.464 | 58.054 | 1.00 | 32.10 | N |
| ATOM | 3358 | CA | LYS | A | 417 | −9.683 | −8.204 | 57.354 | 1.00 | 49.29 | C |
| ATOM | 3359 | C | LYS | A | 417 | −8.630 | −8.163 | 56.267 | 1.00 | 45.69 | C |
| ATOM | 3360 | O | LYS | A | 417 | −7.540 | −8.735 | 56.416 | 1.00 | 47.10 | O |
| ATOM | 3361 | CB | LYS | A | 417 | −9.434 | −7.085 | 58.367 | 1.00 | 44.96 | C |
| ATOM | 3362 | CG | LYS | A | 417 | −9.050 | −5.752 | 57.783 | 1.00 | 42.94 | C |
| ATOM | 3363 | CD | LYS | A | 417 | −8.652 | −4.778 | 58.879 | 1.00 | 39.97 | C |
| ATOM | 3364 | CE | LYS | A | 417 | −8.278 | −3.434 | 58.285 | 1.00 | 43.64 | C |
| ATOM | 3365 | NZ | LYS | A | 417 | −7.867 | −2.502 | 59.348 | 1.00 | 44.31 | N |
| ATOM | 3366 | N | ASN | A | 418 | −8.969 | −7.503 | 55.163 | 1.00 | 32.65 | N |
| ATOM | 3367 | CA | ASN | A | 418 | −8.022 | −7.347 | 54.070 | 1.00 | 43.58 | C |
| ATOM | 3368 | C | ASN | A | 418 | −7.428 | −5.979 | 54.295 | 1.00 | 37.62 | C |
| ATOM | 3369 | O | ASN | A | 418 | −8.064 | −5.147 | 54.916 | 1.00 | 48.11 | O |
| ATOM | 3370 | CB | ASN | A | 418 | −8.720 | −7.331 | 52.715 | 1.00 | 46.04 | C |
| ATOM | 3371 | CG | ASN | A | 418 | −9.403 | −8.630 | 52.396 | 1.00 | 55.61 | C |
| ATOM | 3372 | OD1 | ASN | A | 418 | −10.616 | −8.769 | 52.585 | 1.00 | 62.51 | O |
| ATOM | 3373 | ND2 | ASN | A | 418 | −8.631 | −9.598 | 51.915 | 1.00 | 53.73 | N |
| ATOM | 3374 | N | PHE | A | 419 | −6.208 | −5.749 | 53.828 | 1.00 | 41.98 | N |
| ATOM | 3375 | CA | PHE | A | 419 | −5.617 | −4.418 | 53.963 | 1.00 | 68.08 | C |
| ATOM | 3376 | C | PHE | A | 419 | −5.911 | −3.777 | 52.603 | 1.00 | 55.95 | C |
| ATOM | 3377 | O | PHE | A | 419 | −5.190 | −3.989 | 51.627 | 1.00 | 46.49 | O |
| ATOM | 3378 | CB | PHE | A | 419 | −4.108 | −4.506 | 54.261 | 1.00 | 27.86 | C |
| ATOM | 3379 | CG | PHE | A | 419 | −3.793 | −5.253 | 55.524 | 1.00 | 28.46 | C |
| ATOM | 3380 | CD1 | PHE | A | 419 | −4.578 | −5.070 | 56.676 | 1.00 | 29.34 | C |
| ATOM | 3381 | CD2 | PHE | A | 419 | −2.715 | −6.149 | 55.573 | 1.00 | 36.49 | C |
| ATOM | 3382 | CE1 | PHE | A | 419 | −4.299 | −5.769 | 57.862 | 1.00 | 26.61 | C |
| ATOM | 3383 | CE2 | PHE | A | 419 | −2.419 | −6.858 | 56.758 | 1.00 | 29.91 | C |
| ATOM | 3384 | CZ | PHE | A | 419 | −3.212 | −6.665 | 57.897 | 1.00 | 30.41 | C |
| ATOM | 3385 | N | THR | A | 420 | −7.005 | −3.015 | 52.569 | 1.00 | 65.09 | N |
| ATOM | 3386 | CA | THR | A | 420 | −7.526 | −2.381 | 51.351 | 1.00 | 82.15 | C |
| ATOM | 3387 | C | THR | A | 420 | −6.539 | −1.667 | 50.413 | 1.00 | 86.36 | C |
| ATOM | 3388 | O | THR | A | 420 | −6.504 | −1.939 | 49.202 | 1.00 | 78.51 | O |
| ATOM | 3389 | CB | THR | A | 420 | −8.704 | −1.439 | 51.705 | 1.00 | 75.28 | C |
| ATOM | 3390 | OG1 | THR | A | 420 | −9.704 | −2.184 | 52.412 | 1.00 | 84.90 | O |
| ATOM | 3391 | CG2 | THR | A | 420 | −9.346 | −0.880 | 50.443 | 1.00 | 94.27 | C |
| ATOM | 3392 | N | PRO | A | 421 | −5.756 | −0.723 | 50.938 | 1.00 | 74.46 | N |
| ATOM | 3393 | CA | PRO | A | 421 | −4.823 | −0.081 | 50.001 | 1.00 | 79.03 | C |
| ATOM | 3394 | C | PRO | A | 421 | −3.632 | −1.043 | 49.714 | 1.00 | 83.65 | C |
| ATOM | 3395 | O | PRO | A | 421 | −3.345 | −1.899 | 50.547 | 1.00 | 79.49 | O |
| ATOM | 3396 | CB | PRO | A | 421 | −4.425 | 1.193 | 50.751 | 1.00 | 77.22 | C |
| ATOM | 3397 | CG | PRO | A | 421 | −5.623 | 1.465 | 51.661 | 1.00 | 78.39 | C |
| ATOM | 3398 | CD | PRO | A | 421 | −5.968 | 0.094 | 52.146 | 1.00 | 70.58 | C |
| ATOM | 3399 | N | GLY | A | 422 | −2.979 | −0.931 | 48.545 | 1.00 | 92.65 | N |
| ATOM | 3400 | CA | GLY | A | 422 | −1.818 | −1.779 | 48.188 | 1.00 | 92.85 | C |
| ATOM | 3401 | C | GLY | A | 422 | −0.662 | −0.813 | 47.951 | 1.00 | 100.39 | C |
| ATOM | 3402 | O | GLY | A | 422 | −0.768 | −0.032 | 47.006 | 1.00 | 98.38 | O |
| ATOM | 3403 | N | HIS | A | 423 | 0.434 | −0.850 | 48.750 | 1.00 | 101.16 | N |
| ATOM | 3404 | CA | HIS | A | 423 | 1.406 | 0.255 | 48.578 | 1.00 | 97.71 | C |
| ATOM | 3405 | C | HIS | A | 423 | 2.537 | 0.407 | 49.581 | 1.00 | 94.78 | C |
| ATOM | 3406 | O | HIS | A | 423 | 3.705 | 0.369 | 49.213 | 1.00 | 102.93 | O |
| ATOM | 3407 | CB | HIS | A | 423 | 0.604 | 1.503 | 48.782 | 1.00 | 94.40 | C |
| ATOM | 3408 | CG | HIS | A | 423 | −0.372 | 1.173 | 49.933 | 1.00 | 104.20 | C |
| ATOM | 3409 | ND1 | HIS | A | 423 | −0.383 | −0.066 | 50.547 | 1.00 | 103.08 | N |
| ATOM | 3410 | CD2 | HIS | A | 423 | −1.358 | 1.892 | 50.515 | 1.00 | 103.25 | C |
| ATOM | 3411 | CE1 | HIS | A | 423 | −1.344 | −0.103 | 51.447 | 1.00 | 104.53 | C |
| ATOM | 3412 | NE2 | HIS | A | 423 | −1.951 | 1.072 | 51.449 | 1.00 | 107.04 | N |
| ATOM | 3413 | N | HIS | A | 424 | 2.155 | 0.583 | 50.842 | 1.00 | 81.62 | N |
| ATOM | 3414 | CA | HIS | A | 424 | 3.043 | 0.909 | 51.930 | 1.00 | 89.76 | C |
| ATOM | 3415 | C | HIS | A | 424 | 3.502 | −0.311 | 52.693 | 1.00 | 91.95 | C |
| ATOM | 3416 | O | HIS | A | 424 | 3.707 | −1.398 | 52.129 | 1.00 | 100.16 | O |
| ATOM | 3417 | CB | HIS | A | 424 | 2.358 | 1.903 | 52.853 | 1.00 | 88.30 | C |
| ATOM | 3418 | CG | HIS | A | 424 | 0.987 | 1.428 | 53.343 | 1.00 | 89.86 | C |
| ATOM | 3419 | ND1 | HIS | A | 424 | −0.102 | 2.267 | 53.385 | 1.00 | 95.92 | N |
| ATOM | 3420 | CD2 | HIS | A | 424 | 0.569 | 0.235 | 53.834 | 1.00 | 84.10 | C |
| ATOM | 3421 | CE1 | HIS | A | 424 | −1.136 | 1.612 | 53.886 | 1.00 | 99.16 | C |
| ATOM | 3422 | NE2 | HIS | A | 424 | −0.756 | 0.379 | 54.163 | 1.00 | 90.02 | N |
| ATOM | 3423 | N | HIS | A | 425 | 3.671 | −0.115 | 53.966 | 1.00 | 87.66 | N |
| ATOM | 3424 | CA | HIS | A | 425 | 4.125 | −1.164 | 54.793 | 1.00 | 84.95 | C |
| ATOM | 3425 | C | HIS | A | 425 | 3.237 | −1.199 | 56.007 | 1.00 | 83.31 | C |
| ATOM | 3426 | O | HIS | A | 425 | 2.088 | −0.777 | 56.062 | 1.00 | 72.89 | O |
| ATOM | 3427 | CB | HIS | A | 425 | 5.586 | −0.875 | 55.212 | 1.00 | 78.57 | C |
| ATOM | 3428 | CG | HIS | A | 425 | 6.439 | −2.150 | 55.346 | 1.00 | 94.04 | C |
| ATOM | 3429 | ND1 | HIS | A | 425 | 6.568 | −2.809 | 56.534 | 1.00 | 98.90 | N |

TABLE 1-continued

| | | | | | | | | | | |
|---|---|---|---|---|---|---|---|---|---|---|
| ATOM | 3430 | CD2 | HIS | A | 425 | 7.170 | −2.835 | 54.435 | 1.00 | 100.54 C |
| ATOM | 3431 | CE1 | HIS | A | 425 | 7.341 | −3.864 | 56.349 | 1.00 | 95.43 C |
| ATOM | 3432 | NE2 | HIS | A | 425 | 7.720 | −3.916 | 55.083 | 1.00 | 100.52 N |
| ATOM | 3433 | N | HIS | A | 426 | 3.892 | −1.704 | 56.950 | 1.00 | 91.61 N |
| ATOM | 3434 | CA | HIS | A | 426 | 3.529 | −1.856 | 58.311 | 1.00 | 88.25 C |
| ATOM | 3435 | C | HIS | A | 426 | 4.908 | −1.750 | 58.839 | 1.00 | 83.98 C |
| ATOM | 3436 | O | HIS | A | 426 | 5.509 | −0.671 | 58.875 | 1.00 | 84.81 O |
| ATOM | 3437 | CB | HIS | A | 426 | 2.933 | −3.237 | 58.626 | 1.00 | 83.30 C |
| ATOM | 3438 | CG | HIS | A | 426 | 2.797 | −3.760 | 60.105 | 1.00 | 91.32 C |
| ATOM | 3439 | ND1 | HIS | A | 426 | 2.326 | −3.001 | 61.129 | 1.00 | 98.58 N |
| ATOM | 3440 | CD2 | HIS | A | 426 | 3.070 | −4.986 | 60.649 | 1.00 | 92.32 C |
| ATOM | 3441 | CE1 | HIS | A | 426 | 2.309 | −3.705 | 62.246 | 1.00 | 97.61 C |
| ATOM | 3442 | NE2 | HIS | A | 426 | 2.770 | −4.924 | 61.983 | 1.00 | 104.20 N |
| ATOM | 3443 | N | HIS | A | 427 | 5.391 | −2.890 | 59.242 | 1.00 | 72.73 N |
| ATOM | 3444 | CA | HIS | A | 427 | 6.736 | −3.044 | 59.643 | 1.00 | 82.94 C |
| ATOM | 3445 | C | HIS | A | 427 | 7.036 | −4.408 | 60.207 | 1.00 | 88.84 C |
| ATOM | 3446 | O | HIS | A | 427 | 6.270 | −5.367 | 60.065 | 1.00 | 78.83 O |
| ATOM | 3447 | CB | HIS | A | 427 | 7.185 | −1.880 | 60.485 | 1.00 | 92.52 C |
| ATOM | 3448 | CG | HIS | A | 427 | 7.837 | −1.029 | 59.415 | 1.00 | 93.30 C |
| ATOM | 3449 | ND1 | HIS | A | 427 | 8.692 | 0.015 | 59.621 | 1.00 | 95.51 N |
| ATOM | 3450 | CD2 | HIS | A | 427 | 7.709 | −1.157 | 58.059 | 1.00 | 92.05 C |
| ATOM | 3451 | CE1 | HIS | A | 427 | 9.049 | 0.518 | 58.455 | 1.00 | 100.26 C |
| ATOM | 3452 | NE2 | HIS | A | 427 | 8.476 | −0.179 | 57.494 | 1.00 | 98.98 N |
| ATOM | 3453 | N | HIS | A | 428 | 8.199 | −4.463 | 60.857 | 1.00 | 82.80 N |
| ATOM | 3454 | CA | HIS | A | 428 | 8.667 | −5.734 | 61.354 | 1.00 | 63.27 C |
| ATOM | 3455 | C | HIS | A | 428 | 7.910 | −6.874 | 60.710 | 1.00 | 63.47 C |
| ATOM | 3456 | O | HIS | A | 428 | 7.984 | −7.078 | 59.499 | 1.00 | 65.91 O |
| ATOM | 3457 | CB | HIS | A | 428 | 8.531 | −5.890 | 62.870 | 1.00 | 57.01 C |
| ATOM | 3458 | CG | HIS | A | 428 | 8.991 | −4.664 | 63.672 | 1.00 | 58.32 C |
| ATOM | 3459 | ND1 | HIS | A | 428 | 10.294 | −4.254 | 63.781 | 1.00 | 31.38 N |
| ATOM | 3460 | CD2 | HIS | A | 428 | 8.255 | −3.814 | 64.418 | 1.00 | 46.42 C |
| ATOM | 3461 | CE1 | HIS | A | 428 | 10.359 | −3.185 | 64.568 | 1.00 | 55.84 C |
| ATOM | 3462 | NE2 | HIS | A | 428 | 9.125 | −2.894 | 64.975 | 1.00 | 59.77 N |
| TER | 3463 | | HIS | A | 428 | | | | | |
| HETATM | 3464 | ZN | ZN | A | 429 | 12.084 | −5.131 | 63.058 | 1.00 | 30.18 ZN |
| ATOM | 3465 | N | PRO | B | 430 | −15.098 | 20.030 | 21.692 | 1.00 | 32.67 N |
| ATOM | 3466 | CA | PRO | B | 430 | −14.487 | 21.227 | 22.282 | 1.00 | 56.07 C |
| ATOM | 3467 | C | PRO | B | 430 | −15.372 | 22.356 | 21.898 | 1.00 | 48.45 C |
| ATOM | 3468 | O | PRO | B | 430 | −16.535 | 22.130 | 21.584 | 1.00 | 61.41 O |
| ATOM | 3469 | CB | PRO | B | 430 | −13.128 | 21.411 | 21.646 | 1.00 | 24.77 C |
| ATOM | 3470 | CG | PRO | B | 430 | −12.773 | 20.005 | 21.349 | 1.00 | 41.12 C |
| ATOM | 3471 | CD | PRO | B | 430 | −14.076 | 19.314 | 20.918 | 1.00 | 38.77 C |
| ATOM | 3472 | N | PHE | B | 431 | −14.807 | 23.560 | 21.932 | 1.00 | 46.82 N |
| ATOM | 3473 | CA | PHE | B | 431 | −15.501 | 24.775 | 21.533 | 1.00 | 46.42 C |
| ATOM | 3474 | C | PHE | B | 431 | −16.169 | 24.433 | 20.211 | 1.00 | 36.42 C |
| ATOM | 3475 | O | PHE | B | 431 | −15.558 | 23.833 | 19.314 | 1.00 | 35.73 O |
| ATOM | 3476 | CB | PHE | B | 431 | −14.499 | 25.903 | 21.312 | 1.00 | 49.36 C |
| ATOM | 3477 | CG | PHE | B | 431 | −15.124 | 27.235 | 21.099 | 1.00 | 45.80 C |
| ATOM | 3478 | CD1 | PHE | B | 431 | −15.389 | 28.076 | 22.177 | 1.00 | 56.14 C |
| ATOM | 3479 | CD2 | PHE | B | 431 | −15.436 | 27.673 | 19.814 | 1.00 | 72.07 C |
| ATOM | 3480 | CE1 | PHE | B | 431 | −15.957 | 29.345 | 21.978 | 1.00 | 54.20 C |
| ATOM | 3481 | CE2 | PHE | B | 431 | −16.007 | 28.945 | 19.601 | 1.00 | 61.65 C |
| ATOM | 3482 | CZ | PHE | B | 431 | −16.265 | 29.777 | 20.690 | 1.00 | 50.90 C |
| ATOM | 3483 | N | VAL | B | 432 | −17.442 | 24.784 | 20.128 | 1.00 | 30.43 N |
| ATOM | 3484 | CA | VAL | B | 432 | −18.262 | 24.570 | 18.963 | 1.00 | 45.79 C |
| ATOM | 3485 | C | VAL | B | 432 | −18.411 | 25.899 | 18.302 | 1.00 | 45.10 C |
| ATOM | 3486 | O | VAL | B | 432 | −19.090 | 26.780 | 18.816 | 1.00 | 62.78 O |
| ATOM | 3487 | CB | VAL | B | 432 | −19.644 | 23.980 | 19.398 | 1.00 | 36.88 C |
| ATOM | 3488 | CG1 | VAL | B | 432 | −20.464 | 23.605 | 18.169 | 1.00 | 44.46 C |
| ATOM | 3489 | CG2 | VAL | B | 432 | −19.469 | 22.770 | 20.306 | 1.00 | 45.50 C |
| ATOM | 3490 | N | ASN | B | 433 | −17.797 | 26.075 | 17.131 | 1.00 | 59.60 N |
| ATOM | 3491 | CA | ASN | B | 433 | −17.830 | 27.352 | 16.475 | 1.00 | 68.63 C |
| ATOM | 3492 | C | ASN | B | 433 | −19.186 | 27.782 | 15.924 | 1.00 | 69.04 C |
| ATOM | 3493 | O | ASN | B | 433 | −19.526 | 28.963 | 15.974 | 1.00 | 75.24 O |
| ATOM | 3494 | CB | ASN | B | 433 | −16.775 | 27.391 | 15.383 | 1.00 | 67.75 C |
| ATOM | 3495 | CG | ASN | B | 433 | −15.380 | 27.447 | 15.955 | 1.00 | 77.70 C |
| ATOM | 3496 | OD1 | ASN | B | 433 | −15.098 | 28.255 | 16.846 | 1.00 | 69.06 O |
| ATOM | 3497 | ND2 | ASN | B | 433 | −14.497 | 26.586 | 15.458 | 1.00 | 87.16 N |
| ATOM | 3498 | N | LYS | B | 434 | −19.973 | 26.856 | 15.386 | 1.00 | 63.67 N |
| ATOM | 3499 | CA | LYS | B | 434 | −21.278 | 27.239 | 14.846 | 1.00 | 65.48 C |
| ATOM | 3500 | C | LYS | B | 434 | −22.465 | 26.718 | 15.661 | 1.00 | 69.75 C |
| ATOM | 3501 | O | LYS | B | 434 | −22.381 | 25.652 | 16.274 | 1.00 | 76.81 O |
| ATOM | 3502 | CB | LYS | B | 434 | −21.403 | 26.772 | 13.393 | 1.00 | 65.21 C |
| ATOM | 3503 | CG | LYS | B | 434 | −21.187 | 25.295 | 13.201 | 1.00 | 55.80 C |
| ATOM | 3504 | CD | LYS | B | 434 | −21.549 | 24.873 | 11.778 | 1.00 | 67.63 C |
| ATOM | 3505 | CE | LYS | B | 434 | −20.543 | 25.405 | 10.768 | 1.00 | 77.35 C |
| ATOM | 3506 | NZ | LYS | B | 434 | −20.785 | 24.872 | 9.401 | 1.00 | 72.46 N |
| ATOM | 3507 | N | GLN | B | 435 | −23.565 | 27.474 | 15.662 | 1.00 | 63.05 N |
| ATOM | 3508 | CA | GLN | B | 435 | −24.779 | 27.099 | 16.399 | 1.00 | 66.03 C |

TABLE 1-continued

| | | | | | | | | | | |
|---|---|---|---|---|---|---|---|---|---|---|
| ATOM | 3509 | C | GLN | B | 435 | −25.611 | 26.162 | 15.528 | 1.00 | 65.06 C |
| ATOM | 3510 | O | GLN | B | 435 | −26.124 | 26.560 | 14.487 | 1.00 | 79.05 O |
| ATOM | 3511 | CB | GLN | B | 435 | −25.596 | 28.345 | 16.780 | 1.00 | 67.82 C |
| ATOM | 3512 | CG | GLN | B | 435 | −24.747 | 29.568 | 17.120 | 1.00 | 74.79 C |
| ATOM | 3513 | CD | GLN | B | 435 | −23.995 | 29.396 | 18.418 | 1.00 | 80.77 C |
| ATOM | 3514 | OE1 | GLN | B | 435 | −23.353 | 28.378 | 18.646 | 1.00 | 76.08 O |
| ATOM | 3515 | NE2 | GLN | B | 435 | −23.950 | 30.258 | 19.412 | 1.00 | 80.08 N |
| ATOM | 3516 | N | PHE | B | 436 | −25.736 | 24.916 | 15.965 | 1.00 | 48.95 N |
| ATOM | 3517 | CA | PHE | B | 436 | −26.469 | 23.897 | 15.231 | 1.00 | 49.74 C |
| ATOM | 3518 | C | PHE | B | 436 | −27.921 | 23.777 | 15.689 | 1.00 | 59.50 C |
| ATOM | 3519 | O | PHE | B | 436 | −28.209 | 23.869 | 16.883 | 1.00 | 47.79 O |
| ATOM | 3520 | CB | PHE | B | 436 | −25.811 | 22.525 | 15.411 | 1.00 | 57.06 C |
| ATOM | 3521 | CG | PHE | B | 436 | −24.505 | 22.332 | 14.719 | 1.00 | 58.37 C |
| ATOM | 3522 | CD1 | PHE | B | 436 | −24.484 | 21.958 | 13.375 | 1.00 | 61.75 C |
| ATOM | 3523 | CD2 | PHE | B | 436 | −23.297 | 22.478 | 15.392 | 1.00 | 54.76 C |
| ATOM | 3524 | CE1 | PHE | B | 436 | −23.279 | 21.737 | 12.720 | 1.00 | 67.73 C |
| ATOM | 3525 | CE2 | PHE | B | 436 | −22.082 | 22.259 | 14.743 | 1.00 | 46.76 C |
| ATOM | 3526 | CZ | PHE | B | 436 | −22.072 | 21.888 | 13.412 | 1.00 | 59.60 C |
| ATOM | 3527 | N | ASN | B | 437 | −28.829 | 23.582 | 14.769 | 1.00 | 41.77 N |
| ATOM | 3528 | CA | ASN | B | 437 | −30.235 | 23.381 | 15.023 | 1.00 | 40.68 C |
| ATOM | 3529 | C | ASN | B | 437 | −30.550 | 22.024 | 14.431 | 1.00 | 30.93 C |
| ATOM | 3530 | O | ASN | B | 437 | −30.106 | 21.737 | 13.330 | 1.00 | 41.86 O |
| ATOM | 3531 | CB | ASN | B | 437 | −31.095 | 24.473 | 14.388 | 1.00 | 45.60 C |
| ATOM | 3532 | CG | ASN | B | 437 | −30.753 | 25.843 | 14.935 | 1.00 | 55.50 C |
| ATOM | 3533 | OD1 | ASN | B | 437 | −30.954 | 26.137 | 16.114 | 1.00 | 68.32 O |
| ATOM | 3534 | ND2 | ASN | B | 437 | −30.222 | 26.697 | 14.060 | 1.00 | 60.10 N |
| ATOM | 3535 | N | TYR | B | 438 | −31.306 | 21.185 | 15.122 | 1.00 | 30.19 N |
| ATOM | 3536 | CA | TYR | B | 438 | −31.604 | 19.879 | 14.579 | 1.00 | 30.01 C |
| ATOM | 3537 | C | TYR | B | 438 | −32.261 | 19.958 | 13.190 | 1.00 | 44.01 C |
| ATOM | 3538 | O | TYR | B | 438 | −32.143 | 19.019 | 12.395 | 1.00 | 45.69 O |
| ATOM | 3539 | CB | TYR | B | 438 | −32.500 | 19.100 | 15.548 | 1.00 | 27.25 C |
| ATOM | 3540 | CG | TYR | B | 438 | −32.717 | 17.677 | 15.100 | 1.00 | 42.33 C |
| ATOM | 3541 | CD1 | TYR | B | 438 | −31.712 | 16.725 | 15.264 | 1.00 | 33.76 C |
| ATOM | 3542 | CD2 | TYR | B | 438 | −33.887 | 17.296 | 14.408 | 1.00 | 41.25 C |
| ATOM | 3543 | CE1 | TYR | B | 438 | −31.848 | 15.434 | 14.748 | 1.00 | 40.38 C |
| ATOM | 3544 | CE2 | TYR | B | 438 | −34.027 | 16.000 | 13.886 | 1.00 | 42.70 C |
| ATOM | 3545 | CZ | TYR | B | 438 | −32.993 | 15.084 | 14.061 | 1.00 | 31.69 C |
| ATOM | 3546 | OH | TYR | B | 438 | −33.067 | 13.825 | 13.533 | 1.00 | 50.05 O |
| ATOM | 3547 | N | LYS | B | 439 | −32.924 | 21.089 | 12.908 | 1.00 | 58.48 N |
| ATOM | 3548 | CA | LYS | B | 439 | −33.627 | 21.347 | 11.638 | 1.00 | 50.19 C |
| ATOM | 3549 | C | LYS | B | 439 | −32.711 | 21.688 | 10.458 | 1.00 | 57.44 C |
| ATOM | 3550 | O | LYS | B | 439 | −33.046 | 21.384 | 9.306 | 1.00 | 48.76 O |
| ATOM | 3551 | CB | LYS | B | 439 | −34.616 | 22.504 | 11.800 | 1.00 | 56.46 C |
| ATOM | 3552 | CG | LYS | B | 439 | −35.727 | 22.288 | 12.816 | 1.00 | 68.01 C |
| ATOM | 3553 | CD | LYS | B | 439 | −36.717 | 21.216 | 12.376 | 1.00 | 72.27 C |
| ATOM | 3554 | CE | LYS | B | 439 | −38.026 | 21.340 | 13.168 | 1.00 | 70.70 C |
| ATOM | 3555 | NZ | LYS | B | 439 | −39.013 | 20.291 | 12.786 | 1.00 | 77.99 N |
| ATOM | 3556 | N | ASP | B | 440 | −31.584 | 22.348 | 10.741 | 1.00 | 52.68 N |
| ATOM | 3557 | CA | ASP | B | 440 | −30.612 | 22.730 | 9.709 | 1.00 | 27.10 C |
| ATOM | 3558 | C | ASP | B | 440 | −30.475 | 21.628 | 8.644 | 1.00 | 55.52 C |
| ATOM | 3559 | O | ASP | B | 440 | −30.472 | 20.433 | 8.959 | 1.00 | 40.23 O |
| ATOM | 3560 | CB | ASP | B | 440 | −29.251 | 23.017 | 10.346 | 1.00 | 27.42 C |
| ATOM | 3561 | CG | ASP | B | 440 | −29.291 | 24.174 | 11.350 | 1.00 | 60.03 C |
| ATOM | 3562 | OD1 | ASP | B | 440 | −30.283 | 24.945 | 11.371 | 1.00 | 50.38 O |
| ATOM | 3563 | OD2 | ASP | B | 440 | −28.308 | 24.321 | 12.120 | 1.00 | 65.80 O |
| ATOM | 3564 | N | PRO | B | 441 | −30.365 | 22.018 | 7.361 | 1.00 | 49.86 N |
| ATOM | 3565 | CA | PRO | B | 441 | −30.241 | 21.046 | 6.271 | 1.00 | 53.44 C |
| ATOM | 3566 | C | PRO | B | 441 | −28.891 | 20.328 | 6.199 | 1.00 | 56.71 C |
| ATOM | 3567 | O | PRO | B | 441 | −27.868 | 20.879 | 6.579 | 1.00 | 41.45 O |
| ATOM | 3568 | CB | PRO | B | 441 | −30.482 | 21.897 | 5.028 | 1.00 | 54.05 C |
| ATOM | 3569 | CG | PRO | B | 441 | −29.770 | 23.184 | 5.412 | 1.00 | 50.00 C |
| ATOM | 3570 | CD | PRO | B | 441 | −30.258 | 23.399 | 6.848 | 1.00 | 60.81 C |
| ATOM | 3571 | N | VAL | B | 442 | −28.918 | 19.097 | 5.689 | 1.00 | 50.04 N |
| ATOM | 3572 | CA | VAL | B | 442 | −27.724 | 18.292 | 5.505 | 1.00 | 50.96 C |
| ATOM | 3573 | C | VAL | B | 442 | −26.794 | 18.988 | 4.515 | 1.00 | 55.70 C |
| ATOM | 3574 | O | VAL | B | 442 | −27.247 | 19.552 | 3.528 | 1.00 | 58.72 O |
| ATOM | 3575 | CB | VAL | B | 442 | −28.092 | 16.888 | 4.963 | 1.00 | 52.19 C |
| ATOM | 3576 | CG1 | VAL | B | 442 | −26.872 | 16.202 | 4.362 | 1.00 | 61.27 C |
| ATOM | 3577 | CG2 | VAL | B | 442 | −28.642 | 16.034 | 6.095 | 1.00 | 58.88 C |
| ATOM | 3578 | N | ASN | B | 443 | −25.496 | 18.954 | 4.793 | 1.00 | 55.09 N |
| ATOM | 3579 | CA | ASN | B | 443 | −24.513 | 19.580 | 3.923 | 1.00 | 53.04 C |
| ATOM | 3580 | C | ASN | B | 443 | −23.365 | 18.614 | 3.686 | 1.00 | 45.53 C |
| ATOM | 3581 | O | ASN | B | 443 | −22.321 | 18.987 | 3.165 | 1.00 | 58.48 O |
| ATOM | 3582 | CB | ASN | B | 443 | −23.989 | 20.892 | 4.533 | 1.00 | 50.14 C |
| ATOM | 3583 | CG | ASN | B | 443 | −23.329 | 20.697 | 5.908 | 1.00 | 66.36 C |
| ATOM | 3584 | OD1 | ASN | B | 443 | −22.569 | 19.744 | 6.126 | 1.00 | 50.66 O |
| ATOM | 3585 | ND2 | ASN | B | 443 | −23.599 | 21.622 | 6.828 | 1.00 | 34.02 N |
| ATOM | 3586 | N | GLY | B | 444 | −23.577 | 17.365 | 4.080 | 1.00 | 56.07 N |
| ATOM | 3587 | CA | GLY | B | 444 | −22.572 | 16.334 | 3.898 | 1.00 | 57.70 C |

TABLE 1-continued

| | | | | | | | | | | |
|---|---|---|---|---|---|---|---|---|---|---|
| ATOM | 3588 | C | GLY | B | 444 | −21.239 | 16.566 | 4.588 | 1.00 | 58.86 C |
| ATOM | 3589 | O | GLY | B | 444 | −20.379 | 15.681 | 4.583 | 1.00 | 37.73 O |
| ATOM | 3590 | N | VAL | B | 445 | −21.068 | 17.749 | 5.177 | 1.00 | 45.54 N |
| ATOM | 3591 | CA | VAL | B | 445 | −19.836 | 18.088 | 5.869 | 1.00 | 53.19 C |
| ATOM | 3592 | C | VAL | B | 445 | −19.985 | 17.884 | 7.379 | 1.00 | 59.06 C |
| ATOM | 3593 | O | VAL | B | 445 | −19.550 | 16.861 | 7.925 | 1.00 | 50.13 O |
| ATOM | 3594 | CB | VAL | B | 445 | −19.448 | 19.547 | 5.621 | 1.00 | 58.07 C |
| ATOM | 3595 | CG1 | VAL | B | 445 | −18.006 | 19.780 | 6.064 | 1.00 | 46.86 C |
| ATOM | 3596 | CG2 | VAL | B | 445 | −19.638 | 19.881 | 4.151 | 1.00 | 64.05 C |
| ATOM | 3597 | N | ASP | B | 446 | −20.599 | 18.859 | 8.045 | 1.00 | 42.39 N |
| ATOM | 3598 | CA | ASP | B | 446 | −20.799 | 18.773 | 9.479 | 1.00 | 45.55 C |
| ATOM | 3599 | C | ASP | B | 446 | −22.253 | 18.509 | 9.922 | 1.00 | 43.34 C |
| ATOM | 3600 | O | ASP | B | 446 | −22.563 | 18.578 | 11.112 | 1.00 | 41.54 O |
| ATOM | 3601 | CB | ASP | B | 446 | −20.250 | 20.027 | 10.156 | 1.00 | 42.42 C |
| ATOM | 3602 | CG | ASP | B | 446 | −20.860 | 21.283 | 9.613 | 1.00 | 51.35 C |
| ATOM | 3603 | OD1 | ASP | B | 446 | −21.904 | 21.165 | 8.939 | 1.00 | 59.70 O |
| ATOM | 3604 | OD2 | ASP | B | 446 | −20.314 | 22.378 | 9.869 | 1.00 | 52.23 O |
| ATOM | 3605 | N | ILE | B | 447 | −23.131 | 18.210 | 8.963 | 1.00 | 36.54 N |
| ATOM | 3606 | CA | ILE | B | 447 | −24.531 | 17.879 | 9.241 | 1.00 | 31.48 C |
| ATOM | 3607 | C | ILE | B | 447 | −24.917 | 16.873 | 8.179 | 1.00 | 34.61 C |
| ATOM | 3608 | O | ILE | B | 447 | −25.007 | 17.218 | 7.010 | 1.00 | 37.81 O |
| ATOM | 3609 | CB | ILE | B | 447 | −25.479 | 19.065 | 9.113 | 1.00 | 35.54 C |
| ATOM | 3610 | CG1 | ILE | B | 447 | −25.107 | 20.155 | 10.098 | 1.00 | 39.05 C |
| ATOM | 3611 | CG2 | ILE | B | 447 | −26.902 | 18.615 | 9.427 | 1.00 | 48.63 C |
| ATOM | 3612 | CD1 | ILE | B | 447 | −26.041 | 21.321 | 10.028 | 1.00 | 37.51 C |
| ATOM | 3613 | N | ALA | B | 448 | −25.159 | 15.629 | 8.579 | 1.00 | 40.51 N |
| ATOM | 3614 | CA | ALA | B | 448 | −25.467 | 14.606 | 7.610 | 1.00 | 32.77 C |
| ATOM | 3615 | C | ALA | B | 448 | −26.148 | 13.393 | 8.190 | 1.00 | 44.57 C |
| ATOM | 3616 | O | ALA | B | 448 | −26.292 | 13.257 | 9.403 | 1.00 | 36.95 O |
| ATOM | 3617 | CB | ALA | B | 448 | −24.179 | 14.168 | 6.923 | 1.00 | 43.29 C |
| ATOM | 3618 | N | TYR | B | 449 | −26.566 | 12.509 | 7.287 | 1.00 | 35.30 N |
| ATOM | 3619 | CA | TYR | B | 449 | −27.175 | 11.256 | 7.662 | 1.00 | 30.24 C |
| ATOM | 3620 | C | TYR | B | 449 | −26.043 | 10.254 | 7.574 | 1.00 | 48.80 C |
| ATOM | 3621 | O | TYR | B | 449 | −25.239 | 10.278 | 6.637 | 1.00 | 37.31 O |
| ATOM | 3622 | CB | TYR | B | 449 | −28.321 | 10.907 | 6.717 | 1.00 | 41.36 C |
| ATOM | 3623 | CG | TYR | B | 449 | −29.596 | 11.593 | 7.152 | 1.00 | 49.34 C |
| ATOM | 3624 | CD1 | TYR | B | 449 | −29.913 | 12.886 | 6.707 | 1.00 | 30.83 C |
| ATOM | 3625 | CD2 | TYR | B | 449 | −30.460 | 10.970 | 8.059 | 1.00 | 35.60 C |
| ATOM | 3626 | CE1 | TYR | B | 449 | −31.063 | 13.531 | 7.155 | 1.00 | 47.61 C |
| ATOM | 3627 | CE2 | TYR | B | 449 | −31.619 | 11.607 | 8.512 | 1.00 | 41.27 C |
| ATOM | 3628 | CZ | TYR | B | 449 | −31.915 | 12.887 | 8.054 | 1.00 | 47.57 C |
| ATOM | 3629 | OH | TYR | B | 449 | −33.073 | 13.507 | 8.476 | 1.00 | 48.56 O |
| ATOM | 3630 | N | ILE | B | 450 | −25.970 | 9.383 | 8.569 | 1.00 | 51.58 N |
| ATOM | 3631 | CA | ILE | B | 450 | −24.888 | 8.420 | 8.633 | 1.00 | 32.80 C |
| ATOM | 3632 | C | ILE | B | 450 | −25.356 | 7.069 | 9.119 | 1.00 | 33.91 C |
| ATOM | 3633 | O | ILE | B | 450 | −26.456 | 6.925 | 9.665 | 1.00 | 32.62 O |
| ATOM | 3634 | CB | ILE | B | 450 | −23.826 | 8.887 | 9.626 | 1.00 | 36.03 C |
| ATOM | 3635 | CG1 | ILE | B | 450 | −24.393 | 8.757 | 11.048 | 1.00 | 37.88 C |
| ATOM | 3636 | CG2 | ILE | B | 450 | −23.447 | 10.350 | 9.358 | 1.00 | 20.59 C |
| ATOM | 3637 | CD1 | ILE | B | 450 | −23.376 | 8.754 | 12.120 | 1.00 | 52.23 C |
| ATOM | 3638 | N | LYS | B | 451 | −24.492 | 6.089 | 8.915 | 1.00 | 29.84 N |
| ATOM | 3639 | CA | LYS | B | 451 | −24.732 | 4.725 | 9.352 | 1.00 | 34.08 C |
| ATOM | 3640 | C | LYS | B | 451 | −23.509 | 4.313 | 10.153 | 1.00 | 46.96 C |
| ATOM | 3641 | O | LYS | B | 451 | −22.373 | 4.584 | 9.762 | 1.00 | 36.06 O |
| ATOM | 3642 | CB | LYS | B | 451 | −24.908 | 3.782 | 8.159 | 1.00 | 47.41 C |
| ATOM | 3643 | CG | LYS | B | 451 | −26.185 | 4.016 | 7.367 | 1.00 | 42.44 C |
| ATOM | 3644 | CD | LYS | B | 451 | −26.416 | 2.898 | 6.350 | 1.00 | 67.97 C |
| ATOM | 3645 | CE | LYS | B | 451 | −26.569 | 1.534 | 7.028 | 1.00 | 72.15 C |
| ATOM | 3646 | NZ | LYS | B | 451 | −26.733 | 0.393 | 6.066 | 1.00 | 74.22 N |
| ATOM | 3647 | N | ILE | B | 452 | −23.755 | 3.684 | 11.292 | 1.00 | 33.18 N |
| ATOM | 3648 | CA | ILE | B | 452 | −22.692 | 3.225 | 12.153 | 1.00 | 44.77 C |
| ATOM | 3649 | C | ILE | B | 452 | −22.169 | 1.882 | 11.629 | 1.00 | 53.71 C |
| ATOM | 3650 | O | ILE | B | 452 | −22.940 | 0.951 | 11.359 | 1.00 | 48.04 O |
| ATOM | 3651 | CB | ILE | B | 452 | −23.213 | 3.105 | 13.605 | 1.00 | 43.35 C |
| ATOM | 3652 | CG1 | ILE | B | 452 | −23.576 | 4.502 | 14.119 | 1.00 | 41.87 C |
| ATOM | 3653 | CG2 | ILE | B | 452 | −22.183 | 2.442 | 14.489 | 1.00 | 54.98 C |
| ATOM | 3654 | CD1 | ILE | B | 452 | −24.490 | 4.492 | 15.334 | 1.00 | 60.43 C |
| ATOM | 3655 | N | PRO | B | 453 | −20.840 | 1.772 | 11.440 | 1.00 | 71.62 N |
| ATOM | 3656 | CA | PRO | B | 453 | −20.187 | 0.556 | 10.974 | 1.00 | 74.47 C |
| ATOM | 3657 | C | PRO | B | 453 | −20.378 | −0.525 | 12.016 | 1.00 | 74.41 C |
| ATOM | 3658 | O | PRO | B | 453 | −19.575 | −0.627 | 12.942 | 1.00 | 76.43 O |
| ATOM | 3659 | CB | PRO | B | 453 | −18.699 | 0.923 | 10.905 | 1.00 | 82.69 C |
| ATOM | 3660 | CG | PRO | B | 453 | −18.547 | 1.982 | 11.934 | 1.00 | 65.03 C |
| ATOM | 3661 | CD | PRO | B | 453 | −19.841 | 2.753 | 11.935 | 1.00 | 79.17 C |
| ATOM | 3662 | N | ASN | B | 454 | −21.439 | −1.352 | 11.875 | 1.00 | 74.57 N |
| ATOM | 3663 | CA | ASN | B | 454 | −21.606 | −2.332 | 12.948 | 1.00 | 80.04 C |
| ATOM | 3664 | C | ASN | B | 454 | −22.095 | −3.745 | 12.640 | 1.00 | 84.14 C |
| ATOM | 3665 | O | ASN | B | 454 | −21.377 | −4.702 | 12.902 | 1.00 | 88.39 O |
| ATOM | 3666 | CB | ASN | B | 454 | −22.489 | −1.705 | 13.994 | 1.00 | 87.52 C |

TABLE 1-continued

| | | | | | | | | | | |
|---|---|---|---|---|---|---|---|---|---|---|
| ATOM | 3667 | CG | ASN | B | 454 | −23.854 | −2.353 | 14.086 | 1.00 | 90.02 C |
| ATOM | 3668 | OD1 | ASN | B | 454 | −24.630 | −2.358 | 13.120 | 1.00 | 87.27 O |
| ATOM | 3669 | ND2 | ASN | B | 454 | −24.156 | −2.909 | 15.255 | 1.00 | 90.02 N |
| ATOM | 3670 | N | ALA | B | 455 | −23.302 | −3.895 | 12.100 | 1.00 | 76.04 N |
| ATOM | 3671 | CA | ALA | B | 455 | −23.849 | −5.233 | 11.890 | 1.00 | 87.39 C |
| ATOM | 3672 | C | ALA | B | 455 | −24.932 | −5.347 | 10.816 | 1.00 | 95.41 C |
| ATOM | 3673 | O | ALA | B | 455 | −24.675 | −5.784 | 9.697 | 1.00 | 90.73 O |
| ATOM | 3674 | CB | ALA | B | 455 | −24.366 | −5.763 | 13.223 | 1.00 | 76.10 C |
| ATOM | 3675 | N | GLY | B | 456 | −26.147 | −4.937 | 11.178 | 1.00 | 97.76 N |
| ATOM | 3676 | CA | GLY | B | 456 | −27.266 | −5.004 | 10.256 | 1.00 | 90.18 C |
| ATOM | 3677 | C | GLY | B | 456 | −27.352 | −3.849 | 9.278 | 1.00 | 85.87 C |
| ATOM | 3678 | O | GLY | B | 456 | −26.409 | −3.066 | 9.120 | 1.00 | 79.37 O |
| ATOM | 3679 | N | GLN | B | 457 | −28.503 | −3.749 | 8.620 | 1.00 | 81.99 N |
| ATOM | 3680 | CA | GLN | B | 457 | −28.749 | −2.706 | 7.636 | 1.00 | 87.47 C |
| ATOM | 3681 | C | GLN | B | 457 | −29.569 | −1.592 | 8.283 | 1.00 | 87.78 C |
| ATOM | 3682 | O | GLN | B | 457 | −30.674 | −1.288 | 7.831 | 1.00 | 92.12 O |
| ATOM | 3683 | CB | GLN | B | 457 | −29.471 | −3.305 | 6.398 | 1.00 | 91.96 C |
| ATOM | 3684 | CG | GLN | B | 457 | −28.773 | −4.533 | 5.760 | 1.00 | 91.67 C |
| ATOM | 3685 | CD | GLN | B | 457 | −29.573 | −5.153 | 4.615 | 1.00 | 94.86 C |
| ATOM | 3686 | OE1 | GLN | B | 457 | −30.674 | −5.671 | 4.818 | 1.00 | 87.15 O |
| ATOM | 3687 | NE2 | GLN | B | 457 | −29.226 | −5.190 | 3.329 | 1.00 | 77.64 N |
| ATOM | 3688 | N | MET | B | 458 | −29.033 | −0.994 | 9.348 | 1.00 | 79.85 N |
| ATOM | 3689 | CA | MET | B | 458 | −29.732 | 0.087 | 10.044 | 1.00 | 73.54 C |
| ATOM | 3690 | C | MET | B | 458 | −30.079 | 1.205 | 9.069 | 1.00 | 68.17 C |
| ATOM | 3691 | O | MET | B | 458 | −29.439 | 1.365 | 8.032 | 1.00 | 68.97 O |
| ATOM | 3692 | CB | MET | B | 458 | −28.862 | 0.680 | 11.172 | 1.00 | 79.03 C |
| ATOM | 3693 | CG | MET | B | 458 | −27.840 | 1.726 | 10.723 | 1.00 | 70.80 C |
| ATOM | 3694 | SD | MET | B | 458 | −26.915 | 2.414 | 12.113 | 1.00 | 59.61 S |
| ATOM | 3695 | CE | MET | B | 458 | −27.506 | 4.109 | 12.123 | 1.00 | 53.15 C |
| ATOM | 3696 | N | GLN | B | 459 | −31.102 | 1.977 | 9.399 | 1.00 | 68.68 N |
| ATOM | 3697 | CA | GLN | B | 459 | −31.466 | 3.101 | 8.581 | 1.00 | 67.90 C |
| ATOM | 3698 | C | GLN | B | 459 | −30.641 | 4.275 | 9.079 | 1.00 | 57.04 C |
| ATOM | 3699 | O | GLN | B | 459 | −30.441 | 4.415 | 10.291 | 1.00 | 57.31 O |
| ATOM | 3700 | CB | GLN | B | 459 | −32.975 | 3.387 | 8.637 | 1.00 | 72.03 C |
| ATOM | 3701 | CG | GLN | B | 459 | −33.569 | 3.429 | 10.040 | 1.00 | 80.07 C |
| ATOM | 3702 | CD | GLN | B | 459 | −35.017 | 3.853 | 10.061 | 1.00 | 86.84 C |
| ATOM | 3703 | OE1 | GLN | B | 459 | −35.421 | 4.762 | 9.349 | 1.00 | 95.85 O |
| ATOM | 3704 | NE2 | GLN | B | 459 | −35.967 | 3.322 | 10.808 | 1.00 | 80.80 N |
| ATOM | 3705 | N | PRO | B | 460 | −30.143 | 5.127 | 8.178 | 1.00 | 61.79 N |
| ATOM | 3706 | CA | PRO | B | 460 | −29.332 | 6.274 | 8.576 | 1.00 | 49.44 C |
| ATOM | 3707 | C | PRO | B | 460 | −30.020 | 7.137 | 9.608 | 1.00 | 57.74 C |
| ATOM | 3708 | O | PRO | B | 460 | −31.223 | 7.011 | 9.824 | 1.00 | 70.12 O |
| ATOM | 3709 | CB | PRO | B | 460 | −29.103 | 7.002 | 7.256 | 1.00 | 57.38 C |
| ATOM | 3710 | CG | PRO | B | 460 | −30.340 | 6.702 | 6.510 | 1.00 | 53.34 C |
| ATOM | 3711 | CD | PRO | B | 460 | −30.515 | 5.235 | 6.757 | 1.00 | 57.95 C |
| ATOM | 3712 | N | VAL | B | 461 | −29.236 | 7.988 | 10.266 | 1.00 | 47.95 N |
| ATOM | 3713 | CA | VAL | B | 461 | −29.758 | 8.911 | 11.260 | 1.00 | 40.12 C |
| ATOM | 3714 | C | VAL | B | 461 | −28.975 | 10.195 | 11.105 | 1.00 | 36.28 C |
| ATOM | 3715 | O | VAL | B | 461 | −27.827 | 10.179 | 10.668 | 1.00 | 45.62 O |
| ATOM | 3716 | CB | VAL | B | 461 | −29.634 | 8.374 | 12.726 | 1.00 | 53.56 C |
| ATOM | 3717 | CG1 | VAL | B | 461 | −30.543 | 7.183 | 12.904 | 1.00 | 37.20 C |
| ATOM | 3718 | CG2 | VAL | B | 461 | −28.172 | 8.012 | 13.060 | 1.00 | 39.98 C |
| ATOM | 3719 | N | LYS | B | 462 | −29.620 | 11.302 | 11.443 | 1.00 | 27.97 N |
| ATOM | 3720 | CA | LYS | B | 462 | −29.030 | 12.612 | 11.320 | 1.00 | 27.59 C |
| ATOM | 3721 | C | LYS | B | 462 | −27.962 | 12.868 | 12.386 | 1.00 | 31.06 C |
| ATOM | 3722 | O | LYS | B | 462 | −28.183 | 12.647 | 13.565 | 1.00 | 37.60 O |
| ATOM | 3723 | CB | LYS | B | 462 | −30.140 | 13.646 | 11.391 | 1.00 | 20.26 C |
| ATOM | 3724 | CG | LYS | B | 462 | −29.716 | 15.036 | 10.969 | 1.00 | 42.50 C |
| ATOM | 3725 | CD | LYS | B | 462 | −30.913 | 15.899 | 10.574 | 1.00 | 31.10 C |
| ATOM | 3726 | CE | LYS | B | 462 | −30.465 | 17.299 | 10.195 | 1.00 | 43.14 C |
| ATOM | 3727 | NZ | LYS | B | 462 | −31.565 | 18.190 | 9.739 | 1.00 | 36.27 N |
| ATOM | 3728 | N | ALA | B | 463 | −26.808 | 13.361 | 11.967 | 1.00 | 33.41 N |
| ATOM | 3729 | CA | ALA | B | 463 | −25.728 | 13.594 | 12.894 | 1.00 | 33.84 C |
| ATOM | 3730 | C | ALA | B | 463 | −25.036 | 14.934 | 12.669 | 1.00 | 33.94 C |
| ATOM | 3731 | O | ALA | B | 463 | −25.032 | 15.465 | 11.564 | 1.00 | 36.46 O |
| ATOM | 3732 | CB | ALA | B | 463 | −24.748 | 12.447 | 12.806 | 1.00 | 27.60 C |
| ATOM | 3733 | N | PHE | B | 464 | −24.462 | 15.480 | 13.737 | 1.00 | 36.94 N |
| ATOM | 3734 | CA | PHE | B | 464 | −23.816 | 16.777 | 13.681 | 1.00 | 31.63 C |
| ATOM | 3735 | C | PHE | B | 464 | −22.369 | 16.744 | 14.133 | 1.00 | 37.13 C |
| ATOM | 3736 | O | PHE | B | 464 | −22.054 | 16.274 | 15.232 | 1.00 | 30.28 O |
| ATOM | 3737 | CB | PHE | B | 464 | −24.601 | 17.777 | 14.538 | 1.00 | 29.31 C |
| ATOM | 3738 | CG | PHE | B | 464 | −26.079 | 17.747 | 14.276 | 1.00 | 37.02 C |
| ATOM | 3739 | CD1 | PHE | B | 464 | −26.841 | 16.634 | 14.654 | 1.00 | 20.13 C |
| ATOM | 3740 | CD2 | PHE | B | 464 | −26.702 | 18.793 | 13.573 | 1.00 | 45.33 C |
| ATOM | 3741 | CE1 | PHE | B | 464 | −28.225 | 16.552 | 14.322 | 1.00 | 49.61 C |
| ATOM | 3742 | CE2 | PHE | B | 464 | −28.082 | 18.733 | 13.233 | 1.00 | 34.39 C |
| ATOM | 3743 | CZ | PHE | B | 464 | −28.846 | 17.610 | 13.603 | 1.00 | 28.50 C |
| ATOM | 3744 | N | LYS | B | 465 | −21.483 | 17.266 | 13.290 | 1.00 | 27.04 N |
| ATOM | 3745 | CA | LYS | B | 465 | −20.071 | 17.285 | 13.613 | 1.00 | 21.99 C |

TABLE 1-continued

| | | | | | | | | | | |
|---|---|---|---|---|---|---|---|---|---|---|
| ATOM | 3746 | C | LYS | B | 465 | −19.793 | 18.616 | 14.319 | 1.00 | 39.51 C |
| ATOM | 3747 | O | LYS | B | 465 | −19.677 | 19.663 | 13.685 | 1.00 | 33.79 O |
| ATOM | 3748 | CB | LYS | B | 465 | −19.267 | 17.108 | 12.323 | 1.00 | 31.67 C |
| ATOM | 3749 | CG | LYS | B | 465 | −17.749 | 17.171 | 12.482 | 1.00 | 51.29 C |
| ATOM | 3750 | CD | LYS | B | 465 | −17.056 | 16.770 | 11.177 | 1.00 | 43.45 C |
| ATOM | 3751 | CE | LYS | B | 465 | −15.621 | 17.216 | 11.172 | 1.00 | 58.38 C |
| ATOM | 3752 | NZ | LYS | B | 465 | −14.945 | 16.936 | 9.867 | 1.00 | 68.61 N |
| ATOM | 3753 | N | ILE | B | 466 | −19.700 | 18.577 | 15.644 | 1.00 | 30.38 N |
| ATOM | 3754 | CA | ILE | B | 466 | −19.511 | 19.801 | 16.408 | 1.00 | 24.98 C |
| ATOM | 3755 | C | ILE | B | 466 | −18.076 | 20.274 | 16.581 | 1.00 | 23.09 C |
| ATOM | 3756 | O | ILE | B | 466 | −17.824 | 21.385 | 17.061 | 1.00 | 25.69 O |
| ATOM | 3757 | CB | ILE | B | 466 | −20.172 | 19.664 | 17.803 | 1.00 | 41.81 C |
| ATOM | 3758 | CG1 | ILE | B | 466 | −19.392 | 18.651 | 18.661 | 1.00 | 37.83 C |
| ATOM | 3759 | CG2 | ILE | B | 466 | −21.653 | 19.167 | 17.643 | 1.00 | 26.21 C |
| ATOM | 3760 | CD1 | ILE | B | 466 | −19.788 | 18.678 | 20.141 | 1.00 | 25.41 C |
| ATOM | 3761 | N | HIS | B | 467 | −17.130 | 19.447 | 16.173 | 1.00 | 27.44 N |
| ATOM | 3762 | CA | HIS | B | 467 | −15.712 | 19.790 | 16.280 | 1.00 | 23.57 C |
| ATOM | 3763 | C | HIS | B | 467 | −14.985 | 18.695 | 15.511 | 1.00 | 28.80 C |
| ATOM | 3764 | O | HIS | B | 467 | −15.527 | 17.612 | 15.329 | 1.00 | 23.71 O |
| ATOM | 3765 | CB | HIS | B | 467 | −15.288 | 19.795 | 17.761 | 1.00 | 24.34 C |
| ATOM | 3766 | CG | HIS | B | 467 | −13.959 | 20.436 | 18.015 | 1.00 | 27.36 C |
| ATOM | 3767 | ND1 | HIS | B | 467 | −12.758 | 19.791 | 17.791 | 1.00 | 38.73 N |
| ATOM | 3768 | CD2 | HIS | B | 467 | −13.640 | 21.684 | 18.436 | 1.00 | 35.62 C |
| ATOM | 3769 | CE1 | HIS | B | 467 | −11.756 | 20.612 | 18.058 | 1.00 | 22.99 C |
| ATOM | 3770 | NE2 | HIS | B | 467 | −12.265 | 21.768 | 18.453 | 1.00 | 37.99 N |
| ATOM | 3771 | N | ASN | B | 468 | −13.772 | 18.982 | 15.050 | 1.00 | 32.16 N |
| ATOM | 3772 | CA | ASN | B | 468 | −12.973 | 18.017 | 14.304 | 1.00 | 36.26 C |
| ATOM | 3773 | C | ASN | B | 468 | −13.000 | 16.646 | 15.007 | 1.00 | 21.32 C |
| ATOM | 3774 | O | ASN | B | 468 | −12.797 | 16.573 | 16.201 | 1.00 | 23.93 O |
| ATOM | 3775 | CB | ASN | B | 468 | −11.519 | 18.525 | 14.216 | 1.00 | 40.28 C |
| ATOM | 3776 | CG | ASN | B | 468 | −10.652 | 17.687 | 13.276 | 1.00 | 53.47 C |
| ATOM | 3777 | OD1 | ASN | B | 468 | −9.424 | 17.662 | 13.402 | 1.00 | 68.14 O |
| ATOM | 3778 | ND2 | ASN | B | 468 | −11.286 | 17.008 | 12.324 | 1.00 | 53.55 N |
| ATOM | 3779 | N | LYS | B | 469 | −13.279 | 15.582 | 14.271 | 1.00 | 25.99 N |
| ATOM | 3780 | CA | LYS | B | 469 | −13.306 | 14.240 | 14.863 | 1.00 | 36.04 C |
| ATOM | 3781 | C | LYS | B | 469 | −14.390 | 13.917 | 15.921 | 1.00 | 36.15 C |
| ATOM | 3782 | O | LYS | B | 469 | −14.409 | 12.806 | 16.447 | 1.00 | 26.74 O |
| ATOM | 3783 | CB | LYS | B | 469 | −11.924 | 13.929 | 15.478 | 1.00 | 39.53 C |
| ATOM | 3784 | CG | LYS | B | 469 | −10.739 | 13.884 | 14.463 | 1.00 | 30.18 C |
| ATOM | 3785 | CD | LYS | B | 469 | −11.006 | 12.876 | 13.360 | 1.00 | 36.96 C |
| ATOM | 3786 | CE | LYS | B | 469 | −9.748 | 12.513 | 12.535 | 1.00 | 43.33 C |
| ATOM | 3787 | NZ | LYS | B | 469 | −8.961 | 13.712 | 12.179 | 1.00 | 43.81 N |
| ATOM | 3788 | N | ILE | B | 470 | −15.274 | 14.861 | 16.242 | 1.00 | 26.74 N |
| ATOM | 3789 | CA | ILE | B | 470 | −16.297 | 14.621 | 17.255 | 1.00 | 28.78 C |
| ATOM | 3790 | C | ILE | B | 470 | −17.734 | 14.824 | 16.739 | 1.00 | 36.87 C |
| ATOM | 3791 | O | ILE | B | 470 | −18.097 | 15.903 | 16.271 | 1.00 | 23.71 O |
| ATOM | 3792 | CB | ILE | B | 470 | −16.033 | 15.549 | 18.444 | 1.00 | 24.86 C |
| ATOM | 3793 | CG1 | ILE | B | 470 | −14.657 | 15.207 | 19.069 | 1.00 | 20.49 C |
| ATOM | 3794 | CG2 | ILE | B | 470 | −17.157 | 15.432 | 19.466 | 1.00 | 25.52 C |
| ATOM | 3795 | CD1 | ILE | B | 470 | −14.248 | 16.138 | 20.221 | 1.00 | 26.66 C |
| ATOM | 3796 | N | TRP | B | 471 | −18.544 | 13.781 | 16.813 | 1.00 | 27.89 N |
| ATOM | 3797 | CA | TRP | B | 471 | −19.929 | 13.847 | 16.346 | 1.00 | 25.41 C |
| ATOM | 3798 | C | TRP | B | 471 | −20.993 | 13.595 | 17.434 | 1.00 | 22.54 C |
| ATOM | 3799 | O | TRP | B | 471 | −20.754 | 12.884 | 18.412 | 1.00 | 34.69 O |
| ATOM | 3800 | CB | TRP | B | 471 | −20.167 | 12.823 | 15.227 | 1.00 | 20.43 C |
| ATOM | 3801 | CG | TRP | B | 471 | −19.443 | 13.065 | 13.958 | 1.00 | 41.92 C |
| ATOM | 3802 | CD1 | TRP | B | 471 | −18.098 | 12.927 | 13.748 | 1.00 | 48.00 C |
| ATOM | 3803 | CD2 | TRP | B | 471 | −20.003 | 13.471 | 12.699 | 1.00 | 40.97 C |
| ATOM | 3804 | NE1 | TRP | B | 471 | −17.786 | 13.218 | 12.447 | 1.00 | 30.28 N |
| ATOM | 3805 | CE2 | TRP | B | 471 | −18.933 | 13.560 | 11.775 | 1.00 | 57.19 C |
| ATOM | 3806 | CE3 | TRP | B | 471 | −21.302 | 13.775 | 12.258 | 1.00 | 33.31 C |
| ATOM | 3807 | CZ2 | TRP | B | 471 | −19.118 | 13.943 | 10.436 | 1.00 | 43.57 C |
| ATOM | 3808 | CZ3 | TRP | B | 471 | −21.490 | 14.157 | 10.930 | 1.00 | 33.47 C |
| ATOM | 3809 | CH2 | TRP | B | 471 | −20.400 | 14.238 | 10.034 | 1.00 | 40.56 C |
| ATOM | 3810 | N | VAL | B | 472 | −22.177 | 14.159 | 17.224 | 1.00 | 30.61 N |
| ATOM | 3811 | CA | VAL | B | 472 | −23.315 | 14.003 | 18.124 | 1.00 | 26.49 C |
| ATOM | 3812 | C | VAL | B | 472 | −24.513 | 13.459 | 17.320 | 1.00 | 36.72 C |
| ATOM | 3813 | O | VAL | B | 472 | −24.924 | 14.042 | 16.311 | 1.00 | 37.83 O |
| ATOM | 3814 | CB | VAL | B | 472 | −23.734 | 15.348 | 18.758 | 1.00 | 31.06 C |
| ATOM | 3815 | CG1 | VAL | B | 472 | −24.954 | 15.136 | 19.657 | 1.00 | 34.37 C |
| ATOM | 3816 | CG2 | VAL | B | 472 | −22.594 | 15.925 | 19.557 | 1.00 | 26.61 C |
| ATOM | 3817 | N | ILE | B | 473 | −25.047 | 12.329 | 17.756 | 1.00 | 19.60 N |
| ATOM | 3818 | CA | ILE | B | 473 | −26.190 | 11.698 | 17.113 | 1.00 | 24.90 C |
| ATOM | 3819 | C | ILE | B | 473 | −27.314 | 11.778 | 18.149 | 1.00 | 44.75 C |
| ATOM | 3820 | O | ILE | B | 473 | −27.342 | 11.002 | 19.107 | 1.00 | 29.79 O |
| ATOM | 3821 | CB | ILE | B | 473 | −25.904 | 10.211 | 16.801 | 1.00 | 23.84 C |
| ATOM | 3822 | CG1 | ILE | B | 473 | −24.631 | 10.087 | 15.946 | 1.00 | 29.47 C |
| ATOM | 3823 | CG2 | ILE | B | 473 | −27.104 | 9.596 | 16.097 | 1.00 | 26.33 C |
| ATOM | 3824 | CD1 | ILE | B | 473 | −24.356 | 8.658 | 15.470 | 1.00 | 27.41 C |

TABLE 1-continued

| | | | | | | | | | | |
|---|---|---|---|---|---|---|---|---|---|---|
| ATOM | 3825 | N | PRO | B | 474 | −28.238 | 12.747 | 17.988 | 1.00 | 53.09 N |
| ATOM | 3826 | CA | PRO | B | 474 | −29.328 | 12.870 | 18.957 | 1.00 | 38.45 C |
| ATOM | 3827 | C | PRO | B | 474 | −30.445 | 11.868 | 18.683 | 1.00 | 26.46 C |
| ATOM | 3828 | O | PRO | B | 474 | −31.524 | 12.219 | 18.237 | 1.00 | 42.87 O |
| ATOM | 3829 | CB | PRO | B | 474 | −29.753 | 14.340 | 18.811 | 1.00 | 23.00 C |
| ATOM | 3830 | CG | PRO | B | 474 | −29.489 | 14.624 | 17.437 | 1.00 | 38.47 C |
| ATOM | 3831 | CD | PRO | B | 474 | −28.214 | 13.907 | 17.081 | 1.00 | 29.08 C |
| ATOM | 3832 | N | GLU | B | 475 | −30.147 | 10.612 | 18.966 | 1.00 | 31.76 N |
| ATOM | 3833 | CA | GLU | B | 475 | −31.053 | 9.502 | 18.766 | 1.00 | 37.22 C |
| ATOM | 3834 | C | GLU | B | 475 | −30.806 | 8.543 | 19.929 | 1.00 | 47.01 C |
| ATOM | 3835 | O | GLU | B | 475 | −29.772 | 8.632 | 20.602 | 1.00 | 46.89 O |
| ATOM | 3836 | CB | GLU | B | 475 | −30.699 | 8.761 | 17.470 | 1.00 | 37.66 C |
| ATOM | 3837 | CG | GLU | B | 475 | −30.861 | 9.548 | 16.179 | 1.00 | 61.48 C |
| ATOM | 3838 | CD | GLU | B | 475 | −32.300 | 9.717 | 15.763 | 1.00 | 50.70 C |
| ATOM | 3839 | OE1 | GLU | B | 475 | −33.042 | 8.719 | 15.826 | 1.00 | 49.38 O |
| ATOM | 3840 | OE2 | GLU | B | 475 | −32.674 | 10.840 | 15.361 | 1.00 | 58.50 O |
| ATOM | 3841 | N | ARG | B | 476 | −31.739 | 7.626 | 20.144 | 1.00 | 26.59 N |
| ATOM | 3842 | CA | ARG | B | 476 | −31.600 | 6.614 | 21.176 | 1.00 | 32.93 C |
| ATOM | 3843 | C | ARG | B | 476 | −30.685 | 5.536 | 20.572 | 1.00 | 27.10 C |
| ATOM | 3844 | O | ARG | B | 476 | −30.782 | 5.226 | 19.387 | 1.00 | 36.56 O |
| ATOM | 3845 | CB | ARG | B | 476 | −32.972 | 6.020 | 21.530 | 1.00 | 34.47 C |
| ATOM | 3846 | CG | ARG | B | 476 | −33.942 | 6.985 | 22.242 | 1.00 | 20.56 C |
| ATOM | 3847 | CD | ARG | B | 476 | −33.496 | 7.321 | 23.644 | 1.00 | 26.21 C |
| ATOM | 3848 | NE | ARG | B | 476 | −33.625 | 6.222 | 24.599 | 1.00 | 32.06 N |
| ATOM | 3849 | CZ | ARG | B | 476 | −34.779 | 5.806 | 25.126 | 1.00 | 50.15 C |
| ATOM | 3850 | NH1 | ARG | B | 476 | −35.920 | 6.390 | 24.789 | 1.00 | 40.26 N |
| ATOM | 3851 | NH2 | ARG | B | 476 | −34.788 | 4.828 | 26.020 | 1.00 | 36.22 N |
| ATOM | 3852 | N | ASP | B | 477 | −29.807 | 4.943 | 21.368 | 1.00 | 34.73 N |
| ATOM | 3853 | CA | ASP | B | 477 | −28.904 | 3.955 | 20.806 | 1.00 | 36.46 C |
| ATOM | 3854 | C | ASP | B | 477 | −29.419 | 2.519 | 20.712 | 1.00 | 51.19 C |
| ATOM | 3855 | O | ASP | B | 477 | −29.391 | 1.751 | 21.678 | 1.00 | 37.40 O |
| ATOM | 3856 | CB | ASP | B | 477 | −27.554 | 3.979 | 21.531 | 1.00 | 38.31 C |
| ATOM | 3857 | CG | ASP | B | 477 | −26.571 | 2.939 | 20.972 | 1.00 | 43.23 C |
| ATOM | 3858 | OD1 | ASP | B | 477 | −26.770 | 2.471 | 19.827 | 1.00 | 49.65 O |
| ATOM | 3859 | OD2 | ASP | B | 477 | −25.587 | 2.596 | 21.669 | 1.00 | 44.79 O |
| ATOM | 3860 | N | THR | B | 478 | −29.882 | 2.172 | 19.518 | 1.00 | 33.19 N |
| ATOM | 3861 | CA | THR | B | 478 | −30.373 | 0.840 | 19.243 | 1.00 | 49.12 C |
| ATOM | 3862 | C | THR | B | 478 | −29.507 | 0.301 | 18.091 | 1.00 | 51.86 C |
| ATOM | 3863 | O | THR | B | 478 | −29.891 | −0.629 | 17.391 | 1.00 | 54.58 O |
| ATOM | 3864 | CB | THR | B | 478 | −31.855 | 0.879 | 18.811 | 1.00 | 34.66 C |
| ATOM | 3865 | OG1 | THR | B | 478 | −32.005 | 1.809 | 17.740 | 1.00 | 51.72 O |
| ATOM | 3866 | CG2 | THR | B | 478 | −32.752 | 1.321 | 19.978 | 1.00 | 38.97 C |
| ATOM | 3867 | N | PHE | B | 479 | −28.322 | 0.888 | 17.933 | 1.00 | 56.46 N |
| ATOM | 3868 | CA | PHE | B | 479 | −27.383 | 0.533 | 16.863 | 1.00 | 44.45 C |
| ATOM | 3869 | C | PHE | B | 479 | −26.070 | −0.072 | 17.324 | 1.00 | 37.92 C |
| ATOM | 3870 | O | PHE | B | 479 | −25.563 | −1.003 | 16.720 | 1.00 | 51.95 O |
| ATOM | 3871 | CB | PHE | B | 479 | −27.039 | 1.778 | 16.043 | 1.00 | 41.65 C |
| ATOM | 3872 | CG | PHE | B | 479 | −28.194 | 2.691 | 15.829 | 1.00 | 36.64 C |
| ATOM | 3873 | CD1 | PHE | B | 479 | −29.308 | 2.268 | 15.122 | 1.00 | 47.59 C |
| ATOM | 3874 | CD2 | PHE | B | 479 | −28.168 | 3.981 | 16.327 | 1.00 | 45.68 C |
| ATOM | 3875 | CE1 | PHE | B | 479 | −30.387 | 3.121 | 14.914 | 1.00 | 42.35 C |
| ATOM | 3876 | CE2 | PHE | B | 479 | −29.239 | 4.842 | 16.126 | 1.00 | 46.19 C |
| ATOM | 3877 | CZ | PHE | B | 479 | −30.354 | 4.412 | 15.414 | 1.00 | 44.74 C |
| ATOM | 3878 | N | THR | B | 480 | −25.499 | 0.472 | 18.383 | 1.00 | 42.31 N |
| ATOM | 3879 | CA | THR | B | 480 | −24.218 | −0.027 | 18.844 | 1.00 | 46.20 C |
| ATOM | 3880 | C | THR | B | 480 | −24.191 | −1.475 | 19.308 | 1.00 | 56.55 C |
| ATOM | 3881 | O | THR | B | 480 | −23.140 | −2.107 | 19.306 | 1.00 | 61.30 O |
| ATOM | 3882 | CB | THR | B | 480 | −23.685 | 0.874 | 19.938 | 1.00 | 48.12 C |
| ATOM | 3883 | OG1 | THR | B | 480 | −23.317 | 2.126 | 19.350 | 1.00 | 65.32 O |
| ATOM | 3884 | CG2 | THR | B | 480 | −22.473 | 0.270 | 20.591 | 1.00 | 77.35 C |
| ATOM | 3885 | N | ASN | B | 481 | −25.346 | −2.010 | 19.677 | 1.00 | 52.75 N |
| ATOM | 3886 | CA | ASN | B | 481 | −25.429 | −3.376 | 20.172 | 1.00 | 55.10 C |
| ATOM | 3887 | C | ASN | B | 481 | −26.658 | −4.091 | 19.605 | 1.00 | 72.16 C |
| ATOM | 3888 | O | ASN | B | 481 | −27.788 | −3.638 | 19.808 | 1.00 | 64.90 O |
| ATOM | 3889 | CB | ASN | B | 481 | −25.505 | −3.354 | 21.698 | 1.00 | 52.74 C |
| ATOM | 3890 | CG | ASN | B | 481 | −25.480 | −4.738 | 22.305 | 1.00 | 65.49 C |
| ATOM | 3891 | OD1 | ASN | B | 481 | −25.556 | −5.741 | 21.598 | 1.00 | 68.52 O |
| ATOM | 3892 | ND2 | ASN | B | 481 | −25.372 | −4.799 | 23.624 | 1.00 | 64.00 N |
| ATOM | 3893 | N | PRO | B | 482 | −26.449 | −5.221 | 18.895 | 1.00 | 72.28 N |
| ATOM | 3894 | CA | PRO | B | 482 | −27.519 | −6.022 | 18.287 | 1.00 | 79.62 C |
| ATOM | 3895 | C | PRO | B | 482 | −28.468 | −6.617 | 19.329 | 1.00 | 73.19 C |
| ATOM | 3896 | O | PRO | B | 482 | −29.610 | −6.952 | 19.024 | 1.00 | 73.74 O |
| ATOM | 3897 | CB | PRO | B | 482 | −26.747 | −7.093 | 17.517 | 1.00 | 76.90 C |
| ATOM | 3898 | CG | PRO | B | 482 | −25.544 | −7.302 | 18.381 | 1.00 | 61.08 C |
| ATOM | 3899 | CD | PRO | B | 482 | −25.145 | −5.882 | 18.702 | 1.00 | 72.47 C |
| ATOM | 3900 | N | GLU | B | 483 | −27.982 | −6.743 | 20.560 | 1.00 | 71.97 N |
| ATOM | 3901 | CA | GLU | B | 483 | −28.785 | −7.276 | 21.654 | 1.00 | 78.37 C |
| ATOM | 3902 | C | GLU | B | 483 | −29.656 | −6.171 | 22.262 | 1.00 | 76.66 C |
| ATOM | 3903 | O | GLU | B | 483 | −30.316 | −6.377 | 23.289 | 1.00 | 77.92 O |

TABLE 1-continued

| | | | | | | | | | | |
|---|---|---|---|---|---|---|---|---|---|---|
| ATOM | 3904 | CB | GLU | B | 483 | −27.881 | −7.848 | 22.753 | 1.00 | 85.96 C |
| ATOM | 3905 | CG | GLU | B | 483 | −27.025 | −9.041 | 22.361 | 1.00 | 76.88 C |
| ATOM | 3906 | CD | GLU | B | 483 | −26.173 | −9.528 | 23.524 | 1.00 | 86.27 C |
| ATOM | 3907 | OE1 | GLU | B | 483 | −25.332 | −8.745 | 24.024 | 1.00 | 82.85 O |
| ATOM | 3908 | OE2 | GLU | B | 483 | −26.347 | −10.691 | 23.949 | 1.00 | 97.37 O |
| ATOM | 3909 | N | GLU | B | 484 | −29.639 | −4.995 | 21.641 | 1.00 | 68.90 N |
| ATOM | 3910 | CA | GLU | B | 484 | −30.427 | −3.868 | 22.123 | 1.00 | 64.63 C |
| ATOM | 3911 | C | GLU | B | 484 | −30.987 | −3.103 | 20.943 | 1.00 | 50.87 C |
| ATOM | 3912 | O | GLU | B | 484 | −30.803 | −1.903 | 20.826 | 1.00 | 56.32 O |
| ATOM | 3913 | CB | GLU | B | 484 | −29.566 | −2.949 | 22.994 | 1.00 | 57.56 C |
| ATOM | 3914 | CG | GLU | B | 484 | −28.966 | −3.655 | 24.202 | 1.00 | 74.02 C |
| ATOM | 3915 | CD | GLU | B | 484 | −28.241 | −2.713 | 25.150 | 1.00 | 81.46 C |
| ATOM | 3916 | OE1 | GLU | B | 484 | −28.883 | −1.768 | 25.658 | 1.00 | 88.53 O |
| ATOM | 3917 | OE2 | GLU | B | 484 | −27.032 | −2.917 | 25.394 | 1.00 | 82.88 O |
| ATOM | 3918 | N | GLY | B | 485 | −31.683 | −3.818 | 20.071 | 1.00 | 64.89 N |
| ATOM | 3919 | CA | GLY | B | 485 | −32.259 | −3.203 | 18.894 | 1.00 | 69.21 C |
| ATOM | 3920 | C | GLY | B | 485 | −33.545 | −2.432 | 19.124 | 1.00 | 74.63 C |
| ATOM | 3921 | O | GLY | B | 485 | −34.010 | −1.731 | 18.220 | 1.00 | 69.08 O |
| ATOM | 3922 | N | ASP | B | 486 | −34.129 | −2.554 | 20.314 | 1.00 | 65.49 N |
| ATOM | 3923 | CA | ASP | B | 486 | −35.366 | −1.837 | 20.612 | 1.00 | 60.03 C |
| ATOM | 3924 | C | ASP | B | 486 | −35.323 | −1.213 | 21.997 | 1.00 | 64.42 C |
| ATOM | 3925 | O | ASP | B | 486 | −34.356 | −1.402 | 22.735 | 1.00 | 55.63 O |
| ATOM | 3926 | CB | ASP | B | 486 | −36.567 | −2.769 | 20.498 | 1.00 | 61.40 C |
| ATOM | 3927 | CG | ASP | B | 486 | −36.454 | −3.974 | 21.406 | 1.00 | 79.96 C |
| ATOM | 3928 | OD1 | ASP | B | 486 | −36.410 | −3.781 | 22.649 | 1.00 | 77.61 O |
| ATOM | 3929 | OD2 | ASP | B | 486 | −36.408 | −5.108 | 20.870 | 1.00 | 74.74 O |
| ATOM | 3930 | N | LEU | B | 487 | −36.380 | −0.484 | 22.347 | 1.00 | 53.21 N |
| ATOM | 3931 | CA | LEU | B | 487 | −36.453 | 0.204 | 23.628 | 1.00 | 35.99 C |
| ATOM | 3932 | C | LEU | B | 487 | −37.451 | −0.410 | 24.601 | 1.00 | 53.30 C |
| ATOM | 3933 | O | LEU | B | 487 | −37.930 | 0.241 | 25.539 | 1.00 | 45.27 O |
| ATOM | 3934 | CB | LEU | B | 487 | −36.774 | 1.669 | 23.374 | 1.00 | 29.30 C |
| ATOM | 3935 | CG | LEU | B | 487 | −35.769 | 2.274 | 22.391 | 1.00 | 29.34 C |
| ATOM | 3936 | CD1 | LEU | B | 487 | −36.135 | 3.711 | 22.054 | 1.00 | 35.89 C |
| ATOM | 3937 | CD2 | LEU | B | 487 | −34.367 | 2.189 | 23.003 | 1.00 | 31.10 C |
| ATOM | 3938 | N | ASN | B | 488 | −37.740 | −1.686 | 24.379 | 1.00 | 60.58 N |
| ATOM | 3939 | CA | ASN | B | 488 | −38.652 | −2.421 | 25.225 | 1.00 | 56.24 C |
| ATOM | 3940 | C | ASN | B | 488 | −38.013 | −2.635 | 26.586 | 1.00 | 61.21 C |
| ATOM | 3941 | O | ASN | B | 488 | −36.957 | −3.254 | 26.694 | 1.00 | 62.90 O |
| ATOM | 3942 | CB | ASN | B | 488 | −38.979 | −3.757 | 24.577 | 1.00 | 52.74 C |
| ATOM | 3943 | CG | ASN | B | 488 | −39.833 | −3.595 | 23.361 | 1.00 | 69.15 C |
| ATOM | 3944 | OD1 | ASN | B | 488 | −40.887 | −2.951 | 23.414 | 1.00 | 66.49 O |
| ATOM | 3945 | ND2 | ASN | B | 488 | −39.393 | −4.164 | 22.248 | 1.00 | 83.99 N |
| ATOM | 3946 | N | PRO | B | 489 | −38.649 | −2.111 | 27.644 | 1.00 | 57.35 N |
| ATOM | 3947 | CA | PRO | B | 489 | −38.181 | −2.217 | 29.023 | 1.00 | 60.30 C |
| ATOM | 3948 | C | PRO | B | 489 | −38.439 | −3.607 | 29.598 | 1.00 | 50.89 C |
| ATOM | 3949 | O | PRO | B | 489 | −39.443 | −4.235 | 29.291 | 1.00 | 51.51 O |
| ATOM | 3950 | CB | PRO | B | 489 | −38.993 | −1.139 | 29.732 | 1.00 | 45.96 C |
| ATOM | 3951 | CG | PRO | B | 489 | −40.304 | −1.269 | 29.061 | 1.00 | 55.78 C |
| ATOM | 3952 | CD | PRO | B | 489 | −39.934 | −1.393 | 27.593 | 1.00 | 60.18 C |
| ATOM | 3953 | N | PRO | B | 490 | −37.530 | −4.108 | 30.434 | 1.00 | 36.72 N |
| ATOM | 3954 | CA | PRO | B | 490 | −37.743 | −5.440 | 31.015 | 1.00 | 56.75 C |
| ATOM | 3955 | C | PRO | B | 490 | −38.930 | −5.428 | 31.986 | 1.00 | 44.49 C |
| ATOM | 3956 | O | PRO | B | 490 | −39.393 | −4.365 | 32.395 | 1.00 | 45.80 O |
| ATOM | 3957 | CB | PRO | B | 490 | −36.416 | −5.723 | 31.731 | 1.00 | 31.48 C |
| ATOM | 3958 | CG | PRO | B | 490 | −36.001 | −4.359 | 32.183 | 1.00 | 55.23 C |
| ATOM | 3959 | CD | PRO | B | 490 | −36.306 | −3.486 | 30.966 | 1.00 | 52.46 C |
| ATOM | 3960 | N | PRO | B | 491 | −39.452 | −6.610 | 32.349 | 1.00 | 62.16 N |
| ATOM | 3961 | CA | PRO | B | 491 | −40.584 | −6.625 | 33.288 | 1.00 | 51.75 C |
| ATOM | 3962 | C | PRO | B | 491 | −40.139 | −5.903 | 34.563 | 1.00 | 63.85 C |
| ATOM | 3963 | O | PRO | B | 491 | −38.935 | −5.866 | 34.868 | 1.00 | 64.67 O |
| ATOM | 3964 | CB | PRO | B | 491 | −40.828 | −8.114 | 33.516 | 1.00 | 41.64 C |
| ATOM | 3965 | CG | PRO | B | 491 | −40.412 | −8.726 | 32.209 | 1.00 | 64.09 C |
| ATOM | 3966 | CD | PRO | B | 491 | −39.139 | −7.970 | 31.864 | 1.00 | 56.84 C |
| ATOM | 3967 | N | GLU | B | 492 | −41.094 | −5.332 | 35.300 | 1.00 | 62.49 N |
| ATOM | 3968 | CA | GLU | B | 492 | −40.776 | −4.578 | 36.519 | 1.00 | 57.79 C |
| ATOM | 3969 | C | GLU | B | 492 | −39.958 | −5.342 | 37.535 | 1.00 | 57.17 C |
| ATOM | 3970 | O | GLU | B | 492 | −39.016 | −4.802 | 38.122 | 1.00 | 59.25 O |
| ATOM | 3971 | CB | GLU | B | 492 | −42.051 | −4.067 | 37.195 | 1.00 | 50.18 C |
| ATOM | 3972 | CG | GLU | B | 492 | −42.816 | −3.055 | 36.359 | 1.00 | 71.42 C |
| ATOM | 3973 | CD | GLU | B | 492 | −43.762 | −2.218 | 37.195 | 1.00 | 78.76 C |
| ATOM | 3974 | OE1 | GLU | B | 492 | −43.288 | −1.630 | 38.189 | 1.00 | 87.55 O |
| ATOM | 3975 | OE2 | GLU | B | 492 | −44.969 | −2.140 | 36.863 | 1.00 | 77.86 O |
| ATOM | 3976 | N | ALA | B | 493 | −40.312 | −6.600 | 37.752 | 1.00 | 60.11 N |
| ATOM | 3977 | CA | ALA | B | 493 | −39.587 | −7.416 | 38.711 | 1.00 | 61.39 C |
| ATOM | 3978 | C | ALA | B | 493 | −38.131 | −7.613 | 38.284 | 1.00 | 53.81 C |
| ATOM | 3979 | O | ALA | B | 493 | −37.262 | −7.858 | 39.120 | 1.00 | 52.35 O |
| ATOM | 3980 | CB | ALA | B | 493 | −40.272 | −8.758 | 38.867 | 1.00 | 51.24 C |
| ATOM | 3981 | N | LYS | B | 494 | −37.855 | −7.479 | 36.992 | 1.00 | 36.13 N |
| ATOM | 3982 | CA | LYS | B | 494 | −36.493 | −7.685 | 36.503 | 1.00 | 56.25 C |

TABLE 1-continued

| ATOM | 3983 | C | LYS | B | 494 | −35.647 | −6.419 | 36.363 | 1.00 | 49.82 | C |
|---|---|---|---|---|---|---|---|---|---|---|---|
| ATOM | 3984 | O | LYS | B | 494 | −34.466 | −6.492 | 36.036 | 1.00 | 42.30 | O |
| ATOM | 3985 | CB | LYS | B | 494 | −36.536 | −8.411 | 35.147 | 1.00 | 60.79 | C |
| ATOM | 3986 | CG | LYS | B | 494 | −36.093 | −9.879 | 35.181 | 1.00 | 66.39 | C |
| ATOM | 3987 | CD | LYS | B | 494 | −36.964 | −10.737 | 36.086 | 1.00 | 66.45 | C |
| ATOM | 3988 | CE | LYS | B | 494 | −36.648 | −12.233 | 35.932 | 1.00 | 69.33 | C |
| ATOM | 3989 | NZ | LYS | B | 494 | −36.924 | −12.753 | 34.543 | 1.00 | 57.74 | N |
| ATOM | 3990 | N | GLN | B | 495 | −36.237 | −5.262 | 36.626 | 1.00 | 48.57 | N |
| ATOM | 3991 | CA | GLN | B | 495 | −35.518 | −4.000 | 36.480 | 1.00 | 25.34 | C |
| ATOM | 3992 | C | GLN | B | 495 | −34.595 | −3.623 | 37.632 | 1.00 | 32.37 | C |
| ATOM | 3993 | O | GLN | B | 495 | −34.978 | −3.683 | 38.784 | 1.00 | 41.45 | O |
| ATOM | 3994 | CB | GLN | B | 495 | −36.529 | −2.872 | 36.249 | 1.00 | 42.78 | C |
| ATOM | 3995 | CG | GLN | B | 495 | −37.435 | −3.088 | 35.022 | 1.00 | 37.48 | C |
| ATOM | 3996 | CD | GLN | B | 495 | −38.412 | −1.944 | 34.803 | 1.00 | 40.85 | C |
| ATOM | 3997 | OE1 | GLN | B | 495 | −38.418 | −0.966 | 35.552 | 1.00 | 42.61 | O |
| ATOM | 3998 | NE2 | GLN | B | 495 | −39.234 | −2.056 | 33.767 | 1.00 | 35.65 | N |
| ATOM | 3999 | N | VAL | B | 496 | −33.378 | −3.222 | 37.311 | 1.00 | 29.06 | N |
| ATOM | 4000 | CA | VAL | B | 496 | −32.413 | −2.811 | 38.317 | 1.00 | 36.92 | C |
| ATOM | 4001 | C | VAL | B | 496 | −33.003 | −1.636 | 39.090 | 1.00 | 36.39 | C |
| ATOM | 4002 | O | VAL | B | 496 | −33.623 | −0.765 | 38.501 | 1.00 | 41.77 | O |
| ATOM | 4003 | CB | VAL | B | 496 | −31.112 | −2.330 | 37.651 | 1.00 | 34.39 | C |
| ATOM | 4004 | CG1 | VAL | B | 496 | −30.192 | −1.698 | 38.692 | 1.00 | 58.75 | C |
| ATOM | 4005 | CG2 | VAL | B | 496 | −30.416 | −3.506 | 36.992 | 1.00 | 49.40 | C |
| ATOM | 4006 | N | PRO | B | 497 | −32.822 | −1.601 | 40.419 | 1.00 | 41.96 | N |
| ATOM | 4007 | CA | PRO | B | 497 | −33.354 | −0.498 | 41.245 | 1.00 | 40.90 | C |
| ATOM | 4008 | C | PRO | B | 497 | −32.980 | 0.888 | 40.678 | 1.00 | 51.92 | C |
| ATOM | 4009 | O | PRO | B | 497 | −33.819 | 1.788 | 40.605 | 1.00 | 38.43 | O |
| ATOM | 4010 | CB | PRO | B | 497 | −32.722 | −0.749 | 42.611 | 1.00 | 32.13 | C |
| ATOM | 4011 | CG | PRO | B | 497 | −32.628 | −2.257 | 42.651 | 1.00 | 50.93 | C |
| ATOM | 4012 | CD | PRO | B | 497 | −32.126 | −2.606 | 41.250 | 1.00 | 45.14 | C |
| ATOM | 4013 | N | VAL | B | 498 | −31.720 | 1.049 | 40.284 | 1.00 | 39.63 | N |
| ATOM | 4014 | CA | VAL | B | 498 | −31.243 | 2.302 | 39.702 | 1.00 | 44.67 | C |
| ATOM | 4015 | C | VAL | B | 498 | −31.315 | 2.218 | 38.172 | 1.00 | 29.27 | C |
| ATOM | 4016 | O | VAL | B | 498 | −30.334 | 1.917 | 37.515 | 1.00 | 40.50 | O |
| ATOM | 4017 | CB | VAL | B | 498 | −29.765 | 2.600 | 40.143 | 1.00 | 33.16 | C |
| ATOM | 4018 | CG1 | VAL | B | 498 | −29.240 | 3.822 | 39.430 | 1.00 | 29.28 | C |
| ATOM | 4019 | CG2 | VAL | B | 498 | −29.716 | 2.840 | 41.649 | 1.00 | 28.14 | C |
| ATOM | 4020 | N | SER | B | 499 | −32.491 | 2.482 | 37.622 | 1.00 | 30.62 | N |
| ATOM | 4021 | CA | SER | B | 499 | −32.710 | 2.443 | 36.175 | 1.00 | 37.54 | C |
| ATOM | 4022 | C | SER | B | 499 | −33.935 | 3.298 | 35.874 | 1.00 | 28.18 | C |
| ATOM | 4023 | O | SER | B | 499 | −34.708 | 3.587 | 36.772 | 1.00 | 39.40 | O |
| ATOM | 4024 | CB | SER | B | 499 | −33.009 | 1.015 | 35.724 | 1.00 | 37.10 | C |
| ATOM | 4025 | OG | SER | B | 499 | −34.231 | 0.561 | 36.311 | 1.00 | 29.94 | O |
| ATOM | 4026 | N | TYR | B | 500 | −34.110 | 3.705 | 34.624 | 1.00 | 40.34 | N |
| ATOM | 4027 | CA | TYR | B | 500 | −35.286 | 4.481 | 34.239 | 1.00 | 34.92 | C |
| ATOM | 4028 | C | TYR | B | 500 | −35.634 | 4.180 | 32.794 | 1.00 | 35.90 | C |
| ATOM | 4029 | O | TYR | B | 500 | −34.765 | 4.234 | 31.930 | 1.00 | 40.74 | O |
| ATOM | 4030 | CB | TYR | B | 500 | −35.049 | 5.982 | 34.400 | 1.00 | 36.93 | C |
| ATOM | 4031 | CG | TYR | B | 500 | −36.309 | 6.804 | 34.177 | 1.00 | 53.33 | C |
| ATOM | 4032 | CD1 | TYR | B | 500 | −37.327 | 6.821 | 35.130 | 1.00 | 30.14 | C |
| ATOM | 4033 | CD2 | TYR | B | 500 | −36.482 | 7.565 | 33.010 | 1.00 | 50.40 | C |
| ATOM | 4034 | CE1 | TYR | B | 500 | −38.480 | 7.574 | 34.935 | 1.00 | 43.55 | C |
| ATOM | 4035 | CE2 | TYR | B | 500 | −37.639 | 8.321 | 32.804 | 1.00 | 51.96 | C |
| ATOM | 4036 | CZ | TYR | B | 500 | −38.636 | 8.319 | 33.774 | 1.00 | 49.57 | C |
| ATOM | 4037 | OH | TYR | B | 500 | −39.793 | 9.043 | 33.594 | 1.00 | 48.94 | O |
| ATOM | 4038 | N | TYR | B | 501 | −36.897 | 3.848 | 32.540 | 1.00 | 29.11 | N |
| ATOM | 4039 | CA | TYR | B | 501 | −37.372 | 3.535 | 31.194 | 1.00 | 34.89 | C |
| ATOM | 4040 | C | TYR | B | 501 | −38.510 | 4.412 | 30.699 | 1.00 | 45.26 | C |
| ATOM | 4041 | O | TYR | B | 501 | −39.397 | 4.805 | 31.444 | 1.00 | 47.40 | O |
| ATOM | 4042 | CB | TYR | B | 501 | −37.833 | 2.083 | 31.089 | 1.00 | 35.51 | C |
| ATOM | 4043 | CG | TYR | B | 501 | −36.742 | 1.079 | 31.389 | 1.00 | 36.85 | C |
| ATOM | 4044 | CD1 | TYR | B | 501 | −36.422 | 0.746 | 32.714 | 1.00 | 45.41 | C |
| ATOM | 4045 | CD2 | TYR | B | 501 | −35.992 | 0.500 | 30.359 | 1.00 | 26.28 | C |
| ATOM | 4046 | CE1 | TYR | B | 501 | −35.376 | −0.139 | 33.007 | 1.00 | 44.65 | C |
| ATOM | 4047 | CE2 | TYR | B | 501 | −34.951 | −0.384 | 30.642 | 1.00 | 28.01 | C |
| ATOM | 4048 | CZ | TYR | B | 501 | −34.641 | −0.694 | 31.967 | 1.00 | 34.55 | C |
| ATOM | 4049 | OH | TYR | B | 501 | −33.559 | −1.504 | 32.257 | 1.00 | 35.85 | O |
| ATOM | 4050 | N | ASP | B | 502 | −38.447 | 4.724 | 29.416 | 1.00 | 53.72 | N |
| ATOM | 4051 | CA | ASP | B | 502 | −39.448 | 5.510 | 28.730 | 1.00 | 32.77 | C |
| ATOM | 4052 | C | ASP | B | 502 | −39.061 | 5.433 | 27.277 | 1.00 | 33.76 | C |
| ATOM | 4053 | O | ASP | B | 502 | −38.217 | 6.184 | 26.803 | 1.00 | 38.35 | O |
| ATOM | 4054 | CB | ASP | B | 502 | −39.456 | 6.963 | 29.195 | 1.00 | 45.38 | C |
| ATOM | 4055 | CG | ASP | B | 502 | −40.450 | 7.824 | 28.392 | 1.00 | 51.69 | C |
| ATOM | 4056 | OD1 | ASP | B | 502 | −41.145 | 7.264 | 27.511 | 1.00 | 46.42 | O |
| ATOM | 4057 | OD2 | ASP | B | 502 | −40.527 | 9.054 | 28.632 | 1.00 | 38.07 | O |
| ATOM | 4058 | N | SER | B | 503 | −39.672 | 4.490 | 26.583 | 1.00 | 38.59 | N |
| ATOM | 4059 | CA | SER | B | 503 | −39.430 | 4.270 | 25.167 | 1.00 | 51.03 | C |
| ATOM | 4060 | C | SER | B | 503 | −39.635 | 5.540 | 24.345 | 1.00 | 51.58 | C |
| ATOM | 4061 | O | SER | B | 503 | −39.136 | 5.648 | 23.228 | 1.00 | 46.61 | O |

TABLE 1-continued

| | | | | | | | | | | |
|---|---|---|---|---|---|---|---|---|---|---|
| ATOM | 4062 | CB | SER | B | 503 | −40.385 | 3.187 | 24.647 | 1.00 | 64.01 | C |
| ATOM | 4063 | OG | SER | B | 503 | −41.747 | 3.591 | 24.787 | 1.00 | 56.68 | O |
| ATOM | 4064 | N | THR | B | 504 | −40.358 | 6.498 | 24.918 | 1.00 | 53.88 | N |
| ATOM | 4065 | CA | THR | B | 504 | −40.692 | 7.752 | 24.246 | 1.00 | 55.91 | C |
| ATOM | 4066 | C | THR | B | 504 | −39.676 | 8.909 | 24.279 | 1.00 | 49.35 | C |
| ATOM | 4067 | O | THR | B | 504 | −39.717 | 9.796 | 23.417 | 1.00 | 39.58 | O |
| ATOM | 4068 | CB | THR | B | 504 | −42.063 | 8.242 | 24.779 | 1.00 | 45.82 | C |
| ATOM | 4069 | OG1 | THR | B | 504 | −43.085 | 7.392 | 24.242 | 1.00 | 52.87 | O |
| ATOM | 4070 | CG2 | THR | B | 504 | −42.349 | 9.677 | 24.381 | 1.00 | 60.14 | C |
| ATOM | 4071 | N | TYR | B | 505 | −38.769 | 8.915 | 25.251 | 1.00 | 37.53 | N |
| ATOM | 4072 | CA | TYR | B | 505 | −37.786 | 10.004 | 25.341 | 1.00 | 39.48 | C |
| ATOM | 4073 | C | TYR | B | 505 | −36.913 | 10.108 | 24.088 | 1.00 | 36.59 | C |
| ATOM | 4074 | O | TYR | B | 505 | −36.540 | 9.096 | 23.506 | 1.00 | 34.24 | O |
| ATOM | 4075 | CB | TYR | B | 505 | −36.909 | 9.802 | 26.567 | 1.00 | 34.80 | C |
| ATOM | 4076 | CG | TYR | B | 505 | −35.671 | 10.643 | 26.570 | 1.00 | 29.99 | C |
| ATOM | 4077 | CD1 | TYR | B | 505 | −35.742 | 12.043 | 26.640 | 1.00 | 28.71 | C |
| ATOM | 4078 | CD2 | TYR | B | 505 | −34.409 | 10.038 | 26.490 | 1.00 | 36.76 | C |
| ATOM | 4079 | CE1 | TYR | B | 505 | −34.589 | 12.820 | 26.632 | 1.00 | 26.30 | C |
| ATOM | 4080 | CE2 | TYR | B | 505 | −33.247 | 10.799 | 26.471 | 1.00 | 24.13 | C |
| ATOM | 4081 | CZ | TYR | B | 505 | −33.339 | 12.185 | 26.541 | 1.00 | 32.85 | C |
| ATOM | 4082 | OH | TYR | B | 505 | −32.178 | 12.915 | 26.490 | 1.00 | 36.20 | O |
| ATOM | 4083 | N | LEU | B | 506 | −36.619 | 11.336 | 23.668 | 1.00 | 34.49 | N |
| ATOM | 4084 | CA | LEU | B | 506 | −35.810 | 11.579 | 22.472 | 1.00 | 43.27 | C |
| ATOM | 4085 | C | LEU | B | 506 | −36.371 | 11.015 | 21.160 | 1.00 | 54.87 | C |
| ATOM | 4086 | O | LEU | B | 506 | −35.592 | 10.567 | 20.311 | 1.00 | 46.91 | O |
| ATOM | 4087 | CB | LEU | B | 506 | −34.398 | 11.016 | 22.635 | 1.00 | 29.50 | C |
| ATOM | 4088 | CG | LEU | B | 506 | −33.224 | 11.969 | 22.880 | 1.00 | 48.56 | C |
| ATOM | 4089 | CD1 | LEU | B | 506 | −31.936 | 11.188 | 22.651 | 1.00 | 53.08 | C |
| ATOM | 4090 | CD2 | LEU | B | 506 | −33.240 | 13.137 | 21.959 | 1.00 | 27.93 | C |
| ATOM | 4091 | N | SER | B | 507 | −37.693 | 11.013 | 20.968 | 1.00 | 52.03 | N |
| ATOM | 4092 | CA | SER | B | 507 | −38.220 | 10.488 | 19.704 | 1.00 | 54.39 | C |
| ATOM | 4093 | C | SER | B | 507 | −38.767 | 11.574 | 18.782 | 1.00 | 39.15 | C |
| ATOM | 4094 | O | SER | B | 507 | −39.087 | 11.292 | 17.635 | 1.00 | 54.96 | O |
| ATOM | 4095 | CB | SER | B | 507 | −39.291 | 9.407 | 19.926 | 1.00 | 41.28 | C |
| ATOM | 4096 | OG | SER | B | 507 | −40.428 | 9.909 | 20.592 | 1.00 | 47.82 | O |
| ATOM | 4097 | N | THR | B | 508 | −38.844 | 12.811 | 19.269 | 1.00 | 36.96 | N |
| ATOM | 4098 | CA | THR | B | 508 | −39.352 | 13.915 | 18.462 | 1.00 | 30.84 | C |
| ATOM | 4099 | C | THR | B | 508 | −38.263 | 14.937 | 18.147 | 1.00 | 50.84 | C |
| ATOM | 4100 | O | THR | B | 508 | −37.310 | 15.111 | 18.918 | 1.00 | 54.33 | O |
| ATOM | 4101 | CB | THR | B | 508 | −40.489 | 14.660 | 19.184 | 1.00 | 49.66 | C |
| ATOM | 4102 | OG1 | THR | B | 508 | −39.954 | 15.395 | 20.290 | 1.00 | 45.63 | O |
| ATOM | 4103 | CG2 | THR | B | 508 | −41.533 | 13.672 | 19.693 | 1.00 | 44.73 | C |
| ATOM | 4104 | N | ASP | B | 509 | −38.421 | 15.634 | 17.028 | 1.00 | 37.69 | N |
| ATOM | 4105 | CA | ASP | B | 509 | −37.448 | 16.625 | 16.597 | 1.00 | 43.39 | C |
| ATOM | 4106 | C | ASP | B | 509 | −37.178 | 17.671 | 17.650 | 1.00 | 45.41 | C |
| ATOM | 4107 | O | ASP | B | 509 | −36.056 | 18.167 | 17.781 | 1.00 | 49.79 | O |
| ATOM | 4108 | CB | ASP | B | 509 | −37.900 | 17.327 | 15.311 | 1.00 | 50.80 | C |
| ATOM | 4109 | CG | ASP | B | 509 | −37.975 | 16.386 | 14.119 | 1.00 | 60.32 | C |
| ATOM | 4110 | OD1 | ASP | B | 509 | −37.323 | 15.318 | 14.152 | 1.00 | 71.27 | O |
| ATOM | 4111 | OD2 | ASP | B | 509 | −38.677 | 16.719 | 13.138 | 1.00 | 73.92 | O |
| ATOM | 4112 | N | ASN | B | 510 | −38.200 | 18.014 | 18.413 | 1.00 | 44.76 | N |
| ATOM | 4113 | CA | ASN | B | 510 | −38.018 | 19.028 | 19.432 | 1.00 | 46.17 | C |
| ATOM | 4114 | C | ASN | B | 510 | −37.123 | 18.542 | 20.561 | 1.00 | 46.18 | C |
| ATOM | 4115 | O | ASN | B | 510 | −36.348 | 19.317 | 21.111 | 1.00 | 36.39 | O |
| ATOM | 4116 | CB | ASN | B | 510 | −39.370 | 19.474 | 19.958 | 1.00 | 37.11 | C |
| ATOM | 4117 | CG | ASN | B | 510 | −40.164 | 20.208 | 18.902 | 1.00 | 68.59 | C |
| ATOM | 4118 | OD1 | ASN | B | 510 | −39.942 | 21.406 | 18.652 | 1.00 | 52.73 | O |
| ATOM | 4119 | ND2 | ASN | B | 510 | −41.072 | 19.486 | 18.242 | 1.00 | 54.83 | N |
| ATOM | 4120 | N | GLU | B | 511 | −37.239 | 17.267 | 20.909 | 1.00 | 32.97 | N |
| ATOM | 4121 | CA | GLU | B | 511 | −36.398 | 16.712 | 21.963 | 1.00 | 45.58 | C |
| ATOM | 4122 | C | GLU | B | 511 | −34.953 | 16.629 | 21.442 | 1.00 | 26.46 | C |
| ATOM | 4123 | O | GLU | B | 511 | −34.034 | 17.032 | 22.141 | 1.00 | 42.06 | O |
| ATOM | 4124 | CB | GLU | B | 511 | −36.853 | 15.306 | 22.340 | 1.00 | 38.20 | C |
| ATOM | 4125 | CG | GLU | B | 511 | −38.184 | 15.186 | 23.029 | 1.00 | 50.17 | C |
| ATOM | 4126 | CD | GLU | B | 511 | −38.530 | 13.724 | 23.280 | 1.00 | 44.57 | C |
| ATOM | 4127 | OE1 | GLU | B | 511 | −38.949 | 13.018 | 22.321 | 1.00 | 45.42 | O |
| ATOM | 4128 | OE2 | GLU | B | 511 | −38.352 | 13.277 | 24.434 | 1.00 | 51.72 | O |
| ATOM | 4129 | N | LYS | B | 512 | −34.786 | 16.116 | 20.216 | 1.00 | 31.43 | N |
| ATOM | 4130 | CA | LYS | B | 512 | −33.470 | 15.964 | 19.571 | 1.00 | 29.37 | C |
| ATOM | 4131 | C | LYS | B | 512 | −32.744 | 17.301 | 19.511 | 1.00 | 42.24 | C |
| ATOM | 4132 | O | LYS | B | 512 | −31.543 | 17.391 | 19.792 | 1.00 | 33.01 | O |
| ATOM | 4133 | CB | LYS | B | 512 | −33.631 | 15.376 | 18.171 | 1.00 | 25.01 | C |
| ATOM | 4134 | CG | LYS | B | 512 | −34.184 | 13.985 | 18.205 | 1.00 | 18.54 | C |
| ATOM | 4135 | CD | LYS | B | 512 | −34.383 | 13.347 | 16.853 | 1.00 | 23.72 | C |
| ATOM | 4136 | CE | LYS | B | 512 | −34.946 | 11.931 | 17.105 | 1.00 | 43.75 | C |
| ATOM | 4137 | NZ | LYS | B | 512 | −35.327 | 11.155 | 15.896 | 1.00 | 58.42 | N |
| ATOM | 4138 | N | ASP | B | 513 | −33.491 | 18.353 | 19.199 | 1.00 | 36.06 | N |
| ATOM | 4139 | CA | ASP | B | 513 | −32.901 | 19.673 | 19.140 | 1.00 | 32.27 | C |
| ATOM | 4140 | C | ASP | B | 513 | −32.455 | 20.134 | 20.512 | 1.00 | 41.51 | C |

TABLE 1-continued

| | | | | | | | | | | |
|---|---|---|---|---|---|---|---|---|---|---|
| ATOM | 4141 | O | ASP | B | 513 | −31.476 | 20.871 | 20.654 | 1.00 | 45.56 | O |
| ATOM | 4142 | CB | ASP | B | 513 | −33.895 | 20.689 | 18.593 | 1.00 | 35.28 | C |
| ATOM | 4143 | CG | ASP | B | 513 | −33.267 | 22.045 | 18.405 | 1.00 | 32.06 | C |
| ATOM | 4144 | OD1 | ASP | B | 513 | −32.348 | 22.161 | 17.568 | 1.00 | 50.23 | O |
| ATOM | 4145 | OD2 | ASP | B | 513 | −33.668 | 22.992 | 19.109 | 1.00 | 57.84 | O |
| ATOM | 4146 | N | ASN | B | 514 | −33.180 | 19.717 | 21.538 | 1.00 | 38.38 | N |
| ATOM | 4147 | CA | ASN | B | 514 | −32.802 | 20.133 | 22.877 | 1.00 | 38.03 | C |
| ATOM | 4148 | C | ASN | B | 514 | −31.615 | 19.264 | 23.355 | 1.00 | 22.75 | C |
| ATOM | 4149 | O | ASN | B | 514 | −30.744 | 19.714 | 24.105 | 1.00 | 25.19 | O |
| ATOM | 4150 | CB | ASN | B | 514 | −34.032 | 20.053 | 23.802 | 1.00 | 27.18 | C |
| ATOM | 4151 | CG | ASN | B | 514 | −33.788 | 20.695 | 25.141 | 1.00 | 46.94 | C |
| ATOM | 4152 | OD1 | ASN | B | 514 | −33.562 | 19.996 | 26.136 | 1.00 | 54.44 | O |
| ATOM | 4153 | ND2 | ASN | B | 514 | −33.815 | 22.036 | 25.181 | 1.00 | 31.67 | N |
| ATOM | 4154 | N | TYR | B | 515 | −31.582 | 18.029 | 22.880 | 1.00 | 26.14 | N |
| ATOM | 4155 | CA | TYR | B | 515 | −30.501 | 17.107 | 23.195 | 1.00 | 24.24 | C |
| ATOM | 4156 | C | TYR | B | 515 | −29.182 | 17.698 | 22.658 | 1.00 | 29.74 | C |
| ATOM | 4157 | O | TYR | B | 515 | −28.193 | 17.880 | 23.399 | 1.00 | 33.04 | O |
| ATOM | 4158 | CB | TYR | B | 515 | −30.785 | 15.767 | 22.517 | 1.00 | 42.68 | C |
| ATOM | 4159 | CG | TYR | B | 515 | −29.730 | 14.724 | 22.791 | 1.00 | 27.33 | C |
| ATOM | 4160 | CD1 | TYR | B | 515 | −29.759 | 13.958 | 23.962 | 1.00 | 31.49 | C |
| ATOM | 4161 | CD2 | TYR | B | 515 | −28.663 | 14.551 | 21.907 | 1.00 | 38.82 | C |
| ATOM | 4162 | CE1 | TYR | B | 515 | −28.741 | 13.031 | 24.251 | 1.00 | 38.48 | C |
| ATOM | 4163 | CE2 | TYR | B | 515 | −27.632 | 13.637 | 22.181 | 1.00 | 49.84 | C |
| ATOM | 4164 | CZ | TYR | B | 515 | −27.681 | 12.877 | 23.348 | 1.00 | 38.41 | C |
| ATOM | 4165 | OH | TYR | B | 515 | −26.704 | 11.947 | 23.551 | 1.00 | 35.55 | O |
| ATOM | 4166 | N | LEU | B | 516 | −29.190 | 18.015 | 21.361 | 1.00 | 28.79 | N |
| ATOM | 4167 | CA | LEU | B | 516 | −28.041 | 18.592 | 20.671 | 1.00 | 26.77 | C |
| ATOM | 4168 | C | LEU | B | 516 | −27.506 | 19.847 | 21.364 | 1.00 | 28.25 | C |
| ATOM | 4169 | O | LEU | B | 516 | −26.303 | 19.961 | 21.628 | 1.00 | 32.34 | O |
| ATOM | 4170 | CB | LEU | B | 516 | −28.438 | 18.893 | 19.223 | 1.00 | 33.89 | C |
| ATOM | 4171 | CG | LEU | B | 516 | −27.412 | 19.316 | 18.173 | 1.00 | 49.00 | C |
| ATOM | 4172 | CD1 | LEU | B | 516 | −26.169 | 18.397 | 18.127 | 1.00 | 20.72 | C |
| ATOM | 4173 | CD2 | LEU | B | 516 | −28.153 | 19.319 | 16.844 | 1.00 | 37.64 | C |
| ATOM | 4174 | N | LYS | B | 517 | −28.393 | 20.787 | 21.689 | 1.00 | 29.82 | N |
| ATOM | 4175 | CA | LYS | B | 517 | −27.952 | 22.013 | 22.361 | 1.00 | 19.68 | C |
| ATOM | 4176 | C | LYS | B | 517 | −27.518 | 21.701 | 23.786 | 1.00 | 23.52 | C |
| ATOM | 4177 | O | LYS | B | 517 | −26.670 | 22.376 | 24.357 | 1.00 | 37.30 | O |
| ATOM | 4178 | CB | LYS | B | 517 | −29.079 | 23.061 | 22.375 | 1.00 | 33.70 | C |
| ATOM | 4179 | CG | LYS | B | 517 | −29.511 | 23.556 | 20.968 | 1.00 | 39.13 | C |
| ATOM | 4180 | CD | LYS | B | 517 | −30.636 | 24.602 | 21.080 | 1.00 | 53.42 | C |
| ATOM | 4181 | CE | LYS | B | 517 | −30.933 | 25.308 | 19.762 | 1.00 | 59.15 | C |
| ATOM | 4182 | NZ | LYS | B | 517 | −31.424 | 24.375 | 18.710 | 1.00 | 44.26 | N |
| ATOM | 4183 | N | GLY | B | 518 | −28.119 | 20.680 | 24.387 | 1.00 | 33.16 | N |
| ATOM | 4184 | CA | GLY | B | 518 | −27.710 | 20.351 | 25.732 | 1.00 | 27.95 | C |
| ATOM | 4185 | C | GLY | B | 518 | −26.270 | 19.830 | 25.720 | 1.00 | 30.28 | C |
| ATOM | 4186 | O | GLY | B | 518 | −25.443 | 20.289 | 26.484 | 1.00 | 23.91 | O |
| ATOM | 4187 | N | VAL | B | 519 | −25.976 | 18.875 | 24.844 | 1.00 | 28.79 | N |
| ATOM | 4188 | CA | VAL | B | 519 | −24.639 | 18.311 | 24.768 | 1.00 | 30.03 | C |
| ATOM | 4189 | C | VAL | B | 519 | −23.578 | 19.344 | 24.413 | 1.00 | 38.56 | C |
| ATOM | 4190 | O | VAL | B | 519 | −22.486 | 19.362 | 24.983 | 1.00 | 40.70 | O |
| ATOM | 4191 | CB | VAL | B | 519 | −24.610 | 17.164 | 23.761 | 1.00 | 33.29 | C |
| ATOM | 4192 | CG1 | VAL | B | 519 | −23.164 | 16.661 | 23.537 | 1.00 | 25.70 | C |
| ATOM | 4193 | CG2 | VAL | B | 519 | −25.496 | 16.057 | 24.269 | 1.00 | 20.20 | C |
| ATOM | 4194 | N | THR | B | 520 | −23.916 | 20.214 | 23.474 | 1.00 | 43.03 | N |
| ATOM | 4195 | CA | THR | B | 520 | −23.018 | 21.258 | 23.031 | 1.00 | 23.00 | C |
| ATOM | 4196 | C | THR | B | 520 | −22.694 | 22.189 | 24.171 | 1.00 | 29.54 | C |
| ATOM | 4197 | O | THR | B | 520 | −21.547 | 22.601 | 24.351 | 1.00 | 32.84 | O |
| ATOM | 4198 | CB | THR | B | 520 | −23.662 | 22.056 | 21.893 | 1.00 | 39.22 | C |
| ATOM | 4199 | OG1 | THR | B | 520 | −23.722 | 21.244 | 20.717 | 1.00 | 32.26 | O |
| ATOM | 4200 | CG2 | THR | B | 520 | −22.868 | 23.305 | 21.618 | 1.00 | 41.63 | C |
| ATOM | 4201 | N | LYS | B | 521 | −23.704 | 22.541 | 24.950 | 1.00 | 29.65 | N |
| ATOM | 4202 | CA | LYS | B | 521 | −23.457 | 23.418 | 26.080 | 1.00 | 24.91 | C |
| ATOM | 4203 | C | LYS | B | 521 | −22.591 | 22.725 | 27.127 | 1.00 | 19.89 | C |
| ATOM | 4204 | O | LYS | B | 521 | −21.790 | 23.354 | 27.797 | 1.00 | 22.31 | O |
| ATOM | 4205 | CB | LYS | B | 521 | −24.775 | 23.822 | 26.714 | 1.00 | 37.23 | C |
| ATOM | 4206 | CG | LYS | B | 521 | −24.678 | 25.000 | 27.646 | 1.00 | 37.05 | C |
| ATOM | 4207 | CD | LYS | B | 521 | −26.093 | 25.354 | 28.095 | 1.00 | 48.19 | C |
| ATOM | 4208 | CE | LYS | B | 521 | −26.157 | 26.736 | 28.659 | 1.00 | 34.65 | C |
| ATOM | 4209 | NZ | LYS | B | 521 | −27.544 | 27.089 | 28.956 | 1.00 | 30.91 | N |
| ATOM | 4210 | N | LEU | B | 522 | −22.731 | 21.418 | 27.290 | 1.00 | 33.74 | N |
| ATOM | 4211 | CA | LEU | B | 522 | −21.872 | 20.775 | 28.302 | 1.00 | 44.65 | C |
| ATOM | 4212 | C | LEU | B | 522 | −20.424 | 20.750 | 27.796 | 1.00 | 21.84 | C |
| ATOM | 4213 | O | LEU | B | 522 | −19.482 | 20.957 | 28.562 | 1.00 | 27.57 | O |
| ATOM | 4214 | CB | LEU | B | 522 | −22.383 | 19.369 | 28.669 | 1.00 | 28.73 | C |
| ATOM | 4215 | CG | LEU | B | 522 | −23.764 | 19.338 | 29.364 | 1.00 | 33.23 | C |
| ATOM | 4216 | CD1 | LEU | B | 522 | −24.244 | 17.900 | 29.538 | 1.00 | 27.04 | C |
| ATOM | 4217 | CD2 | LEU | B | 522 | −23.704 | 20.026 | 30.692 | 1.00 | 29.41 | C |
| ATOM | 4218 | N | PHE | B | 523 | −20.245 | 20.563 | 26.494 | 1.00 | 26.51 | N |
| ATOM | 4219 | CA | PHE | B | 523 | −18.889 | 20.556 | 25.946 | 1.00 | 31.20 | C |

TABLE 1-continued

| ATOM | 4220 | C | PHE | B | 523 | −18.244 | 21.917 | 26.199 | 1.00 | 32.03 | C |
|---|---|---|---|---|---|---|---|---|---|---|---|
| ATOM | 4221 | O | PHE | B | 523 | −17.075 | 22.014 | 26.568 | 1.00 | 36.63 | O |
| ATOM | 4222 | CB | PHE | B | 523 | −18.920 | 20.253 | 24.443 | 1.00 | 33.73 | C |
| ATOM | 4223 | CG | PHE | B | 523 | −18.679 | 18.820 | 24.117 | 1.00 | 36.61 | C |
| ATOM | 4224 | CD1 | PHE | B | 523 | −17.381 | 18.312 | 24.101 | 1.00 | 25.15 | C |
| ATOM | 4225 | CD2 | PHE | B | 523 | −19.746 | 17.968 | 23.839 | 1.00 | 33.34 | C |
| ATOM | 4226 | CE1 | PHE | B | 523 | −17.146 | 16.993 | 23.809 | 1.00 | 22.84 | C |
| ATOM | 4227 | CE2 | PHE | B | 523 | −19.527 | 16.636 | 23.546 | 1.00 | 26.35 | C |
| ATOM | 4228 | CZ | PHE | B | 523 | −18.209 | 16.142 | 23.532 | 1.00 | 28.33 | C |
| ATOM | 4229 | N | GLU | B | 524 | −19.013 | 22.975 | 26.001 | 1.00 | 39.97 | N |
| ATOM | 4230 | CA | GLU | B | 524 | −18.483 | 24.315 | 26.225 | 1.00 | 34.10 | C |
| ATOM | 4231 | C | GLU | B | 524 | −18.143 | 24.531 | 27.696 | 1.00 | 27.35 | C |
| ATOM | 4232 | O | GLU | B | 524 | −17.147 | 25.197 | 28.018 | 1.00 | 30.56 | O |
| ATOM | 4233 | CB | GLU | B | 524 | −19.495 | 25.368 | 25.776 | 1.00 | 45.47 | C |
| ATOM | 4234 | CG | GLU | B | 524 | −19.841 | 25.299 | 24.304 | 1.00 | 43.59 | C |
| ATOM | 4235 | CD | GLU | B | 524 | −18.625 | 25.467 | 23.378 | 1.00 | 69.91 | C |
| ATOM | 4236 | OE1 | GLU | B | 524 | −17.537 | 25.913 | 23.839 | 1.00 | 57.99 | O |
| ATOM | 4237 | OE2 | GLU | B | 524 | −18.781 | 25.163 | 22.172 | 1.00 | 50.64 | O |
| ATOM | 4238 | N | ARG | B | 525 | −18.957 | 23.967 | 28.587 | 1.00 | 29.42 | N |
| ATOM | 4239 | CA | ARG | B | 525 | −18.696 | 24.125 | 30.021 | 1.00 | 30.57 | C |
| ATOM | 4240 | C | ARG | B | 525 | −17.389 | 23.392 | 30.366 | 1.00 | 32.12 | C |
| ATOM | 4241 | O | ARG | B | 525 | −16.550 | 23.901 | 31.117 | 1.00 | 31.72 | O |
| ATOM | 4242 | CB | ARG | B | 525 | −19.867 | 23.574 | 30.842 | 1.00 | 31.97 | C |
| ATOM | 4243 | CG | ARG | B | 525 | −19.710 | 23.737 | 32.355 | 1.00 | 25.55 | C |
| ATOM | 4244 | CD | ARG | B | 525 | −21.111 | 23.664 | 32.987 | 1.00 | 56.63 | C |
| ATOM | 4245 | NE | ARG | B | 525 | −21.100 | 23.405 | 34.420 | 1.00 | 31.66 | N |
| ATOM | 4246 | CZ | ARG | B | 525 | −20.505 | 24.190 | 35.312 | 1.00 | 32.93 | C |
| ATOM | 4247 | NH1 | ARG | B | 525 | −19.880 | 25.290 | 34.918 | 1.00 | 35.74 | N |
| ATOM | 4248 | NH2 | ARG | B | 525 | −20.506 | 23.856 | 36.590 | 1.00 | 31.52 | N |
| ATOM | 4249 | N | ILE | B | 526 | −17.222 | 22.195 | 29.813 | 1.00 | 27.27 | N |
| ATOM | 4250 | CA | ILE | B | 526 | −16.000 | 21.438 | 30.029 | 1.00 | 23.64 | C |
| ATOM | 4251 | C | ILE | B | 526 | −14.826 | 22.207 | 29.424 | 1.00 | 27.54 | C |
| ATOM | 4252 | O | ILE | B | 526 | −13.817 | 22.464 | 30.099 | 1.00 | 31.25 | O |
| ATOM | 4253 | CB | ILE | B | 526 | −16.110 | 20.031 | 29.380 | 1.00 | 29.40 | C |
| ATOM | 4254 | CG1 | ILE | B | 526 | −17.085 | 19.190 | 30.207 | 1.00 | 27.45 | C |
| ATOM | 4255 | CG2 | ILE | B | 526 | −14.715 | 19.354 | 29.318 | 1.00 | 30.45 | C |
| ATOM | 4256 | CD1 | ILE | B | 526 | −17.762 | 18.108 | 29.482 | 1.00 | 23.77 | C |
| ATOM | 4257 | N | TYR | B | 527 | −14.967 | 22.581 | 28.153 | 1.00 | 28.08 | N |
| ATOM | 4258 | CA | TYR | B | 527 | −13.921 | 23.311 | 27.429 | 1.00 | 32.05 | C |
| ATOM | 4259 | C | TYR | B | 527 | −13.520 | 24.619 | 28.100 | 1.00 | 39.34 | C |
| ATOM | 4260 | O | TYR | B | 527 | −12.402 | 25.089 | 27.922 | 1.00 | 32.91 | O |
| ATOM | 4261 | CB | TYR | B | 527 | −14.386 | 23.632 | 26.012 | 1.00 | 30.90 | C |
| ATOM | 4262 | CG | TYR | B | 527 | −13.301 | 24.241 | 25.145 | 1.00 | 46.95 | C |
| ATOM | 4263 | CD1 | TYR | B | 527 | −12.241 | 23.466 | 24.679 | 1.00 | 43.71 | C |
| ATOM | 4264 | CD2 | TYR | B | 527 | −13.342 | 25.583 | 24.773 | 1.00 | 48.95 | C |
| ATOM | 4265 | CE1 | TYR | B | 527 | −11.259 | 24.002 | 23.870 | 1.00 | 42.21 | C |
| ATOM | 4266 | CE2 | TYR | B | 527 | −12.352 | 26.135 | 23.957 | 1.00 | 51.63 | C |
| ATOM | 4267 | CZ | TYR | B | 527 | −11.317 | 25.337 | 23.513 | 1.00 | 51.25 | C |
| ATOM | 4268 | OH | TYR | B | 527 | −10.312 | 25.876 | 22.737 | 1.00 | 71.98 | O |
| ATOM | 4269 | N | SER | B | 528 | −14.437 | 25.191 | 28.875 | 1.00 | 34.22 | N |
| ATOM | 4270 | CA | SER | B | 528 | −14.189 | 26.461 | 29.548 | 1.00 | 45.43 | C |
| ATOM | 4271 | C | SER | B | 528 | −13.252 | 26.393 | 30.742 | 1.00 | 44.05 | C |
| ATOM | 4272 | O | SER | B | 528 | −12.917 | 27.423 | 31.312 | 1.00 | 41.88 | O |
| ATOM | 4273 | CB | SER | B | 528 | −15.517 | 27.110 | 29.998 | 1.00 | 40.94 | C |
| ATOM | 4274 | OG | SER | B | 528 | −15.976 | 26.575 | 31.229 | 1.00 | 48.54 | O |
| ATOM | 4275 | N | THR | B | 529 | −12.852 | 25.197 | 31.153 | 1.00 | 32.91 | N |
| ATOM | 4276 | CA | THR | B | 529 | −11.924 | 25.079 | 32.279 | 1.00 | 27.52 | C |
| ATOM | 4277 | C | THR | B | 529 | −10.584 | 24.716 | 31.643 | 1.00 | 26.37 | C |
| ATOM | 4278 | O | THR | B | 529 | −10.557 | 24.186 | 30.530 | 1.00 | 33.34 | O |
| ATOM | 4279 | CB | THR | B | 529 | −12.359 | 23.944 | 33.266 | 1.00 | 35.16 | C |
| ATOM | 4280 | OG1 | THR | B | 529 | −12.439 | 22.690 | 32.558 | 1.00 | 35.19 | O |
| ATOM | 4281 | CG2 | THR | B | 529 | −13.726 | 24.250 | 33.868 | 1.00 | 23.81 | C |
| ATOM | 4282 | N | ASP | B | 530 | −9.479 | 24.999 | 32.325 | 1.00 | 31.40 | N |
| ATOM | 4283 | CA | ASP | B | 530 | −8.150 | 24.649 | 31.806 | 1.00 | 26.13 | C |
| ATOM | 4284 | C | ASP | B | 530 | −8.026 | 23.120 | 31.660 | 1.00 | 43.44 | C |
| ATOM | 4285 | O | ASP | B | 530 | −7.447 | 22.613 | 30.701 | 1.00 | 39.58 | O |
| ATOM | 4286 | CB | ASP | B | 530 | −7.060 | 25.144 | 32.754 | 1.00 | 32.80 | C |
| ATOM | 4287 | CG | ASP | B | 530 | −6.929 | 26.659 | 32.755 | 1.00 | 61.36 | C |
| ATOM | 4288 | OD1 | ASP | B | 530 | −6.631 | 27.233 | 31.692 | 1.00 | 55.17 | O |
| ATOM | 4289 | OD2 | ASP | B | 530 | −7.123 | 27.287 | 33.819 | 1.00 | 84.55 | O |
| ATOM | 4290 | N | LEU | B | 531 | −8.586 | 22.390 | 32.620 | 1.00 | 32.55 | N |
| ATOM | 4291 | CA | LEU | B | 531 | −8.525 | 20.934 | 32.604 | 1.00 | 34.91 | C |
| ATOM | 4292 | C | LEU | B | 531 | −9.303 | 20.324 | 31.408 | 1.00 | 30.98 | C |
| ATOM | 4293 | O | LEU | B | 531 | −8.804 | 19.448 | 30.697 | 1.00 | 31.88 | O |
| ATOM | 4294 | CB | LEU | B | 531 | −9.087 | 20.410 | 33.938 | 1.00 | 27.85 | C |
| ATOM | 4295 | CG | LEU | B | 531 | −8.992 | 18.902 | 34.120 | 1.00 | 37.50 | C |
| ATOM | 4296 | CD1 | LEU | B | 531 | −7.522 | 18.559 | 34.358 | 1.00 | 18.82 | C |
| ATOM | 4297 | CD2 | LEU | B | 531 | −9.898 | 18.436 | 35.286 | 1.00 | 25.06 | C |
| ATOM | 4298 | N | GLY | B | 532 | −10.518 | 20.815 | 31.195 | 1.00 | 28.01 | N |

TABLE 1-continued

| | | | | | | | | | | |
|---|---|---|---|---|---|---|---|---|---|---|
| ATOM | 4299 | CA | GLY | B | 532 | −11.359 | 20.324 | 30.119 | 1.00 | 25.29 | C |
| ATOM | 4300 | C | GLY | B | 532 | −10.856 | 20.636 | 28.725 | 1.00 | 23.14 | C |
| ATOM | 4301 | O | GLY | B | 532 | −11.068 | 19.867 | 27.800 | 1.00 | 32.98 | O |
| ATOM | 4302 | N | ARG | B | 533 | −10.178 | 21.765 | 28.575 | 1.00 | 40.70 | N |
| ATOM | 4303 | CA | ARG | B | 533 | −9.619 | 22.175 | 27.284 | 1.00 | 37.35 | C |
| ATOM | 4304 | C | ARG | B | 533 | −8.499 | 21.202 | 26.927 | 1.00 | 28.92 | C |
| ATOM | 4305 | O | ARG | B | 533 | −8.365 | 20.791 | 25.780 | 1.00 | 35.58 | O |
| ATOM | 4306 | CB | ARG | B | 533 | −9.071 | 23.612 | 27.383 | 1.00 | 39.35 | C |
| ATOM | 4307 | CG | ARG | B | 533 | −8.401 | 24.148 | 26.116 | 1.00 | 43.50 | C |
| ATOM | 4308 | CD | ARG | B | 533 | −7.759 | 25.527 | 26.355 | 1.00 | 49.78 | C |
| ATOM | 4309 | NE | ARG | B | 533 | −7.074 | 26.037 | 25.163 | 1.00 | 78.97 | N |
| ATOM | 4310 | CZ | ARG | B | 533 | −7.606 | 26.877 | 24.271 | 1.00 | 74.79 | C |
| ATOM | 4311 | NH1 | ARG | B | 533 | −8.845 | 27.328 | 24.423 | 1.00 | 75.51 | N |
| ATOM | 4312 | NH2 | ARG | B | 533 | −6.893 | 27.264 | 23.217 | 1.00 | 74.23 | N |
| ATOM | 4313 | N | MET | B | 534 | −7.707 | 20.832 | 27.928 | 1.00 | 34.57 | N |
| ATOM | 4314 | CA | MET | B | 534 | −6.603 | 19.894 | 27.745 | 1.00 | 30.15 | C |
| ATOM | 4315 | C | MET | B | 534 | −7.122 | 18.500 | 27.389 | 1.00 | 47.19 | C |
| ATOM | 4316 | O | MET | B | 534 | −6.615 | 17.858 | 26.448 | 1.00 | 32.08 | O |
| ATOM | 4317 | CB | MET | B | 534 | −5.751 | 19.819 | 29.017 | 1.00 | 37.82 | C |
| ATOM | 4318 | CG | MET | B | 534 | −4.828 | 21.003 | 29.206 | 1.00 | 41.80 | C |
| ATOM | 4319 | SD | MET | B | 534 | −3.678 | 21.094 | 27.793 | 1.00 | 79.22 | S |
| ATOM | 4320 | CE | MET | B | 534 | −4.561 | 22.271 | 26.680 | 1.00 | 71.21 | C |
| ATOM | 4321 | N | LEU | B | 535 | −8.135 | 18.036 | 28.126 | 1.00 | 29.85 | N |
| ATOM | 4322 | CA | LEU | B | 535 | −8.713 | 16.718 | 27.856 | 1.00 | 25.73 | C |
| ATOM | 4323 | C | LEU | B | 535 | −9.285 | 16.663 | 26.439 | 1.00 | 31.80 | C |
| ATOM | 4324 | O | LEU | B | 535 | −8.993 | 15.728 | 25.679 | 1.00 | 44.31 | O |
| ATOM | 4325 | CB | LEU | B | 535 | −9.830 | 16.384 | 28.849 | 1.00 | 26.80 | C |
| ATOM | 4326 | CG | LEU | B | 535 | −10.686 | 15.148 | 28.547 | 1.00 | 23.83 | C |
| ATOM | 4327 | CD1 | LEU | B | 535 | −9.776 | 13.926 | 28.474 | 1.00 | 32.87 | C |
| ATOM | 4328 | CD2 | LEU | B | 535 | −11.728 | 14.941 | 29.643 | 1.00 | 30.69 | C |
| ATOM | 4329 | N | LEU | B | 536 | −10.088 | 17.657 | 26.069 | 1.00 | 23.49 | N |
| ATOM | 4330 | CA | LEU | B | 536 | −10.662 | 17.639 | 24.736 | 1.00 | 27.91 | C |
| ATOM | 4331 | C | LEU | B | 536 | −9.567 | 17.704 | 23.655 | 1.00 | 24.89 | C |
| ATOM | 4332 | O | LEU | B | 536 | −9.700 | 17.092 | 22.615 | 1.00 | 27.35 | O |
| ATOM | 4333 | CB | LEU | B | 536 | −11.708 | 18.758 | 24.590 | 1.00 | 25.55 | C |
| ATOM | 4334 | CG | LEU | B | 536 | −12.948 | 18.547 | 25.484 | 1.00 | 22.57 | C |
| ATOM | 4335 | CD1 | LEU | B | 536 | −13.785 | 19.819 | 25.438 | 1.00 | 27.66 | C |
| ATOM | 4336 | CD2 | LEU | B | 536 | −13.789 | 17.343 | 25.043 | 1.00 | 23.02 | C |
| ATOM | 4337 | N | THR | B | 537 | −8.466 | 18.403 | 23.929 | 1.00 | 30.77 | N |
| ATOM | 4338 | CA | THR | B | 537 | −7.363 | 18.457 | 22.968 | 1.00 | 29.65 | C |
| ATOM | 4339 | C | THR | B | 537 | −6.743 | 17.062 | 22.846 | 1.00 | 22.92 | C |
| ATOM | 4340 | O | THR | B | 537 | −6.462 | 16.600 | 21.750 | 1.00 | 40.55 | O |
| ATOM | 4341 | CB | THR | B | 537 | −6.240 | 19.425 | 23.412 | 1.00 | 48.16 | C |
| ATOM | 4342 | OG1 | THR | B | 537 | −6.780 | 20.736 | 23.622 | 1.00 | 36.47 | O |
| ATOM | 4343 | CG2 | THR | B | 537 | −5.147 | 19.505 | 22.339 | 1.00 | 30.75 | C |
| ATOM | 4344 | N | SER | B | 538 | −6.553 | 16.375 | 23.968 | 1.00 | 28.81 | N |
| ATOM | 4345 | CA | SER | B | 538 | −5.973 | 15.037 | 23.933 | 1.00 | 23.88 | C |
| ATOM | 4346 | C | SER | B | 538 | −6.911 | 14.084 | 23.193 | 1.00 | 25.15 | C |
| ATOM | 4347 | O | SER | B | 538 | −6.466 | 13.224 | 22.434 | 1.00 | 34.02 | O |
| ATOM | 4348 | CB | SER | B | 538 | −5.709 | 14.519 | 25.353 | 1.00 | 31.13 | C |
| ATOM | 4349 | OG | SER | B | 538 | −4.926 | 15.439 | 26.109 | 1.00 | 32.73 | O |
| ATOM | 4350 | N | ILE | B | 539 | −8.215 | 14.259 | 23.382 | 1.00 | 27.44 | N |
| ATOM | 4351 | CA | ILE | B | 539 | −9.183 | 13.407 | 22.705 | 1.00 | 31.43 | C |
| ATOM | 4352 | C | ILE | B | 539 | −9.169 | 13.642 | 21.200 | 1.00 | 20.87 | C |
| ATOM | 4353 | O | ILE | B | 539 | −9.225 | 12.697 | 20.426 | 1.00 | 20.83 | O |
| ATOM | 4354 | CB | ILE | B | 539 | −10.630 | 13.620 | 23.295 | 1.00 | 29.06 | C |
| ATOM | 4355 | CG1 | ILE | B | 539 | −10.752 | 12.863 | 24.623 | 1.00 | 23.12 | C |
| ATOM | 4356 | CG2 | ILE | B | 539 | −11.706 | 13.109 | 22.340 | 1.00 | 17.45 | C |
| ATOM | 4357 | CD1 | ILE | B | 539 | −12.046 | 13.178 | 25.364 | 1.00 | 37.27 | C |
| ATOM | 4358 | N | VAL | B | 540 | −9.079 | 14.901 | 20.778 | 1.00 | 21.26 | N |
| ATOM | 4359 | CA | VAL | B | 540 | −9.074 | 15.186 | 19.331 | 1.00 | 29.24 | C |
| ATOM | 4360 | C | VAL | B | 540 | −7.798 | 14.687 | 18.622 | 1.00 | 27.45 | C |
| ATOM | 4361 | O | VAL | B | 540 | −7.851 | 14.275 | 17.467 | 1.00 | 31.88 | O |
| ATOM | 4362 | CB | VAL | B | 540 | −9.263 | 16.693 | 19.068 | 1.00 | 35.15 | C |
| ATOM | 4363 | CG1 | VAL | B | 540 | −9.023 | 17.010 | 17.592 | 1.00 | 29.27 | C |
| ATOM | 4364 | CG2 | VAL | B | 540 | −10.684 | 17.103 | 19.475 | 1.00 | 18.48 | C |
| ATOM | 4365 | N | ARG | B | 541 | −6.662 | 14.718 | 19.314 | 1.00 | 24.45 | N |
| ATOM | 4366 | CA | ARG | B | 541 | −5.402 | 14.232 | 18.738 | 1.00 | 31.18 | C |
| ATOM | 4367 | C | ARG | B | 541 | −5.338 | 12.710 | 18.818 | 1.00 | 30.53 | C |
| ATOM | 4368 | O | ARG | B | 541 | −4.520 | 12.094 | 18.154 | 1.00 | 32.38 | O |
| ATOM | 4369 | CB | ARG | B | 541 | −4.204 | 14.825 | 19.490 | 1.00 | 39.22 | C |
| ATOM | 4370 | CG | ARG | B | 541 | −4.115 | 16.348 | 19.395 | 1.00 | 37.47 | C |
| ATOM | 4371 | CD | ARG | B | 541 | −3.286 | 16.964 | 20.529 | 1.00 | 42.19 | C |
| ATOM | 4372 | NE | ARG | B | 541 | −1.884 | 17.186 | 20.174 | 1.00 | 57.96 | N |
| ATOM | 4373 | CZ | ARG | B | 541 | −0.945 | 16.246 | 20.218 | 1.00 | 69.09 | C |
| ATOM | 4374 | NH1 | ARG | B | 541 | −1.267 | 15.017 | 20.609 | 1.00 | 67.74 | N |
| ATOM | 4375 | NH2 | ARG | B | 541 | 0.309 | 16.526 | 19.867 | 1.00 | 44.26 | N |
| ATOM | 4376 | N | GLY | B | 542 | −6.233 | 12.115 | 19.614 | 1.00 | 34.18 | N |
| ATOM | 4377 | CA | GLY | B | 542 | −6.257 | 10.661 | 19.796 | 1.00 | 18.67 | C |

TABLE 1-continued

| | | | | | | | | | | |
|---|---|---|---|---|---|---|---|---|---|---|
| ATOM | 4378 | C | GLY | B | 542 | −6.806 | 9.792 | 18.670 | 1.00 | 25.59 C |
| ATOM | 4379 | O | GLY | B | 542 | −7.576 | 8.862 | 18.919 | 1.00 | 33.12 O |
| ATOM | 4380 | N | ILE | B | 543 | −6.400 | 10.057 | 17.434 | 1.00 | 24.88 N |
| ATOM | 4381 | CA | ILE | B | 543 | −6.845 | 9.251 | 16.296 | 1.00 | 26.52 C |
| ATOM | 4382 | C | ILE | B | 543 | −6.543 | 7.748 | 16.480 | 1.00 | 30.51 C |
| ATOM | 4383 | O | ILE | B | 543 | −5.422 | 7.369 | 16.759 | 1.00 | 26.36 O |
| ATOM | 4384 | CB | ILE | B | 543 | −6.137 | 9.671 | 14.985 | 1.00 | 44.30 C |
| ATOM | 4385 | CG1 | ILE | B | 543 | −6.305 | 11.176 | 14.746 | 1.00 | 36.18 C |
| ATOM | 4386 | CG2 | ILE | B | 543 | −6.675 | 8.845 | 13.813 | 1.00 | 25.05 C |
| ATOM | 4387 | CD1 | ILE | B | 543 | −7.730 | 11.619 | 14.772 | 1.00 | 61.00 C |
| ATOM | 4388 | N | PRO | B | 544 | −7.557 | 6.884 | 16.324 | 1.00 | 25.06 N |
| ATOM | 4389 | CA | PRO | B | 544 | −7.333 | 5.443 | 16.470 | 1.00 | 34.70 C |
| ATOM | 4390 | C | PRO | B | 544 | −6.259 | 4.993 | 15.478 | 1.00 | 38.56 C |
| ATOM | 4391 | O | PRO | B | 544 | −6.296 | 5.365 | 14.301 | 1.00 | 32.80 O |
| ATOM | 4392 | CB | PRO | B | 544 | −8.703 | 4.840 | 16.125 | 1.00 | 17.49 C |
| ATOM | 4393 | CG | PRO | B | 544 | −9.657 | 5.877 | 16.648 | 1.00 | 29.69 C |
| ATOM | 4394 | CD | PRO | B | 544 | −8.988 | 7.168 | 16.112 | 1.00 | 20.20 C |
| ATOM | 4395 | N | PHE | B | 545 | −5.330 | 4.169 | 15.943 | 1.00 | 32.64 N |
| ATOM | 4396 | CA | PHE | B | 545 | −4.254 | 3.713 | 15.083 | 1.00 | 34.94 C |
| ATOM | 4397 | C | PHE | B | 545 | −4.691 | 2.983 | 13.800 | 1.00 | 47.42 C |
| ATOM | 4398 | O | PHE | B | 545 | −5.761 | 2.386 | 13.733 | 1.00 | 29.60 O |
| ATOM | 4399 | CB | PHE | B | 545 | −3.293 | 2.853 | 15.875 | 1.00 | 21.70 C |
| ATOM | 4400 | CG | PHE | B | 545 | −2.038 | 2.518 | 15.114 | 1.00 | 34.16 C |
| ATOM | 4401 | CD1 | PHE | B | 545 | −1.185 | 3.526 | 14.704 | 1.00 | 21.98 C |
| ATOM | 4402 | CD2 | PHE | B | 545 | −1.750 | 1.208 | 14.754 | 1.00 | 19.78 C |
| ATOM | 4403 | CE1 | PHE | B | 545 | −0.051 | 3.230 | 13.934 | 1.00 | 40.41 C |
| ATOM | 4404 | CE2 | PHE | B | 545 | −0.627 | 0.901 | 13.990 | 1.00 | 35.63 C |
| ATOM | 4405 | CZ | PHE | B | 545 | 0.223 | 1.911 | 13.578 | 1.00 | 25.39 C |
| ATOM | 4406 | N | TRP | B | 546 | −3.856 | 3.061 | 12.763 | 1.00 | 45.71 N |
| ATOM | 4407 | CA | TRP | B | 546 | −4.172 | 2.415 | 11.488 | 1.00 | 26.74 C |
| ATOM | 4408 | C | TRP | B | 546 | −3.567 | 1.030 | 11.444 | 1.00 | 32.92 C |
| ATOM | 4409 | O | TRP | B | 546 | −2.639 | 0.753 | 10.685 | 1.00 | 37.77 O |
| ATOM | 4410 | CB | TRP | B | 546 | −3.645 | 3.246 | 10.333 | 1.00 | 27.01 C |
| ATOM | 4411 | CG | TRP | B | 546 | −4.561 | 4.349 | 9.914 | 1.00 | 37.81 C |
| ATOM | 4412 | CD1 | TRP | B | 546 | −5.411 | 5.074 | 10.713 | 1.00 | 33.44 C |
| ATOM | 4413 | CD2 | TRP | B | 546 | −4.748 | 4.834 | 8.584 | 1.00 | 26.03 C |
| ATOM | 4414 | NE1 | TRP | B | 546 | −6.122 | 5.968 | 9.951 | 1.00 | 34.72 N |
| ATOM | 4415 | CE2 | TRP | B | 546 | −5.738 | 5.839 | 8.640 | 1.00 | 33.05 C |
| ATOM | 4416 | CE3 | TRP | B | 546 | −4.181 | 4.507 | 7.342 | 1.00 | 33.87 C |
| ATOM | 4417 | CZ2 | TRP | B | 546 | −6.173 | 6.524 | 7.501 | 1.00 | 26.84 C |
| ATOM | 4418 | CZ3 | TRP | B | 546 | −4.613 | 5.187 | 6.213 | 1.00 | 31.00 C |
| ATOM | 4419 | CH2 | TRP | B | 546 | −5.605 | 6.178 | 6.302 | 1.00 | 46.10 C |
| ATOM | 4420 | N | GLY | B | 547 | −4.107 | 0.149 | 12.250 | 1.00 | 21.11 N |
| ATOM | 4421 | CA | GLY | B | 547 | −3.560 | −1.190 | 12.288 | 1.00 | 44.92 C |
| ATOM | 4422 | C | GLY | B | 547 | −4.515 | −2.240 | 11.789 | 1.00 | 32.26 C |
| ATOM | 4423 | O | GLY | B | 547 | −4.635 | −3.299 | 12.384 | 1.00 | 49.94 O |
| ATOM | 4424 | N | GLY | B | 548 | −5.189 | −1.964 | 10.683 | 1.00 | 35.82 N |
| ATOM | 4425 | CA | GLY | B | 548 | −6.119 | −2.940 | 10.178 | 1.00 | 32.97 C |
| ATOM | 4426 | C | GLY | B | 548 | −5.655 | −3.798 | 9.024 | 1.00 | 42.62 C |
| ATOM | 4427 | O | GLY | B | 548 | −6.486 | −4.445 | 8.406 | 1.00 | 45.89 O |
| ATOM | 4428 | N | SER | B | 549 | −4.362 | −3.829 | 8.714 | 1.00 | 35.58 N |
| ATOM | 4429 | CA | SER | B | 549 | −3.921 | −4.660 | 7.592 | 1.00 | 47.80 C |
| ATOM | 4430 | C | SER | B | 549 | −3.325 | −5.986 | 8.046 | 1.00 | 41.81 C |
| ATOM | 4431 | O | SER | B | 549 | −2.789 | −6.091 | 9.147 | 1.00 | 40.77 O |
| ATOM | 4432 | CB | SER | B | 549 | −2.885 | −3.921 | 6.735 | 1.00 | 56.60 C |
| ATOM | 4433 | OG | SER | B | 549 | −2.351 | −4.773 | 5.724 | 1.00 | 58.45 O |
| ATOM | 4434 | N | THR | B | 550 | −3.411 | −6.995 | 7.194 | 1.00 | 35.93 N |
| ATOM | 4435 | CA | THR | B | 550 | −2.830 | −8.299 | 7.529 | 1.00 | 61.46 C |
| ATOM | 4436 | C | THR | B | 550 | −1.321 | −8.285 | 7.203 | 1.00 | 67.86 C |
| ATOM | 4437 | O | THR | B | 550 | −0.534 | −9.031 | 7.797 | 1.00 | 66.22 O |
| ATOM | 4438 | CB | THR | B | 550 | −3.510 | −9.415 | 6.744 | 1.00 | 50.75 C |
| ATOM | 4439 | OG1 | THR | B | 550 | −3.427 | −9.115 | 5.346 | 1.00 | 69.00 O |
| ATOM | 4440 | CG2 | THR | B | 550 | −4.981 | −9.524 | 7.144 | 1.00 | 54.12 C |
| ATOM | 4441 | N | ILE | B | 551 | −0.929 | −7.422 | 6.268 | 1.00 | 59.33 N |
| ATOM | 4442 | CA | ILE | B | 551 | 0.466 | −7.286 | 5.863 | 1.00 | 35.83 C |
| ATOM | 4443 | C | ILE | B | 551 | 1.133 | −6.397 | 6.898 | 1.00 | 49.96 C |
| ATOM | 4444 | O | ILE | B | 551 | 0.764 | −5.231 | 7.045 | 1.00 | 46.44 O |
| ATOM | 4445 | CB | ILE | B | 551 | 0.555 | −6.602 | 4.498 | 1.00 | 50.50 C |
| ATOM | 4446 | CG1 | ILE | B | 551 | −0.252 | −7.406 | 3.473 | 1.00 | 58.94 C |
| ATOM | 4447 | CG2 | ILE | B | 551 | 2.019 | −6.429 | 4.092 | 1.00 | 60.59 C |
| ATOM | 4448 | CD1 | ILE | B | 551 | −0.678 | −6.611 | 2.232 | 1.00 | 48.99 C |
| ATOM | 4449 | N | ASP | B | 552 | 2.136 | −6.924 | 7.590 | 1.00 | 49.84 N |
| ATOM | 4450 | CA | ASP | B | 552 | 2.792 | −6.155 | 8.641 | 1.00 | 58.81 C |
| ATOM | 4451 | C | ASP | B | 552 | 3.505 | −4.856 | 8.253 | 1.00 | 54.96 C |
| ATOM | 4452 | O | ASP | B | 552 | 3.883 | −4.089 | 9.140 | 1.00 | 65.08 O |
| ATOM | 4453 | CB | ASP | B | 552 | 3.745 | −7.055 | 9.451 | 1.00 | 60.20 C |
| ATOM | 4454 | CG | ASP | B | 552 | 5.086 | −7.271 | 8.766 | 1.00 | 75.69 C |
| ATOM | 4455 | OD1 | ASP | B | 552 | 5.092 | −7.660 | 7.581 | 1.00 | 88.34 O |
| ATOM | 4456 | OD2 | ASP | B | 552 | 6.136 | −7.060 | 9.414 | 1.00 | 74.45 O |

TABLE 1-continued

| | | | | | | | | | | |
|---|---|---|---|---|---|---|---|---|---|---|
| ATOM | 4457 | N | THR | B | 553 | 3.681 | −4.578 | 6.963 | 1.00 | 37.50 N |
| ATOM | 4458 | CA | THR | B | 553 | 4.355 | −3.324 | 6.583 | 1.00 | 42.62 C |
| ATOM | 4459 | C | THR | B | 553 | 3.428 | −2.319 | 5.897 | 1.00 | 37.46 C |
| ATOM | 4460 | O | THR | B | 553 | 3.887 | −1.385 | 5.244 | 1.00 | 39.29 O |
| ATOM | 4461 | CB | THR | B | 553 | 5.552 | −3.579 | 5.647 | 1.00 | 43.43 C |
| ATOM | 4462 | OG1 | THR | B | 553 | 5.120 | −4.350 | 4.521 | 1.00 | 54.27 O |
| ATOM | 4463 | CG2 | THR | B | 553 | 6.662 | −4.325 | 6.381 | 1.00 | 41.96 C |
| ATOM | 4464 | N | GLU | B | 554 | 2.124 | −2.522 | 6.070 | 1.00 | 42.05 N |
| ATOM | 4465 | CA | GLU | B | 554 | 1.095 | −1.678 | 5.477 | 1.00 | 35.86 C |
| ATOM | 4466 | C | GLU | B | 554 | 0.184 | −1.048 | 6.531 | 1.00 | 40.47 C |
| ATOM | 4467 | O | GLU | B | 554 | −0.298 | −1.735 | 7.429 | 1.00 | 51.11 O |
| ATOM | 4468 | CB | GLU | B | 554 | 0.244 | −2.540 | 4.540 | 1.00 | 36.70 C |
| ATOM | 4469 | CG | GLU | B | 554 | −0.915 | −1.848 | 3.848 | 1.00 | 38.96 C |
| ATOM | 4470 | CD | GLU | B | 554 | −1.643 | −2.807 | 2.901 | 1.00 | 62.50 C |
| ATOM | 4471 | OE1 | GLU | B | 554 | −2.275 | −3.783 | 3.380 | 1.00 | 65.25 O |
| ATOM | 4472 | OE2 | GLU | B | 554 | −1.569 | −2.601 | 1.672 | 1.00 | 68.39 O |
| ATOM | 4473 | N | LEU | B | 555 | −0.045 | 0.254 | 6.414 | 1.00 | 34.72 N |
| ATOM | 4474 | CA | LEU | B | 555 | −0.935 | 0.968 | 7.313 | 1.00 | 34.39 C |
| ATOM | 4475 | C | LEU | B | 555 | −2.275 | 1.028 | 6.617 | 1.00 | 39.05 C |
| ATOM | 4476 | O | LEU | B | 555 | −2.352 | 1.436 | 5.459 | 1.00 | 34.77 O |
| ATOM | 4477 | CB | LEU | B | 555 | −0.480 | 2.406 | 7.563 | 1.00 | 27.48 C |
| ATOM | 4478 | CG | LEU | B | 555 | 0.762 | 2.673 | 8.406 | 1.00 | 31.68 C |
| ATOM | 4479 | CD1 | LEU | B | 555 | 0.779 | 4.152 | 8.775 | 1.00 | 39.65 C |
| ATOM | 4480 | CD2 | LEU | B | 555 | 0.753 | 1.808 | 9.655 | 1.00 | 33.90 C |
| ATOM | 4481 | N | LYS | B | 556 | −3.322 | 0.636 | 7.342 | 1.00 | 53.52 N |
| ATOM | 4482 | CA | LYS | B | 556 | −4.687 | 0.625 | 6.834 | 1.00 | 34.20 C |
| ATOM | 4483 | C | LYS | B | 556 | −5.667 | 0.872 | 7.978 | 1.00 | 39.34 C |
| ATOM | 4484 | O | LYS | B | 556 | −5.562 | 0.249 | 9.054 | 1.00 | 35.45 O |
| ATOM | 4485 | CB | LYS | B | 556 | −4.989 | −0.728 | 6.198 | 1.00 | 31.63 C |
| ATOM | 4486 | CG | LYS | B | 556 | −6.382 | −0.823 | 5.612 | 1.00 | 32.57 C |
| ATOM | 4487 | CD | LYS | B | 556 | −6.723 | −2.271 | 5.290 | 1.00 | 40.18 C |
| ATOM | 4488 | CE | LYS | B | 556 | −8.118 | −2.390 | 4.693 | 1.00 | 40.92 C |
| ATOM | 4489 | NZ | LYS | B | 556 | −8.355 | −3.737 | 4.105 | 1.00 | 56.00 N |
| ATOM | 4490 | N | VAL | B | 557 | −6.622 | 1.765 | 7.743 | 1.00 | 29.54 N |
| ATOM | 4491 | CA | VAL | B | 557 | −7.601 | 2.096 | 8.769 | 1.00 | 35.25 C |
| ATOM | 4492 | C | VAL | B | 557 | −8.420 | 0.858 | 9.130 | 1.00 | 35.63 C |
| ATOM | 4493 | O | VAL | B | 557 | −8.520 | −0.072 | 8.340 | 1.00 | 41.05 O |
| ATOM | 4494 | CB | VAL | B | 557 | −8.579 | 3.218 | 8.291 | 1.00 | 44.91 C |
| ATOM | 4495 | CG1 | VAL | B | 557 | −9.481 | 2.707 | 7.164 | 1.00 | 32.40 C |
| ATOM | 4496 | CG2 | VAL | B | 557 | −9.428 | 3.694 | 9.452 | 1.00 | 42.46 C |
| ATOM | 4497 | N | ILE | B | 558 | −8.955 | 0.834 | 10.344 | 1.00 | 34.85 N |
| ATOM | 4498 | CA | ILE | B | 558 | −9.826 | −0.257 | 10.769 | 1.00 | 39.44 C |
| ATOM | 4499 | C | ILE | B | 558 | −11.252 | 0.284 | 10.550 | 1.00 | 33.41 C |
| ATOM | 4500 | O | ILE | B | 558 | −11.606 | 1.361 | 11.040 | 1.00 | 35.98 O |
| ATOM | 4501 | CB | ILE | B | 558 | −9.580 | −0.629 | 12.258 | 1.00 | 42.58 C |
| ATOM | 4502 | CG1 | ILE | B | 558 | −8.258 | −1.414 | 12.371 | 1.00 | 29.92 C |
| ATOM | 4503 | CG2 | ILE | B | 558 | −10.771 | −1.442 | 12.801 | 1.00 | 33.29 C |
| ATOM | 4504 | CD1 | ILE | B | 558 | −7.700 | −1.583 | 13.793 | 1.00 | 25.78 C |
| ATOM | 4505 | N | ASP | B | 559 | −12.055 | −0.448 | 9.789 | 1.00 | 41.48 N |
| ATOM | 4506 | CA | ASP | B | 559 | −13.421 | −0.025 | 9.460 | 1.00 | 46.54 C |
| ATOM | 4507 | C | ASP | B | 559 | −14.324 | 0.460 | 10.607 | 1.00 | 44.33 C |
| ATOM | 4508 | O | ASP | B | 559 | −15.062 | 1.427 | 10.438 | 1.00 | 39.39 O |
| ATOM | 4509 | CB | ASP | B | 559 | −14.124 | −1.141 | 8.697 | 1.00 | 44.39 C |
| ATOM | 4510 | CG | ASP | B | 559 | −14.443 | −2.339 | 9.574 | 1.00 | 67.31 C |
| ATOM | 4511 | OD1 | ASP | B | 559 | −13.673 | −2.622 | 10.520 | 1.00 | 76.01 O |
| ATOM | 4512 | OD2 | ASP | B | 559 | −15.464 | −3.014 | 9.311 | 1.00 | 82.04 O |
| ATOM | 4513 | N | THR | B | 560 | −14.239 | −0.169 | 11.776 | 1.00 | 34.67 N |
| ATOM | 4514 | CA | THR | B | 560 | −15.093 | 0.214 | 12.886 | 1.00 | 28.42 C |
| ATOM | 4515 | C | THR | B | 560 | −14.683 | 1.490 | 13.605 | 1.00 | 40.47 C |
| ATOM | 4516 | O | THR | B | 560 | −15.272 | 1.858 | 14.621 | 1.00 | 38.76 O |
| ATOM | 4517 | CB | THR | B | 560 | −15.224 | −0.939 | 13.863 | 1.00 | 49.25 C |
| ATOM | 4518 | OG1 | THR | B | 560 | −13.914 | −1.384 | 14.264 | 1.00 | 42.31 O |
| ATOM | 4519 | CG2 | THR | B | 560 | −15.979 | −2.105 | 13.176 | 1.00 | 31.81 C |
| ATOM | 4520 | N | ASN | B | 561 | −13.667 | 2.162 | 13.066 | 1.00 | 31.54 N |
| ATOM | 4521 | CA | ASN | B | 561 | −13.209 | 3.434 | 13.597 | 1.00 | 33.55 C |
| ATOM | 4522 | C | ASN | B | 561 | −13.697 | 4.564 | 12.654 | 1.00 | 24.85 C |
| ATOM | 4523 | O | ASN | B | 561 | −13.246 | 5.694 | 12.710 | 1.00 | 32.86 O |
| ATOM | 4524 | CB | ASN | B | 561 | −11.689 | 3.457 | 13.722 | 1.00 | 30.42 C |
| ATOM | 4525 | CG | ASN | B | 561 | −11.178 | 2.578 | 14.836 | 1.00 | 29.03 C |
| ATOM | 4526 | OD1 | ASN | B | 561 | −10.042 | 2.103 | 14.785 | 1.00 | 35.76 O |
| ATOM | 4527 | ND2 | ASN | B | 561 | −11.989 | 2.371 | 15.851 | 1.00 | 24.42 N |
| ATOM | 4528 | N | CYS | B | 562 | −14.657 | 4.243 | 11.805 | 1.00 | 40.76 N |
| ATOM | 4529 | CA | CYS | B | 562 | −15.212 | 5.229 | 10.879 | 1.00 | 43.80 C |
| ATOM | 4530 | C | CYS | B | 562 | −16.735 | 5.175 | 10.933 | 1.00 | 44.09 C |
| ATOM | 4531 | O | CYS | B | 562 | −17.313 | 4.305 | 11.592 | 1.00 | 31.81 O |
| ATOM | 4532 | CB | CYS | B | 562 | −14.802 | 4.895 | 9.443 | 1.00 | 46.96 C |
| ATOM | 4533 | SG | CYS | B | 562 | −13.007 | 4.641 | 9.123 | 1.00 | 37.75 S |
| ATOM | 4534 | N | ILE | B | 563 | −17.361 | 6.118 | 10.236 | 1.00 | 32.57 N |
| ATOM | 4535 | CA | ILE | B | 563 | −18.802 | 6.129 | 10.066 | 1.00 | 40.26 C |

TABLE 1-continued

| | | | | | | | | | | |
|---|---|---|---|---|---|---|---|---|---|---|
| ATOM | 4536 | C | ILE | B | 563 | −18.996 | 6.357 | 8.564 | 1.00 | 45.19 | C |
| ATOM | 4537 | O | ILE | B | 563 | −18.105 | 6.887 | 7.881 | 1.00 | 38.27 | O |
| ATOM | 4538 | CB | ILE | B | 563 | −19.527 | 7.261 | 10.828 | 1.00 | 30.13 | C |
| ATOM | 4539 | CG1 | ILE | B | 563 | −18.887 | 8.617 | 10.500 | 1.00 | 43.17 | C |
| ATOM | 4540 | CG2 | ILE | B | 563 | −19.562 | 6.946 | 12.323 | 1.00 | 34.21 | C |
| ATOM | 4541 | CD1 | ILE | B | 563 | −19.682 | 9.805 | 11.054 | 1.00 | 32.97 | C |
| ATOM | 4542 | N | ASN | B | 564 | −20.141 | 5.929 | 8.044 | 1.00 | 42.17 | N |
| ATOM | 4543 | CA | ASN | B | 564 | −20.455 | 6.127 | 6.640 | 1.00 | 29.13 | C |
| ATOM | 4544 | C | ASN | B | 564 | −21.391 | 7.303 | 6.476 | 1.00 | 30.08 | C |
| ATOM | 4545 | O | ASN | B | 564 | −22.562 | 7.235 | 6.855 | 1.00 | 39.64 | O |
| ATOM | 4546 | CB | ASN | B | 564 | −21.098 | 4.878 | 6.050 | 1.00 | 48.34 | C |
| ATOM | 4547 | CG | ASN | B | 564 | −20.100 | 3.764 | 5.846 | 1.00 | 52.34 | C |
| ATOM | 4548 | OD1 | ASN | B | 564 | −18.959 | 4.014 | 5.460 | 1.00 | 51.87 | O |
| ATOM | 4549 | ND2 | ASN | B | 564 | −20.524 | 2.524 | 6.091 | 1.00 | 47.82 | N |
| ATOM | 4550 | N | VAL | B | 565 | −20.853 | 8.393 | 5.939 | 1.00 | 42.48 | N |
| ATOM | 4551 | CA | VAL | B | 565 | −21.621 | 9.606 | 5.682 | 1.00 | 36.07 | C |
| ATOM | 4552 | C | VAL | B | 565 | −22.342 | 9.500 | 4.323 | 1.00 | 45.06 | C |
| ATOM | 4553 | O | VAL | B | 565 | −21.711 | 9.302 | 3.286 | 1.00 | 34.60 | O |
| ATOM | 4554 | CB | VAL | B | 565 | −20.704 | 10.834 | 5.646 | 1.00 | 41.30 | C |
| ATOM | 4555 | CG1 | VAL | B | 565 | −21.503 | 12.055 | 5.231 | 1.00 | 50.87 | C |
| ATOM | 4556 | CG2 | VAL | B | 565 | −20.060 | 11.049 | 7.024 | 1.00 | 37.45 | C |
| ATOM | 4557 | N | ILE | B | 566 | −23.662 | 9.627 | 4.338 | 1.00 | 37.55 | N |
| ATOM | 4558 | CA | ILE | B | 566 | −24.440 | 9.539 | 3.111 | 1.00 | 39.06 | C |
| ATOM | 4559 | C | ILE | B | 566 | −24.251 | 10.736 | 2.205 | 1.00 | 40.84 | C |
| ATOM | 4560 | O | ILE | B | 566 | −24.416 | 11.881 | 2.625 | 1.00 | 43.60 | O |
| ATOM | 4561 | CB | ILE | B | 566 | −25.941 | 9.397 | 3.408 | 1.00 | 44.82 | C |
| ATOM | 4562 | CG1 | ILE | B | 566 | −26.269 | 7.944 | 3.739 | 1.00 | 47.16 | C |
| ATOM | 4563 | CG2 | ILE | B | 566 | −26.757 | 9.825 | 2.209 | 1.00 | 59.91 | C |
| ATOM | 4564 | CD1 | ILE | B | 566 | −27.735 | 7.704 | 4.032 | 1.00 | 72.33 | C |
| ATOM | 4565 | N | GLN | B | 567 | −23.918 | 10.452 | 0.949 | 1.00 | 50.50 | N |
| ATOM | 4566 | CA | GLN | B | 567 | −23.710 | 11.479 | −0.066 | 1.00 | 51.37 | C |
| ATOM | 4567 | C | GLN | B | 567 | −25.032 | 11.861 | −0.753 | 1.00 | 60.71 | C |
| ATOM | 4568 | O | GLN | B | 567 | −26.020 | 11.137 | −0.654 | 1.00 | 47.33 | O |
| ATOM | 4569 | CB | GLN | B | 567 | −22.706 | 10.966 | −1.094 | 1.00 | 50.25 | C |
| ATOM | 4570 | CG | GLN | B | 567 | −21.349 | 10.726 | −0.484 | 1.00 | 58.49 | C |
| ATOM | 4571 | CD | GLN | B | 567 | −20.823 | 11.982 | 0.183 | 1.00 | 66.56 | C |
| ATOM | 4572 | OE1 | GLN | B | 567 | −20.474 | 12.949 | −0.490 | 1.00 | 69.23 | O |
| ATOM | 4573 | NE2 | GLN | B | 567 | −20.788 | 11.985 | 1.516 | 1.00 | 70.76 | N |
| ATOM | 4574 | N | PRO | B | 568 | −25.060 | 13.010 | −1.448 | 1.00 | 64.94 | N |
| ATOM | 4575 | CA | PRO | B | 568 | −26.279 | 13.460 | −2.135 | 1.00 | 65.66 | C |
| ATOM | 4576 | C | PRO | B | 568 | −26.870 | 12.397 | −3.042 | 1.00 | 68.34 | C |
| ATOM | 4577 | O | PRO | B | 568 | −28.094 | 12.274 | −3.168 | 1.00 | 47.17 | O |
| ATOM | 4578 | CB | PRO | B | 568 | −25.800 | 14.679 | −2.917 | 1.00 | 57.41 | C |
| ATOM | 4579 | CG | PRO | B | 568 | −24.764 | 15.270 | −1.971 | 1.00 | 64.24 | C |
| ATOM | 4580 | CD | PRO | B | 568 | −23.991 | 14.025 | −1.555 | 1.00 | 61.24 | C |
| ATOM | 4581 | N | ASP | B | 569 | −25.982 | 11.618 | −3.651 | 1.00 | 65.33 | N |
| ATOM | 4582 | CA | ASP | B | 569 | −26.374 | 10.569 | −4.575 | 1.00 | 56.19 | C |
| ATOM | 4583 | C | ASP | B | 569 | −26.587 | 9.245 | −3.873 | 1.00 | 60.46 | C |
| ATOM | 4584 | O | ASP | B | 569 | −26.419 | 8.188 | −4.476 | 1.00 | 55.97 | O |
| ATOM | 4585 | CB | ASP | B | 569 | −25.301 | 10.411 | −5.643 | 1.00 | 67.35 | C |
| ATOM | 4586 | CG | ASP | B | 569 | −23.919 | 10.207 | −5.044 | 1.00 | 87.11 | C |
| ATOM | 4587 | OD1 | ASP | B | 569 | −23.467 | 11.108 | −4.295 | 1.00 | 73.07 | O |
| ATOM | 4588 | OD2 | ASP | B | 569 | −23.298 | 9.149 | −5.320 | 1.00 | 76.32 | O |
| ATOM | 4589 | N | GLY | B | 570 | −26.939 | 9.299 | −2.593 | 1.00 | 58.62 | N |
| ATOM | 4590 | CA | GLY | B | 570 | −27.192 | 8.079 | −1.850 | 1.00 | 51.71 | C |
| ATOM | 4591 | C | GLY | B | 570 | −26.003 | 7.182 | −1.549 | 1.00 | 61.57 | C |
| ATOM | 4592 | O | GLY | B | 570 | −26.138 | 6.229 | −0.773 | 1.00 | 58.30 | O |
| ATOM | 4593 | N | SER | B | 571 | −24.844 | 7.455 | −2.146 | 1.00 | 55.56 | N |
| ATOM | 4594 | CA | SER | B | 571 | −23.667 | 6.626 | −1.874 | 1.00 | 60.48 | C |
| ATOM | 4595 | C | SER | B | 571 | −23.065 | 6.998 | −0.507 | 1.00 | 67.74 | C |
| ATOM | 4596 | O | SER | B | 571 | −23.273 | 8.113 | 0.011 | 1.00 | 51.33 | O |
| ATOM | 4597 | CB | SER | B | 571 | −22.605 | 6.795 | −2.968 | 1.00 | 50.98 | C |
| ATOM | 4598 | OG | SER | B | 571 | −22.010 | 8.085 | −2.934 | 1.00 | 46.80 | O |
| ATOM | 4599 | N | TYR | B | 572 | −22.323 | 6.057 | 0.072 | 1.00 | 64.33 | N |
| ATOM | 4600 | CA | TYR | B | 572 | −21.705 | 6.266 | 1.378 | 1.00 | 60.44 | C |
| ATOM | 4601 | C | TYR | B | 572 | −20.246 | 6.672 | 1.265 | 1.00 | 59.03 | C |
| ATOM | 4602 | O | TYR | B | 572 | −19.476 | 6.058 | 0.537 | 1.00 | 47.58 | O |
| ATOM | 4603 | CB | TYR | B | 572 | −21.803 | 4.994 | 2.236 | 1.00 | 53.88 | C |
| ATOM | 4604 | CG | TYR | B | 572 | −23.221 | 4.562 | 2.565 | 1.00 | 67.12 | C |
| ATOM | 4605 | CD1 | TYR | B | 572 | −24.029 | 5.315 | 3.417 | 1.00 | 62.67 | C |
| ATOM | 4606 | CD2 | TYR | B | 572 | −23.760 | 3.408 | 2.003 | 1.00 | 81.99 | C |
| ATOM | 4607 | CE1 | TYR | B | 572 | −25.343 | 4.929 | 3.697 | 1.00 | 74.78 | C |
| ATOM | 4608 | CE2 | TYR | B | 572 | −25.071 | 3.011 | 2.272 | 1.00 | 86.72 | C |
| ATOM | 4609 | CZ | TYR | B | 572 | −25.859 | 3.773 | 3.119 | 1.00 | 89.19 | C |
| ATOM | 4610 | OH | TYR | B | 572 | −27.160 | 3.373 | 3.370 | 1.00 | 84.81 | O |
| ATOM | 4611 | N | ARG | B | 573 | −19.892 | 7.738 | 1.971 | 1.00 | 59.32 | N |
| ATOM | 4612 | CA | ARG | B | 573 | −18.522 | 8.212 | 2.027 | 1.00 | 50.59 | C |
| ATOM | 4613 | C | ARG | B | 573 | −18.011 | 7.918 | 3.450 | 1.00 | 55.19 | C |
| ATOM | 4614 | O | ARG | B | 573 | −18.502 | 8.476 | 4.437 | 1.00 | 50.69 | O |

TABLE 1-continued

| ATOM | 4615 | CB | ARG | B | 573 | −18.436 | 9.718 | 1.767 | 1.00 | 51.37 | C |
|---|---|---|---|---|---|---|---|---|---|---|---|
| ATOM | 4616 | CG | ARG | B | 573 | −17.044 | 10.302 | 2.054 | 1.00 | 59.54 | C |
| ATOM | 4617 | CD | ARG | B | 573 | −16.944 | 11.806 | 1.772 | 1.00 | 66.74 | C |
| ATOM | 4618 | NE | ARG | B | 573 | −17.750 | 12.639 | 2.668 | 1.00 | 64.88 | N |
| ATOM | 4619 | CZ | ARG | B | 573 | −17.464 | 12.863 | 3.948 | 1.00 | 71.45 | C |
| ATOM | 4620 | NH1 | ARG | B | 573 | −16.387 | 12.313 | 4.496 | 1.00 | 71.88 | N |
| ATOM | 4621 | NH2 | ARG | B | 573 | −18.247 | 13.647 | 4.680 | 1.00 | 61.70 | N |
| ATOM | 4622 | N | SER | B | 574 | −17.033 | 7.032 | 3.543 | 1.00 | 37.14 | N |
| ATOM | 4623 | CA | SER | B | 574 | −16.441 | 6.662 | 4.819 | 1.00 | 50.28 | C |
| ATOM | 4624 | C | SER | B | 574 | −15.604 | 7.773 | 5.457 | 1.00 | 35.88 | C |
| ATOM | 4625 | O | SER | B | 574 | −14.763 | 8.377 | 4.810 | 1.00 | 41.81 | O |
| ATOM | 4626 | CB | SER | B | 574 | −15.565 | 5.435 | 4.627 | 1.00 | 46.63 | C |
| ATOM | 4627 | OG | SER | B | 574 | −14.648 | 5.345 | 5.693 | 1.00 | 53.97 | O |
| ATOM | 4628 | N | GLU | B | 575 | −15.844 | 8.050 | 6.731 | 1.00 | 44.16 | N |
| ATOM | 4629 | CA | GLU | B | 575 | −15.082 | 9.080 | 7.415 | 1.00 | 36.46 | C |
| ATOM | 4630 | C | GLU | B | 575 | −14.626 | 8.627 | 8.818 | 1.00 | 40.93 | C |
| ATOM | 4631 | O | GLU | B | 575 | −15.372 | 7.965 | 9.557 | 1.00 | 33.20 | O |
| ATOM | 4632 | CB | GLU | B | 575 | −15.894 | 10.369 | 7.528 | 1.00 | 30.54 | C |
| ATOM | 4633 | CG | GLU | B | 575 | −15.120 | 11.485 | 8.185 | 1.00 | 37.55 | C |
| ATOM | 4634 | CD | GLU | B | 575 | −15.909 | 12.780 | 8.283 | 1.00 | 58.81 | C |
| ATOM | 4635 | OE1 | GLU | B | 575 | −16.545 | 13.165 | 7.277 | 1.00 | 68.23 | O |
| ATOM | 4636 | OE2 | GLU | B | 575 | −15.880 | 13.428 | 9.354 | 1.00 | 50.79 | O |
| ATOM | 4637 | N | GLU | B | 576 | −13.393 | 8.988 | 9.165 | 1.00 | 31.86 | N |
| ATOM | 4638 | CA | GLU | B | 576 | −12.791 | 8.644 | 10.457 | 1.00 | 26.71 | C |
| ATOM | 4639 | C | GLU | B | 576 | −13.188 | 9.642 | 11.506 | 1.00 | 28.04 | C |
| ATOM | 4640 | O | GLU | B | 576 | −13.271 | 10.835 | 11.237 | 1.00 | 35.96 | O |
| ATOM | 4641 | CB | GLU | B | 576 | −11.259 | 8.680 | 10.384 | 1.00 | 34.78 | C |
| ATOM | 4642 | CG | GLU | B | 576 | −10.593 | 7.470 | 9.772 | 1.00 | 28.88 | C |
| ATOM | 4643 | CD | GLU | B | 576 | −9.124 | 7.750 | 9.531 | 1.00 | 57.73 | C |
| ATOM | 4644 | OE1 | GLU | B | 576 | −8.314 | 7.789 | 10.504 | 1.00 | 38.93 | O |
| ATOM | 4645 | OE2 | GLU | B | 576 | −8.796 | 7.969 | 8.353 | 1.00 | 57.11 | O |
| ATOM | 4646 | N | LEU | B | 577 | −13.406 | 9.164 | 12.717 | 1.00 | 29.62 | N |
| ATOM | 4647 | CA | LEU | B | 577 | −13.763 | 10.069 | 13.798 | 1.00 | 33.26 | C |
| ATOM | 4648 | C | LEU | B | 577 | −13.272 | 9.451 | 15.088 | 1.00 | 21.33 | C |
| ATOM | 4649 | O | LEU | B | 577 | −13.070 | 8.235 | 15.154 | 1.00 | 19.68 | O |
| ATOM | 4650 | CB | LEU | B | 577 | −15.291 | 10.277 | 13.850 | 1.00 | 25.74 | C |
| ATOM | 4651 | CG | LEU | B | 577 | −16.185 | 9.083 | 14.223 | 1.00 | 31.90 | C |
| ATOM | 4652 | CD1 | LEU | B | 577 | −17.673 | 9.529 | 14.104 | 1.00 | 28.40 | C |
| ATOM | 4653 | CD2 | LEU | B | 577 | −15.933 | 7.901 | 13.304 | 1.00 | 18.40 | C |
| ATOM | 4654 | N | ASN | B | 578 | −13.092 | 10.286 | 16.111 | 1.00 | 22.17 | N |
| ATOM | 4655 | CA | ASN | B | 578 | −12.631 | 9.807 | 17.422 | 1.00 | 30.63 | C |
| ATOM | 4656 | C | ASN | B | 578 | −13.746 | 9.511 | 18.431 | 1.00 | 33.37 | C |
| ATOM | 4657 | O | ASN | B | 578 | −13.712 | 8.508 | 19.143 | 1.00 | 28.84 | O |
| ATOM | 4658 | CB | ASN | B | 578 | −11.707 | 10.839 | 18.047 | 1.00 | 19.96 | C |
| ATOM | 4659 | CG | ASN | B | 578 | −10.427 | 11.013 | 17.266 | 1.00 | 28.26 | C |
| ATOM | 4660 | OD1 | ASN | B | 578 | −10.212 | 10.330 | 16.268 | 1.00 | 25.83 | O |
| ATOM | 4661 | ND2 | ASN | B | 578 | −9.575 | 11.931 | 17.712 | 1.00 | 19.28 | N |
| ATOM | 4662 | N | LEU | B | 579 | −14.738 | 10.392 | 18.461 | 1.00 | 36.59 | N |
| ATOM | 4663 | CA | LEU | B | 579 | −15.813 | 10.314 | 19.418 | 1.00 | 18.46 | C |
| ATOM | 4664 | C | LEU | B | 579 | −17.206 | 10.601 | 18.861 | 1.00 | 30.49 | C |
| ATOM | 4665 | O | LEU | B | 579 | −17.388 | 11.434 | 17.974 | 1.00 | 25.36 | O |
| ATOM | 4666 | CB | LEU | B | 579 | −15.504 | 11.302 | 20.530 | 1.00 | 26.60 | C |
| ATOM | 4667 | CG | LEU | B | 579 | −16.456 | 11.516 | 21.698 | 1.00 | 23.64 | C |
| ATOM | 4668 | CD1 | LEU | B | 579 | −16.384 | 10.364 | 22.650 | 1.00 | 33.82 | C |
| ATOM | 4669 | CD2 | LEU | B | 579 | −16.050 | 12.768 | 22.394 | 1.00 | 21.69 | C |
| ATOM | 4670 | N | VAL | B | 580 | −18.179 | 9.874 | 19.386 | 1.00 | 29.14 | N |
| ATOM | 4671 | CA | VAL | B | 580 | −19.568 | 10.075 | 19.034 | 1.00 | 28.36 | C |
| ATOM | 4672 | C | VAL | B | 580 | −20.343 | 10.168 | 20.347 | 1.00 | 29.42 | C |
| ATOM | 4673 | O | VAL | B | 580 | −20.127 | 9.356 | 21.262 | 1.00 | 29.37 | O |
| ATOM | 4674 | CB | VAL | B | 580 | −20.146 | 8.908 | 18.221 | 1.00 | 21.43 | C |
| ATOM | 4675 | CG1 | VAL | B | 580 | −21.609 | 9.154 | 17.952 | 1.00 | 24.27 | C |
| ATOM | 4676 | CG2 | VAL | B | 580 | −19.387 | 8.732 | 16.929 | 1.00 | 20.54 | C |
| ATOM | 4677 | N | ILE | B | 581 | −21.187 | 11.188 | 20.463 | 1.00 | 32.45 | N |
| ATOM | 4678 | CA | ILE | B | 581 | −22.050 | 11.334 | 21.629 | 1.00 | 30.04 | C |
| ATOM | 4679 | C | ILE | B | 581 | −23.454 | 10.921 | 21.141 | 1.00 | 40.80 | C |
| ATOM | 4680 | O | ILE | B | 581 | −24.010 | 11.508 | 20.210 | 1.00 | 26.19 | O |
| ATOM | 4681 | CB | ILE | B | 581 | −22.120 | 12.774 | 22.144 | 1.00 | 29.28 | C |
| ATOM | 4682 | CG1 | ILE | B | 581 | −20.716 | 13.280 | 22.507 | 1.00 | 27.06 | C |
| ATOM | 4683 | CG2 | ILE | B | 581 | −23.048 | 12.820 | 23.351 | 1.00 | 21.35 | C |
| ATOM | 4684 | CD1 | ILE | B | 581 | −19.985 | 12.401 | 23.527 | 1.00 | 19.35 | C |
| ATOM | 4685 | N | ILE | B | 582 | −24.008 | 9.886 | 21.751 | 1.00 | 27.74 | N |
| ATOM | 4686 | CA | ILE | B | 582 | −25.304 | 9.390 | 21.318 | 1.00 | 35.59 | C |
| ATOM | 4687 | C | ILE | B | 582 | −26.249 | 9.197 | 22.511 | 1.00 | 34.98 | C |
| ATOM | 4688 | O | ILE | B | 582 | −25.793 | 9.056 | 23.652 | 1.00 | 22.35 | O |
| ATOM | 4689 | CB | ILE | B | 582 | −25.128 | 8.045 | 20.572 | 1.00 | 24.01 | C |
| ATOM | 4690 | CG1 | ILE | B | 582 | −26.410 | 7.665 | 19.846 | 1.00 | 39.81 | C |
| ATOM | 4691 | CG2 | ILE | B | 582 | −24.761 | 6.951 | 21.572 | 1.00 | 26.12 | C |
| ATOM | 4692 | CD1 | ILE | B | 582 | −26.266 | 6.483 | 18.911 | 1.00 | 41.33 | C |
| ATOM | 4693 | N | GLY | B | 583 | −27.561 | 9.198 | 22.238 | 1.00 | 36.91 | N |

TABLE 1-continued

| | | | | | | | | | | |
|---|---|---|---|---|---|---|---|---|---|---|
| ATOM | 4694 | CA | GLY | B | 583 | −28.548 | 9.011 | 23.297 | 1.00 | 24.70 | C |
| ATOM | 4695 | C | GLY | B | 583 | −28.521 | 7.628 | 23.956 | 1.00 | 23.50 | C |
| ATOM | 4696 | O | GLY | B | 583 | −28.026 | 6.653 | 23.387 | 1.00 | 25.22 | O |
| ATOM | 4697 | N | PRO | B | 584 | −29.075 | 7.508 | 25.168 | 1.00 | 38.01 | N |
| ATOM | 4698 | CA | PRO | B | 584 | −29.066 | 6.202 | 25.831 | 1.00 | 28.94 | C |
| ATOM | 4699 | C | PRO | B | 584 | −29.940 | 5.129 | 25.162 | 1.00 | 41.66 | C |
| ATOM | 4700 | O | PRO | B | 584 | −30.764 | 5.417 | 24.274 | 1.00 | 28.84 | O |
| ATOM | 4701 | CB | PRO | B | 584 | −29.521 | 6.543 | 27.254 | 1.00 | 36.72 | C |
| ATOM | 4702 | CG | PRO | B | 584 | −30.445 | 7.704 | 27.044 | 1.00 | 40.17 | C |
| ATOM | 4703 | CD | PRO | B | 584 | −29.718 | 8.537 | 26.014 | 1.00 | 29.04 | C |
| ATOM | 4704 | N | SER | B | 585 | −29.729 | 3.889 | 25.589 | 1.00 | 24.04 | N |
| ATOM | 4705 | CA | SER | B | 585 | −30.483 | 2.750 | 25.092 | 1.00 | 36.43 | C |
| ATOM | 4706 | C | SER | B | 585 | −31.761 | 2.638 | 25.968 | 1.00 | 34.52 | C |
| ATOM | 4707 | O | SER | B | 585 | −32.145 | 3.607 | 26.600 | 1.00 | 28.19 | O |
| ATOM | 4708 | CB | SER | B | 585 | −29.614 | 1.490 | 25.212 | 1.00 | 41.43 | C |
| ATOM | 4709 | OG | SER | B | 585 | −30.170 | 0.419 | 24.473 | 1.00 | 55.87 | O |
| ATOM | 4710 | N | ALA | B | 586 | −32.408 | 1.478 | 26.016 | 1.00 | 36.28 | N |
| ATOM | 4711 | CA | ALA | B | 586 | −33.637 | 1.322 | 26.829 | 1.00 | 38.01 | C |
| ATOM | 4712 | C | ALA | B | 586 | −33.567 | 1.969 | 28.212 | 1.00 | 25.36 | C |
| ATOM | 4713 | O | ALA | B | 586 | −34.454 | 2.700 | 28.590 | 1.00 | 34.63 | O |
| ATOM | 4714 | CB | ALA | B | 586 | −33.994 | −0.148 | 26.969 | 1.00 | 28.43 | C |
| ATOM | 4715 | N | ASP | B | 587 | −32.534 | 1.672 | 28.988 | 1.00 | 28.49 | N |
| ATOM | 4716 | CA | ASP | B | 587 | −32.408 | 2.297 | 30.291 | 1.00 | 22.82 | C |
| ATOM | 4717 | C | ASP | B | 587 | −31.775 | 3.665 | 30.013 | 1.00 | 31.83 | C |
| ATOM | 4718 | O | ASP | B | 587 | −30.627 | 3.778 | 29.574 | 1.00 | 34.74 | O |
| ATOM | 4719 | CB | ASP | B | 587 | −31.515 | 1.461 | 31.221 | 1.00 | 38.12 | C |
| ATOM | 4720 | CG | ASP | B | 587 | −31.299 | 2.120 | 32.593 | 1.00 | 36.56 | C |
| ATOM | 4721 | OD1 | ASP | B | 587 | −31.777 | 3.263 | 32.838 | 1.00 | 41.42 | O |
| ATOM | 4722 | OD2 | ASP | B | 587 | −30.635 | 1.482 | 33.434 | 1.00 | 33.79 | O |
| ATOM | 4723 | N | ILE | B | 588 | −32.551 | 4.700 | 30.271 | 1.00 | 28.24 | N |
| ATOM | 4724 | CA | ILE | B | 588 | −32.146 | 6.060 | 30.027 | 1.00 | 28.73 | C |
| ATOM | 4725 | C | ILE | B | 588 | −30.955 | 6.587 | 30.813 | 1.00 | 26.47 | C |
| ATOM | 4726 | O | ILE | B | 588 | −30.168 | 7.365 | 30.285 | 1.00 | 42.87 | O |
| ATOM | 4727 | CB | ILE | B | 588 | −33.353 | 6.973 | 30.226 | 1.00 | 25.78 | C |
| ATOM | 4728 | CG1 | ILE | B | 588 | −34.363 | 6.706 | 29.100 | 1.00 | 34.62 | C |
| ATOM | 4729 | CG2 | ILE | B | 588 | −32.927 | 8.429 | 30.274 | 1.00 | 51.39 | C |
| ATOM | 4730 | CD1 | ILE | B | 588 | −35.645 | 7.463 | 29.260 | 1.00 | 27.06 | C |
| ATOM | 4731 | N | ILE | B | 589 | −30.799 | 6.176 | 32.060 | 1.00 | 31.32 | N |
| ATOM | 4732 | CA | ILE | B | 589 | −29.679 | 6.685 | 32.842 | 1.00 | 33.26 | C |
| ATOM | 4733 | C | ILE | B | 589 | −28.475 | 5.768 | 32.893 | 1.00 | 37.75 | C |
| ATOM | 4734 | O | ILE | B | 589 | −27.658 | 5.895 | 33.789 | 1.00 | 36.46 | O |
| ATOM | 4735 | CB | ILE | B | 589 | −30.083 | 7.023 | 34.299 | 1.00 | 32.89 | C |
| ATOM | 4736 | CG1 | ILE | B | 589 | −30.790 | 5.827 | 34.932 | 1.00 | 38.50 | C |
| ATOM | 4737 | CG2 | ILE | B | 589 | −30.948 | 8.285 | 34.309 | 1.00 | 35.49 | C |
| ATOM | 4738 | CD1 | ILE | B | 589 | −31.332 | 6.084 | 36.289 | 1.00 | 35.96 | C |
| ATOM | 4739 | N | GLN | B | 590 | −28.375 | 4.820 | 31.968 | 1.00 | 34.87 | N |
| ATOM | 4740 | CA | GLN | B | 590 | −27.192 | 3.975 | 31.949 | 1.00 | 40.51 | C |
| ATOM | 4741 | C | GLN | B | 590 | −26.193 | 4.614 | 30.968 | 1.00 | 35.67 | C |
| ATOM | 4742 | O | GLN | B | 590 | −26.251 | 4.371 | 29.767 | 1.00 | 39.90 | O |
| ATOM | 4743 | CB | GLN | B | 590 | −27.545 | 2.570 | 31.499 | 1.00 | 40.99 | C |
| ATOM | 4744 | CG | GLN | B | 590 | −26.339 | 1.706 | 31.245 | 1.00 | 39.02 | C |
| ATOM | 4745 | CD | GLN | B | 590 | −26.717 | 0.254 | 31.114 | 1.00 | 61.78 | C |
| ATOM | 4746 | OE1 | GLN | B | 590 | −26.852 | −0.448 | 32.116 | 1.00 | 77.49 | O |
| ATOM | 4747 | NE2 | GLN | B | 590 | −26.922 | −0.204 | 29.884 | 1.00 | 54.45 | N |
| ATOM | 4748 | N | PHE | B | 591 | −25.312 | 5.466 | 31.477 | 1.00 | 25.56 | N |
| ATOM | 4749 | CA | PHE | B | 591 | −24.336 | 6.121 | 30.627 | 1.00 | 31.08 | C |
| ATOM | 4750 | C | PHE | B | 591 | −23.043 | 5.327 | 30.598 | 1.00 | 49.81 | C |
| ATOM | 4751 | O | PHE | B | 591 | −22.618 | 4.760 | 31.614 | 1.00 | 41.05 | O |
| ATOM | 4752 | CB | PHE | B | 591 | −24.026 | 7.522 | 31.138 | 1.00 | 22.26 | C |
| ATOM | 4753 | CG | PHE | B | 591 | −25.246 | 8.381 | 31.381 | 1.00 | 31.49 | C |
| ATOM | 4754 | CD1 | PHE | B | 591 | −26.400 | 8.259 | 30.585 | 1.00 | 30.06 | C |
| ATOM | 4755 | CD2 | PHE | B | 591 | −25.206 | 9.368 | 32.354 | 1.00 | 28.30 | C |
| ATOM | 4756 | CE1 | PHE | B | 591 | −27.497 | 9.133 | 30.773 | 1.00 | 32.73 | C |
| ATOM | 4757 | CE2 | PHE | B | 591 | −26.287 | 10.250 | 32.552 | 1.00 | 37.42 | C |
| ATOM | 4758 | CZ | PHE | B | 591 | −27.431 | 10.138 | 31.767 | 1.00 | 23.31 | C |
| ATOM | 4759 | N | GLU | B | 592 | −22.399 | 5.285 | 29.442 | 1.00 | 38.18 | N |
| ATOM | 4760 | CA | GLU | B | 592 | −21.139 | 4.564 | 29.362 | 1.00 | 39.56 | C |
| ATOM | 4761 | C | GLU | B | 592 | −20.424 | 4.857 | 28.080 | 1.00 | 36.32 | C |
| ATOM | 4762 | O | GLU | B | 592 | −20.993 | 5.380 | 27.136 | 1.00 | 32.24 | O |
| ATOM | 4763 | CB | GLU | B | 592 | −21.357 | 3.056 | 29.480 | 1.00 | 46.46 | C |
| ATOM | 4764 | CG | GLU | B | 592 | −22.176 | 2.459 | 28.346 | 1.00 | 48.76 | C |
| ATOM | 4765 | CD | GLU | B | 592 | −22.621 | 1.031 | 28.637 | 1.00 | 74.19 | C |
| ATOM | 4766 | OE1 | GLU | B | 592 | −21.748 | 0.158 | 28.867 | 1.00 | 75.61 | O |
| ATOM | 4767 | OE2 | GLU | B | 592 | −23.849 | 0.785 | 28.637 | 1.00 | 71.26 | O |
| ATOM | 4768 | N | CYS | B | 593 | −19.162 | 4.466 | 28.062 | 1.00 | 41.41 | N |
| ATOM | 4769 | CA | CYS | B | 593 | −18.296 | 4.674 | 26.935 | 1.00 | 30.03 | C |
| ATOM | 4770 | C | CYS | B | 593 | −18.027 | 3.315 | 26.301 | 1.00 | 41.20 | C |
| ATOM | 4771 | O | CYS | B | 593 | −17.366 | 2.483 | 26.896 | 1.00 | 35.52 | O |
| ATOM | 4772 | CB | CYS | B | 593 | −17.019 | 5.306 | 27.462 | 1.00 | 35.62 | C |

TABLE 1-continued

| | | | | | | | | | | |
|---|---|---|---|---|---|---|---|---|---|---|
| ATOM | 4773 | SG | CYS | B | 593 | −15.974 | 5.879 | 26.212 | 1.00 | 36.50 S |
| ATOM | 4774 | N | LYS | B | 594 | −18.548 | 3.092 | 25.095 | 1.00 | 48.17 N |
| ATOM | 4775 | CA | LYS | B | 594 | −18.385 | 1.809 | 24.415 | 1.00 | 40.57 C |
| ATOM | 4776 | C | LYS | B | 594 | −17.735 | 1.982 | 23.040 | 1.00 | 52.06 C |
| ATOM | 4777 | O | LYS | B | 594 | −17.637 | 3.104 | 22.526 | 1.00 | 33.44 O |
| ATOM | 4778 | CB | LYS | B | 594 | −19.749 | 1.148 | 24.267 | 1.00 | 44.44 C |
| ATOM | 4779 | CG | LYS | B | 594 | −20.692 | 1.949 | 23.381 | 1.00 | 41.93 C |
| ATOM | 4780 | CD | LYS | B | 594 | −22.129 | 1.923 | 23.911 | 1.00 | 56.68 C |
| ATOM | 4781 | CE | LYS | B | 594 | −22.748 | 0.527 | 23.820 | 1.00 | 51.47 C |
| ATOM | 4782 | NZ | LYS | B | 594 | −22.151 | −0.432 | 24.775 | 1.00 | 51.78 N |
| ATOM | 4783 | N | SER | B | 595 | −17.312 | 0.866 | 22.448 | 1.00 | 29.41 N |
| ATOM | 4784 | CA | SER | B | 595 | −16.638 | 0.885 | 21.160 | 1.00 | 25.42 C |
| ATOM | 4785 | C | SER | B | 595 | −16.652 | −0.489 | 20.505 | 1.00 | 33.22 C |
| ATOM | 4786 | O | SER | B | 595 | −16.849 | −1.504 | 21.178 | 1.00 | 28.34 O |
| ATOM | 4787 | CB | SER | B | 595 | −15.192 | 1.359 | 21.335 | 1.00 | 35.87 C |
| ATOM | 4788 | OG | SER | B | 595 | −14.455 | 0.504 | 22.190 | 1.00 | 31.61 O |
| ATOM | 4789 | N | PHE | B | 596 | −16.442 | −0.518 | 19.193 | 1.00 | 32.97 N |
| ATOM | 4790 | CA | PHE | B | 596 | −16.438 | −1.778 | 18.443 | 1.00 | 31.51 C |
| ATOM | 4791 | C | PHE | B | 596 | −15.115 | −2.492 | 18.581 | 1.00 | 40.15 C |
| ATOM | 4792 | O | PHE | B | 596 | −14.047 | −1.878 | 18.564 | 1.00 | 37.21 O |
| ATOM | 4793 | CB | PHE | B | 596 | −16.754 | −1.508 | 16.971 | 1.00 | 19.28 C |
| ATOM | 4794 | CG | PHE | B | 596 | −18.134 | −0.961 | 16.765 | 1.00 | 28.09 C |
| ATOM | 4795 | CD1 | PHE | B | 596 | −19.244 | −1.800 | 16.857 | 1.00 | 35.95 C |
| ATOM | 4796 | CD2 | PHE | B | 596 | −18.337 | 0.399 | 16.565 | 1.00 | 26.11 C |
| ATOM | 4797 | CE1 | PHE | B | 596 | −20.548 | −1.289 | 16.753 | 1.00 | 49.51 C |
| ATOM | 4798 | CE2 | PHE | B | 596 | −19.636 | 0.928 | 16.457 | 1.00 | 49.85 C |
| ATOM | 4799 | CZ | PHE | B | 596 | −20.747 | 0.077 | 16.554 | 1.00 | 30.99 C |
| ATOM | 4800 | N | GLY | B | 597 | −15.192 | −3.804 | 18.720 | 1.00 | 37.42 N |
| ATOM | 4801 | CA | GLY | B | 597 | −13.982 | −4.578 | 18.871 | 1.00 | 39.10 C |
| ATOM | 4802 | C | GLY | B | 597 | −13.424 | −5.095 | 17.562 | 1.00 | 38.74 C |
| ATOM | 4803 | O | GLY | B | 597 | −14.007 | −4.933 | 16.493 | 1.00 | 31.29 O |
| ATOM | 4804 | N | HIS | B | 598 | −12.264 | −5.720 | 17.663 | 1.00 | 33.87 N |
| ATOM | 4805 | CA | HIS | B | 598 | −11.602 | −6.306 | 16.512 | 1.00 | 55.07 C |
| ATOM | 4806 | C | HIS | B | 598 | −11.676 | −7.818 | 16.715 | 1.00 | 48.25 C |
| ATOM | 4807 | O | HIS | B | 598 | −11.989 | −8.272 | 17.803 | 1.00 | 56.77 O |
| ATOM | 4808 | CB | HIS | B | 598 | −10.152 | −5.863 | 16.486 | 1.00 | 41.14 C |
| ATOM | 4809 | CG | HIS | B | 598 | −9.470 | −6.148 | 15.196 | 1.00 | 54.27 C |
| ATOM | 4810 | ND1 | HIS | B | 598 | −9.618 | −5.345 | 14.088 | 1.00 | 54.73 N |
| ATOM | 4811 | CD2 | HIS | B | 598 | −8.643 | −7.155 | 14.831 | 1.00 | 53.52 C |
| ATOM | 4812 | CE1 | HIS | B | 598 | −8.907 | −5.844 | 13.093 | 1.00 | 59.63 C |
| ATOM | 4813 | NE2 | HIS | B | 598 | −8.306 | −6.940 | 13.518 | 1.00 | 56.60 N |
| ATOM | 4814 | N | GLU | B | 599 | −11.372 | −8.604 | 15.695 | 1.00 | 51.24 N |
| ATOM | 4815 | CA | GLU | B | 599 | −11.454 | −10.051 | 15.859 | 1.00 | 41.78 C |
| ATOM | 4816 | C | GLU | B | 599 | −10.260 | −10.620 | 16.621 | 1.00 | 53.78 C |
| ATOM | 4817 | O | GLU | B | 599 | −10.343 | −11.717 | 17.177 | 1.00 | 62.98 O |
| ATOM | 4818 | CB | GLU | B | 599 | −11.580 | −10.742 | 14.498 | 1.00 | 64.60 C |
| ATOM | 4819 | CG | GLU | B | 599 | −12.472 | −9.996 | 13.494 | 1.00 | 78.68 C |
| ATOM | 4820 | CD | GLU | B | 599 | −11.785 | −8.761 | 12.900 | 1.00 | 82.07 C |
| ATOM | 4821 | OE1 | GLU | B | 599 | −10.802 | −8.946 | 12.141 | 1.00 | 70.30 O |
| ATOM | 4822 | OE2 | GLU | B | 599 | −12.221 | −7.618 | 13.194 | 1.00 | 59.58 O |
| ATOM | 4823 | N | VAL | B | 600 | −9.155 | −9.883 | 16.667 | 1.00 | 41.90 N |
| ATOM | 4824 | CA | VAL | B | 600 | −7.983 | −10.361 | 17.385 | 1.00 | 45.52 C |
| ATOM | 4825 | C | VAL | B | 600 | −7.321 | −9.280 | 18.244 | 1.00 | 54.24 C |
| ATOM | 4826 | O | VAL | B | 600 | −6.845 | −9.556 | 19.345 | 1.00 | 57.86 O |
| ATOM | 4827 | CB | VAL | B | 600 | −6.948 | −10.974 | 16.404 | 1.00 | 58.07 C |
| ATOM | 4828 | CG1 | VAL | B | 600 | −6.526 | −9.958 | 15.383 | 1.00 | 62.35 C |
| ATOM | 4829 | CG2 | VAL | B | 600 | −5.748 | −11.489 | 17.160 | 1.00 | 61.09 C |
| ATOM | 4830 | N | LEU | B | 601 | −7.302 | −8.051 | 17.743 | 1.00 | 52.88 N |
| ATOM | 4831 | CA | LEU | B | 601 | −6.712 | −6.926 | 18.462 | 1.00 | 49.45 C |
| ATOM | 4832 | C | LEU | B | 601 | −7.621 | −6.404 | 19.596 | 1.00 | 42.33 C |
| ATOM | 4833 | O | LEU | B | 601 | −8.833 | −6.327 | 19.435 | 1.00 | 53.96 O |
| ATOM | 4834 | CB | LEU | B | 601 | −6.444 | −5.791 | 17.471 | 1.00 | 47.00 C |
| ATOM | 4835 | CG | LEU | B | 601 | −5.442 | −6.055 | 16.350 | 1.00 | 45.32 C |
| ATOM | 4836 | CD1 | LEU | B | 601 | −5.645 | −5.064 | 15.229 | 1.00 | 39.19 C |
| ATOM | 4837 | CD2 | LEU | B | 601 | −4.037 | −5.959 | 16.902 | 1.00 | 32.83 C |
| ATOM | 4838 | N | ASN | B | 602 | −7.036 | −6.067 | 20.739 | 1.00 | 33.16 N |
| ATOM | 4839 | CA | ASN | B | 602 | −7.792 | −5.495 | 21.866 | 1.00 | 44.49 C |
| ATOM | 4840 | C | ASN | B | 602 | −7.462 | −4.015 | 21.770 | 1.00 | 35.15 C |
| ATOM | 4841 | O | ASN | B | 602 | −6.611 | −3.514 | 22.504 | 1.00 | 44.58 O |
| ATOM | 4842 | CB | ASN | B | 602 | −7.284 | −6.028 | 23.208 | 1.00 | 41.02 C |
| ATOM | 4843 | CG | ASN | B | 602 | −7.367 | −7.535 | 23.300 | 1.00 | 70.15 C |
| ATOM | 4844 | OD1 | ASN | B | 602 | −6.583 | −8.252 | 22.665 | 1.00 | 80.27 O |
| ATOM | 4845 | ND2 | ASN | B | 602 | −8.326 | −8.031 | 24.079 | 1.00 | 65.13 N |
| ATOM | 4846 | N | LEU | B | 603 | −8.134 | −3.331 | 20.852 | 1.00 | 31.13 N |
| ATOM | 4847 | CA | LEU | B | 603 | −7.871 | −1.918 | 20.560 | 1.00 | 23.50 C |
| ATOM | 4848 | C | LEU | B | 603 | −7.814 | −0.944 | 21.722 | 1.00 | 22.18 C |
| ATOM | 4849 | O | LEU | B | 603 | −7.017 | −0.011 | 21.700 | 1.00 | 30.94 O |
| ATOM | 4850 | CB | LEU | B | 603 | −8.890 | −1.411 | 19.531 | 1.00 | 22.08 C |
| ATOM | 4851 | CG | LEU | B | 603 | −9.046 | −2.291 | 18.292 | 1.00 | 33.05 C |

TABLE 1-continued

| | | | | | | | | | | |
|---|---|---|---|---|---|---|---|---|---|---|
| ATOM | 4852 | CD1 | LEU | B | 603 | −10.167 | −1.704 | 17.420 | 1.00 | 24.45 C |
| ATOM | 4853 | CD2 | LEU | B | 603 | −7.693 | −2.371 | 17.512 | 1.00 | 22.59 C |
| ATOM | 4854 | N | THR | B | 604 | −8.661 | −1.139 | 22.725 | 1.00 | 29.16 N |
| ATOM | 4855 | CA | THR | B | 604 | −8.669 | −0.243 | 23.872 | 1.00 | 29.92 C |
| ATOM | 4856 | C | THR | B | 604 | −7.521 | −0.510 | 24.834 | 1.00 | 30.80 C |
| ATOM | 4857 | O | THR | B | 604 | −7.280 | 0.278 | 25.722 | 1.00 | 24.74 O |
| ATOM | 4858 | CB | THR | B | 604 | −9.995 | −0.360 | 24.689 | 1.00 | 46.08 C |
| ATOM | 4859 | OG1 | THR | B | 604 | −10.132 | −1.693 | 25.202 | 1.00 | 37.96 O |
| ATOM | 4860 | CG2 | THR | B | 604 | −11.203 | −0.041 | 23.805 | 1.00 | 33.38 C |
| ATOM | 4861 | N | ARG | B | 605 | −6.803 | −1.607 | 24.635 | 1.00 | 31.86 N |
| ATOM | 4862 | CA | ARG | B | 605 | −5.742 | −1.981 | 25.563 | 1.00 | 38.65 C |
| ATOM | 4863 | C | ARG | B | 605 | −4.380 | −2.347 | 24.981 | 1.00 | 39.07 C |
| ATOM | 4864 | O | ARG | B | 605 | −3.580 | −2.954 | 25.674 | 1.00 | 35.73 O |
| ATOM | 4865 | CB | ARG | B | 605 | −6.220 | −3.152 | 26.418 | 1.00 | 30.64 C |
| ATOM | 4866 | CG | ARG | B | 605 | −7.200 | −2.792 | 27.509 | 1.00 | 47.55 C |
| ATOM | 4867 | CD | ARG | B | 605 | −7.644 | −4.032 | 28.276 | 1.00 | 41.17 C |
| ATOM | 4868 | NE | ARG | B | 605 | −8.989 | −4.432 | 27.891 | 1.00 | 67.13 N |
| ATOM | 4869 | CZ | ARG | B | 605 | −9.348 | −5.669 | 27.577 | 1.00 | 59.81 C |
| ATOM | 4870 | NH1 | ARG | B | 605 | −8.454 | −6.643 | 27.605 | 1.00 | 68.87 N |
| ATOM | 4871 | NH2 | ARG | B | 605 | −10.596 | −5.922 | 27.208 | 1.00 | 66.21 N |
| ATOM | 4872 | N | ASN | B | 606 | −4.117 | −2.008 | 23.724 | 1.00 | 39.12 N |
| ATOM | 4873 | CA | ASN | B | 606 | −2.821 | −2.326 | 23.121 | 1.00 | 42.10 C |
| ATOM | 4874 | C | ASN | B | 606 | −2.184 | −1.049 | 22.593 | 1.00 | 30.28 C |
| ATOM | 4875 | O | ASN | B | 606 | −1.264 | −1.096 | 21.797 | 1.00 | 38.05 O |
| ATOM | 4876 | CB | ASN | B | 606 | −2.982 | −3.340 | 21.977 | 1.00 | 23.30 C |
| ATOM | 4877 | CG | ASN | B | 606 | −3.807 | −2.796 | 20.799 | 1.00 | 51.06 C |
| ATOM | 4878 | OD1 | ASN | B | 606 | −4.215 | −1.617 | 20.787 | 1.00 | 33.43 O |
| ATOM | 4879 | ND2 | ASN | B | 606 | −4.047 | −3.662 | 19.789 | 1.00 | 31.97 N |
| ATOM | 4880 | N | GLY | B | 607 | −2.714 | 0.090 | 23.030 | 1.00 | 41.34 N |
| ATOM | 4881 | CA | GLY | B | 607 | −2.212 | 1.391 | 22.600 | 1.00 | 24.31 C |
| ATOM | 4882 | C | GLY | B | 607 | −2.774 | 1.904 | 21.272 | 1.00 | 27.67 C |
| ATOM | 4883 | O | GLY | B | 607 | −2.467 | 3.032 | 20.853 | 1.00 | 30.95 O |
| ATOM | 4884 | N | TYR | B | 608 | −3.575 | 1.083 | 20.595 | 1.00 | 21.09 N |
| ATOM | 4885 | CA | TYR | B | 608 | −4.135 | 1.493 | 19.302 | 1.00 | 28.28 C |
| ATOM | 4886 | C | TYR | B | 608 | −5.252 | 2.506 | 19.419 | 1.00 | 23.19 C |
| ATOM | 4887 | O | TYR | B | 608 | −5.236 | 3.538 | 18.742 | 1.00 | 35.97 O |
| ATOM | 4888 | CB | TYR | B | 608 | −4.688 | 0.284 | 18.532 | 1.00 | 28.81 C |
| ATOM | 4889 | CG | TYR | B | 608 | −3.663 | −0.539 | 17.782 | 1.00 | 32.59 C |
| ATOM | 4890 | CD1 | TYR | B | 608 | −2.330 | −0.571 | 18.180 | 1.00 | 28.39 C |
| ATOM | 4891 | CD2 | TYR | B | 608 | −4.050 | −1.325 | 16.704 | 1.00 | 32.09 C |
| ATOM | 4892 | CE1 | TYR | B | 608 | −1.411 | −1.366 | 17.516 | 1.00 | 41.48 C |
| ATOM | 4893 | CE2 | TYR | B | 608 | −3.151 | −2.119 | 16.039 | 1.00 | 43.31 C |
| ATOM | 4894 | CZ | TYR | B | 608 | −1.833 | −2.140 | 16.445 | 1.00 | 48.27 C |
| ATOM | 4895 | OH | TYR | B | 608 | −0.948 | −2.951 | 15.776 | 1.00 | 57.65 O |
| ATOM | 4896 | N | GLY | B | 609 | −6.224 | 2.183 | 20.277 | 1.00 | 29.89 N |
| ATOM | 4897 | CA | GLY | B | 609 | −7.392 | 3.020 | 20.470 | 1.00 | 26.87 C |
| ATOM | 4898 | C | GLY | B | 609 | −8.463 | 2.722 | 19.420 | 1.00 | 29.57 C |
| ATOM | 4899 | O | GLY | B | 609 | −8.187 | 2.113 | 18.394 | 1.00 | 28.77 O |
| ATOM | 4900 | N | SER | B | 610 | −9.691 | 3.150 | 19.675 | 1.00 | 30.34 N |
| ATOM | 4901 | CA | SER | B | 610 | −10.793 | 2.935 | 18.750 | 1.00 | 27.13 C |
| ATOM | 4902 | C | SER | B | 610 | −11.833 | 4.032 | 18.976 | 1.00 | 23.44 C |
| ATOM | 4903 | O | SER | B | 610 | −11.895 | 4.619 | 20.046 | 1.00 | 31.30 O |
| ATOM | 4904 | CB | SER | B | 610 | −11.430 | 1.560 | 18.970 | 1.00 | 21.59 C |
| ATOM | 4905 | OG | SER | B | 610 | −11.788 | 1.396 | 20.337 | 1.00 | 34.03 O |
| ATOM | 4906 | N | THR | B | 611 | −12.615 | 4.314 | 17.943 | 1.00 | 24.17 N |
| ATOM | 4907 | CA | THR | B | 611 | −13.651 | 5.321 | 18.014 | 1.00 | 25.33 C |
| ATOM | 4908 | C | THR | B | 611 | −14.552 | 5.004 | 19.210 | 1.00 | 21.88 C |
| ATOM | 4909 | O | THR | B | 611 | −14.981 | 3.866 | 19.376 | 1.00 | 23.51 O |
| ATOM | 4910 | CB | THR | B | 611 | −14.442 | 5.288 | 16.723 | 1.00 | 22.61 C |
| ATOM | 4911 | OG1 | THR | B | 611 | −13.543 | 5.591 | 15.652 | 1.00 | 20.91 O |
| ATOM | 4912 | CG2 | THR | B | 611 | −15.623 | 6.279 | 16.768 | 1.00 | 24.65 C |
| ATOM | 4913 | N | GLN | B | 612 | −14.778 | 5.998 | 20.059 | 1.00 | 20.41 N |
| ATOM | 4914 | CA | GLN | B | 612 | −15.610 | 5.836 | 21.255 | 1.00 | 25.27 C |
| ATOM | 4915 | C | GLN | B | 612 | −17.022 | 6.398 | 21.097 | 1.00 | 21.10 C |
| ATOM | 4916 | O | GLN | B | 612 | −17.199 | 7.505 | 20.600 | 1.00 | 27.77 O |
| ATOM | 4917 | CB | GLN | B | 612 | −14.931 | 6.504 | 22.472 | 1.00 | 26.03 C |
| ATOM | 4918 | CG | GLN | B | 612 | −13.602 | 5.891 | 22.849 | 1.00 | 24.76 C |
| ATOM | 4919 | CD | GLN | B | 612 | −13.735 | 4.395 | 23.096 | 1.00 | 40.49 C |
| ATOM | 4920 | OE1 | GLN | B | 612 | −14.484 | 3.969 | 23.974 | 1.00 | 22.23 O |
| ATOM | 4921 | NE2 | GLN | B | 612 | −13.021 | 3.590 | 22.307 | 1.00 | 30.04 N |
| ATOM | 4922 | N | TYR | B | 613 | −18.005 | 5.611 | 21.530 | 1.00 | 26.19 N |
| ATOM | 4923 | CA | TYR | B | 613 | −19.429 | 5.969 | 21.507 | 1.00 | 28.81 C |
| ATOM | 4924 | C | TYR | B | 613 | −19.913 | 6.130 | 22.952 | 1.00 | 28.89 C |
| ATOM | 4925 | O | TYR | B | 613 | −19.981 | 5.157 | 23.702 | 1.00 | 26.66 O |
| ATOM | 4926 | CB | TYR | B | 613 | −20.259 | 4.878 | 20.832 | 1.00 | 26.68 C |
| ATOM | 4927 | CG | TYR | B | 613 | −20.055 | 4.762 | 19.342 | 1.00 | 24.02 C |
| ATOM | 4928 | CD1 | TYR | B | 613 | −18.838 | 4.318 | 18.815 | 1.00 | 21.09 C |
| ATOM | 4929 | CD2 | TYR | B | 613 | −21.066 | 5.138 | 18.457 | 1.00 | 30.44 C |
| ATOM | 4930 | CE1 | TYR | B | 613 | −18.628 | 4.254 | 17.430 | 1.00 | 24.08 C |

TABLE 1-continued

| | | | | | | | | | | |
|---|---|---|---|---|---|---|---|---|---|---|
| ATOM | 4931 | CE2 | TYR | B | 613 | −20.876 | 5.081 | 17.064 | 1.00 | 35.03 C |
| ATOM | 4932 | CZ | TYR | B | 613 | −19.653 | 4.638 | 16.562 | 1.00 | 37.84 C |
| ATOM | 4933 | OH | TYR | B | 613 | −19.458 | 4.574 | 15.205 | 1.00 | 33.89 O |
| ATOM | 4934 | N | ILE | B | 614 | −20.213 | 7.362 | 23.353 | 1.00 | 25.39 N |
| ATOM | 4935 | CA | ILE | B | 614 | −20.671 | 7.594 | 24.701 | 1.00 | 18.50 C |
| ATOM | 4936 | C | ILE | B | 614 | −22.192 | 7.718 | 24.736 | 1.00 | 21.46 C |
| ATOM | 4937 | O | ILE | B | 614 | −22.743 | 8.595 | 24.098 | 1.00 | 22.90 O |
| ATOM | 4938 | CB | ILE | B | 614 | −20.057 | 8.880 | 25.275 | 1.00 | 27.61 C |
| ATOM | 4939 | CG1 | ILE | B | 614 | −18.521 | 8.745 | 25.364 | 1.00 | 23.96 C |
| ATOM | 4940 | CG2 | ILE | B | 614 | −20.692 | 9.191 | 26.624 | 1.00 | 25.35 C |
| ATOM | 4941 | CD1 | ILE | B | 614 | −17.796 | 10.045 | 25.741 | 1.00 | 15.45 C |
| ATOM | 4942 | N | ARG | B | 615 | −22.848 | 6.802 | 25.439 | 1.00 | 25.74 N |
| ATOM | 4943 | CA | ARG | B | 615 | −24.293 | 6.825 | 25.607 | 1.00 | 25.74 C |
| ATOM | 4944 | C | ARG | B | 615 | −24.454 | 7.842 | 26.728 | 1.00 | 25.17 C |
| ATOM | 4945 | O | ARG | B | 615 | −23.892 | 7.660 | 27.804 | 1.00 | 24.96 O |
| ATOM | 4946 | CB | ARG | B | 615 | −24.796 | 5.455 | 26.053 | 1.00 | 21.29 C |
| ATOM | 4947 | CG | ARG | B | 615 | −25.097 | 4.492 | 24.916 | 1.00 | 26.05 C |
| ATOM | 4948 | CD | ARG | B | 615 | −25.519 | 3.127 | 25.473 | 1.00 | 31.90 C |
| ATOM | 4949 | NE | ARG | B | 615 | −25.788 | 2.142 | 24.438 | 1.00 | 26.75 N |
| ATOM | 4950 | CZ | ARG | B | 615 | −26.113 | 0.884 | 24.712 | 1.00 | 43.97 C |
| ATOM | 4951 | NH1 | ARG | B | 615 | −26.194 | 0.499 | 25.977 | 1.00 | 37.90 N |
| ATOM | 4952 | NH2 | ARG | B | 615 | −26.350 | 0.009 | 23.741 | 1.00 | 26.99 N |
| ATOM | 4953 | N | PHE | B | 616 | −25.228 | 8.898 | 26.497 | 1.00 | 23.53 N |
| ATOM | 4954 | CA | PHE | B | 616 | −25.362 | 9.955 | 27.498 | 1.00 | 24.17 C |
| ATOM | 4955 | C | PHE | B | 616 | −26.590 | 10.794 | 27.270 | 1.00 | 29.46 C |
| ATOM | 4956 | O | PHE | B | 616 | −27.056 | 10.896 | 26.138 | 1.00 | 25.53 O |
| ATOM | 4957 | CB | PHE | B | 616 | −24.139 | 10.883 | 27.389 | 1.00 | 41.18 C |
| ATOM | 4958 | CG | PHE | B | 616 | −24.218 | 12.113 | 28.257 | 1.00 | 30.37 C |
| ATOM | 4959 | CD1 | PHE | B | 616 | −23.969 | 12.029 | 29.619 | 1.00 | 31.22 C |
| ATOM | 4960 | CD2 | PHE | B | 616 | −24.574 | 13.339 | 27.713 | 1.00 | 28.05 C |
| ATOM | 4961 | CE1 | PHE | B | 616 | −24.078 | 13.151 | 30.443 | 1.00 | 29.27 C |
| ATOM | 4962 | CE2 | PHE | B | 616 | −24.690 | 14.469 | 28.513 | 1.00 | 34.98 C |
| ATOM | 4963 | CZ | PHE | B | 616 | −24.437 | 14.379 | 29.891 | 1.00 | 29.29 C |
| ATOM | 4964 | N | SER | B | 617 | −27.114 | 11.409 | 28.330 | 1.00 | 35.27 N |
| ATOM | 4965 | CA | SER | B | 617 | −28.250 | 12.332 | 28.159 | 1.00 | 35.04 C |
| ATOM | 4966 | C | SER | B | 617 | −28.115 | 13.583 | 29.009 | 1.00 | 26.07 C |
| ATOM | 4967 | O | SER | B | 617 | −27.909 | 13.508 | 30.209 | 1.00 | 32.81 O |
| ATOM | 4968 | CB | SER | B | 617 | −29.603 | 11.678 | 28.472 | 1.00 | 47.12 C |
| ATOM | 4969 | OG | SER | B | 617 | −30.646 | 12.653 | 28.452 | 1.00 | 36.37 O |
| ATOM | 4970 | N | PRO | B | 618 | −28.215 | 14.763 | 28.386 | 1.00 | 25.70 N |
| ATOM | 4971 | CA | PRO | B | 618 | −28.107 | 15.990 | 29.160 | 1.00 | 34.06 C |
| ATOM | 4972 | C | PRO | B | 618 | −29.471 | 16.360 | 29.772 | 1.00 | 33.48 C |
| ATOM | 4973 | O | PRO | B | 618 | −29.570 | 17.328 | 30.509 | 1.00 | 31.34 O |
| ATOM | 4974 | CB | PRO | B | 618 | −27.649 | 17.002 | 28.118 | 1.00 | 42.48 C |
| ATOM | 4975 | CG | PRO | B | 618 | −28.379 | 16.560 | 26.907 | 1.00 | 35.77 C |
| ATOM | 4976 | CD | PRO | B | 618 | −28.264 | 15.055 | 26.941 | 1.00 | 28.53 C |
| ATOM | 4977 | N | ASP | B | 619 | −30.503 | 15.559 | 29.490 | 1.00 | 30.18 N |
| ATOM | 4978 | CA | ASP | B | 619 | −31.855 | 15.836 | 29.980 | 1.00 | 31.15 C |
| ATOM | 4979 | C | ASP | B | 619 | −32.264 | 15.259 | 31.344 | 1.00 | 47.72 C |
| ATOM | 4980 | O | ASP | B | 619 | −33.379 | 15.514 | 31.808 | 1.00 | 43.66 O |
| ATOM | 4981 | CB | ASP | B | 619 | −32.865 | 15.412 | 28.907 | 1.00 | 25.10 C |
| ATOM | 4982 | CG | ASP | B | 619 | −32.537 | 16.006 | 27.542 | 1.00 | 29.60 C |
| ATOM | 4983 | OD1 | ASP | B | 619 | −32.311 | 17.244 | 27.475 | 1.00 | 44.04 O |
| ATOM | 4984 | OD2 | ASP | B | 619 | −32.501 | 15.252 | 26.543 | 1.00 | 36.27 O |
| ATOM | 4985 | N | PHE | B | 620 | −31.382 | 14.495 | 31.988 | 1.00 | 27.59 N |
| ATOM | 4986 | CA | PHE | B | 620 | −31.681 | 13.928 | 33.307 | 1.00 | 24.07 C |
| ATOM | 4987 | C | PHE | B | 620 | −30.467 | 14.043 | 34.191 | 1.00 | 22.74 C |
| ATOM | 4988 | O | PHE | B | 620 | −29.365 | 14.235 | 33.697 | 1.00 | 35.87 O |
| ATOM | 4989 | CB | PHE | B | 620 | −32.043 | 12.440 | 33.215 | 1.00 | 27.91 C |
| ATOM | 4990 | CG | PHE | B | 620 | −33.139 | 12.138 | 32.229 | 1.00 | 30.47 C |
| ATOM | 4991 | CD1 | PHE | B | 620 | −32.866 | 12.048 | 30.879 | 1.00 | 22.24 C |
| ATOM | 4992 | CD2 | PHE | B | 620 | −34.455 | 11.968 | 32.655 | 1.00 | 38.13 C |
| ATOM | 4993 | CE1 | PHE | B | 620 | −33.878 | 11.788 | 29.967 | 1.00 | 22.18 C |
| ATOM | 4994 | CE2 | PHE | B | 620 | −35.490 | 11.705 | 31.733 | 1.00 | 26.40 C |
| ATOM | 4995 | CZ | PHE | B | 620 | −35.203 | 11.617 | 30.405 | 1.00 | 27.34 C |
| ATOM | 4996 | N | THR | B | 621 | −30.648 | 13.960 | 35.498 | 1.00 | 24.79 N |
| ATOM | 4997 | CA | THR | B | 621 | −29.485 | 13.984 | 36.385 | 1.00 | 27.11 C |
| ATOM | 4998 | C | THR | B | 621 | −29.866 | 13.219 | 37.649 | 1.00 | 42.53 C |
| ATOM | 4999 | O | THR | B | 621 | −31.039 | 12.924 | 37.852 | 1.00 | 31.94 O |
| ATOM | 5000 | CB | THR | B | 621 | −29.039 | 15.400 | 36.728 | 1.00 | 45.87 C |
| ATOM | 5001 | OG1 | THR | B | 621 | −27.695 | 15.361 | 37.222 | 1.00 | 27.32 O |
| ATOM | 5002 | CG2 | THR | B | 621 | −29.947 | 16.010 | 37.776 | 1.00 | 31.35 C |
| ATOM | 5003 | N | PHE | B | 622 | −28.884 | 12.902 | 38.485 | 1.00 | 31.10 N |
| ATOM | 5004 | CA | PHE | B | 622 | −29.132 | 12.112 | 39.683 | 1.00 | 31.86 C |
| ATOM | 5005 | C | PHE | B | 622 | −29.098 | 12.921 | 40.946 | 1.00 | 22.32 C |
| ATOM | 5006 | O | PHE | B | 622 | −28.273 | 13.813 | 41.105 | 1.00 | 35.75 O |
| ATOM | 5007 | CB | PHE | B | 622 | −28.069 | 11.011 | 39.864 | 1.00 | 29.03 C |
| ATOM | 5008 | CG | PHE | B | 622 | −27.818 | 10.173 | 38.649 | 1.00 | 43.88 C |
| ATOM | 5009 | CD1 | PHE | B | 622 | −27.152 | 10.704 | 37.538 | 1.00 | 52.37 C |

TABLE 1-continued

| | | | | | | | | | | |
|---|---|---|---|---|---|---|---|---|---|---|
| ATOM | 5010 | CD2 | PHE | B | 622 | −28.212 | 8.837 | 38.622 | 1.00 | 44.32 C |
| ATOM | 5011 | CE1 | PHE | B | 622 | −26.881 | 9.910 | 36.417 | 1.00 | 56.43 C |
| ATOM | 5012 | CE2 | PHE | B | 622 | −27.949 | 8.036 | 37.515 | 1.00 | 39.35 C |
| ATOM | 5013 | CZ | PHE | B | 622 | −27.279 | 8.577 | 36.406 | 1.00 | 56.86 C |
| ATOM | 5014 | N | GLY | B | 623 | −29.975 | 12.572 | 41.874 | 1.00 | 31.34 N |
| ATOM | 5015 | CA | GLY | B | 623 | −29.990 | 13.269 | 43.140 | 1.00 | 27.92 C |
| ATOM | 5016 | C | GLY | B | 623 | −29.252 | 12.452 | 44.197 | 1.00 | 47.38 C |
| ATOM | 5017 | O | GLY | B | 623 | −29.324 | 11.219 | 44.190 | 1.00 | 42.45 O |
| ATOM | 5018 | N | PHE | B | 624 | −28.573 | 13.141 | 45.089 | 1.00 | 42.56 N |
| ATOM | 5019 | CA | PHE | B | 624 | −27.825 | 12.515 | 46.172 | 1.00 | 39.37 C |
| ATOM | 5020 | C | PHE | B | 624 | −28.002 | 13.346 | 47.446 | 1.00 | 49.74 C |
| ATOM | 5021 | O | PHE | B | 624 | −28.576 | 14.443 | 47.418 | 1.00 | 45.99 O |
| ATOM | 5022 | CB | PHE | B | 624 | −26.343 | 12.363 | 45.822 | 1.00 | 33.04 C |
| ATOM | 5023 | CG | PHE | B | 624 | −25.602 | 13.654 | 45.565 | 1.00 | 43.40 C |
| ATOM | 5024 | CD1 | PHE | B | 624 | −25.637 | 14.243 | 44.308 | 1.00 | 27.02 C |
| ATOM | 5025 | CD2 | PHE | B | 624 | −24.885 | 14.268 | 46.576 | 1.00 | 39.31 C |
| ATOM | 5026 | CE1 | PHE | B | 624 | −24.965 | 15.420 | 44.051 | 1.00 | 34.23 C |
| ATOM | 5027 | CE2 | PHE | B | 624 | −24.183 | 15.444 | 46.324 | 1.00 | 44.39 C |
| ATOM | 5028 | CZ | PHE | B | 624 | −24.226 | 16.018 | 45.051 | 1.00 | 27.47 C |
| ATOM | 5029 | N | GLU | B | 625 | −27.497 | 12.835 | 48.566 | 1.00 | 50.98 N |
| ATOM | 5030 | CA | GLU | B | 625 | −27.593 | 13.514 | 49.854 | 1.00 | 44.18 C |
| ATOM | 5031 | C | GLU | B | 625 | −26.202 | 13.871 | 50.318 | 1.00 | 45.92 C |
| ATOM | 5032 | O | GLU | B | 625 | −25.233 | 13.221 | 49.950 | 1.00 | 51.64 O |
| ATOM | 5033 | CB | GLU | B | 625 | −28.230 | 12.607 | 50.898 | 1.00 | 40.22 C |
| ATOM | 5034 | CG | GLU | B | 625 | −29.734 | 12.499 | 50.839 | 1.00 | 41.00 C |
| ATOM | 5035 | CD | GLU | B | 625 | −30.300 | 11.492 | 51.814 | 1.00 | 74.55 C |
| ATOM | 5036 | OE1 | GLU | B | 625 | −29.849 | 11.478 | 52.987 | 1.00 | 77.38 O |
| ATOM | 5037 | OE2 | GLU | B | 625 | −31.207 | 10.724 | 51.414 | 1.00 | 69.96 O |
| ATOM | 5038 | N | GLU | B | 626 | −26.105 | 14.880 | 51.157 | 1.00 | 59.53 N |
| ATOM | 5039 | CA | GLU | B | 626 | −24.829 | 15.358 | 51.654 | 1.00 | 62.99 C |
| ATOM | 5040 | C | GLU | B | 626 | −25.070 | 16.687 | 52.343 | 1.00 | 74.87 C |
| ATOM | 5041 | O | GLU | B | 626 | −26.191 | 17.197 | 52.338 | 1.00 | 80.55 O |
| ATOM | 5042 | CB | GLU | B | 626 | −23.813 | 15.534 | 50.527 | 1.00 | 59.03 C |
| ATOM | 5043 | CG | GLU | B | 626 | −22.393 | 15.780 | 51.005 | 1.00 | 73.95 C |
| ATOM | 5044 | CD | GLU | B | 626 | −21.976 | 14.817 | 52.106 | 1.00 | 86.05 C |
| ATOM | 5045 | OE1 | GLU | B | 626 | −22.156 | 13.589 | 51.941 | 1.00 | 91.43 O |
| ATOM | 5046 | OE2 | GLU | B | 626 | −21.462 | 15.288 | 53.142 | 1.00 | 89.64 O |
| ATOM | 5047 | N | SER | B | 627 | −24.022 | 17.239 | 52.944 | 1.00 | 83.48 N |
| ATOM | 5048 | CA | SER | B | 627 | −24.111 | 18.525 | 53.628 | 1.00 | 81.60 C |
| ATOM | 5049 | C | SER | B | 627 | −22.884 | 18.710 | 54.502 | 1.00 | 85.41 C |
| ATOM | 5050 | O | SER | B | 627 | −22.843 | 18.232 | 55.638 | 1.00 | 89.95 O |
| ATOM | 5051 | CB | SER | B | 627 | −25.371 | 18.597 | 54.495 | 1.00 | 82.42 C |
| ATOM | 5052 | OG | SER | B | 627 | −25.584 | 19.912 | 54.985 | 1.00 | 87.77 O |
| ATOM | 5053 | N | LEU | B | 628 | −21.884 | 19.401 | 53.963 | 1.00 | 91.73 N |
| ATOM | 5054 | CA | LEU | B | 628 | −20.642 | 19.659 | 54.689 | 1.00 | 92.90 C |
| ATOM | 5055 | C | LEU | B | 628 | −20.910 | 20.550 | 55.913 | 1.00 | 93.31 C |
| ATOM | 5056 | O | LEU | B | 628 | −21.526 | 21.612 | 55.801 | 1.00 | 84.31 O |
| ATOM | 5057 | CB | LEU | B | 628 | −19.618 | 20.337 | 53.759 | 1.00 | 90.90 C |
| ATOM | 5058 | CG | LEU | B | 628 | −19.177 | 19.599 | 52.481 | 1.00 | 93.47 C |
| ATOM | 5059 | CD1 | LEU | B | 628 | −18.342 | 20.494 | 51.593 | 1.00 | 79.72 C |
| ATOM | 5060 | CD2 | LEU | B | 628 | −18.413 | 18.324 | 52.844 | 1.00 | 89.02 C |
| ATOM | 5061 | N | GLU | B | 629 | −20.448 | 20.128 | 57.084 | 1.00 | 96.11 N |
| ATOM | 5062 | CA | GLU | B | 629 | −20.660 | 20.929 | 58.280 | 1.00 | 90.93 C |
| ATOM | 5063 | C | GLU | B | 629 | −19.538 | 20.755 | 59.294 | 1.00 | 90.11 C |
| ATOM | 5064 | O | GLU | B | 629 | −19.113 | 19.635 | 59.594 | 1.00 | 90.78 O |
| ATOM | 5065 | CB | GLU | B | 629 | −22.031 | 20.635 | 58.906 | 1.00 | 94.04 C |
| ATOM | 5066 | CG | GLU | B | 629 | −23.223 | 21.113 | 58.072 | 1.00 | 92.95 C |
| ATOM | 5067 | CD | GLU | B | 629 | −24.563 | 21.020 | 58.796 | 1.00 | 94.75 C |
| ATOM | 5068 | OE1 | GLU | B | 629 | −24.671 | 21.586 | 59.903 | 1.00 | 89.08 O |
| ATOM | 5069 | OE2 | GLU | B | 629 | −25.486 | 20.386 | 58.246 | 1.00 | 101.94 O |
| ATOM | 5070 | N | VAL | B | 630 | −19.052 | 21.882 | 59.803 | 0.00 | 78.20 N |
| ATOM | 5071 | CA | VAL | B | 630 | −17.974 | 21.889 | 60.781 | 0.00 | 72.52 C |
| ATOM | 5072 | C | VAL | B | 630 | −18.387 | 21.114 | 62.025 | 0.00 | 69.70 C |
| ATOM | 5073 | O | VAL | B | 630 | −17.548 | 20.548 | 62.725 | 0.00 | 68.99 O |
| ATOM | 5074 | CB | VAL | B | 630 | −17.609 | 23.332 | 61.196 | 0.00 | 71.46 C |
| ATOM | 5075 | CG1 | VAL | B | 630 | −16.400 | 23.350 | 62.117 | 0.00 | 70.62 C |
| ATOM | 5076 | CG2 | VAL | B | 630 | −17.334 | 24.176 | 59.961 | 0.00 | 70.62 C |
| ATOM | 5077 | N | ASP | B | 631 | −19.689 | 21.089 | 62.289 | 0.00 | 66.91 N |
| ATOM | 5078 | CA | ASP | B | 631 | −20.222 | 20.393 | 63.452 | 0.00 | 64.49 C |
| ATOM | 5079 | C | ASP | B | 631 | −20.895 | 19.084 | 63.059 | 0.00 | 63.37 C |
| ATOM | 5080 | O | ASP | B | 631 | −20.985 | 18.749 | 61.877 | 0.00 | 63.08 O |
| ATOM | 5081 | CB | ASP | B | 631 | −21.230 | 21.287 | 64.172 | 0.00 | 63.64 C |
| ATOM | 5082 | CG | ASP | B | 631 | −20.670 | 22.659 | 64.478 | 0.00 | 62.91 C |
| ATOM | 5083 | OD1 | ASP | B | 631 | −19.667 | 22.741 | 65.217 | 0.00 | 62.50 O |
| ATOM | 5084 | OD2 | ASP | B | 631 | −21.232 | 23.656 | 63.979 | 0.00 | 62.50 O |
| ATOM | 5085 | N | THR | B | 632 | −21.367 | 18.350 | 64.061 | 0.00 | 62.30 N |
| ATOM | 5086 | CA | THR | B | 632 | −22.037 | 17.078 | 63.831 | 0.00 | 61.41 C |
| ATOM | 5087 | C | THR | B | 632 | −23.445 | 17.097 | 64.423 | 0.00 | 61.37 C |
| ATOM | 5088 | O | THR | B | 632 | −23.886 | 16.122 | 65.032 | 0.00 | 61.02 O |

TABLE 1-continued

| | | | | | | | | | | |
|---|---|---|---|---|---|---|---|---|---|---|
| ATOM | 5089 | CB | THR | B | 632 | −21.244 | 15.910 | 64.455 | 0.00 | 60.96 C |
| ATOM | 5090 | OG1 | THR | B | 632 | −21.137 | 16.103 | 65.870 | 0.00 | 60.57 O |
| ATOM | 5091 | CG2 | THR | B | 632 | −19.848 | 15.834 | 63.852 | 0.00 | 60.57 C |
| ATOM | 5092 | N | ASN | B | 633 | −24.143 | 18.217 | 64.242 | 0.00 | 61.65 N |
| ATOM | 5093 | CA | ASN | B | 633 | −25.507 | 18.375 | 64.744 | 0.00 | 62.58 C |
| ATOM | 5094 | C | ASN | B | 633 | −26.443 | 18.831 | 63.575 | 0.00 | 64.25 C |
| ATOM | 5095 | O | ASN | B | 633 | −26.788 | 19.996 | 63.417 | 0.00 | 63.69 O |
| ATOM | 5096 | CB | ASN | B | 633 | −25.526 | 19.387 | 65.887 | 0.00 | 61.10 C |
| ATOM | 5097 | CG | ASN | B | 633 | −24.714 | 18.919 | 67.081 | 0.00 | 60.27 C |
| ATOM | 5098 | OD1 | ASN | B | 633 | −24.967 | 17.849 | 67.637 | 0.00 | 59.82 O |
| ATOM | 5099 | ND2 | ASN | B | 633 | −23.729 | 19.715 | 67.478 | 0.00 | 59.82 N |
| ATOM | 5100 | N | PRO | B | 634 | −26.822 | 17.794 | 62.764 | 1.00 | 75.13 N |
| ATOM | 5101 | CA | PRO | B | 634 | −27.670 | 17.736 | 61.562 | 1.00 | 65.76 C |
| ATOM | 5102 | C | PRO | B | 634 | −29.173 | 17.582 | 61.854 | 1.00 | 59.92 C |
| ATOM | 5103 | O | PRO | B | 634 | −29.817 | 16.655 | 61.361 | 1.00 | 51.81 O |
| ATOM | 5104 | CB | PRO | B | 634 | −27.133 | 16.504 | 60.832 | 1.00 | 65.33 C |
| ATOM | 5105 | CG | PRO | B | 634 | −26.731 | 15.581 | 61.926 | 1.00 | 69.65 C |
| ATOM | 5106 | CD | PRO | B | 634 | −26.857 | 16.373 | 63.190 | 1.00 | 77.88 C |
| ATOM | 5107 | N | LEU | B | 635 | −29.732 | 18.495 | 62.643 | 1.00 | 64.33 N |
| ATOM | 5108 | CA | LEU | B | 635 | −31.155 | 18.440 | 62.994 | 1.00 | 60.28 C |
| ATOM | 5109 | C | LEU | B | 635 | −32.109 | 18.318 | 61.796 | 1.00 | 57.74 C |
| ATOM | 5110 | O | LEU | B | 635 | −33.069 | 17.555 | 61.848 | 1.00 | 47.22 O |
| ATOM | 5111 | CB | LEU | B | 635 | −31.547 | 19.672 | 63.821 | 1.00 | 70.23 C |
| ATOM | 5112 | CG | LEU | B | 635 | −32.964 | 19.701 | 64.409 | 1.00 | 67.83 C |
| ATOM | 5113 | CD1 | LEU | B | 635 | −33.141 | 18.625 | 65.475 | 1.00 | 70.64 C |
| ATOM | 5114 | CD2 | LEU | B | 635 | −33.262 | 21.082 | 64.971 | 1.00 | 69.29 C |
| ATOM | 5115 | N | LEU | B | 636 | −31.846 | 19.063 | 60.725 | 1.00 | 46.20 N |
| ATOM | 5116 | CA | LEU | B | 636 | −32.707 | 19.020 | 59.546 | 1.00 | 51.70 C |
| ATOM | 5117 | C | LEU | B | 636 | −32.403 | 17.897 | 58.564 | 1.00 | 60.80 C |
| ATOM | 5118 | O | LEU | B | 636 | −33.067 | 17.794 | 57.533 | 1.00 | 64.33 O |
| ATOM | 5119 | CB | LEU | B | 636 | −32.602 | 20.338 | 58.780 | 1.00 | 60.67 C |
| ATOM | 5120 | CG | LEU | B | 636 | −33.135 | 21.598 | 59.468 | 1.00 | 49.81 C |
| ATOM | 5121 | CD1 | LEU | B | 636 | −32.939 | 22.815 | 58.581 | 1.00 | 31.93 C |
| ATOM | 5122 | CD2 | LEU | B | 636 | −34.604 | 21.429 | 59.846 | 1.00 | 45.73 C |
| ATOM | 5123 | N | GLY | B | 637 | −31.407 | 17.067 | 58.870 | 1.00 | 52.68 N |
| ATOM | 5124 | CA | GLY | B | 637 | −31.058 | 15.984 | 57.974 | 1.00 | 52.94 C |
| ATOM | 5125 | C | GLY | B | 637 | −30.171 | 16.491 | 56.854 | 1.00 | 59.48 C |
| ATOM | 5126 | O | GLY | B | 637 | −29.976 | 17.700 | 56.718 | 1.00 | 61.73 O |
| ATOM | 5127 | N | ALA | B | 638 | −29.635 | 15.580 | 56.045 | 1.00 | 57.94 N |
| ATOM | 5128 | CA | ALA | B | 638 | −28.754 | 15.962 | 54.945 | 1.00 | 44.85 C |
| ATOM | 5129 | C | ALA | B | 638 | −29.521 | 16.664 | 53.845 | 1.00 | 42.46 C |
| ATOM | 5130 | O | ALA | B | 638 | −30.715 | 16.441 | 53.649 | 1.00 | 42.84 O |
| ATOM | 5131 | CB | ALA | B | 638 | −28.047 | 14.743 | 54.380 | 1.00 | 58.83 C |
| ATOM | 5132 | N | GLY | B | 639 | −28.822 | 17.540 | 53.142 | 1.00 | 52.12 N |
| ATOM | 5133 | CA | GLY | B | 639 | −29.443 | 18.266 | 52.057 | 1.00 | 50.07 C |
| ATOM | 5134 | C | GLY | B | 639 | −29.595 | 17.324 | 50.891 | 1.00 | 52.21 C |
| ATOM | 5135 | O | GLY | B | 639 | −28.898 | 16.306 | 50.799 | 1.00 | 61.35 O |
| ATOM | 5136 | N | LYS | B | 640 | −30.524 | 17.656 | 50.009 | 1.00 | 44.33 N |
| ATOM | 5137 | CA | LYS | B | 640 | −30.783 | 16.860 | 48.826 | 1.00 | 51.23 C |
| ATOM | 5138 | C | LYS | B | 640 | −30.288 | 17.667 | 47.623 | 1.00 | 55.44 C |
| ATOM | 5139 | O | LYS | B | 640 | −30.817 | 18.742 | 47.325 | 1.00 | 45.95 O |
| ATOM | 5140 | CB | LYS | B | 640 | −32.285 | 16.580 | 48.711 | 1.00 | 57.99 C |
| ATOM | 5141 | CG | LYS | B | 640 | −32.918 | 16.027 | 49.990 | 1.00 | 58.43 C |
| ATOM | 5142 | CD | LYS | B | 640 | −34.438 | 15.975 | 49.870 | 1.00 | 69.25 C |
| ATOM | 5143 | CE | LYS | B | 640 | −35.094 | 15.638 | 51.205 | 1.00 | 76.36 C |
| ATOM | 5144 | NZ | LYS | B | 640 | −34.732 | 14.276 | 51.698 | 1.00 | 69.41 N |
| ATOM | 5145 | N | PHE | B | 641 | −29.270 | 17.144 | 46.940 | 1.00 | 50.89 N |
| ATOM | 5146 | CA | PHE | B | 641 | −28.690 | 17.823 | 45.791 | 1.00 | 36.47 C |
| ATOM | 5147 | C | PHE | B | 641 | −28.720 | 17.028 | 44.493 | 1.00 | 47.43 C |
| ATOM | 5148 | O | PHE | B | 641 | −29.047 | 15.847 | 44.473 | 1.00 | 37.52 O |
| ATOM | 5149 | CB | PHE | B | 641 | −27.247 | 18.223 | 46.078 | 1.00 | 27.32 C |
| ATOM | 5150 | CG | PHE | B | 641 | −27.080 | 19.068 | 47.306 | 1.00 | 24.40 C |
| ATOM | 5151 | CD1 | PHE | B | 641 | −26.959 | 18.470 | 48.568 | 1.00 | 31.96 C |
| ATOM | 5152 | CD2 | PHE | B | 641 | −26.987 | 20.463 | 47.203 | 1.00 | 31.36 C |
| ATOM | 5153 | CE1 | PHE | B | 641 | −26.739 | 19.251 | 49.720 | 1.00 | 39.91 C |
| ATOM | 5154 | CE2 | PHE | B | 641 | −26.770 | 21.269 | 48.333 | 1.00 | 33.85 C |
| ATOM | 5155 | CZ | PHE | B | 641 | −26.643 | 20.668 | 49.601 | 1.00 | 49.13 C |
| ATOM | 5156 | N | ALA | B | 642 | −28.385 | 17.700 | 43.396 | 1.00 | 34.92 N |
| ATOM | 5157 | CA | ALA | B | 642 | −28.358 | 17.056 | 42.098 | 1.00 | 34.51 C |
| ATOM | 5158 | C | ALA | B | 642 | −26.953 | 17.180 | 41.525 | 1.00 | 28.52 C |
| ATOM | 5159 | O | ALA | B | 642 | −26.256 | 18.161 | 41.747 | 1.00 | 29.62 O |
| ATOM | 5160 | CB | ALA | B | 642 | −29.393 | 17.695 | 41.141 | 1.00 | 27.98 C |
| ATOM | 5161 | N | THR | B | 643 | −26.558 | 16.162 | 40.787 | 1.00 | 24.65 N |
| ATOM | 5162 | CA | THR | B | 643 | −25.246 | 16.120 | 40.162 | 1.00 | 32.26 C |
| ATOM | 5163 | C | THR | B | 643 | −25.214 | 16.994 | 38.915 | 1.00 | 33.39 C |
| ATOM | 5164 | O | THR | B | 643 | −26.103 | 16.921 | 38.066 | 1.00 | 31.21 O |
| ATOM | 5165 | CB | THR | B | 643 | −24.902 | 14.674 | 39.736 | 1.00 | 30.69 C |
| ATOM | 5166 | OG1 | THR | B | 643 | −24.649 | 13.893 | 40.908 | 1.00 | 30.54 O |
| ATOM | 5167 | CG2 | THR | B | 643 | −23.681 | 14.646 | 38.803 | 1.00 | 30.13 C |

TABLE 1-continued

| | | | | | | | | | | |
|---|---|---|---|---|---|---|---|---|---|---|
| ATOM | 5168 | N | ASP | B | 644 | −24.183 | 17.802 | 38.793 | 1.00 | 23.55 N |
| ATOM | 5169 | CA | ASP | B | 644 | −24.047 | 18.615 | 37.599 | 1.00 | 29.54 C |
| ATOM | 5170 | C | ASP | B | 644 | −23.700 | 17.705 | 36.408 | 1.00 | 28.55 C |
| ATOM | 5171 | O | ASP | B | 644 | −22.709 | 16.978 | 36.445 | 1.00 | 28.80 O |
| ATOM | 5172 | CB | ASP | B | 644 | −22.920 | 19.613 | 37.782 | 1.00 | 27.84 C |
| ATOM | 5173 | CG | ASP | B | 644 | −22.829 | 20.588 | 36.628 | 1.00 | 31.63 C |
| ATOM | 5174 | OD1 | ASP | B | 644 | −23.229 | 20.233 | 35.490 | 1.00 | 30.56 O |
| ATOM | 5175 | OD2 | ASP | B | 644 | −22.340 | 21.702 | 36.864 | 1.00 | 28.24 O |
| ATOM | 5176 | N | PRO | B | 645 | −24.496 | 17.757 | 35.333 | 1.00 | 22.37 N |
| ATOM | 5177 | CA | PRO | B | 645 | −24.334 | 16.971 | 34.102 | 1.00 | 28.94 C |
| ATOM | 5178 | C | PRO | B | 645 | −22.948 | 17.082 | 33.453 | 1.00 | 26.49 C |
| ATOM | 5179 | O | PRO | B | 645 | −22.494 | 16.167 | 32.781 | 1.00 | 29.67 O |
| ATOM | 5180 | CB | PRO | B | 645 | −25.406 | 17.550 | 33.180 | 1.00 | 22.31 C |
| ATOM | 5181 | CG | PRO | B | 645 | −26.432 | 18.031 | 34.113 | 1.00 | 34.04 C |
| ATOM | 5182 | CD | PRO | B | 645 | −25.636 | 18.673 | 35.212 | 1.00 | 27.86 C |
| ATOM | 5183 | N | ALA | B | 646 | −22.299 | 18.223 | 33.629 | 1.00 | 28.06 N |
| ATOM | 5184 | CA | ALA | B | 646 | −20.971 | 18.436 | 33.061 | 1.00 | 26.27 C |
| ATOM | 5185 | C | ALA | B | 646 | −19.940 | 17.483 | 33.685 | 1.00 | 28.38 C |
| ATOM | 5186 | O | ALA | B | 646 | −18.957 | 17.131 | 33.045 | 1.00 | 23.38 O |
| ATOM | 5187 | CB | ALA | B | 646 | −20.539 | 19.883 | 33.290 | 1.00 | 35.30 C |
| ATOM | 5188 | N | VAL | B | 647 | −20.163 | 17.107 | 34.945 | 1.00 | 30.88 N |
| ATOM | 5189 | CA | VAL | B | 647 | −19.280 | 16.201 | 35.659 | 1.00 | 33.32 C |
| ATOM | 5190 | C | VAL | B | 647 | −19.547 | 14.808 | 35.112 | 1.00 | 26.27 C |
| ATOM | 5191 | O | VAL | B | 647 | −18.613 | 14.075 | 34.815 | 1.00 | 23.64 O |
| ATOM | 5192 | CB | VAL | B | 647 | −19.536 | 16.244 | 37.197 | 1.00 | 32.21 C |
| ATOM | 5193 | CG1 | VAL | B | 647 | −18.672 | 15.220 | 37.908 | 1.00 | 26.87 C |
| ATOM | 5194 | CG2 | VAL | B | 647 | −19.193 | 17.632 | 37.746 | 1.00 | 32.61 C |
| ATOM | 5195 | N | THR | B | 648 | −20.827 | 14.482 | 34.923 | 1.00 | 32.15 N |
| ATOM | 5196 | CA | THR | B | 648 | −21.230 | 13.185 | 34.385 | 1.00 | 23.63 C |
| ATOM | 5197 | C | THR | B | 648 | −20.684 | 13.020 | 32.964 | 1.00 | 29.61 C |
| ATOM | 5198 | O | THR | B | 648 | −20.297 | 11.933 | 32.573 | 1.00 | 28.85 O |
| ATOM | 5199 | CB | THR | B | 648 | −22.784 | 13.034 | 34.345 | 1.00 | 26.42 C |
| ATOM | 5200 | OG1 | THR | B | 648 | −23.313 | 13.206 | 35.646 | 1.00 | 28.44 O |
| ATOM | 5201 | CG2 | THR | B | 648 | −23.191 | 11.668 | 33.880 | 1.00 | 30.17 C |
| ATOM | 5202 | N | LEU | B | 649 | −20.648 | 14.093 | 32.177 | 1.00 | 31.27 N |
| ATOM | 5203 | CA | LEU | B | 649 | −20.094 | 13.954 | 30.833 | 1.00 | 33.14 C |
| ATOM | 5204 | C | LEU | B | 649 | −18.561 | 13.879 | 30.943 | 1.00 | 19.85 C |
| ATOM | 5205 | O | LEU | B | 649 | −17.935 | 13.024 | 30.311 | 1.00 | 18.83 O |
| ATOM | 5206 | CB | LEU | B | 649 | −20.517 | 15.117 | 29.931 | 1.00 | 27.85 C |
| ATOM | 5207 | CG | LEU | B | 649 | −20.044 | 15.127 | 28.475 | 1.00 | 36.68 C |
| ATOM | 5208 | CD1 | LEU | B | 649 | −20.511 | 13.851 | 27.758 | 1.00 | 26.81 C |
| ATOM | 5209 | CD2 | LEU | B | 649 | −20.600 | 16.366 | 27.779 | 1.00 | 20.90 C |
| ATOM | 5210 | N | ALA | B | 650 | −17.957 | 14.731 | 31.771 | 1.00 | 15.42 N |
| ATOM | 5211 | CA | ALA | B | 650 | −16.494 | 14.685 | 31.881 | 1.00 | 29.38 C |
| ATOM | 5212 | C | ALA | B | 650 | −16.026 | 13.251 | 32.261 | 1.00 | 34.23 C |
| ATOM | 5213 | O | ALA | B | 650 | −15.020 | 12.739 | 31.747 | 1.00 | 25.52 O |
| ATOM | 5214 | CB | ALA | B | 650 | −16.009 | 15.679 | 32.902 | 1.00 | 19.40 C |
| ATOM | 5215 | N | HIS | B | 651 | −16.771 | 12.622 | 33.162 | 1.00 | 24.62 N |
| ATOM | 5216 | CA | HIS | B | 651 | −16.460 | 11.263 | 33.585 | 1.00 | 38.20 C |
| ATOM | 5217 | C | HIS | B | 651 | −16.338 | 10.331 | 32.360 | 1.00 | 26.34 C |
| ATOM | 5218 | O | HIS | B | 651 | −15.318 | 9.661 | 32.176 | 1.00 | 25.50 O |
| ATOM | 5219 | CB | HIS | B | 651 | −17.552 | 10.750 | 34.521 | 1.00 | 22.29 C |
| ATOM | 5220 | CG | HIS | B | 651 | −17.275 | 9.395 | 35.075 | 1.00 | 29.17 C |
| ATOM | 5221 | ND1 | HIS | B | 651 | −16.654 | 9.202 | 36.292 | 1.00 | 30.12 N |
| ATOM | 5222 | CD2 | HIS | B | 651 | −17.551 | 8.162 | 34.588 | 1.00 | 17.87 C |
| ATOM | 5223 | CE1 | HIS | B | 651 | −16.567 | 7.908 | 36.537 | 1.00 | 26.97 C |
| ATOM | 5224 | NE2 | HIS | B | 651 | −17.102 | 7.258 | 35.524 | 1.00 | 18.62 N |
| ATOM | 5225 | N | GLN | B | 652 | −17.375 | 10.304 | 31.526 | 1.00 | 18.67 N |
| ATOM | 5226 | CA | GLN | B | 652 | −17.368 | 9.483 | 30.333 | 1.00 | 17.94 C |
| ATOM | 5227 | C | GLN | B | 652 | −16.235 | 9.838 | 29.350 | 1.00 | 30.28 C |
| ATOM | 5228 | O | GLN | B | 652 | −15.652 | 8.952 | 28.715 | 1.00 | 24.08 O |
| ATOM | 5229 | CB | GLN | B | 652 | −18.707 | 9.605 | 29.611 | 1.00 | 22.50 C |
| ATOM | 5230 | CG | GLN | B | 652 | −19.842 | 9.130 | 30.454 | 1.00 | 27.76 C |
| ATOM | 5231 | CD | GLN | B | 652 | −19.660 | 7.681 | 30.846 | 1.00 | 34.90 C |
| ATOM | 5232 | OE1 | GLN | B | 652 | −20.136 | 7.235 | 31.877 | 1.00 | 38.31 O |
| ATOM | 5233 | NE2 | GLN | B | 652 | −18.983 | 6.934 | 30.002 | 1.00 | 47.78 N |
| ATOM | 5234 | N | LEU | B | 653 | −15.933 | 11.123 | 29.210 | 1.00 | 23.12 N |
| ATOM | 5235 | CA | LEU | B | 653 | −14.875 | 11.545 | 28.297 | 1.00 | 31.94 C |
| ATOM | 5236 | C | LEU | B | 653 | −13.492 | 11.078 | 28.804 | 1.00 | 24.10 C |
| ATOM | 5237 | O | LEU | B | 653 | −12.582 | 10.808 | 28.013 | 1.00 | 22.46 O |
| ATOM | 5238 | CB | LEU | B | 653 | −14.896 | 13.081 | 28.129 | 1.00 | 19.05 C |
| ATOM | 5239 | CG | LEU | B | 653 | −16.091 | 13.722 | 27.399 | 1.00 | 31.42 C |
| ATOM | 5240 | CD1 | LEU | B | 653 | −16.035 | 15.258 | 27.559 | 1.00 | 24.13 C |
| ATOM | 5241 | CD2 | LEU | B | 653 | −16.056 | 13.333 | 25.927 | 1.00 | 18.36 C |
| ATOM | 5242 | N | ILE | B | 654 | −13.336 | 11.006 | 30.122 | 1.00 | 22.87 N |
| ATOM | 5243 | CA | ILE | B | 654 | −12.076 | 10.558 | 30.690 | 1.00 | 12.29 C |
| ATOM | 5244 | C | ILE | B | 654 | −11.912 | 9.098 | 30.253 | 1.00 | 20.81 C |
| ATOM | 5245 | O | ILE | B | 654 | −10.834 | 8.700 | 29.853 | 1.00 | 18.05 O |
| ATOM | 5246 | CB | ILE | B | 654 | −12.078 | 10.695 | 32.228 | 1.00 | 21.74 C |

TABLE 1-continued

| | | | | | | | | | | |
|---|---|---|---|---|---|---|---|---|---|---|
| ATOM | 5247 | CG1 | ILE | B | 654 | −12.029 | 12.180 | 32.620 | 1.00 | 32.63 C |
| ATOM | 5248 | CG2 | ILE | B | 654 | −10.883 | 9.955 | 32.831 | 1.00 | 23.57 C |
| ATOM | 5249 | CD1 | ILE | B | 654 | −12.327 | 12.461 | 34.127 | 1.00 | 15.19 C |
| ATOM | 5250 | N | HIS | B | 655 | −12.982 | 8.309 | 30.317 | 1.00 | 17.30 N |
| ATOM | 5251 | CA | HIS | B | 655 | −12.898 | 6.928 | 29.858 | 1.00 | 24.21 C |
| ATOM | 5252 | C | HIS | B | 655 | −12.496 | 6.904 | 28.406 | 1.00 | 30.03 C |
| ATOM | 5253 | O | HIS | B | 655 | −11.740 | 6.038 | 27.988 | 1.00 | 22.21 O |
| ATOM | 5254 | CB | HIS | B | 655 | −14.246 | 6.212 | 29.943 | 1.00 | 19.04 C |
| ATOM | 5255 | CG | HIS | B | 655 | −14.560 | 5.709 | 31.304 | 1.00 | 32.93 C |
| ATOM | 5256 | ND1 | HIS | B | 655 | −13.745 | 4.817 | 31.964 | 1.00 | 30.05 N |
| ATOM | 5257 | CD2 | HIS | B | 655 | −15.542 | 6.040 | 32.170 | 1.00 | 30.44 C |
| ATOM | 5258 | CE1 | HIS | B | 655 | −14.204 | 4.626 | 33.184 | 1.00 | 27.30 C |
| ATOM | 5259 | NE2 | HIS | B | 655 | −15.292 | 5.360 | 33.336 | 1.00 | 37.59 N |
| ATOM | 5260 | N | ALA | B | 656 | −13.049 | 7.847 | 27.641 | 1.00 | 23.70 N |
| ATOM | 5261 | CA | ALA | B | 656 | −12.782 | 7.929 | 26.215 | 1.00 | 38.07 C |
| ATOM | 5262 | C | ALA | B | 656 | −11.297 | 8.233 | 25.980 | 1.00 | 24.68 C |
| ATOM | 5263 | O | ALA | B | 656 | −10.691 | 7.671 | 25.077 | 1.00 | 22.88 O |
| ATOM | 5264 | CB | ALA | B | 656 | −13.670 | 8.980 | 25.572 | 1.00 | 18.96 C |
| ATOM | 5265 | N | GLY | B | 657 | −10.748 | 9.138 | 26.773 | 1.00 | 20.02 N |
| ATOM | 5266 | CA | GLY | B | 657 | −9.325 | 9.432 | 26.678 | 1.00 | 24.87 C |
| ATOM | 5267 | C | GLY | B | 657 | −8.482 | 8.146 | 26.801 | 1.00 | 40.87 C |
| ATOM | 5268 | O | GLY | B | 657 | −7.640 | 7.851 | 25.944 | 1.00 | 31.20 O |
| ATOM | 5269 | N | HIS | B | 658 | −8.714 | 7.362 | 27.853 | 1.00 | 25.08 N |
| ATOM | 5270 | CA | HIS | B | 658 | −7.973 | 6.126 | 28.058 | 1.00 | 39.93 C |
| ATOM | 5271 | C | HIS | B | 658 | −8.081 | 5.191 | 26.861 | 1.00 | 28.68 C |
| ATOM | 5272 | O | HIS | B | 658 | −7.109 | 4.572 | 26.437 | 1.00 | 21.96 O |
| ATOM | 5273 | CB | HIS | B | 658 | −8.506 | 5.347 | 29.271 | 1.00 | 30.84 C |
| ATOM | 5274 | CG | HIS | B | 658 | −8.453 | 6.112 | 30.548 | 1.00 | 26.67 C |
| ATOM | 5275 | ND1 | HIS | B | 658 | −9.268 | 5.823 | 31.613 | 1.00 | 27.12 N |
| ATOM | 5276 | CD2 | HIS | B | 658 | −7.690 | 7.161 | 30.930 | 1.00 | 29.85 C |
| ATOM | 5277 | CE1 | HIS | B | 658 | −9.016 | 6.661 | 32.599 | 1.00 | 26.44 C |
| ATOM | 5278 | NE2 | HIS | B | 658 | −8.061 | 7.484 | 32.210 | 1.00 | 36.88 N |
| ATOM | 5279 | N | ARG | B | 659 | −9.296 | 5.052 | 26.364 | 1.00 | 23.59 N |
| ATOM | 5280 | CA | ARG | B | 659 | −9.555 | 4.147 | 25.272 | 1.00 | 21.75 C |
| ATOM | 5281 | C | ARG | B | 659 | −9.072 | 4.586 | 23.900 | 1.00 | 23.12 C |
| ATOM | 5282 | O | ARG | B | 659 | −8.708 | 3.737 | 23.083 | 1.00 | 24.83 O |
| ATOM | 5283 | CB | ARG | B | 659 | −11.042 | 3.828 | 25.228 | 1.00 | 19.09 C |
| ATOM | 5284 | CG | ARG | B | 659 | −11.536 | 3.170 | 26.494 | 1.00 | 31.86 C |
| ATOM | 5285 | CD | ARG | B | 659 | −13.095 | 3.118 | 26.581 | 1.00 | 23.95 C |
| ATOM | 5286 | NE | ARG | B | 659 | −13.495 | 1.843 | 27.153 | 1.00 | 50.79 N |
| ATOM | 5287 | CZ | ARG | B | 659 | −14.160 | 0.887 | 26.508 | 1.00 | 53.66 C |
| ATOM | 5288 | NH1 | ARG | B | 659 | −14.544 | 1.050 | 25.245 | 1.00 | 26.40 N |
| ATOM | 5289 | NH2 | ARG | B | 659 | −14.375 | −0.276 | 27.122 | 1.00 | 42.23 N |
| ATOM | 5290 | N | LEU | B | 660 | −9.106 | 5.890 | 23.626 | 1.00 | 23.40 N |
| ATOM | 5291 | CA | LEU | B | 660 | −8.652 | 6.394 | 22.341 | 1.00 | 20.29 C |
| ATOM | 5292 | C | LEU | B | 660 | −7.129 | 6.136 | 22.243 | 1.00 | 25.00 C |
| ATOM | 5293 | O | LEU | B | 660 | −6.613 | 5.897 | 21.166 | 1.00 | 21.79 O |
| ATOM | 5294 | CB | LEU | B | 660 | −8.957 | 7.897 | 22.213 | 1.00 | 18.61 C |
| ATOM | 5295 | CG | LEU | B | 660 | −10.409 | 8.247 | 21.846 | 1.00 | 21.93 C |
| ATOM | 5296 | CD1 | LEU | B | 660 | −10.640 | 9.708 | 22.004 | 1.00 | 18.35 C |
| ATOM | 5297 | CD2 | LEU | B | 660 | −10.678 | 7.823 | 20.390 | 1.00 | 20.59 C |
| ATOM | 5298 | N | TYR | B | 661 | −6.440 | 6.146 | 23.383 | 1.00 | 30.83 N |
| ATOM | 5299 | CA | TYR | B | 661 | −4.996 | 5.914 | 23.443 | 1.00 | 25.87 C |
| ATOM | 5300 | C | TYR | B | 661 | −4.630 | 4.467 | 23.761 | 1.00 | 29.21 C |
| ATOM | 5301 | O | TYR | B | 661 | −3.460 | 4.148 | 23.989 | 1.00 | 25.82 O |
| ATOM | 5302 | CB | TYR | B | 661 | −4.352 | 6.851 | 24.460 | 1.00 | 25.22 C |
| ATOM | 5303 | CG | TYR | B | 661 | −4.241 | 8.283 | 23.973 | 1.00 | 37.26 C |
| ATOM | 5304 | CD1 | TYR | B | 661 | −5.344 | 9.142 | 24.009 | 1.00 | 28.12 C |
| ATOM | 5305 | CD2 | TYR | B | 661 | −3.052 | 8.755 | 23.398 | 1.00 | 21.65 C |
| ATOM | 5306 | CE1 | TYR | B | 661 | −5.272 | 10.431 | 23.480 | 1.00 | 21.41 C |
| ATOM | 5307 | CE2 | TYR | B | 661 | −2.976 | 10.037 | 22.857 | 1.00 | 23.13 C |
| ATOM | 5308 | CZ | TYR | B | 661 | −4.090 | 10.869 | 22.900 | 1.00 | 23.02 C |
| ATOM | 5309 | OH | TYR | B | 661 | −4.034 | 12.126 | 22.352 | 1.00 | 27.98 O |
| ATOM | 5310 | N | GLY | B | 662 | −5.636 | 3.595 | 23.775 | 1.00 | 28.16 N |
| ATOM | 5311 | CA | GLY | B | 662 | −5.397 | 2.183 | 24.027 | 1.00 | 19.62 C |
| ATOM | 5312 | C | GLY | B | 662 | −4.698 | 1.856 | 25.337 | 1.00 | 29.62 C |
| ATOM | 5313 | O | GLY | B | 662 | −3.909 | 0.940 | 25.383 | 1.00 | 36.41 O |
| ATOM | 5314 | N | ILE | B | 663 | −4.997 | 2.575 | 26.410 | 1.00 | 30.84 N |
| ATOM | 5315 | CA | ILE | B | 663 | −4.364 | 2.295 | 27.687 | 1.00 | 29.39 C |
| ATOM | 5316 | C | ILE | B | 663 | −5.360 | 2.002 | 28.780 | 1.00 | 30.45 C |
| ATOM | 5317 | O | ILE | B | 663 | −5.067 | 2.191 | 29.962 | 1.00 | 38.66 O |
| ATOM | 5318 | CB | ILE | B | 663 | −3.460 | 3.442 | 28.161 | 1.00 | 25.28 C |
| ATOM | 5319 | CG1 | ILE | B | 663 | −4.250 | 4.726 | 28.321 | 1.00 | 24.28 C |
| ATOM | 5320 | CG2 | ILE | B | 663 | −2.290 | 3.652 | 27.166 | 1.00 | 28.70 C |
| ATOM | 5321 | CD1 | ILE | B | 663 | −3.421 | 5.861 | 28.974 | 1.00 | 20.74 C |
| ATOM | 5322 | N | ALA | B | 664 | −6.538 | 1.527 | 28.386 | 1.00 | 32.00 N |
| ATOM | 5323 | CA | ALA | B | 664 | −7.587 | 1.204 | 29.352 | 1.00 | 36.12 C |
| ATOM | 5324 | C | ALA | B | 664 | −7.177 | −0.060 | 30.081 | 1.00 | 43.99 C |
| ATOM | 5325 | O | ALA | B | 664 | −6.347 | −0.810 | 29.585 | 1.00 | 45.25 O |

TABLE 1-continued

| ATOM | 5326 | CB | ALA | B | 664 | -8.922 | 0.994 | 28.655 | 1.00 | 27.72 | C |
| ATOM | 5327 | N | ILE | B | 665 | -7.752 | -0.291 | 31.254 | 1.00 | 43.06 | N |
| ATOM | 5328 | CA | ILE | B | 665 | -7.426 | -1.466 | 32.038 | 1.00 | 39.67 | C |
| ATOM | 5329 | C | ILE | B | 665 | -8.566 | -2.422 | 31.935 | 1.00 | 43.01 | C |
| ATOM | 5330 | O | ILE | B | 665 | -9.720 | -2.020 | 32.043 | 1.00 | 44.24 | O |
| ATOM | 5331 | CB | ILE | B | 665 | -7.242 | -1.144 | 33.551 | 1.00 | 49.91 | C |
| ATOM | 5332 | CG1 | ILE | B | 665 | -6.161 | -0.082 | 33.751 | 1.00 | 42.66 | C |
| ATOM | 5333 | CG2 | ILE | B | 665 | -6.852 | -2.415 | 34.300 | 1.00 | 49.60 | C |
| ATOM | 5334 | CD1 | ILE | B | 665 | -4.849 | -0.441 | 33.121 | 1.00 | 51.85 | C |
| ATOM | 5335 | N | ASN | B | 666 | -8.257 | -3.696 | 31.744 | 1.00 | 46.89 | N |
| ATOM | 5336 | CA | ASN | B | 666 | -9.308 | -4.704 | 31.660 | 1.00 | 45.65 | C |
| ATOM | 5337 | C | ASN | B | 666 | -10.222 | -4.571 | 32.896 | 1.00 | 45.92 | C |
| ATOM | 5338 | O | ASN | B | 666 | -9.747 | -4.491 | 34.025 | 1.00 | 36.63 | O |
| ATOM | 5339 | CB | ASN | B | 666 | -8.672 | -6.092 | 31.638 | 1.00 | 44.55 | C |
| ATOM | 5340 | CG | ASN | B | 666 | -9.645 | -7.167 | 31.244 | 1.00 | 53.76 | C |
| ATOM | 5341 | OD1 | ASN | B | 666 | -10.782 | -7.214 | 31.730 | 1.00 | 61.69 | O |
| ATOM | 5342 | ND2 | ASN | B | 666 | -9.211 | -8.047 | 30.353 | 1.00 | 57.90 | N |
| ATOM | 5343 | N | PRO | B | 667 | -11.544 | -4.529 | 32.695 | 1.00 | 53.61 | N |
| ATOM | 5344 | CA | PRO | B | 667 | -12.422 | -4.403 | 33.867 | 1.00 | 57.66 | C |
| ATOM | 5345 | C | PRO | B | 667 | -12.437 | -5.580 | 34.854 | 1.00 | 60.98 | C |
| ATOM | 5346 | O | PRO | B | 667 | -13.005 | -5.465 | 35.942 | 1.00 | 41.21 | O |
| ATOM | 5347 | CB | PRO | B | 667 | -13.798 | -4.128 | 33.250 | 1.00 | 58.34 | C |
| ATOM | 5348 | CG | PRO | B | 667 | -13.705 | -4.727 | 31.890 | 1.00 | 54.64 | C |
| ATOM | 5349 | CD | PRO | B | 667 | -12.305 | -4.368 | 31.445 | 1.00 | 47.44 | C |
| ATOM | 5350 | N | ASN | B | 668 | -11.818 | -6.704 | 34.501 | 1.00 | 63.89 | N |
| ATOM | 5351 | CA | ASN | B | 668 | -11.798 | -7.823 | 35.440 | 1.00 | 67.24 | C |
| ATOM | 5352 | C | ASN | B | 668 | -10.756 | -7.545 | 36.518 | 1.00 | 60.69 | C |
| ATOM | 5353 | O | ASN | B | 668 | -10.695 | -8.231 | 37.535 | 1.00 | 59.06 | O |
| ATOM | 5354 | CB | ASN | B | 668 | -11.514 | -9.174 | 34.751 | 1.00 | 40.70 | C |
| ATOM | 5355 | CG | ASN | B | 668 | -10.117 | -9.277 | 34.154 | 1.00 | 63.99 | C |
| ATOM | 5356 | OD1 | ASN | B | 668 | -9.129 | -8.738 | 34.681 | 1.00 | 60.02 | O |
| ATOM | 5357 | ND2 | ASN | B | 668 | -10.024 | -10.015 | 33.050 | 1.00 | 66.67 | N |
| ATOM | 5358 | N | ARG | B | 669 | -9.940 | -6.526 | 36.290 | 1.00 | 56.51 | N |
| ATOM | 5359 | CA | ARG | B | 669 | -8.922 | -6.150 | 37.253 | 1.00 | 49.47 | C |
| ATOM | 5360 | C | ARG | B | 669 | -9.604 | -5.205 | 38.241 | 1.00 | 61.56 | C |
| ATOM | 5361 | O | ARG | B | 669 | -9.967 | -4.076 | 37.895 | 1.00 | 52.45 | O |
| ATOM | 5362 | CB | ARG | B | 669 | -7.756 | -5.481 | 36.527 | 1.00 | 37.62 | C |
| ATOM | 5363 | CG | ARG | B | 669 | -7.109 | -6.395 | 35.496 | 1.00 | 61.25 | C |
| ATOM | 5364 | CD | ARG | B | 669 | -6.428 | -7.564 | 36.186 | 1.00 | 64.85 | C |
| ATOM | 5365 | NE | ARG | B | 669 | -5.426 | -7.044 | 37.103 | 1.00 | 61.97 | N |
| ATOM | 5366 | CZ | ARG | B | 669 | -4.203 | -6.687 | 36.733 | 1.00 | 71.97 | C |
| ATOM | 5367 | NH1 | ARG | B | 669 | -3.825 | -6.815 | 35.467 | 1.00 | 62.82 | N |
| ATOM | 5368 | NH2 | ARG | B | 669 | -3.376 | -6.154 | 37.619 | 1.00 | 61.29 | N |
| ATOM | 5369 | N | VAL | B | 669 | -9.796 | -5.684 | 39.468 | 1.00 | 56.35 | N |
| ATOM | 5370 | CA | VAL | B | 670 | -10.478 | -4.905 | 40.491 | 1.00 | 44.88 | C |
| ATOM | 5371 | C | VAL | B | 670 | -9.727 | -4.857 | 41.822 | 1.00 | 63.84 | C |
| ATOM | 5372 | O | VAL | B | 670 | -8.854 | -5.687 | 42.078 | 1.00 | 61.33 | O |
| ATOM | 5373 | CB | VAL | B | 670 | -11.868 | -5.487 | 40.746 | 1.00 | 56.35 | C |
| ATOM | 5374 | CG1 | VAL | B | 670 | -12.543 | -5.811 | 39.428 | 1.00 | 38.64 | C |
| ATOM | 5375 | CG2 | VAL | B | 670 | -11.752 | -6.735 | 41.586 | 1.00 | 55.23 | C |
| ATOM | 5376 | N | PHE | B | 671 | -10.064 | -3.869 | 42.655 | 1.00 | 53.43 | N |
| ATOM | 5377 | CA | PHE | B | 671 | -9.451 | -3.716 | 43.968 | 1.00 | 46.15 | C |
| ATOM | 5378 | C | PHE | B | 671 | -10.553 | -3.691 | 45.006 | 1.00 | 57.16 | C |
| ATOM | 5379 | O | PHE | B | 671 | -11.637 | -3.165 | 44.759 | 1.00 | 48.76 | O |
| ATOM | 5380 | CB | PHE | B | 671 | -8.643 | -2.418 | 44.082 | 1.00 | 43.36 | C |
| ATOM | 5381 | CG | PHE | B | 671 | -7.472 | -2.336 | 43.149 | 1.00 | 56.40 | C |
| ATOM | 5382 | CD1 | PHE | B | 671 | -6.331 | -3.100 | 43.369 | 1.00 | 55.52 | C |
| ATOM | 5383 | CD2 | PHE | B | 671 | -7.504 | -1.477 | 42.050 | 1.00 | 55.09 | C |
| ATOM | 5384 | CE1 | PHE | B | 671 | -5.231 | -3.009 | 42.510 | 1.00 | 64.50 | C |
| ATOM | 5385 | CE2 | PHE | B | 671 | -6.414 | -1.377 | 41.186 | 1.00 | 66.18 | C |
| ATOM | 5386 | CZ | PHE | B | 671 | -5.274 | -2.146 | 41.416 | 1.00 | 67.22 | C |
| ATOM | 5387 | N | LYS | B | 672 | -10.270 | -4.278 | 46.165 | 1.00 | 70.78 | N |
| ATOM | 5388 | CA | LYS | B | 672 | -11.225 | -4.323 | 47.264 | 1.00 | 71.78 | C |
| ATOM | 5389 | C | LYS | B | 672 | -11.162 | -2.958 | 47.919 | 1.00 | 60.09 | C |
| ATOM | 5390 | O | LYS | B | 672 | -10.077 | -2.413 | 48.122 | 1.00 | 64.60 | O |
| ATOM | 5391 | CB | LYS | B | 672 | -10.828 | -5.426 | 48.259 | 1.00 | 67.85 | C |
| ATOM | 5392 | CG | LYS | B | 672 | -11.381 | -5.249 | 49.674 | 1.00 | 82.60 | C |
| ATOM | 5393 | CD | LYS | B | 672 | -12.912 | -5.357 | 49.759 | 1.00 | 85.14 | C |
| ATOM | 5394 | CE | LYS | B | 672 | -13.418 | -6.789 | 49.551 | 1.00 | 87.83 | C |
| ATOM | 5395 | NZ | LYS | B | 672 | -14.866 | -6.953 | 49.919 | 1.00 | 73.34 | N |
| ATOM | 5396 | N | VAL | B | 673 | -12.316 | -2.391 | 48.239 | 1.00 | 61.32 | N |
| ATOM | 5397 | CA | VAL | B | 673 | -12.291 | -1.041 | 48.853 | 1.00 | 80.90 | C |
| ATOM | 5398 | C | VAL | B | 673 | -12.820 | -1.000 | 50.278 | 1.00 | 78.21 | C |
| ATOM | 5399 | O | VAL | B | 673 | -13.495 | -0.021 | 50.612 | 1.00 | 84.08 | O |
| ATOM | 5400 | CB | VAL | B | 673 | -13.179 | -0.058 | 48.052 | 1.00 | 69.08 | C |
| ATOM | 5401 | CG1 | VAL | B | 673 | -12.504 | 0.331 | 46.745 | 1.00 | 77.65 | C |
| ATOM | 5402 | CG2 | VAL | B | 673 | -14.550 | -0.680 | 47.790 | 1.00 | 67.12 | C |
| ATOM | 5403 | N | ASN | B | 674 | -12.587 | -1.962 | 51.154 | 1.00 | 80.15 | N |
| ATOM | 5404 | CA | ASN | B | 674 | -13.239 | -1.716 | 52.436 | 1.00 | 86.71 | C |

TABLE 1-continued

| ATOM | 5405 | C   | ASN | B | 674 | −12.580 | −0.709  | 53.319 | 1.00 | 85.05 | C |
|------|------|-----|-----|---|-----|---------|---------|--------|------|-------|---|
| ATOM | 5406 | O   | ASN | B | 674 | −11.448 | −0.763  | 53.808 | 1.00 | 96.58 | O |
| ATOM | 5407 | CB  | ASN | B | 674 | −13.497 | −2.950  | 53.285 | 1.00 | 91.21 | C |
| ATOM | 5408 | CG  | ASN | B | 674 | −14.149 | −2.470  | 54.592 | 1.00 | 98.43 | C |
| ATOM | 5409 | OD1 | ASN | B | 674 | −14.816 | −3.232  | 55.293 | 1.00 | 96.68 | O |
| ATOM | 5410 | ND2 | ASN | B | 674 | −13.938 | −1.202  | 54.904 | 1.00 | 98.51 | N |
| ATOM | 5411 | N   | THR | B | 675 | −13.517 | 0.210   | 53.390 | 0.00 | 72.42 | N |
| ATOM | 5412 | CA  | THR | B | 675 | −13.645 | 1.433   | 54.052 | 0.00 | 65.70 | C |
| ATOM | 5413 | C   | THR | B | 675 | −15.036 | 1.288   | 54.652 | 0.00 | 62.62 | C |
| ATOM | 5414 | O   | THR | B | 675 | −16.025 | 1.697   | 54.034 | 0.00 | 61.74 | O |
| ATOM | 5415 | CB  | THR | B | 675 | −13.709 | 2.612   | 53.058 | 0.00 | 64.42 | C |
| ATOM | 5416 | OG1 | THR | B | 675 | −12.475 | 2.703   | 52.346 | 0.00 | 63.36 | O |
| ATOM | 5417 | CG2 | THR | B | 675 | −13.991 | 3.900   | 53.813 | 0.00 | 63.36 | C |
| ATOM | 5418 | N   | ASN | B | 676 | −15.137 | 0.694   | 55.838 | 0.00 | 59.58 | N |
| ATOM | 5419 | CA  | ASN | B | 676 | −16.429 | 0.474   | 56.519 | 0.00 | 56.99 | C |
| ATOM | 5420 | C   | ASN | B | 676 | −17.291 | −0.654  | 55.927 | 0.00 | 55.51 | C |
| ATOM | 5421 | O   | ASN | B | 676 | −18.504 | −0.501  | 55.790 | 0.00 | 55.27 | O |
| ATOM | 5422 | CB  | ASN | B | 676 | −17.275 | 1.753   | 56.534 | 0.00 | 56.50 | C |
| ATOM | 5423 | CG  | ASN | B | 676 | −16.668 | 2.851   | 57.377 | 0.00 | 56.05 | C |
| ATOM | 5424 | OD1 | ASN | B | 676 | −15.587 | 3.355   | 57.076 | 0.00 | 55.84 | O |
| ATOM | 5425 | ND2 | ASN | B | 676 | −17.364 | 3.231   | 58.443 | 0.00 | 55.84 | N |
| ATOM | 5426 | N   | ALA | B | 677 | −16.693 | −1.785  | 55.563 | 0.00 | 53.90 | N |
| ATOM | 5427 | CA  | ALA | B | 677 | −17.458 | −2.902  | 54.986 | 0.00 | 52.34 | C |
| ATOM | 5428 | C   | ALA | B | 677 | −16.648 | −4.199  | 55.043 | 0.00 | 51.30 | C |
| ATOM | 5429 | O   | ALA | B | 677 | −16.136 | −4.673  | 54.028 | 0.00 | 51.13 | O |
| ATOM | 5430 | CB  | ALA | B | 677 | −17.852 | −2.613  | 53.542 | 0.00 | 52.30 | C |
| ATOM | 5431 | N   | TYR | B | 678 | −16.538 | −4.788  | 56.231 | 0.00 | 50.11 | N |
| ATOM | 5432 | CA  | TYR | B | 678 | −15.750 | −6.005  | 56.404 | 0.00 | 48.99 | C |
| ATOM | 5433 | C   | TYR | B | 678 | −16.573 | −7.283  | 56.514 | 0.00 | 48.57 | C |
| ATOM | 5434 | O   | TYR | B | 678 | −16.109 | −8.266  | 57.093 | 0.00 | 48.46 | O |
| ATOM | 5435 | CB  | TYR | B | 678 | −14.866 | −5.896  | 57.655 | 0.00 | 48.39 | C |
| ATOM | 5436 | CG  | TYR | B | 678 | −13.994 | −4.661  | 57.734 | 0.00 | 47.74 | C |
| ATOM | 5437 | CD1 | TYR | B | 678 | −14.524 | −3.429  | 58.120 | 0.00 | 47.46 | C |
| ATOM | 5438 | CD2 | TYR | B | 678 | −12.632 | −4.728  | 57.441 | 0.00 | 47.46 | C |
| ATOM | 5439 | CE1 | TYR | B | 678 | −13.717 | −2.294  | 58.212 | 0.00 | 47.20 | C |
| ATOM | 5440 | CE2 | TYR | B | 678 | −11.818 | −3.600  | 57.530 | 0.00 | 47.20 | C |
| ATOM | 5441 | CZ  | TYR | B | 678 | −12.366 | −2.389  | 57.917 | 0.00 | 47.14 | C |
| ATOM | 5442 | OH  | TYR | B | 678 | −11.563 | −1.276  | 58.011 | 0.00 | 47.00 | O |
| ATOM | 5443 | N   | TYR | B | 679 | −17.782 | −7.286  | 55.965 | 0.00 | 48.14 | N |
| ATOM | 5444 | CA  | TYR | B | 679 | −18.619 | −8.476  | 56.056 | 0.00 | 47.80 | C |
| ATOM | 5445 | C   | TYR | B | 679 | −19.149 | −9.005  | 54.730 | 0.00 | 47.89 | C |
| ATOM | 5446 | O   | TYR | B | 679 | −18.981 | −8.385  | 53.679 | 0.00 | 47.83 | O |
| ATOM | 5447 | CB  | TYR | B | 679 | −19.790 | −8.219  | 57.008 | 0.00 | 47.29 | C |
| ATOM | 5448 | CG  | TYR | B | 679 | −19.365 | −7.936  | 58.432 | 0.00 | 46.78 | C |
| ATOM | 5449 | CD1 | TYR | B | 679 | −18.787 | −6.715  | 58.780 | 0.00 | 46.56 | C |
| ATOM | 5450 | CD2 | TYR | B | 679 | −19.522 | −8.898  | 59.429 | 0.00 | 46.56 | C |
| ATOM | 5451 | CE1 | TYR | B | 679 | −18.375 | −6.460  | 60.087 | 0.00 | 46.36 | C |
| ATOM | 5452 | CE2 | TYR | B | 679 | −19.113 | −8.654  | 60.737 | 0.00 | 46.36 | C |
| ATOM | 5453 | CZ  | TYR | B | 679 | −18.542 | −7.433  | 61.059 | 0.00 | 46.31 | C |
| ATOM | 5454 | OH  | TYR | B | 679 | −18.138 | −7.189  | 62.351 | 0.00 | 46.21 | O |
| ATOM | 5455 | N   | GLU | B | 680 | −19.790 | −10.169 | 54.803 | 0.00 | 48.10 | N |
| ATOM | 5456 | CA  | GLU | B | 680 | −20.365 | −10.835 | 53.640 | 0.00 | 48.42 | C |
| ATOM | 5457 | C   | GLU | B | 680 | −21.338 | −9.934  | 52.908 | 0.00 | 48.94 | C |
| ATOM | 5458 | O   | GLU | B | 680 | −21.305 | −9.833  | 51.681 | 0.00 | 48.89 | O |
| ATOM | 5459 | CB  | GLU | B | 680 | −21.102 | −12.100 | 54.070 | 0.00 | 48.03 | C |
| ATOM | 5460 | CG  | GLU | B | 680 | −20.240 | −13.111 | 54.787 | 0.00 | 47.58 | C |
| ATOM | 5461 | CD  | GLU | B | 680 | −21.045 | −14.286 | 55.294 | 0.00 | 47.34 | C |
| ATOM | 5462 | OE1 | GLU | B | 680 | −21.701 | −14.957 | 54.470 | 0.00 | 47.20 | O |
| ATOM | 5463 | OE2 | GLU | B | 680 | −21.024 | −14.536 | 56.517 | 0.00 | 47.20 | O |
| ATOM | 5464 | N   | MET | B | 681 | −22.216 | −9.288  | 53.668 | 0.00 | 49.68 | N |
| ATOM | 5465 | CA  | MET | B | 681 | −23.203 | −8.395  | 53.088 | 0.00 | 50.57 | C |
| ATOM | 5466 | C   | MET | B | 681 | −22.515 | −7.337  | 52.242 | 0.00 | 51.53 | C |
| ATOM | 5467 | O   | MET | B | 681 | −23.127 | −6.371  | 51.794 | 0.00 | 51.47 | O |
| ATOM | 5468 | CB  | MET | B | 681 | −24.031 | −7.727  | 54.191 | 0.00 | 50.18 | C |
| ATOM | 5469 | CG  | MET | B | 681 | −24.855 | −8.707  | 55.015 | 0.00 | 49.84 | C |
| ATOM | 5470 | SD  | MET | B | 681 | −25.908 | −7.913  | 56.247 | 0.00 | 49.61 | S |
| ATOM | 5471 | CE  | MET | B | 681 | −27.427 | −7.704  | 55.316 | 0.00 | 49.44 | C |
| ATOM | 5472 | N   | SER | B | 682 | −21.209 | −7.519  | 52.007 | 0.00 | 52.91 | N |
| ATOM | 5473 | CA  | SER | B | 682 | −20.534 | −6.503  | 51.219 | 0.00 | 54.59 | C |
| ATOM | 5474 | C   | SER | B | 682 | −19.158 | −6.759  | 50.623 | 0.00 | 56.38 | C |
| ATOM | 5475 | O   | SER | B | 682 | −18.211 | −6.077  | 50.982 | 0.00 | 55.99 | O |
| ATOM | 5476 | CB  | SER | B | 682 | −20.419 | −5.253  | 52.100 | 0.00 | 54.07 | C |
| ATOM | 5477 | OG  | SER | B | 682 | −19.966 | −5.600  | 53.399 | 0.00 | 53.81 | O |
| ATOM | 5478 | N   | GLY | B | 683 | −19.046 | −7.687  | 49.711 | 0.00 | 59.09 | N |
| ATOM | 5479 | CA  | GLY | B | 683 | −17.795 | −7.714  | 49.057 | 0.00 | 63.16 | C |
| ATOM | 5480 | C   | GLY | B | 683 | −17.786 | −6.371  | 48.367 | 0.00 | 66.27 | C |
| ATOM | 5481 | O   | GLY | B | 683 | −18.782 | −5.972  | 47.759 | 0.00 | 65.83 | O |
| ATOM | 5482 | N   | LEU | B | 684 | −16.667 | −5.682  | 48.433 | 1.00 | 77.24 | N |
| ATOM | 5483 | CA  | LEU | B | 684 | −16.550 | −4.433  | 47.734 | 1.00 | 74.24 | C |

TABLE 1-continued

| ATOM | 5484 | C | LEU | B | 684 | −15.246 | −4.318 | 46.967 | 1.00 | 71.08 | C |
| --- | --- | --- | --- | --- | --- | --- | --- | --- | --- | --- | --- |
| ATOM | 5485 | O | LEU | B | 684 | −14.206 | −4.010 | 47.529 | 1.00 | 69.39 | O |
| ATOM | 5486 | CB | LEU | B | 684 | −16.727 | −3.249 | 48.678 | 1.00 | 77.81 | C |
| ATOM | 5487 | CG | LEU | B | 684 | −18.126 | −2.629 | 48.655 | 1.00 | 85.06 | C |
| ATOM | 5488 | CD1 | LEU | B | 684 | −18.156 | −1.332 | 49.438 | 1.00 | 68.95 | C |
| ATOM | 5489 | CD2 | LEU | B | 684 | −18.581 | −2.408 | 47.217 | 1.00 | 69.00 | C |
| ATOM | 5490 | N | GLU | B | 685 | −15.352 | −4.564 | 45.668 | 1.00 | 72.85 | N |
| ATOM | 5491 | CA | GLU | B | 685 | −14.210 | −4.469 | 44.779 | 1.00 | 71.18 | C |
| ATOM | 5492 | C | GLU | B | 685 | −14.609 | −3.650 | 43.564 | 1.00 | 73.25 | C |
| ATOM | 5493 | O | GLU | B | 685 | −15.408 | −4.084 | 42.742 | 1.00 | 66.53 | O |
| ATOM | 5494 | CB | GLU | B | 685 | −13.687 | −5.852 | 44.361 | 1.00 | 70.08 | C |
| ATOM | 5495 | CG | GLU | B | 685 | −14.626 | −7.025 | 44.612 | 1.00 | 85.91 | C |
| ATOM | 5496 | CD | GLU | B | 685 | −15.742 | −7.126 | 43.584 | 1.00 | 99.93 | C |
| ATOM | 5497 | OE1 | GLU | B | 685 | −16.591 | −6.202 | 43.529 | 1.00 | 99.90 | O |
| ATOM | 5498 | OE2 | GLU | B | 685 | −15.765 | −8.133 | 42.832 | 1.00 | 96.26 | O |
| ATOM | 5499 | N | VAL | B | 686 | −14.027 | −2.464 | 43.495 | 1.00 | 69.51 | N |
| ATOM | 5500 | CA | VAL | B | 686 | −14.263 | −1.546 | 42.403 | 1.00 | 48.70 | C |
| ATOM | 5501 | C | VAL | B | 686 | −13.167 | −1.786 | 41.374 | 1.00 | 45.14 | C |
| ATOM | 5502 | O | VAL | B | 686 | −12.016 | −2.035 | 41.728 | 1.00 | 39.98 | O |
| ATOM | 5503 | CB | VAL | B | 686 | −14.195 | −0.111 | 42.912 | 1.00 | 50.97 | C |
| ATOM | 5504 | CG1 | VAL | B | 686 | −14.473 | 0.860 | 41.778 | 1.00 | 60.67 | C |
| ATOM | 5505 | CG2 | VAL | B | 686 | −15.193 | 0.062 | 44.039 | 1.00 | 46.59 | C |
| ATOM | 5506 | N | SER | B | 687 | −13.517 | −1.704 | 40.099 | 1.00 | 47.74 | N |
| ATOM | 5507 | CA | SER | B | 687 | −12.533 | −1.939 | 39.071 | 1.00 | 39.06 | C |
| ATOM | 5508 | C | SER | B | 687 | −11.488 | −0.837 | 39.083 | 1.00 | 38.29 | C |
| ATOM | 5509 | O | SER | B | 687 | −11.772 | 0.308 | 39.465 | 1.00 | 38.43 | O |
| ATOM | 5510 | CB | SER | B | 687 | −13.204 | −2.011 | 37.704 | 1.00 | 47.27 | C |
| ATOM | 5511 | OG | SER | B | 687 | −13.730 | −0.756 | 37.348 | 1.00 | 49.64 | O |
| ATOM | 5512 | N | PHE | B | 688 | −10.275 | −1.223 | 38.702 | 1.00 | 28.60 | N |
| ATOM | 5513 | CA | PHE | B | 688 | −9.123 | −0.338 | 38.601 | 1.00 | 30.55 | C |
| ATOM | 5514 | C | PHE | B | 688 | −9.509 | 0.848 | 37.676 | 1.00 | 43.80 | C |
| ATOM | 5515 | O | PHE | B | 688 | −9.216 | 2.014 | 37.988 | 1.00 | 34.80 | O |
| ATOM | 5516 | CB | PHE | B | 688 | −7.972 | −1.154 | 38.002 | 1.00 | 33.62 | C |
| ATOM | 5517 | CG | PHE | B | 688 | −6.626 | −0.481 | 38.028 | 1.00 | 43.75 | C |
| ATOM | 5518 | CD1 | PHE | B | 688 | −6.491 | 0.884 | 38.237 | 1.00 | 42.88 | C |
| ATOM | 5519 | CD2 | PHE | B | 688 | −5.481 | −1.226 | 37.754 | 1.00 | 42.83 | C |
| ATOM | 5520 | CE1 | PHE | B | 688 | −5.232 | 1.503 | 38.164 | 1.00 | 56.68 | C |
| ATOM | 5521 | CE2 | PHE | B | 688 | −4.224 | −0.623 | 37.678 | 1.00 | 42.52 | C |
| ATOM | 5522 | CZ | PHE | B | 688 | −4.098 | 0.741 | 37.880 | 1.00 | 48.41 | C |
| ATOM | 5523 | N | GLU | B | 689 | −10.172 | 0.546 | 36.552 | 1.00 | 39.02 | N |
| ATOM | 5524 | CA | GLU | B | 689 | −10.610 | 1.586 | 35.598 | 1.00 | 47.04 | C |
| ATOM | 5525 | C | GLU | B | 689 | −11.398 | 2.714 | 36.262 | 1.00 | 27.02 | C |
| ATOM | 5526 | O | GLU | B | 689 | −11.090 | 3.884 | 36.052 | 1.00 | 34.63 | O |
| ATOM | 5527 | CB | GLU | B | 689 | −11.457 | 0.986 | 34.472 | 1.00 | 40.38 | C |
| ATOM | 5528 | CG | GLU | B | 689 | −10.757 | 0.901 | 33.106 | 1.00 | 55.51 | C |
| ATOM | 5529 | CD | GLU | B | 689 | −10.266 | 2.246 | 32.559 | 1.00 | 59.37 | C |
| ATOM | 5530 | OE1 | GLU | B | 689 | −11.097 | 3.119 | 32.208 | 1.00 | 48.40 | O |
| ATOM | 5531 | OE2 | GLU | B | 689 | −9.030 | 2.422 | 32.469 | 1.00 | 54.36 | O |
| ATOM | 5532 | N | GLU | B | 690 | −12.407 | 2.357 | 37.065 | 1.00 | 39.77 | N |
| ATOM | 5533 | CA | GLU | B | 690 | −13.232 | 3.338 | 37.780 | 1.00 | 25.17 | C |
| ATOM | 5534 | C | GLU | B | 690 | −12.521 | 4.141 | 38.846 | 1.00 | 50.93 | C |
| ATOM | 5535 | O | GLU | B | 690 | −12.725 | 5.361 | 38.961 | 1.00 | 37.63 | O |
| ATOM | 5536 | CB | GLU | B | 690 | −14.409 | 2.684 | 38.495 | 1.00 | 33.10 | C |
| ATOM | 5537 | CG | GLU | B | 690 | −15.517 | 2.211 | 37.635 | 1.00 | 35.77 | C |
| ATOM | 5538 | CD | GLU | B | 690 | −15.953 | 3.240 | 36.625 | 1.00 | 31.47 | C |
| ATOM | 5539 | OE1 | GLU | B | 690 | −16.364 | 4.338 | 37.018 | 1.00 | 45.62 | O |
| ATOM | 5540 | OE2 | GLU | B | 690 | −15.885 | 2.933 | 35.427 | 1.00 | 47.77 | O |
| ATOM | 5541 | N | LEU | B | 691 | −11.736 | 3.460 | 39.674 | 1.00 | 30.62 | N |
| ATOM | 5542 | CA | LEU | B | 691 | −11.056 | 4.170 | 40.743 | 1.00 | 26.09 | C |
| ATOM | 5543 | C | LEU | B | 691 | −10.140 | 5.225 | 40.161 | 1.00 | 26.71 | C |
| ATOM | 5544 | O | LEU | B | 691 | −10.021 | 6.333 | 40.686 | 1.00 | 39.49 | O |
| ATOM | 5545 | CB | LEU | B | 691 | −10.275 | 3.182 | 41.629 | 1.00 | 24.11 | C |
| ATOM | 5546 | CG | LEU | B | 691 | −11.155 | 2.187 | 42.410 | 1.00 | 43.34 | C |
| ATOM | 5547 | CD1 | LEU | B | 691 | −10.273 | 1.068 | 43.027 | 1.00 | 51.69 | C |
| ATOM | 5548 | CD2 | LEU | B | 691 | −11.946 | 2.942 | 43.499 | 1.00 | 31.65 | C |
| ATOM | 5549 | N | ARG | B | 692 | −9.492 | 4.887 | 39.062 | 1.00 | 26.56 | N |
| ATOM | 5550 | CA | ARG | B | 692 | −8.590 | 5.825 | 38.441 | 1.00 | 26.97 | C |
| ATOM | 5551 | C | ARG | B | 692 | −9.360 | 6.972 | 37.772 | 1.00 | 23.73 | C |
| ATOM | 5552 | O | ARG | B | 692 | −8.931 | 8.120 | 37.803 | 1.00 | 37.49 | O |
| ATOM | 5553 | CB | ARG | B | 692 | −7.730 | 5.100 | 37.408 | 1.00 | 40.49 | C |
| ATOM | 5554 | CG | ARG | B | 692 | −7.520 | 5.881 | 36.135 | 1.00 | 41.02 | C |
| ATOM | 5555 | CD | ARG | B | 692 | −6.861 | 5.040 | 35.065 | 1.00 | 47.78 | C |
| ATOM | 5556 | NE | ARG | B | 692 | −5.565 | 4.554 | 35.517 | 1.00 | 73.13 | N |
| ATOM | 5557 | CZ | ARG | B | 692 | −4.705 | 3.899 | 34.745 | 1.00 | 66.68 | C |
| ATOM | 5558 | NH1 | ARG | B | 692 | −5.018 | 3.666 | 33.485 | 1.00 | 34.08 | N |
| ATOM | 5559 | NH2 | ARG | B | 692 | −3.546 | 3.470 | 35.244 | 1.00 | 52.53 | N |
| ATOM | 5560 | N | THR | B | 693 | −10.488 | 6.660 | 37.157 | 1.00 | 25.87 | N |
| ATOM | 5561 | CA | THR | B | 693 | −11.297 | 7.686 | 36.499 | 1.00 | 24.91 | C |
| ATOM | 5562 | C | THR | B | 693 | −11.872 | 8.690 | 37.504 | 1.00 | 26.70 | C |

TABLE 1-continued

| ATOM | 5563 | O | THR | B | 693 | −11.848 | 9.883 | 37.260 | 1.00 | 23.19 | O |
|---|---|---|---|---|---|---|---|---|---|---|---|
| ATOM | 5564 | CB | THR | B | 693 | −12.427 | 7.028 | 35.702 | 1.00 | 32.34 | C |
| ATOM | 5565 | OG1 | THR | B | 693 | −11.834 | 6.289 | 34.642 | 1.00 | 39.33 | O |
| ATOM | 5566 | CG2 | THR | B | 693 | −13.403 | 8.069 | 35.098 | 1.00 | 40.88 | C |
| ATOM | 5567 | N | PHE | B | 694 | −12.379 | 8.213 | 38.630 | 1.00 | 26.49 | N |
| ATOM | 5568 | CA | PHE | B | 694 | −12.922 | 9.119 | 39.646 | 1.00 | 32.83 | C |
| ATOM | 5569 | C | PHE | B | 694 | −11.804 | 9.874 | 40.360 | 1.00 | 34.28 | C |
| ATOM | 5570 | O | PHE | B | 694 | −11.954 | 11.052 | 40.700 | 1.00 | 36.32 | O |
| ATOM | 5571 | CB | PHE | B | 694 | −13.718 | 8.360 | 40.707 | 1.00 | 44.27 | C |
| ATOM | 5572 | CG | PHE | B | 694 | −14.315 | 9.268 | 41.762 | 1.00 | 63.02 | C |
| ATOM | 5573 | CD1 | PHE | B | 694 | −15.619 | 9.763 | 41.620 | 1.00 | 59.33 | C |
| ATOM | 5574 | CD2 | PHE | B | 694 | −13.560 | 9.670 | 42.867 | 1.00 | 55.43 | C |
| ATOM | 5575 | CE1 | PHE | B | 694 | −16.158 | 10.643 | 42.561 | 1.00 | 56.37 | C |
| ATOM | 5576 | CE2 | PHE | B | 694 | −14.084 | 10.549 | 43.813 | 1.00 | 62.10 | C |
| ATOM | 5577 | CZ | PHE | B | 694 | −15.390 | 11.037 | 43.659 | 1.00 | 64.96 | C |
| ATOM | 5578 | N | GLY | B | 695 | −10.692 | 9.181 | 40.602 | 1.00 | 27.66 | N |
| ATOM | 5579 | CA | GLY | B | 695 | −9.550 | 9.793 | 41.268 | 1.00 | 29.39 | C |
| ATOM | 5580 | C | GLY | B | 695 | −9.780 | 10.209 | 42.710 | 1.00 | 29.85 | C |
| ATOM | 5581 | O | GLY | B | 695 | −10.524 | 9.575 | 43.440 | 1.00 | 38.66 | O |
| ATOM | 5582 | N | GLY | B | 696 | −9.131 | 11.290 | 43.116 | 1.00 | 41.87 | N |
| ATOM | 5583 | CA | GLY | B | 696 | −9.294 | 11.780 | 44.468 | 1.00 | 46.96 | C |
| ATOM | 5584 | C | GLY | B | 696 | −9.013 | 10.748 | 45.555 | 1.00 | 58.96 | C |
| ATOM | 5585 | O | GLY | B | 696 | −8.193 | 9.838 | 45.398 | 1.00 | 48.40 | O |
| ATOM | 5586 | N | HIS | B | 697 | −9.712 | 10.896 | 46.667 | 1.00 | 43.94 | N |
| ATOM | 5587 | CA | HIS | B | 697 | −9.537 | 9.997 | 47.783 | 1.00 | 61.70 | C |
| ATOM | 5588 | C | HIS | B | 697 | −9.747 | 8.532 | 47.439 | 1.00 | 59.31 | C |
| ATOM | 5589 | O | HIS | B | 697 | −9.333 | 7.667 | 48.189 | 1.00 | 51.24 | O |
| ATOM | 5590 | CB | HIS | B | 697 | −10.457 | 10.423 | 48.921 | 1.00 | 50.95 | C |
| ATOM | 5591 | CG | HIS | B | 697 | −9.945 | 11.607 | 49.681 | 1.00 | 65.93 | C |
| ATOM | 5592 | ND1 | HIS | B | 697 | −8.743 | 11.589 | 50.360 | 1.00 | 77.97 | N |
| ATOM | 5593 | CD2 | HIS | B | 697 | −10.461 | 12.845 | 49.865 | 1.00 | 67.18 | C |
| ATOM | 5594 | CE1 | HIS | B | 697 | −8.541 | 12.764 | 50.929 | 1.00 | 53.33 | C |
| ATOM | 5595 | NE2 | HIS | B | 697 | −9.569 | 13.543 | 50.645 | 1.00 | 74.36 | N |
| ATOM | 5596 | N | ASP | B | 698 | −10.373 | 8.248 | 46.300 | 1.00 | 59.69 | N |
| ATOM | 5597 | CA | ASP | B | 698 | −10.604 | 6.860 | 45.912 | 1.00 | 55.52 | C |
| ATOM | 5598 | C | ASP | B | 698 | −9.462 | 6.273 | 45.094 | 1.00 | 49.04 | C |
| ATOM | 5599 | O | ASP | B | 698 | −9.428 | 5.080 | 44.863 | 1.00 | 61.34 | O |
| ATOM | 5600 | CB | ASP | B | 698 | −11.912 | 6.722 | 45.127 | 1.00 | 55.46 | C |
| ATOM | 5601 | CG | ASP | B | 698 | −13.118 | 7.144 | 45.935 | 1.00 | 67.49 | C |
| ATOM | 5602 | OD1 | ASP | B | 698 | −13.277 | 6.639 | 47.060 | 1.00 | 70.75 | O |
| ATOM | 5603 | OD2 | ASP | B | 698 | −13.908 | 7.980 | 45.452 | 1.00 | 75.41 | O |
| ATOM | 5604 | N | ALA | B | 699 | −8.523 | 7.103 | 44.659 | 1.00 | 54.26 | N |
| ATOM | 5605 | CA | ALA | B | 699 | −7.404 | 6.593 | 43.873 | 1.00 | 68.87 | C |
| ATOM | 5606 | C | ALA | B | 699 | −6.277 | 6.100 | 44.779 | 1.00 | 63.82 | C |
| ATOM | 5607 | O | ALA | B | 699 | −5.192 | 5.755 | 44.309 | 1.00 | 55.23 | O |
| ATOM | 5608 | CB | ALA | B | 699 | −6.883 | 7.669 | 42.922 | 1.00 | 56.16 | C |
| ATOM | 5609 | N | LYS | B | 700 | −6.532 | 6.069 | 46.081 | 1.00 | 63.26 | N |
| ATOM | 5610 | CA | LYS | B | 700 | −5.516 | 5.608 | 47.017 | 1.00 | 59.86 | C |
| ATOM | 5611 | C | LYS | B | 700 | −5.663 | 4.132 | 47.328 | 1.00 | 64.89 | C |
| ATOM | 5612 | O | LYS | B | 700 | −4.818 | 3.541 | 48.004 | 1.00 | 58.48 | O |
| ATOM | 5613 | CB | LYS | B | 700 | −5.559 | 6.431 | 48.302 | 1.00 | 61.07 | C |
| ATOM | 5614 | CG | LYS | B | 700 | −4.605 | 7.627 | 48.253 | 1.00 | 81.37 | C |
| ATOM | 5615 | CD | LYS | B | 700 | −3.154 | 7.176 | 47.985 | 1.00 | 80.11 | C |
| ATOM | 5616 | CE | LYS | B | 700 | −2.193 | 8.363 | 47.881 | 1.00 | 86.87 | C |
| ATOM | 5617 | NZ | LYS | B | 700 | −2.531 | 9.262 | 46.736 | 1.00 | 79.03 | N |
| ATOM | 5618 | N | PHE | B | 701 | −6.734 | 3.541 | 46.808 | 1.00 | 47.21 | N |
| ATOM | 5619 | CA | PHE | B | 701 | −7.004 | 2.139 | 47.015 | 1.00 | 37.51 | C |
| ATOM | 5620 | C | PHE | B | 701 | −6.412 | 1.325 | 45.880 | 1.00 | 57.95 | C |
| ATOM | 5621 | O | PHE | B | 701 | −6.542 | 0.102 | 45.832 | 1.00 | 58.48 | O |
| ATOM | 5622 | CB | PHE | B | 701 | −8.504 | 1.926 | 47.095 | 1.00 | 36.25 | C |
| ATOM | 5623 | CG | PHE | B | 701 | −9.145 | 2.663 | 48.229 | 1.00 | 55.27 | C |
| ATOM | 5624 | CD1 | PHE | B | 701 | −8.710 | 2.459 | 49.542 | 1.00 | 56.47 | C |
| ATOM | 5625 | CD2 | PHE | B | 701 | −10.188 | 3.553 | 47.999 | 1.00 | 59.88 | C |
| ATOM | 5626 | CE1 | PHE | B | 701 | −9.303 | 3.124 | 50.612 | 1.00 | 56.52 | C |
| ATOM | 5627 | CE2 | PHE | B | 701 | −10.790 | 4.226 | 49.061 | 1.00 | 62.45 | C |
| ATOM | 5628 | CZ | PHE | B | 701 | −10.343 | 4.007 | 50.375 | 1.00 | 61.32 | C |
| ATOM | 5629 | N | ILE | B | 702 | −5.751 | 2.009 | 44.961 | 1.00 | 54.97 | N |
| ATOM | 5630 | CA | ILE | B | 702 | −5.146 | 1.332 | 43.832 | 1.00 | 57.72 | C |
| ATOM | 5631 | C | ILE | B | 702 | −3.712 | 0.907 | 44.103 | 1.00 | 48.13 | C |
| ATOM | 5632 | O | ILE | B | 702 | −2.859 | 1.747 | 44.359 | 1.00 | 49.95 | O |
| ATOM | 5633 | CB | ILE | B | 702 | −5.172 | 2.228 | 42.581 | 1.00 | 52.98 | C |
| ATOM | 5634 | CG1 | ILE | B | 702 | −6.622 | 2.343 | 42.073 | 1.00 | 63.90 | C |
| ATOM | 5635 | CG2 | ILE | B | 702 | −4.237 | 1.649 | 41.513 | 1.00 | 56.42 | C |
| ATOM | 5636 | CD1 | ILE | B | 702 | −6.803 | 3.139 | 40.801 | 1.00 | 44.84 | C |
| ATOM | 5637 | N | ASP | B | 703 | −3.453 | −0.395 | 44.029 | 1.00 | 51.86 | N |
| ATOM | 5638 | CA | ASP | B | 703 | −2.110 | −0.934 | 44.256 | 1.00 | 53.62 | C |
| ATOM | 5639 | C | ASP | B | 703 | −1.071 | −0.175 | 43.429 | 1.00 | 55.67 | C |
| ATOM | 5640 | O | ASP | B | 703 | −1.154 | −0.121 | 42.199 | 1.00 | 52.53 | O |
| ATOM | 5641 | CB | ASP | B | 703 | −2.083 | −2.422 | 43.882 | 1.00 | 74.43 | C |

TABLE 1-continued

| | | | | | | | | | | |
|---|---|---|---|---|---|---|---|---|---|---|
| ATOM | 5642 | CG | ASP | B | 703 | −0.735 | −3.084 | 44.175 | 1.00 | 72.41 | C |
| ATOM | 5643 | OD1 | ASP | B | 703 | −0.277 | −2.758 | 43.505 | 1.00 | 72.38 | O |
| ATOM | 5644 | OD2 | ASP | B | 703 | −0.693 | −3.939 | 45.085 | 1.00 | 72.49 | O |
| ATOM | 5645 | N | SER | B | 704 | −0.088 | 0.403 | 44.101 | 1.00 | 51.28 | N |
| ATOM | 5646 | CA | SER | B | 704 | 0.950 | 1.156 | 43.409 | 1.00 | 69.60 | C |
| ATOM | 5647 | C | SER | B | 704 | 1.740 | 0.310 | 42.412 | 1.00 | 64.00 | C |
| ATOM | 5648 | O | SER | B | 704 | 1.943 | 0.720 | 41.274 | 1.00 | 67.58 | O |
| ATOM | 5649 | CB | SER | B | 704 | 1.913 | 1.791 | 44.419 | 1.00 | 73.41 | C |
| ATOM | 5650 | OG | SER | B | 704 | 1.271 | 2.816 | 45.161 | 1.00 | 71.79 | O |
| ATOM | 5651 | N | LEU | B | 705 | 2.180 | −0.870 | 42.828 | 1.00 | 67.56 | N |
| ATOM | 5652 | CA | LEU | B | 705 | 2.954 | −1.724 | 41.934 | 1.00 | 73.24 | C |
| ATOM | 5653 | C | LEU | B | 705 | 2.177 | −2.056 | 40.672 | 1.00 | 72.16 | C |
| ATOM | 5654 | O | LEU | B | 705 | 2.644 | −1.780 | 39.565 | 1.00 | 61.97 | O |
| ATOM | 5655 | CB | LEU | B | 705 | 3.378 | −3.005 | 42.648 | 1.00 | 67.25 | C |
| ATOM | 5656 | CG | LEU | B | 705 | 4.422 | −2.750 | 43.737 | 1.00 | 72.06 | C |
| ATOM | 5657 | CD1 | LEU | B | 705 | 4.793 | −4.065 | 44.410 | 1.00 | 75.30 | C |
| ATOM | 5658 | CD2 | LEU | B | 705 | 5.650 | −2.089 | 43.118 | 1.00 | 73.71 | C |
| ATOM | 5659 | N | GLN | B | 706 | 1.000 | −2.652 | 40.836 | 1.00 | 64.57 | N |
| ATOM | 5660 | CA | GLN | B | 706 | 0.159 | −2.978 | 39.693 | 1.00 | 66.81 | C |
| ATOM | 5661 | C | GLN | B | 706 | 0.023 | −1.754 | 38.794 | 1.00 | 65.19 | C |
| ATOM | 5662 | O | GLN | B | 706 | 0.017 | −1.864 | 37.571 | 1.00 | 73.40 | O |
| ATOM | 5663 | CB | GLN | B | 706 | −1.224 | −3.406 | 40.152 | 1.00 | 53.40 | C |
| ATOM | 5664 | CG | GLN | B | 706 | −1.268 | −4.767 | 40.757 | 1.00 | 61.29 | C |
| ATOM | 5665 | CD | GLN | B | 706 | −2.671 | −5.166 | 41.100 | 1.00 | 79.26 | C |
| ATOM | 5666 | OE1 | GLN | B | 706 | −3.557 | −5.140 | 40.243 | 1.00 | 82.25 | O |
| ATOM | 5667 | NE2 | GLN | B | 706 | −2.897 | −5.534 | 42.360 | 1.00 | 79.87 | N |
| ATOM | 5668 | N | GLU | B | 707 | −0.084 | −0.586 | 39.414 | 1.00 | 54.79 | N |
| ATOM | 5669 | CA | GLU | B | 707 | −0.215 | 0.651 | 38.675 | 1.00 | 59.87 | C |
| ATOM | 5670 | C | GLU | B | 707 | 1.058 | 0.855 | 37.875 | 1.00 | 53.21 | C |
| ATOM | 5671 | O | GLU | B | 707 | 1.030 | 1.238 | 36.709 | 1.00 | 55.25 | O |
| ATOM | 5672 | CB | GLU | B | 707 | −0.424 | 1.806 | 39.650 | 1.00 | 56.80 | C |
| ATOM | 5673 | CG | GLU | B | 707 | −0.796 | 3.123 | 39.001 | 1.00 | 64.14 | C |
| ATOM | 5674 | CD | GLU | B | 707 | −1.157 | 4.187 | 40.035 | 1.00 | 80.95 | C |
| ATOM | 5675 | OE1 | GLU | B | 707 | −0.246 | 4.682 | 40.745 | 1.00 | 80.11 | O |
| ATOM | 5676 | OE2 | GLU | B | 707 | −2.358 | 4.522 | 40.145 | 1.00 | 77.50 | O |
| ATOM | 5677 | N | ASN | B | 708 | 2.182 | 0.578 | 38.520 | 1.00 | 67.09 | N |
| ATOM | 5678 | CA | ASN | B | 708 | 3.488 | 0.736 | 37.896 | 1.00 | 54.67 | C |
| ATOM | 5679 | C | ASN | B | 708 | 3.658 | −0.248 | 36.235 | 1.00 | 46.58 | C |
| ATOM | 5680 | O | ASN | B | 708 | 4.188 | 0.101 | 35.682 | 1.00 | 47.39 | O |
| ATOM | 5681 | CB | ASN | B | 708 | 4.587 | 0.512 | 38.939 | 1.00 | 53.94 | C |
| ATOM | 5682 | CG | ASN | B | 708 | 5.914 | 1.103 | 38.518 | 1.00 | 71.88 | C |
| ATOM | 5683 | OD1 | ASN | B | 708 | 6.974 | 0.652 | 38.963 | 1.00 | 84.12 | O |
| ATOM | 5684 | ND2 | ASN | B | 708 | 5.868 | 2.133 | 37.665 | 1.00 | 64.05 | N |
| ATOM | 5685 | N | GLU | B | 709 | 3.200 | −1.478 | 36.928 | 1.00 | 36.28 | N |
| ATOM | 5686 | CA | GLU | B | 709 | 3.309 | −2.470 | 35.884 | 1.00 | 41.47 | C |
| ATOM | 5687 | C | GLU | B | 709 | 2.574 | −2.052 | 34.614 | 1.00 | 58.67 | C |
| ATOM | 5688 | O | GLU | B | 709 | 3.116 | −2.186 | 33.514 | 1.00 | 50.31 | O |
| ATOM | 5689 | CB | GLU | B | 709 | 2.785 | −3.809 | 36.389 | 1.00 | 51.03 | C |
| ATOM | 5690 | CG | GLU | B | 709 | 3.834 | −4.580 | 37.197 | 1.00 | 72.34 | C |
| ATOM | 5691 | CD | GLU | B | 709 | 3.221 | −5.525 | 38.210 | 1.00 | 80.29 | C |
| ATOM | 5692 | OE1 | GLU | B | 709 | 2.342 | −6.329 | 37.824 | 1.00 | 80.79 | O |
| ATOM | 5693 | OE2 | GLU | B | 709 | 3.621 | −5.460 | 39.394 | 1.00 | 84.71 | O |
| ATOM | 5694 | N | PHE | B | 710 | 1.351 | −1.541 | 34.763 | 1.00 | 47.57 | N |
| ATOM | 5695 | CA | PHE | B | 710 | 0.571 | −1.107 | 33.608 | 1.00 | 36.55 | C |
| ATOM | 5696 | C | PHE | B | 710 | 1.254 | 0.021 | 32.826 | 1.00 | 21.25 | C |
| ATOM | 5697 | O | PHE | B | 710 | 1.285 | 0.013 | 31.606 | 1.00 | 39.64 | O |
| ATOM | 5698 | CB | PHE | B | 710 | −0.834 | −0.707 | 34.059 | 1.00 | 28.66 | C |
| ATOM | 5699 | CG | PHE | B | 710 | −1.780 | −1.869 | 34.137 | 1.00 | 30.08 | C |
| ATOM | 5700 | CD1 | PHE | B | 710 | −2.138 | −2.554 | 32.986 | 1.00 | 30.61 | C |
| ATOM | 5701 | CD2 | PHE | B | 710 | −2.272 | −2.302 | 35.350 | 1.00 | 28.14 | C |
| ATOM | 5702 | CE1 | PHE | B | 710 | −2.986 | −3.652 | 33.040 | 1.00 | 47.78 | C |
| ATOM | 5703 | CE2 | PHE | B | 710 | −3.117 | −3.390 | 35.420 | 1.00 | 42.33 | C |
| ATOM | 5704 | CZ | PHE | B | 710 | −3.473 | −4.077 | 34.257 | 1.00 | 40.99 | C |
| ATOM | 5705 | N | ARG | B | 711 | 1.810 | 0.988 | 33.524 | 1.00 | 29.92 | N |
| ATOM | 5706 | CA | ARG | B | 711 | 2.509 | 2.061 | 32.833 | 1.00 | 41.00 | C |
| ATOM | 5707 | C | ARG | B | 711 | 3.658 | 1.496 | 31.977 | 1.00 | 55.78 | C |
| ATOM | 5708 | O | ARG | B | 711 | 3.931 | 2.008 | 30.886 | 1.00 | 53.18 | O |
| ATOM | 5709 | CB | ARG | B | 711 | 3.084 | 3.060 | 33.842 | 1.00 | 27.73 | C |
| ATOM | 5710 | CG | ARG | B | 711 | 3.915 | 4.147 | 33.206 | 1.00 | 34.12 | C |
| ATOM | 5711 | CD | ARG | B | 711 | 4.184 | 5.298 | 34.161 | 1.00 | 47.94 | C |
| ATOM | 5712 | NE | ARG | B | 711 | 5.610 | 5.606 | 34.250 | 1.00 | 79.71 | N |
| ATOM | 5713 | CZ | ARG | B | 711 | 6.526 | 4.791 | 34.779 | 1.00 | 88.85 | C |
| ATOM | 5714 | NH1 | ARG | B | 711 | 6.167 | 3.608 | 35.270 | 1.00 | 82.81 | N |
| ATOM | 5715 | NH2 | ARG | B | 711 | 7.804 | 5.159 | 34.827 | 1.00 | 77.02 | N |
| ATOM | 5716 | N | LEU | B | 712 | 4.324 | 0.447 | 32.473 | 1.00 | 40.77 | N |
| ATOM | 5717 | CA | LEU | B | 712 | 5.455 | −0.154 | 31.767 | 1.00 | 42.90 | C |
| ATOM | 5718 | C | LEU | B | 712 | 4.917 | −0.940 | 30.578 | 1.00 | 33.15 | C |
| ATOM | 5719 | O | LEU | B | 712 | 5.432 | −0.870 | 29.480 | 1.00 | 36.88 | O |
| ATOM | 5720 | CB | LEU | B | 712 | 6.221 | −1.090 | 32.704 | 1.00 | 48.58 | C |

TABLE 1-continued

| | | | | | | | | | | |
|---|---|---|---|---|---|---|---|---|---|---|
| ATOM | 5721 | CG | LEU | B | 712 | 7.738 | −1.191 | 32.500 | 1.00 | 69.59 C |
| ATOM | 5722 | CD1 | LEU | B | 712 | 8.074 | −1.794 | 31.128 | 1.00 | 48.04 C |
| ATOM | 5723 | CD2 | LEU | B | 712 | 8.344 | 0.208 | 32.669 | 1.00 | 65.91 C |
| ATOM | 5724 | N | TYR | B | 713 | 3.870 | −1.694 | 30.830 | 1.00 | 32.06 N |
| ATOM | 5725 | CA | TYR | B | 713 | 3.225 | −2.471 | 29.804 | 1.00 | 36.09 C |
| ATOM | 5726 | C | TYR | B | 713 | 2.741 | −1.520 | 28.674 | 1.00 | 48.14 C |
| ATOM | 5727 | O | TYR | B | 713 | 2.975 | −1.782 | 27.503 | 1.00 | 50.19 O |
| ATOM | 5728 | CB | TYR | B | 713 | 2.047 | −3.211 | 30.434 | 1.00 | 28.32 C |
| ATOM | 5729 | CG | TYR | B | 713 | 1.180 | −4.003 | 29.475 | 1.00 | 40.97 C |
| ATOM | 5730 | CD1 | TYR | B | 713 | 1.466 | −5.336 | 29.193 | 1.00 | 46.17 C |
| ATOM | 5731 | CD2 | TYR | B | 713 | 0.069 | −3.419 | 28.853 | 1.00 | 42.67 C |
| ATOM | 5732 | CE1 | TYR | B | 713 | 0.678 | −6.079 | 28.316 | 1.00 | 37.80 C |
| ATOM | 5733 | CE2 | TYR | B | 713 | −0.743 | −4.159 | 27.968 | 1.00 | 32.88 C |
| ATOM | 5734 | CZ | TYR | B | 713 | −0.420 | −5.482 | 27.712 | 1.00 | 40.25 C |
| ATOM | 5735 | OH | TYR | B | 713 | −1.155 | −6.213 | 26.844 | 1.00 | 35.73 O |
| ATOM | 5736 | N | TYR | B | 714 | 2.095 | −0.405 | 28.999 | 1.00 | 37.73 N |
| ATOM | 5737 | CA | TYR | B | 714 | 1.632 | 0.460 | 27.903 | 1.00 | 42.13 C |
| ATOM | 5738 | C | TYR | B | 714 | 2.763 | 1.184 | 27.213 | 1.00 | 24.51 C |
| ATOM | 5739 | O | TYR | B | 714 | 2.681 | 1.436 | 26.012 | 1.00 | 36.65 O |
| ATOM | 5740 | CB | TYR | B | 714 | 0.531 | 1.444 | 28.369 | 1.00 | 23.24 C |
| ATOM | 5741 | CG | TYR | B | 714 | −0.788 | 0.712 | 28.567 | 1.00 | 32.16 C |
| ATOM | 5742 | CD1 | TYR | B | 714 | −1.367 | 0.013 | 27.508 | 1.00 | 31.53 C |
| ATOM | 5743 | CD2 | TYR | B | 714 | −1.377 | 0.593 | 29.837 | 1.00 | 31.71 C |
| ATOM | 5744 | CE1 | TYR | B | 714 | −2.470 | −0.792 | 27.701 | 1.00 | 30.23 C |
| ATOM | 5745 | CE2 | TYR | B | 714 | −2.495 | −0.220 | 30.037 | 1.00 | 23.98 C |
| ATOM | 5746 | CZ | TYR | B | 714 | −3.023 | −0.914 | 28.963 | 1.00 | 29.74 C |
| ATOM | 5747 | OH | TYR | B | 714 | −4.053 | −1.801 | 29.144 | 1.00 | 43.43 O |
| ATOM | 5748 | N | TYR | B | 715 | 3.800 | 1.544 | 27.965 | 1.00 | 27.97 N |
| ATOM | 5749 | CA | TYR | B | 715 | 4.990 | 2.198 | 27.389 | 1.00 | 33.91 C |
| ATOM | 5750 | C | TYR | B | 715 | 5.524 | 1.278 | 26.286 | 1.00 | 39.04 C |
| ATOM | 5751 | O | TYR | B | 715 | 5.970 | 1.731 | 25.237 | 1.00 | 38.79 O |
| ATOM | 5752 | CB | TYR | B | 715 | 6.091 | 2.362 | 28.443 | 1.00 | 32.02 C |
| ATOM | 5753 | CG | TYR | B | 715 | 7.479 | 2.658 | 27.880 | 1.00 | 31.96 C |
| ATOM | 5754 | CD1 | TYR | B | 715 | 7.810 | 3.917 | 27.392 | 1.00 | 37.02 C |
| ATOM | 5755 | CD2 | TYR | B | 715 | 8.475 | 1.687 | 27.896 | 1.00 | 50.82 C |
| ATOM | 5756 | CE1 | TYR | B | 715 | 9.102 | 4.205 | 26.938 | 1.00 | 46.49 C |
| ATOM | 5757 | CE2 | TYR | B | 715 | 9.774 | 1.963 | 27.448 | 1.00 | 40.87 C |
| ATOM | 5758 | CZ | TYR | B | 715 | 10.085 | 3.219 | 26.974 | 1.00 | 50.89 C |
| ATOM | 5759 | OH | TYR | B | 715 | 11.378 | 3.496 | 26.551 | 1.00 | 47.62 O |
| ATOM | 5760 | N | ASN | B | 716 | 5.475 | −0.025 | 26.540 | 1.00 | 34.36 N |
| ATOM | 5761 | CA | ASN | B | 716 | 5.947 | −0.979 | 25.574 | 1.00 | 31.64 C |
| ATOM | 5762 | C | ASN | B | 716 | 5.034 | −1.028 | 24.364 | 1.00 | 41.45 C |
| ATOM | 5763 | O | ASN | B | 716 | 5.508 | −1.116 | 23.224 | 1.00 | 42.91 O |
| ATOM | 5764 | CB | ASN | B | 716 | 6.072 | −2.359 | 26.232 | 1.00 | 43.70 C |
| ATOM | 5765 | CG | ASN | B | 716 | 7.397 | −2.529 | 26.987 | 1.00 | 50.97 C |
| ATOM | 5766 | OD1 | ASN | B | 716 | 7.566 | −3.462 | 27.765 | 1.00 | 55.46 O |
| ATOM | 5767 | ND2 | ASN | B | 716 | 8.340 | −1.618 | 26.747 | 1.00 | 58.73 N |
| ATOM | 5768 | N | LYS | B | 717 | 3.722 | −0.986 | 24.601 | 1.00 | 40.68 N |
| ATOM | 5769 | CA | LYS | B | 717 | 2.773 | −1.001 | 123.499 | 1.00 | 30.01 C |
| ATOM | 5770 | C | LYS | B | 717 | 3.073 | 0.186 | 22.587 | 1.00 | 23.78 C |
| ATOM | 5771 | O | LYS | B | 717 | 3.002 | 0.077 | 21.369 | 1.00 | 43.12 O |
| ATOM | 5772 | CB | LYS | B | 717 | 1.334 | −0.916 | 24.024 | 1.00 | 55.18 C |
| ATOM | 5773 | CG | LYS | B | 717 | 0.811 | −2.199 | 24.665 | 1.00 | 30.92 C |
| ATOM | 5774 | CD | LYS | B | 717 | 0.911 | −3.349 | 23.692 | 1.00 | 43.04 C |
| ATOM | 5775 | CE | LYS | B | 717 | 0.691 | −4.700 | 24.363 | 1.00 | 39.82 C |
| ATOM | 5776 | NZ | LYS | B | 717 | 0.698 | −5.822 | 23.377 | 1.00 | 56.37 N |
| ATOM | 5777 | N | PHE | B | 718 | 3.438 | 1.318 | 23.173 | 1.00 | 32.94 N |
| ATOM | 5778 | CA | PHE | B | 718 | 3.754 | 2.504 | 22.380 | 1.00 | 37.54 C |
| ATOM | 5779 | C | PHE | B | 718 | 5.032 | 2.307 | 21.568 | 1.00 | 44.22 C |
| ATOM | 5780 | O | PHE | B | 718 | 5.187 | 2.862 | 20.467 | 1.00 | 37.75 O |
| ATOM | 5781 | CB | PHE | B | 718 | 3.903 | 3.737 | 23.281 | 1.00 | 35.06 C |
| ATOM | 5782 | CG | PHE | B | 718 | 2.578 | 4.372 | 23.688 | 1.00 | 30.09 C |
| ATOM | 5783 | CD1 | PHE | B | 718 | 1.435 | 3.605 | 23.849 | 1.00 | 26.97 C |
| ATOM | 5784 | CD2 | PHE | B | 718 | 2.503 | 5.735 | 23.955 | 1.00 | 27.51 C |
| ATOM | 5785 | CE1 | PHE | B | 718 | 0.229 | 4.184 | 24.276 | 1.00 | 32.15 C |
| ATOM | 5786 | CE2 | PHE | B | 718 | 1.317 | 6.317 | 24.378 | 1.00 | 45.92 C |
| ATOM | 5787 | CZ | PHE | B | 718 | 0.174 | 5.537 | 24.539 | 1.00 | 26.97 C |
| ATOM | 5788 | N | LYS | B | 719 | 5.945 | 1.517 | 22.121 | 1.00 | 42.51 N |
| ATOM | 5789 | CA | LYS | B | 719 | 7.209 | 1.224 | 21.456 | 1.00 | 28.94 C |
| ATOM | 5790 | C | LYS | B | 719 | 6.948 | 0.335 | 20.271 | 1.00 | 25.48 C |
| ATOM | 5791 | O | LYS | B | 719 | 7.568 | 0.502 | 19.235 | 1.00 | 27.29 O |
| ATOM | 5792 | CB | LYS | B | 719 | 8.179 | 0.559 | 22.428 | 1.00 | 31.98 C |
| ATOM | 5793 | CG | LYS | B | 719 | 8.845 | 1.576 | 23.356 | 1.00 | 37.37 C |
| ATOM | 5794 | CD | LYS | B | 719 | 9.690 | 0.920 | 24.458 | 1.00 | 61.86 C |
| ATOM | 5795 | CE | LYS | B | 719 | 10.733 | −0.045 | 23.921 | 1.00 | 54.47 C |
| ATOM | 5796 | NZ | LYS | B | 719 | 11.582 | −0.633 | 25.011 | 1.00 | 63.17 N |
| ATOM | 5797 | N | ASP | B | 720 | 6.004 | −0.593 | 20.420 | 1.00 | 26.23 N |
| ATOM | 5798 | CA | ASP | B | 720 | 5.662 | −1.488 | 19.335 | 1.00 | 27.44 C |
| ATOM | 5799 | C | ASP | B | 720 | 5.052 | −0.669 | 18.207 | 1.00 | 53.23 C |

TABLE 1-continued

| ATOM | 5800 | O   | ASP | B | 720 | 5.306  | −0.923 | 17.030 | 1.00 | 67.76 | O |
|------|------|-----|-----|---|-----|--------|--------|--------|------|-------|---|
| ATOM | 5801 | CB  | ASP | B | 720 | 4.642  | −2.519 | 19.781 | 1.00 | 42.66 | C |
| ATOM | 5802 | CG  | ASP | B | 720 | 5.156  | −3.399 | 20.886 | 1.00 | 65.31 | C |
| ATOM | 5803 | OD1 | ASP | B | 720 | 6.248  | −3.988 | 20.719 | 1.00 | 76.31 | O |
| ATOM | 5804 | OD2 | ASP | B | 720 | 4.469  | −3.506 | 21.922 | 1.00 | 83.03 | O |
| ATOM | 5805 | N   | ILE | B | 721 | 4.234  | 0.313  | 18.561 | 1.00 | 50.39 | N |
| ATOM | 5806 | CA  | ILE | B | 721 | 3.623  | 1.142  | 17.542 | 1.00 | 47.09 | C |
| ATOM | 5807 | C   | ILE | B | 721 | 4.722  | 1.901  | 16.818 | 1.00 | 31.89 | C |
| ATOM | 5808 | O   | ILE | B | 721 | 4.697  | 1.992  | 15.597 | 1.00 | 40.70 | O |
| ATOM | 5809 | CB  | ILE | B | 721 | 2.568  | 2.095  | 18.153 | 1.00 | 32.56 | C |
| ATOM | 5810 | CG1 | ILE | B | 721 | 1.354  | 1.276  | 18.571 | 1.00 | 30.69 | C |
| ATOM | 5811 | CG2 | ILE | B | 721 | 2.150  | 3.158  | 17.167 | 1.00 | 34.05 | C |
| ATOM | 5812 | CD1 | ILE | B | 721 | 0.251  | 2.119  | 19.198 | 1.00 | 50.30 | C |
| ATOM | 5813 | N   | ALA | B | 722 | 5.684  | 2.435  | 17.562 | 1.00 | 31.81 | N |
| ATOM | 5814 | CA  | ALA | B | 722 | 6.801  | 3.149  | 16.935 | 1.00 | 42.29 | C |
| ATOM | 5815 | C   | ALA | B | 722 | 7.536  | 2.241  | 15.915 | 1.00 | 55.38 | C |
| ATOM | 5816 | O   | ALA | B | 722 | 7.904  | 2.701  | 14.827 | 1.00 | 39.82 | O |
| ATOM | 5817 | CB  | ALA | B | 722 | 7.780  | 3.637  | 17.985 | 1.00 | 36.45 | C |
| ATOM | 5818 | N   | SER | B | 723 | 7.738  | 0.960  | 16.251 | 1.00 | 37.23 | N |
| ATOM | 5819 | CA  | SER | B | 723 | 8.409  | 0.055  | 15.313 | 1.00 | 50.35 | C |
| ATOM | 5820 | C   | SER | B | 723 | 7.530  | −0.212 | 14.079 | 1.00 | 48.65 | C |
| ATOM | 5821 | O   | SER | B | 723 | 8.031  | −0.262 | 12.951 | 1.00 | 39.69 | O |
| ATOM | 5822 | CB  | SER | B | 723 | 8.799  | −1.267 | 15.999 | 1.00 | 40.05 | C |
| ATOM | 5823 | OG  | SER | B | 723 | 7.675  | −2.076 | 16.249 | 1.00 | 69.07 | O |
| ATOM | 5824 | N   | THR | B | 724 | 6.225  | −0.373 | 14.290 | 1.00 | 39.13 | N |
| ATOM | 5825 | CA  | THR | B | 724 | 5.300  | −0.596 | 13.174 | 1.00 | 36.50 | C |
| ATOM | 5826 | C   | THR | B | 724 | 5.415  | 0.606  | 12.215 | 1.00 | 34.73 | C |
| ATOM | 5827 | O   | THR | B | 724 | 5.534  | 0.459  | 11.015 | 1.00 | 32.53 | O |
| ATOM | 5828 | CB  | THR | B | 724 | 3.850  | −0.717 | 13.696 | 1.00 | 35.31 | C |
| ATOM | 5829 | OG1 | THR | B | 724 | 3.767  | −1.845 | 14.566 | 1.00 | 39.51 | O |
| ATOM | 5830 | CG2 | THR | B | 724 | 2.843  | −0.889 | 12.560 | 1.00 | 20.71 | C |
| ATOM | 5831 | N   | LEU | B | 725 | 5.408  | 1.808  | 12.757 | 1.00 | 30.61 | N |
| ATOM | 5832 | CA  | LEU | B | 725 | 5.521  | 2.971  | 11.905 | 1.00 | 35.11 | C |
| ATOM | 5833 | C   | LEU | B | 725 | 6.869  | 2.961  | 11.175 | 1.00 | 47.12 | C |
| ATOM | 5834 | O   | LEU | B | 725 | 6.939  | 3.270  | 9.988  | 1.00 | 38.15 | O |
| ATOM | 5835 | CB  | LEU | B | 725 | 5.376  | 4.248  | 12.744 | 1.00 | 36.92 | C |
| ATOM | 5836 | CG  | LEU | B | 725 | 3.973  | 4.449  | 13.330 | 1.00 | 36.58 | C |
| ATOM | 5837 | CD1 | LEU | B | 725 | 3.972  | 5.628  | 14.287 | 1.00 | 32.35 | C |
| ATOM | 5838 | CD2 | LEU | B | 725 | 2.975  | 4.661  | 12.171 | 1.00 | 18.06 | C |
| ATOM | 5839 | N   | ASN | B | 726 | 7.927  | 2.593  | 11.896 | 1.00 | 38.63 | N |
| ATOM | 5840 | CA  | ASN | B | 726 | 9.277  | 2.567  | 11.340 | 1.00 | 48.40 | C |
| ATOM | 5841 | C   | ASN | B | 726 | 9.406  | 1.558  | 10.207 | 1.00 | 47.43 | C |
| ATOM | 5842 | O   | ASN | B | 726 | 10.110 | 1.804  | 9.240  | 1.00 | 60.56 | O |
| ATOM | 5843 | CB  | ASN | B | 726 | 10.300 | 2.248  | 12.440 | 1.00 | 33.09 | C |
| ATOM | 5844 | CG  | ASN | B | 726 | 10.578 | 3.433  | 13.355 | 1.00 | 30.88 | C |
| ATOM | 5845 | OD1 | ASN | B | 726 | 11.131 | 3.263  | 14.444 | 1.00 | 46.61 | O |
| ATOM | 5846 | ND2 | ASN | B | 726 | 10.204 | 4.633  | 12.924 | 1.00 | 32.32 | N |
| ATOM | 5847 | N   | LYS | B | 727 | 8.711  | 0.433  | 10.316 | 1.00 | 47.47 | N |
| ATOM | 5848 | CA  | LYS | B | 727 | 8.752  | −0.591 | 9.286  | 1.00 | 32.59 | C |
| ATOM | 5849 | C   | LYS | B | 727 | 7.697  | −0.454 | 8.193  | 1.00 | 38.71 | C |
| ATOM | 5850 | O   | LYS | B | 727 | 7.623  | −1.298 | 7.308  | 1.00 | 46.60 | O |
| ATOM | 5851 | CB  | LYS | B | 727 | 8.622  | −1.967 | 9.946  | 1.00 | 39.20 | C |
| ATOM | 5852 | CG  | LYS | B | 727 | 9.901  | −2.375 | 10.654 | 1.00 | 57.76 | C |
| ATOM | 5853 | CD  | LYS | B | 727 | 9.693  | −3.409 | 11.755 | 1.00 | 68.49 | C |
| ATOM | 5854 | CE  | LYS | B | 727 | 11.033 | −3.676 | 12.474 | 1.00 | 78.63 | C |
| ATOM | 5855 | NZ  | LYS | B | 727 | 10.956 | −4.591 | 13.663 | 1.00 | 71.75 | N |
| ATOM | 5856 | N   | ALA | B | 728 | 6.878  | 0.592  | 8.240  | 1.00 | 35.89 | N |
| ATOM | 5857 | CA  | ALA | B | 728 | 5.823  | 0.760  | 7.241  | 1.00 | 43.96 | C |
| ATOM | 5858 | C   | ALA | B | 728 | 6.371  | 1.082  | 5.862  | 1.00 | 45.70 | C |
| ATOM | 5859 | O   | ALA | B | 728 | 7.143  | 2.026  | 5.707  | 1.00 | 58.78 | O |
| ATOM | 5860 | CB  | ALA | B | 728 | 4.884  | 1.849  | 7.664  | 1.00 | 25.40 | C |
| ATOM | 5861 | N   | LYS | B | 729 | 5.957  | 0.317  | 4.859  | 1.00 | 44.89 | N |
| ATOM | 5862 | CA  | LYS | B | 729 | 6.417  | 0.550  | 3.498  | 1.00 | 28.76 | C |
| ATOM | 5863 | C   | LYS | B | 729 | 5.280  | 1.014  | 2.590  | 1.00 | 47.96 | C |
| ATOM | 5864 | O   | LYS | B | 729 | 5.507  | 1.671  | 1.567  | 1.00 | 36.42 | O |
| ATOM | 5865 | CB  | LYS | B | 729 | 7.028  | −0.727 | 2.943  | 1.00 | 45.74 | C |
| ATOM | 5866 | CG  | LYS | B | 729 | 8.277  | −1.152 | 3.665  | 1.00 | 40.88 | C |
| ATOM | 5867 | CD  | LYS | B | 729 | 9.340  | −0.059 | 3.542  | 1.00 | 46.17 | C |
| ATOM | 5868 | CE  | LYS | B | 729 | 10.537 | −0.338 | 4.456  | 1.00 | 69.40 | C |
| ATOM | 5869 | NZ  | LYS | B | 729 | 11.573 | 0.751  | 4.364  | 1.00 | 70.58 | N |
| ATOM | 5870 | N   | SER | B | 730 | 4.047  | 0.686  | 2.957  | 1.00 | 39.19 | N |
| ATOM | 5871 | CA  | SER | B | 730 | 2.918  | 1.099  | 2.125  | 1.00 | 38.24 | C |
| ATOM | 5872 | C   | SER | B | 730 | 1.667  | 1.553  | 2.907  | 1.00 | 34.06 | C |
| ATOM | 5873 | O   | SER | B | 730 | 1.626  | 1.450  | 4.125  | 1.00 | 32.29 | O |
| ATOM | 5874 | CB  | SER | B | 730 | 2.565  | −0.052 | 1.190  | 1.00 | 35.40 | C |
| ATOM | 5875 | OG  | SER | B | 730 | 2.217  | −1.196 | 1.950  | 1.00 | 38.29 | O |
| ATOM | 5876 | N   | ILE | B | 731 | 0.645  | 2.025  | 2.189  | 1.00 | 34.12 | N |
| ATOM | 5877 | CA  | ILE | B | 731 | −0.573 | 2.496  | 2.816  | 1.00 | 28.22 | C |
| ATOM | 5878 | C   | ILE | B | 731 | −1.833 | 2.333  | 1.941  | 1.00 | 33.39 | C |

TABLE 1-continued

| ATOM | 5879 | O   | ILE | B | 731 | −1.796 | 2.496  | 0.719  | 1.00 | 38.09 | O |
|------|------|-----|-----|---|-----|--------|--------|--------|------|-------|---|
| ATOM | 5880 | CB  | ILE | B | 731 | −0.403 | 3.998  | 3.248  | 1.00 | 36.12 | C |
| ATOM | 5881 | CG1 | ILE | B | 731 | −1.610 | 4.462  | 4.080  | 1.00 | 24.13 | C |
| ATOM | 5882 | CG2 | ILE | B | 731 | −0.289 | 4.878  | 2.028  | 1.00 | 26.37 | C |
| ATOM | 5883 | CD1 | ILE | B | 731 | −1.479 | 5.865  | 4.580  | 1.00 | 41.65 | C |
| ATOM | 5884 | N   | VAL | B | 732 | −2.947 | 1.986  | 2.574  | 1.00 | 38.12 | N |
| ATOM | 5885 | CA  | VAL | B | 732 | −4.218 | 1.815  | 1.872  | 1.00 | 31.23 | C |
| ATOM | 5886 | C   | VAL | B | 732 | −5.039 | 3.101  | 2.044  | 1.00 | 44.39 | C |
| ATOM | 5887 | O   | VAL | B | 732 | −5.053 | 3.709  | 3.121  | 1.00 | 37.91 | O |
| ATOM | 5888 | CB  | VAL | B | 732 | −5.006 | 0.624  | 2.453  | 1.00 | 40.37 | C |
| ATOM | 5889 | CG1 | VAL | B | 732 | −6.363 | 0.473  | 1.755  | 1.00 | 35.36 | C |
| ATOM | 5890 | CG2 | VAL | B | 732 | −4.196 | −0.627 | 2.308  | 1.00 | 27.59 | C |
| ATOM | 5891 | N   | GLY | B | 733 | −5.721 | 3.510  | 0.985  | 1.00 | 39.55 | N |
| ATOM | 5892 | CA  | GLY | B | 733 | −6.518 | 4.719  | 1.062  | 1.00 | 56.10 | C |
| ATOM | 5893 | C   | GLY | B | 733 | −6.173 | 5.599  | −0.118 | 1.00 | 50.83 | C |
| ATOM | 5894 | O   | GLY | B | 733 | −5.143 | 5.392  | −0.747 | 1.00 | 47.06 | O |
| ATOM | 5895 | N   | THR | B | 734 | −6.996 | 6.601  | −0.403 | 1.00 | 54.20 | N |
| ATOM | 5896 | CA  | THR | B | 734 | −6.726 | 7.434  | −1.558 | 1.00 | 56.94 | C |
| ATOM | 5897 | C   | THR | B | 734 | −6.185 | 8.826  | −1.290 | 1.00 | 57.53 | C |
| ATOM | 5898 | O   | THR | B | 734 | −5.326 | 9.308  | −2.032 | 1.00 | 52.93 | O |
| ATOM | 5899 | CB  | THR | B | 734 | −7.976 | 7.544  | −2.440 | 1.00 | 59.53 | C |
| ATOM | 5900 | OG1 | THR | B | 734 | −9.020 | 8.206  | −1.719 | 1.00 | 75.88 | O |
| ATOM | 5901 | CG2 | THR | B | 734 | −8.447 | 6.168  | −2.829 | 1.00 | 64.04 | C |
| ATOM | 5902 | N   | THR | B | 735 | −6.670 | 9.470  | −0.236 | 1.00 | 58.08 | N |
| ATOM | 5903 | CA  | THR | B | 735 | −6.208 | 10.815 | 0.090  | 1.00 | 50.41 | C |
| ATOM | 5904 | C   | THR | B | 735 | −4.925 | 10.886 | 0.903  | 1.00 | 52.15 | C |
| ATOM | 5905 | O   | THR | B | 735 | −4.021 | 11.641 | 0.558  | 1.00 | 65.78 | O |
| ATOM | 5906 | CB  | THR | B | 735 | −7.287 | 11.611 | 0.854  | 1.00 | 66.77 | C |
| ATOM | 5907 | OG1 | THR | B | 735 | −8.301 | 12.033 | −0.068 | 1.00 | 77.62 | O |
| ATOM | 5908 | CG2 | THR | B | 735 | −6.670 | 12.836 | 1.563  | 1.00 | 54.12 | C |
| ATOM | 5909 | N   | ALA | B | 736 | −4.842 | 10.113 | 1.980  | 1.00 | 56.45 | N |
| ATOM | 5910 | CA  | ALA | B | 736 | −3.668 | 10.151 | 2.848  | 1.00 | 41.52 | C |
| ATOM | 5911 | C   | ALA | B | 736 | −2.413 | 9.389  | 2.405  | 1.00 | 50.79 | C |
| ATOM | 5912 | O   | ALA | B | 736 | −2.474 | 8.216  | 2.016  | 1.00 | 39.30 | O |
| ATOM | 5913 | CB  | ALA | B | 736 | −4.064 | 9.694  | 4.243  | 1.00 | 48.30 | C |
| ATOM | 5914 | N   | SER | B | 737 | −1.272 | 10.071 | 2.489  | 1.00 | 39.67 | N |
| ATOM | 5915 | CA  | SER | B | 737 | 0.015  | 9.483  | 2.154  | 1.00 | 39.16 | C |
| ATOM | 5916 | C   | SER | B | 737 | 0.603  | 8.906  | 3.434  | 1.00 | 37.71 | C |
| ATOM | 5917 | O   | SER | B | 737 | 0.306  | 9.363  | 4.533  | 1.00 | 34.53 | O |
| ATOM | 5918 | CB  | SER | B | 737 | 0.986  | 10.536 | 1.624  | 1.00 | 40.83 | C |
| ATOM | 5919 | OG  | SER | B | 737 | 1.664  | 11.175 | 2.698  | 1.00 | 45.63 | O |
| ATOM | 5920 | N   | LEU | B | 738 | 1.472  | 7.923  | 3.264  | 1.00 | 42.55 | N |
| ATOM | 5921 | CA  | LEU | B | 738 | 2.118  | 7.259  | 4.378  | 1.00 | 46.40 | C |
| ATOM | 5922 | C   | LEU | B | 738 | 2.809  | 8.232  | 5.321  | 1.00 | 43.75 | C |
| ATOM | 5923 | O   | LEU | B | 738 | 2.527  | 8.246  | 6.527  | 1.00 | 53.78 | O |
| ATOM | 5924 | CB  | LEU | B | 738 | 3.115  | 6.236  | 3.843  | 1.00 | 39.46 | C |
| ATOM | 5925 | CG  | LEU | B | 738 | 3.935  | 5.497  | 4.898  | 1.00 | 33.50 | C |
| ATOM | 5926 | CD1 | LEU | B | 738 | 3.010  | 4.844  | 5.895  | 1.00 | 42.98 | C |
| ATOM | 5927 | CD2 | LEU | B | 738 | 4.817  | 4.464  | 4.217  | 1.00 | 31.72 | C |
| ATOM | 5928 | N   | GLN | B | 739 | 3.697  | 9.057  | 4.775  | 1.00 | 43.65 | N |
| ATOM | 5929 | CA  | GLN | B | 739 | 4.428  | 10.022 | 5.586  | 1.00 | 30.22 | C |
| ATOM | 5930 | C   | GLN | B | 739 | 3.448  | 10.873 | 6.382  | 1.00 | 43.99 | C |
| ATOM | 5931 | O   | GLN | B | 739 | 3.668  | 11.200 | 7.553  | 1.00 | 37.09 | O |
| ATOM | 5932 | CB  | GLN | B | 739 | 5.312  | 10.882 | 4.706  | 1.00 | 36.34 | C |
| ATOM | 5933 | CG  | GLN | B | 739 | 6.208  | 11.843 | 5.487  | 1.00 | 53.09 | C |
| ATOM | 5934 | CD  | GLN | B | 739 | 7.264  | 12.465 | 4.604  | 1.00 | 74.04 | C |
| ATOM | 5935 | OE1 | GLN | B | 739 | 7.021  | 13.453 | 3.931  | 1.00 | 76.55 | O |
| ATOM | 5936 | NE2 | GLN | B | 739 | 8.515  | 12.046 | 4.460  | 1.00 | 45.92 | N |
| ATOM | 5937 | N   | TYR | B | 740 | 2.341  | 11.232 | 5.736  | 1.00 | 35.41 | N |
| ATOM | 5938 | CA  | TYR | B | 740 | 1.300  | 12.014 | 6.377  | 1.00 | 35.78 | C |
| ATOM | 5939 | C   | TYR | B | 740 | 0.759  | 11.272 | 7.607  | 1.00 | 28.85 | C |
| ATOM | 5940 | O   | TYR | B | 740 | 0.709  | 11.828 | 8.701  | 1.00 | 37.36 | O |
| ATOM | 5941 | CB  | TYR | B | 740 | 0.152  | 12.265 | 5.402  | 1.00 | 24.70 | C |
| ATOM | 5942 | CG  | TYR | B | 740 | −0.945 | 13.082 | 6.023  | 1.00 | 36.09 | C |
| ATOM | 5943 | CD1 | TYR | B | 740 | −0.850 | 14.469 | 6.096  | 1.00 | 45.48 | C |
| ATOM | 5944 | CD2 | TYR | B | 740 | −2.061 | 12.470 | 6.586  | 1.00 | 39.70 | C |
| ATOM | 5945 | CE1 | TYR | B | 740 | −1.849 | 15.231 | 6.722  | 1.00 | 55.84 | C |
| ATOM | 5946 | CE2 | TYR | B | 740 | −3.062 | 13.215 | 7.212  | 1.00 | 46.86 | C |
| ATOM | 5947 | CZ  | TYR | B | 740 | −2.952 | 14.591 | 7.279  | 1.00 | 56.38 | C |
| ATOM | 5948 | OH  | TYR | B | 740 | −3.940 | 15.343 | 7.882  | 1.00 | 55.54 | O |
| ATOM | 5949 | N   | MET | B | 741 | 0.369  | 10.009 | 7.428  | 1.00 | 39.85 | N |
| ATOM | 5950 | CA  | MET | B | 741 | −0.170 | 9.244  | 8.541  | 1.00 | 30.39 | C |
| ATOM | 5951 | C   | MET | B | 741 | 0.882  | 9.027  | 9.624  | 1.00 | 32.55 | C |
| ATOM | 5952 | O   | MET | B | 741 | 0.584  | 9.138  | 10.811 | 1.00 | 35.16 | O |
| ATOM | 5953 | CB  | MET | B | 741 | −0.698 | 7.901  | 8.054  | 1.00 | 25.96 | C |
| ATOM | 5954 | CG  | MET | B | 741 | −2.109 | 7.979  | 7.531  | 1.00 | 56.95 | C |
| ATOM | 5955 | SD  | MET | B | 741 | −3.246 | 8.695  | 8.736  | 1.00 | 52.73 | S |
| ATOM | 5956 | CE  | MET | B | 741 | −3.190 | 10.435 | 8.295  | 1.00 | 21.29 | C |
| ATOM | 5957 | N   | LYS | B | 742 | 2.117  | 8.729  | 9.222  | 1.00 | 32.93 | N |

TABLE 1-continued

| ATOM | 5958 | CA | LYS | B | 742 | 3.167 | 8.528 | 10.221 | 1.00 | 34.73 | C |
|---|---|---|---|---|---|---|---|---|---|---|---|
| ATOM | 5959 | C | LYS | B | 742 | 3.280 | 9.797 | 11.044 | 1.00 | 31.91 | C |
| ATOM | 5960 | O | LYS | B | 742 | 3.471 | 9.742 | 12.241 | 1.00 | 35.22 | O |
| ATOM | 5961 | CB | LYS | B | 742 | 4.519 | 8.211 | 9.572 | 1.00 | 30.54 | C |
| ATOM | 5962 | CG | LYS | B | 742 | 4.577 | 6.825 | 8.951 | 1.00 | 42.14 | C |
| ATOM | 5963 | CD | LYS | B | 742 | 5.881 | 6.621 | 8.187 | 1.00 | 38.45 | C |
| ATOM | 5964 | CE | LYS | B | 742 | 7.096 | 6.692 | 9.102 | 1.00 | 50.59 | C |
| ATOM | 5965 | NZ | LYS | B | 742 | 8.344 | 6.317 | 8.377 | 1.00 | 65.02 | N |
| ATOM | 5966 | N | ASN | B | 743 | 3.141 | 10.951 | 10.403 | 1.00 | 39.52 | N |
| ATOM | 5967 | CA | ASN | B | 743 | 3.251 | 12.176 | 11.171 | 1.00 | 39.30 | C |
| ATOM | 5968 | C | ASN | B | 743 | 2.050 | 12.342 | 12.106 | 1.00 | 38.15 | C |
| ATOM | 5969 | O | ASN | B | 743 | 2.193 | 12.876 | 13.198 | 1.00 | 44.99 | O |
| ATOM | 5970 | CB | ASN | B | 743 | 3.388 | 13.395 | 10.261 | 1.00 | 40.18 | C |
| ATOM | 5971 | CG | ASN | B | 743 | 3.588 | 14.672 | 11.056 | 1.00 | 59.05 | C |
| ATOM | 5972 | OD1 | ASN | B | 743 | 2.755 | 15.580 | 11.023 | 1.00 | 50.34 | O |
| ATOM | 5973 | ND2 | ASN | B | 743 | 4.688 | 14.739 | 11.799 | 1.00 | 64.83 | N |
| ATOM | 5974 | N | VAL | B | 744 | 0.871 | 11.891 | 11.678 | 1.00 | 33.01 | N |
| ATOM | 5975 | CA | VAL | B | 744 | −0.304 | 11.994 | 12.526 | 1.00 | 33.34 | C |
| ATOM | 5976 | C | VAL | B | 744 | −0.041 | 11.213 | 13.812 | 1.00 | 38.00 | C |
| ATOM | 5977 | O | VAL | B | 744 | −0.297 | 11.707 | 14.911 | 1.00 | 35.07 | O |
| ATOM | 5978 | CB | VAL | B | 744 | −1.577 | 11.422 | 11.846 | 1.00 | 32.11 | C |
| ATOM | 5979 | CG1 | VAL | B | 744 | −2.693 | 11.286 | 12.852 | 1.00 | 21.58 | C |
| ATOM | 5980 | CG2 | VAL | B | 744 | −2.036 | 12.360 | 10.732 | 1.00 | 42.47 | C |
| ATOM | 5981 | N | PHE | B | 745 | 0.500 | 10.004 | 13.671 | 1.00 | 30.91 | N |
| ATOM | 5982 | CA | PHE | B | 745 | 0.763 | 9.184 | 14.825 | 1.00 | 30.81 | C |
| ATOM | 5983 | C | PHE | B | 745 | 1.960 | 9.644 | 15.623 | 1.00 | 32.60 | C |
| ATOM | 5984 | O | PHE | B | 745 | 2.015 | 9.461 | 16.844 | 1.00 | 27.59 | O |
| ATOM | 5985 | CB | PHE | B | 745 | 0.840 | 7.722 | 14.404 | 1.00 | 23.66 | C |
| ATOM | 5986 | CG | PHE | B | 745 | −0.486 | 7.211 | 13.901 | 1.00 | 31.05 | C |
| ATOM | 5987 | CD1 | PHE | B | 745 | −1.604 | 7.260 | 14.731 | 1.00 | 30.76 | C |
| ATOM | 5988 | CD2 | PHE | B | 745 | −0.657 | 6.829 | 12.571 | 1.00 | 26.20 | C |
| ATOM | 5989 | CE1 | PHE | B | 745 | −2.878 | 6.943 | 14.242 | 1.00 | 38.43 | C |
| ATOM | 5990 | CE2 | PHE | B | 745 | −1.928 | 6.517 | 12.079 | 1.00 | 24.77 | C |
| ATOM | 5991 | CZ | PHE | B | 745 | −3.037 | 6.577 | 12.911 | 1.00 | 24.34 | C |
| ATOM | 5992 | N | LYS | B | 746 | 2.901 | 10.281 | 14.948 | 1.00 | 28.40 | N |
| ATOM | 5993 | CA | LYS | B | 746 | 4.052 | 10.800 | 15.646 | 1.00 | 36.73 | C |
| ATOM | 5994 | C | LYS | B | 746 | 3.550 | 11.867 | 16.625 | 1.00 | 30.71 | C |
| ATOM | 5995 | O | LYS | B | 746 | 4.027 | 11.943 | 17.756 | 1.00 | 44.65 | O |
| ATOM | 5996 | CB | LYS | B | 746 | 5.050 | 11.396 | 14.645 | 1.00 | 46.61 | C |
| ATOM | 5997 | CG | LYS | B | 746 | 6.162 | 12.216 | 15.270 | 1.00 | 45.13 | C |
| ATOM | 5998 | CD | LYS | B | 746 | 6.922 | 12.964 | 14.177 | 1.00 | 57.56 | C |
| ATOM | 5999 | CE | LYS | B | 746 | 7.780 | 14.053 | 14.761 | 1.00 | 49.93 | C |
| ATOM | 6000 | NZ | LYS | B | 746 | 8.566 | 13.512 | 15.892 | 1.00 | 58.69 | N |
| ATOM | 6001 | N | GLU | B | 747 | 2.582 | 12.682 | 16.201 | 1.00 | 33.91 | N |
| ATOM | 6002 | CA | GLU | B | 747 | 2.031 | 13.716 | 17.085 | 1.00 | 28.44 | C |
| ATOM | 6003 | C | GLU | B | 747 | 1.158 | 13.091 | 18.181 | 1.00 | 38.00 | C |
| ATOM | 6004 | O | GLU | B | 747 | 1.147 | 13.554 | 19.327 | 1.00 | 41.20 | O |
| ATOM | 6005 | CB | GLU | B | 747 | 1.203 | 14.723 | 16.292 | 1.00 | 31.22 | C |
| ATOM | 6006 | CG | GLU | B | 747 | 1.970 | 15.406 | 15.173 | 1.00 | 45.66 | C |
| ATOM | 6007 | CD | GLU | B | 747 | 1.088 | 16.315 | 14.324 | 1.00 | 79.03 | C |
| ATOM | 6008 | OE1 | GLU | B | 747 | 0.017 | 15.847 | 13.866 | 1.00 | 86.53 | O |
| ATOM | 6009 | OE2 | GLU | B | 747 | 1.465 | 17.494 | 14.103 | 1.00 | 79.24 | O |
| ATOM | 6010 | N | LYS | B | 748 | 0.429 | 12.039 | 17.836 | 1.00 | 33.82 | N |
| ATOM | 6011 | CA | LYS | B | 748 | −0.423 | 11.407 | 18.826 | 1.00 | 36.48 | C |
| ATOM | 6012 | C | LYS | B | 748 | 0.370 | 10.825 | 19.990 | 1.00 | 33.66 | C |
| ATOM | 6013 | O | LYS | B | 748 | 0.139 | 11.168 | 21.147 | 1.00 | 37.33 | O |
| ATOM | 6014 | CB | LYS | B | 748 | −1.267 | 10.289 | 18.211 | 1.00 | 22.66 | C |
| ATOM | 6015 | CG | LYS | B | 748 | −2.139 | 9.599 | 19.263 | 1.00 | 24.76 | C |
| ATOM | 6016 | CD | LYS | B | 748 | −2.961 | 8.476 | 18.708 | 1.00 | 23.66 | C |
| ATOM | 6017 | CE | LYS | B | 748 | −3.713 | 7.752 | 19.827 | 1.00 | 20.75 | C |
| ATOM | 6018 | NZ | LYS | B | 748 | −4.473 | 6.565 | 19.315 | 1.00 | 21.41 | N |
| ATOM | 6019 | N | TYR | B | 749 | 1.287 | 9.913 | 19.676 | 1.00 | 41.55 | N |
| ATOM | 6020 | CA | TYR | B | 749 | 2.077 | 9.260 | 20.706 | 1.00 | 45.58 | C |
| ATOM | 6021 | C | TYR | B | 749 | 3.330 | 10.033 | 21.126 | 1.00 | 37.21 | C |
| ATOM | 6022 | O | TYR | B | 749 | 4.166 | 9.499 | 21.841 | 1.00 | 41.71 | O |
| ATOM | 6023 | CB | TYR | B | 749 | 2.434 | 7.851 | 20.245 | 1.00 | 43.75 | C |
| ATOM | 6024 | CG | TYR | B | 749 | 1.226 | 6.989 | 19.898 | 1.00 | 46.46 | C |
| ATOM | 6025 | CD1 | TYR | B | 749 | 0.476 | 6.348 | 20.892 | 1.00 | 31.79 | C |
| ATOM | 6026 | CD2 | TYR | B | 749 | 0.835 | 6.814 | 18.564 | 1.00 | 38.74 | C |
| ATOM | 6027 | CE1 | TYR | B | 749 | −0.628 | 5.563 | 20.561 | 1.00 | 25.13 | C |
| ATOM | 6028 | CE2 | TYR | B | 749 | −0.255 | 6.035 | 18.226 | 1.00 | 21.71 | C |
| ATOM | 6029 | CZ | TYR | B | 749 | −0.983 | 5.416 | 19.222 | 1.00 | 38.66 | C |
| ATOM | 6030 | OH | TYR | B | 749 | −2.080 | 4.670 | 18.866 | 1.00 | 25.85 | O |
| ATOM | 6031 | N | LEU | B | 750 | 3.436 | 11.288 | 20.680 | 1.00 | 38.22 | N |
| ATOM | 6032 | CA | LEU | B | 750 | 4.556 | 12.176 | 21.001 | 1.00 | 47.17 | C |
| ATOM | 6033 | C | LEU | B | 750 | 5.936 | 11.510 | 20.831 | 1.00 | 53.18 | C |
| ATOM | 6034 | O | LEU | B | 750 | 6.776 | 11.576 | 21.727 | 1.00 | 51.79 | O |
| ATOM | 6035 | CB | LEU | B | 750 | 4.402 | 12.675 | 22.443 | 1.00 | 44.01 | C |
| ATOM | 6036 | CG | LEU | B | 750 | 3.035 | 13.258 | 22.817 | 1.00 | 40.35 | C |

TABLE 1-continued

| ATOM | 6037 | CD1 | LEU | B | 750 | 2.973 | 13.468 | 24.310 | 1.00 | 41.43 | C |
|------|------|-----|-----|---|-----|-------|--------|--------|------|-------|---|
| ATOM | 6038 | CD2 | LEU | B | 750 | 2.794 | 14.570 | 22.086 | 1.00 | 40.31 | C |
| ATOM | 6039 | N | LEU | B | 751 | 6.165 | 10.887 | 19.679 | 1.00 | 48.15 | N |
| ATOM | 6040 | CA | LEU | B | 751 | 7.416 | 10.187 | 19.411 | 1.00 | 32.40 | C |
| ATOM | 6041 | C | LEU | B | 751 | 8.560 | 11.092 | 19.013 | 1.00 | 44.83 | C |
| ATOM | 6042 | O | LEU | B | 751 | 8.347 | 12.221 | 18.563 | 1.00 | 47.37 | O |
| ATOM | 6043 | CB | LEU | B | 751 | 7.216 | 9.162 | 18.292 | 1.00 | 40.09 | C |
| ATOM | 6044 | CG | LEU | B | 751 | 5.988 | 8.271 | 18.437 | 1.00 | 29.62 | C |
| ATOM | 6045 | CD1 | LEU | B | 751 | 5.796 | 7.409 | 17.189 | 1.00 | 29.54 | C |
| ATOM | 6046 | CD2 | LEU | B | 751 | 6.147 | 7.434 | 19.678 | 1.00 | 31.62 | C |
| ATOM | 6047 | N | SER | B | 752 | 9.779 | 10.585 | 19.185 | 1.00 | 47.96 | N |
| ATOM | 6048 | CA | SER | B | 752 | 10.968 | 11.323 | 18.783 | 1.00 | 61.52 | C |
| ATOM | 6049 | C | SER | B | 752 | 11.316 | 10.799 | 17.386 | 1.00 | 52.35 | C |
| ATOM | 6050 | O | SER | B | 752 | 11.158 | 9.606 | 17.096 | 1.00 | 47.20 | O |
| ATOM | 6051 | CB | SER | B | 752 | 12.147 | 11.057 | 19.736 | 1.00 | 50.05 | C |
| ATOM | 6052 | OG | SER | B | 752 | 11.793 | 11.296 | 21.083 | 1.00 | 56.51 | O |
| ATOM | 6053 | N | GLU | B | 753 | 11.767 | 11.695 | 16.521 | 1.00 | 47.71 | N |
| ATOM | 6054 | CA | GLU | B | 753 | 12.157 | 11.324 | 15.165 | 1.00 | 63.89 | C |
| ATOM | 6055 | C | GLU | B | 753 | 13.666 | 11.562 | 15.103 | 1.00 | 73.95 | C |
| ATOM | 6056 | O | GLU | B | 753 | 14.113 | 12.687 | 14.888 | 1.00 | 81.33 | O |
| ATOM | 6057 | CB | GLU | B | 753 | 11.429 | 12.211 | 14.157 | 1.00 | 56.64 | C |
| ATOM | 6058 | CG | GLU | B | 753 | 11.530 | 11.755 | 12.703 | 1.00 | 77.79 | C |
| ATOM | 6059 | CD | GLU | B | 753 | 10.843 | 12.724 | 11.741 | 1.00 | 73.60 | C |
| ATOM | 6060 | OE1 | GLU | B | 753 | 9.603 | 12.880 | 11.814 | 1.00 | 78.27 | O |
| ATOM | 6061 | OE2 | GLU | B | 753 | 11.547 | 13.338 | 10.912 | 1.00 | 84.20 | O |
| ATOM | 6062 | N | ASP | B | 754 | 14.444 | 10.501 | 15.303 | 1.00 | 73.25 | N |
| ATOM | 6063 | CA | ASP | B | 754 | 15.904 | 10.593 | 15.324 | 1.00 | 70.67 | C |
| ATOM | 6064 | C | ASP | B | 754 | 16.532 | 11.234 | 14.090 | 1.00 | 63.82 | C |
| ATOM | 6065 | O | ASP | B | 754 | 15.844 | 11.588 | 13.135 | 1.00 | 54.11 | O |
| ATOM | 6066 | CB | ASP | B | 754 | 16.512 | 9.203 | 15.533 | 1.00 | 62.82 | C |
| ATOM | 6067 | CG | ASP | B | 754 | 16.842 | 8.512 | 14.225 | 1.00 | 80.71 | C |
| ATOM | 6068 | OD1 | ASP | B | 754 | 16.087 | 8.701 | 13.244 | 1.00 | 82.30 | O |
| ATOM | 6069 | OD2 | ASP | B | 754 | 17.852 | 7.774 | 14.177 | 1.00 | 91.76 | O |
| ATOM | 6070 | N | THR | B | 755 | 17.855 | 11.368 | 14.131 | 1.00 | 71.74 | N |
| ATOM | 6071 | CA | THR | B | 755 | 18.627 | 11.961 | 13.042 | 1.00 | 76.47 | C |
| ATOM | 6072 | C | THR | B | 755 | 18.426 | 11.239 | 11.707 | 1.00 | 69.90 | C |
| ATOM | 6073 | O | THR | B | 755 | 18.667 | 11.816 | 10.646 | 1.00 | 72.48 | O |
| ATOM | 6074 | CB | THR | B | 755 | 20.133 | 11.966 | 13.386 | 1.00 | 79.02 | C |
| ATOM | 6075 | OG1 | THR | B | 755 | 20.325 | 12.641 | 14.634 | 1.00 | 82.76 | O |
| ATOM | 6076 | CG2 | THR | B | 755 | 20.933 | 12.687 | 12.311 | 1.00 | 84.78 | C |
| ATOM | 6077 | N | SER | B | 756 | 17.978 | 9.985 | 11.765 | 1.00 | 74.12 | N |
| ATOM | 6078 | CA | SER | B | 756 | 17.753 | 9.188 | 10.561 | 1.00 | 66.71 | C |
| ATOM | 6079 | C | SER | B | 756 | 16.292 | 9.087 | 10.119 | 1.00 | 68.23 | C |
| ATOM | 6080 | O | SER | B | 756 | 16.015 | 8.527 | 9.064 | 1.00 | 69.30 | O |
| ATOM | 6081 | CB | SER | B | 756 | 18.326 | 7.773 | 10.744 | 1.00 | 72.32 | C |
| ATOM | 6082 | OG | SER | B | 756 | 17.668 | 7.053 | 11.781 | 1.00 | 72.55 | O |
| ATOM | 6083 | N | GLY | B | 757 | 15.362 | 9.622 | 10.908 | 1.00 | 56.45 | N |
| ATOM | 6084 | CA | GLY | B | 757 | 13.960 | 9.548 | 10.521 | 1.00 | 64.83 | C |
| ATOM | 6085 | C | GLY | B | 757 | 13.189 | 8.437 | 11.220 | 1.00 | 66.98 | C |
| ATOM | 6086 | O | GLY | B | 757 | 11.980 | 8.289 | 11.039 | 1.00 | 59.50 | O |
| ATOM | 6087 | N | LYS | B | 758 | 13.907 | 7.657 | 12.020 | 1.00 | 66.56 | N |
| ATOM | 6088 | CA | LYS | B | 758 | 13.342 | 6.556 | 12.783 | 1.00 | 63.38 | C |
| ATOM | 6089 | C | LYS | B | 758 | 12.621 | 7.110 | 14.037 | 1.00 | 65.54 | C |
| ATOM | 6090 | O | LYS | B | 758 | 13.168 | 7.944 | 14.769 | 1.00 | 50.20 | O |
| ATOM | 6091 | CB | LYS | B | 758 | 14.481 | 5.607 | 13.180 | 1.00 | 55.94 | C |
| ATOM | 6092 | CG | LYS | B | 758 | 14.064 | 4.385 | 13.968 | 1.00 | 67.30 | C |
| ATOM | 6093 | CD | LYS | B | 758 | 15.282 | 3.637 | 14.508 | 1.00 | 68.82 | C |
| ATOM | 6094 | CE | LYS | B | 758 | 14.854 | 2.464 | 15.390 | 1.00 | 78.74 | C |
| ATOM | 6095 | NZ | LYS | B | 758 | 16.001 | 1.825 | 16.096 | 1.00 | 78.37 | N |
| ATOM | 6096 | N | PHE | B | 759 | 11.396 | 6.644 | 14.275 | 1.00 | 61.94 | N |
| ATOM | 6097 | CA | PHE | B | 759 | 10.613 | 7.094 | 15.426 | 1.00 | 50.93 | C |
| ATOM | 6098 | C | PHE | B | 759 | 10.958 | 6.346 | 16.696 | 1.00 | 36.64 | C |
| ATOM | 6099 | O | PHE | B | 759 | 11.198 | 5.139 | 16.686 | 1.00 | 34.50 | O |
| ATOM | 6100 | CB | PHE | B | 759 | 9.104 | 6.903 | 15.195 | 1.00 | 52.08 | C |
| ATOM | 6101 | CG | PHE | B | 759 | 8.518 | 7.787 | 14.132 | 1.00 | 33.95 | C |
| ATOM | 6102 | CD1 | PHE | B | 759 | 9.012 | 9.071 | 13.909 | 1.00 | 51.32 | C |
| ATOM | 6103 | CD2 | PHE | B | 759 | 7.437 | 7.350 | 13.383 | 1.00 | 48.52 | C |
| ATOM | 6104 | CE1 | PHE | B | 759 | 8.433 | 9.906 | 12.952 | 1.00 | 36.55 | C |
| ATOM | 6105 | CE2 | PHE | B | 759 | 6.851 | 8.173 | 12.421 | 1.00 | 39.90 | C |
| ATOM | 6106 | CZ | PHE | B | 759 | 7.346 | 9.447 | 12.206 | 1.00 | 46.39 | C |
| ATOM | 6107 | N | SER | B | 760 | 10.937 | 7.069 | 17.802 | 1.00 | 35.28 | N |
| ATOM | 6108 | CA | SER | B | 760 | 11.210 | 6.464 | 19.093 | 1.00 | 43.94 | C |
| ATOM | 6109 | C | SER | B | 760 | 10.315 | 7.093 | 20.163 | 1.00 | 32.37 | C |
| ATOM | 6110 | O | SER | B | 760 | 9.899 | 8.243 | 20.025 | 1.00 | 41.88 | O |
| ATOM | 6111 | CB | SER | B | 760 | 12.675 | 6.672 | 19.461 | 1.00 | 46.43 | C |
| ATOM | 6112 | OG | SER | B | 760 | 12.887 | 6.322 | 20.814 | 1.00 | 62.01 | O |
| ATOM | 6113 | N | VAL | B | 761 | 10.039 | 6.344 | 21.225 | 1.00 | 37.27 | N |
| ATOM | 6114 | CA | VAL | B | 761 | 9.215 | 6.833 | 22.328 | 1.00 | 55.52 | C |
| ATOM | 6115 | C | VAL | B | 761 | 9.965 | 7.728 | 23.315 | 1.00 | 49.39 | C |

TABLE 1-continued

| | | | | | | | | | | |
|---|---|---|---|---|---|---|---|---|---|---|
| ATOM | 6116 | O | VAL | B | 761 | 10.840 | 7.281 | 24.054 | 1.00 | 46.88 O |
| ATOM | 6117 | CB | VAL | B | 761 | 8.595 | 5.670 | 23.125 | 1.00 | 51.02 C |
| ATOM | 6118 | CG1 | VAL | B | 761 | 7.862 | 6.213 | 24.348 | 1.00 | 56.75 C |
| ATOM | 6119 | CG2 | VAL | B | 761 | 7.640 | 4.896 | 22.245 | 1.00 | 47.35 C |
| ATOM | 6120 | N | ASP | B | 762 | 9.596 | 9.003 | 23.315 | 1.00 | 65.74 N |
| ATOM | 6121 | CA | ASP | B | 762 | 10.182 | 10.017 | 24.193 | 1.00 | 55.32 C |
| ATOM | 6122 | C | ASP | B | 762 | 9.710 | 9.743 | 25.630 | 1.00 | 58.87 C |
| ATOM | 6123 | O | ASP | B | 762 | 8.564 | 10.047 | 25.991 | 1.00 | 51.13 O |
| ATOM | 6124 | CB | ASP | B | 762 | 9.697 | 11.390 | 23.717 | 1.00 | 65.04 C |
| ATOM | 6125 | CG | ASP | B | 762 | 10.360 | 12.541 | 24.438 | 1.00 | 62.42 C |
| ATOM | 6126 | OD1 | ASP | B | 762 | 10.607 | 12.449 | 25.664 | 1.00 | 65.60 O |
| ATOM | 6127 | OD2 | ASP | B | 762 | 10.610 | 13.558 | 23.762 | 1.00 | 66.33 O |
| ATOM | 6128 | N | LYS | B | 763 | 10.582 | 9.164 | 26.447 | 1.00 | 56.13 N |
| ATOM | 6129 | CA | LYS | B | 763 | 10.219 | 8.843 | 27.831 | 1.00 | 59.41 C |
| ATOM | 6130 | C | LYS | B | 763 | 9.705 | 10.047 | 28.617 | 1.00 | 46.80 C |
| ATOM | 6131 | O | LYS | B | 763 | 8.792 | 9.938 | 29.428 | 1.00 | 48.86 O |
| ATOM | 6132 | CB | LYS | B | 763 | 11.413 | 8.229 | 28.544 | 1.00 | 31.35 C |
| ATOM | 6133 | CG | LYS | B | 763 | 11.808 | 6.886 | 27.968 | 1.00 | 61.43 C |
| ATOM | 6134 | CD | LYS | B | 763 | 13.213 | 6.445 | 28.398 | 1.00 | 65.28 C |
| ATOM | 6135 | CE | LYS | B | 763 | 13.665 | 5.286 | 27.527 | 1.00 | 62.86 C |
| ATOM | 6136 | NZ | LYS | B | 763 | 14.990 | 4.771 | 27.887 | 1.00 | 72.38 N |
| ATOM | 6137 | N | LEU | B | 764 | 10.294 | 11.199 | 28.359 | 1.00 | 54.47 N |
| ATOM | 6138 | CA | LEU | B | 764 | 9.891 | 12.412 | 29.043 | 1.00 | 55.84 C |
| ATOM | 6139 | C | LEU | B | 764 | 8.452 | 12.748 | 28.663 | 1.00 | 65.91 C |
| ATOM | 6140 | O | LEU | B | 764 | 7.589 | 12.917 | 29.524 | 1.00 | 56.43 O |
| ATOM | 6141 | CB | LEU | B | 764 | 10.824 | 13.555 | 28.648 | 1.00 | 62.89 C |
| ATOM | 6142 | CG | LEU | B | 764 | 11.226 | 14.474 | 29.797 | 1.00 | 65.62 C |
| ATOM | 6143 | CD1 | LEU | B | 764 | 10.021 | 15.286 | 30.248 | 1.00 | 74.50 C |
| ATOM | 6144 | CD2 | LEU | B | 764 | 11.791 | 13.632 | 30.935 | 1.00 | 58.84 C |
| ATOM | 6145 | N | LYS | B | 765 | 8.208 | 12.833 | 27.360 | 1.00 | 53.19 N |
| ATOM | 6146 | CA | LYS | B | 765 | 6.892 | 13.145 | 26.843 | 1.00 | 51.58 C |
| ATOM | 6147 | C | LYS | B | 765 | 5.878 | 12.052 | 27.136 | 1.00 | 43.00 C |
| ATOM | 6148 | O | LYS | B | 765 | 4.722 | 12.338 | 27.437 | 1.00 | 45.37 O |
| ATOM | 6149 | CB | LYS | B | 765 | 6.987 | 13.427 | 25.355 | 1.00 | 52.51 C |
| ATOM | 6150 | CG | LYS | B | 765 | 7.685 | 14.753 | 25.067 | 1.00 | 42.86 C |
| ATOM | 6151 | CD | LYS | B | 765 | 7.800 | 15.017 | 23.569 | 1.00 | 65.64 C |
| ATOM | 6152 | CE | LYS | B | 765 | 8.110 | 16.479 | 23.299 | 1.00 | 57.96 C |
| ATOM | 6153 | NZ | LYS | B | 765 | 8.071 | 16.785 | 21.840 | 1.00 | 80.76 N |
| ATOM | 6154 | N | PHE | B | 766 | 6.300 | 10.801 | 27.071 | 1.00 | 36.56 N |
| ATOM | 6155 | CA | PHE | B | 766 | 5.383 | 9.722 | 27.385 | 1.00 | 25.89 C |
| ATOM | 6156 | C | PHE | B | 766 | 4.868 | 9.832 | 28.816 | 1.00 | 42.74 C |
| ATOM | 6157 | O | PHE | B | 766 | 3.655 | 9.903 | 29.034 | 1.00 | 45.66 O |
| ATOM | 6158 | CB | PHE | B | 766 | 6.056 | 8.371 | 27.240 | 1.00 | 24.36 C |
| ATOM | 6159 | CG | PHE | B | 766 | 5.226 | 7.244 | 27.757 | 1.00 | 25.91 C |
| ATOM | 6160 | CD1 | PHE | B | 766 | 4.156 | 6.761 | 27.016 | 1.00 | 31.19 C |
| ATOM | 6161 | CD2 | PHE | B | 766 | 5.485 | 6.690 | 29.004 | 1.00 | 36.21 C |
| ATOM | 6162 | CE1 | PHE | B | 766 | 3.340 | 5.727 | 27.503 | 1.00 | 41.76 C |
| ATOM | 6163 | CE2 | PHE | B | 766 | 4.676 | 5.647 | 29.512 | 1.00 | 47.71 C |
| ATOM | 6164 | CZ | PHE | B | 766 | 3.601 | 5.163 | 28.759 | 1.00 | 28.94 C |
| ATOM | 6165 | N | ASP | B | 767 | 5.791 | 9.824 | 29.787 | 1.00 | 35.23 N |
| ATOM | 6166 | CA | ASP | B | 767 | 5.426 | 9.907 | 31.204 | 1.00 | 47.44 C |
| ATOM | 6167 | C | ASP | B | 767 | 4.377 | 10.985 | 31.490 | 1.00 | 46.72 C |
| ATOM | 6168 | O | ASP | B | 767 | 3.399 | 10.750 | 32.211 | 1.00 | 38.58 O |
| ATOM | 6169 | CB | ASP | B | 767 | 6.655 | 10.184 | 32.078 | 1.00 | 54.70 C |
| ATOM | 6170 | CG | ASP | B | 767 | 7.488 | 8.943 | 32.331 | 1.00 | 61.30 C |
| ATOM | 6171 | OD1 | ASP | B | 767 | 6.925 | 7.822 | 32.293 | 1.00 | 79.03 O |
| ATOM | 6172 | OD2 | ASP | B | 767 | 8.702 | 9.092 | 32.595 | 1.00 | 71.66 O |
| ATOM | 6173 | N | LYS | B | 768 | 4.607 | 12.165 | 30.931 | 1.00 | 26.43 N |
| ATOM | 6174 | CA | LYS | B | 768 | 3.720 | 13.292 | 31.106 | 1.00 | 41.55 C |
| ATOM | 6175 | C | LYS | B | 768 | 2.333 | 13.004 | 30.527 | 1.00 | 52.46 C |
| ATOM | 6176 | O | LYS | B | 768 | 1.320 | 13.273 | 31.177 | 1.00 | 41.90 O |
| ATOM | 6177 | CB | LYS | B | 768 | 4.318 | 14.512 | 30.418 | 1.00 | 38.23 C |
| ATOM | 6178 | CG | LYS | B | 768 | 3.935 | 15.840 | 31.055 | 1.00 | 54.95 C |
| ATOM | 6179 | CD | LYS | B | 768 | 5.097 | 16.815 | 30.912 | 1.00 | 72.44 C |
| ATOM | 6180 | CE | LYS | B | 768 | 6.352 | 16.276 | 31.612 | 1.00 | 69.85 C |
| ATOM | 6181 | NZ | LYS | B | 768 | 7.584 | 17.002 | 31.220 | 1.00 | 72.64 N |
| ATOM | 6182 | N | LEU | B | 769 | 2.308 | 12.448 | 29.315 | 1.00 | 34.93 N |
| ATOM | 6183 | CA | LEU | B | 769 | 1.064 | 12.132 | 28.630 | 1.00 | 40.98 C |
| ATOM | 6184 | C | LEU | B | 769 | 0.263 | 11.117 | 29.416 | 1.00 | 37.81 C |
| ATOM | 6185 | O | LEU | B | 769 | −0.939 | 11.300 | 29.651 | 1.00 | 35.86 O |
| ATOM | 6186 | CB | LEU | B | 769 | 1.331 | 11.571 | 27.228 | 1.00 | 39.83 C |
| ATOM | 6187 | CG | LEU | B | 769 | 0.075 | 11.043 | 26.501 | 1.00 | 54.05 C |
| ATOM | 6188 | CD1 | LEU | B | 769 | −0.934 | 12.188 | 26.254 | 1.00 | 34.03 C |
| ATOM | 6189 | CD2 | LEU | B | 769 | 0.487 | 10.382 | 25.184 | 1.00 | 42.88 C |
| ATOM | 6190 | N | TYR | B | 770 | 0.940 | 10.047 | 29.802 | 1.00 | 27.16 N |
| ATOM | 6191 | CA | TYR | B | 770 | 0.325 | 8.982 | 30.569 | 1.00 | 27.31 C |
| ATOM | 6192 | C | TYR | B | 770 | −0.258 | 9.545 | 31.871 | 1.00 | 45.59 C |
| ATOM | 6193 | O | TYR | B | 770 | −1.425 | 9.294 | 32.206 | 1.00 | 45.01 O |
| ATOM | 6194 | CB | TYR | B | 770 | 1.373 | 7.938 | 30.924 | 1.00 | 34.27 C |

TABLE 1-continued

| ATOM | 6195 | CG | TYR | B | 770 | 0.796 | 6.651 | 31.430 | 1.00 | 34.73 | C |
| --- | --- | --- | --- | --- | --- | --- | --- | --- | --- | --- | --- |
| ATOM | 6196 | CD1 | TYR | B | 770 | 0.222 | 5.737 | 30.551 | 1.00 | 36.42 | C |
| ATOM | 6197 | CD2 | TYR | B | 770 | 0.798 | 6.346 | 32.797 | 1.00 | 28.17 | C |
| ATOM | 6198 | CE1 | TYR | B | 770 | −0.340 | 4.542 | 31.015 | 1.00 | 24.11 | C |
| ATOM | 6199 | CE2 | TYR | B | 770 | 0.230 | 5.158 | 33.260 | 1.00 | 35.40 | C |
| ATOM | 6200 | CZ | TYR | B | 770 | −0.331 | 4.270 | 32.361 | 1.00 | 23.74 | C |
| ATOM | 6201 | OH | TYR | B | 770 | −0.893 | 3.105 | 32.819 | 1.00 | 39.55 | O |
| ATOM | 6202 | N | LYS | B | 771 | 0.567 | 10.294 | 32.604 | 1.00 | 40.71 | N |
| ATOM | 6203 | CA | LYS | B | 771 | 0.143 | 10.878 | 33.873 | 1.00 | 44.90 | C |
| ATOM | 6204 | C | LYS | B | 771 | −1.099 | 11.748 | 33.658 | 1.00 | 33.26 | C |
| ATOM | 6205 | O | LYS | B | 771 | −2.074 | 11.647 | 34.382 | 1.00 | 36.46 | O |
| ATOM | 6206 | CB | LYS | B | 771 | 1.246 | 11.736 | 34.477 | 1.00 | 32.18 | C |
| ATOM | 6207 | CG | LYS | B | 771 | 0.907 | 12.245 | 35.881 | 1.00 | 49.84 | C |
| ATOM | 6208 | CD | LYS | B | 771 | 1.988 | 13.192 | 36.411 | 1.00 | 58.90 | C |
| ATOM | 6209 | CE | LYS | B | 771 | 1.698 | 13.639 | 37.834 | 1.00 | 52.02 | C |
| ATOM | 6210 | NZ | LYS | B | 771 | 1.651 | 12.460 | 38.728 | 1.00 | 61.64 | N |
| ATOM | 6211 | N | MET | B | 772 | −1.041 | 12.613 | 32.666 | 1.00 | 37.51 | N |
| ATOM | 6212 | CA | MET | B | 772 | −2.166 | 13.480 | 32.353 | 1.00 | 35.70 | C |
| ATOM | 6213 | C | MET | B | 772 | −3.443 | 12.631 | 32.106 | 1.00 | 34.53 | C |
| ATOM | 6214 | O | MET | B | 772 | −4.494 | 12.892 | 32.698 | 1.00 | 33.01 | O |
| ATOM | 6215 | CB | MET | B | 772 | −1.823 | 14.278 | 31.105 | 1.00 | 35.39 | C |
| ATOM | 6216 | CG | MET | B | 772 | −2.779 | 15.380 | 30.760 | 1.00 | 63.14 | C |
| ATOM | 6217 | SD | MET | B | 772 | −2.363 | 16.853 | 31.664 | 1.00 | 64.68 | S |
| ATOM | 6218 | CE | MET | B | 772 | −0.691 | 17.063 | 31.148 | 1.00 | 64.90 | C |
| ATOM | 6219 | N | LEU | B | 773 | −3.331 | 11.600 | 31.263 | 1.00 | 31.75 | N |
| ATOM | 6220 | CA | LEU | B | 773 | −4.485 | 10.771 | 30.922 | 1.00 | 41.17 | C |
| ATOM | 6221 | C | LEU | B | 773 | −5.013 | 9.929 | 32.062 | 1.00 | 44.68 | C |
| ATOM | 6222 | O | LEU | B | 773 | −6.229 | 9.741 | 32.178 | 1.00 | 29.73 | O |
| ATOM | 6223 | CB | LEU | B | 773 | −4.176 | 9.848 | 29.745 | 1.00 | 36.93 | C |
| ATOM | 6224 | CG | LEU | B | 773 | −4.033 | 10.427 | 28.326 | 1.00 | 36.70 | C |
| ATOM | 6225 | CD1 | LEU | B | 773 | −3.361 | 9.394 | 27.418 | 1.00 | 33.20 | C |
| ATOM | 6226 | CD2 | LEU | B | 773 | −5.398 | 10.802 | 27.779 | 1.00 | 29.27 | C |
| ATOM | 6227 | N | THR | B | 774 | −4.118 | 9.453 | 32.921 | 1.00 | 23.19 | N |
| ATOM | 6228 | CA | THR | B | 774 | −4.550 | 8.608 | 34.009 | 1.00 | 35.33 | C |
| ATOM | 6229 | C | THR | B | 774 | −4.698 | 9.227 | 35.389 | 1.00 | 39.98 | C |
| ATOM | 6230 | O | THR | B | 774 | −5.366 | 8.633 | 36.227 | 1.00 | 41.41 | O |
| ATOM | 6231 | CB | THR | B | 774 | −3.634 | 7.375 | 34.162 | 1.00 | 46.14 | C |
| ATOM | 6232 | OG1 | THR | B | 774 | −2.321 | 7.802 | 34.560 | 1.00 | 41.76 | O |
| ATOM | 6233 | CG2 | THR | B | 774 | −3.544 | 6.612 | 32.836 | 1.00 | 37.05 | C |
| ATOM | 6234 | N | GLU | B | 775 | −4.086 | 10.378 | 35.659 | 1.00 | 31.57 | N |
| ATOM | 6235 | CA | GLU | B | 775 | −4.245 | 10.950 | 37.002 | 1.00 | 42.74 | C |
| ATOM | 6236 | C | GLU | B | 775 | −4.566 | 12.439 | 37.105 | 1.00 | 28.97 | C |
| ATOM | 6237 | O | GLU | B | 775 | −4.936 | 12.916 | 38.172 | 1.00 | 37.37 | O |
| ATOM | 6238 | CB | GLU | B | 775 | −3.054 | 10.589 | 37.915 | 1.00 | 27.57 | C |
| ATOM | 6239 | CG | GLU | B | 775 | −1.684 | 11.008 | 37.465 | 1.00 | 62.34 | C |
| ATOM | 6240 | CD | GLU | B | 775 | −0.598 | 10.585 | 38.480 | 1.00 | 77.76 | C |
| ATOM | 6241 | OE1 | GLU | B | 775 | −0.498 | 11.226 | 39.551 | 1.00 | 49.26 | O |
| ATOM | 6242 | OE2 | GLU | B | 775 | 0.141 | 9.603 | 38.209 | 1.00 | 60.66 | O |
| ATOM | 6243 | N | ILE | B | 776 | −4.421 | 13.181 | 36.019 | 1.00 | 24.72 | N |
| ATOM | 6244 | CA | ILE | B | 776 | −4.790 | 14.586 | 36.066 | 1.00 | 26.90 | C |
| ATOM | 6245 | C | ILE | B | 776 | −6.244 | 14.677 | 35.594 | 1.00 | 27.36 | C |
| ATOM | 6246 | O | ILE | B | 776 | −7.039 | 15.414 | 36.161 | 1.00 | 30.36 | O |
| ATOM | 6247 | CB | ILE | B | 776 | −3.861 | 15.440 | 35.181 | 1.00 | 39.38 | C |
| ATOM | 6248 | CG1 | ILE | B | 776 | −2.423 | 15.310 | 35.707 | 1.00 | 47.22 | C |
| ATOM | 6249 | CG2 | ILE | B | 776 | −4.292 | 16.912 | 35.206 | 1.00 | 31.23 | C |
| ATOM | 6250 | CD1 | ILE | B | 776 | −1.394 | 16.077 | 34.882 | 1.00 | 43.55 | C |
| ATOM | 6251 | N | TYR | B | 777 | −6.598 | 13.895 | 34.575 | 1.00 | 31.06 | N |
| ATOM | 6252 | CA | TYR | B | 777 | −7.972 | 13.898 | 34.063 | 1.00 | 24.82 | C |
| ATOM | 6253 | C | TYR | B | 777 | −8.822 | 12.974 | 34.920 | 1.00 | 26.65 | C |
| ATOM | 6254 | O | TYR | B | 777 | −8.906 | 11.782 | 34.644 | 1.00 | 22.41 | O |
| ATOM | 6255 | CB | TYR | B | 777 | −8.048 | 13.400 | 32.614 | 1.00 | 26.09 | C |
| ATOM | 6256 | CG | TYR | B | 777 | −7.274 | 14.206 | 31.606 | 1.00 | 23.08 | C |
| ATOM | 6257 | CD1 | TYR | B | 777 | −7.016 | 15.556 | 31.807 | 1.00 | 25.44 | C |
| ATOM | 6258 | CD2 | TYR | B | 777 | −6.801 | 13.617 | 30.443 | 1.00 | 23.46 | C |
| ATOM | 6259 | CE1 | TYR | B | 777 | −6.291 | 16.292 | 30.884 | 1.00 | 36.44 | C |
| ATOM | 6260 | CE2 | TYR | B | 777 | −6.085 | 14.348 | 29.505 | 1.00 | 26.99 | C |
| ATOM | 6261 | CZ | TYR | B | 777 | −5.824 | 15.681 | 29.736 | 1.00 | 24.97 | C |
| ATOM | 6262 | OH | TYR | B | 777 | −5.063 | 16.388 | 28.848 | 1.00 | 30.92 | O |
| ATOM | 6263 | N | THR | B | 778 | −9.422 | 13.509 | 35.977 | 1.00 | 29.70 | N |
| ATOM | 6264 | CA | THR | B | 778 | −10.272 | 12.704 | 36.847 | 1.00 | 30.51 | C |
| ATOM | 6265 | C | THR | B | 778 | −11.543 | 13.468 | 37.227 | 1.00 | 35.37 | C |
| ATOM | 6266 | O | THR | B | 778 | −11.581 | 14.706 | 37.207 | 1.00 | 28.28 | O |
| ATOM | 6267 | CB | THR | B | 778 | −9.566 | 12.363 | 38.172 | 1.00 | 32.06 | C |
| ATOM | 6268 | OG1 | THR | B | 778 | −9.331 | 13.582 | 38.892 | 1.00 | 30.73 | O |
| ATOM | 6269 | CG2 | THR | B | 778 | −8.237 | 11.663 | 37.916 | 1.00 | 31.83 | C |
| ATOM | 6270 | N | GLU | B | 779 | −12.579 | 12.723 | 37.587 | 1.00 | 24.74 | N |
| ATOM | 6271 | CA | GLU | B | 779 | −13.814 | 13.339 | 38.037 | 1.00 | 26.59 | C |
| ATOM | 6272 | C | GLU | B | 779 | −13.502 | 14.289 | 39.196 | 1.00 | 24.87 | C |
| ATOM | 6273 | O | GLU | B | 779 | −13.984 | 15.415 | 39.222 | 1.00 | 37.14 | O |

TABLE 1-continued

| ATOM | 6274 | CB | GLU | B | 779 | −14.808 | 12.283 | 38.505 | 1.00 | 25.28 | C |
|---|---|---|---|---|---|---|---|---|---|---|---|
| ATOM | 6275 | CG | GLU | B | 779 | −16.152 | 12.894 | 38.929 | 1.00 | 43.92 | C |
| ATOM | 6276 | CD | GLU | B | 779 | −17.272 | 11.860 | 39.071 | 1.00 | 38.41 | C |
| ATOM | 6277 | OE1 | GLU | B | 779 | −17.396 | 10.972 | 38.193 | 1.00 | 38.16 | O |
| ATOM | 6278 | OE2 | GLU | B | 779 | −18.044 | 11.951 | 40.052 | 1.00 | 37.50 | O |
| ATOM | 6279 | N | ASP | B | 780 | −12.690 | 13.825 | 40.146 | 1.00 | 25.59 | N |
| ATOM | 6280 | CA | ASP | B | 780 | −12.309 | 14.627 | 41.311 | 1.00 | 27.78 | C |
| ATOM | 6281 | C | ASP | B | 780 | −11.722 | 15.963 | 40.899 | 1.00 | 29.71 | C |
| ATOM | 6282 | O | ASP | B | 780 | −12.094 | 16.995 | 41.434 | 1.00 | 36.92 | O |
| ATOM | 6283 | CB | ASP | B | 780 | −11.265 | 13.899 | 42.166 | 1.00 | 44.44 | C |
| ATOM | 6284 | CG | ASP | B | 780 | −10.801 | 14.736 | 43.363 | 1.00 | 42.58 | C |
| ATOM | 6285 | OD1 | ASP | B | 780 | −11.631 | 14.999 | 44.259 | 1.00 | 46.52 | O |
| ATOM | 6286 | OD2 | ASP | B | 780 | −9.609 | 15.128 | 43.401 | 1.00 | 62.27 | O |
| ATOM | 6287 | N | ASN | B | 781 | −10.782 | 15.953 | 39.960 | 1.00 | 35.82 | N |
| ATOM | 6288 | CA | ASN | B | 781 | −10.206 | 17.219 | 39.526 | 1.00 | 33.98 | C |
| ATOM | 6289 | C | ASN | B | 781 | −11.220 | 18.104 | 38.812 | 1.00 | 24.39 | C |
| ATOM | 6290 | O | ASN | B | 781 | −11.214 | 19.309 | 39.010 | 1.00 | 45.20 | O |
| ATOM | 6291 | CB | ASN | B | 781 | −8.957 | 16.985 | 38.672 | 1.00 | 38.43 | C |
| ATOM | 6292 | CG | ASN | B | 781 | −7.778 | 16.576 | 39.528 | 1.00 | 54.41 | C |
| ATOM | 6293 | OD1 | ASN | B | 781 | −7.680 | 17.049 | 40.649 | 1.00 | 48.15 | O |
| ATOM | 6294 | ND2 | ASN | B | 781 | −6.890 | 15.697 | 39.024 | 1.00 | 31.97 | N |
| ATOM | 6295 | N | PHE | B | 782 | −12.111 | 17.524 | 38.011 | 1.00 | 28.48 | N |
| ATOM | 6296 | CA | PHE | B | 782 | −13.114 | 18.331 | 37.325 | 1.00 | 31.70 | C |
| ATOM | 6297 | C | PHE | B | 782 | −14.045 | 19.006 | 38.347 | 1.00 | 32.99 | C |
| ATOM | 6298 | O | PHE | B | 782 | −14.449 | 20.150 | 38.178 | 1.00 | 32.88 | O |
| ATOM | 6299 | CB | PHE | B | 782 | −13.952 | 17.474 | 36.356 | 1.00 | 30.12 | C |
| ATOM | 6300 | CG | PHE | B | 782 | −13.402 | 17.437 | 34.971 | 1.00 | 41.55 | C |
| ATOM | 6301 | CD1 | PHE | B | 782 | −13.491 | 18.558 | 34.146 | 1.00 | 47.31 | C |
| ATOM | 6302 | CD2 | PHE | B | 782 | −12.670 | 16.339 | 34.534 | 1.00 | 35.73 | C |
| ATOM | 6303 | CE1 | PHE | B | 782 | −12.845 | 18.582 | 32.902 | 1.00 | 33.01 | C |
| ATOM | 6304 | CE2 | PHE | B | 782 | −12.028 | 16.357 | 33.313 | 1.00 | 30.67 | C |
| ATOM | 6305 | CZ | PHE | B | 782 | −12.112 | 17.487 | 32.498 | 1.00 | 27.46 | C |
| ATOM | 6306 | N | VAL | B | 783 | −14.396 | 18.275 | 39.396 | 1.00 | 33.58 | N |
| ATOM | 6307 | CA | VAL | B | 783 | −15.246 | 18.809 | 40.438 | 1.00 | 33.28 | C |
| ATOM | 6308 | C | VAL | B | 783 | −14.604 | 20.063 | 41.035 | 1.00 | 51.29 | C |
| ATOM | 6309 | O | VAL | B | 783 | −15.295 | 21.030 | 41.386 | 1.00 | 44.57 | O |
| ATOM | 6310 | CB | VAL | B | 783 | −15.473 | 17.771 | 41.543 | 1.00 | 42.83 | C |
| ATOM | 6311 | CG1 | VAL | B | 783 | −15.984 | 18.472 | 42.783 | 1.00 | 32.70 | C |
| ATOM | 6312 | CG2 | VAL | B | 783 | −16.489 | 16.666 | 41.046 | 1.00 | 17.71 | C |
| ATOM | 6313 | N | LYS | B | 784 | −13.281 | 20.067 | 41.142 | 1.00 | 34.97 | N |
| ATOM | 6314 | CA | LYS | B | 784 | −12.632 | 21.244 | 41.682 | 1.00 | 38.23 | C |
| ATOM | 6315 | C | LYS | B | 784 | −12.775 | 22.418 | 40.731 | 1.00 | 32.82 | C |
| ATOM | 6316 | O | LYS | B | 784 | −13.224 | 23.485 | 41.127 | 1.00 | 44.98 | O |
| ATOM | 6317 | CB | LYS | B | 784 | −11.156 | 20.973 | 41.960 | 1.00 | 48.34 | C |
| ATOM | 6318 | CG | LYS | B | 784 | −10.925 | 20.115 | 43.177 | 1.00 | 45.65 | C |
| ATOM | 6319 | CD | LYS | B | 784 | −9.477 | 19.669 | 43.250 | 1.00 | 30.09 | C |
| ATOM | 6320 | CE | LYS | B | 784 | −9.299 | 18.625 | 44.336 | 1.00 | 39.47 | C |
| ATOM | 6321 | NZ | LYS | B | 784 | −7.931 | 18.017 | 44.330 | 1.00 | 51.72 | N |
| ATOM | 6322 | N | PHE | B | 785 | −12.403 | 22.222 | 39.473 | 1.00 | 33.42 | N |
| ATOM | 6323 | CA | PHE | B | 785 | −12.499 | 23.298 | 38.503 | 1.00 | 44.78 | C |
| ATOM | 6324 | C | PHE | B | 785 | −13.903 | 23.848 | 38.381 | 1.00 | 59.73 | C |
| ATOM | 6325 | O | PHE | B | 785 | −14.076 | 25.061 | 38.284 | 1.00 | 55.44 | O |
| ATOM | 6326 | CB | PHE | B | 785 | −12.016 | 22.842 | 37.132 | 1.00 | 38.22 | C |
| ATOM | 6327 | CG | PHE | B | 785 | −10.541 | 22.926 | 36.968 | 1.00 | 38.14 | C |
| ATOM | 6328 | CD1 | PHE | B | 785 | −9.706 | 22.049 | 37.644 | 1.00 | 49.00 | C |
| ATOM | 6329 | CD2 | PHE | B | 785 | −9.977 | 23.901 | 36.150 | 1.00 | 48.88 | C |
| ATOM | 6330 | CE1 | PHE | B | 785 | −8.343 | 22.128 | 37.509 | 1.00 | 35.99 | C |
| ATOM | 6331 | CE2 | PHE | B | 785 | −8.599 | 23.994 | 36.008 | 1.00 | 41.50 | C |
| ATOM | 6332 | CZ | PHE | B | 785 | −7.782 | 23.106 | 36.690 | 1.00 | 46.46 | C |
| ATOM | 6333 | N | PHE | B | 786 | −14.903 | 22.962 | 38.392 | 1.00 | 50.30 | N |
| ATOM | 6334 | CA | PHE | B | 786 | −16.294 | 23.390 | 38.270 | 1.00 | 33.96 | C |
| ATOM | 6335 | C | PHE | B | 786 | −16.858 | 24.061 | 39.523 | 1.00 | 36.21 | C |
| ATOM | 6336 | O | PHE | B | 786 | −17.883 | 24.744 | 39.454 | 1.00 | 44.80 | O |
| ATOM | 6337 | CB | PHE | B | 786 | −17.208 | 22.210 | 37.905 | 1.00 | 31.97 | C |
| ATOM | 6338 | CG | PHE | B | 786 | −17.027 | 21.697 | 36.503 | 1.00 | 29.63 | C |
| ATOM | 6339 | CD1 | PHE | B | 786 | −16.792 | 22.565 | 35.442 | 1.00 | 27.10 | C |
| ATOM | 6340 | CD2 | PHE | B | 786 | −17.117 | 20.341 | 36.245 | 1.00 | 28.31 | C |
| ATOM | 6341 | CE1 | PHE | B | 786 | −16.646 | 22.084 | 34.132 | 1.00 | 28.47 | C |
| ATOM | 6342 | CE2 | PHE | B | 786 | −16.975 | 19.834 | 34.941 | 1.00 | 33.87 | C |
| ATOM | 6343 | CZ | PHE | B | 786 | −16.738 | 20.707 | 33.880 | 1.00 | 29.56 | C |
| ATOM | 6344 | N | LYS | B | 787 | −16.206 | 23.867 | 40.664 | 1.00 | 42.30 | N |
| ATOM | 6345 | CA | LYS | B | 787 | −16.703 | 24.441 | 41.909 | 1.00 | 42.70 | C |
| ATOM | 6346 | C | LYS | B | 787 | −18.136 | 23.948 | 42.148 | 1.00 | 44.56 | C |
| ATOM | 6347 | O | LYS | B | 787 | −19.038 | 24.731 | 42.429 | 1.00 | 46.12 | O |
| ATOM | 6348 | CB | LYS | B | 787 | −16.684 | 25.982 | 41.853 | 1.00 | 49.51 | C |
| ATOM | 6349 | CG | LYS | B | 787 | −15.338 | 26.631 | 42.144 | 1.00 | 43.19 | C |
| ATOM | 6350 | CD | LYS | B | 787 | −14.389 | 26.613 | 40.956 | 1.00 | 61.77 | C |
| ATOM | 6351 | CE | LYS | B | 787 | −14.818 | 27.578 | 39.830 | 1.00 | 74.25 | C |
| ATOM | 6352 | NZ | LYS | B | 787 | −14.801 | 29.014 | 40.249 | 1.00 | 73.50 | N |

TABLE 1-continued

| ATOM | 6353 | N | VAL | B | 788 | −18.353 | 22.647 | 42.011 | 1.00 | 40.68 | N |
|---|---|---|---|---|---|---|---|---|---|---|---|
| ATOM | 6354 | CA | VAL | B | 788 | −19.686 | 22.086 | 42.240 | 1.00 | 33.04 | C |
| ATOM | 6355 | C | VAL | B | 788 | −19.658 | 21.089 | 43.392 | 1.00 | 39.98 | C |
| ATOM | 6356 | O | VAL | B | 788 | −18.594 | 20.651 | 43.842 | 1.00 | 35.63 | O |
| ATOM | 6357 | CB | VAL | B | 788 | −20.241 | 21.326 | 41.005 | 1.00 | 47.71 | C |
| ATOM | 6358 | CG1 | VAL | B | 788 | −20.673 | 22.313 | 39.924 | 1.00 | 45.28 | C |
| ATOM | 6359 | CG2 | VAL | B | 788 | −19.183 | 20.357 | 40.475 | 1.00 | 23.39 | C |
| ATOM | 6360 | N | LEU | B | 789 | −20.839 | 20.762 | 43.885 | 1.00 | 34.99 | N |
| ATOM | 6361 | CA | LEU | B | 789 | −20.949 | 19.791 | 44.946 | 1.00 | 38.58 | C |
| ATOM | 6362 | C | LEU | B | 789 | −21.093 | 18.488 | 44.171 | 1.00 | 43.41 | C |
| ATOM | 6363 | O | LEU | B | 789 | −21.845 | 18.421 | 43.191 | 1.00 | 49.94 | O |
| ATOM | 6364 | CB | LEU | B | 789 | −22.207 | 20.037 | 45.790 | 1.00 | 26.64 | C |
| ATOM | 6365 | CG | LEU | B | 789 | −22.332 | 19.116 | 47.007 | 1.00 | 50.02 | C |
| ATOM | 6366 | CD1 | LEU | B | 789 | −21.103 | 19.302 | 47.903 | 1.00 | 31.24 | C |
| ATOM | 6367 | CD2 | LEU | B | 789 | −23.609 | 19.428 | 47.785 | 1.00 | 38.71 | C |
| ATOM | 6368 | N | ASN | B | 790 | −20.361 | 17.464 | 44.577 | 1.00 | 32.62 | N |
| ATOM | 6369 | CA | ASN | B | 790 | −20.435 | 16.177 | 43.898 | 1.00 | 41.13 | C |
| ATOM | 6370 | C | ASN | B | 790 | −20.197 | 15.132 | 44.979 | 1.00 | 38.15 | C |
| ATOM | 6371 | O | ASN | B | 790 | −19.670 | 15.468 | 46.045 | 1.00 | 33.53 | O |
| ATOM | 6372 | CB | ASN | B | 790 | −19.335 | 16.098 | 42.817 | 1.00 | 38.32 | C |
| ATOM | 6373 | CG | ASN | B | 790 | −19.481 | 14.884 | 41.900 | 1.00 | 55.86 | C |
| ATOM | 6374 | OD1 | ASN | B | 790 | −20.364 | 14.837 | 41.013 | 1.00 | 34.79 | O |
| ATOM | 6375 | ND2 | ASN | B | 790 | −18.611 | 13.886 | 42.109 | 1.00 | 35.35 | N |
| ATOM | 6376 | N | ARG | B | 791 | −20.589 | 13.886 | 44.715 | 1.00 | 32.46 | N |
| ATOM | 6377 | CA | ARG | B | 791 | −20.366 | 12.791 | 45.670 | 1.00 | 47.36 | C |
| ATOM | 6378 | C | ARG | B | 791 | −18.893 | 12.861 | 46.073 | 1.00 | 45.40 | C |
| ATOM | 6379 | O | ARG | B | 791 | −18.027 | 13.128 | 45.233 | 1.00 | 44.79 | O |
| ATOM | 6380 | CB | ARG | B | 791 | −20.625 | 11.449 | 44.994 | 1.00 | 44.46 | C |
| ATOM | 6381 | CG | ARG | B | 791 | −19.766 | 11.265 | 43.740 | 1.00 | 56.95 | C |
| ATOM | 6382 | CD | ARG | B | 791 | −20.133 | 10.021 | 42.925 | 1.00 | 60.22 | C |
| ATOM | 6383 | NE | ARG | B | 791 | −19.385 | 9.970 | 41.666 | 1.00 | 55.19 | N |
| ATOM | 6384 | CZ | ARG | B | 791 | −19.525 | 9.022 | 40.746 | 1.00 | 60.02 | C |
| ATOM | 6385 | NH1 | ARG | B | 791 | −20.389 | 8.028 | 40.931 | 1.00 | 59.31 | N |
| ATOM | 6386 | NH2 | ARG | B | 791 | −18.797 | 9.066 | 39.640 | 1.00 | 58.77 | N |
| ATOM | 6387 | N | LYS | B | 792 | −18.595 | 12.627 | 47.346 | 1.00 | 55.53 | N |
| ATOM | 6388 | CA | LYS | B | 792 | −17.204 | 12.682 | 47.795 | 1.00 | 61.28 | C |
| ATOM | 6389 | C | LYS | B | 792 | −16.446 | 11.423 | 47.375 | 1.00 | 55.31 | C |
| ATOM | 6390 | O | LYS | B | 792 | −15.290 | 11.484 | 46.959 | 1.00 | 67.60 | O |
| ATOM | 6391 | CB | LYS | B | 792 | −17.145 | 12.838 | 49.315 | 1.00 | 65.89 | C |
| ATOM | 6392 | CG | LYS | B | 792 | −18.063 | 13.920 | 49.852 | 1.00 | 71.73 | C |
| ATOM | 6393 | CD | LYS | B | 792 | −17.750 | 15.300 | 49.269 | 1.00 | 62.56 | C |
| ATOM | 6394 | CE | LYS | B | 792 | −18.926 | 16.250 | 49.536 | 1.00 | 75.31 | C |
| ATOM | 6395 | NZ | LYS | B | 792 | −18.714 | 17.643 | 49.065 | 1.00 | 69.21 | N |
| ATOM | 6396 | N | THR | B | 793 | −17.100 | 10.281 | 47.489 | 1.00 | 41.04 | N |
| ATOM | 6397 | CA | THR | B | 793 | −16.481 | 9.024 | 47.112 | 1.00 | 61.16 | C |
| ATOM | 6398 | C | THR | B | 793 | −17.292 | 8.409 | 45.998 | 1.00 | 69.32 | C |
| ATOM | 6399 | O | THR | B | 793 | −18.526 | 8.455 | 46.024 | 1.00 | 61.47 | O |
| ATOM | 6400 | CB | THR | B | 793 | −16.486 | 7.985 | 48.265 | 1.00 | 65.11 | C |
| ATOM | 6401 | OG1 | THR | B | 793 | −15.760 | 8.489 | 49.390 | 1.00 | 78.61 | O |
| ATOM | 6402 | CG2 | THR | B | 793 | −15.839 | 6.692 | 47.802 | 1.00 | 63.40 | C |
| ATOM | 6403 | N | PHE | B | 794 | −16.596 | 7.821 | 45.032 | 1.00 | 58.97 | N |
| ATOM | 6404 | CA | PHE | B | 794 | −17.248 | 7.140 | 43.929 | 1.00 | 61.05 | C |
| ATOM | 6405 | C | PHE | B | 794 | −18.241 | 6.148 | 44.544 | 1.00 | 71.16 | C |
| ATOM | 6406 | O | PHE | B | 794 | −19.194 | 5.716 | 43.897 | 1.00 | 63.74 | O |
| ATOM | 6407 | CB | PHE | B | 794 | −16.202 | 6.381 | 43.112 | 1.00 | 74.38 | C |
| ATOM | 6408 | CG | PHE | B | 794 | −16.779 | 5.549 | 42.013 | 1.00 | 66.88 | C |
| ATOM | 6409 | CD1 | PHE | B | 794 | −17.240 | 6.147 | 40.845 | 1.00 | 62.50 | C |
| ATOM | 6410 | CD2 | PHE | B | 794 | −16.896 | 4.169 | 42.161 | 1.00 | 68.22 | C |
| ATOM | 6411 | CE1 | PHE | B | 794 | −17.814 | 5.387 | 39.835 | 1.00 | 65.39 | C |
| ATOM | 6412 | CE2 | PHE | B | 794 | −17.471 | 3.393 | 41.156 | 1.00 | 70.50 | C |
| ATOM | 6413 | CZ | PHE | B | 794 | −17.933 | 4.004 | 39.989 | 1.00 | 73.33 | C |
| ATOM | 6414 | N | LEU | B | 795 | −18.006 | 5.809 | 45.812 | 1.00 | 75.76 | N |
| ATOM | 6415 | CA | LEU | B | 795 | −18.839 | 4.863 | 46.547 | 1.00 | 71.12 | C |
| ATOM | 6416 | C | LEU | B | 795 | −20.041 | 5.472 | 47.255 | 1.00 | 74.94 | C |
| ATOM | 6417 | O | LEU | B | 795 | −20.418 | 5.016 | 48.336 | 1.00 | 73.08 | O |
| ATOM | 6418 | CB | LEU | B | 795 | −17.989 | 4.110 | 47.573 | 1.00 | 72.55 | C |
| ATOM | 6419 | CG | LEU | B | 795 | −16.839 | 3.287 | 46.990 | 1.00 | 75.13 | C |
| ATOM | 6420 | CD1 | LEU | B | 795 | −16.062 | 2.650 | 48.119 | 1.00 | 81.27 | C |
| ATOM | 6421 | CD2 | LEU | B | 795 | −17.380 | 2.229 | 46.046 | 1.00 | 72.59 | C |
| ATOM | 6422 | N | ASN | B | 796 | −20.638 | 6.499 | 46.654 | 1.00 | 85.12 | N |
| ATOM | 6423 | CA | ASN | B | 796 | −21.820 | 7.144 | 47.232 | 1.00 | 70.86 | C |
| ATOM | 6424 | C | ASN | B | 796 | −23.055 | 6.624 | 46.530 | 1.00 | 55.51 | C |
| ATOM | 6425 | O | ASN | B | 796 | −22.956 | 6.115 | 45.414 | 1.00 | 76.93 | O |
| ATOM | 6426 | CB | ASN | B | 796 | −21.745 | 8.664 | 47.081 | 1.00 | 72.25 | C |
| ATOM | 6427 | CG | ASN | B | 796 | −20.929 | 9.315 | 48.187 | 1.00 | 84.15 | C |
| ATOM | 6428 | OD1 | ASN | B | 796 | −21.178 | 9.075 | 49.370 | 1.00 | 79.76 | O |
| ATOM | 6429 | ND2 | ASN | B | 796 | −19.954 | 10.144 | 47.810 | 1.00 | 82.20 | N |
| ATOM | 6430 | N | PHE | B | 797 | −24.214 | 6.749 | 47.170 | 1.00 | 38.80 | N |
| ATOM | 6431 | CA | PHE | B | 797 | −25.448 | 6.256 | 46.567 | 1.00 | 56.30 | C |

TABLE 1-continued

| ATOM | 6432 | C | PHE | B | 797 | −26.386 | 7.350 | 46.109 | 1.00 | 51.73 | C |
|------|------|------|-----|---|-----|---------|--------|--------|------|-------|---|
| ATOM | 6433 | O | PHE | B | 797 | −26.661 | 8.294 | 46.845 | 1.00 | 59.51 | O |
| ATOM | 6434 | CB | PHE | B | 797 | −26.210 | 5.352 | 47.537 | 1.00 | 59.19 | C |
| ATOM | 6435 | CG | PHE | B | 797 | −25.360 | 4.301 | 48.175 | 1.00 | 72.62 | C |
| ATOM | 6436 | CD1 | PHE | B | 797 | −24.553 | 3.473 | 47.399 | 1.00 | 73.43 | C |
| ATOM | 6437 | CD2 | PHE | B | 797 | −25.359 | 4.141 | 49.556 | 1.00 | 68.16 | C |
| ATOM | 6438 | CE1 | PHE | B | 797 | −23.752 | 2.494 | 47.997 | 1.00 | 81.28 | C |
| ATOM | 6439 | CE2 | PHE | B | 797 | −24.567 | 3.170 | 50.161 | 1.00 | 70.17 | C |
| ATOM | 6440 | CZ | PHE | B | 797 | −23.761 | 2.344 | 49.380 | 1.00 | 75.59 | C |
| ATOM | 6441 | N | ASP | B | 798 | −26.883 | 7.212 | 44.888 | 1.00 | 39.83 | N |
| ATOM | 6442 | CA | ASP | B | 798 | −27.824 | 8.169 | 44.336 | 1.00 | 43.81 | C |
| ATOM | 6443 | C | ASP | B | 798 | −29.195 | 7.845 | 44.920 | 1.00 | 46.35 | C |
| ATOM | 6444 | O | ASP | B | 798 | −29.497 | 6.682 | 45.155 | 1.00 | 47.93 | O |
| ATOM | 6445 | CB | ASP | B | 798 | −27.862 | 8.040 | 42.811 | 1.00 | 50.85 | C |
| ATOM | 6446 | CG | ASP | B | 798 | −26.554 | 8.459 | 42.151 | 1.00 | 67.08 | C |
| ATOM | 6447 | OD1 | ASP | B | 798 | −26.037 | 9.561 | 42.476 | 1.00 | 59.54 | O |
| ATOM | 6448 | OD2 | ASP | B | 798 | −26.058 | 7.689 | 41.299 | 1.00 | 70.20 | O |
| ATOM | 6449 | N | LYS | B | 799 | −30.023 | 8.860 | 45.151 | 1.00 | 44.94 | N |
| ATOM | 6450 | CA | LYS | B | 799 | −31.358 | 8.644 | 45.712 | 1.00 | 51.49 | C |
| ATOM | 6451 | C | LYS | B | 799 | −32.506 | 8.719 | 44.699 | 1.00 | 44.70 | C |
| ATOM | 6452 | O | LYS | B | 799 | −33.528 | 8.060 | 44.881 | 1.00 | 33.03 | O |
| ATOM | 6453 | CB | LYS | B | 799 | −31.622 | 9.650 | 46.830 | 1.00 | 58.24 | C |
| ATOM | 6454 | CG | LYS | B | 799 | −30.599 | 9.623 | 47.941 | 1.00 | 54.59 | C |
| ATOM | 6455 | CD | LYS | B | 799 | −30.923 | 8.545 | 48.937 | 1.00 | 58.62 | C |
| ATOM | 6456 | CE | LYS | B | 799 | −29.759 | 8.320 | 49.882 | 1.00 | 74.70 | C |
| ATOM | 6457 | NZ | LYS | B | 799 | −28.545 | 7.839 | 49.147 | 1.00 | 65.18 | N |
| ATOM | 6458 | N | ALA | B | 800 | −32.352 | 9.522 | 43.642 | 1.00 | 34.59 | N |
| ATOM | 6459 | CA | ALA | B | 800 | −33.413 | 9.629 | 42.647 | 1.00 | 35.80 | C |
| ATOM | 6460 | C | ALA | B | 800 | −32.965 | 10.185 | 41.303 | 1.00 | 35.87 | C |
| ATOM | 6461 | O | ALA | B | 800 | −31.830 | 10.628 | 41.153 | 1.00 | 32.31 | O |
| ATOM | 6462 | CB | ALA | B | 800 | −34.559 | 10.477 | 43.187 | 1.00 | 46.61 | C |
| ATOM | 6463 | N | VAL | B | 801 | −33.881 | 10.124 | 40.335 | 1.00 | 30.49 | N |
| ATOM | 6464 | CA | VAL | B | 801 | −33.665 | 10.645 | 38.993 | 1.00 | 47.70 | C |
| ATOM | 6465 | C | VAL | B | 801 | −34.519 | 11.923 | 38.862 | 1.00 | 42.11 | C |
| ATOM | 6466 | O | VAL | B | 801 | −35.695 | 11.931 | 39.244 | 1.00 | 36.38 | O |
| ATOM | 6467 | CB | VAL | B | 801 | −34.180 | 9.700 | 37.881 | 1.00 | 26.32 | C |
| ATOM | 6468 | CG1 | VAL | B | 801 | −33.716 | 10.210 | 36.539 | 1.00 | 35.85 | C |
| ATOM | 6469 | CG2 | VAL | B | 801 | −33.714 | 8.333 | 38.085 | 1.00 | 42.72 | C |
| ATOM | 6470 | N | PHE | B | 802 | −33.940 | 12.957 | 38.265 | 1.00 | 31.92 | N |
| ATOM | 6471 | CA | PHE | B | 802 | −34.603 | 14.253 | 38.067 | 1.00 | 34.47 | C |
| ATOM | 6472 | C | PHE | B | 802 | −34.628 | 14.691 | 36.613 | 1.00 | 25.64 | C |
| ATOM | 6473 | O | PHE | B | 802 | −33.621 | 14.604 | 35.931 | 1.00 | 47.77 | O |
| ATOM | 6474 | CB | PHE | B | 802 | −33.871 | 15.330 | 38.858 | 1.00 | 26.98 | C |
| ATOM | 6475 | CG | PHE | B | 802 | −34.149 | 15.307 | 40.326 | 1.00 | 35.93 | C |
| ATOM | 6476 | CD1 | PHE | B | 802 | −35.407 | 15.671 | 40.816 | 1.00 | 44.67 | C |
| ATOM | 6477 | CD2 | PHE | B | 802 | −33.153 | 14.944 | 41.229 | 1.00 | 41.96 | C |
| ATOM | 6478 | CE1 | PHE | B | 802 | −35.667 | 15.677 | 42.182 | 1.00 | 41.18 | C |
| ATOM | 6479 | CE2 | PHE | B | 802 | −33.403 | 14.946 | 42.607 | 1.00 | 49.03 | C |
| ATOM | 6480 | CZ | PHE | B | 802 | −34.659 | 15.314 | 43.082 | 1.00 | 42.01 | C |
| ATOM | 6481 | N | LYS | B | 803 | −35.772 | 15.151 | 36.123 | 1.00 | 34.71 | N |
| ATOM | 6482 | CA | LYS | B | 803 | −35.818 | 15.639 | 34.741 | 1.00 | 32.04 | C |
| ATOM | 6483 | C | LYS | B | 803 | −35.282 | 17.056 | 34.836 | 1.00 | 34.96 | C |
| ATOM | 6484 | O | LYS | B | 803 | −35.603 | 17.763 | 35.785 | 1.00 | 31.04 | O |
| ATOM | 6485 | CB | LYS | B | 803 | −37.241 | 15.686 | 34.188 | 1.00 | 36.24 | C |
| ATOM | 6486 | CG | LYS | B | 803 | −37.320 | 16.176 | 32.714 | 1.00 | 30.64 | C |
| ATOM | 6487 | CD | LYS | B | 803 | −37.041 | 15.039 | 31.744 | 1.00 | 37.76 | C |
| ATOM | 6488 | CE | LYS | B | 803 | −37.004 | 15.488 | 30.284 | 1.00 | 35.84 | C |
| ATOM | 6489 | NZ | LYS | B | 803 | −35.836 | 16.392 | 30.035 | 1.00 | 49.70 | N |
| ATOM | 6490 | N | ILE | B | 804 | −34.438 | 17.462 | 33.896 | 1.00 | 27.93 | N |
| ATOM | 6491 | CA | ILE | B | 804 | −33.913 | 18.811 | 33.938 | 1.00 | 20.61 | C |
| ATOM | 6492 | C | ILE | B | 804 | −33.898 | 19.384 | 32.528 | 1.00 | 29.72 | C |
| ATOM | 6493 | O | ILE | B | 804 | −34.160 | 18.674 | 31.544 | 1.00 | 20.61 | O |
| ATOM | 6494 | CB | ILE | B | 804 | −32.466 | 18.857 | 34.513 | 1.00 | 30.91 | C |
| ATOM | 6495 | CG1 | ILE | B | 804 | −31.465 | 18.255 | 33.512 | 1.00 | 28.60 | C |
| ATOM | 6496 | CG2 | ILE | B | 804 | −32.417 | 18.127 | 35.834 | 1.00 | 45.12 | C |
| ATOM | 6497 | CD1 | ILE | B | 804 | −30.040 | 18.095 | 34.052 | 1.00 | 25.28 | C |
| ATOM | 6498 | N | ASN | B | 805 | −33.624 | 20.683 | 32.435 | 1.00 | 33.44 | N |
| ATOM | 6499 | CA | ASN | B | 805 | −33.512 | 21.329 | 31.132 | 1.00 | 40.47 | C |
| ATOM | 6500 | C | ASN | B | 805 | −32.459 | 22.391 | 31.237 | 1.00 | 28.56 | C |
| ATOM | 6501 | O | ASN | B | 805 | −32.712 | 23.471 | 31.718 | 1.00 | 41.55 | O |
| ATOM | 6502 | CB | ASN | B | 805 | −34.814 | 21.962 | 30.662 | 1.00 | 47.95 | C |
| ATOM | 6503 | CG | ASN | B | 805 | −34.696 | 22.500 | 29.241 | 1.00 | 64.07 | C |
| ATOM | 6504 | OD1 | ASN | B | 805 | −33.605 | 22.491 | 28.643 | 1.00 | 39.48 | O |
| ATOM | 6505 | ND2 | ASN | B | 805 | −35.807 | 22.972 | 28.696 | 1.00 | 43.97 | N |
| ATOM | 6506 | N | ILE | B | 806 | −31.276 | 22.061 | 30.751 | 1.00 | 32.53 | N |
| ATOM | 6507 | CA | ILE | B | 806 | −30.107 | 22.914 | 30.805 | 1.00 | 22.67 | C |
| ATOM | 6508 | C | ILE | B | 806 | −29.938 | 23.928 | 29.666 | 1.00 | 40.68 | C |
| ATOM | 6509 | O | ILE | B | 806 | −29.102 | 24.818 | 29.748 | 1.00 | 37.03 | O |
| ATOM | 6510 | CB | ILE | B | 806 | −28.871 | 21.987 | 30.879 | 1.00 | 45.27 | C |

TABLE 1-continued

| | | | | | | | | | | |
|---|---|---|---|---|---|---|---|---|---|---|
| ATOM | 6511 | CG1 | ILE | B | 806 | −28.728 | 21.475 | 32.305 | 1.00 | 33.13 | C |
| ATOM | 6512 | CG2 | ILE | B | 806 | −27.633 | 22.649 | 30.365 | 1.00 | 59.17 | C |
| ATOM | 6513 | CD1 | ILE | B | 806 | −27.509 | 20.636 | 32.500 | 1.00 | 61.71 | C |
| ATOM | 6514 | N | VAL | B | 807 | −30.728 | 23.812 | 28.608 | 1.00 | 37.33 | N |
| ATOM | 6515 | CA | VAL | B | 807 | −30.563 | 24.722 | 27.497 | 1.00 | 35.46 | C |
| ATOM | 6516 | C | VAL | B | 807 | −30.808 | 26.190 | 27.860 | 1.00 | 52.14 | C |
| ATOM | 6517 | O | VAL | B | 807 | −29.935 | 27.023 | 27.638 | 1.00 | 34.27 | O |
| ATOM | 6518 | CB | VAL | B | 807 | −31.417 | 24.245 | 26.305 | 1.00 | 52.95 | C |
| ATOM | 6519 | CG1 | VAL | B | 807 | −31.423 | 25.293 | 25.161 | 1.00 | 41.17 | C |
| ATOM | 6520 | CG2 | VAL | B | 807 | −30.836 | 22.900 | 25.810 | 1.00 | 43.35 | C |
| ATOM | 6521 | N | PRO | B | 808 | −31.965 | 26.519 | 28.468 | 1.00 | 46.84 | N |
| ATOM | 6522 | CA | PRO | B | 808 | −32.244 | 27.911 | 28.836 | 1.00 | 22.19 | C |
| ATOM | 6523 | C | PRO | B | 808 | −31.138 | 28.514 | 29.676 | 1.00 | 33.48 | C |
| ATOM | 6524 | O | PRO | B | 808 | −30.733 | 27.943 | 30.676 | 1.00 | 43.96 | O |
| ATOM | 6525 | CB | PRO | B | 808 | −33.548 | 27.802 | 29.622 | 1.00 | 32.97 | C |
| ATOM | 6526 | CG | PRO | B | 808 | −34.242 | 26.664 | 28.964 | 1.00 | 39.96 | C |
| ATOM | 6527 | CD | PRO | B | 808 | −33.114 | 25.653 | 28.798 | 1.00 | 40.95 | C |
| ATOM | 6528 | N | LYS | B | 809 | −30.652 | 29.683 | 29.295 | 1.00 | 40.94 | N |
| ATOM | 6529 | CA | LYS | B | 809 | −29.591 | 30.307 | 30.061 | 1.00 | 33.75 | C |
| ATOM | 6530 | C | LYS | B | 809 | −30.043 | 30.727 | 31.456 | 1.00 | 41.48 | C |
| ATOM | 6531 | O | LYS | B | 809 | −29.210 | 30.994 | 32.319 | 1.00 | 46.52 | O |
| ATOM | 6532 | CB | LYS | B | 809 | −29.042 | 31.509 | 29.310 | 1.00 | 29.43 | C |
| ATOM | 6533 | CG | LYS | B | 809 | −27.797 | 32.073 | 29.958 | 1.00 | 42.91 | C |
| ATOM | 6534 | CD | LYS | B | 809 | −26.990 | 32.944 | 29.004 | 1.00 | 51.56 | C |
| ATOM | 6535 | CE | LYS | B | 809 | −25.713 | 33.437 | 29.688 | 1.00 | 67.51 | C |
| ATOM | 6536 | NZ | LYS | B | 809 | −24.897 | 34.370 | 28.855 | 1.00 | 62.52 | N |
| ATOM | 6537 | N | VAL | B | 810 | −31.356 | 30.809 | 31.682 | 1.00 | 46.78 | N |
| ATOM | 6538 | CA | VAL | B | 810 | −31.849 | 31.175 | 33.013 | 1.00 | 46.12 | C |
| ATOM | 6539 | C | VAL | B | 810 | −31.837 | 29.971 | 33.975 | 1.00 | 39.20 | C |
| ATOM | 6540 | O | VAL | B | 810 | −31.946 | 30.134 | 35.179 | 1.00 | 39.74 | O |
| ATOM | 6541 | CB | VAL | B | 810 | −33.265 | 31.780 | 32.938 | 1.00 | 47.60 | C |
| ATOM | 6542 | CG1 | VAL | B | 810 | −33.197 | 33.107 | 32.191 | 1.00 | 43.04 | C |
| ATOM | 6543 | CG2 | VAL | B | 810 | −34.221 | 30.828 | 32.233 | 1.00 | 33.21 | C |
| ATOM | 6544 | N | ASN | B | 811 | −31.672 | 28.769 | 33.429 | 1.00 | 31.61 | N |
| ATOM | 6545 | CA | ASN | B | 811 | −31.610 | 27.538 | 34.224 | 1.00 | 39.72 | C |
| ATOM | 6546 | C | ASN | B | 811 | −30.185 | 27.063 | 34.498 | 1.00 | 42.87 | C |
| ATOM | 6547 | O | ASN | B | 811 | −29.883 | 26.584 | 35.591 | 1.00 | 41.02 | O |
| ATOM | 6548 | CB | ASN | B | 811 | −32.326 | 26.391 | 33.503 | 1.00 | 31.55 | C |
| ATOM | 6549 | CG | ASN | B | 811 | −33.825 | 26.588 | 33.412 | 1.00 | 47.70 | C |
| ATOM | 6550 | OD1 | ASN | B | 811 | −34.369 | 27.556 | 33.959 | 1.00 | 40.45 | O |
| ATOM | 6551 | ND2 | ASN | B | 811 | −34.511 | 25.660 | 32.724 | 1.00 | 30.92 | N |
| ATOM | 6552 | N | TYR | B | 812 | −29.309 | 27.215 | 33.506 | 1.00 | 45.76 | N |
| ATOM | 6553 | CA | TYR | B | 812 | −27.937 | 26.706 | 33.603 | 1.00 | 39.97 | C |
| ATOM | 6554 | C | TYR | B | 812 | −26.941 | 27.452 | 32.687 | 1.00 | 41.50 | C |
| ATOM | 6555 | O | TYR | B | 812 | −27.253 | 27.753 | 31.533 | 1.00 | 33.45 | O |
| ATOM | 6556 | CB | TYR | B | 812 | −28.014 | 25.212 | 33.223 | 1.00 | 33.67 | C |
| ATOM | 6557 | CG | TYR | B | 812 | −26.756 | 24.368 | 33.332 | 1.00 | 48.57 | C |
| ATOM | 6558 | CD1 | TYR | B | 812 | −25.819 | 24.344 | 32.301 | 1.00 | 32.64 | C |
| ATOM | 6559 | CD2 | TYR | B | 812 | −26.530 | 23.543 | 34.455 | 1.00 | 47.95 | C |
| ATOM | 6560 | CE1 | TYR | B | 812 | −24.686 | 23.524 | 32.369 | 1.00 | 50.82 | C |
| ATOM | 6561 | CE2 | TYR | B | 812 | −25.399 | 22.724 | 34.536 | 1.00 | 31.63 | C |
| ATOM | 6562 | CZ | TYR | B | 812 | −24.480 | 22.722 | 33.486 | 1.00 | 39.13 | C |
| ATOM | 6563 | OH | TYR | B | 812 | −23.351 | 21.963 | 33.552 | 1.00 | 29.21 | O |
| ATOM | 6564 | N | THR | B | 813 | −25.742 | 27.745 | 33.185 | 1.00 | 39.32 | N |
| ATOM | 6565 | CA | THR | B | 813 | −24.779 | 28.408 | 32.329 | 1.00 | 35.72 | C |
| ATOM | 6566 | C | THR | B | 813 | −23.458 | 27.677 | 32.256 | 1.00 | 42.15 | C |
| ATOM | 6567 | O | THR | B | 813 | −23.130 | 26.862 | 33.127 | 1.00 | 38.91 | O |
| ATOM | 6568 | CB | THR | B | 813 | −24.489 | 29.861 | 32.768 | 1.00 | 37.14 | C |
| ATOM | 6569 | OG1 | THR | B | 813 | −23.678 | 29.859 | 33.941 | 1.00 | 42.92 | O |
| ATOM | 6570 | CG2 | THR | B | 813 | −25.793 | 30.620 | 33.044 | 1.00 | 40.30 | C |
| ATOM | 6571 | N | ILE | B | 814 | −22.709 | 28.013 | 31.208 | 1.00 | 39.15 | N |
| ATOM | 6572 | CA | ILE | B | 814 | −21.397 | 27.459 | 30.904 | 1.00 | 41.81 | C |
| ATOM | 6573 | C | ILE | B | 814 | −20.429 | 27.700 | 32.038 | 1.00 | 37.59 | C |
| ATOM | 6574 | O | ILE | B | 814 | −19.624 | 26.844 | 32.358 | 1.00 | 43.59 | O |
| ATOM | 6575 | CB | ILE | B | 814 | −20.826 | 28.089 | 29.603 | 1.00 | 39.46 | C |
| ATOM | 6576 | CG1 | ILE | B | 814 | −21.631 | 27.601 | 28.413 | 1.00 | 36.55 | C |
| ATOM | 6577 | CG2 | ILE | B | 814 | −19.358 | 27.714 | 29.396 | 1.00 | 47.07 | C |
| ATOM | 6578 | CD1 | ILE | B | 814 | −21.179 | 28.172 | 27.079 | 1.00 | 61.87 | C |
| ATOM | 6579 | N | TYR | B | 815 | −20.528 | 28.860 | 32.668 | 1.00 | 38.18 | N |
| ATOM | 6580 | CA | TYR | B | 815 | −19.626 | 29.180 | 33.751 | 1.00 | 27.43 | C |
| ATOM | 6581 | C | TYR | B | 815 | −20.085 | 28.816 | 35.148 | 1.00 | 40.87 | C |
| ATOM | 6582 | O | TYR | B | 815 | −19.260 | 28.598 | 36.008 | 1.00 | 34.26 | O |
| ATOM | 6583 | CB | TYR | B | 815 | −19.267 | 30.673 | 33.723 | 1.00 | 55.70 | C |
| ATOM | 6584 | CG | TYR | B | 815 | −18.088 | 31.015 | 32.830 | 1.00 | 62.62 | C |
| ATOM | 6585 | CD1 | TYR | B | 815 | −18.208 | 31.000 | 31.439 | 1.00 | 49.87 | C |
| ATOM | 6586 | CD2 | TYR | B | 815 | −16.831 | 31.295 | 33.385 | 1.00 | 74.22 | C |
| ATOM | 6587 | CE1 | TYR | B | 815 | −17.105 | 31.248 | 30.617 | 1.00 | 59.22 | C |
| ATOM | 6588 | CE2 | TYR | B | 815 | −15.714 | 31.545 | 32.573 | 1.00 | 69.19 | C |
| ATOM | 6589 | CZ | TYR | B | 815 | −15.860 | 31.517 | 31.190 | 1.00 | 71.42 | C |

TABLE 1-continued

| | | | | | | | | | | |
|---|---|---|---|---|---|---|---|---|---|---|
| ATOM | 6590 | OH | TYR | B | 815 | −14.765 | 31.747 | 30.387 | 1.00 | 69.97 O |
| ATOM | 6591 | N | ASP | B | 816 | −21.386 | 28.752 | 35.398 | 1.00 | 36.57 N |
| ATOM | 6592 | CA | ASP | B | 816 | −21.826 | 28.451 | 36.758 | 1.00 | 52.26 C |
| ATOM | 6593 | C | ASP | B | 816 | −22.639 | 27.189 | 36.915 | 1.00 | 30.18 C |
| ATOM | 6594 | O | ASP | B | 816 | −22.928 | 26.801 | 38.030 | 1.00 | 47.49 O |
| ATOM | 6595 | CB | ASP | B | 816 | −22.663 | 29.595 | 37.328 | 1.00 | 54.31 C |
| ATOM | 6596 | CG | ASP | B | 816 | −21.906 | 30.897 | 37.415 | 1.00 | 60.60 C |
| ATOM | 6597 | OD1 | ASP | B | 816 | −20.776 | 30.916 | 37.965 | 1.00 | 57.46 O |
| ATOM | 6598 | OD2 | ASP | B | 816 | −22.467 | 31.902 | 36.936 | 1.00 | 61.98 O |
| ATOM | 6599 | N | GLY | B | 817 | −23.013 | 26.568 | 35.804 | 1.00 | 30.64 N |
| ATOM | 6600 | CA | GLY | B | 817 | −23.819 | 25.375 | 35.876 | 1.00 | 35.32 C |
| ATOM | 6601 | C | GLY | B | 817 | −25.199 | 25.764 | 36.386 | 1.00 | 56.36 C |
| ATOM | 6602 | O | GLY | B | 817 | −25.900 | 26.578 | 35.770 | 1.00 | 43.67 O |
| ATOM | 6603 | N | PHE | B | 818 | −25.585 | 25.183 | 37.516 | 1.00 | 29.42 N |
| ATOM | 6604 | CA | PHE | B | 818 | −26.875 | 25.469 | 38.128 | 1.00 | 35.81 C |
| ATOM | 6605 | C | PHE | B | 818 | −26.795 | 26.581 | 39.163 | 1.00 | 31.45 C |
| ATOM | 6606 | O | PHE | B | 818 | −27.813 | 27.184 | 39.479 | 1.00 | 26.19 O |
| ATOM | 6607 | CB | PHE | B | 818 | −27.431 | 24.242 | 38.840 | 1.00 | 28.81 C |
| ATOM | 6608 | CG | PHE | B | 818 | −28.000 | 23.225 | 37.932 | 1.00 | 26.84 C |
| ATOM | 6609 | CD1 | PHE | B | 818 | −29.151 | 23.485 | 37.221 | 1.00 | 24.35 C |
| ATOM | 6610 | CD2 | PHE | B | 818 | −27.410 | 21.963 | 37.840 | 1.00 | 37.34 C |
| ATOM | 6611 | CE1 | PHE | B | 818 | −29.732 | 22.500 | 36.433 | 1.00 | 21.15 C |
| ATOM | 6612 | CE2 | PHE | B | 818 | −27.975 | 20.959 | 37.058 | 1.00 | 25.10 C |
| ATOM | 6613 | CZ | PHE | B | 818 | −29.135 | 21.220 | 36.352 | 1.00 | 32.00 C |
| ATOM | 6614 | N | ASN | B | 819 | −25.597 | 26.815 | 39.693 | 1.00 | 35.91 N |
| ATOM | 6615 | CA | ASN | B | 819 | −25.381 | 27.817 | 40.732 | 1.00 | 40.99 C |
| ATOM | 6616 | C | ASN | B | 819 | −25.176 | 29.207 | 40.149 | 1.00 | 44.82 C |
| ATOM | 6617 | O | ASN | B | 819 | −24.131 | 29.824 | 40.327 | 1.00 | 39.25 O |
| ATOM | 6618 | CB | ASN | B | 819 | −24.175 | 27.426 | 41.590 | 1.00 | 37.58 C |
| ATOM | 6619 | CG | ASN | B | 819 | −24.317 | 26.025 | 42.204 | 1.00 | 36.97 C |
| ATOM | 6620 | OD1 | ASN | B | 819 | −25.404 | 25.629 | 42.644 | 1.00 | 37.72 O |
| ATOM | 6621 | ND2 | ASN | B | 819 | −23.218 | 25.283 | 42.242 | 1.00 | 33.23 N |
| ATOM | 6622 | N | LEU | B | 820 | −26.205 | 29.690 | 39.462 | 1.00 | 46.71 N |
| ATOM | 6623 | CA | LEU | B | 820 | −26.191 | 30.990 | 38.808 | 1.00 | 39.93 C |
| ATOM | 6624 | C | LEU | B | 820 | −25.723 | 32.149 | 39.695 | 1.00 | 39.11 C |
| ATOM | 6625 | O | LEU | B | 820 | −26.190 | 32.312 | 40.828 | 1.00 | 46.42 O |
| ATOM | 6626 | CB | LEU | B | 820 | −27.592 | 31.260 | 38.257 | 1.00 | 39.10 C |
| ATOM | 6627 | CG | LEU | B | 820 | −28.121 | 30.176 | 37.316 | 1.00 | 40.43 C |
| ATOM | 6628 | CD1 | LEU | B | 820 | −29.528 | 30.508 | 36.892 | 1.00 | 32.86 C |
| ATOM | 6629 | CD2 | LEU | B | 820 | −27.217 | 30.057 | 36.084 | 1.00 | 45.18 C |
| ATOM | 6630 | N | ARG | B | 821 | −24.777 | 32.940 | 39.189 | 1.00 | 41.16 N |
| ATOM | 6631 | CA | ARG | B | 821 | −24.281 | 34.092 | 39.942 | 1.00 | 47.02 C |
| ATOM | 6632 | C | ARG | B | 821 | −25.372 | 35.175 | 40.060 | 1.00 | 40.78 C |
| ATOM | 6633 | O | ARG | B | 821 | −26.311 | 35.228 | 39.256 | 1.00 | 32.42 O |
| ATOM | 6634 | CB | ARG | B | 821 | −23.023 | 34.677 | 39.283 | 1.00 | 40.35 C |
| ATOM | 6635 | CG | ARG | B | 821 | −23.241 | 35.264 | 37.892 | 1.00 | 55.11 C |
| ATOM | 6636 | CD | ARG | B | 821 | −21.911 | 35.572 | 37.226 | 1.00 | 66.39 C |
| ATOM | 6637 | NE | ARG | B | 821 | −21.198 | 34.348 | 36.865 | 1.00 | 56.39 N |
| ATOM | 6638 | CZ | ARG | B | 821 | −19.973 | 34.306 | 36.348 | 1.00 | 61.04 C |
| ATOM | 6639 | NH1 | ARG | B | 821 | −19.286 | 35.418 | 36.122 | 1.00 | 60.23 N |
| ATOM | 6640 | NH2 | ARG | B | 821 | −19.440 | 33.141 | 36.033 | 1.00 | 64.35 N |
| ATOM | 6641 | N | ASN | B | 822 | −25.248 | 36.017 | 41.086 | 1.00 | 43.83 N |
| ATOM | 6642 | CA | ASN | B | 822 | −26.197 | 37.105 | 41.340 | 1.00 | 48.83 C |
| ATOM | 6643 | C | ASN | B | 822 | −27.638 | 36.688 | 41.551 | 1.00 | 50.50 C |
| ATOM | 6644 | O | ASN | B | 822 | −28.559 | 37.426 | 41.211 | 1.00 | 57.98 O |
| ATOM | 6645 | CB | ASN | B | 822 | −26.134 | 38.145 | 40.218 | 1.00 | 40.56 C |
| ATOM | 6646 | CG | ASN | B | 822 | −24.716 | 38.619 | 39.954 | 1.00 | 34.70 C |
| ATOM | 6647 | OD1 | ASN | B | 822 | −23.923 | 38.813 | 40.887 | 1.00 | 38.16 O |
| ATOM | 6648 | ND2 | ASN | B | 822 | −24.389 | 38.808 | 38.690 | 1.00 | 38.33 N |
| ATOM | 6649 | N | THR | B | 823 | −27.827 | 35.484 | 42.079 | 1.00 | 54.61 N |
| ATOM | 6650 | CA | THR | B | 823 | −29.156 | 34.982 | 42.416 | 1.00 | 38.79 C |
| ATOM | 6651 | C | THR | B | 823 | −28.883 | 34.292 | 43.749 | 1.00 | 56.94 C |
| ATOM | 6652 | O | THR | B | 823 | −27.705 | 34.207 | 44.183 | 1.00 | 43.11 O |
| ATOM | 6653 | CB | THR | B | 823 | −29.686 | 33.948 | 41.393 | 1.00 | 50.32 C |
| ATOM | 6654 | OG1 | THR | B | 823 | −28.976 | 32.718 | 41.541 | 1.00 | 51.99 O |
| ATOM | 6655 | CG2 | THR | B | 823 | −29.502 | 34.455 | 39.966 | 1.00 | 43.88 C |
| ATOM | 6656 | N | ASN | B | 824 | −29.923 | 33.811 | 44.425 | 1.00 | 45.06 N |
| ATOM | 6657 | CA | ASN | B | 824 | −29.666 | 33.137 | 45.699 | 1.00 | 52.13 C |
| ATOM | 6658 | C | ASN | B | 824 | −29.278 | 31.675 | 45.441 | 1.00 | 59.36 C |
| ATOM | 6659 | O | ASN | B | 824 | −29.343 | 30.838 | 46.341 | 1.00 | 55.05 O |
| ATOM | 6660 | CB | ASN | B | 824 | −30.887 | 33.195 | 46.618 | 1.00 | 53.82 C |
| ATOM | 6661 | CG | ASN | B | 824 | −31.875 | 32.095 | 46.339 | 1.00 | 50.04 C |
| ATOM | 6662 | OD1 | ASN | B | 824 | −32.319 | 31.415 | 45.205 | 1.00 | 57.03 O |
| ATOM | 6663 | ND2 | ASN | B | 824 | −32.230 | 31.347 | 47.377 | 1.00 | 45.49 N |
| ATOM | 6664 | N | LEU | B | 825 | −28.853 | 31.395 | 44.209 | 1.00 | 56.91 N |
| ATOM | 6665 | CA | LEU | B | 825 | −28.451 | 30.062 | 43.776 | 1.00 | 50.30 C |
| ATOM | 6666 | C | LEU | B | 825 | −26.945 | 29.900 | 43.749 | 1.00 | 53.67 C |
| ATOM | 6667 | O | LEU | B | 825 | −26.441 | 28.785 | 43.573 | 1.00 | 47.71 O |
| ATOM | 6668 | CB | LEU | B | 825 | −29.004 | 29.790 | 42.380 | 1.00 | 26.70 C |

TABLE 1-continued

| ATOM | 6669 | CG | LEU | B | 825 | −30.279 | 28.954 | 42.336 | 1.00 | 56.33 | C |
| --- | --- | --- | --- | --- | --- | --- | --- | --- | --- | --- | --- |
| ATOM | 6670 | CD1 | LEU | B | 825 | −31.227 | 29.372 | 43.459 | 1.00 | 43.33 | C |
| ATOM | 6671 | CD2 | LEU | B | 825 | −30.979 | 29.075 | 40.994 | 1.00 | 28.12 | C |
| ATOM | 6672 | N | ALA | B | 826 | −26.221 | 30.996 | 43.943 | 1.00 | 37.99 | N |
| ATOM | 6673 | CA | ALA | B | 826 | −24.764 | 30.928 | 43.875 | 1.00 | 42.71 | C |
| ATOM | 6674 | C | ALA | B | 826 | −24.041 | 30.528 | 45.150 | 1.00 | 45.82 | C |
| ATOM | 6675 | O | ALA | B | 826 | −22.857 | 30.184 | 45.122 | 1.00 | 61.70 | O |
| ATOM | 6676 | CB | ALA | B | 826 | −24.222 | 32.280 | 43.413 | 1.00 | 50.68 | C |
| ATOM | 6677 | N | ALA | B | 827 | −24.742 | 30.572 | 46.271 | 1.00 | 47.11 | N |
| ATOM | 6678 | CA | ALA | B | 827 | −24.126 | 30.229 | 47.547 | 1.00 | 60.57 | C |
| ATOM | 6679 | C | ALA | B | 827 | −24.530 | 28.844 | 48.037 | 1.00 | 60.07 | C |
| ATOM | 6680 | O | ALA | B | 827 | −25.662 | 28.404 | 47.807 | 1.00 | 43.96 | O |
| ATOM | 6681 | CB | ALA | B | 827 | −24.472 | 31.267 | 48.605 | 1.00 | 58.64 | C |
| ATOM | 6682 | N | ASN | B | 828 | −23.591 | 28.175 | 48.708 | 1.00 | 45.76 | N |
| ATOM | 6683 | CA | ASN | B | 828 | −23.829 | 26.849 | 49.264 | 1.00 | 46.91 | C |
| ATOM | 6684 | C | ASN | B | 828 | −24.442 | 25.889 | 48.258 | 1.00 | 47.55 | C |
| ATOM | 6685 | O | ASN | B | 828 | −25.287 | 25.066 | 48.621 | 1.00 | 42.19 | O |
| ATOM | 6686 | CB | ASN | B | 828 | −24.724 | 26.951 | 50.493 | 1.00 | 54.29 | C |
| ATOM | 6687 | CG | ASN | B | 828 | −24.251 | 28.006 | 51.479 | 1.00 | 64.96 | C |
| ATOM | 6688 | OD1 | ASN | B | 828 | −25.025 | 28.536 | 52.267 | 1.00 | 63.81 | O |
| ATOM | 6689 | ND2 | ASN | B | 828 | −22.950 | 28.318 | 51.434 | 1.00 | 52.10 | N |
| ATOM | 6690 | N | PHE | B | 829 | −24.016 | 26.011 | 47.002 | 1.00 | 31.56 | N |
| ATOM | 6691 | CA | PHE | B | 829 | −24.502 | 25.173 | 45.927 | 1.00 | 34.16 | C |
| ATOM | 6692 | C | PHE | B | 829 | −26.022 | 25.113 | 45.940 | 1.00 | 45.67 | C |
| ATOM | 6693 | O | PHE | B | 829 | −26.624 | 24.060 | 45.700 | 1.00 | 44.58 | O |
| ATOM | 6694 | CB | PHE | B | 829 | −23.919 | 23.771 | 46.043 | 1.00 | 37.81 | C |
| ATOM | 6695 | CG | PHE | B | 829 | −22.451 | 23.760 | 46.411 | 1.00 | 45.68 | C |
| ATOM | 6696 | CD1 | PHE | B | 829 | −21.496 | 24.012 | 45.437 | 1.00 | 33.15 | C |
| ATOM | 6697 | CD2 | PHE | B | 829 | −22.029 | 23.490 | 47.709 | 1.00 | 34.81 | C |
| ATOM | 6698 | CE1 | PHE | B | 829 | −20.136 | 23.992 | 45.748 | 1.00 | 45.50 | C |
| ATOM | 6699 | CE2 | PHE | B | 829 | −20.671 | 23.472 | 48.027 | 1.00 | 48.27 | C |
| ATOM | 6700 | CZ | PHE | B | 829 | −19.728 | 23.720 | 47.054 | 1.00 | 40.14 | C |
| ATOM | 6701 | N | ASN | B | 830 | −26.654 | 26.247 | 46.236 | 1.00 | 38.24 | N |
| ATOM | 6702 | CA | ASN | B | 830 | −28.106 | 26.279 | 46.283 | 1.00 | 27.95 | C |
| ATOM | 6703 | C | ASN | B | 830 | −28.704 | 25.874 | 44.946 | 1.00 | 41.31 | C |
| ATOM | 6704 | O | ASN | B | 830 | −29.774 | 25.266 | 44.880 | 1.00 | 35.49 | O |
| ATOM | 6705 | CB | ASN | B | 830 | −28.612 | 27.669 | 46.682 | 1.00 | 34.34 | C |
| ATOM | 6706 | CG | ASN | B | 830 | −28.586 | 27.902 | 48.183 | 1.00 | 46.89 | C |
| ATOM | 6707 | OD1 | ASN | B | 830 | −28.527 | 26.962 | 48.958 | 1.00 | 43.49 | O |
| ATOM | 6708 | ND2 | ASN | B | 830 | −28.618 | 29.167 | 48.599 | 1.00 | 49.52 | N |
| ATOM | 6709 | N | GLY | B | 831 | −27.998 | 26.159 | 43.864 | 1.00 | 37.53 | N |
| ATOM | 6710 | CA | GLY | B | 831 | −28.499 | 25.816 | 42.545 | 1.00 | 38.45 | C |
| ATOM | 6711 | C | GLY | B | 831 | −28.598 | 24.300 | 42.353 | 1.00 | 24.57 | C |
| ATOM | 6712 | O | GLY | B | 831 | −29.423 | 23.809 | 41.576 | 1.00 | 30.94 | O |
| ATOM | 6713 | N | GLN | B | 832 | −27.751 | 23.558 | 43.048 | 1.00 | 28.29 | N |
| ATOM | 6714 | CA | GLN | B | 832 | −27.794 | 22.101 | 42.965 | 1.00 | 45.69 | C |
| ATOM | 6715 | C | GLN | B | 832 | −28.770 | 21.541 | 43.979 | 1.00 | 36.99 | C |
| ATOM | 6716 | O | GLN | B | 832 | −29.158 | 20.376 | 43.887 | 1.00 | 35.84 | O |
| ATOM | 6717 | CB | GLN | B | 832 | −26.411 | 21.502 | 43.164 | 1.00 | 23.97 | C |
| ATOM | 6718 | CG | GLN | B | 832 | −25.472 | 21.812 | 42.040 | 1.00 | 27.93 | C |
| ATOM | 6719 | CD | GLN | B | 832 | −24.103 | 21.229 | 42.257 | 1.00 | 29.86 | C |
| ATOM | 6720 | OE1 | GLN | B | 832 | −23.915 | 20.012 | 42.113 | 1.00 | 33.01 | O |
| ATOM | 6721 | NE2 | GLN | B | 832 | −22.993 | 21.882 | 42.605 | 1.00 | 28.38 | N |
| ATOM | 6722 | N | ASN | B | 833 | −29.175 | 22.372 | 44.944 | 1.00 | 41.29 | N |
| ATOM | 6723 | CA | ASN | B | 833 | −30.113 | 21.922 | 45.969 | 1.00 | 31.40 | C |
| ATOM | 6724 | C | ASN | B | 833 | −31.471 | 21.716 | 45.331 | 1.00 | 29.96 | C |
| ATOM | 6725 | O | ASN | B | 833 | −32.041 | 22.634 | 44.754 | 1.00 | 44.08 | O |
| ATOM | 6726 | CB | ASN | B | 833 | −30.239 | 22.924 | 47.104 | 1.00 | 27.39 | C |
| ATOM | 6727 | CG | ASN | B | 833 | −31.087 | 22.390 | 48.239 | 1.00 | 26.66 | C |
| ATOM | 6728 | OD1 | ASN | B | 833 | −32.204 | 21.920 | 48.030 | 1.00 | 31.39 | O |
| ATOM | 6729 | ND2 | ASN | B | 833 | −30.554 | 22.475 | 49.450 | 1.00 | 37.71 | N |
| ATOM | 6730 | N | THR | B | 834 | −31.995 | 20.498 | 45.480 | 1.00 | 42.44 | N |
| ATOM | 6731 | CA | THR | B | 834 | −33.252 | 20.153 | 44.870 | 1.00 | 36.32 | C |
| ATOM | 6732 | C | THR | B | 834 | −34.506 | 20.653 | 45.607 | 1.00 | 34.02 | C |
| ATOM | 6733 | O | THR | B | 834 | −35.618 | 20.547 | 45.076 | 1.00 | 32.77 | O |
| ATOM | 6734 | CB | THR | B | 834 | −33.299 | 18.636 | 44.675 | 1.00 | 36.27 | C |
| ATOM | 6735 | OG1 | THR | B | 834 | −32.430 | 18.261 | 43.605 | 1.00 | 57.03 | O |
| ATOM | 6736 | CG2 | THR | B | 834 | −34.705 | 18.174 | 44.351 | 1.00 | 57.01 | C |
| ATOM | 6737 | N | GLU | B | 835 | −34.347 | 21.174 | 46.815 | 1.00 | 32.37 | N |
| ATOM | 6738 | CA | GLU | B | 835 | −35.519 | 21.686 | 47.535 | 1.00 | 47.97 | C |
| ATOM | 6739 | C | GLU | B | 835 | −35.612 | 23.150 | 47.147 | 1.00 | 36.90 | C |
| ATOM | 6740 | O | GLU | B | 835 | −36.642 | 23.615 | 46.680 | 1.00 | 61.82 | O |
| ATOM | 6741 | CB | GLU | B | 835 | −35.341 | 21.607 | 49.053 | 1.00 | 27.88 | C |
| ATOM | 6742 | CG | GLU | B | 835 | −34.661 | 20.355 | 49.569 | 1.00 | 68.13 | C |
| ATOM | 6743 | CD | GLU | B | 835 | −35.641 | 19.300 | 50.029 | 1.00 | 70.61 | C |
| ATOM | 6744 | OE1 | GLU | B | 835 | −36.300 | 18.676 | 49.169 | 1.00 | 83.89 | O |
| ATOM | 6745 | OE2 | GLU | B | 835 | −35.752 | 19.102 | 51.258 | 1.00 | 56.28 | O |
| ATOM | 6746 | N | ILE | B | 836 | −34.509 | 23.858 | 47.347 | 1.00 | 33.28 | N |
| ATOM | 6747 | CA | ILE | B | 836 | −34.400 | 25.270 | 47.048 | 1.00 | 34.94 | C |

TABLE 1-continued

| | | | | | | | | | | |
|---|---|---|---|---|---|---|---|---|---|---|
| ATOM | 6748 | C | ILE | B | 836 | −34.696 | 25.558 | 45.580 | 1.00 | 52.95 C |
| ATOM | 6749 | O | ILE | B | 836 | −35.726 | 26.142 | 45.256 | 1.00 | 63.31 O |
| ATOM | 6750 | CB | ILE | B | 836 | −32.985 | 25.781 | 47.423 | 1.00 | 47.91 C |
| ATOM | 6751 | CG1 | ILE | B | 836 | −32.793 | 25.687 | 48.941 | 1.00 | 36.60 C |
| ATOM | 6752 | CG2 | ILE | B | 836 | −32.775 | 27.197 | 46.929 | 1.00 | 43.69 C |
| ATOM | 6753 | CD1 | ILE | B | 836 | −31.491 | 26.272 | 49.421 | 1.00 | 43.31 C |
| ATOM | 6754 | N | ASN | B | 837 | −33.809 | 25.125 | 44.691 | 1.00 | 49.83 N |
| ATOM | 6755 | CA | ASN | B | 837 | −33.966 | 25.350 | 43.254 | 1.00 | 29.63 C |
| ATOM | 6756 | C | ASN | B | 837 | −34.910 | 24.323 | 42.656 | 1.00 | 29.75 C |
| ATOM | 6757 | O | ASN | B | 837 | −34.661 | 23.800 | 41.577 | 1.00 | 43.90 O |
| ATOM | 6758 | CB | ASN | B | 837 | −32.583 | 25.262 | 42.591 | 1.00 | 35.51 C |
| ATOM | 6759 | CG | ASN | B | 837 | −32.597 | 25.646 | 41.120 | 1.00 | 49.11 C |
| ATOM | 6760 | OD1 | ASN | B | 837 | −33.568 | 26.214 | 40.605 | 1.00 | 44.43 O |
| ATOM | 6761 | ND2 | ASN | B | 837 | −31.502 | 25.351 | 40.437 | 1.00 | 35.12 N |
| ATOM | 6762 | N | ASN | B | 838 | −36.014 | 24.052 | 43.347 | 1.00 | 37.53 N |
| ATOM | 6763 | CA | ASN | B | 838 | −36.981 | 23.047 | 42.906 | 1.00 | 33.18 C |
| ATOM | 6764 | C | ASN | B | 838 | −37.585 | 23.171 | 41.519 | 1.00 | 40.31 C |
| ATOM | 6765 | O | ASN | B | 838 | −38.093 | 22.180 | 40.976 | 1.00 | 37.18 O |
| ATOM | 6766 | CB | ASN | B | 838 | −38.119 | 22.943 | 43.918 | 1.00 | 49.28 C |
| ATOM | 6767 | CG | ASN | B | 838 | −38.807 | 24.263 | 44.145 | 1.00 | 47.73 C |
| ATOM | 6768 | OD1 | ASN | B | 838 | −38.367 | 25.071 | 44.955 | 1.00 | 41.45 O |
| ATOM | 6769 | ND2 | ASN | B | 838 | −39.877 | 24.504 | 43.399 | 1.00 | 39.73 N |
| ATOM | 6770 | N | MET | B | 839 | −37.563 | 24.374 | 40.955 | 1.00 | 43.68 N |
| ATOM | 6771 | CA | MET | B | 839 | −38.115 | 24.595 | 39.622 | 1.00 | 44.00 C |
| ATOM | 6772 | C | MET | B | 839 | −37.194 | 24.069 | 38.519 | 1.00 | 49.23 C |
| ATOM | 6773 | O | MET | B | 839 | −37.592 | 23.945 | 37.359 | 1.00 | 54.24 O |
| ATOM | 6774 | CB | MET | B | 839 | −38.390 | 26.088 | 39.409 | 1.00 | 58.41 C |
| ATOM | 6775 | CG | MET | B | 839 | −39.610 | 26.602 | 40.176 | 1.00 | 67.27 C |
| ATOM | 6776 | SD | MET | B | 839 | −41.216 | 25.893 | 39.625 | 1.00 | 100.64 S |
| ATOM | 6777 | CE | MET | B | 839 | −41.383 | 24.370 | 40.643 | 1.00 | 68.50 C |
| ATOM | 6778 | N | ASN | B | 840 | −35.961 | 23.753 | 38.883 | 1.00 | 46.03 N |
| ATOM | 6779 | CA | ASN | B | 840 | −35.034 | 23.232 | 37.912 | 1.00 | 41.04 C |
| ATOM | 6780 | C | ASN | B | 840 | −34.912 | 21.715 | 37.917 | 1.00 | 53.28 C |
| ATOM | 6781 | O | ASN | B | 840 | −34.279 | 21.137 | 37.028 | 1.00 | 46.16 O |
| ATOM | 6782 | CB | ASN | B | 840 | −33.673 | 23.876 | 38.106 | 1.00 | 41.38 C |
| ATOM | 6783 | CG | ASN | B | 840 | −33.518 | 25.114 | 37.260 | 1.00 | 43.25 C |
| ATOM | 6784 | OD1 | ASN | B | 840 | −33.703 | 25.062 | 36.044 | 1.00 | 42.09 O |
| ATOM | 6785 | ND2 | ASN | B | 840 | −33.198 | 26.233 | 37.889 | 1.00 | 49.54 N |
| ATOM | 6786 | N | PHE | B | 841 | −35.545 | 21.065 | 38.889 | 1.00 | 40.89 N |
| ATOM | 6787 | CA | PHE | B | 841 | −35.465 | 19.609 | 38.994 | 1.00 | 33.83 C |
| ATOM | 6788 | C | PHE | B | 841 | −36.835 | 19.001 | 39.213 | 1.00 | 29.38 C |
| ATOM | 6789 | O | PHE | B | 841 | −37.502 | 19.332 | 40.171 | 1.00 | 51.74 O |
| ATOM | 6790 | CB | PHE | B | 841 | −34.547 | 19.230 | 40.174 | 1.00 | 27.54 C |
| ATOM | 6791 | CG | PHE | B | 841 | −33.162 | 19.827 | 40.085 | 1.00 | 28.57 C |
| ATOM | 6792 | CD1 | PHE | B | 841 | −32.181 | 19.240 | 39.289 | 1.00 | 33.32 C |
| ATOM | 6793 | CD2 | PHE | B | 841 | −32.851 | 21.009 | 40.758 | 1.00 | 24.56 C |
| ATOM | 6794 | CE1 | PHE | B | 841 | −30.918 | 19.824 | 39.158 | 1.00 | 32.94 C |
| ATOM | 6795 | CE2 | PHE | B | 841 | −31.596 | 21.597 | 40.636 | 1.00 | 29.66 C |
| ATOM | 6796 | CZ | PHE | B | 841 | −30.623 | 21.000 | 39.828 | 1.00 | 27.97 C |
| ATOM | 6797 | N | THR | B | 842 | −37.244 | 18.089 | 38.348 | 1.00 | 40.02 N |
| ATOM | 6798 | CA | THR | B | 842 | −38.542 | 17.429 | 38.486 | 1.00 | 29.17 C |
| ATOM | 6799 | C | THR | B | 842 | −38.297 | 15.944 | 38.747 | 1.00 | 35.40 C |
| ATOM | 6800 | O | THR | B | 842 | −37.880 | 15.220 | 37.843 | 1.00 | 36.35 O |
| ATOM | 6801 | CB | THR | B | 842 | −39.369 | 17.556 | 37.191 | 1.00 | 40.76 C |
| ATOM | 6802 | OG1 | THR | B | 842 | −39.420 | 18.932 | 36.797 | 1.00 | 44.74 O |
| ATOM | 6803 | CG2 | THR | B | 842 | −40.782 | 17.021 | 37.399 | 1.00 | 39.24 C |
| ATOM | 6804 | N | LYS | B | 843 | −38.581 | 15.483 | 39.964 | 1.00 | 39.54 N |
| ATOM | 6805 | CA | LYS | B | 843 | −38.353 | 14.085 | 40.308 | 1.00 | 38.30 C |
| ATOM | 6806 | C | LYS | B | 843 | −39.222 | 13.157 | 39.493 | 1.00 | 30.70 C |
| ATOM | 6807 | O | LYS | B | 843 | −40.410 | 13.375 | 39.342 | 1.00 | 48.43 O |
| ATOM | 6808 | CB | LYS | B | 843 | −38.584 | 13.826 | 41.797 | 1.00 | 44.29 C |
| ATOM | 6809 | CG | LYS | B | 843 | −38.126 | 12.431 | 42.217 | 1.00 | 49.26 C |
| ATOM | 6810 | CD | LYS | B | 843 | −38.608 | 11.999 | 43.609 | 1.00 | 45.49 C |
| ATOM | 6811 | CE | LYS | B | 843 | −38.130 | 12.926 | 44.710 | 1.00 | 59.11 C |
| ATOM | 6812 | NZ | LYS | B | 843 | −36.651 | 12.996 | 44.825 | 1.00 | 55.65 N |
| ATOM | 6813 | N | LEU | B | 844 | −38.608 | 12.125 | 38.946 | 1.00 | 31.65 N |
| ATOM | 6814 | CA | LEU | B | 844 | −39.320 | 11.149 | 38.126 | 1.00 | 44.50 C |
| ATOM | 6815 | C | LEU | B | 844 | −39.440 | 9.818 | 38.839 | 1.00 | 28.65 C |
| ATOM | 6816 | O | LEU | B | 844 | −40.317 | 9.016 | 38.530 | 1.00 | 46.09 O |
| ATOM | 6817 | CB | LEU | B | 844 | −38.570 | 10.913 | 36.813 | 1.00 | 43.11 C |
| ATOM | 6818 | CG | LEU | B | 844 | −38.595 | 12.061 | 35.814 | 1.00 | 50.73 C |
| ATOM | 6819 | CD1 | LEU | B | 844 | −37.560 | 11.816 | 34.712 | 1.00 | 46.07 C |
| ATOM | 6820 | CD2 | LEU | B | 844 | −40.011 | 12.160 | 35.238 | 1.00 | 36.20 C |
| ATOM | 6821 | N | LYS | B | 845 | −38.538 | 9.584 | 39.779 | 1.00 | 34.07 N |
| ATOM | 6822 | CA | LYS | B | 845 | −38.527 | 8.326 | 40.481 | 1.00 | 51.12 C |
| ATOM | 6823 | C | LYS | B | 845 | −37.482 | 8.301 | 41.578 | 1.00 | 41.17 C |
| ATOM | 6824 | O | LYS | B | 845 | −36.402 | 8.867 | 41.448 | 1.00 | 48.59 O |
| ATOM | 6825 | CB | LYS | B | 845 | −38.310 | 7.206 | 39.465 | 1.00 | 52.35 C |
| ATOM | 6826 | CG | LYS | B | 845 | −37.873 | 5.870 | 40.050 | 1.00 | 40.80 C |

TABLE 1-continued

| ATOM | 6827 | CD  | LYS | B | 845 | −37.496 | 4.889  | 38.949 | 1.00 | 45.43  | C |
| ---- | ---- | --- | --- | - | --- | ------- | ------ | ------ | ---- | ------ | - |
| ATOM | 6828 | CE  | LYS | B | 845 | −37.090 | 3.544  | 39.546 | 1.00 | 33.10  | C |
| ATOM | 6829 | NZ  | LYS | B | 845 | −36.750 | 2.555  | 38.488 | 1.00 | 43.44  | N |
| ATOM | 6830 | N   | ASN | B | 846 | −37.818 | 7.660  | 42.674 | 1.00 | 40.60  | N |
| ATOM | 6831 | CA  | ASN | B | 846 | −36.870 | 7.468  | 43.769 | 1.00 | 46.81  | C |
| ATOM | 6832 | C   | ASN | B | 846 | −36.265 | 6.094  | 43.542 | 1.00 | 34.74  | C |
| ATOM | 6833 | O   | ASN | B | 846 | −36.885 | 5.220  | 42.945 | 1.00 | 56.62  | O |
| ATOM | 6834 | CB  | ASN | B | 846 | −37.571 | 7.451  | 45.123 | 1.00 | 46.21  | C |
| ATOM | 6835 | CG  | ASN | B | 846 | −38.253 | 8.749  | 45.450 | 1.00 | 57.63  | C |
| ATOM | 6836 | OD1 | ASN | B | 846 | −39.462 | 8.896  | 45.250 | 1.00 | 69.95  | O |
| ATOM | 6837 | ND2 | ASN | B | 846 | −37.485 | 9.706  | 45.954 | 1.00 | 57.10  | N |
| ATOM | 6838 | N   | PHE | B | 847 | −35.053 | 5.867  | 44.020 | 1.00 | 51.36  | N |
| ATOM | 6839 | CA  | PHE | B | 847 | −34.458 | 4.539  | 43.920 | 1.00 | 70.24  | C |
| ATOM | 6840 | C   | PHE | B | 847 | −34.731 | 3.885  | 45.283 | 1.00 | 60.39  | C |
| ATOM | 6841 | O   | PHE | B | 847 | −34.025 | 4.133  | 46.258 | 1.00 | 54.18  | O |
| ATOM | 6842 | CB  | PHE | B | 847 | −32.955 | 4.612  | 43.597 | 1.00 | 29.91  | C |
| ATOM | 6843 | CG  | PHE | B | 847 | −32.642 | 5.390  | 42.342 | 1.00 | 31.14  | C |
| ATOM | 6844 | CD1 | PHE | B | 847 | −33.411 | 5.189  | 41.180 | 1.00 | 35.96  | C |
| ATOM | 6845 | CD2 | PHE | B | 847 | −31.605 | 6.296  | 42.303 | 1.00 | 35.22  | C |
| ATOM | 6846 | CE1 | PHE | B | 847 | −33.123 | 5.885  | 40.022 | 1.00 | 26.19  | C |
| ATOM | 6847 | CE2 | PHE | B | 847 | −31.333 | 6.969  | 41.121 | 1.00 | 27.04  | C |
| ATOM | 6848 | CZ  | PHE | B | 847 | −32.083 | 6.759  | 39.995 | 1.00 | 29.98  | C |
| ATOM | 6849 | N   | THR | B | 848 | −35.761 | 3.047  | 45.330 | 1.00 | 68.10  | N |
| ATOM | 6850 | CA  | THR | B | 848 | −36.248 | 2.448  | 46.571 | 1.00 | 79.00  | C |
| ATOM | 6851 | C   | THR | B | 848 | −35.269 | 1.664  | 47.476 | 1.00 | 79.53  | C |
| ATOM | 6852 | O   | THR | B | 848 | −35.098 | 2.040  | 48.642 | 1.00 | 76.40  | O |
| ATOM | 6853 | CB  | THR | B | 848 | −37.463 | 1.555  | 46.248 | 1.00 | 73.10  | C |
| ATOM | 6854 | OG1 | THR | B | 848 | −38.430 | 2.315  | 45.517 | 1.00 | 80.01  | O |
| ATOM | 6855 | CG2 | THR | B | 848 | −38.091 | 1.042  | 47.540 | 1.00 | 93.78  | C |
| ATOM | 6856 | N   | PRO | B | 849 | −34.625 | 0.572  | 46.994 | 1.00 | 71.96  | N |
| ATOM | 6857 | CA  | PRO | B | 849 | −33.735 | −0.294 | 47.826 | 1.00 | 77.46  | C |
| ATOM | 6858 | C   | PRO | B | 849 | −32.622 | 0.355  | 48.666 | 1.00 | 87.70  | C |
| ATOM | 6859 | O   | PRO | B | 849 | −32.170 | 1.447  | 48.353 | 1.00 | 82.08  | O |
| ATOM | 6860 | CB  | PRO | B | 849 | −33.139 | −1.252 | 46.781 | 1.00 | 76.31  | C |
| ATOM | 6861 | CG  | PRO | B | 849 | −34.255 | −1.408 | 45.785 | 1.00 | 79.46  | C |
| ATOM | 6862 | CD  | PRO | B | 849 | −34.932 | −0.062 | 45.699 | 1.00 | 71.02  | C |
| ATOM | 6863 | N   | GLY | B | 850 | −32.183 | −0.350 | 49.754 | 1.00 | 96.87  | N |
| ATOM | 6864 | CA  | GLY | B | 850 | −31.061 | 0.087  | 50.637 | 1.00 | 93.70  | C |
| ATOM | 6865 | C   | GLY | B | 850 | −29.889 | 0.287  | 49.699 | 1.00 | 96.70  | C |
| ATOM | 6866 | O   | GLY | B | 850 | −29.824 | 1.320  | 49.049 | 1.00 | 100.55 | O |
| ATOM | 6867 | N   | HIS | B | 851 | −28.913 | −0.649 | 49.578 | 1.00 | 90.34  | N |
| ATOM | 6868 | CA  | HIS | B | 851 | −28.061 | −0.355 | 48.437 | 1.00 | 91.91  | C |
| ATOM | 6869 | C   | HIS | B | 851 | −26.815 | −1.111 | 47.973 | 1.00 | 89.31  | C |
| ATOM | 6870 | O   | HIS | B | 851 | −26.101 | −1.836 | 48.662 | 1.00 | 87.59  | O |
| ATOM | 6871 | CB  | HIS | B | 851 | −27.751 | 1.112  | 48.450 | 1.00 | 91.51  | C |
| ATOM | 6872 | CG  | HIS | B | 851 | −28.535 | 1.666  | 47.232 | 1.00 | 94.30  | C |
| ATOM | 6873 | ND1 | HIS | B | 851 | −28.259 | 2.840  | 46.640 | 1.00 | 97.39  | N |
| ATOM | 6874 | CD2 | HIS | B | 851 | −29.585 | 1.107  | 46.562 | 1.00 | 97.59  | C |
| ATOM | 6875 | CE1 | HIS | B | 851 | −29.108 | 3.002  | 45.640 | 1.00 | 90.52  | C |
| ATOM | 6876 | NE2 | HIS | B | 851 | −29.918 | 1.967  | 45.574 | 1.00 | 97.08  | N |
| ATOM | 6877 | N   | HIS | B | 852 | −26.709 | −0.794 | 46.689 | 1.00 | 91.82  | N |
| ATOM | 6878 | CA  | HIS | B | 852 | −25.801 | −1.178 | 45.656 | 1.00 | 92.50  | C |
| ATOM | 6879 | C   | HIS | B | 852 | −25.253 | 0.075  | 44.946 | 1.00 | 92.87  | C |
| ATOM | 6880 | O   | HIS | B | 852 | −24.684 | 0.964  | 45.589 | 1.00 | 97.44  | O |
| ATOM | 6881 | CB  | HIS | B | 852 | −26.549 | −2.013 | 44.622 | 1.00 | 87.50  | C |
| ATOM | 6882 | CG  | HIS | B | 852 | −28.024 | −1.579 | 44.557 | 1.00 | 91.47  | C |
| ATOM | 6883 | ND1 | HIS | B | 852 | −29.011 | −2.184 | 45.300 | 1.00 | 91.69  | N |
| ATOM | 6884 | CD2 | HIS | B | 852 | −28.626 | −0.584 | 43.859 | 1.00 | 88.45  | C |
| ATOM | 6885 | CE1 | HIS | B | 852 | −30.168 | −1.581 | 45.065 | 1.00 | 98.16  | C |
| ATOM | 6886 | NE2 | HIS | B | 852 | −29.961 | −0.608 | 44.197 | 1.00 | 96.47  | N |
| ATOM | 6887 | N   | HIS | B | 853 | −25.423 | 0.122  | 43.622 | 1.00 | 86.71  | N |
| ATOM | 6888 | CA  | HIS | B | 853 | −24.890 | 1.250  | 42.867 | 1.00 | 83.42  | C |
| ATOM | 6889 | C   | HIS | B | 853 | −25.542 | 1.418  | 41.515 | 1.00 | 85.07  | C |
| ATOM | 6890 | O   | HIS | B | 853 | −26.737 | 1.217  | 41.319 | 1.00 | 64.56  | O |
| ATOM | 6891 | CB  | HIS | B | 853 | −23.376 | 1.060  | 42.717 | 1.00 | 80.74  | C |
| ATOM | 6892 | CG  | HIS | B | 853 | −22.571 | 2.369  | 42.581 | 1.00 | 96.43  | C |
| ATOM | 6893 | ND1 | HIS | B | 853 | −22.556 | 3.118  | 41.424 | 1.00 | 103.01 | N |
| ATOM | 6894 | CD2 | HIS | B | 853 | −21.772 | 3.021  | 43.460 | 1.00 | 102.87 | C |
| ATOM | 6895 | CE1 | HIS | B | 853 | −21.780 | 4.176  | 41.595 | 1.00 | 97.73  | C |
| ATOM | 6896 | NE2 | HIS | B | 853 | −21.292 | 4.140  | 42.821 | 1.00 | 99.31  | N |
| ATOM | 6897 | N   | HIS | B | 854 | −24.710 | 1.785  | 40.592 | 1.00 | 94.66  | N |
| ATOM | 6898 | CA  | HIS | B | 854 | −25.112 | 1.977  | 39.278 | 1.00 | 90.81  | C |
| ATOM | 6899 | C   | HIS | B | 854 | −23.829 | 1.721  | 38.561 | 1.00 | 88.92  | C |
| ATOM | 6900 | O   | HIS | B | 854 | −23.545 | 0.661  | 38.015 | 1.00 | 89.96  | O |
| ATOM | 6901 | CB  | HIS | B | 854 | −25.786 | 3.375  | 39.124 | 1.00 | 80.69  | C |
| ATOM | 6902 | CG  | HIS | B | 854 | −25.891 | 3.964  | 37.699 | 1.00 | 91.31  | C |
| ATOM | 6903 | ND1 | HIS | B | 854 | −26.405 | 3.209  | 36.667 | 1.00 | 97.11  | N |
| ATOM | 6904 | CD2 | HIS | B | 854 | −25.543 | 5.156  | 37.158 | 1.00 | 96.96  | C |
| ATOM | 6905 | CE1 | HIS | B | 854 | −26.396 | 3.910  | 35.548 | 1.00 | 94.91  | C |

TABLE 1-continued

| | | | | | | | | | | |
|---|---|---|---|---|---|---|---|---|---|---|
| ATOM | 6906 | NE2 | HIS | B | 854 | −25.877 | 5.094 | 35.818 | 1.00 | 104.94 N |
| ATOM | 6907 | N | HIS | B | 855 | −23.076 | 2.792 | 38.643 | 1.00 | 76.19 N |
| ATOM | 6908 | CA | HIS | B | 855 | −21.760 | 2.867 | 38.104 | 1.00 | 79.83 C |
| ATOM | 6909 | C | HIS | B | 855 | −21.475 | 4.238 | 37.511 | 1.00 | 90.02 C |
| ATOM | 6910 | O | HIS | B | 855 | −22.375 | 4.983 | 37.167 | 1.00 | 78.75 O |
| ATOM | 6911 | CB | HIS | B | 855 | −21.538 | 1.781 | 37.081 | 1.00 | 91.55 C |
| ATOM | 6912 | CG | HIS | B | 855 | −20.116 | 1.243 | 37.318 | 1.00 | 97.22 C |
| ATOM | 6913 | ND1 | HIS | B | 855 | −19.767 | 0.663 | 38.501 | 1.00 | 104.10 N |
| ATOM | 6914 | CD2 | HIS | B | 855 | −18.995 | 1.235 | 36.544 | 1.00 | 94.24 C |
| ATOM | 6915 | CE1 | HIS | B | 855 | −18.497 | 0.321 | 38.455 | 1.00 | 102.02 C |
| ATOM | 6916 | NE2 | HIS | B | 855 | −17.994 | 0.668 | 37.277 | 1.00 | 99.90 N |
| ATOM | 6917 | N | HIS | B | 856 | −20.185 | 4.537 | 37.390 | 1.00 | 84.27 N |
| ATOM | 6918 | CA | HIS | B | 856 | −19.776 | 5.777 | 36.758 | 1.00 | 66.99 C |
| ATOM | 6919 | C | HIS | B | 856 | −20.181 | 6.984 | 37.575 | 1.00 | 63.28 C |
| ATOM | 6920 | O | HIS | B | 856 | −20.806 | 6.866 | 38.622 | 1.00 | 53.73 O |
| ATOM | 6921 | CB | HIS | B | 856 | −20.374 | 5.817 | 35.343 | 1.00 | 55.45 C |
| ATOM | 6922 | CG | HIS | B | 856 | −19.909 | 4.684 | 34.356 | 1.00 | 59.56 C |
| ATOM | 6923 | ND1 | HIS | B | 856 | −18.569 | 4.417 | 34.167 | 1.00 | 41.28 N |
| ATOM | 6924 | CD2 | HIS | B | 856 | −20.577 | 3.814 | 33.562 | 1.00 | 59.56 C |
| ATOM | 6925 | CE1 | HIS | B | 856 | −18.433 | 3.456 | 33.271 | 1.00 | 59.17 C |
| ATOM | 6926 | NE2 | HIS | B | 856 | −19.636 | 3.080 | 32.882 | 1.00 | 65.60 N |

What is claimed is:

1. A crystal of a double mutant of the light chain of botulinum neurotoxin serotype A protein, wherein the double mutant of the light chain of botulinum neurotoxin serotype A protein consists of the amino acid sequence according to SEQ ID NO: 9, and wherein the crystal is in space group P2, and wherein said crystal comprises a unit cell having dimensions of a, b, and c, wherein a is between about 53 and about 61 Å, b is between about 39 and about 43 Å, and c is between about 185 and about 205 Å, and wherein said crystal consists of atoms arranged in a spatial relationship having the structure coordinates having a root mean square deviation of less than about 0.2 Å from the structure coordinates listed in Table 1.

2. A crystal of a SNARE domain of the SNAP-25 protein in complex with a double mutant of the light chain of botulinum neurotoxin serotype A protein, wherein the double mutant of the light chain of botulinum neurotoxin serotype A protein consists of the amino acid sequence according to SEQ ID NO: 10, and wherein the SNARE domain is a polypeptide consisting of amino acids 141 through 204 of the amino acid sequence listed in SEQ ID NO: 2, and wherein the crystal is in space group $P4_32_12$, and wherein said crystal comprises a unit cell having dimensions of a, b, and c, wherein a is between about 80 and about 90 Å, b is between about 80 and about 90 Å, and c is between about 154 and about 174 Å, and wherein said crystal comprises atoms arranged in a spatial relationship having a root mean square deviation of less than about 0.2 Å from the structure coordinates listed in Table 2.

* * * * *

SEQUENCE LISTING

<160> NUMBER OF SEQ ID NOS: 6

<210> SEQ ID NO 1
<211> LENGTH: 419
<212> TYPE: PRT
<213> ORGANISM: Clostridium Botulinum

<400> SEQUENCE: 1

```
Pro Phe Val Asn Lys Gln Phe Asn Tyr Lys Asp Pro Val Asn Gly Val
1               5                   10                  15

Asp Ile Ala Tyr Ile Lys Ile Pro Asn Ala Gly Gln Met Gln Pro Val
            20                  25                  30

Lys Ala Phe Lys Ile His Asn Lys Ile Trp Val Ile Pro Glu Arg Asp
        35                  40                  45

Thr Phe Thr Asn Pro Glu Glu Gly Asp Leu Asn Pro Pro Glu Ala
    50                  55                  60

Lys Gln Val Pro Val Ser Tyr Tyr Asp Ser Thr Tyr Leu Ser Thr Asp
65                  70                  75                  80

Asn Glu Lys Asp Asn Tyr Leu Lys Gly Val Thr Lys Leu Phe Glu Arg
                85                  90                  95

Ile Tyr Ser Thr Asp Leu Gly Arg Met Leu Leu Thr Ser Ile Val Arg
            100                 105                 110

Gly Ile Pro Phe Trp Gly Gly Ser Thr Ile Asp Thr Glu Leu Lys Val
        115                 120                 125

Ile Asp Thr Asn Cys Ile Asn Val Ile Gln Pro Asp Gly Ser Tyr Arg
    130                 135                 140

Ser Glu Glu Leu Asn Leu Val Ile Gly Pro Ser Ala Asp Ile Ile
145                 150                 155                 160

Gln Phe Glu Cys Lys Ser Phe Gly His Glu Val Leu Asn Leu Thr Arg
                165                 170                 175

Asn Gly Tyr Gly Ser Thr Gln Tyr Ile Arg Phe Ser Pro Asp Phe Thr
            180                 185                 190

Phe Gly Phe Glu Glu Ser Leu Glu Val Asp Thr Asn Pro Leu Leu Gly
        195                 200                 205

Ala Gly Lys Phe Ala Thr Asp Pro Ala Val Thr Leu Ala His Gln Leu
```

-continued

```
                210                 215                 220
Ile His Ala Gly His Arg Leu Tyr Gly Ile Ala Ile Asn Pro Asn Arg
225                 230                 235                 240

Val Phe Lys Val Asn Thr Asn Ala Tyr Tyr Glu Met Ser Gly Leu Glu
                245                 250                 255

Val Ser Phe Glu Glu Leu Arg Thr Phe Gly His Asp Ala Lys Phe
                260                 265                 270

Ile Asp Ser Leu Gln Glu Asn Glu Phe Arg Leu Tyr Tyr Asn Lys
            275                 280                 285

Phe Lys Asp Ile Ala Ser Thr Leu Asn Lys Ala Lys Ser Ile Val Gly
        290                 295                 300

Thr Thr Ala Ser Leu Gln Tyr Met Lys Asn Val Phe Lys Glu Lys Tyr
305                 310                 315                 320

Leu Leu Ser Glu Asp Thr Ser Gly Lys Phe Ser Val Asp Lys Leu Lys
                325                 330                 335

Phe Asp Lys Leu Tyr Lys Met Leu Thr Glu Ile Tyr Thr Glu Asp Asn
                340                 345                 350

Phe Val Lys Phe Phe Lys Val Leu Asn Arg Lys Thr Phe Leu Asn Phe
                355                 360                 365

Asp Lys Ala Val Phe Lys Ile Asn Ile Val Pro Lys Val Asn Tyr Thr
        370                 375                 380

Ile Tyr Asp Gly Phe Asn Leu Arg Asn Thr Asn Leu Ala Ala Asn Phe
385                 390                 395                 400

Asn Gly Gln Asn Thr Glu Ile Asn Asn Met Asn Phe Thr Lys Leu Lys
                405                 410                 415

Asn Phe Thr

<210> SEQ ID NO 2
<211> LENGTH: 206
<212> TYPE: PRT
<213> ORGANISM: Homo sapiens

<400> SEQUENCE: 2

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
                20                  25                  30

Leu Gln Leu Val Glu Glu Ser Lys Asp Ala Gly Ile Arg Thr Leu Val
            35                  40                  45

Met Leu Asp Glu Gln Gly Glu Gln Leu Glu Arg Ile Glu Glu Gly Met
        50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
                100                 105                 110

Val Ala Ser Gln Pro Ala Arg Val Val Asp Glu Arg Glu Gln Met Ala
            115                 120                 125

Ile Ser Gly Gly Phe Ile Arg Arg Val Thr Asn Asp Ala Arg Glu Asn
        130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
```

-continued

```
                  165                 170                 175
Gln Ile Asp Arg Ile Met Glu Lys Ala Asp Ser Asn Lys Thr Arg Ile
            180                 185                 190
Asp Glu Ala Asn Gln Arg Ala Thr Lys Met Leu Gly Ser Gly
        195                 200                 205

<210> SEQ ID NO 3
<211> LENGTH: 33
<212> TYPE: DNA
<213> ORGANISM: Artificial
<220> FEATURE:
<223> OTHER INFORMATION: Forward PCR primer for amplification of
      BoNT/A-LC

<400> SEQUENCE: 3
acagaattcg caattaagga gataataggt atg                                    33

<210> SEQ ID NO 4
<211> LENGTH: 62
<212> TYPE: DNA
<213> ORGANISM: Artificial
<220> FEATURE:
<223> OTHER INFORMATION: Reverse PCR primer for amplification of
      BoNT/A-LC

<400> SEQUENCE: 4
gctcccggga gtaaaatttt ttagtttagt aaaattcata ttattaattt ctgtattttg       60
ac                                                                     62

<210> SEQ ID NO 5
<211> LENGTH: 20
<212> TYPE: DNA
<213> ORGANISM: Artificial
<220> FEATURE:
<223> OTHER INFORMATION: forward PCR primer for affinity tag

<400> SEQUENCE: 5
ctggttccgc gcgtggatct                                                   20

<210> SEQ ID NO 6
<211> LENGTH: 18
<212> TYPE: DNA
<213> ORGANISM: Artificial
<220> FEATURE:
<223> OTHER INFORMATION: reverse PCR primer for affinity tag

<400> SEQUENCE: 6
agatccacgc ggaaccag                                                     18
```